United States Patent
Liu et al.

(10) Patent No.: US 12,331,044 B2
(45) Date of Patent: Jun. 17, 2025

(54) INHIBITORS OF HISTONE DEACETYLASE USEFUL FOR THE TREATMENT OR PREVENTION OF HIV INFECTION

(71) Applicant: Merck Sharp & Dohme LLC, Rahway, NJ (US)

(72) Inventors: Jian Liu, Edison, NJ (US); Dane James Clausen, Rahway, NJ (US); Wensheng Yu, Edison, NJ (US); Joseph M. Kelly, Parlin, NJ (US); Hyunjin M. Kim, Livingston, NJ (US); Joseph A. Kozlowski, Princeton, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 1032 days.

(21) Appl. No.: 17/261,982

(22) PCT Filed: Jul. 26, 2019

(86) PCT No.: PCT/US2019/043543
§ 371 (c)(1),
(2) Date: Jan. 21, 2021

(87) PCT Pub. No.: WO2020/028150
PCT Pub. Date: Feb. 6, 2020

(65) Prior Publication Data
US 2021/0276992 A1    Sep. 9, 2021

Related U.S. Application Data

(60) Provisional application No. 62/713,177, filed on Aug. 1, 2018.

(51) Int. Cl.
| | | |
|---|---|---|
| *C07D 413/14* | (2006.01) | |
| *C07D 413/12* | (2006.01) | |
| *C07D 417/14* | (2006.01) | |
| *C07D 471/04* | (2006.01) | |
| *C07D 487/04* | (2006.01) | |
| *C07D 498/04* | (2006.01) | |
| *C07D 498/10* | (2006.01) | |
| *C07D 513/04* | (2006.01) | |

(52) U.S. Cl.
CPC ......... *C07D 413/14* (2013.01); *C07D 413/12* (2013.01); *C07D 417/14* (2013.01); *C07D 471/04* (2013.01); *C07D 487/04* (2013.01); *C07D 498/04* (2013.01); *C07D 498/10* (2013.01); *C07D 513/04* (2013.01)

(58) Field of Classification Search
CPC .. C07D 413/14; C07D 413/12; C07D 417/14; C07D 471/04; C07D 487/04; C07D 498/04; C07D 498/10; C07D 513/04
See application file for complete search history.

(56) References Cited

U.S. PATENT DOCUMENTS 5,750,532 A    5/1998    Girijavallabhan et al.

FOREIGN PATENT DOCUMENTS

| WO | 1991013876 A1 | 9/1991 |
|---|---|---|
| WO | 2006061638 A2 | 6/2006 |
| WO | 2007052073 A2 | 5/2007 |
| WO | 2014023754 A1 | 2/2014 |
| WO | 2014067985 A1 | 5/2014 |
| WO | 2017222951 A1 | 12/2017 |
| WO | 2020025631 A1 | 2/2020 |
| WO | 2020096916 A2 | 5/2020 |
| WO | 2020150091 A1 | 7/2020 |
| WO | 2020190827 A1 | 9/2020 |

OTHER PUBLICATIONS

Pubchem, PubChem CID 87331625, created Feb. 12, 2015 (Year: 2015).*
Vasudevan et al., Bioorganic & Medicinal Chemistry Letters 13, 2003, 3909-3913 (Year: 2003).*
PubChem-CID-44350688, Create Date: Nov. 19, 2009 (Nov. 19, 2009), p. 2, Fig.
PubChem-CID-87331625, Create Date: Feb. 12, 2015 (Feb. 12, 2015), p. 2, Fig.
International Search Report and Written Opinion issued for corresponding application PCT/US19/43543, Dec. 3, 2019, 10 pages.
Database PubChem Compound [Online] Jun. 10, 2006 (Jun. 10, 2006), American Chemical Society: "1 H-Indole-3-acetamide, N-[(1 S)-7-(2-furanyl)-1-[5-(2-naphthalenyl)-1 H-imidazol-2-yl]-7-oxoheptyl]-5-methoxy-2-methyl", XP55890590, Database accession No. 891264-91-8 (1 page).
Database PubChem Compound [Online] American Chemical Society; Jan. 1, 2006 (Jan. 1, 2006), Attenni Barbara et al: "Preparation of heterocycle derivatives as histone deacetylase inhibitors", XP55890680, Database accession No. 145:62907* Compounds with RN 891264-92-9 and 891268-95-4 * (3 pages).

(Continued)

*Primary Examiner* — Susanna Moore
*Assistant Examiner* — Luisalberto Gonzalez
(74) *Attorney, Agent, or Firm* — Eric Greenwald; John C. Todaro

(57) ABSTRACT

The present invention relates to Compounds of Formula (I): Formula (I) and pharmaceutically acceptable salts or prodrug thereof, wherein $R^1$, $R^2$, $R^3$, $R^a$, $R^b$, A and B are as defined herein. The present invention also relates to compositions comprising at least one compound of Formula (I), and methods of using the compounds of Formula (I) for treating or preventing HIV infection in a subject.

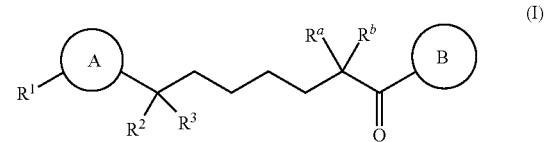

(I)

12 Claims, No Drawings

(56) References Cited

OTHER PUBLICATIONS

Vasudevan, Anil et al., Heterocyclic Ketones as Inhibitors of Histone Deacetylase, Bioorganic & Medicinal Chemistry Letters, 2003, 3909-3913, 13.

* cited by examiner

INHIBITORS OF HISTONE DEACETYLASE USEFUL FOR THE TREATMENT OR PREVENTION OF HIV INFECTION

CROSS REFERENCE TO RELATED APPLICATIONS

This application is a U.S. National Phase application under 35 U.S.C. § 371 of PCT Application No. PCT/US2019/043543 filed Jul. 26, 2019, which claims priority to U.S. Ser. No. 62/713,177 filed Aug. 1, 2018.

FIELD OF THE INVENTION

The present invention relates to inhibitors of histone deacetylase, compositions comprising at least one inhibitor of histone deacetylase, and methods of using the inhibitors of histone deacetylase for treating or preventing HIV infection in a subject.

BACKGROUND OF THE INVENTION

DNA in the nucleus of the cell exists as a hierarchy of compacted chromatin structures. The basic repeating unit in chromatin is the nucleosome, which consists of a histone octamer of proteins in the nucleus of the cell around which DNA is wrapped twice. The orderly packaging of DNA in the nucleus plays an important role in the functional aspects of gene regulation. Covalent modifications of the histones have a key role in altering chromatin higher order structure and function, and ultimately, gene expression. The covalent modification of histones, such as acetylation, occurs by enzymatically mediated process.

Regulation of gene expression through the inhibition of the nuclear enzyme histone deacetylase (HDAC) is one of the several possible regulatory mechanisms whereby chromatin actively can be affected. The dynamic homeostasis of the nuclear acetylation of histone can be regulated by the opposing activity of the enzymes histone acetyl transferase (HAT) and histone deacetylase (HDAC). Transcriptionally silent chromatin can be characterized by nucleosomes with low levels of acetylated histones. Acetylation reduces the positive charge of histones, thereby expanding the structure of the nucleosome and facilitating the interaction of transcription factors with the DNA. Removal of the acetyl group restores the positive charge, condensing the structure of the nucleosome. While histone acetylation can activate DNA transcription, enhancing gene expression, histone deacetylase can reverse the process and can serve to repress gene expression. Inhibition of the histone deacetylase (HDAC inhibition) can also increase the activation of DNA transcription. See, for example, Grunstein, Nature, 389, 349-352 (1997); Pazin et al., Cell 89, 325-328 (1997); Wade et al., Trends Biochem Sci. 22, 128-132 (1997); and Wolffe, Science 272, 371-372 (1996).

With the introduction of combination antiretroviral therapy (ART), HIV became a controllable chronic disease. The combination of ART (cART) targets specific stages of the viral life cycle, and is effective at combatting active viral load down to undetectable levels. However, HIV persists within the body of infected individuals undergoing therapy, and cessation of ART leads to a viral rebound within 3-4 weeks. The HIV can persist in resting memory and naïve CD4+ T cells and other long-lived cells, such as infected astrocytes and cells of macrophage lineage. HIV can persist in these resting cells by establishing a latent or "silent" infection. In these cells, virus is integrated into the host genome, but viral production does not occur as a result of inhibition of both viral transcriptions from proteins. However, these latently infected cells still do contain replication competent virus, and once cART is stopped, rebound in plasma HIV RNA is observed in nearly all patients.

One approach currently being explored to eliminate latently infected CD4+ T cells is to activate viral production from these cells in the presence of cART, when the production of the virus should kill the infected cells. Histone deacetylase inhibitors have shown promise in vitro in activating virus production from latent infected cells, and therefore this class of drugs is being studied as part of a strategy aimed at a cure of HIV.

Eleven members of the HDAC family has been identified in humans, which share a conserved catalytic domain and are grouped into two classes: class I (1,2,3,8), homologous to yeast Rpd3; and class IIa (4,5,7,9) and IIb (6, 10), homologous to yeast Hda1. HDAC 11 shares homology with both classes, but is at the same time distinct from all the other ten subtypes. The first generation of HDAC inhibitors (HDACi) are promising therapeutic agents against cancer and other diseases, and showed in vitro activation of virus production from latent infected cells. However, due to their poor selectivity, those that entered clinical trials, all show similar adverse effects. The poorly selective HDACi's are not suitable for healthy HIV patents on cART, thus the interest is high for the discovery and development of novel and subtype selective HDAC inhibitors.

SUMMARY OF THE INVENTION

In one aspect, the present invention provides Compounds of Formula I:

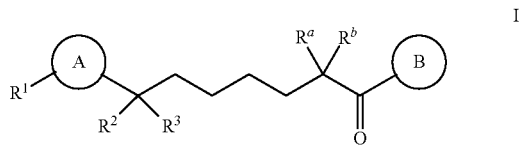

or a pharmaceutically acceptable salt thereof,
wherein

is a five-membered heteroaryl ring which is optionally substituted with halo, cyano or $C_{1-3}$ alkyl;

is a five-membered heteroaryl ring which is optionally substituted with $C_{1-3}$ alkyl;

$R^1$ is phenyl or heteroaryl, which may be monocyclic or bicyclic, wherein said phenyl and heteroaryl groups are optionally substituted with one to three groups independently selected from the group consisting of halo, oxo, cyano, $R^4$, $R^6$, $OR^4$, $OR^6$ and $SO_2R^4$;

$R^2$ is selected from the group consisting of hydrogen, $NH(C=O)R^6$, $NH(C=O)CH_2R^6$, $NH(C=O)R^4$, $NH(C=O)R^5$, $NH(C=O)OR^5$, $NH_2$, $NHR^4$, $NHR^6$, $NHCH_2R^6$ and $R^6$;

$R^3$ is selected from hydrogen or $C_{1-6}$ alkyl;

or $R^2$ and $R^3$ can be taken together with the atoms to which they are attached to form a 5, 6 or 7 membered heterocyclyl group which is optionally substituted with oxo;

each $R^4$ is independently hydrogen or $C_{1-6}$ alkyl, which is optionally substituted with one to three halo;

each $R^5$ is independently hydrogen or $C_{1-6}$ alkyl, which is optionally substituted with $N(R^4)_2$ or $OR^4$;

$R^6$ is (a) heterocyclyl, which may be monocyclic or bicyclic, (b) $C_{3-6}$ cycloalkyl, (c) phenyl, or (d) heteroaryl, which may be monocyclic or bicyclic, wherein said heterocyclyl, cycloalkyl, phenyl and heteroaryl groups are optionally substituted with one to two groups independently selected from the group of oxo, $R^5$, $OR^4$ and heteroaryl;

$R^a$ is hydrogen or halo;

$R^b$ is hydrogen or halo.

The Compounds of Formula I and pharmaceutically acceptable salts or prodrugs thereof may be useful, for example, for activating HIV latency for potential complete cure of HIV infection alone or in combination with cART and/or other HIV treatments.

Accordingly, the present invention provides methods for treating or preventing HIV infection in a subject, comprising administering to the subject an effective amount of at least one compound of Formula I.

The details of the invention are set forth in the accompanying detailed description below.

Although any methods and materials similar to those described herein may be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention includes to inhibitors of histone deacetylase, compositions comprising at least one inhibitor of histone deacetylase, and methods of using the inhibitors of histone deacetylase for treating or preventing HIV infection in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of Tricyclic Heterocycle Compound and/or an additional therapeutic agent, or a composition thereof that is effective in inhibiting HIV replication and in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The terms "treating" or "treatment" as used herein with respect to an HIV viral infection or AIDS, includes inhibiting the severity of HIV infection or AIDS, i.e., arresting or reducing the development of the HIV infection or AIDS or its clinical symptoms; or relieving the HIV infection or AIDS, i.e., causing regression of the severity of HIV infection or AIDS or its clinical symptoms.

The terms "preventing," or "prohylaxis," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "alkenyl, as used herein, refers to an aliphatic hydrocarbon group having at least one carbon to carbon double bond. An alkenyl group may be straight or branched and contain from about 2 to about 10 carbon atoms. In one embodiment, an alenyl group contains from about 2 to about 6 carbon atoms. In different embodiments, an alkenyl group contains from 2 to 3 carbon atoms ($C_{2-3}$ alkyl). Non-limiting examples of alkenyl groups include ethenyl, propenyl, butenyl, pentenyl and hexenyl. In one embodiment, an alkenyl group is linear. In another embodiment, an alkenyl group is branched. Unless otherwise indicated, an alkenyl group is unsubstituted.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on. Bicyclic cycloalkyl ring systems include fused ring systems, where two rings share two atoms, and spiro ring systems, where two rings share one atom.

The term "heteroaryl", as used herein, represents a stable monocyclic or bicyclic ring system of up to 10 atoms in each ring, wherein at least one ring is aromatic, and at least one ring contains from 1 to 4 heteroatoms selected from the group consisting of O, N and S. Bicyclic heteroaryl ring systems include fused ring systems, where two rings share two atoms, and spiro ring systems, where two rings share one atom. Heteroaryl groups within the scope of this definition include but are not limited to: azaindolyl, benzoimidazolyl, benzisoxazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyrazolopyrimidinyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, dihydrobenzodioxinyl, dihydropyrazoloxazinyl, dihydropyrazolyothiazinedioxidyl, methylenedioxybenzene, benzothiazolyl, benzothienyl, quinolinyl, isoquinolinyl, oxazolyl, tetra-hydroquinoline and 3-oxo-3,4dihydro-2N-benzo[b][1,4]thiazine. If the heteroaryl contains nitrogen atoms, it is understood that the corresponding N-oxides thereof are also encompassed by this definition.

The term "heterocycle" or "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of O, N, S, SO, or $SO_2$. Bicyclic heterocyclic ring systems include fused ring systems, where two rings share two atoms, and spiro ring systems, where two rings share one atom. "Heterocyclyl" therefore includes, but is not limited to the following: azaspirononanyl, azaspirooctanyl, azetidinyl, dioxanyl, oxadiazaspirodecenyl, oxaspirooctanyl, oxazolidinonyl, piperazinyl, piperidinyl, pyrrolidinyl, morpholinyl, thiomorpholinyl, tetrahydrofurnayl, tetrahydropyranyl, dihydropiperidinyl, tetrahydrothiophenyl and the like. If the heterocycle contains a nitrogen, it is understood that the corresponding N-oxides thereof are also encompassed by this definition.

"Celite®" (Fluka) diatomite is diatomaceous earth, and can be referred to as "celite".

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., $R^4$) occurs more than one time in any constituent or in Formula I, its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a compound of Formula I or a pharmaceutically acceptable salt of the compound. The transformation may occur by various mechanisms (e.g., by metabolic or chemical processes), such as, for example, through hydrolysis in blood. For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-Cu_1)$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1$-$C_2)$alkylamino$(C_2$-$C_3)$alkyl (such as β-dimethylaminoethyl), carbamoyl-$(C_1$-$C_2)$alkyl, N,N-di $(C_1$-$C_2)$alkylcarbamoyl-$(C_1$-$C_2)$alkyl and piperidino-, pyrrolidino- or morpholino$(C_2$-$C_3)$alkyl, and the like.

Similarly, if a compound of Formula I contains an alcohol functional group, a prodrug can be formed by the replacement of one or more of the hydrogen atoms of the alcohol groups with a group such as, for example, $(C_1$-$C_6)$alkanoyloxymethyl, 1-(($C_1$-$C_6$)alkanoyloxy)ethyl, 1-methyl-1-(($C_1$-$C_6$)alkanoyloxy)ethyl, $(C_1$-$C_6$)alkoxycarbonyloxymethyl, N—$(C_1$-$C_6$)alkoxycarbonylaminomethyl, succinoyl, $(C_1$-$C_6$)alkanoyl, α-amino$(C_1$-$C_4$)alkyl, α-amino$(C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a compound of Formula I incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$) alkyl, ($C_3$-$C_7$) cycloalkyl, benzyl, a natural α-aminoacyl, —C(OH)C(O)OY' wherein $Y^1$ is H, ($C_1$-$C_6$)alkyl or benzyl, —C($OY^2$)$Y^3$ wherein $Y^2$ is ($C_1$-$C_4$) alkyl and $Y^3$ is ($C_1$-$C_6$) alkyl; carboxy ($C_1$-$C_6$)alkyl; amino($C_1$-$C_4$)alkyl or mono-N— or di-N,N—($C_1$-$C_6$)alkylaminoalkyl; —C($Y^4$)$Y^5$ wherein $Y^4$ is H or methyl and $Y^5$ is mono-N— or di-N, N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvates, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The compound of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. *Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the compound of Formula I may be atropisomers (e.g., substituted biaryls) and are considered as part of this invention. Enantiomers can also be directly separated using chiral chromatographic techniques.

It is also possible that the compound of Formula I may exist in different tautomeric forms, and all such forms are embraced within the scope of the invention. For example, all keto-enol and imine-enamine forms of the compounds are included in the invention.

Unless otherwise indicated, all stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a compound of Formula I incorporates a double bond or a fused ring, both the cis- and trans-forms, as well as mixtures, are embraced within the scope of the invention.

When a subsituent on a chiral carbon atom is depicted without specific stereochemistry (by using a straight line bond to a chiral center), it is to be understood that both the alpha and beta configurations of said subtituent group are to be considered part of the present invention. For example, the compound of the present invention, which is drawn as follows:

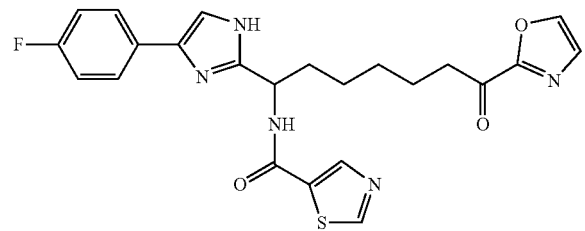 [SMILES: O=C(CCCCCC(NC(=O)c1cncs1)c1nc(-c2ccc(F)cc2)c[nH]1)c1ncco1]

is understood to encompass both stereoisomers at the indicated chiral center, the structures of which are as follows:

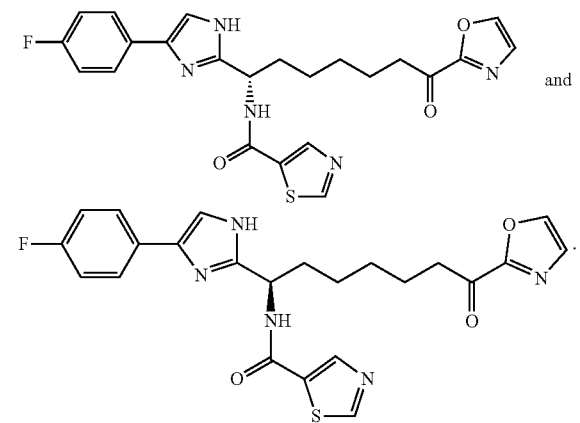

In the Examples section below, compounds of the present invention that have been purified as individual stereoisomers are sometimes depicted in non-stereospecific form but identified using one or more of the terms: "diastereomer 1," "diastereomer 2," "isomer 1," "isomer 2," "enantiomer A" and "enantiomer B." In this instance, the absolute stereochemistry of each isolated diastereomer and enantiomeric center has not been determined and the terms used above are used to represent each individual purified stereochemically pure compound.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (H) and deuterium (2H). Protium is the predominant hydrogen isotope found in nature. Enriching for deuterium may provide certain therapeutic advantages, such as increasing in vivo half-life or reducing dosage requirements, or may provide a compound useful as a standard for characterization of biological samples.

Isotopically-enriched Compounds of Formula I can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula I has one or more of its hydrogen atoms replaced with deuterium.

The compounds of Formula I may be useful in human and veterinary medicine for treating or preventing HIV infection in a subject. In one embodiment, the compounds of Formula I can be inhibitors of HIV viral replication. In a specific embodiment, the compound of Formula I are inhibitors of HIV-1. Accordingly, the compounds of Formula I may be useful for treating HIV infections and AIDS. In accordance with the invention, the compounds of Formula I can be administered to a subject in need of treatment or prevention of HIV infection.

Accordingly, in one embodiment, the invention provides methods for treating HIV infection in a subject comprising administering to the subject an effective amount of at least one compound of Formula I or a pharmaceutically acceptable salt thereof. In a specific embodiment, the present invention provides methods for treating AIDS in a subject comprising administering to the subject an effective amount of at least one compound of Formula I or a pharmaceutically acceptable salt thereof.

The Compounds of Formula I

The present invention provides Compounds of Formula I.

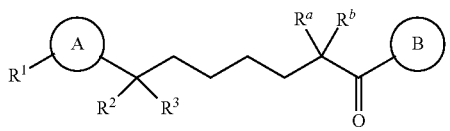

wherein

is a five-membered heteroaryl ring which is optionally substituted with halo, cyano or $C_{1-3}$ alkyl;

is a five-membered heteroaryl ring which is optionally substituted with $C_{1-3}$ alkyl;

$R^1$ is phenyl or heteroaryl, which may be monocyclic or bicyclic, wherein said phenyl and heteroaryl groups are optionally substituted with one to three groups independently selected from the group consisting of halo, oxo, cyano, $R^4$, $R^6$, $OR^4$, $OR^6$ and $SO_2R^4$;

$R^2$ is selected from the group consisting of hydrogen, $NH(C=O)R^6$, $NH(C=O)CH_2R^6$, $NH(C=O)R^4$, $NH(C=O)R^5$, $NH(C=O)OR^5$, $NH_2$, $NHR^4$, $NHR^6$, $NHCH_2R^6$ and $R^6$;

$R^3$ is selected from hydrogen or $C_{1-6}$ alkyl;

or $R^2$ and $R^3$ can be taken together with the atoms to which they are attached to form a 5, 6 or 7 membered heterocyclyl group which is optionally substituted with oxo;

each $R^4$ is independently hydrogen or $C_{1-6}$ alkyl, which is optionally substituted with one to three halo;

each $R^5$ is independently hydrogen or $C_{1-6}$ alkyl, which is optionally substituted with $N(R^4)_2$ or $OR^4$;

$R^6$ is (a) heterocyclyl, which may be monocyclic or bicyclic,
(b) $C_{3-6}$ cycloalkyl,
(c) phenyl, or
(d) heteroaryl, which may be monocyclic or bicyclic, wherein said heterocyclyl, cycloalkyl, phenyl and heteroaryl groups are optionally substituted with one to two groups independently selected from the group of oxo, $R^5$, $OR^4$ and heteroaryl;

$R^a$ is hydrogen or halo;
$R^b$ is hydrogen or halo;
or a pharmaceutically acceptable salt thereof.

In an embodiment of the invention,

is selected from imidazolyl, isoxazolyl, oxadiazolyl, oxazolyl, pyrazolyl or triazolyl, wherein said groups are optionally substituted with halo, cyano or $C_{1-3}$ alkyl. In a class of the embodiment,

is selected from imidazolyl. In another embodiment of the invention,

is isoxazolyl. In another class of the embodiment,

is oxadiazolyl. In another class of the embodiment,

is oxazolyl. In another class of the embodiment,

is pyrazolyl. In another embodiment of the invention,

is triazolyl.

In an embodiment of the invention, is

isoxazolyl, oxazolyl or thiazolyl, wherein said groups are optionally substituted with $C_{1-3}$ alkyl. In a class of the embodiment,

is isoxazolyl. In another class of the embodiment,

is oxazolyl. In another class of the embodiment,

is thiazolyl.

In an embodiment of the invention, $R^1$ is dishydroisoquinolinyl, imidazolyl, isoquinolinyl, napthyridinyl, phenyl, pyrazinyl, pyridinyl, quinolinyl or quinoxalinyl, wherein said groups are optionally substituted with one to three groups optionally selected from the group consisting of halo, oxo, cyano, $R^4$, $R^6$, $OR^4$, $OR^6$ and $SO_2R^4$.

In an embodiment of the invention, $R^2$ is $NH(C=O)R^6$ or $NH(C=O)CH_2R^6$, and $R^6$ is selected from the group consisting of azaindolyl, azaspirononanyl, azaspirooctanyl, azetidinyl, benzisoxazolyl, cyclobutyl, cyclopentyl, cyclopropyl, dihydrobenzodioxinyl, dihydropyrazoloxazinyl, dihydropyrazolyothiazinedioxidyl, dioxanyl, morpholinyl, oxadiazaspirodecenyl, oxaspirooctanyl, oxazolidinonyl, oxazolyl, phenyl, piperazinyl, piperidinyl, pyrazolopyrimidinyl, pyrazolyl, pyrimidinyl, pyrrolidinyl, pyrrolyl, tetrahydrofuranyl, tetrahydropyranyl and thiazolyl. In another embodiment of the invention, $R^2$ is $NH_2$.

In an embodiment of the invention, $R^3$ is hydrogen.
In an embodiment of the invention, $R^a$ is hydrogen.
In an embodiment of the invention, $R^b$ is hydrogen.

In another embodiment, the Compounds of Formula I are in substantially purified form.

It is to be understood that any of the aforementioned embodiments may be combined with one or more separate embodiments.

Other embodiments of the present invention include the following:

(a) A pharmaceutical composition comprising an effective amount of a Compound of Formula I, and a pharmaceutically acceptable carrier.

(b) The pharmaceutical composition of (a), further comprising a second therapeutic agent selected from the group consisting of HIV antiviral agents, immunomodulators, anti-infective agents, vaccines, and antibodies.

(c) The pharmaceutical composition of (b), wherein the HIV antiviral agent is an antiviral selected from the group consisting of HIV protease inhibitors, HIV integrase inhibitors and HIV NNRTI inhibitors.

(d) A pharmaceutical combination that is (i) a Compound of Formula I and (ii) a second therapeutic agent selected from the group consisting of HIV antiviral agents, immunomodulators, and anti-infective agents, vaccines, and antibodies; wherein the Compound of Formula I and the second therapeutic agent are each employed in an amount that renders the combination effective for inhibiting HIV replication, or for treating HIV infection and/or reducing the likelihood or severity of symptoms of HIV infection, and eradicates HIV infection.

(e) The combination of (d), wherein the HIV antiviral agent is an antiviral selected from the group consisting of HIV protease inhibitors, HIV integrase inhibitors and HIV NNRTI inhibitors.

(f) A method of inhibiting HIV replication in a subject in need thereof which comprises administering to the subject an effective amount of a Compound of Formula I.

(g) A method of treating HIV infection and/or reducing the likelihood or severity of symptoms of HIV infection in a subject in need thereof which comprises administering to the subject an effective amount of a Compound of Formula I.

(h) The method of (g), wherein the Compound of Formula I is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors, HIV integrase inhibitors and HIV NNRTI inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

Additional embodiments of the present invention include the following:

(l) A pharmaceutical composition comprising an effective amount of a pharmaceutically acceptable salt of a Compound of Formula I, and a pharmaceutically acceptable carrier.

(m) The pharmaceutical composition of (l), further comprising a second therapeutic agent selected from the group consisting of HIV antiviral agents, immunomodulators, anti-infective agents, vaccines and antibodies.

(n) The pharmaceutical composition of (m), wherein the HIV antiviral agent is an antiviral selected from the group consisting of HIV protease inhibitors and HIV NNRTI inhibitors.

(o) A pharmaceutical combination that is (i) a pharmaceutically acceptable salt of a Compound of Formula I and (ii) a second therapeutic agent selected from the group consisting of HIV antiviral agents, immunomodulators, and anti-infective agents; wherein the pharmaceutically acceptable salt of the Compound of Formula I and the second therapeutic agent are each employed in an amount that renders the combination effective for inhibiting HIV replication, or for treating HIV infection and/or reducing the likelihood or severity of symptoms of HIV infection.

(p) The combination of (o), wherein the HIV antiviral agent is an antiviral selected from the group consisting of HIV protease inhibitors and HIV NNRTI inhibitors.

(q) A method of inhibiting HIV replication in a subject in need thereof which comprises administering to the subject an effective amount of a pharmaceutically acceptable salt of a Compound of Formula I.

(r) A method of treating HIV infection and/or reducing the likelihood or severity of symptoms of HIV infection in a subject in need thereof which comprises administering to the subject an effective amount of a pharmaceutically acceptable salt of a Compound of Formula I.

(s) The method of (r), wherein the pharmaceutically acceptable salt of the Compound of Formula I is administered in combination with an effective amount of at least one second therapeutic agent selected from the group consisting of HIV antiviral agents, immunomodulators, and anti-infective agents.

(t) The method of (s), wherein the HIV antiviral agent is an antiviral selected from the group consisting of HIV protease inhibitors and HIV NS5B polymerase inhibitors.

(u) A method of inhibiting HIV replication in a subject in need thereof which comprises administering to the subject the pharmaceutical composition of (1), (m) or (n) or the combination of (o) or (p).

(v) A method of treating HIV infection and/or reducing the likelihood or severity of symptoms of HIV infection in a subject in need thereof which comprises administering to the subject the pharmaceutical composition of (1), (m) or (n) or the combination of (o) or (p).

Further embodiments of the present invention include the following:

(w) A pharmaceutical composition comprising an effective amount of a Compound of Formula I or a pharmaceutically acceptable salt thereof, and a pharmaceutically acceptable carrier.

(x) The pharmaceutical composition of (w), further comprising a second therapeutic agent selected from the group consisting of HIV antiviral agents, immunomodulators, and anti-infective agents.

(y) The pharmaceutical composition of (x), wherein the HIV antiviral agent is an antiviral selected from the group consisting of HIV protease inhibitors and HIV NNRTI inhibitors.

(z) A pharmaceutical combination that is (i) a Compound of Formula I and (ii) or a pharmaceutically acceptable salt thereof, a second therapeutic agent selected from the group consisting of HIV antiviral agents, immunomodulators, and anti-infective agents; wherein the Compound of Formula I and the second therapeutic agent are each employed in an amount that renders the combination effective for inhibiting HIV replication, or for treating HIV infection and/or reducing the likelihood or severity of symptoms of HIV infection.

(aa) The combination of (z), wherein the HIV antiviral agent is an antiviral selected from the group consisting of HIV protease inhibitors and HIV NNRTI inhibitors.

(bb) A method of inhibiting HIV replication in a subject in need thereof which comprises administering to the subject an effective amount of a Compound of Formula I or a pharmaceutically acceptable salt thereof.

(cc) A method of treating HIV infection and/or reducing the likelihood or severity of symptoms of HIV infection in a subject in need thereof which comprises administering to the subject an effective amount of a Compound of Formula I or a pharmaceutically acceptable salt thereof.

(dd) The method of (cc), wherein the Compound of Formula I or pharmaceutically acceptable salt thereof, is administered in combination with an effective amount of at least one second therapeutic agent selected from the group consisting of HIV antiviral agents, immunomodulators, and anti-infective agents.

(ee) The method of (dd), wherein the HIV antiviral agent is an antiviral selected from the group consisting of HIV protease inhibitors and HIV NNRTI inhibitors.

(ff) A method of inhibiting HIV replication in a subject in need thereof which comprises administering to the subject the pharmaceutical composition of (w), (x) or (y) or the combination of (z) or (aa).

(gg) A method of treating HIV infection and/or reducing the likelihood or severity of symptoms of HIV infection in a subject in need thereof which comprises administering to the subject the pharmaceutical composition of (w), (x) or (y) or the combination of (z) or (aa).

The present invention also includes a compound of the present invention for use I in, (ii) as a medicament for, or (iii) in the preparation of a medicament for: (a) medicine; (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(gg) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (gg) above are understood to include all embodiments of the compounds, including such embodiments as result from combinations of embodiments.

Non-limiting examples of the Compounds of Formula I include compounds 1-196 as set forth in the Examples below, and pharmaceutically acceptable salts thereof.

Methods for Making the Compounds of Formula I

The Compounds of Formula I may be prepared from known or readily prepared starting materials, following methods known to one skilled in the art of organic synthesis. Methods useful for making the Compounds of Formula I are set forth in the Examples below and generalized in the Schemes below. Alternative synthetic pathways and analogous structures will be apparent to those skilled in the art of organic synthesis.

General List of Abbreviations

Abbreviations and acronyms herein include the following:

| | |
|---|---|
| Ac | Acetyl |
| Aq | Aqueous |
| ACN | Acetonitrile |
| AIBN | Azobisisobutyronitrile |
| AUC | Area under the curve |
| BAST | Bis(2-methoxyethyl)aminosulfur trifluoride |
| BOC | tert-butyloxycarbonyl |
| Bu | Butyl |
| Bz | Benzoyl |
| CDI | Carbonyldiimidazole |
| DBDMH | 1,3-Dibromo-5,5-dimethylhydantoin |
| DCM | Dichloromethane |
| DCE | 1,2-Dichloroethane |
| DHP | 3,4-dihydro-2H-pyran |
| DIBAL-H | Diisobutylaluminium hydride |
| DIEA, DIPEA or Hünig's base | N,N-diisopropylethylamine |
| DMAP | 4-dimethylaminopyridine |
| DME | dimethyoxyethane |
| DMF | dimethylformamide |
| DMP | Dess-Martin periodinane |
| Dppf | 1,1'-Bis(diphenylphosphino)ferrocene |
| DMSO | dimethyl sulfoxide |
| DTBPF | 1,1'-bis(di-tert-butylphosphino)ferrocene |
| EA | Ethyl Acetate |
| EDCI | N-ethyl-N'-(3-dimethylaminopropyl)carbodiimide hydrochloride |

-continued

General List of Abbreviations

Abbreviations and acronyms herein include the following:

| | |
|---|---|
| Et | Ethyl |
| EtOH | Ethanol |
| EtOAc | ethyl acetate |
| G | Grams |
| GI | Gastrointestinal |
| H | Hour |
| HATU | 1-[Bis(dimethylamino)methylene]-1H-1,2,3-triazolo[4,5-b]pyridinium 3-oxide hexafluorophosphate |
| HIV | human immunodeficiency virus |
| HOBT, HOBt | 1-Hydroxybenzotriazole hydrate |
| HPBCD | hydroxypropyl β-cyclodextrin |
| HPLC | high-performance liquid chromatography |
| mCPBA, CPBA | meta-Chloroperoxybenzoic |
| Hz | Hertz |
| IPA | Isopropanol |
| IV | Intravenous |
| iPr | Isopropyl |
| Ir[dF(CF$_3$)ppy]$_2$(dtbpy)PF$_6$ | [4,4'-Bis(1,1-dimethylethyl)-2,2'-bipyridine-N1,N1']bis[3,5-difluoro-2-[5-(trifluoromethyl)-2-pyridinyl-N]phenyl-C] Iridium(III) hexafluorophosphate |
| L | Liter |
| LC | liquid chromatography |
| LC/MS | liquid chromatography mass spectrometry |
| LED | light-emitting diode |
| LiHMDS | lithium bis(trimethylsilyl)amide |
| Me | Methyl |
| MeOH | Methanol |
| Mg | Milligrams |
| MHz | Megahertz |
| Min | Minute |
| μL | Microliters |
| mL | Milliliters |
| Mmol | Millimoles |
| MOM-Cl | chloromethyl methyl ether |
| MPLC | medium pressure liquid chromatography |
| MS | mass spectrometry |
| NBS | N-Bromosuccinimide |
| NCS | N-Chlorosuccinimide |
| NHS | normal human serum |
| NIS | N-Iodosuccinimide |
| NMO | 4-methylmorpholine N-oxide |
| NMR | nuclear magnetic resonance spectroscopy |
| PBMC | peripheral blood mononuclear cell |
| Pd$_2$(dba)$_3$ | Tris(dibenzylideneacetone)dipalladium(0) |
| Ph | Phenyl |
| P.O. | Oral |
| PPTS | Pyridinium p-toluenesulfonate |
| PTSA | para-toluenesulfonic acid |
| Pr | Propyl |
| Rpm | revolutions per minute |
| RT or rt | room temperature (ambient, about 25° C.) |
| sat or sat'd | Saturated |
| SEMCl | 2-Chloromethoxyethyl)trimethylsilane |
| SFC | supercritical fluid chromatography |
| T3P, T$_3$P | 1-Propanephosphonic anhydride solution |
| TBAF | Tetra-n-butylammonium fluoride |
| TBDPSCl | tert-Butyldiphenylchlorosilane |
| TBSCl | tert-Butyldimethylsilyl chloride |
| tBu | tert-butyl |
| TEA | triethylamine (Et$_3$N) |
| TEMED | Tetramethylethylenediamine |
| TFA | trifluoroacetic acid |
| TFV | Tenofovir |
| TFV-MP | Tenofovir monophosphoate |
| TFV-DP | Tenofovir diphosphate |
| THF | Tetrahydrofuran |
| TMS | Tetramethylsilane |
| TosMIC | Toluenesulfonylmethyl isocyanide |
| TPAP | Tetrapropylammonium perruthenate |
| Ts | Tosyl |
| UPLC | ultrahigh pressure liquid chromatography |
| UV | Ultraviolet |
| UV/VIS | ultraviolet/visible |
| W | Watt |
| XPhos | 2-Dicyclohexylphosphino-2',4',6'-triisopropylbiphenyl |

General Procedures

Starting materials and intermediates are purchased or are made using known procedures, or as otherwise illustrated. The general route applied to the synthesis of compounds of Formula I is described in the Schemes that follows. In some cases the order of carrying out the reaction steps in the schemes may be varied to facilitate the reaction or to avoid unwanted reaction products.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC/MS).

Typically the analytical LC-MS system used consisted of a Waters ZQ™ platform with electrospray ionization in positive ion detection mode with an Agilent 1100 series HPLC with autosampler. The column was commonly a Waters Xterra MS C18, 3.0×50 mm, 5 μm or a Waters Acquity UPLC® BEH C18 1.0×50 mm, 1.7 μm. The flow rate was 1 mL/min, and the injection volume was 10 μL. UV detection was in the range 210-400 nm. The mobile phase consisted of solvent A (water plus 0.05% TFA) and solvent B (MeCN plus 0.05% TFA) with a gradient of 100% solvent A for 0.7 min changing to 100% solvent B over 3.75 min, maintained for 1.1 min, then reverting to 100% solvent A over 0.2 min. Alternatively, the column was commonly a Waters Acquity UPLC® BEH C18 1.0×50 mm, 1.7 μm. The flow rate was 0.3 mL/min, and the injection volume was 0.5 μL. UV detection was 215 or 254 nm. Either the mobile phase consisted of solvent A (water plus 0.05% TFA) and solvent B (MeCN plus 0.05% TFA) with a gradient of 90% solvent A changing to 99% solvent B over 1.6 min, maintained for 0.4 min, then reverting to 90% solvent A over 0.1 min or the mobile phase consisted of solvent A (water plus 0.05% TFA) and solvent B (MeCN plus 0.05% TFA) with a gradient of 97% solvent A changing to 4% then 50% solvent B over 0.5 min and 0.9 min, 50%-99% solvent B over 0.2 min, maintained for 0.4 min, then reverting to 90% solvent A over 0.1 min.

Preparative HPLC purifications were usually performed using either a mass spectrometry directed system or a non-mass guided system. Usually they were performed on a Waters Chromatography Workstation configured with LC-MS System consisting of: Waters ZQ™ single quad MS system with Electrospray Ionization, Waters 2525 Gradient Pump, Waters 2767 Injecto/Collector, Waters 996 PDA Detector, the MS Conditions of: 150-750 amu, Positive Electrospray, Collection Triggered by MS, and a Waters SUNFIRE® C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 μL, and the UV detection range was 210-400 nm. An alternate preparative HPLC system used was a Gilson Workstation consisting of: Gilson GX-281 Injector/Collector, Gilson UV/VIS-155 Detector, Gilson 322, 333, and 334 Pumps, and a Phenomenex Gemini-NX C-18 5 micron, 50 mm (id)×250 mm column, a Waters XBridge™ C-18 5 micron OBD™, 30 mm (id)×250 mm column, or a Waters SUNFIRE™ C-18 OBD™ 10 micron, 30 mm (id)×150 mm column. The mobile phases consisted of mixtures of acetonitrile (0-90%) in water containing 0.1% or 0.05% TFA. Flow rates were maintained at 50 mL/min for the Waters Xbridge™ column, 90 mL/min for the Phenomenex Gemini column, and 30 mL/min for the Waters SUNFIRE™ column. The injection volume ranged from 1000-8000 µL, and the UV detection range was 210-400 nm. Mobile phase gradients were optimized for the individual compounds. Reactions performed using microwave irradiation were normally carried out using an Emrys Optimizer manufactured by Personal Chemistry, or an Initiator manufactured by Biotage. Reactions performed using photon irradiation were normally carried out using either a second generation Merck photoreactor or a Kessil 34 W blue LED lamp. Concentration of solutions was carried out on a rotary evaporator under reduced pressure. Flash chromatography was usually performed using either a Biotage® Flash Chromatography apparatus (Dyax Corp.), an ISCO CombiFlash® Rf apparatus, or an ISCO CombiFlash® Companion XL on silica gel (32-63 microns, 60 Å pore size) in pre-packed cartridges of the size noted. ¹H NMR spectra were acquired at 500 MHz spectrometers in CDCl₃ solutions unless otherwise noted. Chemical shifts were reported in parts per million (ppm). Tetramethylsilane (TMS) was used as internal reference in CDCl₃ solutions, and residual CH₃OH peak or TMS was used as internal reference in CD₃OD solutions. Coupling constants (J) were reported in hertz (Hz). Chiral analytical chromatography was most commonly performed on one of CHIRALPAK® AS, CHIRALPAK®AD, CHIRALCEL® OD, CHIRALCEL® IA, or CHIRALCEL® OJ columns (250×4.6 mm) (Daicel Chemical Industries, Ltd.) with noted percentage of ethanol in hexane (% EtOH/Hex), isopropanol in heptane (% IPA/Hep), ethanol in carbon dioxide (% EtOH/CO₂), or isopropanol in carbon dioxide (% IPA/CO₂) as isocratic solvent systems. Chiral preparative chromatography was conducted on one of CHIRALPAK AS, of CHIRALPAK AD, CHIRALCEL® OD, CHIRALCEL® IA, CHIRALCEL® OJ columns (20×250 mm) (Daicel Chemical Industries, Ltd.) with desired isocratic solvent systems identified on chiral analytical chromatography or by supercritical fluid (SFC) conditions.

Several catalysts are used in the following procedures. "UMICORE M71 SIPR" is also known as Umicore Hoveyda Grubbs Catalyst M71 SIPr" and [1,3-Bis(2,6-diisopropylphenyl)-2-imidazolidinylidene]dichloro[(2-isopropoxy)(5-trifluoroacetamido)benzylidene]ruthenium(II). It is available from Umicore Precious Metals Chemistry USA, LLC, 1305 Main Parkway Catoosa, OK 74015. "Zhan's catalyst" is available from Sigma Aldrich.

Several methods for preparing the compounds of this invention are also described in the Examples. Starting materials and intermediates were purchased commercially from common catalog sources or were made using known procedures, or as otherwise illustrated.

Intermediate 1

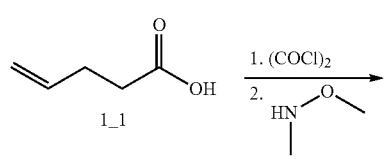

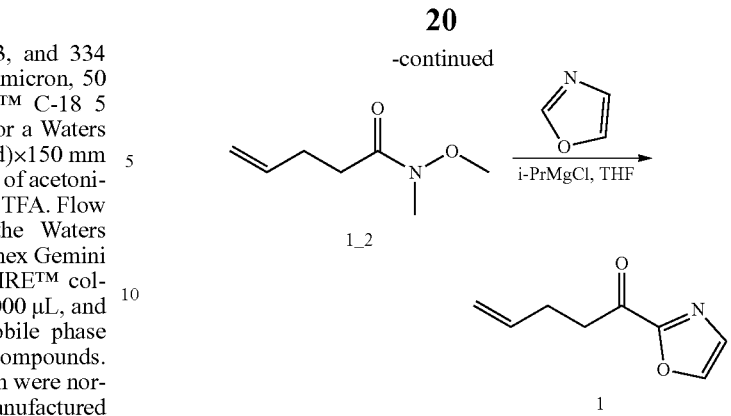

Step 1: Preparation of N-methoxy-N-methylpent-4-enamide (1_2)

Oxalyl chloride (5.25 ml, 59.9 mmol) was added to the solution of DMF (0.046 ml, 0.599 mmol) and pent-4-enoic acid (11, 3.00 g, 30.0 mmol) in DCM (50 ml), the resultant mixture was stirred at 25° C. for 2 h. The reaction mixture was poured to a stirred solution of N,O-dimethylhydroxylamine hydrochloride (9.75 g, 0.10 mol) in water (30 mL) at 0° C., and stirred for 1 h. The reaction mixture was separated and the organic layer was washed with brine (30 mL) and dried. The solvent was removed in vacuo to give N-methoxy-N-methylpent-4-enamide (1_2) which was used to the next step without further purification. ¹H NMR (400 MHz, CDCl₃) δ 5.86 (m, 1H), 5.06 (d, J=19.6 Hz, 1H), 4.98 (d, J=10.0 Hz, 1H), 3.8 (s, 3H), 3.17 (s, 3H), 2.46-2.60 (m, 2H), 2.35-2.40 (m, 2H).

Step 2: Preparation of 1-(oxazol-2-yl)pent-4-en-1-one (1)

To a solution of oxazole (0.904 g, 13.10 mmol) in THF (15 ml) was added drop wise isopropylmagnesium chloride (6.55 ml, 13.10 mmol) at −15° C. The resultant mixture was stirred at −15° C. for 40 min, then a solution of N-methoxy-N-methylpent-4-enamide (1_2, 1.50 g, 10.48 mmol) in THF (5 mL) was added to the reaction mixture, and stirred at room temperature for 16 h. The mixture was quenched with aqueous NH₄Cl (saturated, 10 mL), and the mixture was extracted with ethyl acetate (15×2 mL). The combined organic fractions were washed with brine (saturated, 10 mL), dried (Na₂SO₄), filtered and the solvent was evaporated under reduced pressure. The residue was purified by silica gel flash chromatography (ISCORF75; Sepa flash column), eluting with petroleum ether/EtOAc=20:1-5:1 to give 1-(oxazol-2-yl)pent-4-en-1-one (1). ¹H NMR (400 MHz, CDCl₃) δ 7.76 (s, 1H), 7.27 (s, 1H), 5.81 (m, 1H), 4.90-5.08 (m, 2H), 3.13 (t, J=7.43 Hz, 3H), 2.45 (q, J=6.78 Hz, 3H).

Intermediate 2

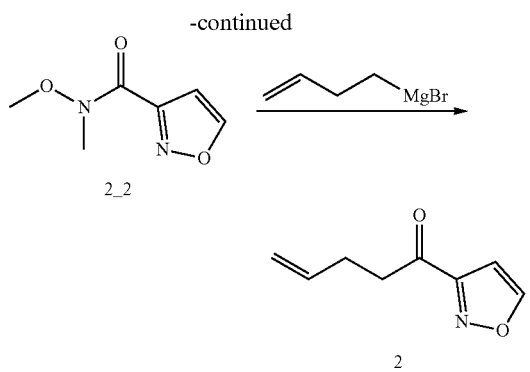

Step 1: Preparation of N-methoxy-N-methylisoxazole-3-carboxamide (2_2)

HOBt (4.5 g, 29.4 mmol) and EDCI (5.4 g, 28.2 mmol) were added to solution of isoxazole-3-carboxylic acid (21, 3 g, 26.5 mmol) and N,O-dimethylhydroxylamine hydrochloride (2.7 g, 27.7 mmol) in DMF (5 ml) and DCM (7 ml). 4-methylmorpholine (3 ml, 27.3 mmol) was added, then the mixture was stirred overnight. It was extracted with ether (300 ml) and brine (100 ml), the organic layer was separated, it was washed with brine, dried over $Na_2SO_4$, then filtered and the solvent was evaporated. The residue was purified by chromatography (Redisep 40 g column) eluting with 1/1 EtOAc/Hexanes yielding N-methoxy-N-methylisoxazole-3-carboxamide (2_2). LCMS (ESI) calc'd for $C_6H_8N_2O_3$[M+H]$^+$: 157.1, found: 157.1

Step 2: Preparation of 1-(isoxazol-3-yl)pent-4-en-1-one (2)

But-3-en-1-ylmagnesium bromide (50 ml, 25.00 mmol) was added to solution of N-methoxy-N-methylisoxazole-3-carboxamide (2_2, 3 g, 19.21 mmol) in THF (15 ml) at rt, and it was stirred at 60° C. for 3 h. It was cooled to room temperature, sat. $NH_4Cl$ (2 ml) was added, then it was extracted with EtOAc (250 ml) and water (100 ml). The organic layer was separated, it was washed with brine, dried over $Na_2SO_4$, then filtered and the solvent was evaporated. The residue was purified by chromatography (Redisep 40 g column) eluting with 20% EtOAc-Hexanes yielding 1-(isoxazol-3-yl)pent-4-en-1-one (2). LCMS (ESI) calc'd for $C_8H_9NO_2$ [M+H]$^+$: 152.1, found: 152.1

Intermediate 3

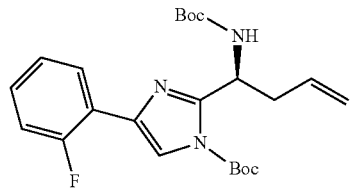 [SMILES: C=CC[C@H](NC(=O)OC(C)(C)C)c1nc(-c2ccccc2F)cn1C(=O)OC(C)(C)C]

Step 1: (S)-2-(2-fluorophenyl)-2-oxoethyl 2-((tert-butoxycarbonyl)amino)pent-4-enoate A 250 ml one neck round bottom flask was charged with (S)-2-((tert-butoxycarbonyl)amino)pent-4-enoic acid (1.60 g, 7.43 mmol) along with cesium carbonate (1.695 g, 5.20 mmol) and DMF (15 ml). The mixture was stirred and 2-bromo-1-(2-fluorophenyl)ethanone (1.694 g, 7.81 mmol) was added, and the resulting reaction mixture was stirred at room temperature for 2 hrs. The mixture was diluted with ethyl acetate (40 mL), the solid was filtered and washed with ethyl acetate (3×). The filtrate was then concentrated and the crude was purified by MPLC (40 g solica gel, 0 to 40% ethyl acetate in hexanes, 18 CV) to afford white solid product (S)-2-(2-fluorophenyl)-2-oxoethyl 2-((tert-butoxycarbonyl)amino)pent-4-enoate. LC-MS: [M+H]$^+$=352.0.

Step 2: (S)-tert-butyl (1-(5-(2-fluorophenyl)-1H-imidazol-2-yl)but-3-en-1-yl)carbamate A 100 ml one neck round bottom flask was charged with (S)-2-(2-fluorophenyl)-2-oxoethyl 2-((tert-butoxycarbonyl)amino)pent-4-enoate (2.60 g, 7.40 mmol) along with ammonium acetate (5.70 g, 74.0 mmol) in toluene (20 ml). The mixture was then stirred and heated in an oil bath at 110° C. for 3 hrs. After it was cooled to room temperature, the mixture was diluted with ethyl acetate (100 mL), washed with $NaHCO_3$ (sat, 30 mL), water, dried over $MgSO_4$, filtered and concentrated to afford (S)-tert-butyl (1-(5-(2-fluorophenyl)-1H-imidazol-2-yl)but-3-en-1-yl)carbamate which is used directly to next step without further purification. LC-MS: [M+H]$^+$=332.0.

Step 3: (S)-tert-butyl 2-(1-((tert-butoxycarbonyl)amino)but-3-en-1-yl)-4-(2-fluorophenyl)-1H-imidazole-1-carboxylate A round bottom flask was charged with (S)-tert-butyl (1-(5-(2-fluorophenyl)-1H-imidazol-2-yl)but-3-en-1-yl)carbamate (2.452 g, 7.40 mmol) along with DMAP (0.045 g, 0.370 mmol) in $CH_2Cl_2$ (20 ml). The mixture was stirred while di-tert-butyl dicarbonate (1.696 g, 7.77 mmol) was added in one portion. The resulting reaction mixture was then stirred at room temperature for 3 hrs. The mixture was then concentrated and the crude was purified by MPLC (80 g silica gel, 0 to 30% ethyl acetate in hexanes, 18 CV) to afford the product (S)-tert-butyl 2-(1-((tert-butoxycarbonyl)amino)but-3-en-1-yl)-4-(2-fluorophenyl)-1H-imidazole-1-carboxylate. LC-MS: [M+H]$^+$=432.0.

Intermediate 4 tert-butyl (S)-2-(1-((tert-butoxycarbonyl)amino)but-3-en-1-yl)-4-(4-fluorophenyl)-1H-imidazole-1-carboxylate

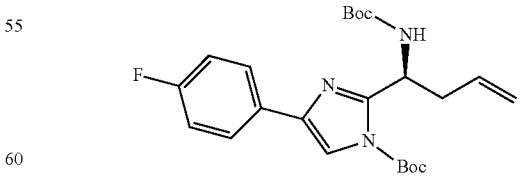

Using similar chemistry as the preparation of intermediate 3, starting with 2-bromo-1-(4-fluorophenyl)ethanone, the intermediate 4 tert-butyl (S)-2-(1-((tert-butoxycarbonyl)amino)but-3-en-1-yl)-4-(4-fluorophenyl)-1H-imidazole-1-carboxylate (4) can be prepared.

Intermediate 5

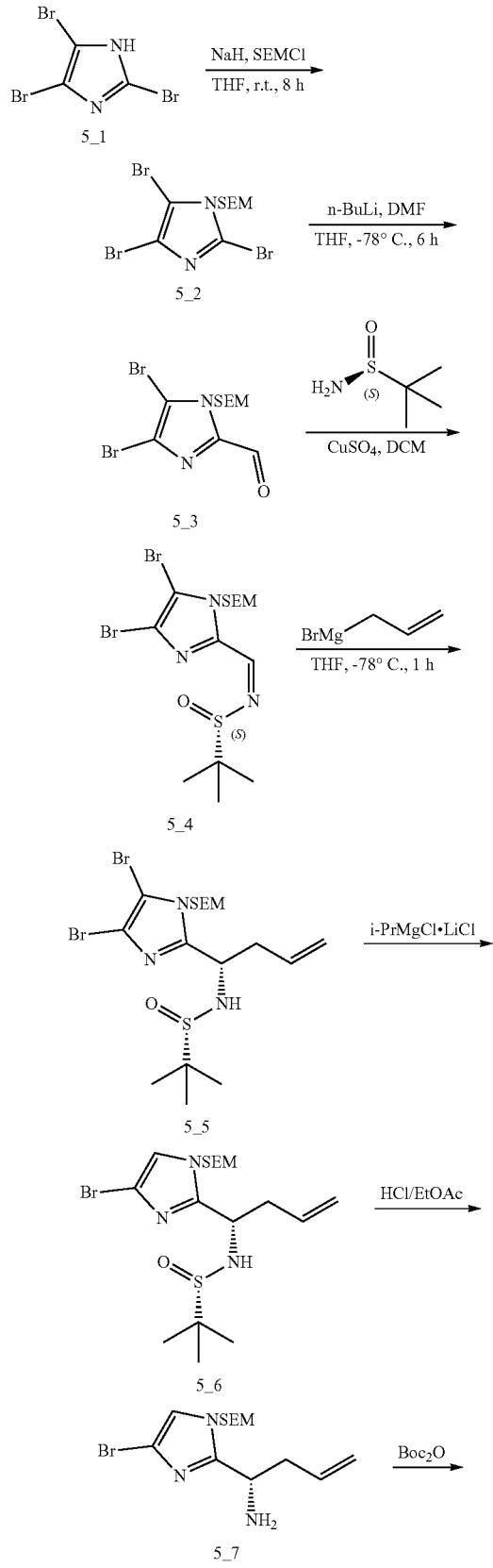

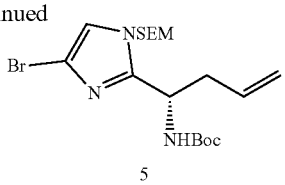

Step 1: Preparation of 2,4,5-tribromo-1-((2-(trimethylsilyl)ethoxy)methyl)-1H-imidazole (5_2)

A dried 500 mL round bottom flask was charged with 2,4,5-tribromoimidazole (51, 20.0 g, 65.6 mmol) and anhydrous DMF (100 mL), and the resulting solution was cooled to 0° C. To this cold solution was added NaH (60% in mineral oil, 2.80 g, 70.0 mmol) portionwise with gas evolution under control and an internal temperature maintained below 10° C. After addition, the cold bath was removed and the resulting mixture was stirred at ambient temperature for 30 minutes. The reaction mixture was cooled back to 0° C., and SEMCl (12.2 mL, 69.5 mmol) was added to the reaction via syringe pump over 30 minutes. The reaction was stirred at 0° C. for an additional 30 minutes and at room temperature for another 30 minutes. The mixture was partitioned between EtOAc (150 mL) and water (300 mL), the organic phase was washed with dilute aqueous NaCl (5 percent w/w) twice, then brine (100 mL), dried ($Na_2SO_4$), and concentrated. The crude material was re-crystallized from hot petroleum ether (30 mL) and the solids were harvested from the mother liquor at 0° C. The product was washed with cold petroleum ether (30 mL) and dried under vacuum to afford 2,4,5-tribromo-1-((2-(trimethylsilyl)ethoxy)methyl)-1H-imidazole (5_2). $^1$H NMR (400 MHz, $CDCl_3$) δ 5.31 (s, 2H), 3.59 (t, J=7.2 Hz, 2H), 0.92 (t, J=7.2 Hz, 2H), −0.01 (s, 9H).

Step 2: Preparation of 4,5-dibromo-1-((2-(trimethylsilyl)ethoxy)methyl)-1H-imidazole-2-carbaldehyde (5_3)

To a cooled (−78° C.) solution of 2,4,5-tribromo-1-((2-(trimethylsilyl)ethoxy)methyl)-1H-imidazole (5_2, 16 g, 0.03 mol) in THF (160 mL) was added a solution of n-BuLi (13.5 mL, 3 M in hexane; 0.04 mol) dropwise. After 1 h, DMF (14 mL, 0.2 mol) was added dropwise. After 1 h, the reaction was quenched with saturated ammonium chloride solution and then the reaction was allowed to warm to rt. The reaction was extracted with ethyl acetate (2×100 mL). The organic layers were combined and washed with 10 percent sodium bicarbonate solution, water, brine and then concentrated. The residue was purified by flash chromatography (gradient elution pet ether: ethyl acetate) gave 4,5-dibromo-1-((2-(trimethylsilyl)ethoxy)methyl)-1H-imidazole-2-carbaldehyde (53).

Step 3: Preparation of (S,Z)-N-((4,5-dibromo-1-((2-(trimethylsilyl)ethoxy)methyl)-1H-imidazol-2-yl)methylene)-2-methylpropane-2-sulfinamide (5_4)

To a solution of 4,5-dibromo-1-((2-(trimethylsilyl)ethoxy)methyl)-1H-imidazole-2-carbaldehyde (53, 35 g, 0.09 mol) in DCM (350 mL) was added (S)-2-methylpropane-2-sulfinamide (22 g, 0.18 mole) and anhydrous copper sulfate (72 g, 0.45 mol). The resulting suspension was stirred at rt for 20 h. The reaction was filtered through Celite. The filtrate was concentrated and purification by flash chromatography (gradient elution pet ether/ethyl acetate) gave (S,Z)-N-((4,5-dibromo-1-((2-(trimethylsilyl)ethoxy)methyl)-1H-imidazol-2-yl)methylene)-2-methylpropane-2-sulfinamide (5_4).

Step 4: Preparation of (S)-N-((S)-1-(4,5-dibromo-1-((2-(trimethylsilyl)ethoxy)methyl)-1H-imidazol-2-yl)but-3-en-1-yl)-2-methylpropane-2-sulfinamide (5_5)

To a cooled (−78° C.) solution of (S,Z)-N-((4,5-dibromo-1-((2-(trimethylsilyl)ethoxy)methyl)-1H-imidazol-2-yl)methylene)-2-methylpropane-2-sulfinamide (5_4, 17 g, 0.03 mole) in THF (170 mL) was added allylmagnesium bromide (1 M in diethylether, 52.3 mL, 0.05 mol) dropwise. After 1 h, the reaction was quenched with saturated ammonium chloride solution and then the reaction was allowed to warm to rt. The reaction mixture was extracted with ethyl acetate (2×250 mL). The organic layers were combined and washed with sodium bicarbonate solution, brine, water, dried over anhydrous sodium sulfate, filtered and concentrated. Purification by flash phase chromatography gave (S)-N-((S)-1-(4,5-dibromo-1-((2-(trimethylsilyl)ethoxy)methyl)-1H-imidazol-2-yl)but-3-en-1-yl)-2-methylpropane-2-sulfinamide. $^1$H NMR (400 MHz, CDCl$_3$) δ 5.71 (m, 1H), 5.60 (d, J=11.6 Hz, 1H), 5.28 (m, 1H), 5.06 (m, 2H), 4.57 (q, J=7.2 Hz 1H), 3.98 (d, J=8.4 Hz, 1H), 3.55 (m, 2H), 2.70 (t, J=7.2 Hz, 2H), 1.2 (s, 9H), 0.92 (m, 2H), −0.01 (s, 9H).

Step 5: Preparation of (S)-N-((S)-1-(4-bromo-1-((2-(trimethylsilyl)ethoxy)methyl)-1H-imidazol-2-yl)but-3-en-1-yl)-2-methylpropane-2-sulfinamide (5_6)

A solution of (S)-N-((S)-1-(4,5-dibromo-1-((2-(trimethylsilyl)ethoxy)methyl)-1H-imidazol-2-yl)but-3-en-1-yl)-2-methylpropane-2-sulfinamide (55, 5.25 g, 9.92 mmol) in THF (33.1 mL) was degassed with argon for 15 min. The solution was cooled to −3° C. (ice/brine) and isopropylmagnesium chloride, lithium chloride complex in THF (8.00 mL, 10.4 mmol) was added dropwise over 20 min, keeping the temperature below 0° C. during the addition. After 30 min, the second equivalent of isopropylmagnesium chloride, lithium chloride complex in THF (8.00 mL, 10.4 mmol) was added dropwise over 20 min, keeping the temperature below 0° C. during the addition. After 30 min, the reaction was quenched with sat. ammonium chloride (30 mL) and the reaction was allowed to warm to rt. The reaction was partitioned between EtOAc and sat. ammonium chloride. The aqueous layer was extracted with EtOAc. The organic layers were combined and washed with sat. NaHCO$_3$, brine, dried over sodium sulfate, filtered and concentrated. Purification by flash chromatography gave (S)-N-((S)-1-(4-bromo-1-((2-(trimethylsilyl)ethoxy)methyl)-1H-imidazol-2-yl)but-3-en-1-yl)-2-methylpropane-2-sulfinamide (5_6).

Step 6: Preparation of (S)-1-(4-bromo-1-((2-(trimethylsilyl)ethoxy)methyl)-1H-imidazol-2-yl)but-3-en-1-amine (5_7)

Hydrogen chloride (~4 M in EtOAc, 8 ml, 32.0 mmol) was added to a stirred mixture of (S)-N-((S)-1-(4-bromo-1-((2-(trimethylsilyl)ethoxy)methyl)-1H-imidazol-2-yl)but-3-en-1-yl)-2-methylpropane-2-sulfinamide (56, 1.0 g, 2.220 mmol) in DCM (10 ml) at room temperature and the mixture was stirred at room temperature for 1 h. The mixture was concentrated to afford (S)-1-(4-bromo-1-((2-(trimethylsilyl)ethoxy)methyl)-1H-imidazol-2-yl)but-3-en-1-amine (57) which was used to the next step without further purification. LCMS (ESI) calc'd for C$_{13}$H$_{24}$BrN$_3$OSi [M+H]$^+$: 346.1, found: 346.1

Step 7: Preparation of (S)-tert-butyl (1-(4-bromo-1-((2-(trimethylsilyl)ethoxy)methyl)-1H-imidazol-2-yl)but-3-en-1-yl)carbamate (5)

Bo15O (0.77 ml, 3.32 mmol) was added to a stirred mixture of DIEA (0.70 ml, 4.01 mmol) and (S)-1-(4-bromo-1-((2-(trimethylsilyl)ethoxy)methyl)-1H-imidazol-2-yl)but-3-en-1-amine (57, 0.769 g, 2.220 mmol) in DCM (10 ml) at room temperature and the mixture was stirred at room temperature for 1 h. The mixture was concentrated. The residue was purified by silica gel column flash chromatography, eluting with petroleum ether/EtOAc=10:1 to give (S)-tert-butyl (1-(4-bromo-1-((2-(trimethylsilyl)ethoxy)methyl)-1H-imidazol-2-yl)but-3-en-1-yl)carbamate (5). LCMS (ESI) calc'd for C$_{18}$H$_{32}$BrN$_3$O$_3$Si [M+H]$^+$: 446.1, found: 448.1

Preparation of Intermediate 6

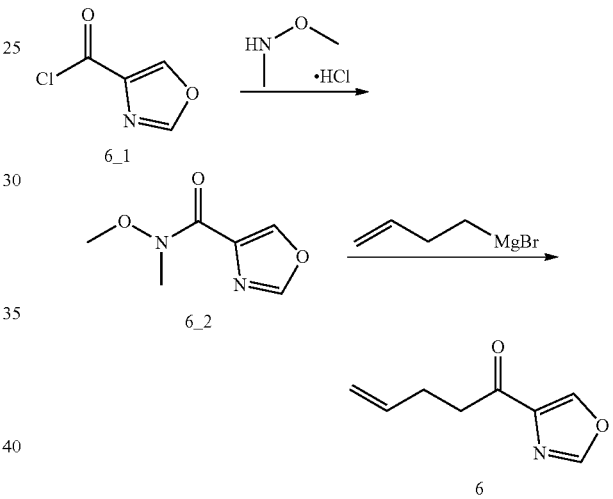

Step 1: Preparation of N-methoxy-N-methyloxazole-4-carboxamide (6_2)

A mixture of oxazole-4-carbonyl chloride (61, 696 mg, 5.3 mmol), N,O-dimethylhydroxylamine hydrochloride (1550 mg, 15.9 mmol) and Na$_2$CO$_3$ in water was stirred at rt for 1 h. The product was extracted with DCM. The combined organic layers were washed with brine, dried over anhydrous Na$_2$SO$_4$ and concentrated in vacuo to afford N-methoxy-N-methyloxazole-4-carboxamide (6_2) which was used to the next step without further purification. LCMS (ESI) calc'd for C$_6$H$_8$N$_2$O$_3$[M+H]$^+$: 157.1, found: 157.0

Step 2: Preparation of 1-(oxazol-4-yl)pent-4-en-1-one (6)

But-3-en-1-ylmagnesium bromide (1.7 g, 10.67 mmol) (THF solution) was added to a stirred mixture of N-methoxy-N-methyloxazole-4-carboxamide (6_2, 450 mg, 2.88 mmol) in THF (10 ml) at rt, then the mixture was stirred at rt for 2 h. The mixture was quenched with aqueous NH$_4$Cl (saturated, 20 mL), and extracted with ethyl acetate (3×20 mL). The combined organic fractions were washed with brine (saturated, 15 mL), dried (Na₂SO₄), filtered and the solvent was evaporated under reduced pressure. The residue was purified by silica gel column flash chromatography, eluting with petroleum ether/EtOAc=0~10% to give 1-(oxazol-4-yl)pent-4-en-1-one (6). LCMS (ESI) calc'd for $C_8H_9NO_2$ [M+H]⁺: 152.1, found: 151.9.

Intermediate 7

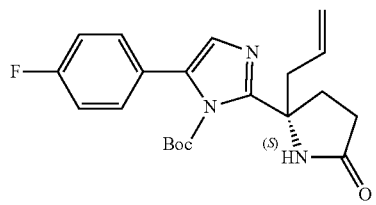

Step 1: ethyl (S)-5-oxopyrrolidine-2-carboxylate Into a 5-L 3-necked round-bottom flask purged and maintained with an inert atmosphere of nitrogen, was placed N,N-dimethylpyridin-4-amine (21.3 g, 174.35 mmol, 0.11 equiv), N-(N-cyclohexylcarboximidoyl)cyclohexanamine (409 g, 1.98 mol, 1.25 equiv), ethanol (2 L). This was followed by the addition of (2S)-5-oxopyrrolidine-2-carboxylic acid (205 g, 1.59 mol, 1.00 equiv) at −10° C. The resulting solution was stirred overnight at 20° C. The solids were filtered out. The residue was applied onto a silica gel column with ethyl acetate/petroleum ether (1:100-1:5). This resulted in ethyl (2S)-5-oxopyrrolidine-2-carboxylate.

Step 2: ethyl 2-allyl-5-oxopyrrolidine-2-carboxylate

Into a 10-L 3-necked round-bottom flask purged and maintained with an inert atmosphere of nitrogen, was placed ethyl (2S)-5-oxopyrrolidine-2-carboxylate (205 g, 1.30 mol, 1.00 equiv), tetrahydrofuran (1.6 L), 3-bromoprop-1-ene (610.6 g, 5.05 mol, 4.00 equiv). This was followed by the addition of LiHMDS (1N in THF) (2.6 L, 2.10 equiv) dropwise with stirring at −40° C. in 40 min. The resulting solution was stirred for 2 h at 20° C. The reaction was then quenched by the addition of 3 L of NH₄Cl. The resulting solution was extracted with 3×5 L of ethyl acetate and the organic layers combined and dried over anhydrous sodium sulfate and concentrated. The residue was applied onto a silica gel column with ethyl acetate/petroleum ether (1:100-1:5). This resulted in ethyl (2R)-5-oxo-2-(prop-2-en-1-yl)pyrrolidine-2-carboxylate.

Step 3: (S)-2-allyl-5-oxopyrrolidine-2-carboxylic acid and (R)-2-allyl-5-oxopyrrolidine-2-carboxylic acid Into a 2-L 3-necked round-bottom flask purged and maintained with an inert atmosphere of nitrogen, was placed ethyl (2R)-5-oxo-2-(prop-2-en-1-yl)pyrrolidine-2-carboxylate (110 g, 557.72 mmol, 1.00 equiv), methanol (660 mL), water (330 mL). This was followed by the addition of potassium hydroxide (62 g, 2.00 equiv), in portions. The resulting solution was stirred for 2 h at 20° C. The pH value of the solution was adjusted to 2 with hydrogen chloride (1 mol/L). The resulting solution was extracted with 3×3 L of ethyl acetate and the organic layers combined and dried over anhydrous sodium sulfate and concentrated under vacuum. The crude product was purified by Prep-SFC with the following conditions: Column, CHIRALPAK AS-3 4.6*100 mm, 3 um; mobile phase, methanol (0.1% DEA); Detector, UV 220 nm. This resulted in (2S)-5-oxo-2-(prop-2-en-1-yl)pyrrolidine-2-carboxylic acid and (2R)-5-oxo-2-(prop-2-en-1-yl)pyrrolidine-2-carboxylic acid.

(S)-2-allyl-5-oxopyrrolidine-2-carboxylic acid: (ES, m/z): 170 [M+H]⁺, ¹H-NMR: (400 MHz, CD₃OD, ppm): δ 2.14-2.17 (1H, t), 2.3-2.45, (3H, q), 2.45-2.6 (1H, t), 2.6-2.75 (1H, t), 5.15-5.30 (2H, t), 5.7-5.9 (1H, q)

(R)-2-allyl-5-oxopyrrolidine-2-carboxylic acid: (ES, m/z): 170 [M+H]⁺; ¹H-NMR: (400 MHz, CDCl₃, ppm): δ 2.01-2.10 (1H, q), 2.45-2.53, (4H, t), 2.66-2.71 (1H, d), 5.19-5.22 (2H, d), 5.69-5.79 (1H, t), 7.78 (1H, s), 10.795 (1H, s).

Step 4: (S)-5-allyl-5-(5-(4-fluorophenyl)-1H-imidazol-2-yl)pyrrolidin-2-one

A 250 ml one necked round bottom flask was charged with 2-bromo-4'-fluoroacetylphenone (2.3 g, 10.60 mmol) and a solution of (S)-2-allyl-5-oxopyrrolidine-2-carboxylic acid (1.5 g, 8.87 mmol) and N-ethyl-N-isopropylpropan-2-amine (2 ml, 11.48 mmol) in DMF (10 ml), then it was stirred overnight. The mixture was diluted with EtOAc (100 ml) and H₂O (40 ml), the organic layer was separated, dried (Na₂SO₄), then filtered and the solution was concentrated. The crude was purified by chromatography (Redisep 40 g column) eluting with 3% MeOH/MeCl₂, yielding intermediate 2-(4-fluorophenyl)-2-oxoethyl (S)-2-allyl-5-oxopyrrolidine-2-carboxylate. LCMS: [M+H]⁺=306.1. This intermediate was then dissolved in toluene (20 ml), ammonium acetate (2 g, 25.9 mmol) was added, then it was stirred at 90° C. overnight. After it was cooled to room temperature, it was diluted with EtOAc (200 ml) and washed with satd NaHCO₃ (100 ml), then dried (Na₂SO₄), filtered and the solvent was evaporated yielding (S)-5-allyl-5-(5-(4-fluorophenyl)-1H-imidazol-2-yl)pyrrolidin-2-one. LC-MS: [M+H]⁺=286.0.

Step 5: (S)-tert-butyl 2-(2-allyl-5-oxopyrrolidin-2-yl)-5-(4-fluorophenyl)-1H-imidazole-1-carboxylate To a 250 ml one necked round bottom flask was added di-tert-butyl dicarbonate (1.3 g, 5.96 mmol) in CH₂Cl₂ (5 ml) to a solution of (S)-5-allyl-5-(5-(4-fluorophenyl)-1H-imidazol-2-yl)pyrrolidin-2-one (1.8 g, 6.31 mmol) in CH₂Cl₂ (20 ml). DMAP (0.1 g, 0.819 mmol) was added. The mixture was then stirred at room temperature for 2 hours. The mixture was concentrated to about 5 ml, then purified by chromatography on Analogix (40 g Redisep column) eluting with 3% MeOH/MeCl₂ yielding (S)-tert-butyl 2-(2-allyl-5-oxopyrrolidin-2-yl)-5-(4-fluorophenyl)-1H-imidazole-1-carboxylate (7). LC-MS: [M+H]⁺=386.0

Intermediate 8

(R)-2-allyl-6-oxopiperidine-2-carboxylic acid and (S)-2-allyl-6-oxopiperidine-2-carboxylic acid

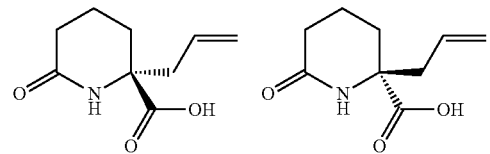

Step 1: 6-oxopiperidine-2-carboxylic acid

Into a 5-L 4-necked round-bottom flask purged and maintained with an inert atmosphere of nitrogen, was placed 2-aminohexanedioic acid (300 g, 1.86 mol, 1.00 equiv), AcOH (3000 mL). The resulting solution was stirred for 6 h at reflux. The reaction mixture was cooled to room temperature. The resulting mixture was concentrated under vacuum. The residue was dissolved in 2000/120 mL of toluene/ether. The resulting mixture was concentrated under vacuum. The residue was dissolved in 2000 mL of ether. The solid was filtrated and washed with ether. This resulted in 6-oxopiperidine-2-carboxylic acid.

Step 2: ethyl 6-oxopiperidine-2-carboxylate

Into a 5-L 4-necked round-bottom flask purged and maintained with an inert atmosphere of nitrogen, was placed ethanol (2500 mL). This was followed by the addition of thionyl chloride (229 g, 1.92 mol, 1.10 equiv) dropwise with stirring at −5° C. To this was added 6-oxopiperidine-2-carboxylic acid (250 g, 1.75 mol, 1.00 equiv), in portions at −5° C. The resulting solution was stirred overnight at room temperature. The resulting mixture was concentrated under vacuum. The residue was dissolved in 2000/450 mL of toluene/triethylamine. The solids were filtered out and the filtrate was concentrated under vacuum. The residue was treated with 1500 ml of ether and the solids were filtered out. The filtrate was concentrated under vacuum. This resulted in ethyl 6-oxopiperidine-2-carboxylate.

Step 3: ethyl 2-allyl-6-oxopiperidine-2-carboxylate

Into a 10-L 4-necked round-bottom flask purged and maintained with an inert atmosphere of nitrogen, was placed ethyl 6-oxopiperidine-2-carboxylate (270 g, 1.58 mol, 1.00 equiv), tetrahydrofuran (3000 mL). This was followed by the addition of LiHMDS (3300 mL, 2.10 equiv, 1M in tetrahydrofuran) dropwise with stirring at −40° C. The resulting solution was stirred for 10 min at −40° C. To this was added 3-bromoprop-1-ene (765 g, 6.32 mol, 4.00 equiv) dropwise with stirring at −40° C. The resulting solution was stirred for 10 min at −40° C. The resulting solution was allowed to react, with stirring, for an additional 2 h at room temperature. The reaction was then quenched by the addition of 3.5 L of saturated NH₄Cl. The resulting solution was extracted with 3×5 L of ethyl acetate and the organic layers combined and dried over anhydrous sodium sulfate and concentrated under vacuum. The residue was applied onto a silica gel column with ethyl acetate/petroleum ether (1:2). This resulted in ethyl 6-oxo-2-(prop-2-en-1-yl)piperidine-2-carboxylate.

Step 4: (R)-2-allyl-6-oxopiperidine-2-carboxylic acid and (S)-2-allyl-6-oxopiperidine-2-carboxylic acid Into a 5-L 4-necked round-bottom flask purged and maintained with an inert atmosphere of nitrogen, was placed ethyl 6-oxo-2-(prop-2-en-1-yl)piperidine-2-carboxylate (230 g, 1.09 mol, 1.00 equiv), ethanol (1600 mL), water (800 mL). This was followed by the addition of sodium hydroxide (86.5 g, 2.16 mol, 2.00 equiv), in portions. The resulting solution was stirred for 2 h at room temperature. The ethanol was concentrated under vacuum. The pH value of the residue was adjusted to 2 with hydrogen chloride (1 mol/L). The resulting solution was extracted with 5×1 L of ethyl acetate and the organic layers combined. The mixture was dried over anhydrous sodium sulfate and concentrated under vacuum. The crude product was purified by Prep-SFC with the following conditions: Column, CHTRALPAK AD-H 4.6*100 mm, 5 um; mobile phase, IPA (0.1% DEA); Detector, UV 220 nm. This resulted in (2R)-6-oxo-2-(prop-2-en-1-yl)piperidine-2-carboxylic acid and (2S)-6-oxo-2-(prop-2-en-1-yl)piperidine-2-carboxylic acid.

(R)-2-allyl-6-oxopiperidine-2-carboxylic acid: LC-MS: (ES, m/z): 184.2 [M+H]⁺; ¹H-NMR: (400 MHz, CDCl₃, ppm): δ 1.76-1.89 (3H, m), 2.15-2.18, (1H, m), 2.20-2.48 (3H, m), 2.50-2.65 (1H, m), 5.17-5.21 (2H, t), 5.70-5.78 (1H, q), 7.78 (1H, s).

(S)-2-allyl-6-oxopiperidine-2-carboxylic acid: LC-MS: (ES, m/z): 184.2 [M+H]⁺; ¹H-NMR: (300 MHz, CDCl₃, ppm): δ 1.70-1.90 (3H, m), 2.13-2.19 (1H, m), 2.22-2.50 (3H, m), 2.60-2.67 (1H, m), 5.17-5.22 (2H, t), 5.66-5.80 (1H, q), 7.85 (1H, s), 11.17-11.33 (1H, s).

Intermediate 9

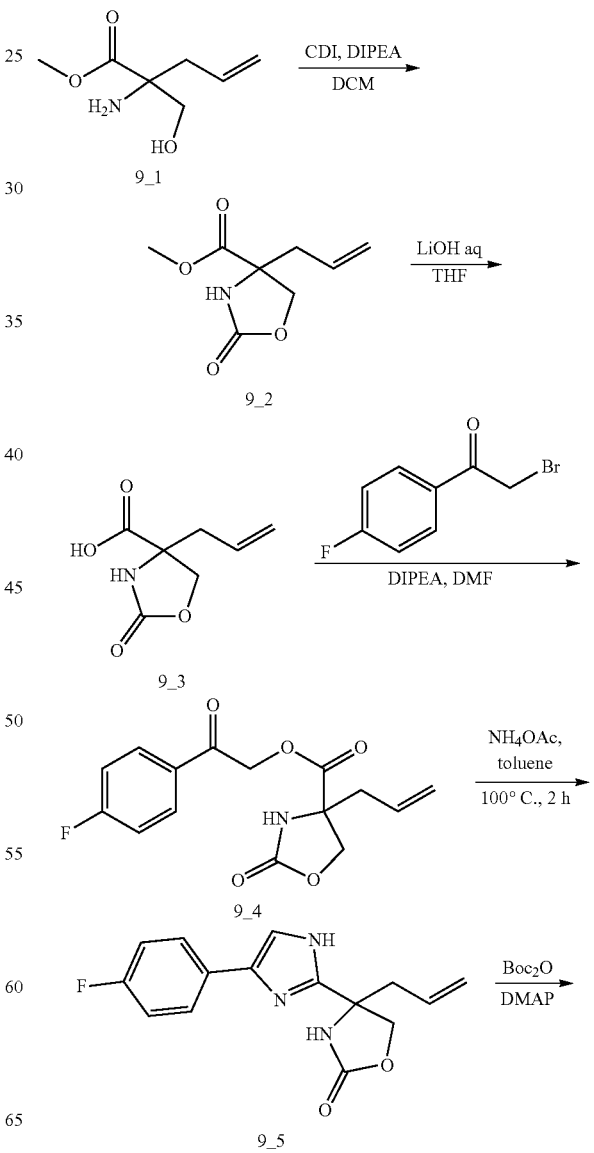

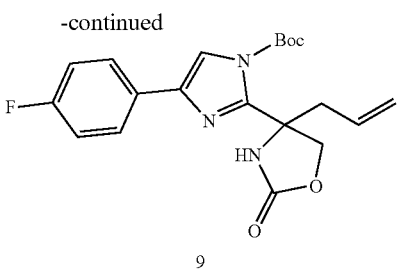

9

Step 1: Preparation of methyl 4-allyl-2-oxooxazolidine-4-carboxylate (9_2)

CDI (2445 mg, 15.08 mmol) was added to the solution of methyl 2-amino-2-(hydroxymethyl) pent-4-enoate (9_1, 2000 mg, 12.56 mmol) and DIPEA (3.29 ml, 18.85 mmol) in DCM (2 ml), and the reaction mixture was stirred at 30° C. for 2 h. The mixture was concentrated in vacuo and the residue was purified by silica gel flash chromatography (ISCORF75; Sepa flash column), eluting with petroleum ether/EtOAc=5:1-1:1 to give methyl 4-allyl-2-oxooxazolidine-4-carboxylate (9_2).

Step 2: Preparation of 4-allyl-2-oxooxazolidine-4-carboxylic acid (9_3)

LiOH·H$_2$O (0.570 g, 13.58 mmol) was added to the solution of methyl 4-allyl-2-oxooxazolidine-4-carboxylate (9_2, 1.70 g, 9.18 mmol) in THF (15 ml) and water (2.00 ml), and the resultant mixture was stirred at rt for 1.5 h. The mixture was quenched with hydrochloric acid (4 M, 3.3 mL), and the mixture was extracted with ethyl acetate (3×30 mL) and dried (Na$_2$SO$_4$), filtered and the solvent was evaporated under reduced pressure to give 4-allyl-2-oxooxazolidine-4-carboxylic acid (9_3) which was used to the next step without further purification.

Step 3: Preparation of 2-(4-fluorophenyl)-2-oxoethyl 4-allyl-2-oxooxazolidine-4-carboxylate (9_4)

DIPEA (2.403 ml, 13.76 mmol) was added to the solution of 4-allyl-2-oxo-oxazolidine-4-carboxylic acid (9_3, 1.57 g, 9.17 mmol) and 2-bromo-1-(4-fluorophenyl)ethanone (2.011 g, 9.26 mmol) in DMF (30 ml), the resultant mixture was stirred at rt for 1.5 h. The mixture was quenched with aqueous NH$_4$Cl (saturated, 10 mL), and the mixture was extracted with ethyl acetate (3×30 mL). The combined organic fractions were washed with brine (saturated, 15 mL), dried (Na$_2$SO$_4$), filtered and the solvent was evaporated under reduced pressure to give 2-(4-fluorophenyl)-2-oxoethyl 4-allyl-2-oxooxazolidine-4-carboxylate (9_4) which was used to the next step without further purification. LCMS (ESI) calc'd for C$_{15}$H$_{14}$FNO$_5$ [M+H]$^+$: 308.1, found: 308.1. $^1$H NMR (400 MHz, CDCl$_3$) δ 7.87 (dd, J=5.48, 8.61 Hz, 2H), 7.13 (t, J=8.41 Hz, 2H), 5.68-5.91 (m, 1H), 5.16-5.51 (m, 5H), 4.73 (d, J=9.00 Hz, 1H), 4.26 (d, J=9.00 Hz, 1H), 2.80 (dd, J=6.26, 14.09 Hz, 1H), 2.56 (dd, J=8.22, 13.69 Hz, 1H).

Step 4: Preparation of 4-allyl-4-(4-(4-fluorophenyl)-1H-imidazol-2-yl)oxazolidin-2-one (9_5)

NH$_4$OAc (331 mg, 4.30 mmol) was added to the solution of 2-(4-fluorophenyl)-2-oxoethyl 4-allyl-2-oxooxazolidine-4-carboxylate (9_4, 330 mg, 1.074 mmol) in toluene (5 ml), and the resultant mixture was stirred at 100° C. for 2.5 h. The mixture was concentrated in vacuo and the residue was purified by silica gel flash chromatography (ISCORF75; Sepa flash column), eluting with petroleum ether/EtOAc=10:1-1:2 to give 4-allyl-4-(4-(4-fluorophenyl)-1H-imidazol-2-yl)oxazolidin-2-one (95). LCMS (ESI) calc'd for C$_{15}$H$_{14}$FN$_3$O$_2$[M+H]$^+$: 288.1, found: 288.1

Step 5: Preparation of tert-butyl 2-(4-allyl-2-oxooxazolidin-4-yl)-4-(4-fluorophenyl)-1H-imidazole-1-carboxylate (9)

DMAP (12 mg, 0.098 mmol) was added to the solution of Boc$_2$O (0.412 ml, 1.775 mmol) and 4-allyl-4-(4-(4-fluorophenyl)-1H-imidazol-2-yl)oxazolidin-2-one (95, 300 mg, 1.044 mmol) in DCM (10 ml), the resultant mixture was stirred at rt for 6 h. The reaction mixture was concentrated in vacuo and the residue was purified by silica gel flash chromatography (ISCORF75; Sepa flash column), eluting with petroleum ether/EtOAc=10:1-2:1 to give tert-butyl 2-(4-allyl-2-oxooxazolidin-4-yl)-4-(4-fluorophenyl)-1H-imidazole-1-carboxylate (9). LCMS (ESI) calc'd for 15$_0$H$_{22}$FN$_3$O$_4$[M+H]$^+$: 388.1, found: 388.1.

Intermediate 10

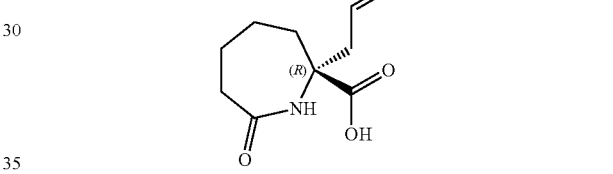

A10

Step 1: ethyl 1-allyl-2-oxocyclohexane-1-carboxylate

Into a 10000-mL 4-necked round-bottom flask purged and maintained with an inert atmosphere of nitrogen, was placed a solution of ethyl 2-oxocyclohexane-1-carboxylate (500 g, 2.94 mol, 1.00 equiv) in tetrahydrofuran (6 L). This was followed by the addition of (tert-butoxy)potassium (346 g, 3.08 mol, 1.05 equiv) in several batches. To this was added 3-bromoprop-1-ene (373 g, 3.08 mol, 1.05 equiv). The resulting solution was stirred for 18 h at 65° C. The resulting solution was quenched by the addition of H$_2$O, extracted with ethyl acetate and the organic layers combined and dried over anhydrous sodium sulfate. The residue was applied onto a silica gel column with petroleum ether (1). This resulted in ethyl 2-oxo-1-(prop-2-en-1-yl)cyclohexane-1-carboxylate.

Step 2: ethyl (E)-1-allyl-2-(hydroximino)cyclohexane-1-carbpxylate

Into a 10000-mL 4-necked round-bottom flask, was placed ethanol (5100 mL), ethyl 2-oxo-1-(prop-2-en-1-yl)cyclohexane-1-carboxylate (510 g, 2.43 mol, 1.00 equiv), CH$_3$COONa (637 g, 7.77 mol, 3.20 equiv), and hydroxylamine hydrochloride (506 g, 7.28 mol, 3.00 equiv). The resulting solution was stirred for 12 h at 25° C. The resulting solution was quenched by the addition of H$_2$O, extracted with ethyl acetate and the organic layers combined and dried over anhydrous sodium sulfate. The crude product was purified by re-crystallization from PE. This resulted in ethyl (2E)-2-(hydroxyimino)-1-(prop-2-en-1-yl)cyclohexane-1-carboxylate.

Step 3: ethyl (E)-1-allyl-2-((tosyloxy)imino)cyclohexane-1-carboxylate

Into a 10000-mL 4-necked round-bottom flask (1 atm), was placed pyridine (2100 mL), ethyl (2E)-2-(hydroxyimino)-1-(prop-2-en-1-yl)cyclohexane-1-carboxylate (420 g, 1.86 mol, 1.00 equiv), 4-dimethylaminopyridine (1.8 g, 14.73 mmol, 0.01 equiv), 4-methylbenzene-1-sulfonyl chloride (710 g, 3.72 mol, 2.00 equiv). The resulting solution was stirred for 14 h at 25° C. The reaction was then quenched by the addition of water. The resulting solution was extracted with dichloromethane and the organic layers combined. The mixture was washed by sodium bicarbonate solution and dried over anhydrous sodium sulfate and concentrated under vacuum. This resulted in ethyl (2E)-2-([[(4-methylbenzene)sulfonyl]oxy]imino)-1-(prop-2-en-1-yl)cyclohexane-1-carboxylate.

Step 4: Ethyl (2R)-7-oxo-2-(prop-2-en-1-yl)azepane-2-carboxylate and ethyl (2S)-7-oxo-2-(prop-2-en-1-yl)azepane-2-carboxylate Into a 20000-mL 4-necked round-bottom flask, was placed ethyl (2E)-2-([[(4-methylbenzene)sulfonyl]oxy]imino)-1-(prop-2-en-1-yl)cyclohexane-1-carboxylate (250 g, 658.81 mmol, 1.00 equiv), dichloromethane (10500 mL), and Silica gel (5500 g, 1500% wt). The resulting solution was stirred for 14 h at 25° C. The residue was applied onto a silica gel column with ethyl acetate/petroleum ether (100:1). The crude product was purified by re-crystallization from EA. The same process was repeated and the overall mixture was combined to work up. The crude product was purified by Prep-SFC with the following conditions: Column, CHIRALPAK-IC-SFC-025 cm*25 cm (5 um) Chiral-P(IC) 006S90ICOSCY-SL001; mobile phase, Solvent A:Solvent B=CO$_2$:(DCM:ACN=1:1)=60:40; Detector, uv. This resulted in ethyl (2R)-7-oxo-2-(prop-2-en-1-yl)azepane-2-carboxylate and ethyl (2S)-7-oxo-2-(prop-2-en-1-yl)azepane-2-carboxylate.

Step 5: (R)-2-allyl-7-oxoazepane-2-carboxylic acid

Into a 3000-mL 4-necked round-bottom flask, was placed ethyl (2R)-7-oxo-2-(prop-2-en-1-yl)azepane-2-carboxylate (83 g, 368.42 mmol, 1.00 equiv), oxolane (830 mL). This was followed by the addition of a solution of LiOH (17.7 g, 739.04 mmol, 2.00 equiv) in water (737 mL). The resulting solution was stirred for 2 h at 25° C. The reaction was then quenched by the addition of 500 mL of H$_2$O. The resulting solution was extracted with ethyl acetate and the organic layers combined. The mixture was dried over anhydrous sodium sulfate and concentrated under vacuum. This resulted in (2R)-7-oxo-2-(prop-2-en-1-yl)azepane-2-carboxylic acid. LC-MS: (ES, m/z): 198 [M+H]$^+$; 239 [M+ACN+H]$^+$; 261 [M+2ACN+Na]$^+$; 302 [M+ACN+Na]$^+$; 395 [2M+H]$^+$.

Step 6: (S)-2-allyl-7-oxoazepane-2-carboxylic acid

Into a 3000-mL 4-necked round-bottom flask (1 atm), was placed ethyl (2S)-7-oxo-2-(prop-2-en-1-yl)azepane-2-carboxylate (83 g, 368.42 mmol, 1.00 equiv), oxolane (830 mL), and a solution of LiOH (17.7 g, 2.00 equiv) in water (737 mL). The resulting solution was stirred for 2 h at 25° C. The reaction was then quenched by the addition of 500 mL of H$_2$O. The resulting solution was extracted with ethyl acetate and the organic layers were combined. The mixture was dried over anhydrous sodium sulfate and concentrated under vacuum. This resulted in (2S)-7-oxo-2-(prop-2-en-1-yl)azepane-2-carboxylic acid. LC-MS: (ES, m/z): 198 [M+H]$^+$; 220 [M+Na]$^+$; 261 [M+2ACN+Na]$^+$; 417 [2M+Na]$^+$. $^1$H-NMR: (400 MHz, CD$_3$OD, ppm): δ 5.76 (dddd, J=16.7, 10.1, 8.3, 6.4 Hz, 1H), 5.30-5.18 (m, 2H), 2.68-2.37 (m, 4H), 2.31-2.21 (m, 1H), 2.00-1.88 (m, 1H), 1.82-1.59 (m, 3H), 1.52 (dddd, J=15.4, 12.9, 6.3, 3.7 Hz, 1H).

Intermediate 11

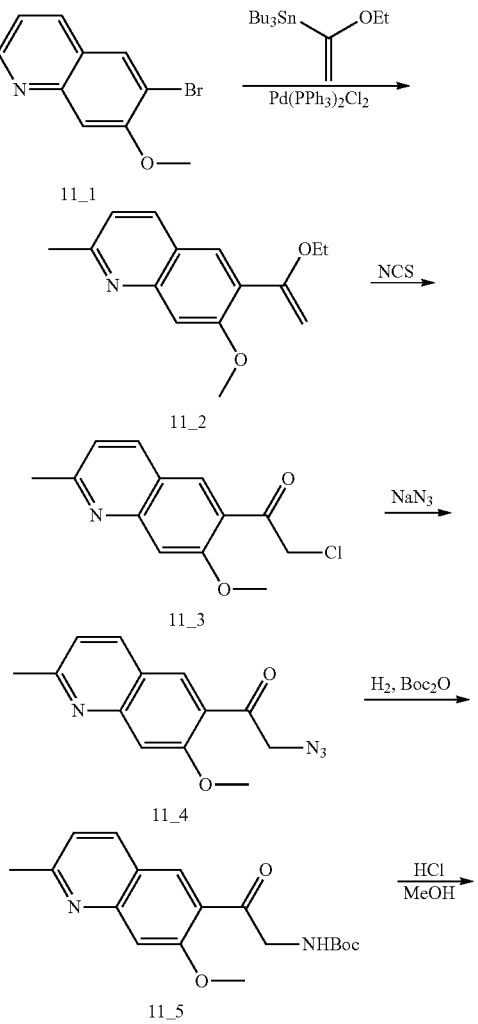

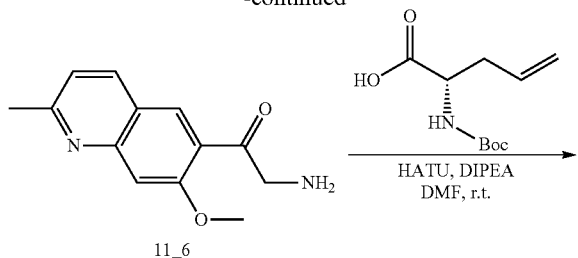

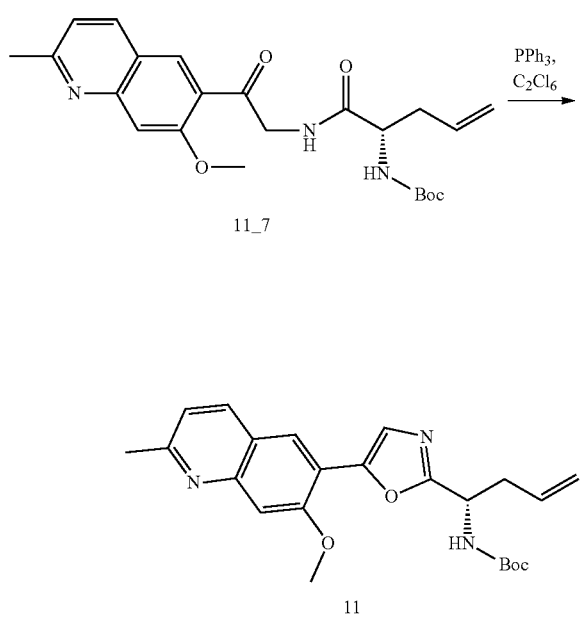

Step 1: Preparation of 6-(1-ethoxyvinyl)-7-methoxy-2-methylquinoline (11_2)

Tributyl(1-ethoxyvinyl)stannane (8.5 ml, 25.2 mmol) was added to a stirred mixture of $PdCl_2(PPh_3)_2$ (0.974 g, 1.388 mmol), and 6-bromo-7-methoxy-2-methylquinoline (11I, 3.5 g, 13.88 mmol) in DMF (100 ml) at room temperature and the mixture was stirred at 80° C. for 16 h under $N_2$. The mixture was cooled to room temperature, and KF (saturated, 50 mL) was added and the mixture was extracted with ethyl acetate (3×40 mL). The combined organic fractions were washed with brine (saturated, 40 mL), dried ($Na_2SO_4$), filtered and the solvent was evaporated under reduced pressure. The residue was purified by silica gel column flash chromatography, eluting with petroleum ether/EtOAc=0-40% to give 6-(1-ethoxyvinyl)-7-methoxy-2-methylquinoline (11_2). LCMS (ESI) calc'd for $C_{15}H_{17}NO_2$ [M+H]$^+$: 244.1, found: 244.1.

Step 2: Preparation of 2-chloro-1-(7-methoxy-2-methylquinolin-6-yl)ethanone (11_3) NCS (1.767 g, 13.23 mmol) was added to a stirred mixture of 6-(1-ethoxyvinyl)-7-methoxy-2-methylquinoline (11_2, 3.5 g, 14.39 mmol) in MeCN (30 ml) and water (7.5 ml) at room temperature and the mixture was stirred at room temperature for 30 min. The mixture was washed with water (100 mL), diluted with ethyl acetate (2*100 mL), washed with brine (50 mL), dried ($Na_2SO_4$), filtered and the solvent was evaporated under reduced pressure. The residue was purified by silica gel column flash chromatography, eluting with petroleum ether/EtOAc=0-40% to give 2-chloro-1-(7-methoxy-2-methylquinolin-6-yl)ethanone (11_3). LCMS (ESI) calc'd for $C_{13}H_{12}ClNO_2$ [M+H]$^+$: 250.1, found: 250.0

Step 3: Preparation of 2-azido-1-(7-methoxy-2-methylquinolin-6-yl)ethanone (11_4) $NaN_3$ (0.69 g, 10.61 mmol) was added to a stirred mixture of 2-chloro-1-(7-methoxy-2-methylquinolin-6-yl)ethanone (113, 2.2 g, 8.81 mmol) in DMF (20 ml) and the mixture was stirred at rt for 1.5 h. The mixture was diluted with water (10 mL), extracted with ethyl acetate (3×8 mL). The combined organic fractions were washed with water (3×6 mL), brine (saturated, 5 mL), dried ($Na_2SO_4$), and filtered to give 2-azido-1-(7-methoxy-2-methylquinolin-6-yl)ethanone ethyl acetate which was used directly to next step without further purification. LCMS (ESI) calc'd for $C_{13}H_{12}N_4O_2$ [M+H]$^+$: 257.1, found: 257.1

Step 4: Preparation of tert-butyl (2-(7-methoxy-2-methylquinolin-6-yl)-2-oxoethyl)carbamate (11_5)

10% Pd—C (0.332 g, 0.312 mmol) was added to a stirred mixture of 2-azido-1-(7-methoxy-2-methylquinolin-6-yl)ethanone (11_4, ethyl acetate solution) and $Boc_2O$ (3.4 ml, 14.64 mmol) in MeOH (2 ml) at rt and the mixture was degassed and backfilled with $H_2$ three times and then stirred at rt for 2 h. The mixture was filtered and the filter cake was washed with MeOH (2 mL). The filtrate was concentrated to dryness. The residue was purified by silica gel column flash chromatography, eluting with petroleum ether/EtOAc=0-45% to give tert-butyl (2-(7-methoxy-2-methylquinolin-6-yl)-2-oxoethyl)carbamate (11_5). LCMS (ESI) calc'd for $C_{18}H_{22}N_2O_4$ [M+H]$^+$: 331.2, found: 331.1

Step 5: Preparation of 2-amino-1-(7-methoxy-2-methylquinolin-6-yl)ethanone (11_6)

HCl/MeOH (4 M, 3 ml, 12.00 mmol) was added to a stirred mixture of tert-butyl (2-(7-methoxy-2-methylquinolin-6-yl)-2-oxoethyl)carbamate (115, 1.3 g, 3.93 mmol) in MeOH (3 ml) at room temperature and the mixture was stirred at room temperature for 21 h. The residue was concentrated to give 2-amino-1-(7-methoxy-2-methylquinolin-6-yl)ethanone hydrochloride (11_6) which was used to the next step without further purification. LCMS (ESI) calc'd for $C_{13}H_{14}N_2O_2 \cdot ClH$ [M+H]$^+$: 231.1, found: 231.1

Step 6: Preparation of (S)-tert-butyl (1-((2-(7-methoxy-2-methylquinolin-6-yl)-2-oxoethyl)amino)-1-oxopent-4-en-2-yl)carbamate (11_7)

HATU (1.882 g, 4.95 mmol) was added to a stirred mixture of DIPEA (7 ml, 40.1 mmol), and (S)-2-((tert-butoxycarbonyl)amino)pent-4-enoic acid (1.065 g, 4.95 mmol) in DMF (20 ml) at room temperature and the mixture was stirred at room temperature for 15 min. Then 2-amino-1-(7-methoxy-2-methylquinolin-6-yl)ethanone hydrochloride (116, 1.1 g, 4.12 mmol) was added, and the mixture was stirred at rt for 2 h. The mixture was diluted with ethyl acetate (10 mL), washed with brine (saturated, 3×10 mL), dried (Na$_2$SO$_4$), filtered and the solvent was evaporated under reduced pressure. The residue was purified by silica gel column flash chromatography, eluting with EtOAc/petroleum ether=50-100% to give (S)-tert-butyl (1-((2-(7-methoxy-2-methylquinolin-6-yl)-2-oxoethyl)amino)-1-oxopent-4-en-2-yl)carbamate (11_7). LCMS (ESI) calc'd for $15_3H_{29}N_3O_5$ [M+H]$^+$: 428.2, found: 428.2

Step 7: Preparation of (S)-tert-butyl (1-(5-(7-methoxy-2-methylquinolin-6-yl)oxazol-2-yl)but-3-en-1-yl)carbamate (11)

Burgess reagent (1.449 g, 6.08 mmol) was added to a stirred mixture of (S)-tert-butyl (1-((2-(7-methoxy-2-methylquinolin-6-yl)-2-oxoethyl)amino)-1-oxopent-4-en-2-yl)carbamate (11_7, 1.3 g, 3.04 mmol) in DCM (8 ml). The mixture was stirred at rt for 16 h. The mixture was diluted with dichloromethane (3×15 mL), washed with brine (saturated, 2×20 mL), dried (Na$_2$SO$_4$), filtered and the solvent was evaporated under reduced pressure. The residue was purified by silica gel column flash chromatography, eluting with EtOAc/petroleum ether=10-80% to give (S)-tert-butyl (1-(5-(7-methoxy-2-methylquinolin-6-yl)oxazol-2-yl)but-3-en-1-yl)carbamate (11). LCMS (ESI) calc'd for $15_3H_{27}N_3O_4$ [M+H]$^+$: 410.2, found: 410.2

Intermediate 12

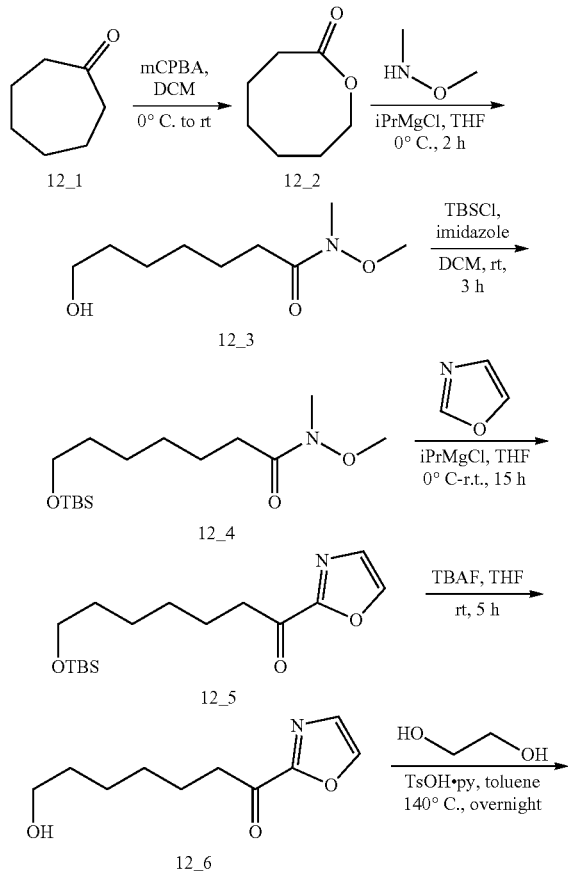

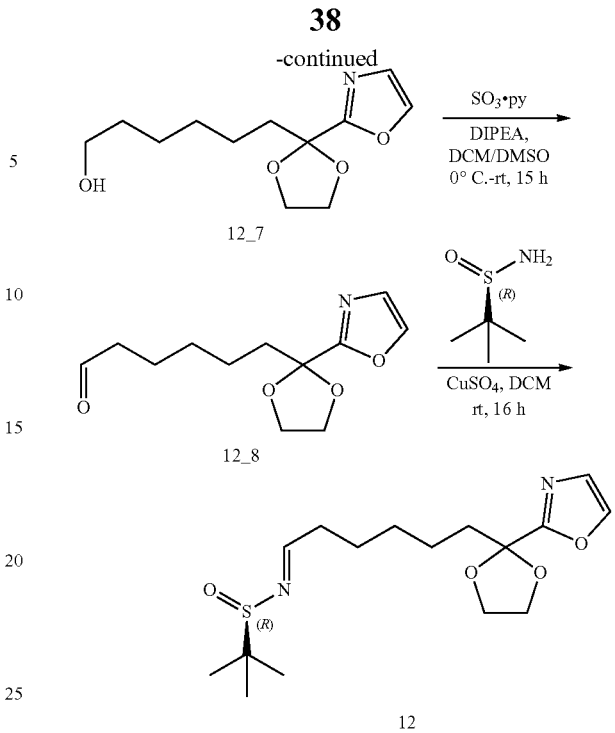

Step 1: Preparation of oxocan-2-one (12_2)

3-chlorobenzoperoxoic acid (41.0 g, 178 mmol) was added to a stirred mixture of cycloheptanone (10 g, 89 mmol) in DCM (200 ml) at 0° C. and the mixture was stirred at room temperature for 6 days. The mixture was combined with a same scale reaction, filtered and washed with DCM (50 mL). The resulting filtrate was washed with a sat. solution of Na$_2$S2O3 (200 mL) and water (200 mL), and aqueous NaHCO$_3$ (3*300 mL), dried (Na$_2$SO$_4$), filtered and the solvent was evaporated under reduced pressure to get oxocan-2-one (12_2) and used directly without further purification.

Step 2: Preparation of 7-hydroxy-N-methoxy-N-methylheptanamide (12_3)

N,O-dimethylhydroxylamine (9.37 g, 153 mmol) was added to a stirred mixture of oxepan-2-one (12_2, 14 g, 123 mmol) in THF (260 ml) at 0° C. Then isopropylmagnesium chloride (153 ml, 307 mmol) was added dropwise into the mixture (10 min) and stirred at 0° C. for 2 h. The mixture was combined with a 10 scale reaction, quenched with a sat. solution of NH$_4$Cl (600 mL) and water (500 mL). It was extracted with EtOAc (3×300 mL), dried over Na$_2$SO$_4$, filtered and concentrated. The residue was purified by silica gel column flash chromatography, eluting with petroleum ether/EtOAc=0-60% to give 7-hydroxy-N-methoxy-N-methylheptanamide (12_3).

Step 3: Preparation of 7-((tert-butyldimethylsilyl)oxy)-N-methoxy-N-methylheptanamide (12_4)

To a mixture of 7-hydroxy-N-methoxy-N-methylheptanamide (12_3, 10 g, 52.8 mmol) in DCM (100 ml) was added imidazole (3.60 g, 52.8 mmol) and a solution of TBSCl (7.96 g, 52.8 mmol) in DCM (20 mL) at room temperature. The mixture was stirred at 30° C. for 2 h. Then the mixture was quenched with a sat. solution of NH₄Cl (100 mL) and water (100 mL). The mixture was extracted with DCM (3×200 mL), dried over Na₂SO₄, filtered and concentrated to afford 7-((tert-butyldimethylsilyl)oxy)-N-methoxy-N-methylheptanamide (12_4) and used in the next step without further purification.

Step 4: Preparation of 7-((tert-butyldimethylsilyl)oxy)-1-(oxazol-2-yl)heptan-1-one (12_5)

To a mixture of oxazole (4.9 ml, 74.5 mmol) in THF (200 ml) at 0° C. was added isopropylmagnesium chloride (24.7 ml, 49.4 mmol) dropwise. The reaction was stirred for 30 minutes before adding 7-((tert-butyldimethylsilyl)oxy)-N-methoxy-N-methylheptanamide (12_4, g, 49.4 mmol) in THF dropwise. The mixture was warmed to 30° C. and stirred overnight. The residue was quenched with a sat. solution of NH₄Cl (300 mL) and water (200 mL). It was extracted with EtOAc (3×200 mL), dried over Na₂SO₄, filtered and concentrated. The residue was purified by silica gel column flash chromatography, eluting with petroleum ether/EtOAc=0-30% to give 7-((tert-butyldimethylsilyl)oxy)-1-(oxazol-2-yl)heptan-1-one (12_5).

Step 5: Preparation of 7-hydroxy-1-(oxazol-2-yl)heptan-1-one (12_6)

To a mixture of 7-((tert-butyldimethylsilyl)oxy)-1-(oxazol-2-yl)heptan-1-one (125, 7 g, 22.47 mmol) in THF (100 ml) at room temperature was added TBAF (22.5 ml, 22.50 mmol) in THF. The reaction was stirred for 5 h. The residue was evaporated under pressure to get 7-hydroxy-1-(oxazol-2-yl)heptan-1-one (12_6, 5 g crude) which was used to next step.

Step 6: Preparation of 6-(2-(oxazol-2-yl)-1,3-dioxolan-2-yl)hexan-1-ol (12_7)

To a mixture of 7-hydroxy-1-(oxazol-2-yl)heptan-1-one (12_6, 5 g, 25.4 mmol) in toluene (250 ml) at room temperature was added ethane-1,2-diol (31.5 g, 507 mmol) and PPTS (0.319 g, 1.268 mmol). Then the mixture was heated to 130° C. and stirred for 15 h. The mixture was evaporated under reduced pressure. The residue was purified by silica gel column flash chromatography, eluting with petroleum ether/EtOAc=0-50% to give 6-(2-(oxazol-2-yl)-1,3-dioxolan-2-yl)hexan-1-ol (12_7).

Step 7: Preparation of 6-(2-(oxazol-2-yl)-1,3-dioxolan-2-yl)hexanal (12_8)

TPAP (0.255 g, 0.725 mmol) was added into a mixture of 6-(2-(oxazol-2-yl)-1,3-dioxolan-2-yl)hexan-1-ol (127, 3.5 g, 14.51 mmol), and NMO (2.55 g, 21.76 mmol) in DCM (20 ml) at 0° C., then stirred at room temperature for 3 h. The mixture was washed with water (150 mL), and brine (20 mL), the water layer was extracted with DCM (50 mL*2), the combined organic layer was filtered and the solvent was evaporated under reduced pressure. The residue was purified by silica gel column flash chromatography, eluting with petroleum ether/EtOAc=0-50% to give 6-(2-(oxazol-2-yl)-1,3-dioxolan-2-yl)hexanal (128). LCMS (ESI) calc'd for C₁₂H₁₇NO₄ [M+H]⁺: 240.1, found: 240.1

Step 8: Preparation of (R,E)-2-methyl-N-(6-(2-(oxazol-2-yl)-1,3-dioxolan-2-yl)hexylidene)propane-2-sulfinamide (12)

To a mixture of 6-(2-(oxazol-2-yl)-1,3-dioxolan-2-yl)hexanal (128, 1.2 g, 5.02 mmol) in DCM (10 ml) at room temperature was added copper(II) sulfate (8.00 g, 50.2 mmol) and (R)-2-methylpropane-2-sulfinamide (0.912 g, 7.52 mmol). The mixture was stirred at rt for 16 h, filtered through a pad of Celite. The resulting filtrate was concentrated and purified by silica gel column flash chromatography, eluting with petroleum ether/EtOAc=0-60% to give (R,E)-2-methyl-N-(6-(2-(oxazol-2-yl)-1,3-dioxolan-2-yl)hexylidene)propane-2-sulfinamide (12). LCMS (ESI) calc'd for C₁₆H₂₆N₂O₄S [M+H]⁺: 343.2, found: 343.2. ¹H NMR (400 MHz, CDCl₃) δ 8.04 (t, J=4.63 Hz, 1H), 7.61-7.64 (m, 1H), 7.09 (s, 1H), 4.11 (s, 5H), 2.39-2.53 (m, 2H), 2.08-2.19 (m, 2H), 1.58-1.66 (m, 2H), 1.32-1.47 (m, 5H), 1.26 (t, J=7.17 Hz, 3H), 1.18 (s, 5H).

Intermediate 13

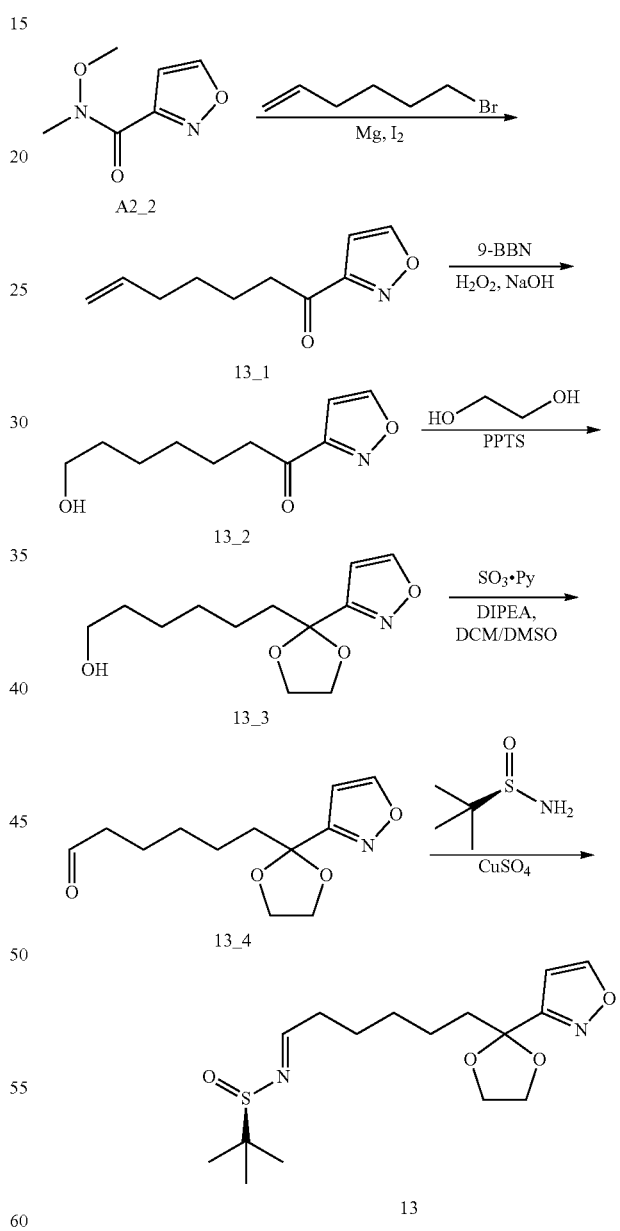

Step 1: Preparation of 1-(isoxazol-3-yl)hept-6-en-1-one (13_1)

Magnesium (7.45 g, 307 mmol) was stirred vigorously for 15 minutes under N₂ before adding THF (20 ml) and I₂

(0.039 g, 0.153 mmol), and 6-bromohex-1-ene (25 g, 153 mmol) in THF (210 ml) was added dropwise via an addition funnel over 2 h. The resulting solution was added to a stirred mixture of N-methoxy-N-methylisoxazole-3-carboxamide (A2_2, 13 g, 83 mmol) in THF (150 ml) at 0° C., stirred for 30 min, and the mixture was stirred at rt for 15 h. The mixture was quenched with NH$_4$Cl (100 mL), extracted with EtOAc (100 mL*3), and the combined organic layers were washed with brine (100 mL), dried over Na$_2$SO$_4$, filtered and concentrated. The crude product was purified by flash silica gel chromatography (ISCO®; 120 g SepaFlash® Silica Flash Column, Eluent of 0~10% EtOAc/Petroleum ether gradient @40 mL/min) to give 1-(isoxazol-3-yl)hept-6-en-1-one (13_1).

Step 2: Preparation of 7-hydroxy-1-(isoxazol-3-yl) heptan-1-one (13_2)

9-BBN (151 ml, 75 mmol) was added to a stirred mixture of 1-(isoxazol-3-yl)hept-6-en-1-one (13_1, 9 g, 50.2 mmol) in THF (100 ml) at rt, the mixture was stirred for 2 h before cooling to 0° C. and adding NaOH (20 ml, 100 mmol) dropwise followed by H$_2$O$_2$ (8.8 ml, 101 mmol)) dropwise. The mixture was warmed to room temperature and stirred for 1 h. The mixture was taken up in H$_2$O (50 mL) and EtOAc (50 mL). It was extracted with EtOAc (3×50 mL), and the combined organic layers were washed with brine (10 mL), dried over Na$_2$SO$_4$, filtered and concentrated. The crude product was purified by flash silica gel chromatography (ISCO®; 80 g SepaFlash® Silica Flash Column, Eluent of 0~10% EtOAc/Petroleum ether gradient @40 mL/min) to give 7-hydroxy-1-(isoxazol-3-yl)heptan-1-one (13_2).

Step 3: Preparation of 6-(2-(isoxazol-3-yl)-1,3-dioxolan-2-yl)hexan-1-ol (13_3)

A mixture of 7-hydroxy-1-(isoxazol-3-yl)heptan-1-one (13_2, 5.4 g, 27.4 mmol), ethane-1,2-diol (15.27 ml, 274 mmol) and TsOH (0.260 g, 1.369 mmol) in toluene (200 ml) was stirred at 130° C. for 13 h. The mixture was cooled, the solvent was evaporated under reduced pressure. The resulting residue was taken up in EtOAc (100 mL), washed with a sat. solution of NaHCO$_3$ (100 mL), dried over Na$_2$SO$_4$, and concentrated to get the crude, the crude was purified by flash silica gel chromatography (ISCO®; 40 g SepaFlash® Silica Flash Column, Eluent of 0~10% EtOAc/Petroleum ether gradient @40 mL/min) to give 6-(2-(isoxazol-3-yl)-1,3-dioxolan-2-yl)hexan-1-ol (13_3). LCMS (ESI) calc'd for C$_{12}$H$_{19}$NO$_4$ [M+H]$^+$: 242.2, found: 242.1

Step 4: Preparation of 6-(2-(isoxazol-3-yl)-1,3-dioxolan-2-yl)hexanal (13_4)

To a mixture of 6-(2-(isoxazol-3-yl)-1,3-dioxolan-2-yl)hexan-1-ol (13_3, 4.7 g, 19.48 mmol) in DCM (35 ml) and DMSO (23 ml) was added DIPEA (10.2 ml, 58.4 mmol) and sulfur trioxide pyridine complex (4.65 g, 29.2 mmol) at 0° C., and the mixture was stirred at rt for 3 h. The reaction was quenched with water (50 mL) and taken up in EtOAc (50 mL). The mixture was washed with H$_2$O (100 mL), washed with 1 M HCl (50 mL), and sat. solution of NaHCO$_3$ (50 mL), dried over Na$_2$SO$_4$, and concentrated to get the crude product. The crude product was purified by flash silica gel chromatography (ISCO®; 20 g SepaFlash® Silica Flash Column, Eluent of 0-10% EtOAc/Petroleum ether gradient @40 mL/min) to give 6-(2-(isoxazol-3-yl)-1,3-dioxolan-2-yl)hexanal (13_4).

Step 5: Preparation of (R,E)-N-(6-(2-(isoxazol-3-yl)-1,3-dioxolan-2-yl)hexylidene)-2-methylpropane-2-sulfinamide (13)

Copper(II) sulfate (7.74 g, 48.5 mmol) was added to a stirred mixture of 6-(2-(isoxazol-3-yl)-1,3-dioxolan-2-yl) hexanal (13_4, 2.9 g, 12.12 mmol), (R)-2-methylpropane-2-sulfinamide (2.203 g, 18.18 mmol) in DCM (100 ml) at rt, and the mixture was stirred at rt for 20 h. The mixture was combined with a 0.7 g scale reaction, filtered and the filtrate was concentrated to dryness to get the crude product. The crude product was purified by flash silica gel chromatography (ISCO®; 20 g SepaFlash® Silica Flash Column, Eluent of 0~10% EtOAc/Petroleum ether gradient @40 mL/min) to give (R,E)-N-(6-(2-(isoxazol-3-yl)-1,3-dioxolan-2-yl)hexylidene)-2-methylpropane-2-sulfinamide (13). $^1$H NMR (400 MHz, CDCl$_3$) δ 8.37 (d, J=1.5 Hz, 1H), 8.04 (s, 1H), 6.32 (d, J=1.5 Hz, 1H), 4.11-4.06 (m, 2H), 3.99-3.94 (m, 2H), 2.50 (dt, J=4.9, 7.4 Hz, 2H), 2.04-1.99 (m, 2H), 1.67-1.58 (m, 3H), 1.49-134 (m, 4H), 1.19 (s, 9H).

Intermediate 14

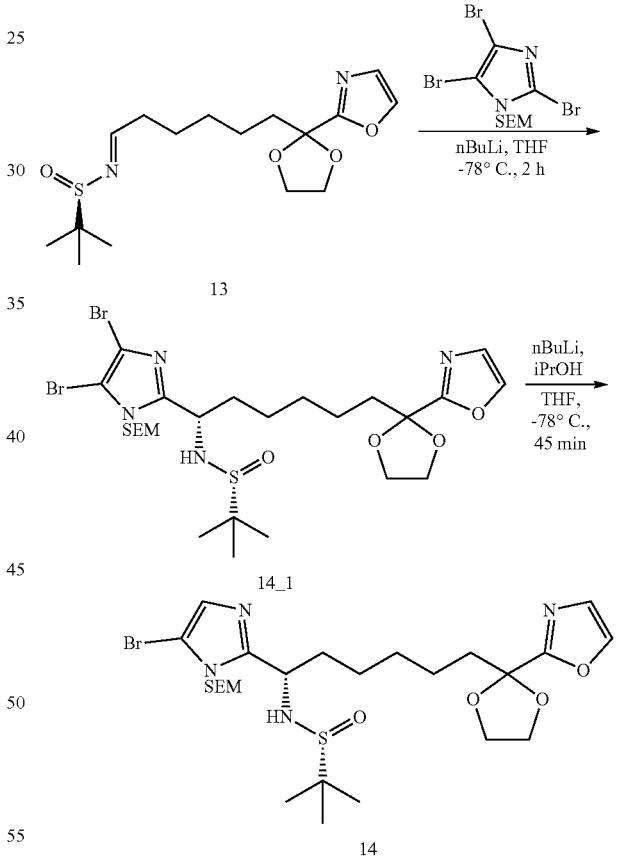

Step 1: Preparation of (R)-N-((S)-1-(4,5-dibromo-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (14_1)

Butyllithium (14 ml, 35.0 mmol) was added to a stirred mixture of 2,4,5-tribromo-1-((2-(trimethylsilyl)ethoxy)methyl)-1H-imidazole (15.24 g, 35.0 mmol) in THF (80.0 ml) at −78° C. and the mixture was stirred at −78° C. for 30 min. (R,E)-2-methyl-N-(6-(2-(oxazol-2-yl)-1,3-dioxolan-2-yl)hexylidene)propane-2-sulfinamide (12, 8.0 g, 23.36 mmol) in THF (20 mL) was added. The mixture was stirred at −78° C. for 2 h. The mixture was quenched with aqueous NH$_4$Cl (saturated, 80 mL) and the mixture was extracted with ethyl acetate (3×80 mL). The combined organic fractions were washed with brine (saturated, 50 mL), dried (Na$_2$SO$_4$), filtered and the solvent was evaporated under reduced pressure. The residue was purified by silica gel column flash chromatography, eluting with petroleum ether/EtOAc=1:1-1:2 to give (R)-N-((S)-1-(4,5-dibromo-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (141). LCMS (ESI) calc'd for $15_5H_{42}Br_2N_4O_5SSi$ [M+H]$^+$: 697.1, found: 697.1.

Step 2: Preparation of (R)-N-((S)-1-(5-bromo-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (14)

BuLi (8.8 ml, 22.00 mmol) was added to a stirred mixture of (R)-N-((S)-1-(4,5-dibromo-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (14_1, 9.0 g, 12.88 mmol) in THF (100.0 ml) at −78° C. and the mixture was stirred at −78° C. for 1 h. Propan-2-ol (3.87 g, 64.4 mmol) was added dropwise. The mixture was stirred at −78° C. for 20 min. The mixture was quenched further with aqueous NH$_4$Cl (saturated, 80 mL) and the mixture was extracted with ethyl acetate (3×80 mL). The combined organic fractions were washed with brine (saturated, 2×50 mL), dried (Na$_2$SO$_4$), filtered and the solvent was evaporated under reduced pressure. The residue was purified by silica gel column flash chromatography, eluting with petroleum ether/EtOAc=1:1-0:1 to give (R)-N-((S)-1-(5-bromo-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (14). LCMS (ESI) calc'd for $15_5H_{43}BrN_4O_5SSi$ [M+H]$^+$: 619.2, found: 621.2. $^1$H NMR (400 MHz, CDCl$_3$) δ 7.61 (s, 1H), 7.07 (s, 1H), 6.88 (s, 1H), 5.39 (d, J=11.04 Hz, 1H), 5.13 (d, J=11.04 Hz, 1H), 4.02-4.15 (m, 5H), 3.72 (d, J=7.53 Hz, 1H), 3.50 (t, J=8.28 Hz, 2H), 2.17-2.19 (m, 1H), 2.06-2.19 (m, 2H), 2.02 (d, J=6.78 Hz, 1H), 1.63-1.73 (m, 1H), 1.26-1.48 (m, 7H), 1.08-1.21 (m, 10H), 0.85-0.96 (m, 2H), 0.01 (s, 9H).
Intermediate 15

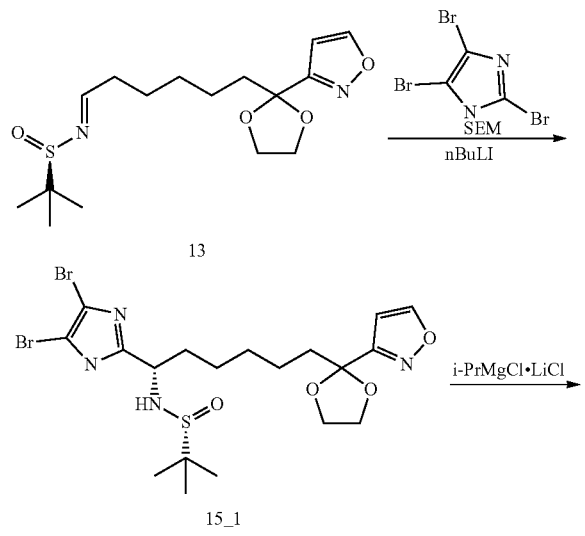

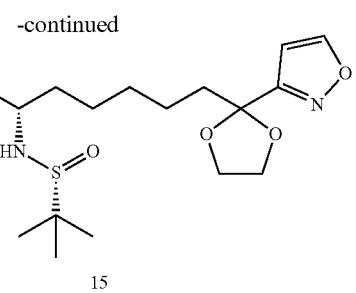

Step 1: Preparation of ((R)-N-((S)-1-(4,5-dibromo-1-((2-(trimethylsilyl) ethoxy)methyl)-1H-imidazol-2-yl)-6-(2-(isoxazol-3-yl)-1,3-dioxolan-2-yl) hexyl)-2-methylpropane-2-sulfinamide (15_1)

Butyllithium (6.13 ml, 15.33 mmol) was added to a stirred mixture of 2,4,5-tribromo-1-((2-(trimethylsilyl)ethoxy)methyl)-1H-imidazole (6.67 g, 15.33 mmol) in THF (35 ml) at −78° C., and the mixture was stirred at −78° C. for 30 min. (R,E)-N-(6-(2-(isoxazol-3-yl)-1,3-dioxolan-2-yl)hexylidene)-2-methylpropane-2-sulfinamide (13, 3.5 g, 10.22 mmol) in THF (5 ml) was added, and the mixture was stirred at −78° C. for 2 h. The mixture was quenched with NH$_4$Cl (100 mL), extracted with EtOAc (100 mL*3), the combined organic layers were washed with brine (100 mL), dried over Na$_2$SO$_4$, filtered and concentrated. The crude product was purified by flash silica gel chromatography (ISCO®; 20 g SepaFlash® Silica Flash Column, Eluent of 0~10% EtOAc/Petroleum ether gradient @40 mL/min) to give (R)-N-((S)-1-(4,5-dibromo-1-((2-(trimethylsilyl)ethoxy)methyl)-1H-imidazol-2-yl)-6-(2-(isoxazol-3-yl)-1,3-dioxolan-2-yl) hexyl)-2-methylpropane-2-sulfinamide (15_1). LC/MS (ESI) calc'd for $C_{15}H_{42}Br_2N_4O_5SSi$ [M+H]$^+$: 699.5, found: 698.9.

Step 2: Preparation of (R)-N-((S)-1-(5-bromo-1-((2-(trimethylsilyl)ethoxy)methyl)-1H-imidazol-2-yl)-6-(2-(isoxazol-3-yl)-1,3-dioxolan-2-yl)hexyl)-2-methylpropane-2-sulfinamide (15)

iPrMgCl·LiCl (6.17 ml, 8.02 mmol) was added to a stirred mixture of (R)-N-((S)-1-(4,5-dibromo-1-((2-(trimethylsilyl)ethoxy)methyl)-1H-imidazol-2-yl)-6-(2-(isoxazol-3-yl)-1,3-dioxolan-2-yl)hexyl)-2-methylpropane-2-sulfinamide (15_1, 2.8 g, 4.01 mmol) in THF (30 ml) at 0° C., and the mixture was stirred at rt for 30 min. The mixture was quenched with NH$_4$Cl (50 mL), extracted with EtOAc (50 mL*3), the combined organic layers were washed with brine (50 mL), dried over Na$_2$SO$_4$, filtered and concentrated. The crude product was purified by flash silica gel chromatography (ISCO®; 20 g SepaFlash® Silica Flash Column, Eluent of 0~50% EtOAc/Petroleum ether gradient @40 mL/min) to give (R)-N-((S)-1-(5-bromo-1-((2-(trimethylsilyl)ethoxy)methyl)-1H-imidazol-2-yl)-6-(2-(isoxazol-3-yl)-1,3-dioxolan-2-yl)hexyl)-2-methylpropane-2-sulfinamide (15). $^1$H NMR (400 MHz, CDCl$_3$) δ 8.35 (d, J=1.6 Hz, 1H), 6.89 (s, 1H), 6.31 (d, J=1.6 Hz, 1H), 5.43-5.34 (m, 1H), 5.17-5.10 (m, 1H), 4.53-4.44 (m, 1H), 4.10-4.03 (m, 2H), 3.99-3.92 (m, 2H), 3.76-3.69 (m, 1H), 3.54-3.45 (m, 2H), 2.18-2.07 (m, 1H), 2.02-1.93 (m, 3H), 1.44-1.29 (m, 6H), 1.16 (s, 11H), 0.97-0.86 (m, 3H), 0.01 (s, 9H).

Intermediate 16

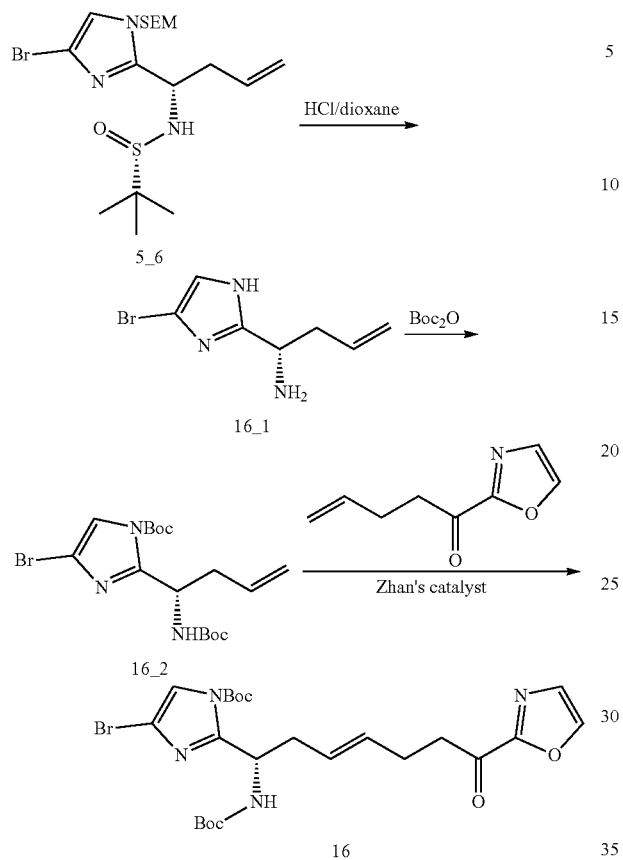

Step 1: Preparation of (S)-1-(4-bromo-1H-imidazol-2-yl)but-3-en-1-amine (16_1)

To a solution of (S)-N-((S)-1-(4-bromo-1-((2-(trimethylsilyl)ethoxy)methyl)-1H-imidazol-2-yl)but-3-en-1-yl)-2-methylpropane-2-sulfinamide (5_6, 7.1 g, 15.76 mmol) in ethyl acetate (5 ml) was added HCl/dioxane (2 ml, 8.00 mmol). The mixture was stirred at rt for 2 h. The reaction was concentrated to give (S)-1-(4-bromo-1H-imidazol-2-yl)but-3-en-1-amine (16_1) which was used directly in next step.

Step 2: Preparation of (S)-tert-butyl 4-bromo-2-(1-((tert-butoxycarbonyl)amino)but-3-en-1-yl)-1H-imidazole-1-carboxylate (16_2)

A mixture of DIEA (8 ml, 45.8 mmol), (S)-1-(4-bromo-1H-imidazol-2-yl)but-3-en-1-amine (161, 4 g crude, 18.51 mmol), DMAP (0.226 g, 1.851 mmol) and Bo15O (10 ml, 43.1 mmol) in DCM (20 ml) was stirred at rt for 10 h. The mixture was concentrated to dryness and purified by silica gel column flash chromatography, eluting with petroleum ether/EtOAc=10:1-20:1 to give (S)-tert-butyl 4-bromo-2-(1-((tert-butoxycarbonyl)amino)but-3-en-1-yl)-1H-imidazole-1-carboxylate (16_2). LCMS (ESI) calc'd for $C_{17}H_{26}BrN_3O_4[M+H]^+$: 416.1, 418.1, found: 416.1, 418.1.

Step 3: Preparation of (S,E)-tert-butyl 4-bromo-2-(1-((tert-butoxycarbonyl)amino)-7-(oxazol-2-yl)-7-oxohept-3-en-1-yl)-1H-imidazole-1-carboxylate (16)

A mixture of 1-(oxazol-2-yl)pent-4-en-1-one (1, 290 mg, 1.922 mmol), (S)-tert-butyl 4-bromo-2-(1-((tert-butoxycarbonyl)amino)but-3-en-1-yl)-1H-imidazole-1-carboxylate (16_2, 500 mg, 1.201 mmol) and Zhan's catalyst (44 mg, 0.060 mmol) in toluene (2 mL) was degassed and backfilled with $N_2$ three times. The mixture was heated at 140° C. for 3 h. The mixture was cooled, diluted with ethyl acetate (20 mL), washed with brine (saturated, 5 mL), dried ($Na_2SO_4$), filtered and the solvent was evaporated under reduced pressure. The residue was purified by silica gel column flash chromatography, eluting with petroleum ether/EtOAc=20:1-1:3 to give (S,E)-tert-butyl 4-bromo-2-(1-((tert-butoxycarbonyl)amino)-7-(oxazol-2-yl)-7-oxohept-3-en-1-yl)-1H-imidazole-1-carboxylate (16). LCMS (ESI) calc'd for $C_{13}H_{31}BrN_4O_6$ $[M+H]^+$: 539.0, 541.0, found: 539.1, 541.1

Intermediate 17

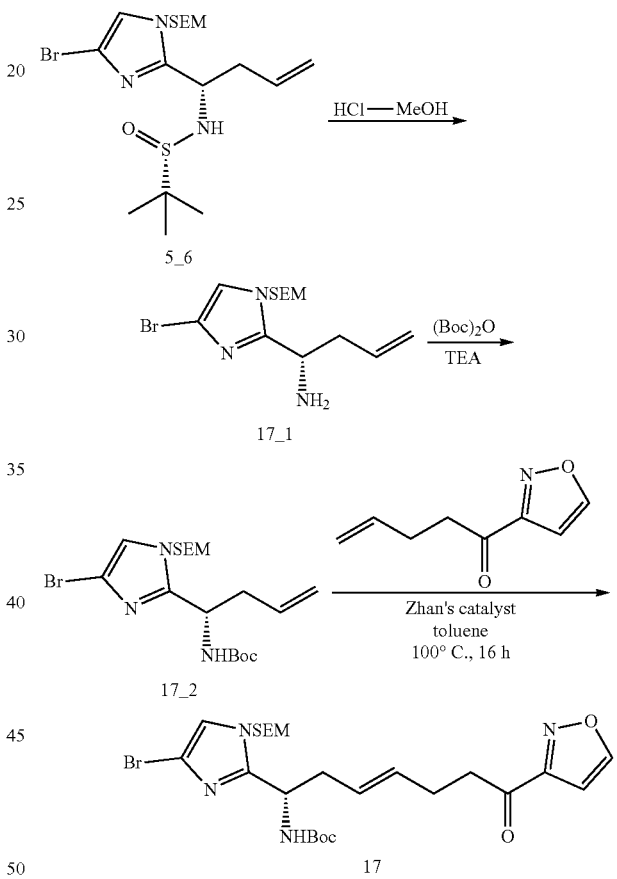

Step 1: Preparation of (S)-1-(4-bromo-1-((2-(trimethylsilyl) ethoxy)methyl)-1H-imidazol-2-yl)but-3-en-1-amine (17_1)

To a solution of (S)-N-((S)-1-(4-bromo-1-((2-(trimethylsilyl)ethoxy)methyl)-1H-imidazol-2-yl)but-3-en-1-yl)-2-methylpropane-2-sulfinamide (5_6, 9 g, 19.98 mmol) in MeOH (60 ml) was added HCl/MeOH (5 ml, 20.00 mmol). The mixture was stirred at rt for 1 h and then concentrated to give (S)-1-(4-bromo-1-((2-(trimethylsilyl)ethoxy) methyl)-1H-imidazol-2-yl) but-3-en-1-amine (171) which was used directly in next step. LCMS (ESI) calc'd for $C_{13}H_{24}BrN_3OSi$ $[M+H]^+$: 348.0, found: 348.1

Step 2: Preparation of (S)-tert-butyl (1-(4-bromo-1-((2-(trimethylsilyl)ethoxy) methyl)-1H-imidazol-2-yl)but-3-en-1-yl)carbamate (17_2)

A mixture of (S)-1-(4-bromo-1-((2-(trimethylsilyl)ethoxy)methyl)-1H-imidazol-2-yl)but-3-en-1-amine (171, 6900 mg), TEA (4.17 ml, 29.9 mmol) and Bo15O (5.80 ml, 24.90 mmol) in DCM (100 ml) was stirred at rt for 16 h. The mixture was concentrated to dryness and purified by silica gel column flash chromatography, eluting with petroleum ether/EtOAc=100:1-30:1 to give (S)-tert-butyl (1-(4-bromo-1-((2-(trimethylsilyl)ethoxy)methyl)-1H-imidazol-2-yl)but-3-en-1-yl)carbamate (17_2). LCMS (ESI) calc'd for $C_{18}H_{32}BrN_3O_3Si$ [M+H]$^+$: 446.1 found: 446.2

Step 3: Preparation of (S,E)-tert-butyl(1-(4-bromo-1-((2-(trimethylsilyl)eth oxy)methyl)-1H-imidazol-2-yl)-7-(isoxazol-3-yl)-7-oxohept-3-en-1-yl)carbamate (17)

Zhan's catalyst (82 mg, 0.112 mmol) was added to a mixture of (S)-tert-butyl (1-(4-bromo-1-((2-(trimethylsilyl)ethoxy)methyl)-1H-imidazol-2-yl)but-3-en-1-yl)carbamate (17_2, 1000 mg, 2.240 mmol) and 1-(isoxazol-3-yl)pent-4-en-1-one (A1, 745 mg, 4.93 mmol) in toluene (8 ml) which was bubbled with $N_2$ for 20 mins at rt. The mixture was degassed and backfilled with $N_2$ three times and stirred at 100° C. for 16 h. Five parallel reactions were combined and concentrated to dryness, then purified by silica gel chromatography eluted with Petro.Ether:EtOAc=5:1 to give (S,E)-tert-butyl(1-(4-bromo-1-((2-(trimethylsilyl)ethoxy)methyl)-1H-imidazol-2-yl)-7-(isoxazol-3-yl)-7-oxohept-3-en-1-yl)carbamate (17). LCMS (ESI) calc'd for $C_{14}H_{37}BrN_4O_5Si$ [M+H]$^+$: 569.2, found: 571.0

Intermediate 18 tert-butyl (S)-(1-(1-(2-methyl-2H-indazol-5-yl)-1H-pyrazol-3-yl)but-3-en-1-yl)carbamate

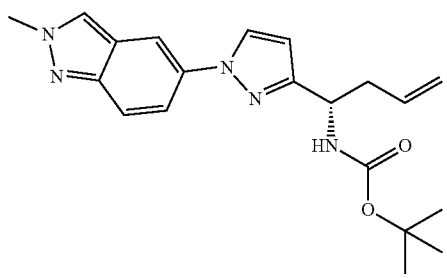 [SMILES: C=CC[C@H](NC(=O)OC(C)(C)C)c1ccn(-c2ccc3nn(C)cc3c2)n1]

Step 1: 1-tosyl-1H-pyrazole-3-carbaldehyde

To a solution of 1H-pyrazole-3-carbaldehyde (5 g, 52.0 mmol) in THF (80 ml) and DMF (40 ml) at 0° C. was added NaH (2.289 g, 57.2 mmol) in three equal portions. The reaction mixture was stirred at 0° C. under $N_2$. After 20 min of stirring, the reaction mixture was treated with Ts-Cl (10.91 g, 57.2 mmol) in three equal portions. The reaction mixture was stirred under $N_2$ while allowed to warm to RT slowly. After 2 hr of stirring, the reaction mixture was quenched carefully with sat. NaHCO$_3$(aq) (5 mL). The reaction mixture was diluted with H$_2$O (200 mL) and extracted with EtOAc (3×100 mL). The organic extracts were combined, washed with H$_2$O (3×100 mL), brine (1×50 mL), dried over MgSO$_4$, filtered and concentrated. The crude product was purified by normal phase silica gel column chromatography using EtOAc/Hexanes as eluents to yield the title compound.

Step 2: (S,E)-2-methyl-N-((1-tosyl-1H-pyrazol-3-yl)methylene)propane-2-sulfinamide To a solution of 1-tosyl-1H-pyrazole-3-carbaldehyde (4.56 g, 18.22 mmol) in CH$_2$Cl$_2$ (50 ml) were added (S)-2-methylpropane-2-sulfinamide (3.31 g, 27.3 mmol) and copper(II) sulfate (11.63 g, 72.9 mmol). The reaction mixture was stirred at RT under $N_2$. After 3 days of stirring, the reaction mixture was filtered through a pad of Celite with CH$_2$Cl$_2$ and the filtrate was concentrated. The crude product was purified by normal phase silica gel column chromatography using EtOAc/Hexanes as eluents to yield the title compound.

Step 3: (S)-2-methyl-N-((S)-1-(1-tosyl-1H-pyrazol-3-yl)but-3-en-1-yl)propane-2-sulfinamide To a solution of (S,E)-2-methyl-N-((1-tosyl-1H-pyrazol-3-yl)methylene)propane-2-sulfinamide (5.67 g, 16.04 mmol) in THF (100 ml) at −78° C. was added allylmagnesium chloride (10.43 ml, 20.85 mmol) dropwise. The reaction mixture was stirred at −78° C. under $N_2$. After 1 hr of stirring, the reaction mixture was quenched by addition of sat NH$_4$Cl(aq) (1 mL) at −78° C. The reaction mixture was warmed to room temperature. The reaction mixture was diluted with H$_2$O (50 mL) and EtOAc (100 mL). The layers were separated and the organic layer was washed with sat. NaHCO$_3$(aq) (1×50 mL), dried over MgSO$_4$, filtered, and concentrated. The crude product was purified by normal phase silica gel column chromatography using EtOAc/Hexanes as eluents to yield the title compound.

Step 4: tert-butyl (S)-(1-(1H-pyrazol-3-yl)but-3-en-1-yl)carbamate

To a solution of (S)-2-methyl-N-((S)-1-(1-tosyl-1H-pyrazol-3-yl)but-3-en-1-yl)propane-2-sulfinamide (1.3 g, 3.29 mmol) in MeOH (30 ml) was added HCl (4.11 ml, 16.43 mmol) (4.0 M in dioxane) at RT. The reaction mixture was stirred at 50° C. under $N_2$. After 1 day of stirring, the reaction mixture was cooled to RT, concentrated by rotorvap, and dried in vacuo. To a solution of the crude product in THF (20 ml) were added Boc$_2$O (0.916 ml, 3.95 mmol) and TEA (2.292 ml, 16.44 mmol). The reaction mixture was stirred at RT under $N_2$. After 2 hr of stirring, the reaction mixture was diluted with EtOAc (50 mL) and washed with sat NaHCO$_3$(aq) (3×50 mL), dried over MgSO$_4$, filtered, and concentrated. The crude product was purified by normal phase silica gel column chromatography using EtOAc/CH$_2$Cl$_2$ as eluents to yield the title compound.

Step 5: tert-butyl (S)-(1-(1-(2-methyl-2H-indazol-5-yl)-1H-pyrazol

To a solution of (S)-tert-butyl (1-(1H-pyrazol-3-yl)but-3-en-1-yl)carbamate (250 mg, 1.054 mmol) and 5-iodo-2-methyl-2H-indazole (408 mg, 1.580 mmol) in dioxane (5 mL) were added cuprous iodide (20.06 mg, 0.105 mmol), trans-n,n'-dimethylcyclohexane-1,2-diamine (0.034 mL, 0.211 mmol), and Cs$_2$CO$_3$ (687 mg, 2.107 mmol). The reaction mixture was degassed by being under vacuum briefly and flushed with N₂ three times. Then, the reaction mixture was heated at reflux under N₂. After 2 days of heating, the reaction mixture was cooled to RT and filtered with the help of EtOAc. Then, the filtrate was diluted with EtOAc (50 mL) and washed with sat. NaHCO₃(aq) (1×50 mL), sat NH₄Cl (1×50 mL), brine (1×50 mL), dried over MgSO₄, filtered, and concentrated. The crude product was purified by normal phase silica gel column chromatography using EtOAc/Hexanes as eluents to yield the title compound.
Intermediate 19 tert-butyl (S)-(1-(1-(4-fluorophenyl)-1H-pyrazol-3-yl)but-3-en-1-yl)carbamate

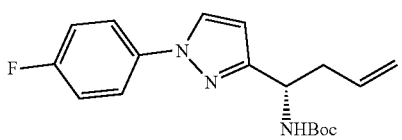 [SMILES: C=CC[C@H](NC(=O)OC(C)(C)C)c1ccn(-c2ccc(F)cc2)n1]

The title compound was prepared from the appropriate commercially available starting materials using procedures similar to those for the Intermediate 18 Step E.
Intermediate 20 tert-butyl (1-(5-(4-fluorophenyl)isoxazol-3-yl)but-3-en-1-yl)carbamate

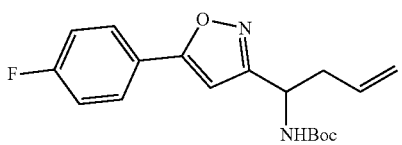 [SMILES: C=CCC(NC(=O)OC(C)(C)C)c1cc(-c2ccc(F)cc2)on1]

Step 1: (E)-N-((5-(4-fluorophenyl)isoxazol-3-yl)methylene)-2-methylpropane-2-sulfinamide To a solution of 5-(4-fluorophenyl)isoxazole-3-carbaldehyde (0.3 g, 1.569 mmol) in CH₂Cl₂ (5 ml) were added 2-methylpropane-2-sulfinamide (0.285 g, 2.354 mmol) and copper(II) sulfate (1.002 g, 6.28 mmol). The reaction mixture was stirred at RT under N₂ overnight. The reaction mixture was filtered through a pad of Celite and the filtrate was concentrated. The crude product was purified by normal phase silica gel column chromatography using EtOAc/Hexanes as eluents to yield the title compound.

Step 2: N-(1-(5-(4-fluorophenyl)isoxazol-3-yl)but-3-en-1-yl)-2-methylpropane-2-sulfinamide To a solution of (E)-N-((5-(4-fluorophenyl)isoxazol-3-yl)methylene)-2-methylpropane-2-sulfinamide (410 mg, 1.393 mmol) in THF (20 ml) at −78° C. was added allylmagnesium chloride (0.905 ml, 1.811 mmol) dropwise. The reaction mixture was stirred at −78° C. under N₂. After 1 hr of stirring, the reaction mixture was quenched by addition of sat NH₄Cl$_{(aq)}$ (1 mL) at −78° C. The reaction mixture was warmed to RT. The reaction mixture was diluted with H₂O (50 mL) and EtOAc (100 mL). The layers were separated and the organic layer was washed with sat NaHCO₃(aq) (1×50 mL), dried over MgSO₄, filtered, concentrated, and dried in vacuo. The title compound was used for the next reaction without further purification.

Step 3: tert-butyl (1-(5-(4-fluorophenyl)isoxazol-3-yl)but-3-en-1-yl)carbamate

To a solution of N-(1-(5-(4-fluorophenyl)isoxazol-3-yl)but-3-en-1-yl)-2-methylpropane-2-sulfinamide (469 mg, 1.394 mmol) in MeOH (5 ml) was added HCl (0.523 ml, 2.091 mmol) (4.0 M in dioxane) at room temperature. The reaction mixture was stirred at RT under N₂. After 1 hr of stirring, the reaction mixture was concentrated by rotorvap and further dried in vacuo. To a suspension of the crude product in THF (10 ml) were added Boc₂O (0.421 ml, 1.814 mmol) and TEA (0.973 ml, 6.98 mmol). The reaction mixture was stirred at RT under N₂ overnight. The reaction mixture was diluted with EtOAc (50 mL) and washed with sat NaHCO₃(aq) (2×50 mL), dried over MgSO₄, filtered, and concentrated. The crude product was purified by normal phase silica gel column chromatography using EtOAc/Hexanes as eluents to yield the title compound.
Intermediate 21 tert-butyl (1-(1-(4-fluorophenyl)-1H-pyrazol-4-yl)but-3-en-1-yl)carbamate

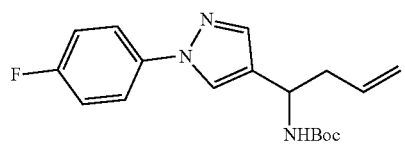 [SMILES: C=CCC(NC(=O)OC(C)(C)C)c1cnn(-c2ccc(F)cc2)c1]

The title compound was prepared from the appropriate commercially available starting materials using procedures similar to those for Intermediate 20.
Intermediate 22 tert-butyl (1-(2-(4-fluorophenyl)-2H-1,2,3-triazol-4-yl)but-3-en-1-yl)carbamate

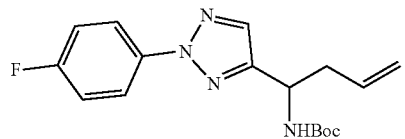

The title compound was prepared from the appropriate commercially available starting materials using procedures similar to those for Intermediate 20.
Intermediate 23 tert-butyl (S)-(1-(5-(2-fluorophenyl)isoxazol-3-yl)but-3-en-1-yl)carbamate

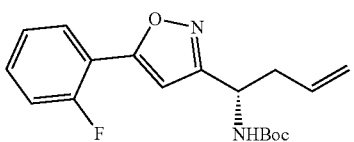 [SMILES: C=CC[C@H](NC(=O)OC(C)(C)C)c1cc(-c2ccccc2F)on1]

Step 1: 5-(2-fluorophenyl)-N-methoxy-N-methyl-isoxazole-3-carboxamide

To a solution of n,o-dimethylhydroxylamine hydrochloride (1.85 g, 18.97 mmol) and 5-(2-fluorophenyl)isoxazole-3-carboxylic acid (2.5 g, 11.46 mmol) in DMF (50 ml) were added EDC (2.5 g, 13.04 mmol), HOBt (0.018 g, 0.115 mmol), and TEA (7.99 ml, 57.3 mmol). The reaction mixture was stirred at RT under $N_2$ overnight. The reaction mixture was diluted with $H_2O$ (200 mL) and extracted with EtOAc (3×50 mL). All the organic extracts were combined and washed with sat $NaHCO_3$(aq) (2×100 mL), $H_2O$ (5×100 mL), dried over $MgSO_4$, filtered, and concentrated. The crude product was purified by normal phase silica gel column chromatography using EtOAc/Hexanes as eluents to yield the title compound.

Step 2: 5-(2-fluorophenyl)isoxazole-3-carbaldehyde

To a solution of 5-(2-fluorophenyl)-N-methoxy-N-methylisoxazole-3-carboxamide (1.48 g, 5.91 mmol) in THF (50 ml) at −78° C. under $N_2$ was added DIBAL-H (14.79 ml, 14.79 mmol) dropwise. The reaction mixture was stirred at −78° C. under $N_2$. After 2 hr of stirring, the reaction mixture was quenched by addition of 5 mL sat. Rochell salt(aq) at −78° C. The reaction mixture was warmed to RT and diluted with sat. Rochelle salt(aq)(100 mL) and $Et_2O$ (50 mL). The crude reaction mixture was stirred vigorously at RT overnight. The layers were separated and the aqueous layer was extracted with EtOAc (1×50 mL). All the organic layers were combined, dried over $MgSO_4$, filtered, concentrated and dried in vacuo to yield the title compound.

Step 3: (S,E)-N-((5-(2-fluorophenyl)isoxazol-3-yl)methylene)-2-methylpropane-2-sulfinamide To a solution of 5-(2-fluorophenyl)isoxazole-3-carbaldehyde (1.50 g, 7.85 mmol) in $CH_2Cl_2$ (20 ml) were added (S)-2-methylpropane-2-sulfinamide (1.427 g, 11.77 mmol) and copper(II) sulfate (5.01 g, 31.4 mmol). The reaction mixture was stirred at room temperature under $N_2$ overnight. The reaction mixture was filtered through a pad of Celite and the filtrate was concentrated down. The crude product was purified by normal phase silica gel column chromatography using EtOAc/Hexanes as eluents to yield the title compound.

Step 4: (S)-N-((S)-1-(5-(2-fluorophenyl)isoxazol-3-yl)but-3-en-1-yl)-2-methylpropane-2-sulfinamide To a solution of (S,E)-N-((5-(2-fluorophenyl)isoxazol-3-yl)methylene)-2-methylpropane-2-sulfinamide (1.08 g, 3.67 mmol) in THF (25 ml) at −78° C. was added allylmagnesium chloride (2.385 ml, 4.77 mmol) dropwise. The reaction mixture was stirred at −78° C. under $N_2$. After 1 hr of stirring, the reaction mixture was quenched by addition of sat $NH_4Cl$(aq) (5 mL) at −78° C. The reaction mixture was warmed to RT. The reaction mixture was diluted with $H_2O$ (50 mL) and EtOAc (100 mL). The layers were separated and the organic layer was washed with sat. $NaHCO_3$(aq) (1×50 mL), dried over $MgSO_4$, filtered, and concentrated. The crude product was purified by normal phase silica gel column chromatography using EtOAc/Hexanes as eluents to yield the title compound.

Step 5: tert-butyl (S)-(1-(5-(2-fluorophenyl)isoxazol-3-yl)but-3-en-1-yl)carbamate To a solution of (S)-N-((S)-1-(5-(2-fluorophenyl)isoxazol-3-yl)but-3-en-1-yl)-2-methylpropane-2-sulfinamide (1.14 g, 3.39 mmol) in MeOH (20 ml) was added HCl (1.271 ml, 5.08 mmol) (4.0M in dioxane) at RT. The reaction mixture was stirred at RT under $N_2$. After 1 hr of stirring, the reaction mixture was concentrated down by rotorvap and further dried in vacuo. To a suspension of the crude product in THF (10 ml) were added $Boc_2O$ (1.023 ml, 4.41 mmol) and TEA (2.363 ml, 16.95 mmol). The reaction mixture was stirred at RT under $N_2$ overnight. The reaction mixture was diluted with EtOAc (50 mL) and washed with sat $NaHCO_3$ (aq) (2×50 mL), dried over $MgSO_4$, filtered, and concentrated. The crude product was purified by normal phase silica gel column chromatography using EtOAc/Hexanes as eluents to yield the title compound.

Intermediate 24 tert-butyl (S)-(1-(5-(2-methyl-2H-indazol-5-yl)isoxazol-3-yl)but-3-en-1-yl)carbamate

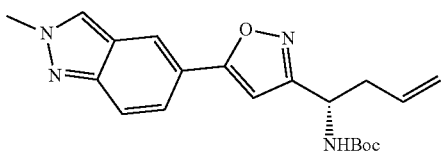 [SMILES: C=CC[C@H](NC(=O)OC(C)(C)C)c1cc(-c2ccc3nn(C)cc3c2)on1]

Step 1: ethyl 5-(2-methyl-2H-indazol-5-yl)isoxazole-3-carboxylate

To a suspension of ethyl 5-bromoisoxazole-3-carboxylate (4.8 g, 21.82 mmol) and (2-methyl-2H-indazol-5-yl)boronic acid (4.61 g, 26.2 mmol) in 1,4-Dioxane (100 ml) and Water (20.00 ml) were added 2nd generation xphos precatalyst (0.858 g, 1.091 mmol) and $Cs_2CO_3$ (11.6 g, 35.6 mmol). The reaction mixture was degassed by $N_2$ stream for 20 min. Then the reaction mixture was stirred at 90° C. under $N_2$ overnight. The reaction mixture was cooled to RT. The reaction mixture was filtered thru a pad of Celite to remove most of the insoluble ppts and concentrated by rotorvap to remove most of volatiles. Then, the reaction mixture was diluted with EtOAc (200 mL) and $H_2O$ (200 mL). The layers were separated and the aqueous layer was extracted with EtOAc (1×200 mL). All of the organic layers were combined, washed with $H_2O$ (1×50 mL), sat. $NaHCO_{3(aq)}$ (2×100 mL), dried over $MgSO_4$, filtered and concentrated. The crude reaction mixture was purified by normal phase silica gel column chromatography using EtOAc/hexanes as eluents to yield the title compound.

Step 2: (5-(2-methyl-2H-indazol-5-yl)isoxazol-3-yl)methanol

To a solution of ethyl 5-(2-methyl-2H-indazol-5-yl)isoxazole-3-carboxylate (3.55 g, 13.09 mmol) in THF (100 ml) and $CH_2Cl_2$ (20 mL) at −78° C. under $N_2$ was added DIBAL-H (31.4 ml, 31.4 mmol) dropwise. The reaction mixture was stirred under $N_2$ and allowed to warm slowly up to RT. After 18 hr of stirring, the reaction mixture was cooled to −78° C. and quenched by addition of 5 mL sat. Rochelle salt(aq) at −78° C. The reaction mixture was warmed to RT and diluted with sat. Rochelle salt(aq) (200 mL) and $Et_2O$ (200 mL). The crude reaction mixture was stirred vigorously at RT. The layers were separated and the aqueous layer was extracted with EtOAc (3×100 mL). All of the organic layers were combined, dried over $MgSO_4$, filtered, and concentrated. The crude product was purified by normal phase silica gel column chromatography using EtOAc/Hexanes as eluents to yield the title compounds.

Step 3: 5-(2-methyl-2H-indazol-5-yl)isoxazole-3-carbaldehyde

To a solution of (5-(2-methyl-2H-indazol-5-yl)isoxazol-3-yl)methanol (1.96 g, 8.55 mmol) in 1,4-dioxane (50 ml) was added manganese dioxide (3.72 g, 42.8 mmol). The suspension was heated at reflux under $N_2$ overnight. The reaction mixture was cooled to room temperature. The reaction mixture was filtered through a pad of Celite. The filtrate was concentrated and dried in vacuo to yield the title compound.

Step 4: (S,E)-2-methyl-N-((5-(2-methyl-2H-indazol-5-yl)isoxazol-3-yl)methylene)propane-2-sulfinamide To a solution of 5-(2-methyl-2H-indazol-5-yl)isoxazole-3-carbaldehyde (1.943 g, 8.55 mmol) in $CH_2Cl_2$ (40 ml) were added (S)-2-methylpropane-2-sulfinamide (1.555 g, 12.83 mmol) and copper(II) sulfate (5.46 g, 34.2 mmol). The reaction mixture was stirred at room temperature under $N_2$ overnight. The reaction mixture was filtered through a pad of Celite with $CH_2Cl_2$ and the filtrate was concentrated. The crude product was purified by normal phase silica gel column chromatography using EtOAc/$CH_2Cl_2$ as eluents to yield the title compound.

Step 5: (S)-2-methyl-N-((S)-1-(5-(2-methyl-2H-indazol-5-yl)isoxazol-3-yl)but-3-en-1-yl)propane-2-sulfinamide To a solution of (S,E)-2-methyl-N-((5-(2-methyl-2H-indazol-5-yl)isoxazol-3-yl)methylene)propane-2-sulfinamide (550 mg, 1.665 mmol) in THF (20 ml) at −78° C. was added allylmagnesium chloride (1.082 ml, 2.164 mmol) dropwise. The reaction mixture was stirred at −78° C. under $N_2$. After 1 hr of stirring, the reaction mixture was quenched by addition of sat. $NH_4Cl$(aq) (5 mL) at −78° C. The reaction mixture was warmed to RT. The reaction mixture was diluted with $H_2O$ (50 mL) and EtOAc (100 mL). The layers were separated and the organic layer was washed with sat $NaHCO_3$(aq) (1×50 mL), dried over $MgSO_4$, filtered, and concentrated. The crude product was purified by column chromatography using MeOH/$CH_2Cl_2$ as eluents to yield the title compound.

Step 6: tert-butyl (S)-(1-(5-(2-methyl-2H-indazol-5-yl)isoxazol-3-yl)but-3-en-1-yl)carbamate To a solution of (S)-2-methyl-N-((S)-1-(5-(2-methyl-2H-indazol-5-yl)isoxazol-3-yl)but-3-en-1-yl)propane-2-sulfinamide (536.2 mg, 1.440 mmol) in MeOH (5 ml) was added HCl (0.540 ml, 2.159 mmol) (4.0M in dioxane) at RT. The reaction mixture was stirred at RT under $N_2$. After 1 hr of stirring, the reaction mixture was concentrated down by rotorvap and dried in vacuo. To a suspension of crude product in THF (15 ml) were added $Boc_2O$ (0.502 ml, 2.161 mmol) and TEA (1.004 ml, 7.20 mmol). The reaction mixture was stirred at RT under $N_2$ overnight. The reaction mixture was diluted with EtOAc (50 mL) and washed with sat $NaHCO_3$(aq) (2×50 mL), dried over $MgSO_4$, filtered, and concentrated. The crude product was purified by normal phase silica gel column chromatography using EtOAc/Hexanes as eluents to yield the title compound.

Intermediate 25 tert-butyl (S)-(1-(5-(7-methoxy-2-methylquinolin-6-yl)isoxazol-3-yl)but-3-en-1-yl)carbamate

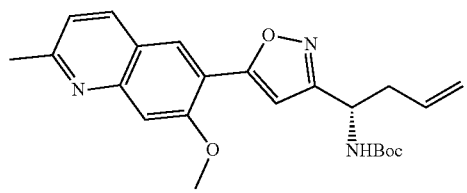 [SMILES: C=CC[C@H](NC(=O)OC(C)(C)C)c1cc(-c2cc3ccc(C)nc3cc2OC)on1]

The title compound was prepared from the appropriate commercially available starting materials using procedures similar to those for Intermediate 24.

Example 1

(S)-N-(1-(4-(4-fluorophenyl)-1H-imidazol-2-yl)-7-(oxazol-2-yl)-7-oxoheptyl)-1-methylazetidine-3-carboxamide

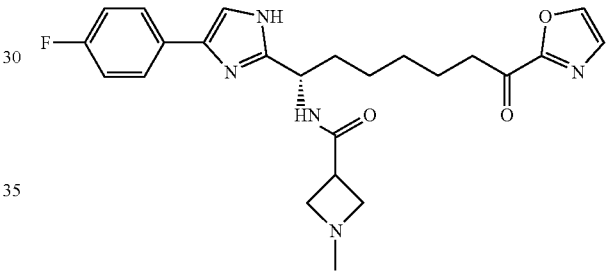

Step 1: tert-butyl (S,E)-2-(1-((tert-butoxycarbonyl)amino)-7-(oxazol-2-yl)-7-oxohept-3-en-1-yl)-4-(4-fluorophenyl)-1H-imidazole-1-carboxylate To a 50 ml one neck round bottom flaks was added toluene (5 ml) to mixture of (S)-tert-butyl 2-(1-((tert-butoxycarbonyl)amino)but-3-en-1-yl)-4-(4-fluorophenyl)-1H-imidazole-1-carboxylate (Intermediate 4, 1 g, 2.317 mmol); Zhan catalyst-1B (100 mg, 0.136 mmol) and 1-(oxazol-2-yl)pent-4-en-1-one (Intermediate 1, 900 mg, 5.95 mmol). The mixture was degassed and refilled with nitrogen and then was stirred at 50° C. overnight. The reaction mixture was directly purified by Analogix (Redisep 40 g column) eluting with 20% EtOAc-hexanes yielding (S,E)-tert-butyl 2-(1-((tert-butoxycarbonyl)amino)-7-(oxazol-2-yl)-7-oxohept-3-en-1-yl)-4-(4-fluorophenyl)-1H-imidazole-1-carboxylate. LC-MS: $C_{29}H_{35}FN_4O_6$, Calcd $[M+H]^+$: 555.3, found $[M+H]^+$: 555.1.

Step 2: (S,E)-7-amino-7-(4-(4-fluorophenyl)-1H-imidazol-2-yl)-1-(oxazol-2-yl)hept-4-en-1-one To a 50 ml one neck round bottom flask was charged a solution of (S,E)-tert-butyl 2-(1-((tert-butoxycarbonyl)amino)-7-(oxazol-2-yl)-7-oxohept-3-en-1-yl)-4-(4-fluorophenyl)-1H-imidazole-1-carboxylate (500 mg, 0.902 mmol) in DCM (5 ml)/TFA (1 ml) and it was stirred overnight. The solvent was evaporated to provide (S,E)-7-amino-7-(4-(4-fluorophenyl)-1H-imidazol-2-yl)-1-(oxazol-2-yl)hept-4-en-1-one, TFA salt. $C_{19}H_{19}FN_4O_2$, calced Calcd $[M+H]^+$: 355.2, found $[M+H]^+$: 355.1.

Step 3: (S)-7-amino-7-(4-(4-fluorophenyl)-1H-imidazol-2-yl)-1-(oxazol-2-yl)heptan-1-one A 50 ml one neck round bottom flask was charged with (S,E)-7-amino-7-(4-(4-fluorophenyl)-1H-imidazol-2-yl)-1-(oxazol-2-yl)hept-4-en-1-one, TFA (350 mg, 0.747 mmol) and 10% Pd/C (5 mg) in methanol (10 ml). The flask was connected to a hydrogen balloon through a three-way joint. The flask was vacuumed and refilled with hydrogen three times. The mixture was stirred under a hydrogen balloon for 2 hours. The mixture was then filtered through a Celite pad, and washed with MeOH (10 ml). The filtrate was concentrated and the residue was dissolved in $CH_2Cl_2$ (100 ml), water was added (30 ml) and the solution was basified with conc. $NH_4OH$ (1 ml). The organic layer was separated, dried over $Na_2SO_4$, then filtered and evaporated to afford (S)-7-amino-7-(4-(4-fluorophenyl)-1H-imidazol-2-yl)-1-(oxazol-2-yl)heptan-1-one. LC-MS: $C_{19}H_{23}FN_4O_2$, Calcd $[M+H]^+$: 357.2, found $[M+H]^+$: 357.1.

Step 4: (S)-N-(1-(4-(4-fluorophenyl)-1H-imidazol-2-yl)-7-(oxazol-2-yl)-7-oxoheptyl-1-methylazetidine-3-carboxamide To a 25 ml one neck round bottom flask was added 1-hydroxybenzotriazole (15 mg, 0.111 mmol) and EDCI (20 mg, 0.104 mmol) to solution of 1-methyl-3-azetidine carboxylic acid (15 mg, 0.130 mmol) and (S)-7-amino-7-(4-(4-fluorophenyl)-1H-imidazol-2-yl)-1-(oxazol-2-yl)heptan-1-one (30 mg, 0.084 mmol) in DMF (1 ml). The mixture was then stirred at room temperature overnight. The mixture was partitioned in EtOAc (50 ml) and brine (10 ml). The organic layer was separated and dried over $Na_2SO_4$, then filtered and concentrated. The crude was purified on Analogix (Redisep 24 g column) eluting with 700 $MeOH/MeCl_2$ yielding (S)-N-(1-(4-(4-fluorophenyl)-1H-imidazol-2-yl)-7-(oxazol-2-yl)-7-oxoheptyl)-1-methylazetidine-3-carboxamide.
LC-MS: $C_{24}H_{28}FN_5O_3$, Calcd $[M+H]^+$: 454.2, found $[M+H]^+$: 454.0. 1HNMR ($CD_3OD$, 500 MHz) δ: 8.11 (1, 1H), 7.67 (t, 2H), 7.40 (s, 1H), 7.25 (s, 1H), 7.09 (t, 2H), 5.05 (t, 1H), 3.52 (m, 2H), 3.32 (s, 3H), 3.05 (m, 1H), 2.02 (m, 1H), 1.88 (m, 1H), 1.72 (m, 2H), 1.25-1.45 (in, 4H) ppm.

Using similar chemistry as described above, the following compounds were prepared by using a different acid in Step 4 to provide the final amide coupling products:

| Example | Structure | IUPAC Name | Exact Mass $[M + H]^+$ | Retention time (min) |
|---|---|---|---|---|
| 2 | 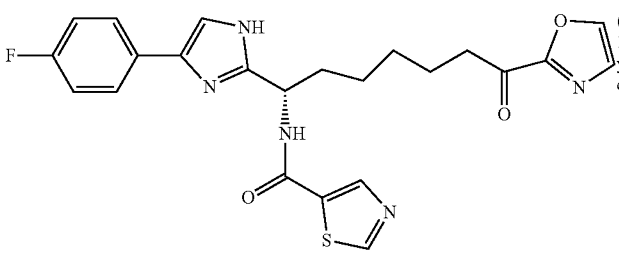 [SMILES: O=C(CCCCC[C@H](NC(=O)c1cncs1)c1nc(-c2ccc(F)cc2)c[nH]1)c1ncco1] | (S)-N-(1-(4-(4-fluorophenyl)-1H-imidazol-2-yl)-7-(oxazol-2-yl)-7-oxoheptyl)thiazole-5-carboxamide | 468.1 | 2.52 |
| 3 | 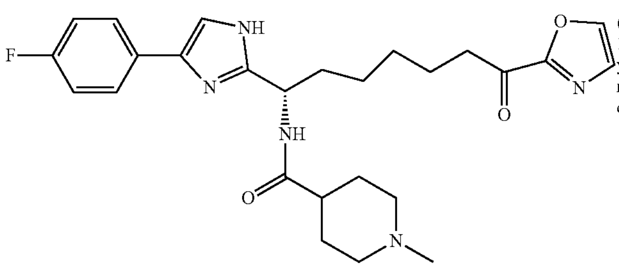 | (S)-N-(1-(4-(4-fluorophenyl)-1H-imidazol-2-yl)-7-(oxazol-2-yl)-7-oxoheptyl)-1-methylpiperidine-4-carboxamide | 482.1 | 2.15 |
| 4 | 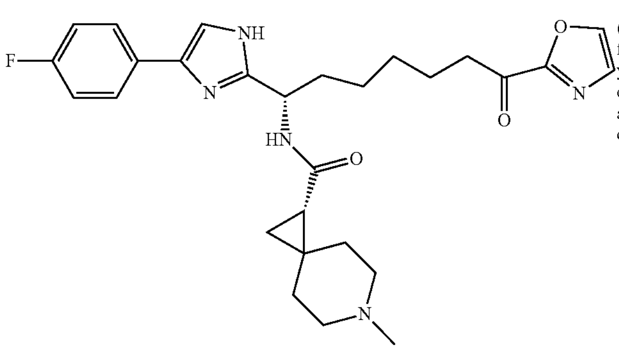 [SMILES: CN1CCC2(CC1)C[C@@H]2C(=O)N[C@@H](CCCCCC(=O)c1ncco1)c1nc(-c2ccc(F)cc2)c[nH]1] | (S)-N-((S)-1-(4-(4-fluorophenyl)-1H-imidazol-2-yl)-7-(oxazol-2-yl)-7-oxoheptyl)-6-methyl-6-azaspiro[2.5]octane-1-carboxamide | 508.1 | 2.10 |

-continued

| Example | Structure | IUPAC Name | Exact Mass [M + H]+ | Retention time (min) |
|---|---|---|---|---|
| 5 | 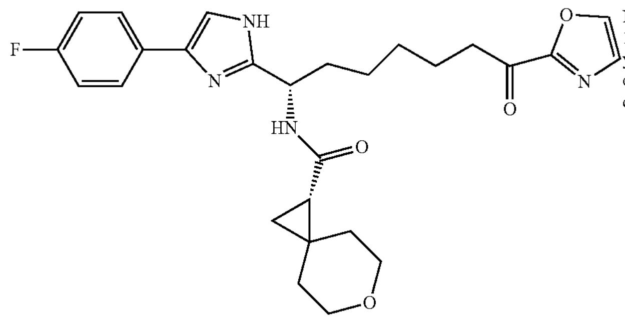 [SMILES: O=C(CCCCC[C@H](NC(=O)[C@H]1CC12CCOCC2)c1nc(-c2ccc(F)cc2)c[nH]1)c1ncco1] | N-((S)-1-(4-(4-fluorophenyl)-1H-imidazol-2-yl)-7-(oxazol-2-yl)-7-oxoheptyl)-6-oxaspiro[2.5]octane-1-carboxamide | 495.0 | 1.45 |
| 6 | 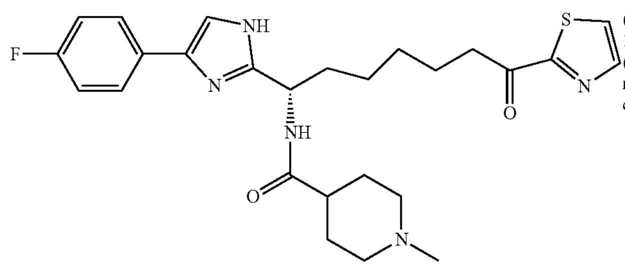 [SMILES: CN1CCC(C(=O)N[C@@H](CCCCCC(=O)c2nccs2)c2nc(-c3ccc(F)cc3)c[nH]2)CC1] | (S)-N-(1-(4-(4-fluorophenyl)-1H-imidazol-2-yl)-7-oxo-7-(thiazol-2-yl)heptyl)-1-methylpiperidine-4-carboxamide | 498.2 | 2.36 |
| 7 | 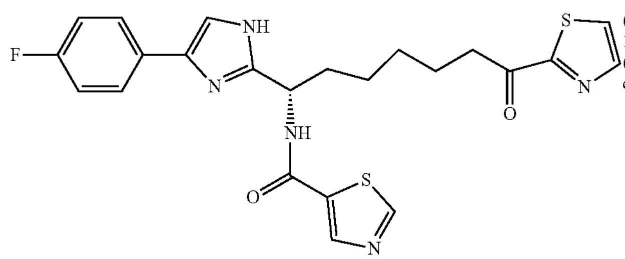 [SMILES: O=C(N[C@@H](CCCCCC(=O)c1nccs1)c1nc(-c2ccc(F)cc2)c[nH]1)c1cncs1] | (S)-N-(1-(4-(4-fluorophenyl)-1H-imidazol-2-yl)-7-oxo-7-(thiazol-2-yl)heptyl)thiazole-5-carboxamide | 483.9 | 1.25 |
| 8 | 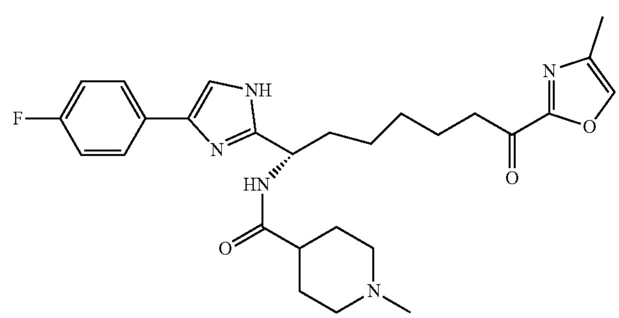 [SMILES: Cc1coc(C(=O)CCCCC[C@H](NC(=O)C2CCN(C)CC2)c2nc(-c3ccc(F)cc3)c[nH]2)n1] | (S)-N-(1-(4-(4-fluorophenyl)-1H-imidazol-2-yl)-7-(4-methyloxazol-2-yl)-7-oxoheptyl)-1-methylpiperidine-4-carboxamide | 496.4 | 1.17 |

((S)-7-amino-7-(4-(2-methylquinolin-6-yl)-1H-imidazol-2-yl)-1-(oxazol-2-yl)heptan-1-one

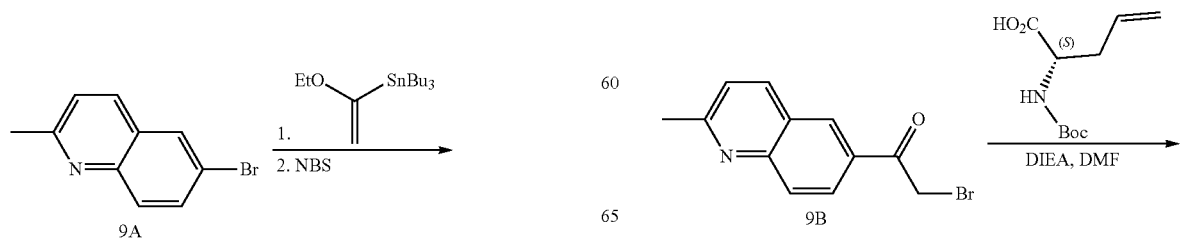

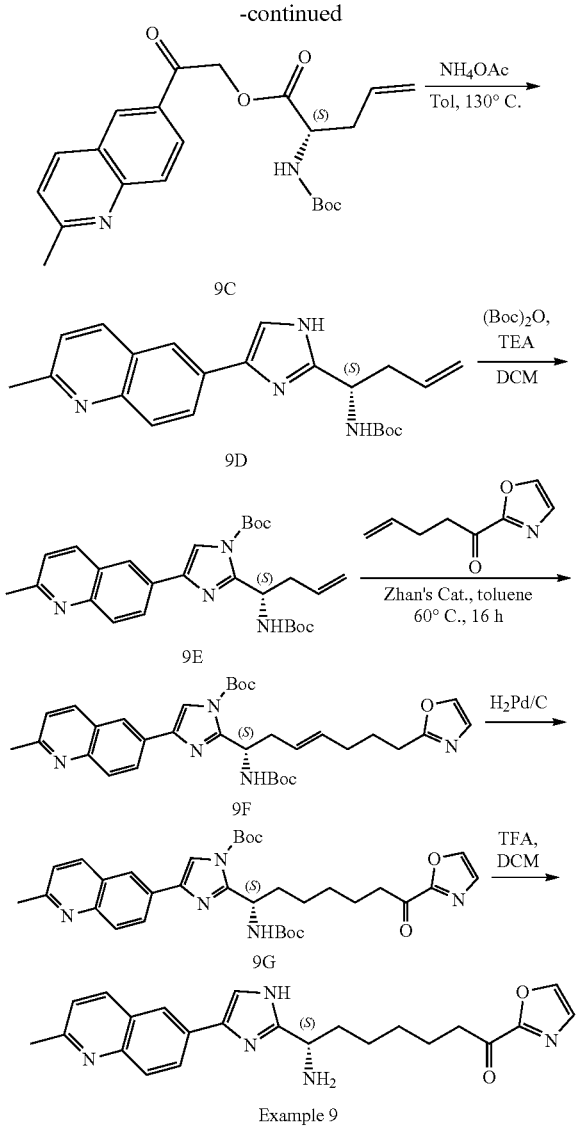

Example 9

Step 1: Preparation of 2-bromo-1-(2-methylquinolin-6-yl)ethanone (9B)

A mixture of 6-bromo-2-methylquinoline (9A, 2 g, 9.01 mmol), tributyl(1-ethoxyvinyl)stannane (5.41 g, 14.98 mmol) and Pd(PPh$_3$)$_2$Cl$_2$ (0.316 g, 0.450 mmol) in toluene (20 mL) was degassed and backfilled with N$_2$ three times. The mixture was heated at 60° C. for 12 h. The mixture was cooled and filtered, and the filter cake was washed with ethyl acetate (50 mL). The filtrate was concentrated to dryness. The crude product was purified by silica gel column flash chromatography (ISCO®; 4 g SepaFlash® Silica Flash Column, Eluent of 0~20% EtOAc/Petro.Ether gradient @40 mL/min) to give 6-(1-ethoxyvinyl)-2-methylquinoline.

NBS (701 mg, 3.94 mmol) was added to a stirred solution of 6-(1-ethoxyvinyl)-2-methylquinoline (700 mg, 3.28 mmol) in THF (10 mL) at rt and the mixture was stirred at room temperature for 30 min. To the mixture water (30 mL) was added, and the mixture was extracted with ethyl acetate (2×20 mL). The combined organic fractions were washed with brine (saturated, 10 mL), dried (Na$_2$SO$_4$), filtered and the solvent was evaporated under reduced pressure to give 2-bromo-1-(2-methylquinolin-6-yl)ethanone (9B) which was used in next step without purification. LCMS (ESI) calc'd for C$_{12}$H$_{10}$BrNO [M+H]$^+$: 264.0, 266.0, found: 263.9, 265.9.

Step 2: Preparation of (S)-2-(2-methylquinolin-6-yl)-2-oxoethyl 2-((tert-butoxycarbonyl)amino)pent-4-enoate (9C)

DIEA (1 mL, 5.73 mmol) was added to a stirred solution of (S)-2-((tert-butoxycarbonyl)amino)pent-4-enoic acid (570 mg, 2.65 mmol) and 2-bromo-1-(2-methylquinolin-6-yl)ethanone (9B, 700 mg, 2.65 mmol) in DMF (2 mL) at rt and the mixture was stirred at rt for 10 h. Water (20 mL) was added to the reaction and the mixture was extracted with ethyl acetate (10×2 mL). The combined organic fractions were washed with brine (saturated, 10 mL), dried (Na$_2$SO$_4$), filtered and the solvent was evaporated under reduced pressure. The crude product was purified by silica gel column flash chromatography (ISCO®; 4 g SepaFlash® Silica Flash Column, Eluent of 0-70% EtOAc/Petro.Ether gradient @40 mL/min) to give (S)-2-(2-methylquinolin-6-yl)-2-oxoethyl 2-((tert-butoxycarbonyl)amino)pent-4-enoate (9C). LCMS (ESI) calc'd for 15$_2$H$_{26}$N$_2$O$_5$ [M+H]$^+$: 399.2, found: 399.1

Step 3: Preparation of (S)-tert-butyl (1-(4-(2-methylquinolin-6-yl)-1H-imidazol-2-yl)but-3-en-1-yl)carbamate (9D)

NH$_4$OAc (1.935 g, 25.10 mmol) was added to a stirred mixture of (S)-2-(2-methylquinolin-6-yl)-2-oxoethyl 2-((tert-butoxycarbonyl)amino)pent-4-enoate (9C, 1 g, 2.510 mmol) in toluene (20 mL) at rt and the mixture was stirred at rt for 12 h. The mixture was washed with water (20 mL) and extracted with EtOAc (20×3 mL). The combined organic fractions were washed with brine (saturated, 20 mL), dried (Na$_2$SO$_4$), filtered and the solvent was evaporated under reduced pressure. The filtrate was concentrated to dryness. The crude product was purified by silica gel column flash chromatography (ISCO®; 12 g SepaFlash® Silica Flash Column, Eluent of 0~70% EtOAc/Petro.Ether gradient @40 mL/min) to give (S)-tert-butyl (1-(4-(2-methylquinolin-6-yl)-1H-imidazol-2-yl)but-3-en-1-yl)carbamate (9D). LCMS (ESI) calc'd for 15$_2$H$_{26}$N$_4$O$_2$ [M+H]$^+$: 379.2, found: 379.1

Step 4: Preparation of (S)-tert-butyl 2-(1-((tert-butoxycarbonyl)amino)but-3-en-1-yl)-4-(2-methylquinolin-6-yl)-1H-imidazole-1-carboxylate (9E)

DMAP (16 mg, 0.131 mmol) was added to a stirred mixture of Bo15O (0.4 mL, 1.723 mmol) and (S)-tert-butyl (1-(4-(2-methylquinolin-6-yl)-1H-imidazol-2-yl)but-3-en-1-yl)carbamate (9D, 500 mg, 1.321 mmol) in DCM (10 mL) at rt and the mixture was stirred at rt for 2 h. The mixture was concentrated to dryness. The crude product was purified by silica gel column flash chromatography (ISCO®; 12 g SepaFlash® Silica Flash Column, Eluent of 0~70% EtOAc/Petro.Ether gradient @40 mL/min) to give (S)-tert-butyl 2-(1-((tert-butoxycarbonyl)amino)but-3-en-1-yl)-4-(2-methylquinolin-6-yl)-1H-imidazole-1-carboxylate (9E). LCMS (ESI) calc'd for 15$_7$H$_{34}$N$_4$O$_4$ [M+H]$^+$: 479.3, found: 479.3

Step 5: Preparation of (S,E)-tert-butyl (1-(4-(2-methylquinolin-6-yl)-1H-imidazol-2-yl)-7-(oxazol-2-yl)-7-oxohept-3-en-1-yl)carbamate (9F)

A mixture of 1-(oxazol-2-yl)pent-4-en-1-one (1, 120 mg, 0.794 mmol), (S)-tert-butyl 2-(1-(((tert-butoxycarbonyl)

amino)but-3-en-1-yl)-4-(2-methylquinolin-6-yl)-1H-imidazole-1-carboxylate (9E, 380 mg, 0.794 mmol) and Zhan's catalyst (14 mg, 0.019 mmol) in toluene (5 mL) was degassed and backfilled with $N_2$ three times. The mixture was heated at 60° C. for 12 h. The mixture was concentrated to dryness. The residue was purified by preparative HPLC (reverse phase C-18 column), eluting with acetonitrile/water+0.1% TFA, to give (S,E)-tert-butyl (1-(4-(2-methylquinolin-6-yl)-1H-imidazol-2-yl)-7-(oxazol-2-yl)-7-oxohept-3-en-1-yl)carbamate (9F). LCMS (ESI) calc'd for $15_8H_{31}N_5O_4$ [M+H]$^+$: 502.2, found: 502.0

Step 6: Preparation of (S)-tert-butyl (1-(4-(2-methylquinolin-6-yl)-1H-imidazol-2-yl)-7-(oxazol-2-yl)-7-oxoheptyl)carbamate (9G)

A solution of (S,E)-tert-butyl (1-(4-(2-methylquinolin-6-yl)-1H-imidazol-2-yl)-7-(oxazol-2-yl)-7-oxohept-3-en-1-yl) carbamate (9F, 140 mg, 0.279 mmol) in MeOH (5 mL) was added to a 100 mL flask and then Pd/C (30 mg, 0.028 mmol) (10%, wet) was added under Ar. The suspension was degassed under vacuum and purged with $N_2$ several times. The mixture was then stirred under $H_2$ (1 atm) at 20° C. for 2 h. The mixture was filtered and the filter cake was washed with MeOH (5 mL×3). The filtrate was concentrated to give (S)-tert-butyl (1-(4-(2-methylquinolin-6-yl)-1H-imidazol-2-yl)-7-(oxazol-2-yl)-7-oxoheptyl)carbamate (9G) which was used to the next step without further purification. LCMS (ESI) calc'd for $15_8H_{33}N_5O_4$ [M+H]$^+$: 504.2, found: 504.1

Step 7: Preparation of (S)-7-amino-7-(4-(2-methylquinolin-6-yl)-1H-imidazol-2-yl)-1-(oxazol-2-yl) heptan-1-one (9)

TFA (1 mL, 12.98 mmol) was added to a stirred mixture of (S)-tert-butyl 2-(1-((tert-butoxycarbonyl)amino)-7-(oxazol-2-yl)-7-oxoheptyl)-4-(2-methylquinolin-6-yl)-1H-imidazole-1-carboxylate (9G, 100 mg, 0.166 mmol) in DCM (1 mL) at rt and the mixture was stirred at room temperature for 2 h. The mixture was concentrated and the residue was purified by preparative HPLC (reverse phase C-18 column), eluting with acetonitrile/water+0.1% TFA, and the solution was concentrated and adjusted to pH=8 with $Na_2CO_3$ (sat.). The solution was extracted with DCM (10 mL×3) and concentrated to give (S)-7-amino-7-(4-(2-methylquinolin-6-yl)-1H-imidazol-2-yl)-1-(oxazol-2-yl)heptan-1-one (9). The solid was dissolved in water and HCl (0.2 mL, 1 M) was added. The solution was lyophilized to give the HCl salt. LCMS (ESI) calc'd for $C_{23}H_{25}N_5O_2$ [M+H]$^+$: 404.2, found: 404.2. $^1$H NMR (400 MHz, MeOD) δ 9.00-9.08 (m, 1H), 8.69-8.76 (m, 1H), 8.58-8.62 (m, 1H), 8.16-8.28 (m, 1H), 8.05-8.14 (m, 2H), 7.93-8.00 (m, 1H), 7.33-7.41 (m, 1H), 2.96-3.14 (m, 8H), 1.66-1.82 (m, 3H), 1.31-1.57 (m, 5H).

Example 10

(S)-6-(2-(1-amino-7-(oxazol-2-yl)-7-oxoheptyl)-1H-imidazol-4-yl)-2-ethylisoquinolin-1(2H)-one

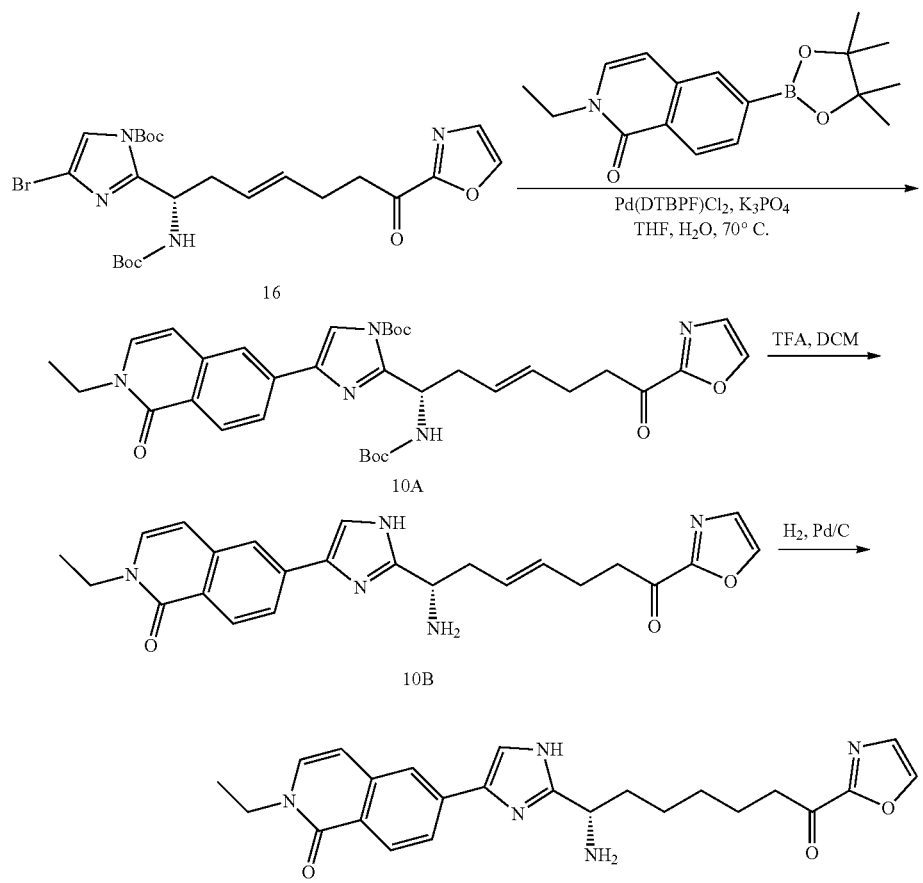

Example 10

Step 1: Preparation of (S,E)-tert-butyl 2-(1-((tert-butoxycarbonyl)amino)-7-(oxazol-2-yl)-7-oxohept-3-en-1-yl)-4-(2-ethyl-1-oxo-1,2-dihydroisoquinolin-6-yl)-1H-imidazole-1-carboxylate (10A)

PdCl$_2$(DTBPF) (18 mg, 0.028 mmol) was added to a stirred mixture of (S,E)-tert-butyl-4-bromo-2-(1-((tert-butoxycarbonyl)amino)-7-(oxazol-2-yl)-7-oxohept-3-en-1-yl)-1H-imidazole-1-carboxylate (16, 150 mg, 0.278 mmol), 2-ethyl-6-(4,4,5,5-tetramethyl-1,3,2-dioxaborolan-2-yl)isoquinolin-1(2H)-one (56 mg, 0.187 mmol) and K$_3$PO$_4$ (177 mg, 0.834 mmol) in THF (2 ml) and water (0.5 ml) at room temperature and the mixture was heated with stirring at 70° C. for 16 h. The mixture was cooled to room temperature, water (2 mL) was added and the mixture was extracted with ethyl acetate (3×5 mL). The combined organic fractions were washed with brine (saturated, 1×5 mL), dried (Na$_2$SO$_4$), filtered and the solvent was evaporated under reduced pressure. The residue was purified by silica gel flash chromatography (ISCORF75; Sepa flash column), eluting with petroleum ether/EtOAc=100/0~1/2 to give (S,E)-tert-butyl 2-(1-((tert-butoxycarbonyl)amino)-7-(oxazol-2-yl)-7-oxohept-3-en-1-yl)-4-(2-ethyl-1-oxo-1,2-dihydroisoquinolin-6-yl)-1H-imidazole-1-carboxylate (10A). LCMS (ESI) calc'd for C$_{34}$H$_{41}$N$_5$O$_7$ [M+H]$^+$: 632.3, found: 632.4

Step 2: Preparation of (S,E)-6-(2-(1-amino-7-(oxazol-2-yl)-7-oxohept-3-en-1-yl)-1H-imidazol-4-yl)-2-ethylisoquinolin-1(2H)-one (10B)

TFA (0.6 ml, 0.095 mmol) was added to a stirred mixture of (S,E)-tert-butyl-2-(1-((tert-butoxycarbonyl)amino)-7-(oxazol-2-yl)-7-oxohept-3-en-1-yl)-4-(2-ethyl-1-oxo-1,2-dihydroisoquinolin-6-yl)-1H-imidazole-1-carboxylate (4A, 60 mg, 0.095 mmol) in DCM (6 ml) at rt and the mixture was stirred at room temperature for 2 h. All the volatiles were removed by evaporator to give (S,E)-6-(2-(1-amino-7-(oxazol-2-yl)-7-oxohept-3-en-1-yl)-1H-imidazol-4-yl)-2-ethylisoquinolin-1(2H)-one (4B) which was used directly for hydrogenation. A pure batch was purified by preparative HPLC (reverse phase C-18 column), eluting with acetonitrile/water+0.1% TFA, to give (S,E)-6-(2-(1-amino-7-(oxazol-2-yl)-7-oxohept-3-en-1-yl)-1H-imidazol-4-yl)-2-ethylisoquinolin-1(2H)-one as a white solid. LCMS (ESI) calc'd for 15$_4$H$_{25}$N$_5$O$_3$ [M+H]$^+$: 432.2, found: 432.2. $^1$H NMR (400 MHz, MeOD) δ 8.22-8.33 (m, 1H), 7.85-8.05 (m, 3H), 7.69-7.76 (m, 1H), 7.32-7.44 (m, 2H), 6.66-6.75 (m, 1H), 5.59-5.75 (m, 1H), 5.36-5.52 (m, 1H), 4.47-4.58 (m, 1H), 4.04-4.16 (m, 2H), 2.97-3.13 (m, 2H), 2.72-2.88 (m, 2H), 2.37-2.46 (m, 2H), 1.36 (t, J=8.0 Hz, 3H).

Step 3: Preparation of (S)-6-(2-(1-amino-7-(oxazol-2-yl)-7-oxoheptyl)-1H-imidazol-4-yl)-2-ethylisoquinolin-1(2H)-one (Example 10)

A solution of (S,E)-6-(2-(1-amino-7-(oxazol-2-yl)-7-oxohept-3-en-1-yl)-1H-imidazol-4-yl)-2-ethylisoquinolin-1 (2H)-one (35 mg, 0.081 mmol) in MeOH (2 ml) was added to a flask and then Pd—C (20 mg, 0.019 mmol) (10%, wet) was added under Ar. The suspension was degassed under vacuum and purged with N$_2$ several times. The mixture was then stirred under H$_2$ (Pressure: 15 psi) at rt for 4 h. It was filtered on Celite then the filter cake was washed with methanol (3×5 mL). The filtrate was concentrated under reduced pressure. The residue was purified by preparative HPLC (reverse phase C-18 column), eluting with acetonitrile/water+0.05% NH$_3$·H$_2$O, to give (S)-6-(2-(1-amino-7-(oxazol-2-yl)-7-oxoheptyl)-1H-imidazol-4-yl)-2-ethylisoquinolin-1(2H)-one (Example 10). LCMS (ESI) calc'd for C$_{24}$H$_{27}$N$_5$O$_3$ [M+H]$^+$: 434.2, found: 434.2

L-(+)-tartaric acid (7 mg, 0.047 mmol) was added to a stirred mixture of (S)-6-(2-(1-amino-7-(oxazol-2-yl)-7-oxoheptyl)-1H-imidazol-4-yl)-2-ethylisoquinolin-1(2H)-one (4, 15 mg, 0.035 mmol) in acetonitrile (1 ml) and water (1 ml) at rt and the mixture was lyophylized to give (S)-6-(2-(1-amino-7-(oxazol-2-yl)-7-oxoheptyl)-1H-imidazol-4-yl)-2-ethylisoquinolin-1(2H)-one (2R,3R)-2,3-dihydroxysuccinate (4). $^1$H NMR (400 MHz, MeOD) δ 8.25-8.31 (m, 1H), 8.05-8.09 (m, 1H), 7.98-8.04 (m, 1H), 7.89-7.95 (m, 1H), 7.68-7.73 (m, 1H), 7.35-7.40 (m, 2H), 6.66-6.79 (m, 1H), 4.52 (s, 2H), 4.09 (d, J=7.3 Hz, 2H), 3.03 (s, 2H), 2.14-2.27 (m, 1H), 2.01-2.13 (m, 1H), 1.64-1.77 (m, 2H), 1.28-1.47 (m, 8H).

The following compounds were prepared using similar procedures to those described above via Suzuki coupling from intermediate 16 and commercially available reagents or intermediates:

| Example # | Structure | Exact Mass [M + H]$^+$ | Observed [M + H]$^+$ |
|---|---|---|---|
| 11 | 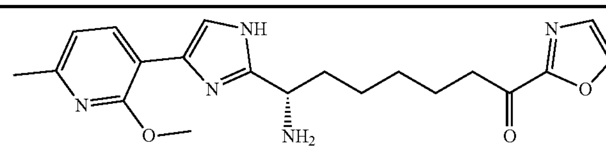 | Calc'd 384.2, | found 384.1 |
| 12 | 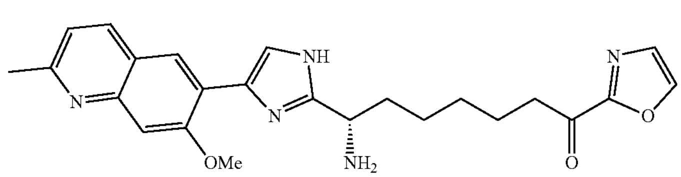 [SMILES: COc1cc2nc(C)ccc2cc1-c1c[nH]c([C@@H](N)CCCCCC(=O)c2ncco2)n1] | Calc'd 434.2, | found 434.0 |
| 13 | 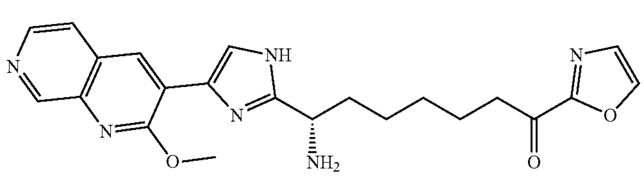 [SMILES: COc1nc2cnccc2cc1-c1c[nH]c([C@@H](N)CCCCCC(=O)c2ncco2)n1] | Calc'd 421.2, | found 421.1 |

-continued
| Example # | Structure | Exact Mass [M + H]+ | Observed [M + H]+ |
|---|---|---|---|
| 14 | 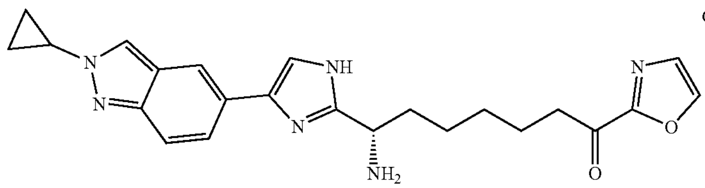 [SMILES: N[C@@H](CCCCCC(=O)c1ncco1)c1nc(-c2ccc3nn(C4CC4)cc3c2)c[nH]1] | Calc'd 419.2, | found 419.1 |
| 15 | 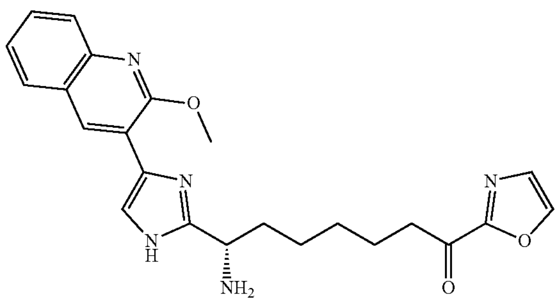 [SMILES: COc1nc2ccccc2cc1-c1c[nH]c([C@@H](N)CCCCCC(=O)c2ncco2)n1] | Calc'd 420.2, | Found 420.1 |
Example 16
(S)-7-amino-1-(oxazol-2-yl)-7-(5-(quinolin-6-yl)-1H-imidazol-2-yl)heptan-1-one
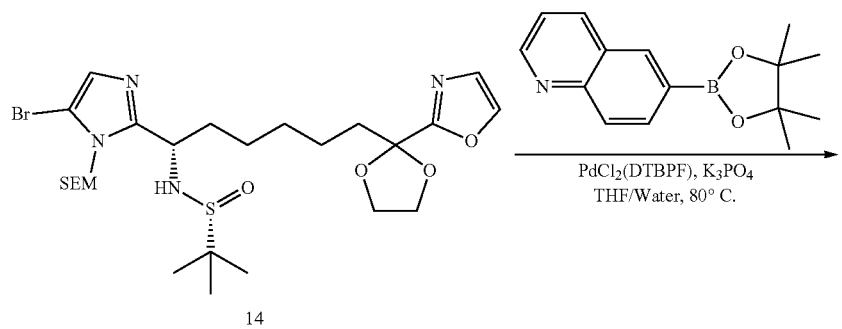
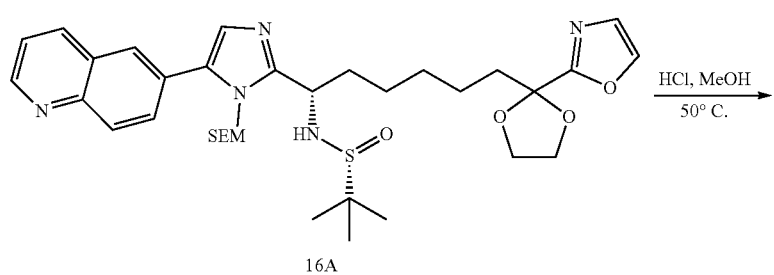
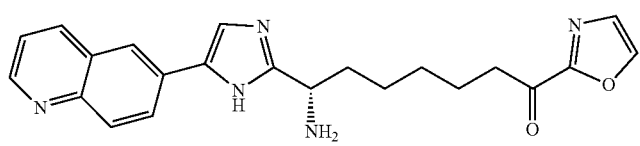
Example 16

Step 1: Preparation of (R)-2-methyl-N-((S)-6-(2-(oxazol-2-yl)-1,3-dioxolan-2-yl)-1-(5-(quinolin-6-yl)-1-((2-(trimethylsilyl)ethoxy)methyl)-1H-imidazol-2-yl)hexyl)propane-2-sulfinamide (16A)

PdCl₂(DTBPF) (15 mg, 0.023 mmol) was added to a mixture of (R)-N-((S)-1-(5-bromo-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (14, 132 mg, 0.213 mmol), K₃PO₄ (142 mg, 0.669 mmol) and 6-(4,4,5,5-tetramethyl-1,3,2-dioxaborolan-2-yl)quinoline (67 mg, 0.263 mmol) in co-solvents of THF (2 ml) and water (0.2 ml) at rt and the mixture was stirred at 80° C. for 5 h. The mixture was diluted with water (10 mL), and extracted with ethyl acetate (3×10 mL). The combined organic fractions were washed with brine (saturated, 8 mL), dried (Na₂SO₄), filtered and the solvent was evaporated under reduced pressure. The residue was purified by preparative TLC on silica gel, eluting with EtOAc to give (R)-2-methyl-N-((S)-6-(2-(oxazol-2-yl)-1,3-dioxolan-2-yl)-1-(5-(quinolin-6-yl)-1-((2-(trimethylsilyl)ethoxy)methyl)-1H-imidazol-2-yl)hexyl)propane-2-sulfinamide (16A). LCMS (ESI) calc'd for C₃₄H₄₉N₅O₅SSi [M+H]⁺: 668.9, found: 668.5

Step 2: Preparation of (S)-7-amino-1-(oxazol-2-yl)-7-(5-(quinolin-6-yl)-1H-imidazol-2-yl)heptan-1-one (Example 16)

HCl (0.014 ml, 0.172 mmol) was added to a stirred mixture of (R)-2-methyl-N-((S)-6-(2-(oxazol-2-yl)-1,3-dioxolan-2-yl)-1-(5-(quinolin-6-yl)-1-((2-(trimethylsilyl)ethoxy)methyl)-1H-imidazol-2-yl)hexyl)propane-2-sulfinamide (16A, 115 mg, 0.172 mmol) in co-solvents of MeOH (2 ml) and water (0.2 ml) at 50° C. and the mixture was stirred at 50° C. for 16 h. The solvent was evaporated under reduced pressure. The residue was purified by preparative HPLC (reverse phase C-18 column), eluting with acetonitrile/water+0.1% TFA, to give a TFA salt of (S)-7-amino-1-(oxazol-2-yl)-7-(5-(quinolin-6-yl)-1H-imidazol-2-yl)heptan-1-one. The TFA salt was neutralized with aqueous Na₂CO₃ (saturated, 20 mL), and extracted with DCM (3×15 mL). The combined organic fractions were washed with brine (saturated, 10 mL), dried (Na₂SO₄), filtered and the solvent was evaporated under reduced pressure to give (S)-7-amino-1-(oxazol-2-yl)-7-(5-(quinolin-6-yl)-1H-imidazol-2-yl)heptan-1-one (6). LCMS (ESI) calc'd for C₂₂H₂₃N₅O₂ [M+H]⁺: 390.4, found: 390.2.

L-tartaric acid (17 mg, 0.113 mmol) was added to (S)-7-amino-1-(oxazol-2-yl)-7-(5-(quinolin-6-yl)-1H-imidazol-2-yl)heptan-1-one (6, 45 mg, 0.116 mmol) in co-solvents of acetonitrile (5 ml) and water (30 ml) at rt and the mixture was stirred at rt for 20 mins. The mixture was lyophilized to give (S)-7-amino-1-(oxazol-2-yl)-7-(5-(quinolin-6-yl)-1H-imidazol-2-yl)heptan-1-one 2,3-dihydroxysuccinate (Example 16). ¹H NMR (400 MHz, D₂O) δ 8.72 (d, J=5.07 Hz, 1H), 8.62 (d, J=8.16 Hz, 1H), 8.01-8.10 (m, 2H), 7.88 (d, J=8.82 Hz, 1H), 7.66 (dd, J=8.38, 5.29 Hz, 1H), 7.61 (s, 1H), 7.51 (s, 1H), 6.96 (s, 1H), 4.36-4.45 (m, 1H), 4.23 (s, 2H), 2.60-2.80 (m, 2H), 1.89-2.06 (m, 2H), 1.44 (t, J=6.84 Hz, 2H), 0.97-1.29 (m, 5H).

The following compounds were prepared using similar procedures to those described above via Suzuki coupling from intermediate 16 and commercially available reagents or intermediates:

| Example # | Structure | Exact Mass [M + H]⁺ | Observed [M + H]⁺ |
|---|---|---|---|
| 17 | 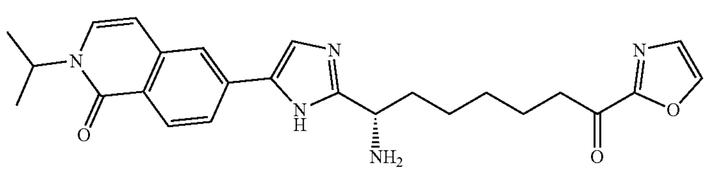 [SMILES: CC(C)n1ccc2cc(-c3cnc([C@@H](N)CCCCCC(=O)c4ncco4)[nH]3)ccc2c1=O] | Calc'd 448.2, found | 448.2 |
| 18 | 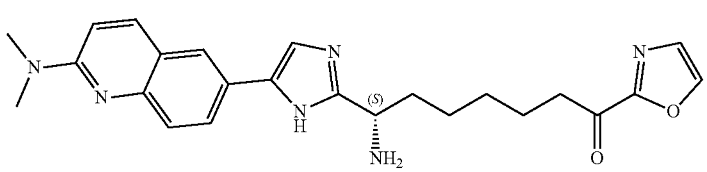 | Calc'd 433.2, found | 433.1 |
| 19 | 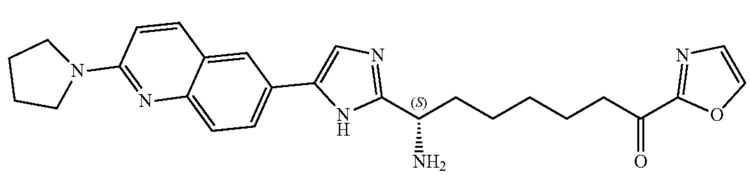 | Calc'd 459.2, found | 459.1 |
| 20 | 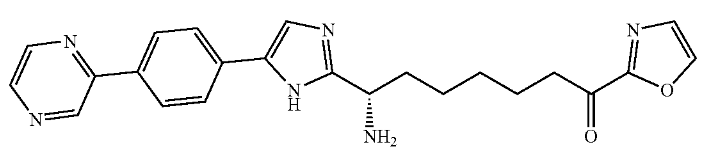 [SMILES: N[C@@H](CCCCCC(=O)c1ncco1)c1ncc(-c2ccc(-c3cnccn3)cc2)[nH]1] | Calc'd 417.2, found | 417.0 |

| Example # | Structure | Exact Mass [M + H]+ | Observed [M + H]+ |
|---|---|---|---|
| 21 | 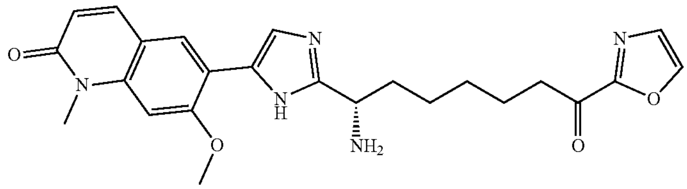 [SMILES: COc1cc2c(ccc(=O)n2C)cc1-c1cnc([C@@H](N)CCCCCC(=O)c2ncco2)[nH]1] | Calc'd 450.2, found | 450.0 |
| 22 | 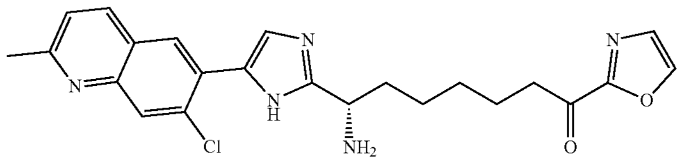 [SMILES: Cc1ccc2cc(-c3cnc([C@@H](N)CCCCCC(=O)c4ncco4)[nH]3)c(Cl)cc2n1] | Calc'd 438.2, found | 438.0 |

Example 23

(S)-7-amino-7-(4-(7-methoxyquinolin-6-yl)-1H-imidazol-2-yl)-1-(oxazol-2-yl)heptan-1-one

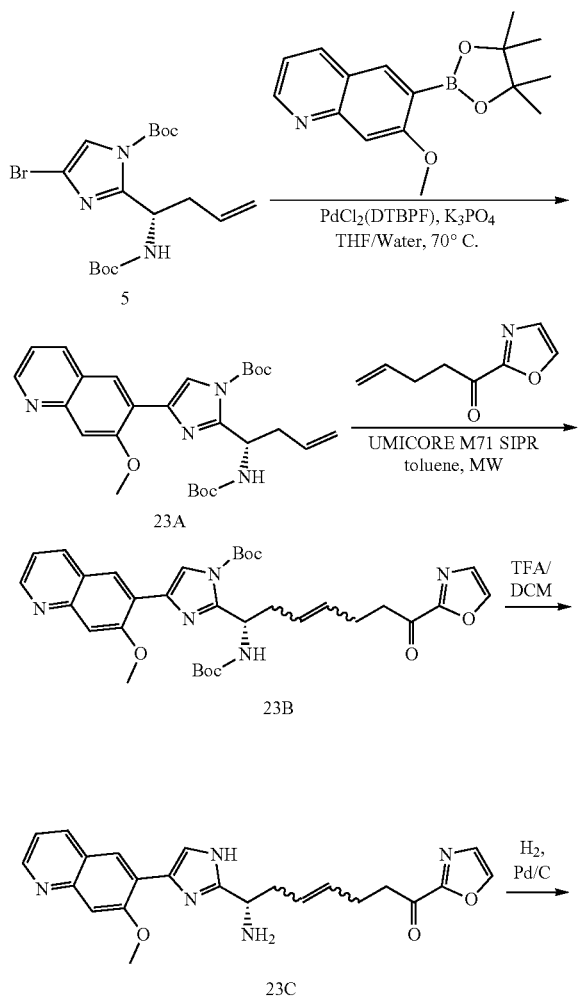

Example 23

Step 1: Preparation of (S)-tert-butyl 2-(1-((tert-butoxycarbonyl)amino)but-3-en-1-yl)-4-(7-methoxyquinolin-6-yl)-1H-imidazole-1-carboxylate (23A)

PdCl$_2$(DTBPF) (100 mg, 0.153 mmol) was added to a mixture of (S)-tert-butyl 4-bromo-2-(1-((tert-butoxycarbonyl)amino)but-3-en-1-yl)-1H-imidazole-1-carboxylate (5, 1 g, 2.402 mmol), 7-methoxy-6-(4,4,5,5-tetramethyl-1,3,2-dioxaborolan-2-yl)quinoline (1.020 g, 3.58 mmol) and K$_3$PO$_4$ (1.56 g, 7.35 mmol) in co-solvents of THF (20 ml) and water (2 ml) at rt and the mixture was stirred at 80° C. for 3.5 h. The mixture was cooled to rt, diluted with water (20 mL), extracted with DCM (3×20 mL). The combined organic fractions were washed with brine (15 mL), dried (Na$_2$SO$_4$), filtered and the solvent was evaporated under reduced pressure. The residue was purified by silica gel column flash chromatography, eluting with petroleum ether/EtOAc=0-50% to give (S)-tert-butyl 2-(1-((tert-butoxycarbonyl)amino)but-3-en-1-yl)-4-(7-methoxyquinolin-6-yl)-1H-imidazole-1-carboxylate (23A). LCMS (ESI) calc'd for C$_{27}$H$_{34}$N$_4$O$_5$ [M+Na]$^+$: 495.3, found: 517.0 (M+Na$^+$). $^1$H NMR (400 MHz, CDCl$_3$) δ 8.81 (d, J=3.09 Hz, 1H), 8.60-8.67 (m, 1H), 8.20 (d, J=7.50 Hz, 1H), 7.98 (s, 1H), 7.50 (s, 1H), 7.30 (dd, J=7.94, 4.41 Hz, 1H), 5.76-5.87 (m, 2H), 5.61 (d, J=6.17 Hz, 1H), 5.05-5.13 (m, 2H), 4.08-4.12 (m, 3H), 2.68-2.80 (m, 1H), 2.48-2.59 (m, 1H), 1.68 (s, 8H), 1.43-1.53 (m, 8H).

Step 2: Preparation of (S)-tert-butyl 2-(1-((tert-butoxycarbonyl)amino)-7-(oxazol-2-yl)-7-oxohept-3-en-1-yl)-4-(7-methoxyquinolin-6-yl)-1H-imidazole-1-carboxylate (23B) UMICORE M71 SIPR (11 mg, 0.013 mmol) was added to a mixture of (S)-tert-butyl 2-(1-((tert-butoxycarbonyl)amino)but-3-en- 1-yl)-4-(7-methoxyquinolin-6-yl)-1H-imidazole-1-carboxylate (5A, 97 mg, 0.196 mmol) and 1-(oxazol-2-yl)pent-4-en-1-one (5, 112 mg, 0.741 mmol) in toluene (1 ml) which was bubbled with $N_2$ for 10 mins at rt. The mixture was degassed and backfilled with $N_2$ three times and stirred at 100° C. for 60 min under microwave. The residue was purified by preparative TLC on silica gel, eluting with DCM/MeOH=20:1 to give (S)-tert-butyl 2-(1-((tert-butoxycarbonyl)amino)-7-(oxazol-2-yl)-7-oxohept-3-en-1-yl)-4-(7-methoxyquinolin-6-yl)-1H-imidazole-1-carboxylate (23B). LCMS (ESI) calc'd for $C_{23}H_{39}N_5O_7$ [M+H]$^+$: 618.3, found: 618.3

Step 3: Preparation of (S)-7-amino-7-(4-(7-methoxyquinolin-6-yl)-1H-imidazol-2-yl)-1-(oxazol-2-yl)hept-4-en-1-one (23C)

TFA (0.5 ml, 6.49 mmol) was added to a stirred mixture of (S)-tert-butyl 2-(1-((tert-butoxycarbonyl)amino)-7-(oxazol-2-yl)-7-oxohept-3-en-1-yl)-4-(7-methoxyquinolin-6-yl)-1H-imidazole-1-carboxylate (23B, 32 mg, 0.052 mmol) in DCM (5 ml) at rt and the mixture was stirred at rt for 2 h. The solvent was evaporated under reduced pressure. Half of the residue was purified by preparative HPLC (reverse phase C-18 column), eluting with acetonitrile/water+0.1% TFA, to give (S)-7-amino-7-(4-(7-methoxyquinolin-6-yl)-1H-imidazol-2-yl)-1-(oxazol-2-yl)hept-4-en-1-one (23C). LCMS (ESI) calc'd for $C_{23}H_{23}N_5O_3$ [M+H]$^+$: 418.2, found: 418.2. $^1$H NMR (400 MHz, MeOD) δ 8.95-9.06 (m, 1H), 8.95 (s, 1H), 8.87-9.07 (m, 1H), 8.90 (brs, 1H), 8.87-8.88 (m, 1H), 8.68-8.77 (m, 1H), 8.03-8.08 (m, 1H), 8.06 (s, 1H), 7.92-7.96 (m, 1H), 7.91-7.92 (m, 1H), 7.83-7.92 (m, 1H), 7.61-7.66 (m, 1H), 7.60-7.66 (m, 1H), 7.63 (s, 1H), 7.56-7.56 (m, 1H), 7.54 (brs, 1H), 7.32-7.36 (m, 1H), 7.32-7.37 (m, 1H), 7.32-7.37 (m, 1H), 7.35 (s, 1H), 7.28-7.28 (m, 1H), 7.26 (brs, 1H), 5.70 (d, J=6.61 Hz, 1H), 5.34-5.53 (m, 1H), 4.84 (brs, 1H), 4.54 (d, J=6.84 Hz, 1H), 4.17-4.18 (m, 1H), 4.14-4.31 (m, 1H), 3.31 (brs, 7H), 3.09 (t, J=6.62 Hz, 2H), 2.62-2.88 (m, 2H), 2.28-2.52 (m, 2H).

Step 5: Preparation of (S)-7-amino-7-(4-(7-methoxyquinolin-6-yl)-1H-imidazol-2-yl)-1-(oxazol-2-yl)heptan-1-one (23)

Pd—C (10%, 40 mg, 0.038 mmol) was added to a stirred mixture of (S)-7-amino-7-(4-(7-methoxyquinolin-6-yl)-1H-imidazol-2-yl)-1-(oxazol-2-yl)hept-4-en-1-one (23C, 30 mg, 0.072 mmol) in MeOH (10 ml) at rt and the mixture was stirred at rt for 4 h under a $H_2$ balloon.

The mixture was filtered and the filter cake was washed with MeOH (20 mL). The filtrate was concentrated to dryness. The residue was purified by preparative HPLC (reverse phase C-18 column), eluting with acetonitrile/water+0.05% $NH_3·H_2O$, to give (S)-7-amino-7-(4-(7-methoxyquinolin-6-yl)-1H-imidazol-2-yl)-1-(oxazol-2-yl)heptan-1-one (5). LCMS (ESI) calc'd for $C_{23}H_{25}N_5O_3$ [M+H]$^+$: 420.2, found: 420.0

L-tartaric acid (6 mg, 0.040 mmol) was added to (S)-7-amino-7-(4-(7-methoxyquinolin-6-yl)-1H-imidazol-2-yl)-1-(oxazol-2-yl)heptan-1-one (23, 15 mg, 0.036 mmol) in co-solvents of acetonitrile (5 ml) and water (30 ml) and the mixture was stirred at rt for 20 mins. The mixture was lyophilized to give (S)-7-amino-7-(4-(7-methoxyquinolin-6-yl)-1H-imidazol-2-yl)-1-(oxazol-2-yl)heptan-1-one 2,3-dihydroxysuccinate (23). $^1$H NMR (400 MHz, $D_2O$) δ 8.64-8.76 (m, 2H), 8.28 (s, 1H), 7.61-7.68 (m, 3H), 7.28 (s, 1H), 6.99 (s, 1H), 4.43-4.50 (m, 2H), 4.38 (s, 6H), 3.94 (s, 3H), 2.60-2.78 (m, 2H), 1.91-2.08 (m, 2H), 1.44 (brs, 2H), 1.18-1.31 (m, 1H), 1.09 (brs, 3H).

Example 24

(S)-7-amino-7-(4-(6-cyclopropyl-2-methoxypyridin-3-yl)-1H-imidazol-2-yl)-1-(oxazol-2-yl)heptan-1-one

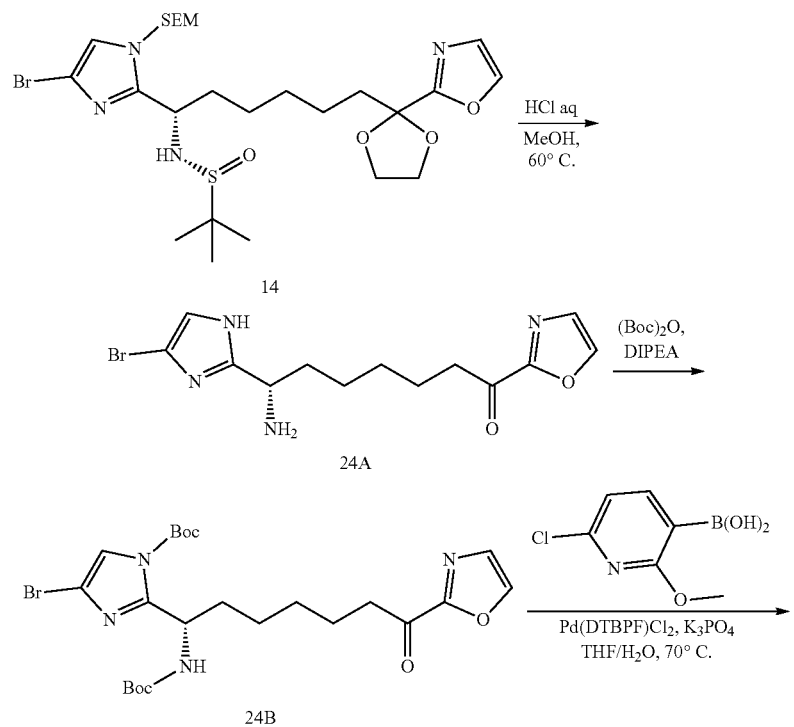

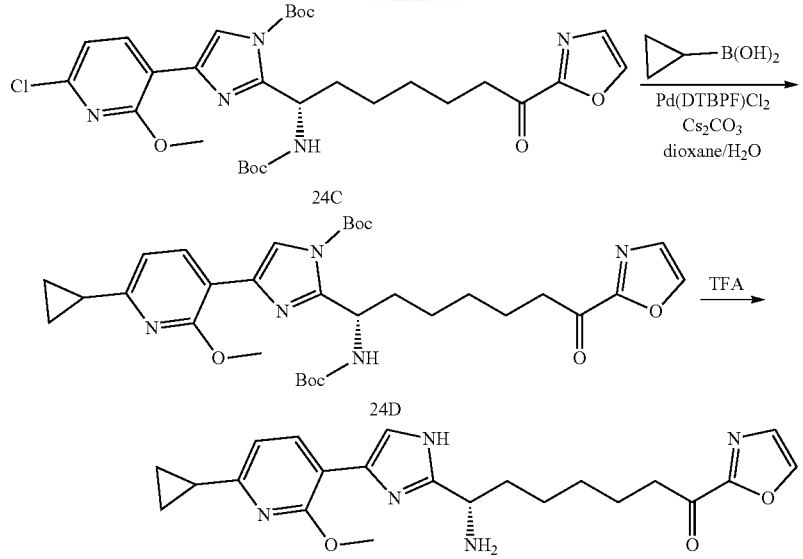

Example 24

Step 1: (S)-7-amino-7-(4-bromo-1H-imidazol-2-yl)-1-(oxazol-2-yl)heptan-1-one (24A)

Conc. HCl (5 ml, 60.9 mmol) was added to a stirred mixture of (R)-N-((S)-1-(4-bromo-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (14, 1.365 g, 2.203 mmol) in co-solvents of MeOH (20 ml) and water (2 mL) and the mixture was stirred at 60° C. for 6 h. The mixture was diluted with MeOH (50 mL) and concentrated in vacuo to give (S)-7-amino-7-(4-bromo-1H-imidazol-2-yl)-1-(oxazol-2-yl)heptan-1-one (60A) which was used to the next step without purification. LCMS (ESI) calc'd for $C_{13}H_{17}BrN_4O_2$ [M+H]$^+$: 341.1, found: 343.0

Step 2: (S)-tert-butyl 4-bromo-2-(1-((tert-butoxycarbonyl)amino)-7-(oxazol-2-yl)-7-oxoheptyl)-1H-imidazole-1-carboxylate (24B)

Bo15O (2.128 ml, 9.16 mmol) was added to a stirred mixture of DIPEA (3 ml, 17.18 mmol) and (S)-7-amino-7-(4-bromo-1H-imidazol-2-yl)-1-(oxazol-2-yl)heptan-1-one (24A, 650 mg, 1.905 mmol) in DCM (20 ml) and the mixture was stirred at rt for 16 h. The mixture was diluted with DCM (60 mL), washed with brine (saturated, 3×20 mL), dried ($Na_2SO_4$), filtered and the solvent was evaporated under reduced pressure. The residue was purified by silica gel column flash chromatography, eluting with petroleum ether/EtOAc=0-40% to give (S)-tert-butyl 4-bromo-2-(1-((tert-butoxycarbonyl)amino)-7-(oxazol-2-yl)-7-oxoheptyl)-1H-imidazole-1-carboxylate (24B).

Step 3: (S)-tert-butyl 2-(1-((tert-butoxycarbonyl)amino)-7-(oxazol-2-yl)-7-oxoheptyl)-4-(6-chloro-2-methoxypyridin-3-yl)-1H-imidazole-1-carboxylate (24C)

PdCl$_2$(DTBPF) (45 mg, 0.069 mmol) was added to a stirred mixture of (S)-tert-butyl 4-bromo-2-(1-((tert-butoxycarbonyl)amino)-7-(oxazol-2-yl)-7-oxoheptyl)-1H-imidazole-1-carboxylate (24B, 634 mg, 1.171 mmol), (6-chloro-2-methoxypyridin-3-yl)boronic acid (252 mg, 1.345 mmol) and $K_3PO_4$ (810 mg, 3.82 mmol) in co-solvents of THF (7 ml) and water (0.7 ml) at rt and the mixture was stirred at 60° C. for 2 h. The mixture was diluted with water (20 mL), extracted with DCM (3×15 mL). The combined organic fractions were washed with brine (saturated, 20 mL), dried ($Na_2SO_4$), filtered and the solvent was evaporated under reduced pressure. The residue was purified by silica gel column flash chromatography, eluting with petroleum ether/EtOAc=0-20 to give (S)-tert-butyl 2-(1-((tert-butoxycarbonyl)amino)-7-(oxazol-2-yl)-7-oxoheptyl)-4-(6-chloro-2-methoxypyridin-3-yl)-1H-imidazole-1-carboxylate (24C). LCMS (ESI) calc'd for $C_{29}H_{38}ClN_5O_7$ [M+H]$^+$: 604.2, found: 604.3

Step 4: (S)-tert-butyl (1-(4-(6-cyclopropyl-2-methoxypyridin-3-yl)-1H-imidazol-2-yl)-7-(oxazol-2-yl)-7-oxoheptyl)carbamate (24D)

PdCl$_2$(DTBPF) (80 mg, 0.123 mmol) was added to a stirred mixture of cyclopropylboronic acid (543 mg, 6.32 mmol), (S)-tert-butyl 2-(1-((tert-butoxycarbonyl)amino)-7-(oxazol-2-yl)-7-oxoheptyl)-4-(6-chloro-2-methoxypyridin-3-yl)-1H-imidazole-1-carboxylate (60C, 420 mg, 0.695 mmol) and $Cs_2CO_3$ (2.43 g, 7.46 mmol) in co-solvents of 1,4-dioxane (6 ml) and water (0.6 ml) at rt and the mixture was stirred at 80° C. for 12 h. The mixture was diluted with water (15 mL), extracted with DCM (3×15 mL). The combined organic fractions were washed with brine (saturated, 20 mL), dried ($Na_2SO_4$), filtered and the solvent was evaporated under reduced pressure. The residue was purified by silica gel column flash chromatography, eluting with petroleum ether/EtOAc=0-40% to give (S)-tert-butyl (1-(4-(6-cyclopropyl-2-methoxypyridin-3-yl)-1H-imidazol-2-yl)-7-(oxazol-2-yl)-7-oxoheptyl)carbamate (24D). LCMS (ESI) calc'd for $C_{22}H_{43}N_5O_7$ [M+H]$^+$: 610.3, found: 610.3

Step 5: (S)-7-amino-7-(4-(6-cyclopropyl-2-methoxypyridin-3-yl)-1H-imidazol-2-yl)-1-(oxazol-2-yl)heptan-1-one (Example 24)

TFA (2 mL, 26.0 mmol) was added to (S)-tert-butyl (1-(4-(6-cyclopropyl-2-methoxypyridin-3-yl)-1H-imidazol- 2-yl)-7-(oxazol-2-yl)-7-oxoheptyl)carbamate (24D, 80 mg, 0.157 mmol) in DCM (2 ml) and the mixture was stirred at rt for 1 h. TFA and DCM was removed under $N_2$ flow. The residue was purified by preparative HPLC (reverse phase C-18 column), eluting with acetonitrile/water+0.1% TFA, to give (S)-7-amino-7-(4-(6-cyclopropyl-2-methoxypyridin-3-yl)-1H-imidazol-2-yl)-1-(oxazol-2-yl)heptan-1-one (Example 24). LCMS (ESI) calc'd for $C_{22}H_{27}N_5O_3$ [M+H]$^+$: 410.2, found: 410.2. $^1$H NMR (400 MHz, MeOD) δ 8.03-8.11 (m, 2H), 7.66 (s, 1H), 7.38 (s, 1H), 6.93 (d, J=7.72 Hz, 1H), 4.50-4.60 (m, 1H), 4.56 (dd, J=6.17, 8.82 Hz, 1H), 3.99 (s, 3H), 3.04 (t, J=7.28 Hz, 2H), 2.05-2.21 (m, 1H), 2.05-2.22 (m, 1H), 2.05-2.22 (m, 1H), 2.02-2.04 (m, 1H), 1.98-2.02 (m, 1H), 1.72 (m, 2H), 1.23-1.49 (m, 1H), 1.23-1.50 (m, 3H), 0.89-1.07 (m, 4H).

Example 25

(S)-7-amino-7-(4-chloro-2-(4-fluorophenyl)-1H-imidazol-5-yl)-1-(oxazol-2-yl)heptan-1-one

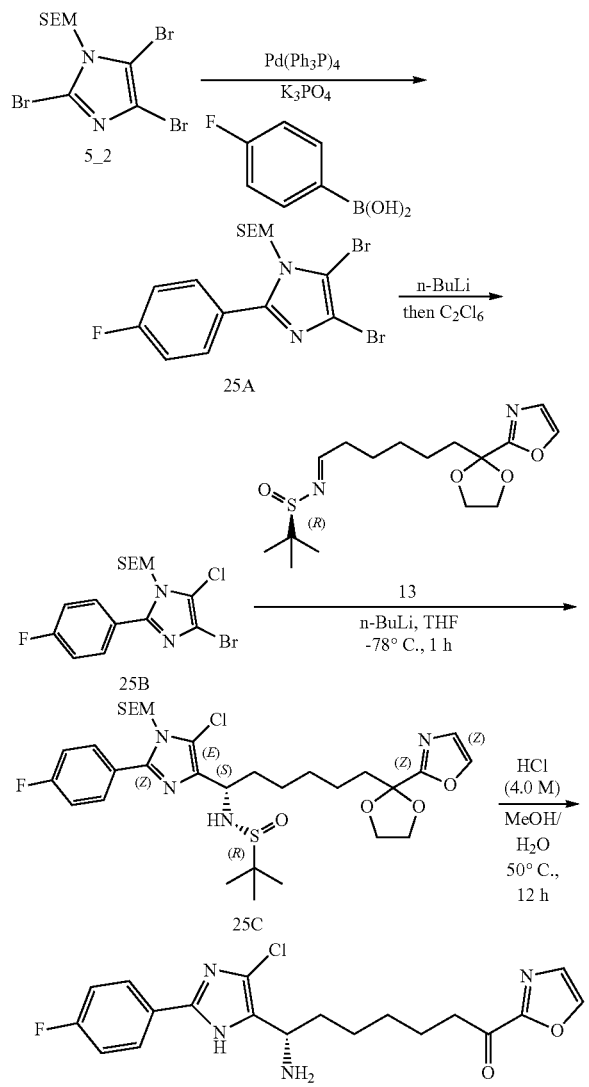

Example 25

Step 1: 4,5-dibromo-2-(4-fluorophenyl)-1-((2-(trimethylsilyl)ethoxy)methyl)-1H-imidazole (25A)

To a mixture of 2,4,5-tribromo-1-((2-(trimethylsilyl)ethoxy)methyl)-1H-imidazole (5_2) (10.50 g, 24.14 mmol) in Dioxane (97 ml) at ambient temperature was added (4-fluorophenyl)boronic acid (3.38 g, 24.14 mmol) and $K_3PO_4$ (12.81 g, 60.3 mmol) dissolved in Water (24.14 ml). Pd(Ph$_3$P)$_4$ (0.837 g, 0.724 mmol) was added and the mixture was heated to 100° C. and stirred for 2 hours. The mixture was cooled and water (100 mL) was added. Extract with EtOAc (3×@100 mL), dry over Na$_2$SO$_4$, and concentrate. The resulting residue was purified using an ISCO (220 g, silica) with a solvent system of 2% to 40% 3:1 EtOAc: EtOH/hexanes to give 4,5-dibromo-2-(4-fluorophenyl)-1-((2-(trimethylsilyl)ethoxy)methyl)-1H-imidazole (25A).

Step 2: Preparation of 4-bromo-5-chloro-2-(4-fluorophenyl)-1-((2-(trimethylsilyl)ethoxy)methyl)-1H-imidazole (25B)

nBuLi (1.75 ml, 4.38 mmol) was added to a stirred mixture of 4,5-dibromo-2-(4-fluorophenyl)-1-((2-(trimethylsilyl)ethoxy)methyl)-1H-imidazole (25A, 2.0 g, 4.44 mmol) in THF (20 ml) at −78° C. and the mixture was stirred at −78° C. for 30 min. Hexachloroethane (0.65 ml, 5.74 mmol) was added. The mixture was stirred at −78° C. for 2 h. The mixture was quenched with aqueous NH$_4$Cl (saturated, 30 mL) and the mixture was extracted with ethyl acetate (3×30 mL). The combined organic fractions were washed with brine (saturated, 2×30 mL), dried (Na$_2$SO$_4$), filtered and the solvent was evaporated under reduced pressure. The residue was purified by silica gel column flash chromatography, eluting with petroleum ether/EtOAc=10:1 to give 4-bromo-5-chloro-2-(4-fluorophenyl)-1-((2-(trimethylsilyl)ethoxy)methyl)-1H-imidazole (25B). LCMS (ESI) calc'd for $C_{15}H_{19}BrClFN_2OSi$ [M+H]$^+$: 405.0, found: 407.1.

Step 3: Preparation of (R)-N-((S)-1-(4-chloro-2-(4-fluorophenyl)-1-((2-(trimethylsilyl)ethoxy)methyl)-1H-imidazol-5-yl)-6-(2-(oxazol-2-yl)-1,3-dioxolan-2-yl)hexyl)-2-methylpropane-2-sulfinamide (25C)

nBuLi (0.3 ml, 0.750 mmol) was added to a stirred mixture of 4-bromo-5-chloro-2-(4-fluorophenyl)-1-((2-(trimethylsilyl)ethoxy)methyl)-1H-imidazole (25B, 251 mg, 0.619 mmol) in THF (2.0 ml) at −78° C. and the mixture was stirred at −78° C. for 10 min. (R,E)-2-methyl-N-(6-(2-(oxazol-2-yl)-1,3-dioxolan-2-yl)hexylidene)propane-2-sulfinamide (12, 200 mg, 0.584 mmol) in THF (0.5 mL) was added. The mixture was stirred at −78° C. for 1 h. The mixture was quenched with water (20 mL) and the mixture was extracted with ethyl acetate (3×20 mL). The combined organic fractions were washed with brine (saturated, 20 mL), dried (Na$_2$SO$_4$), filtered and the solvent was evaporated under reduced pressure. The residue was purified by silica gel column flash chromatography, eluting with DCM/MeOH=10:1 to give (R)-N-((S)-1-(4-chloro-2-(4-fluorophenyl)-1-((2-(trimethylsilyl)ethoxy)methyl)-1H-imidazol-5-yl)-6-(2-(oxazol-2-yl)-1,3-dioxolan-2-yl)hexyl)-2-methylpropane-2-sulfinamide (25C). LCMS (ESI) calc'd for $C_{21}H_{46}ClFN_4O_5SSi$ [M+H]$^+$: 669.3, found: 669.3

Step 4: Preparation of (S)-7-amino-7-(4-chloro-2-(4-fluorophenyl)-1H-imidazol-5-yl)-1-(oxazol-2-yl)heptan-1-one (Example 25)

Hydrogen chloride (0.8 ml, 3.20 mmol) was added to the solution of (R)-N-((S)-1-(4-chloro-2-(4-fluorophenyl)-1-

((2-(trimethylsilyl)ethoxy)methyl)-1H-imidazol-5-yl)-6-(2-(oxazol-2-yl)-1,3-dioxolan-2-yl)hexyl)-2-methylpropane-2-sulfinamide (25C, 360 mg, 0.538 mmol) in MeOH (2.0 ml) and water (0.8 ml), and the resultant mixture was stirred at 50° C. for 12 h. The mixture was quenched with aqueous NaHCO$_3$ (saturated) to pH=7-8 and the mixture was extracted with DCM (3×10 mL). The combined organic fractions were washed with brine (saturated, 20 mL), dried (Na$_2$SO$_4$), filtered and the solvent was evaporated under reduced pressure. The residue was purified by preparative HPLC (reverse phase C-18 column), eluting with acetonitrile/water+0.05% HCl, to give (S)-7-amino-7-(4-chloro-2-(4-fluorophenyl)-1H-imidazol-5-yl)-1-(oxazol-2-yl)heptan-1-one (Example 25). LCMS (ESI) calc'd for C$_{19}$H$_{20}$ClFN$_4$O$_2$[M+H]$^+$: 391.1, found: 391.1. $^1$H NMR (400 MHz, MeOD) δ 8.10 (s, 1H), 7.92-8.06 (m, 2H), 7.39 (s, 1H), 7.25-7.36 (m, 2H), 4.50 (dd, J=5.29, 9.92 Hz, 1H), 3.06 (t, J=7.17 Hz, 2H), 2.25 (d, J=8.38 Hz, 1H), 2.02-2.14 (m, 1H), 1.69-1.83 (m, 2H), 1.27-1.55 (m, 4H).

Example 26

7-amino-7-(5-(2-methylquinolin-6-yl)oxazol-2-yl)-1-(oxazol-2-yl)heptan-1-one (35, L-006157881-001T) and (37, L-006157885-001C)

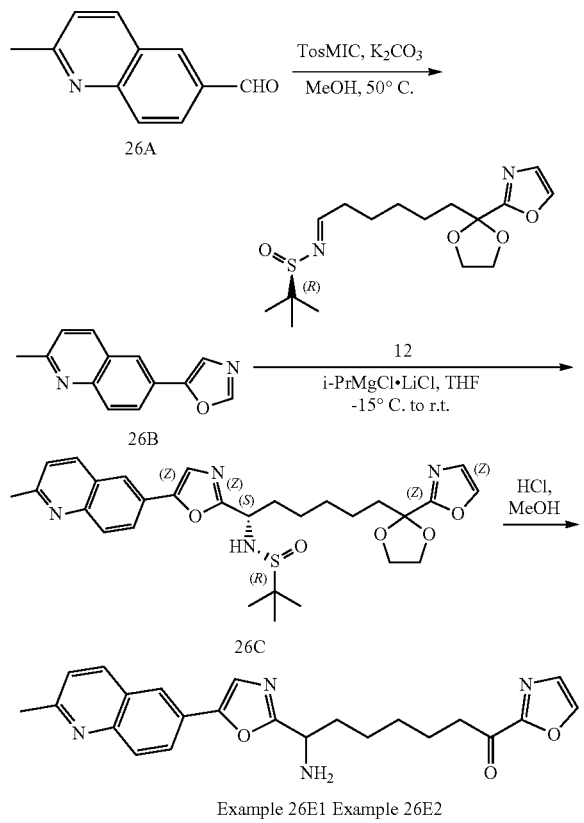

Step 1: Preparation of 5-(2-methylquinolin-6-yl)oxazole (26B)

To a mixture of 2-methylquinoline-6-carbaldehyde (26A, 0.26 g, 1.52 mmol) and K$_2$CO$_3$ in MeOH (10 mL) was added TosMIC (0.36 g, 1.83 mmol). Then the mixture was stirred at 50° C. under N$_2$ atmosphere for 14 h. The reaction mixture was concentrated under reduced pressure. The residue was purified by silica gel column flash chromatography, eluting with Petro.ether/EtOAc=1:1 to give 5-(2-methylquinolin-6-yl)oxazole (26B). LCMS (ESI) calc'd for C$_{13}$H$_{10}$N$_2$O [M+H]$^+$: 211.1, found: 211.0.

Step 2: Preparation of (R)-2-methyl-N-((S)-1-(5-(2-methylquinolin-6-yl)oxazol-2-yl)-6-(2-(oxazol-2-yl)-1,3-dioxolan-2-yl)hexyl)propane-2-sulfinamide (26C)

To a cooled (−15° C.) solution of 5-(2-methylquinolin-6-yl)oxazole (26B, 223 mg, 1.06 mmol) in THF (3 mL) was added dropwise a solution of i-PrMgCl·LiCl (0.9 mL, 1.3 M in THF, 1.17 mmol). After stirring at −15° C. for 0.5 h, a solution of (R,E)-2-methyl-N-(6-(2-(oxazol-2-yl)-1,3-dioxolan-2-yl)hexylidene)propane-2-sulfinamide (12, 191 mg, 0.558 mmol) in THF (2 mL) was added dropwise into the above mixture. Then the reaction mixture was warmed to rt and stirred for another 24 h. The reaction mixture was quenched with NH$_4$Cl solution (aq. saturated, 50 mL) and extracted with EtOAc (30×2 mL). The organic layers were combined, washed with brine (saturated, 40 mL), dried over anhydrous Na$_2$SO$_4$, filtered and concentrated. The residue was purified by prep-HPLC (Column: Phenomenex Synergi C18 150×30 mm×4 μm), eluting with water (0.1% TFA)-acetonitrile (Gradient: 17% to 47%) to give (R)-2-methyl-N-((S)-1-(5-(2-methylquinolin-6-yl)oxazol-2-yl)-6-(2-(oxazol-2-yl)-1,3-dioxolan-2-yl)hexyl)propane-2-sulfinamide (26C). LCMS (ESI) calc'd for C$_{19}$H$_{36}$N$_4$O$_5$S [M+Na]$^+$: 553.2, found: 575.1 (M+Na$^+$).

Step 3: Preparation of 7-amino-7-(5-(2-methylquinolin-6-yl)oxazol-2-yl)-1-(oxazol-2-yl) heptan-1-one hydrochloride (Example 26)

To a solution of (R)-2-methyl-N-((S)-1-(5-(2-methylquinolin-6-yl)oxazol-2-yl)-6-(2-(oxazol-2-yl)-1,3-dioxolan-2-yl)hexyl)propane-2-sulfinamide (26C, peak 1, 54 mg, 97.7 mol) in MeOH (1 mL) was added HCl (0.15 mL, 4.0 M, aq.) and H$_2$O (0.08 mL). The reaction mixture was stirred at 50° C. for 16 h. Then HCl (0.15 mL, 4.0 M, aq.) and H$_2$O (0.08 mL) was added and the mixture was stirred at 50° C. for another 13 h. The reaction mixture was evaporated under reduced pressure. The residue was purified by prep-HPLC (Column: Phenomenex Synergi C18 250×21.2 mm×4 m), eluting with water (0.1% TFA)-acetonitrile (Gradient: 4% to 24%) to give the product. To this product was added HCl (1.5 mL, 0.1 M, aq.) and the mixture was shaken up for 10 min. The above mixture was lyophilized to give 7-amino-7-(5-(2-methylquinolin-6-yl)oxazol-2-yl)-1-(oxazol-2-yl) heptan-1-one hydrochloride (Example 26E1). LCMS (ESI) calc'd for C$_{13}$H$_{24}$N$_4$O$_3$ [M+H]$^+$: 405.2, found: 405.1. $^1$H NMR (400 MHz, MeOD) δ 9.08 (d, J=8.6 Hz, 1H), 8.65 (s, 1H), 8.47-8.52 (m, 1H), 8.26 (d, J=8.8 Hz, 1H), 8.09 (s, 1H), 8.00 (d, J=8.6 Hz, 1H), 7.92 (s, 1H), 7.38 (d, J=0.6 Hz, 1H), 4.76 (t, J=6.8 Hz, 1H), 3.08 (t, J=7.2 Hz, 2H), 3.03 (s, 3H), 2.08-2.28 (m, 2H), 1.76 (t, J=7.0 Hz, 2H), 1.51 (brs, 4H).

Compound Example 26E2 was obtained from peak 2 in step 2 using similar methodology. LCMS (ESI) calc'd for C$_{13}$H$_{24}$N$_4$O$_3$ [M+H]$^+$: 405.2, found: 405.1. $^1$H NMR (400 MHz, MeOD) δ 9.02 (d, J=8.4 Hz, 1H), 8.60 (d, J=1.2 Hz, 1H), 8.45 (dd, J=1.6, 8.8 Hz, 1H), 8.22 (d, J=8.8 Hz, 1H), 8.07 (s, 1H), 7.95 (d, J=7.6 Hz, 1H), 7.89 (s, 1H) 7.36 (s, 1H), 4.72-4.76 (m, 1H), 3.06 (t, J=7.2 Hz, 2H), 3.00 (s, 3H), 2.12-2.19 (m, 2H), 1.73-1.77 (m, 2H), 1.27-1.49 (m, 4H).

Example 27

(S)-7-amino-7-(5-(7-methoxy-2-methylquinolin-6-yl)oxazol-2-yl)-1-(oxazol-2-yl)heptan-1-one

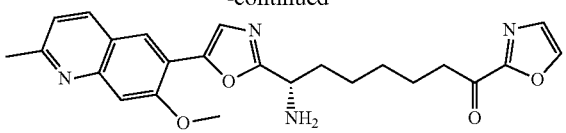

Example 27

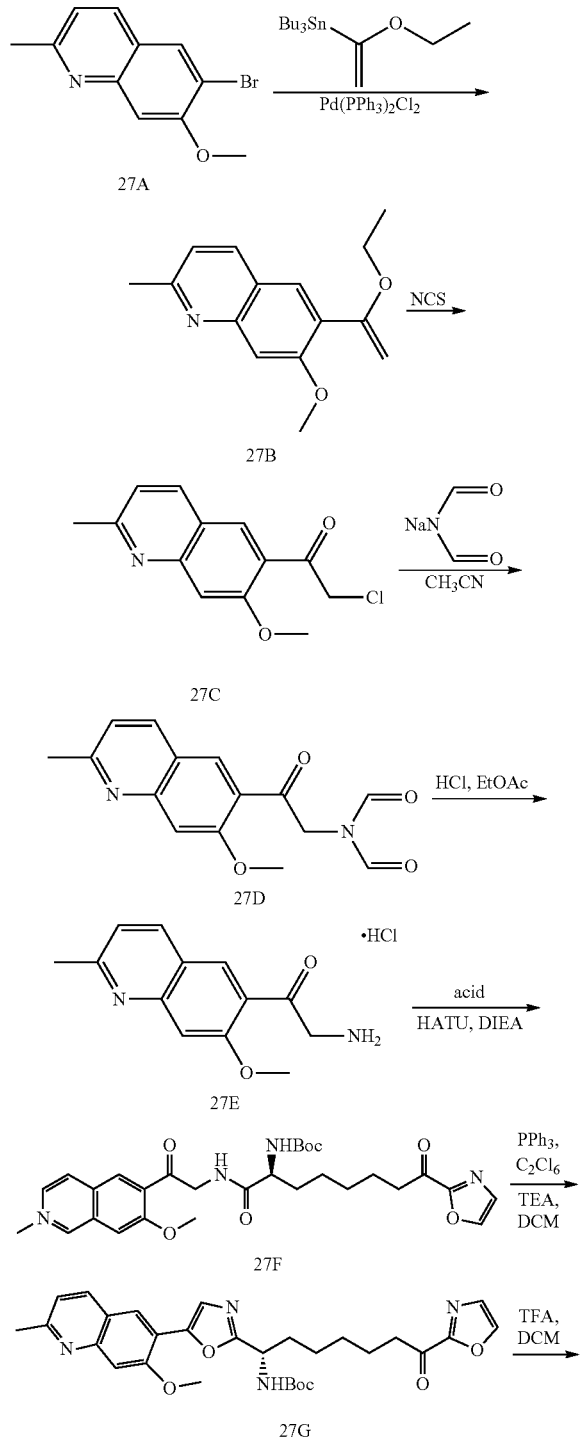

Step 1: Preparation of 6-(1-ethoxyvinyl)-7-methoxy-2-methylquinoline (27B)

Tributyl(1-ethoxyvinyl)stannane (11.53 ml, 34.1 mmol) was added to a stirred mixture of PdCl$_2$(PPh$_3$)$_2$ (1.580 g, 2.251 mmol), and 6-bromo-2-methylquinoline (27A, 5 g, 22.51 mmol) in DMF (50 ml) at room temperature and the mixture was stirred at 80° C. for 16 h under N$_2$. The mixture was cooled to room temperature, KF (saturated, 50 mL) was added and the mixture was extracted with ethyl acetate (3×40 mL). The combined organic fractions were washed with brine (saturated, 1×40 mL), dried (Na$_2$SO$_4$), filtered and the solvent was evaporated under reduced pressure. The residue was purified by silica gel column flash chromatography, eluting with petroleum ether/EtOAc=4/1 to give 6-(1-ethoxyvinyl)-2-methylquinoline (27B). LCMS (ESI) calc'd for C$_{14}$H$_{15}$NO [M+H]$^+$: 214.1, found: 214.4

Step 2: Preparation of 2-chloro-1-(7-methoxy-2-methylquinolin-6-yl)ethanone (27C)

NCS (1.537 g, 11.51 mmol) was added to a stirred mixture of 6-(1-ethoxyvinyl)-7-methoxy-2-methylquinoline (27B, 2.80 g, 11.51 mmol) in MeCN (30 ml) and water (15.0 ml) at room temperature and the mixture was stirred at room temperature for 30 min. Water (20 mL) was added and the mixture was extracted with ethyl acetate (3×20 mL). The combined organic fractions were washed with brine (saturated, 2×15 mL), dried (Na$_2$SO$_4$), filtered and the solvent was evaporated under reduced pressure. The residue was purified by silica gel column flash chromatography, eluting with petroleum ether/EtOAc=3/1 to give 2-chloro-1-(7-methoxy-2-methylquinolin-6-yl)ethanone (27C).

Step 3: Preparation of N-formyl-N-(2-(7-methoxy-2-methylquinolin-6-yl)-2-oxoethyl)formamide (27D)

Sodium diformylamide (951 mg, 10.01 mmol) was added to a stirred mixture of 2-chloro-1-(7-methoxy-2-methylquinolin-6-yl)ethanone (27C, 1000 mg, 4.00 mmol) in acetonitrile (15 ml) at room temperature, and the mixture was stirred at 60° C. for 24 h. The mixture was quenched with brine (saturated, 20 mL), and the mixture was extracted with ethyl acetate (2×30 mL). The combined organic fractions were washed with brine (saturated, 20 mL), dried (Na$_2$SO$_4$), filtered and the solvent was evaporated under reduced pressure. The residue was purified by silica gel flash chromatography (ISCORF75; Sepa flash column), eluting with petroleum ether/EtOAc=5:1-1:1 to give N-formyl-N-(2-(7-methoxy-2-methylquinolin-6-yl)-2-oxoethyl)formamide (27D). LCMS (ESI) calc'd for C$_{15}$H$_{14}$N$_2$O$_4$ [M+H]$^+$: 287.1, found: 287.0

Step 4: Preparation of 2-amino-1-(7-methoxy-2-methylquinolin-6-yl)ethanone hydrochloride (27E)

HCl (1.2 ml, 14.61 mmol) was added to a stirred mixture of N-formyl-N-(2-(7-methoxy-2-methylquinolin-6-yl)-2- oxoethyl)formamide (27D, 520 mg, 1.816 mmol) in EtOH (10 ml) at room temperature, and the mixture was stirred at 60° C. for 2 h. The reaction mixture was concentrated in vacuo to give 2-amino-1-(7-methoxy-2-methylquinolin-6-yl)ethanone hydrochloride (27E) which was used to the next step without further purification. LCMS (ESI) calc'd for $C_{13}H_{14}N_2O_2 \cdot ClH$ [M+H]$^+$: 231.1, found: 231.1

Step 5: Preparation of (S)-tert-butyl (1-((2-(7-methoxy-2-methylquinolin-6-yl)-2-oxoethyl)amino)-8-(oxazol-2-yl)-1,8-dioxooctan-2-yl)carbamate (27F)

HATU (270 mg, 0.710 mmol) was added to the solution of (S)-2-((tert-butoxycarbonyl)amino)-8-(oxazol-2-yl)-8-oxooctanoic acid (230 mg, 0.676 mmol) in DMF (5 ml), and stirred at 25° C. for 10 min, then DIPEA (0.590 ml, 3.38 mmol) and 2-amino-1-(7-methoxy-2-methylquinolin-6-yl)ethanone hydrochloride (27E, 234 mg, 0.878 mmol) was added to the reaction mixture, and it was stirred at 25° C. for 2 h. The mixture was quenched with brine (saturated, 10 mL), and the mixture was extracted with ethyl acetate (3×20 mL). The combined organic fractions were washed with brine (saturated, 10 mL), dried (Na$_2$SO$_4$), filtered and the solvent was evaporated under reduced pressure. The residue was purified by silica gel flash chromatography (ISCORF75; Sepa flash column), eluting with EtOAc/MeOH/NH$_3$ aq.) =10:1:0.02 to give (S)-tert-butyl (1-((2-(7-methoxy-2-methylquinolin-6-yl)-2-oxoethyl)amino)-8-(oxazol-2-yl)-1,8-dioxooctan-2-yl)carbamate (27F). LCMS (ESI) calc'd for $C_{19}H_{36}N_4O_7$ [M+H]$^+$: 553.3, found: 553.2

Step 6: Preparation of (S)-tert-butyl (1-(5-(7-methoxy-2-methylquinolin-6-yl)oxazol-2-yl)-7-(oxazol-2-yl)-7-oxoheptyl)carbamate (27G)

TEA (0.651 ml, 4.67 mmol) and perchloroethane (368 mg, 1.556 mmol) and triphenylphosphine (408 mg, 1.556 mmol) were added to a stirred mixture of (S)-tert-butyl (1-((2-(7-methoxy-2-methylquinolin-6-yl)-2-oxoethyl)amino)-8-(oxazol-2-yl)-1,8-dioxooctan-2-yl)carbamate (27F, 430 mg, 0.778 mmol) in DCM (10 ml). The mixture was stirred at rt for 16 h, and another potion of perchloroethane (368 mg, 1.556 mmol) and triphenylphosphine (408 mg, 1.556 mmol) was added. The mixture was stirred for another 2 h. The mixture was quenched with water (10 mL), and the mixture was extracted with ethyl acetate (3×10 mL). The combined organic fractions were washed with brine (saturated, 10 mL), dried (Na$_2$SO$_4$), filtered and the solvent was evaporated under reduced pressure. The residue was purified by silica gel flash chromatography (ISCORF75; Sepa flash column), eluting with petroleum ether/EtOAc=3:1-1:1 to give (S)-tert-butyl (1-(5-(7-methoxy-2-methylquinolin-6-yl)oxazol-2-yl)-7-(oxazol-2-yl)-7-oxoheptyl)carbamate (27G). LCMS (ESI) calc'd for $C_{19}H_{34}N_4O_6$ [M+H]$^+$: 535.2, found: 535.3

Step 7: Preparation of (S)-7-amino-7-(5-(7-methoxy-2-methylquinolin-6-yl)oxazol-2-yl)-1-(oxazol-2-yl)heptan-1-one (Example 27)

TFA (0.5 ml, 6.49 mmol) was added to the solution of (S)-tert-butyl (1-(5-(7-methoxy-2-methylquinolin-6-yl)oxazol-2-yl)-7-(oxazol-2-yl)-7-oxoheptyl)carbamate (27G, 240 mg, 0.449 mmol) in DCM (10 ml), and the resultant mixture was stirred at rt for 5 h. The reaction mixture was concentrated in vacuo to give (S)-7-amino-7-(5-(7-methoxy-2-methylquinolin-6-yl)oxazol-2-yl)-1-(oxazol-2-yl)heptan-1-one 2,2,2-trifluoroacetate (Example 27) which can be used without further purification.

A pure sample was purified by preparative HPLC (reverse phase C-18 column), eluting with acetonitrile/water+0.1% TFA, to give the title compound. LCMS (ESI) calc'd for $C_{14}H_{26}N_4O_4 \cdot 15HF_3O_2$[M+H]$^+$: 435.2, found: 435. $^1$H NMR (400 MHz, MeOD) δ 8.99 (d, J=8.61 Hz, 1H), 8.66 (s, 1H), 8.06 (s, 1H), 7.72-7.88 (m, 2H), 7.62 (s, 1H), 7.35 (s, 1H), 4.74 (t, J=6.85 Hz, 1H), 4.25 (s, 3H), 3.04 (t, J=7.14 Hz, 2H), 2.96 (s, 3H), 2.05-2.27 (m, 2H), 1.73 (t, J=7.14 Hz, 2H), 1.48 (d, J=6.26 Hz, 4H).

Example 28

(S)-7-amino-7-(5-(2-methoxypyridin-3-yl)oxazol-2-yl)-1-(oxazol-2-yl)heptan-1-one

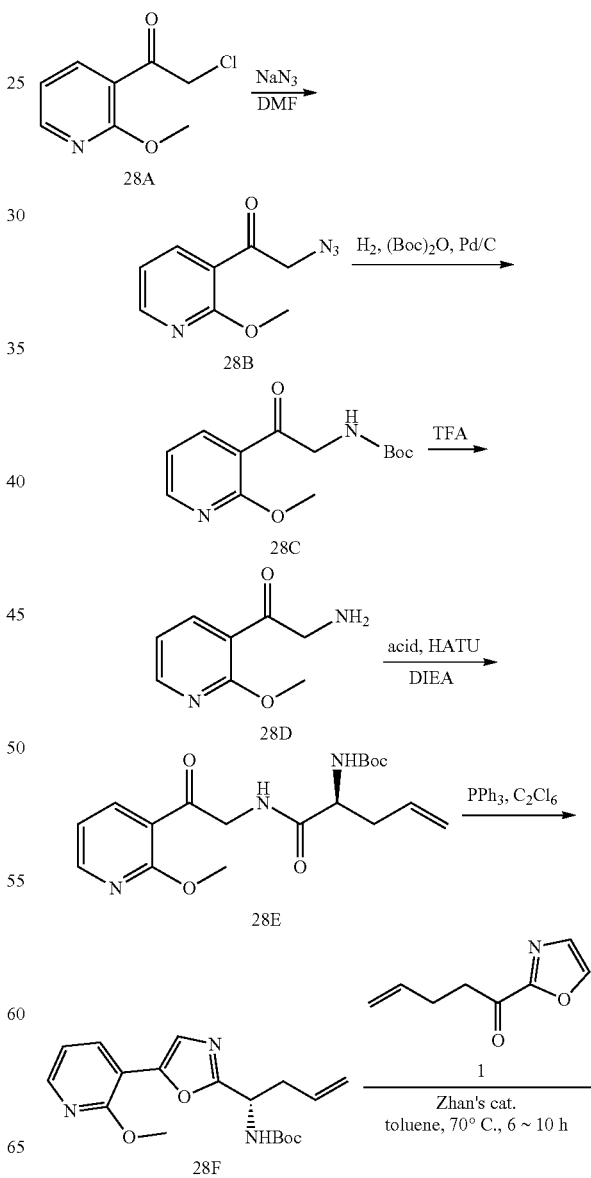

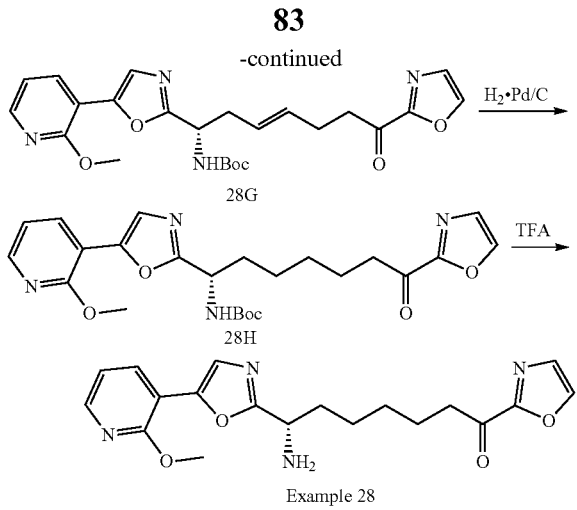

Example 28

Step 1: 2-azido-1-(2-methoxypyridin-3-yl)ethanone (28B)

NaN₃ (1.13 g, 17.38 mmol) was added to a stirred mixture of 2-chloro-1-(2-methoxypyridin-3-yl)ethanone (28A, 2.17 g, 11.69 mmol) in DMF (10 ml) and the mixture was stirred at rt for 2 h. The mixture was diluted with water (40 mL), and extracted with ethyl acetate (4×20 mL). The combined organic fractions were washed with water (3×15 mL), brine (saturated, 10 mL), dried (Na₂SO₄), and filtered to give 2-azido-1-(2-methoxypyridin-3-yl)ethanone (28B, ethyl acetate solution) which was used to the step without purification. LCMS (ESI) calc'd for $C_8H_8N_4O_2$[M+H]$^+$: 193.1, found: 193.0

Step 2: tert-butyl (2-(2-methoxypyridin-3-yl)-2-oxoethyl)carbamate (28C)

Pd—C (10%, 436 mg, 0.410 mmol) was added to a stirred mixture of 2-azido-1-(2-methoxypyridin-3-yl)ethanone (28B, ethyl acetate solution) and Bo15O (4.6 ml, 19.81 mmol) in MeOH (60 ml) at 25° C. and the mixture was degassed and backfilled with H₂ (three times) and stirred at 25° C. for 2 h under H₂ (15 psi). The mixture was filtered and the filter cake was washed with MeOH (20 mL). The filtrate was concentrated to dryness. The residue was purified by silica gel column flash chromatography, eluting with petroleum ether/EtOAc=0~15% to give tert-butyl (2-(2-methoxypyridin-3-yl)-2-oxoethyl)carbamate (28C). LCMS (ESI) calc'd for $C_{13}H_{18}N_2O_4$ [M+H]$^+$: 267.1, found: 267.1

Step 3: 2-amino-1-(2-methoxypyridin-3-yl)ethanone (28D)

TFA (4 mL, 51.9 mmol) was added to a stirred mixture of tert-butyl (2-(2-methoxypyridin-3-yl)-2-oxoethyl)carbamate (28C, 1.7 g, 6.38 mmol) in DCM (20 ml) and the mixture was stirred at rt for 3 h. The solvent was evaporated under reduced pressure to give 2-amino-1-(2-methoxypyridin-3-yl)ethanone (28D) which was used to the next step without purification.

Step 4: (S)-tert-butyl (1-((2-(2-methoxypyridin-3-yl)-2-oxoethyl)amino)-1-oxopent-4-en-2-yl)carbamate (28E)

A mixture of HATU (2.516 g, 6.62 mmol), (S)-2-((tert-butoxycarbonyl)amino)pent-4-enoic acid (1.452 g, 6.75 mmol) and DIEA (5.1 ml, 29.2 mmol) in DMF (10 ml) was stirred at rt for 1 h, then was added 2-amino-1-(2-methoxypyridin-3-yl)ethanone (28D, 1 g, 6.02 mmol) dissolved in DMF (3 ml) and the mixture was stirred at rt for 2 h. The mixture was diluted with water (50 mL), and extracted with ethyl acetate (3×20 mL). The combined organic fractions were washed with water (3×10 mL), brine (saturated, 10 mL), dried (Na₂SO₄), filtered and the solvent was evaporated under reduced pressure. The residue was purified by silica gel column flash chromatography, eluting with petroleum ether/EtOAc=0~15% to give (S)-tert-butyl (1-((2-(2-methoxypyridin-3-yl)-2-oxoethyl)amino)-1-oxopent-4-en-2-yl)carbamate (28E). LCMS (ESI) calc'd for $C_{18}H_{25}N_3O_5$ [M+H]$^+$: 364.2, found: 364.1

Step 5: (S)-tert-butyl (1-(5-(2-methoxypyridin-3-yl)oxazol-2-yl)but-3-en-1-yl)carbamate (28F)

A mixture of (S)-tert-butyl (1-((2-(2-methoxypyridin-3-yl)-2-oxoethyl)amino)-1-oxopent-4-en-2-yl)carbamate (28E, 1.56 g, 4.29 mmol), triphenylphosphine (1.680 g, 6.41 mmol), hexachloroethane (0.734 ml, 6.48 mmol) and TEA (4 ml, 28.7 mmol) in DCM (16 ml) was degassed and backfilled with N₂ three times and stirred at rt for 3 h. The mixture was quenched with water (50 mL), and extracted with DCM (3×30 mL). The combined organic fractions were washed with brine (saturated, 20 mL), dried (Na₂SO₄), filtered and the solvent was evaporated under reduced pressure. The residue was purified by silica gel column flash chromatography, eluting with petroleum ether/EtOAc=0-15% to give (S)-tert-butyl (1-(5-(2-methoxypyridin-3-yl)oxazol-2-yl)but-3-en-1-yl)carbamate (28F). LCMS (ESI) calc'd for $C_{18}H_{23}N_3O_4$ [M+H]$^+$: 346.2, found: 346.2.

Step 6: (S,E)-tert-butyl (1-(5-(2-methoxypyridin-3-yl)oxazol-2-yl)-7-(oxazol-2-yl)-7-oxohept-3-en-1-yl)carbamate (28G)

Zhan's catalyst (146 mg, 0.199 mmol) was added to a mixture of (S)-tert-butyl (1-(5-(2-methoxypyridin-3-yl)oxazol-2-yl)but-3-en-1-yl)carbamate (28F, 950 mg, 2.75 mmol) and 1-(oxazol-2-yl)pent-4-en-1-one (1, 1436 mg, 9.50 mmol) in toluene (7 ml) which was bubbled with N₂ for 20 mins at rt. The mixture was degassed and backfilled with N₂ (three times) and stirred at 70° C. for 10 h. The mixture was concentrated under reduced pressure. The residue was purified by silica gel column flash chromatography, eluting with petroleum ether/EtOAc=0-33% to give (S,E)-tert-butyl (1-(5-(2-methoxypyridin-3-yl)oxazol-2-yl)-7-(oxazol-2-yl)-7-oxohept-3-en-1-yl)carbamate (28G). LCMS (ESI) calc'd for $C_{14}H_{28}N_4O_6$ [M+H]$^+$: 469.2, found: 469.2

Step 7: (S)-tert-butyl (1-(5-(2-methoxypyridin-3-yl)oxazol-2-yl)-7-(oxazol-2-yl)-7-oxoheptyl)carbamate (28H)

Pd—C (10%, 126 mg, 0.118 mmol) was added to (S,E)-tert-butyl (1-(5-(2-methoxypyridin-3-yl)oxazol-2-yl)-7-(oxazol-2-yl)-7-oxohept-3-en-1-yl)carbamate (28G, 590 mg, 1.259 mmol) in MeOH (10 ml) at 26° C. and the mixture was degassed and backfilled with H₂ (three times) and stirred at 26° C. for 1 h under H₂ (15 psi). The mixture was filtered and the solvent was evaporated under reduced pressure to give (S)-tert-butyl (1-(5-(2-methoxypyridin-3-yl)oxazol-2-yl)-7-(oxazol-2-yl)-7-oxoheptyl)carbamate (28H)

which was used to the next step without further purification. LCMS (ESI) calc'd for $C_{14}H_{30}N_4O_6$ [M+H]$^+$: 471.2, found: 471.3

Step 8: (S)-7-amino-7-(5-(2-methoxypyridin-3-yl)oxazol-2-yl)-1-(oxazol-2-yl)heptan-1-one Example 28

TFA (0.6 mL, 7.79 mmol) was added to (S)-tert-butyl (1-(5-(2-methoxypyridin-3-yl)oxazol-2-yl)-7-(oxazol-2-yl)-7-oxoheptyl)carbamate (28H, 25 mg, 0.053 mmol) in DCM (3 ml) and the mixture was stirred at rt for 1 h. The solvent was evaporated under reduced pressure. The residue was purified by preparative HPLC (reverse phase C-18 column), eluting with acetonitrile/water+0.1% TFA, to give (S)-7-amino-7-(5-(2-methoxypyridin-3-yl)oxazol-2-yl)-1-(oxazol-2-yl)heptan-1-one (Example 28). LCMS (ESI) calc'd for $C_{19}H_{22}N_4O_4$ [M+H]$^+$: 371.2, found: 371.2. $^1$H NMR (400 MHz, MeOD) δ 8.14-8.18 (m, 1H), 8.10-8.13 (m, 1H), 8.09 (s, 1H), 7.61 (s, 1H), 7.38 (s, 1H), 7.10 (dd, J=5.09, 7.43 Hz, 1H), 4.66 (t, J=7.04 Hz, 1H), 4.10 (s, 3H), 3.05 (t, J=7.24 Hz, 2H), 2.02-2.22 (m, 2H), 1.74 (t, J=6.85 Hz, 2H), 1.47 (d, J=2.74 Hz, 4H).

Example 29

(S)-7-amino-7-(1-methyl-4-(2-methylquinolin-6-yl)-1H-imidazol-2-yl)-1-(oxazol-2-yl)heptan-1-one

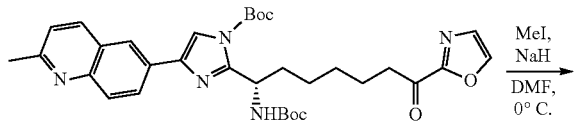

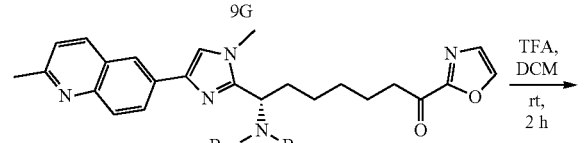

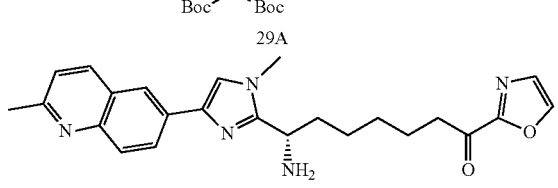

Example 29

Step 1: Preparation of compound 29A

To a solution of (S)-tert-butyl 2-(1-(((tert-butoxycarbonyl)amino)-7-(oxazol-2-yl)-7-oxoheptyl)-4-(2-methylquinolin-6-yl)-1H-imidazole-1-carboxylate (9G, 80 mg, 0.133 mmol) in DMF (1 ml) was added NaH (6 mg, 0.150 mmol) at 0° C. The mixture was stirred at 0° C. for 30 min. Then, iodomethane (18 mg, 0.127 mmol) was added. The mixture was stirred at rt for 2 h. Aqueous NH$_4$Cl (saturated, 10 mL) was added and the mixture was extracted with ethyl acetate (5×2 mL). The combined organic fractions were washed with brine (saturated, 10 mL), dried (Na$_2$SO$_4$), filtered and the solvent was evaporated under reduced pressure. The crude product was used directly in the next step. LCMS (ESI) calc'd for $16_4H_{41}N_5O_6$ [M+H]$^+$: 618.3, found: 618.4. The structure of compound 29A was not confirmed and derived from de-protection product in next step.

Step 2: Preparation of (S)-7-amino-7-(1-methyl-4-(2-methylquinolin-6-yl)-1H-imidazol-2-yl)-1-(oxazol-2-yl)heptan-1-one (Example 29)

A solution of compound 29A (80 mg crude, 0.130 mmol) in DCM (1 ml) was added to TFA (1 ml, 12.98 mmol). The mixture was then stirred at rt for 2 h. The mixture was concentrated and the residue was purified by preparative HPLC (reverse phase C-18 column), eluting with acetonitrile/water+0.1% TFA, to give (S)-7-(methylamino)-7-(5-(2-methylquinolin-6-yl)-1H-imidazol-2-yl)-1-(oxazol-2-yl)heptan-1-one (Example 29). LCMS (ESI) calc'd for $C_{14}H_{27}N_5O_2$ [M+H]$^+$: 418.2, found: 418.3

HCl (0.1 M, 0.5 ml, 0.050 mmol) was added to a stirred mixture of (S)-7-(methylamino)-7-(5-(2-methylquinolin-6-yl)-1H-imidazol-2-yl)-1-(oxazol-2-yl)heptan-1-one (Example 29, 10 mg, 0.024 mmol) in acetonitrile (2 ml) at room temperature, then it was lyophilized to give (S)-7-(methylamino)-7-(5-(2-methylquinolin-6-yl)-1H-imidazol-2-yl)-1-(oxazol-2-yl)heptan-1-one hydrochloride (Example 29). $^1$H NMR (400 MHz, MeOD) δ 8.97 (d, J=8.61 Hz, 1H), 8.64 (brs, 1H), 8.56 (d, J=9.00 Hz, 1H), 8.15 (d, J=8.61 Hz, 1H), 8.06 (s, 1H), 7.87-7.94 (m, 2H), 7.35 (s, 1H), 4.68-4.76 (m, 1H), 3.86 (brs, 3H), 2.96-3.05 (m, 6H), 1.72 (t, J=7.24 Hz, 2H), 1.35-1.47 (m, 2H), 1.28 (brs, 4H).

Example 30

(S)-7-amino-7-(1-ethyl-4-(2-methylquinolin-6-yl)-1H-imidazol-2-yl)-1-(oxazol-2-yl)heptan-1-one

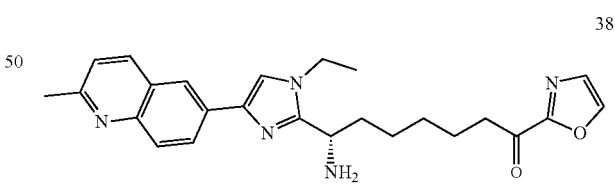

(S)-7-amino-7-(1-ethyl-4-(2-methylquinolin-6-yl)-1H-imidazol-2-yl)-1-(oxazol-2-yl)heptan-1-one (Example 30) was obtained from EtI with same method described above. LCMS (ESI) calc'd for $C_{15}H_{30}ClN_5O_2$[M+H]$^+$: 432.2, found: 432.0. $^1$H NMR (400 MHz, MeOD) δ 8.98 (brs, 1H), 9.00 (brs, 1H), 8.65-8.71 (m, 1H), 8.58 (d, J=7.83 Hz, 1H), 8.18 (d, J=8.61 Hz, 1H), 8.03-8.10 (m, 2H), 7.89-7.94 (m, 1H), 7.33-7.37 (m, 1H), 4.79 (brs, 1H), 4.16-4.29 (m, 2H), 3.01-3.03 (m, 2H), 2.98-3.00 (m, 3H), 1.66-1.78 (m, 2H), 1.54 (t, J=7.04 Hz, 3H), 1.37-1.47 (m, 3H), 1.20-1.33 (m, 3H).

Example 31

(S)-7-amino-1-(isoxazol-3-yl)-7-(4-(7-methoxy-2-methylquinolin-6-yl)-1H-imidazol-2-yl)heptan-1-one

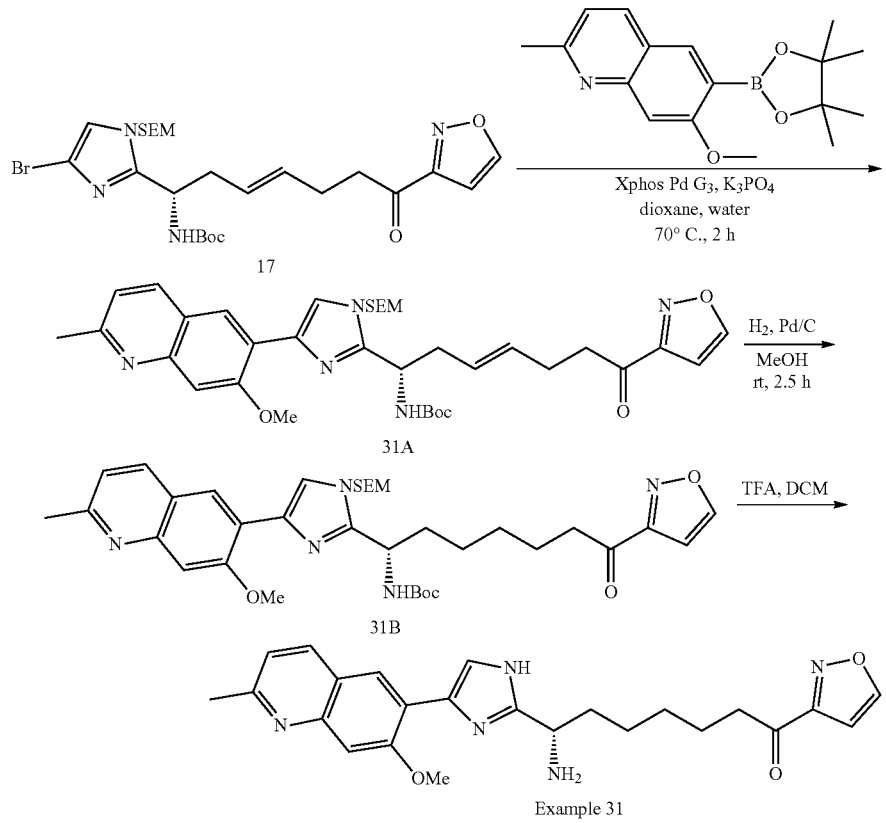

Example 31

Step 1: Preparation of (S,E)-tert-butyl (7-(isoxazol-3-yl)-1-(4-(7-methoxy-2-methylquinolin-6-yl)-1-((2-(trimethylsilyl)ethoxy)methyl)-1H-imidazol-2-yl)-7-oxohept-3-en-1-yl)carbamate (31A)

A stirred mixture of (S,Z)-tert-butyl (1-(4-bromo-1-((2-(trimethylsilyl)ethoxy)methyl)-1H-imidazol-2-yl)-7-(isoxazol-3-yl)-7-oxohept-3-en-1-yl)carbamate (17, 300 mg, 0.527 mmol), 7-methoxy-2-methyl-6-(4,4,5,5-tetramethyl-1,3,2-dioxaborolan-2-yl)quinoline (236 mg, 0.790 mmol) and $K_3PO_4$ (335 mg, 1.580 mmol), XPhos Pd G3 (22 mg, 0.026 mmol) in THF (2 ml) and water (0.05 ml) was sealed in a 10 mL vial and stirred at 70° C. for 2 h under $N_2$ protection. The reaction mixture was concentrated to dryness, and purified by silica gel chromatography eluted with Petro.Ether:EtOAc=1:2 to give (S,E)-tert-butyl (7-(isoxazol-3-yl)-1-(4-(7-methoxy-2-methylquinolin-6-yl)-1-((2-(trimethylsilyl)ethoxy)methyl)-1H-imidazol-2-yl)-7-oxohept-3-en-1-yl)carbamate (31A). LCMS (ESI) calc'd for $C_{35}H_{47}N_5O_6Si$ [M+H]$^+$: 662.3, found: 662.4

Step 2: Preparation of (S)-tert-butyl (7-(isoxazol-3-yl)-1-(4-(7-methoxy-2-methylquinolin-6-yl)-1-((2-(trimethylsilyl)ethoxy)methyl)-1H-imidazol-2-yl)-7-oxoheptyl)carbamate (31B)

To a solution of ((S,E)-tert-butyl (7-(isoxazol-3-yl)-1-(4-(7-methoxy-2-methylquinolin-6-yl)-1-((2-(trimethylsilyl) ethoxy)methyl)-1H-imidazol-2-yl)-7-oxohept-3-en-1-yl) carbamate (31A, 100 mg, 0.151 mmol) in MeOH (2 ml) was added Pd/C (16 mg, 0.015 mmol) (10%, wet) under Ar. The suspension was degassed under vacuum and purged with $N_2$ several times. The mixture was then stirred under $H_2$ (Pressure: 15 psi) at rt for 2 h. It was filtered on Celite then the filter cake was washed with methanol (3×5 mL). The filtrate was concentrated under reduced pressure to give (S)-tert-butyl (7-(isoxazol-3-yl)-1-(4-(7-methoxy-2-methylquinolin-6-yl)-1-((2-(trimethylsilyl)ethoxy)methyl)-1H-imidazol-2-yl)-7-oxoheptyl)carbamate (31B) which was used directly for next step without purification. LCMS (ESI) calc'd for $C_{35}H_{49}N_5O_6Si$ [M+H]$^+$: 664.3, found: 664.4

Step 3: Preparation of (S)-7-amino-1-(isoxazol-3-yl)-7-(4-(7-methoxy-2-methylquinolin-6-yl)-1H-imidazol-2-yl)heptan-1-one (Example 31)

TFA (3 mL, 38.9 mmol) was added to a stirred mixture of (S)-tert-butyl (7-(isoxazol-3-yl)-1-(4-(7-methoxy-2-methylquinolin-6-yl)-1-((2-(trimethylsilyl)ethoxy)methyl)-1H-imidazol-2-yl)-7-oxoheptyl)carbamate (31B, 65 mg, 0.098 mmol) at room temperature and the mixture was stirred at rt for 2 h. The mixture was concentrated and purified by preparative HPLC (reverse phase C-18 column), eluting with acetonitrile/water+0.1% TFA, to give (S)-7-amino-1-(isoxazol-3-yl)-7-(4-(7-methoxy-2-methylquinolin-6-yl)-1H-imidazol-2-yl)heptan-1-one (Example 31).

HCl aq (0.1 M, 3.88 ml, 0.388 mmol) was added to a stirred mixture of (S)-7-amino-1-(isoxazol-3-yl)-7-(4-(7-methoxy-2-methylquinolin-6-yl)-1H-imidazol-2-yl)heptan-1-one (Example 31, 42 mg, 0.097 mmol) in water (2.0 ml) at room temperature and the mixture was lyophilized to give (S)-7-amino-1-(isoxazol-3-yl)-7-(4-(7-methoxy-2-methylquinolin-6-yl)-1H-imidazol-2-yl)heptan-1-one dihydrochloride (Example 31). $^1$H NMR (400 MHz, MeOD) δ 9.00

(s, 1H), 8.98 (s, 1H), 8.86 (s, 1H), 8.77 (d, J=1.56 Hz, 1H), 8.23 (s, 1H), 7.80-7.85 (m, 1H), 7.69 (s, 1H), 6.76 (d, J=1.76 Hz, 1H), 4.85-4.88 (m, 1H), 4.28 (s, 3H), 3.31 (td, J=1.64, 3.18 Hz, 5H), 3.06 (s, 1H), 3.04-3.09 (m, 1H), 2.99-3.03 (m, 3H), 2.17-2.47 (m, 2H), 1.69-1.82 (m, 2H), 1.30-1.35 (m, 4H).

Example 32

(S)-6-(2-(1-amino-7-(isoxazol-3-yl)-7-oxoheptyl)-1H-imidazol-4-yl)-1-methylquinolin-2(1H)-one

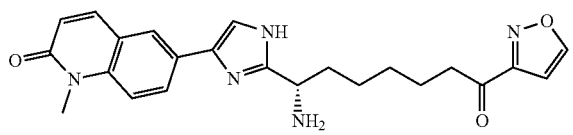

(S)-6-(2-(1-amino-7-(isoxazol-3-yl)-7-oxoheptyl)-1H-imidazol-4-yl)-1-methylquinolin-2(1H)-one (Example 31) was obtained from 17 utilizing same method as described above. LCMS (ESI) calc'd for $C_{13}H_{25}N_5O_3 \cdot 2ClH$ [M+H]+: 420.2, found: 420.0. $^1$HNMR (400 MHz, MeOD) δ 8.77 (d, J=1.76 Hz, 1H), 8.17 (s, 1H), 8.09 (dd, J=1.98, 8.82 Hz, 1H), 7.94-8.05 (m, 2H), 7.75 (s, 1H), 6.76 (dd, J=3.86, 5.62 Hz, 2H), 4.79 (d, J=7.28 Hz, 1H), 3.78 (s, 3H), 3.07 (t, J=7.17 Hz, 2H), 2.15-2.38 (m, 2H), 1.76 (quin, J=7.28 Hz, 2H), 1.29-1.56 (m, 4H).

Example 33

(S)-7-amino-1-(isoxazol-3-yl)-7-(4-(2-methoxypyridin-3-yl)-1H-imidazol-2-yl)heptan-1-one

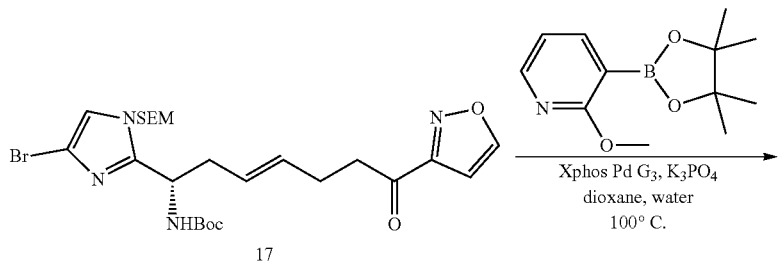

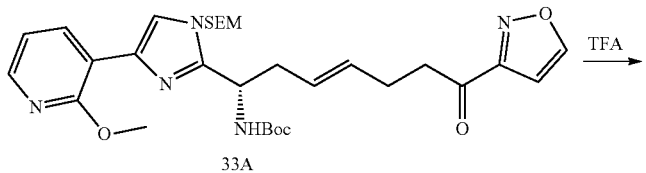

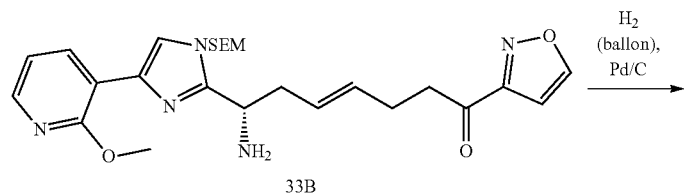

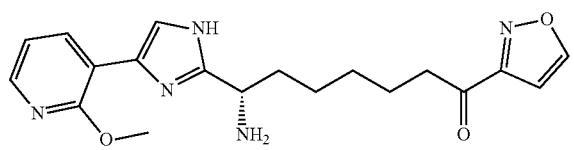

Example 33

Step 1: Preparation of (S)-tert-butyl (7-(isoxazol-3-yl)-1-(4-(2-methoxypyridin-3-yl)-1-((2-(trimethylsilyl)ethoxy)methyl)-1H-imidazol-2-yl)-7-oxohept-3-en-1-yl)carbamate (33A)

XPhos Pd G3 (10 mg, 0.012 mmol) was added to a mixture of (S)-tert-butyl (1-(4-bromo-1-((2-(trimethylsilyl)ethoxy)methyl)-1H-imidazol-2-yl)-7-(isoxazol-3-yl)-7-oxohept-3-en-1-yl)carbamate (17, 106 mg, 0.186 mmol), 2-methoxy-3-(4,4,5,5-tetramethyl-1,3,2-dioxaborolan-2-yl)pyridine (110 mg, 0.468 mmol) and $K_3PO_4$ (123 mg, 0.579 mmol) in co-solvents of dioxane (1.5 ml) and water (0.15 ml) at rt and the mixture was stirred at 100° C. for 2 h under $N_2$ protection. The mixture was cooled, diluted with water (15 mL), and extracted with ethyl acetate (3×8 mL). The combined organic fractions were washed with brine (saturated, 8 mL), dried ($Na_2SO_4$), filtered and the solvent was evaporated under reduced pressure. The residue was purified by silica gel column flash chromatography, eluting with petroleum ether/EtOAc=0~50% to give (S)-tert-butyl (7-(isoxazol-3-yl)-1-(4-(2-methoxypyridin-3-yl)-1-((2-(trimethylsilyl)ethoxy)methyl)-1H-imidazol-2-yl)-7-oxohept-3-en-1-yl)carbamate (33A). LCMS (ESI) calc'd for $C_{30}H_{43}N_5O_6Si$ [M+H]$^+$: 598.3, found: 598.2

Step 2: Preparation of (S)-7-amino-1-(isoxazol-3-yl)-7-(4-(2-methoxypyridin-3-yl)-1H-imidazol-2-yl)hept-4-en-1-one (33B)

TFA (4 mL, 51.9 mmol) was added to (S)-tert-butyl (7-(isoxazol-3-yl)-1-(4-(2-methoxypyridin-3-yl)-1-((2-(trimethylsilyl)ethoxy)methyl)-1H-imidazol-2-yl)-7-oxohept-3-en-1-yl)carbamate (18A, 42 mg, 0.070 mmol) and the mixture was stirred at rt for 3.5 h. The solvent was evaporated under reduced pressure to give (S)-7-amino-1-(isoxazol-3-yl)-7-(4-(2-methoxypyridin-3-yl)-1H-imidazol-2-yl)hept-4-en-1-one (33B) which was used to the next step without further purification. LCMS (ESI) calc'd for $C_{19}H_{21}N_5O_3$ [M+H]$^+$: 368.2, found: 368.2.

Step 3: Preparation of (S)-7-amino-1-(isoxazol-3-yl)-7-(4-(2-methoxypyridin-3-yl)-1H-imidazol-2-yl)heptan-1-one (Example 33)

10% Pd—C (45 mg, 0.042 mmol) was added to (S)-7-amino-1-(isoxazol-3-yl)-7-(4-(2-methoxypyridin-3-yl)-1H-imidazol-2-yl)hept-4-en-1-one (33B, 25 mg, 0.068 mmol) in MeOH (10 ml). The mixture was degassed and backfilled with $H_2$ (three times) and then stirred at rt for 6 h under $H_2$ atmosphere (15 psi). The mixture was filtered and the filter cake was washed with MeOH (30 mL). The filtrate was concentrated to dryness. The residue was purified by preparative HPLC (reverse phase C-18 column), eluting with acetonitrile/water+0.1% TFA, to give (S)-7-amino-1-(isoxazol-3-yl)-7-(4-(2-methoxypyridin-3-yl)-1H-imidazol-2-yl)heptan-1-one (Example 33). LCMS (ESI) calc'd for $C_{19}H_{23}N_5O_3$ [M+H]$^+$: 370.2, found: 370.2. $^1$H NMR (400 MHz, MeOD) δ 8.76 (d, J=1.32 Hz, 1H), 8.30-8.37 (m, 1H), 8.03-8.09 (m, 1H), 7.70 (s, 1H), 7.04 (dd, J=7.28, 5.07 Hz, 1H), 6.75 (d, J=1.32 Hz, 1H), 4.46-4.55 (m, 1H), 4.07 (s, 3H), 3.04 (t, J=7.28 Hz, 2H), 1.98-2.20 (m, 2H), 1.68-1.81 (m, 2H), 1.28-1.48 (m, 1H), 1.26-1.50 (m, 4H).

Example 34

(S)-7-amino-1-(isoxazol-3-yl)-7-(4-(7-methoxyquinolin-6-yl)-1H-imidazol-2-yl)heptan-1-one

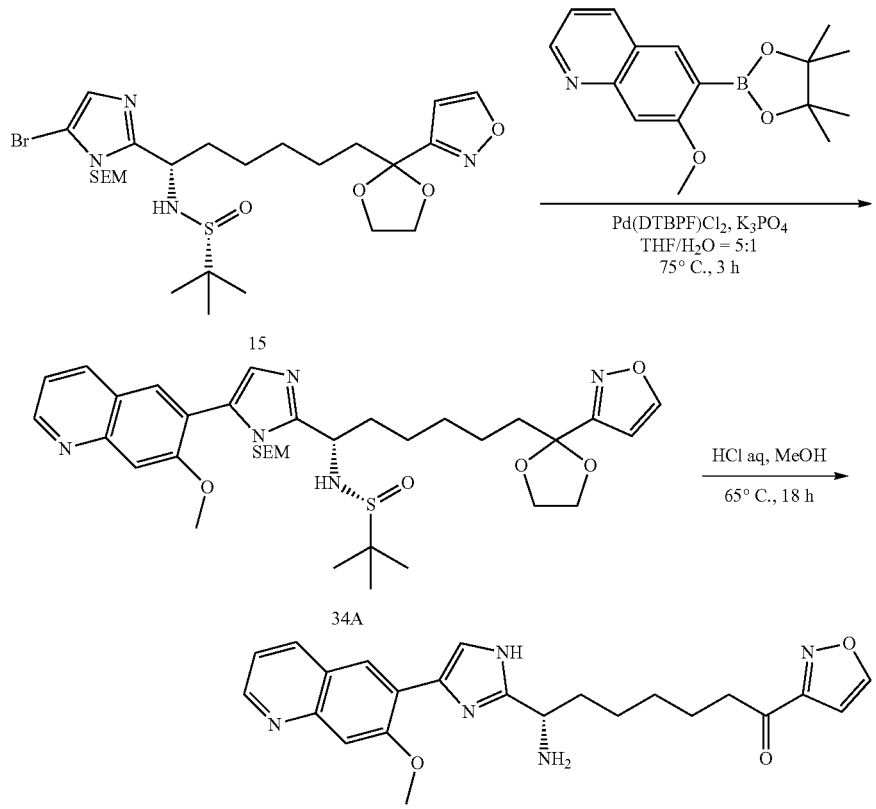

Example 34

Step 1: Preparation of (R)-N-((S)-6-(2-(isoxazol-3-yl)-1,3-dioxolan-2-yl)-1-(5-(7-methoxyquinolin-6-yl)-1-((2-(trimethylsilyl)ethoxy)methyl)-1H-imidazol-2-yl)hexyl)-2-methylpropane-2-sulfinamide (34A)

Pd(DTBPF)Cl$_2$ (16 mg, 0.025 mmol) was added to a stirred mixture of 7-methoxy-6-(4,4,5,5-tetramethyl-1,3,2-dioxaborolan-2-yl)quinoline (69 mg, 0.242 mmol), (R)-N-((S)-1-(5-bromo-1-((2-(trimethylsilyl)ethoxy)methyl)-1H-imidazol-2-yl)-6-(2-(isoxazol-3-yl)-1,3-dioxolan-2-yl)hexyl)-2-methylpropane-2-sulfinamide (15, 100 mg, 0.161 mmol) and K$_3$PO$_4$ (86 mg, 0.403 mmol) in THF (3 ml)/water (0.6 ml) at room temperature and the mixture was stirred at 75° C. for 3 h. The mixture was cooled to room temperature, filtered, evaporated under reduced pressure to afford (R)-N-((S)-6-(2-(isoxazol-3-yl)-1,3-dioxolan-2-yl)-1-(5-(7-methoxyquinolin-6-yl)-1-((2-(trimethylsilyl)ethoxy)methyl)-1H-imidazol-2-yl)hexyl)-2-methylpropane-2-sulfinamide (24A) which was used to the next step without further purification. LCMS (ESI) calc'd for C$_{35}$H$_{51}$N$_5$O$_6$SSi [M+H]$^+$: 698.3, found: 698.4

Step 2: Preparation of (S)-7-amino-1-(isoxazol-3-yl)-7-(4-(7-methoxyquinolin-6-yl)-1H-imidazol-2-yl)heptan-1-one (Example 34)

Hydrogen chloride (2 ml, 8.00 mmol) was added to a stirred mixture of (R)-N-((S)-6-(2-(isoxazol-3-yl)-1,3-dioxolan-2-yl)-1-(5-(7-methoxyquinolin-6-yl)-1-((2-(trimethylsilyl)ethoxy)methyl)-1H-imidazol-2-yl)hexyl)-2-methylpropane-2-sulfinamide (34A, 120 mg, 0.172 mmol) in MeOH (2 ml)/water (0.2 ml) at room temperature and the mixture was stirred at 65° C. for 18 h. The mixture was cooled to room temperature and the residue was purified by preparative HPLC (reverse phase C-18 column), eluting with acetonitrile/water+0.1% TFA, then transferred to HCl salt to give (S)-7-amino-1-(isoxazol-3-yl)-7-(5-(7-methoxyquinolin-6-yl)-1H-imidazol-2-yl)heptan-1-one hydrochloride (Example 34). LCMS (ESI) calc'd for C$_{23}$H$_{25}$N$_5$O$_3$·ClH [M+H]$^+$: 420.2, found: 420.2. $^1$H NMR (400 MHz, CDCl$_3$) δ 8.89-9.09 (m, 3H), 8.46 (s, 1H), 7.96-8.17 (m, 2H), 7.81 (brs, 1H), 6.69 (s, 1H), 5.28 (s, 1H), 5.19 (brs, 1H), 4.23 (brs, 3H), 3.38 (brs, 1H), 3.01 (d, J=6.46 Hz, 2H), 2.15 (s, 1H), 1.70 (brs, 2H), 1.44 (brs, 3H), 1.16-1.26 (m, 1H), 1.22 (brs, 2H).

Example 35

(S)-6-(2-(1-amino-7-(isoxazol-3-yl)-7-oxoheptyl)-1H-imidazol-5-yl)-7-methoxy-1-methylquinolin-2(1H)-one

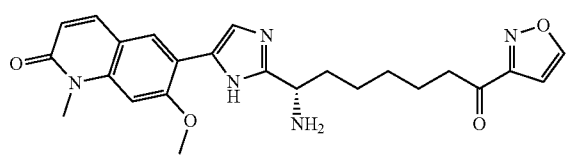

Example 35

(S)-6-(2-(1-amino-7-(isoxazol-3-yl)-7-oxoheptyl)-1H-imidazol-5-yl)-7-methoxy-1-methylquinolin-2(1H)-one (Example 35) was obtained from 15 using similar methodology as described above. LCMS (ESI) calc'd for C$_{24}$H$_{27}$N$_5$O$_4$·ClH [M+H]$^+$: 450.2, found: 450.0. $^1$H NMR (400 MHz, MeOD) δ 8.75 (d, J=1.8 Hz, 1H), 8.17 (s, 1H), 8.06 (s, 1H), 7.90 (d, J=9.4 Hz, 1H), 7.17 (s, 1H), 6.74 (d, J=1.8 Hz, 1H), 6.60 (d, J=9.4 Hz, 1H), 4.95-4.93 (m, 1H), 4.17 (s, 3H), 3.77 (s, 3H), 3.05 (t, J=7.1 Hz, 2H), 2.42-2.31 (m, 1H), 2.26-2.24 (m, 1H), 1.76-1.72 (m, 2H), 1.50-1.45 (m, 3H), 1.40-1.21 (m, 1H).

Example 36

(S)-7-amino-7-(5-(2-fluorophenyl)-1H-imidazol-2-yl)-1-(oxazol-4-yl)heptan-1-one

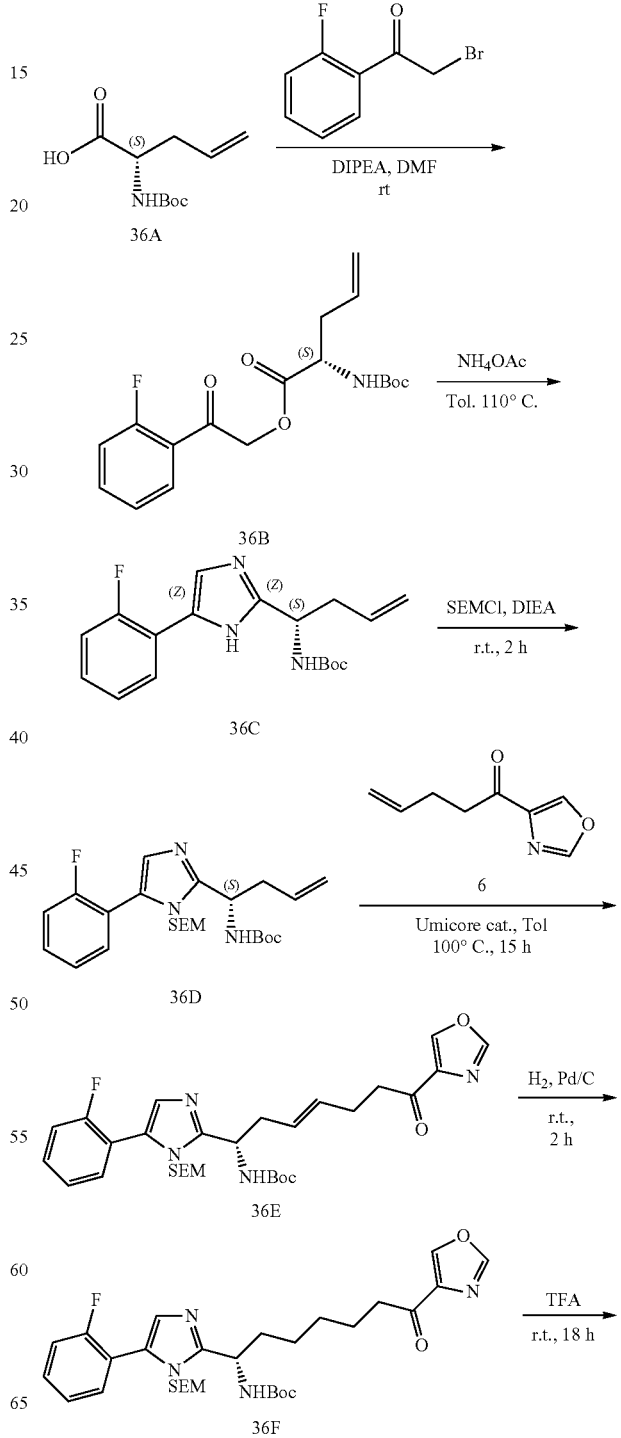

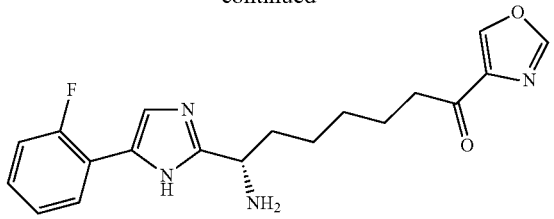

Example 36

Step 1: Preparation of (S)-2-(2-fluorophenyl)-2-oxoethyl 2-((tert-butoxycarbonyl)amino)pent-4-enoate (36B)

DIPEA (2 ml, 11.45 mmol) was added to a solution of (S)-2-((tert-butoxycarbonyl)amino)pent-4-enoic acid (36A, 1.5 g, 6.97 mmol) and 2-bromo-1-(2-fluorophenyl)ethanone (1.528 g, 7.04 mmol) in DMF (20 ml), the resultant mixture was stirred at rt for 1.5 h. The mixture was combined with a 0.5 g reaction and quenched with aqueous $NH_4Cl$ (saturated, 10 mL), and extracted with ethyl acetate (3×50 mL). The combined organic fractions were washed with brine (saturated, 15 mL), dried ($Na_2SO_4$), filtered and the solvent was evaporated under reduced pressure. The residue was purified by silica gel column flash chromatography, eluting with petroleum ether/EtOAc=0-20% to give (S)-2-(2-fluorophenyl)-2-oxoethyl 2-((tert-butoxycarbonyl)amino)pent-4-enoate (36B). LCMS (ESI) calc'd for $C_{18}H_{22}FNO_5$ [M+H]$^+$: 352.1, found: 352.1

Step 2: Preparation of (S)-tert-butyl (1-(5-(2-fluorophenyl)-1H-imidazol-2-yl)but-3-en-1-yl)carbamate (36C)

Ammonium acetate (3.07 g, 39.8 mmol) was added to a stirred mixture of (S)-2-(2-fluorophenyl)-2-oxoethyl 2-((tert-butoxycarbonyl)amino)pent-4-enoate (36B, 3.5 g, 9.96 mmol) in toluene (40 ml) at room temperature and the mixture was stirred at 110° C. for 18 h. The mixture was cooled and evaporated under reduced pressure. The residue was combined with a 0.5 g reaction and purified by silica gel column flash chromatography, eluting with petroleum ether/EtOAc=0-40% to give (S)-tert-butyl (1-(5-(2-fluorophenyl)-1H-imidazol-2-yl)but-3-en-1-yl)carbamate (36C). LCMS (ESI) calc'd for $C_{18}H_{22}FN_3O_2$[M+H]$^+$: 332.2, found: 332.2

Step 3: Preparation of (S)-tert-butyl (1-(5-(2-fluorophenyl)-1-((2-(trimethylsilyl)ethoxy)methyl)-1H-imidazol-2-yl)but-3-en-1-yl)carbamate (36D)

DIPEA (5 ml, 28.6 mmol) was added to a stirred mixture of (S)-tert-butyl (1-(5-(2-fluorophenyl)-1H-imidazol-2-yl)but-3-en-1-yl)carbamate (36C, 3.2 g, 9.66 mmol) and (2-(chloromethoxy)ethyl)trimethylsilane (2.6 ml, 14.69 mmol) in DMF (30 ml) at room temperature and the mixture was stirred at room temperature for 2 h. It was combined with a 1.2 g reaction. Water (50 mL) was added and the mixture was extracted with EtOAc (3×100 mL). The combined organic fractions were washed with brine (saturated, 1×20 mL), dried ($Na_2SO_4$), filtered and the solvent was evaporated under reduced pressure. The residue was purified by silica gel column flash chromatography, eluting with petroleum ether/EtOAc=0~30% to give (S)-tert-butyl (1-(5-(2-fluorophenyl)-1-((2-(trimethylsilyl)ethoxy)methyl)-1H-imidazol-2-yl)but-3-en-1-yl)carbamate (36D). LCMS (ESI) calc'd for $C_{24}H_{36}FN_3O_3Si$ [M+H]$^+$: 462.3, found: 462.3

Step 4: Preparation of (S,E)-tert-butyl (1-(5-(2-fluorophenyl)-1-((2-(trimethylsilyl)ethoxy)methyl)-1H-imidazol-2-yl)-7-(oxazol-4-yl)-7-oxohept-3-en-1-yl)carbamate (36E)

UMICORE M71 SIPR (10 mg, 0.014 mmol) was added to a mixture of (S)-tert-butyl (1-(5-(2-fluorophenyl)-1-((2-(trimethylsilyl)ethoxy)methyl)-1H-imidazol-2-yl)but-3-en-1-yl)carbamate (36D, 100 mg, 0.217 mmol) and 1-(oxazol-4-yl)pent-4-en-1-one (6, 66 mg, 0.437 mmol) in toluene (1 ml) which was bubbled with $N_2$ for 20 mins at rt. The mixture was degassed and backfilled with $N_2$ three times and stirred at 100° C. for 15 h. The reaction mixture was concentrated to dryness, and purified by silica gel chromatography eluted with Petro.Ether:EtOAc=0-50% to give (S,E)-tert-butyl (1-(5-(2-fluorophenyl)-1-((2-(trimethylsilyl)ethoxy)methyl)-1H-imidazol-2-yl)-7-(oxazol-4-yl)-7-oxohept-3-en-1-yl)carbamate (36E, E, Z mixture). LCMS (ESI) calc'd for $C_{30}H_{41}FN_4O_5Si$ [M+H]$^+$: 585.3, found: 585.8

Step 5: Preparation of (S)-tert-butyl (1-(5-(2-fluorophenyl)-1-((2-(trimethylsilyl)ethoxy)methyl)-1H-imidazol-2-yl)-7-(oxazol-4-yl)-7-oxoheptyl)carbamate (36F)

10% Pd—C (4 mg, 0.019 mmol) was added to a stirred mixture of (S,E)-tert-butyl (1-(5-(2-fluorophenyl)-1-((2-(trimethylsilyl)ethoxy)methyl)-1H-imidazol-2-yl)-7-(oxazol-4-yl)-7-oxohept-3-en-1-yl)carbamate (36E, 20 mg, 0.034 mmol) in MeOH (2 ml) at room temperature and the mixture was stirred at room temperature for 2 h. The mixture was filtered and the filtrate was evaporated in vacuo to give (S)-tert-butyl (1-(5-(2-fluorophenyl)-1-((2-(trimethylsilyl)ethoxy)methyl)-1H-imidazol-2-yl)-7-(oxazol-4-yl)-7-oxoheptyl)carbamate (36F,) which was used to the next step without further purification. LCMS (ESI) calc'd for $C_{30}H_{43}FN_4O_5Si$ [M+H]$^+$: 587.3, found: 587.4

Step 6: Preparation of (S)-7-amino-7-(5-(2-fluorophenyl)-1H-imidazol-2-yl)-1-(oxazol-4-yl)heptan-1-one (Example 36)

TFA (1 mL, 12.98 mmol) was added to a stirred mixture of (S)-tert-butyl (1-(5-(2-fluorophenyl)-1-((2-(trimethylsilyl)ethoxy)methyl)-1H-imidazol-2-yl)-7-(oxazol-4-yl)-7-oxoheptyl)carbamate (36F, 20 mg, 0.034 mmol) at room temperature and the mixture was stirred at room temperature for 18 h. The mixture was evaporated in vacuo to remove TFA. The residue was purified by preparative HPLC (reverse phase C-18 column), eluting with acetonitrile/water+ 0.1% TFA, to give (S)-7-amino-7-(5-(2-fluorophenyl)-1H-imidazol-2-yl)-1-(oxazol-4-yl)heptan-1-one (Example 36). LCMS (ESI) calc'd for $C_{19}H_{21}FN_4O_2$[M+H]$^+$: 357.2, found: 357.1. $^1$H NMR (400 MHz, MeOD) δ 8.58 (s, 1H), 8.24 (s, 1H), 8.00 (t, J=6.75 Hz, 1H), 7.50 (d, J=3.72 Hz, 1H), 7.11-7.28 (m, 3H), 4.41-4.47 (m, 1H), 2.88 (t, J=7.14 Hz, 2H), 2.07-2.18 (m, 1H), 1.98-2.07 (m, 1H), 1.65-1.74 (m, 2H), 1.31-1.46 (m, 4H), 1.26-1.31 (m, 2H).

Example 37

(S)-7-amino-7-(5-(2-fluorophenyl)-1H-imidazol-2-yl)-1-(isoxazol-3-yl)heptan-1-one

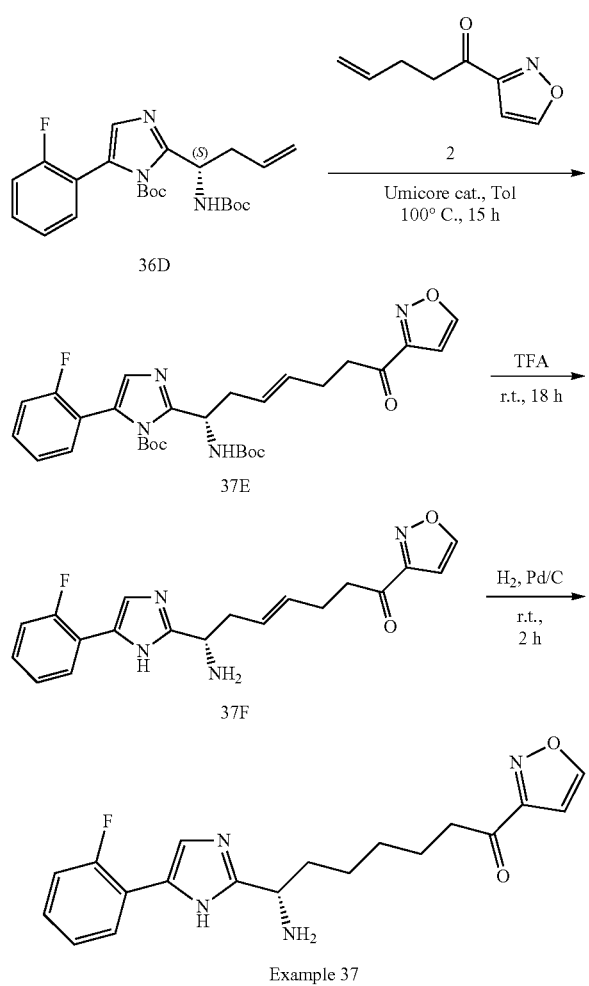

Step 1: tert-butyl (S,E)-2-(1-((tert-butoxycarbonyl)amino)-7-(isoxazol-3-yl)-7-oxohept-3-en-1-yl)-5-(2-fluorophenyl)-1H-imidazole-1-carboxylate (37E)

A100 ml one neck round bottom flask was charged with toluene (8 ml) and a mixture of (S)-tert-butyl 2-(1-((tert-butoxycarbonyl)amino)but-3-en-1-yl)-4-(2-fluorophenyl)-1H-imidazole-1-carboxylate (36D, 1.1 g, 2.55 mmol); 1-(isoxazol-3-yl)pent-4-en-1-one (2, 800 mg, 5.29 mmol) and UMICOREM71 SIPR (80 mg, 0.097 mmol). The mixture was degassed and refilled with nitrogen, and then stirred at 65° C. overnight. After it was cooled to room temperature, the mixture was Purified on Analogix (Redisep 80 g column) eluting with 30% EtOAc-Hexanes yielding (S,E)-tert-butyl 2-(1-((tert-butoxycarbonyl)amino)-7-(isoxazol-3-yl)-7-oxo-hept-3-en-1-yl)-4-(2-fluorophenyl)-1H-imidazole-1-carboxylate (37E). LCMS (ESI) calc'd for $C_{29}H_{35}FN_4O_6[M+H]^+$: 555.1, found: 555.1.

Step 2: (S,E)-7-amino-7-(5-(2-fluorophenyl)-1H-imidazol-2-yl)-1-(isoxazol-3-yl)hept-4-en-1-one (37F)

A 50 ml one neck round bottom flask was charged with (S,E)-tert-butyl 2-(1-((tert-butoxycarbonyl)amino)-7-(isoxazol-3-yl)-7-oxohept-3-en-1-yl)-4-(2-fluorophenyl)-1H-imidazole-1-carboxylate (37E) (280 mg, 0.865 mmol) in TFA (2 ml)/DCM (10 ml). The mixture was then stirred at room temperature for 1 hour. The reaction mixture was then concentrated, and the residue was dissolved in $CH_2Cl_2$ (20 ml). The re-evaporation provided (S,E)-7-amino-7-(4-(2-fluorophenyl)-1H-imidazol-2-yl)-1-(isoxazol-3-yl)hept-4-en-1-one (37F), TFA crude which was used directly to next step. LCMS (ESI) calc'd for $C_{19}H_{19}FN_4O_2[M+H]^+$: 355.1, found: 355.0.

Step 3: (S)-7-amino-7-(5-(2-fluorophenyl)-1H-imidazol-2-yl)-1-(isoxazol-3-yl)heptan-1-one

Example 37

To a 50 ml one neck round bottom flask was added 10% Pd/C, 50% in $H_2O$ (10 mg) to solution of (S,E)-7-amino-7-(4-(2-fluorophenyl)-1H-imidazol-2-yl)-1-(isoxazol-3-yl) hept-4-en-1-one, TFA (37F) (280 mg, 0.213 mmol) in MeOH (5 ml). The system was connected to a hydrogen balloon through a three way joint. It was vacuumed and refilled with hydrogen three times. The mixture was then stirred under hydrogen atmosphere for 3 hours. The mixture was filtered through celite, washed with methanol, and the filtrate was evaporated to provide residue, which was purified by RP-HPLC (TFA_50 ml_10_40_8m_V3_C1 yielding (S)-7-amino-7-(4-(2-fluorophenyl)-1H-imidazol-2-yl)-1-(isoxazol-3-yl)heptan-1-one (Example 37), TFA. LCMS (ESI) calc'd for $C_{19}H_{21}FN_4O_2[M+H]^+$: 356.1, found: 357.0.

Example 38

(S)-N-(1-(5-(2-fluorophenyl)-1H-imidazol-2-yl)-7-(isoxazol-3-yl)-7-oxoheptyl)-1-methylazetidine-3-carboxamide

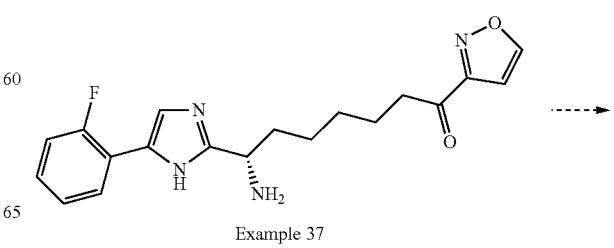

Example 37

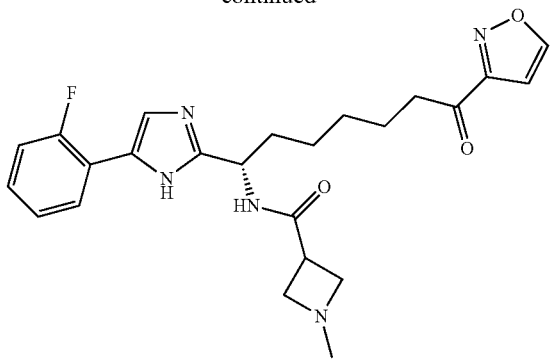

Example 38

To a 25 ml one neck round bottom flask was added dissolved (S)-7-amino-7-(4-(2-fluorophenyl)-1H-imidazol-2-yl)-1-(isoxazol-3-yl)heptan-1-one (from Example 37) (20 mg, 0.053 mmol) in methylene chloride (1 mL). Then 1-hydroxybenzotriazole (10 mg, 0.074 mmol) and 1-(3-dimethylaminopropyl)-3-ethylcarbodiimide hydrochloride (15 mg, 0.078 mmol) was added to the solution, followed by 1-methyl-3-azetidinecarboxylic acid (10 mg, 0.087 mmol) in DMF (1 ml). Finally, 4-methylmorpholine (0.05 ml, 0.455 mmol) was added and the resulting reaction mixture was stirred at room temperature overnight. The mixture was purified by RP HPLC yielding the product which was dissolved in acetonitrile/water and freeze dried/lyophilized yielding (S)-N-(1-(4-(2-fluorophenyl)-1H-imidazol-2-yl)-7-(isoxazol-3-yl)-7-oxoheptyl)-1-methylazetidine-3-carboxamide (Example 38), TFA. LCMS (ESI) calc'd for $C_{24}H_{28}FN_5O_3[M+H]^+$: 454.2.1, found: 454.0. $^1$H NMR (400 MHz, MeOD) δ 8.77 (1H, s), 7.92 (1H, s), 7.34 (1H, s), 7.29 (2H, m), 7.13 (1H, m), 6.77 (1H, s), 5.04 (1H, t), 3.65 (2H, m), 3.42 (2H, m), 3.31 (3H, s), 3.05 (2H, m), 1.95 (2H, m), 1.79 (2H, m), 1.2-1.5 (8H, m) ppm.

The following examples were prepared using the same procedure as Example 38, using different acids and amines for coupling.

| Example # | Structure | Exact Mass [M + H]⁺ | Observed [M + H]⁺ |
|---|---|---|---|
| 39 | 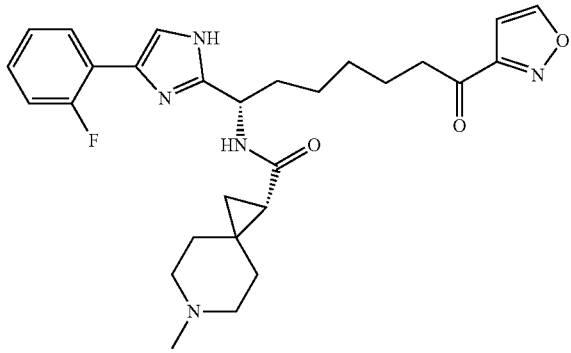<br>Exact Mass: 507.26 | Calc'd 508.2 | 508.1 |
| 40 | 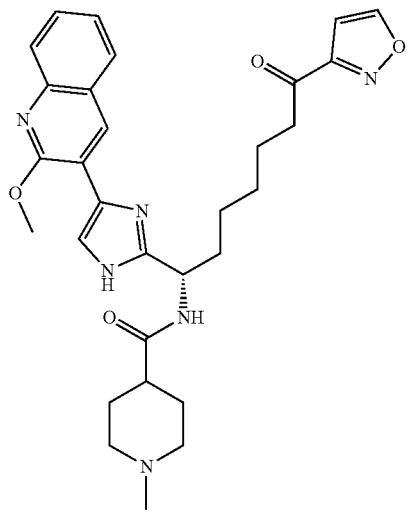<br>Exact Mass: 544.28 | Calc'd 545.2 | 545.3 |

-continued
| Example # | Structure | Exact Mass [M + H]+ | Observed [M + H]+ |
|---|---|---|---|
| 41 | 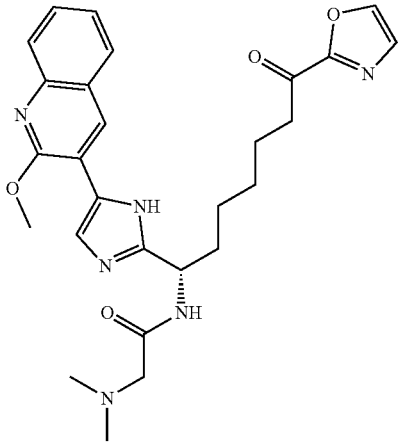<br>Exact Mass: 504.25 | Calc'd 505.3 | 505.3 |
| 42 | 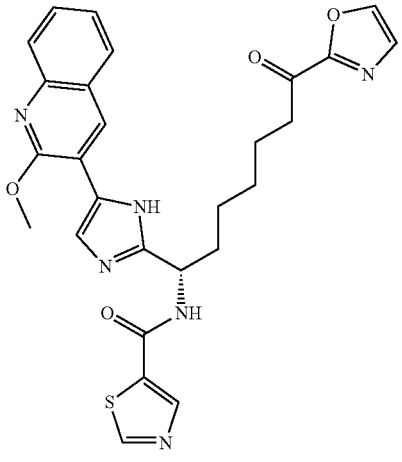<br>Exact Mass: 530.17 | Calc'd 531.2 | 530.9 |
| 43 | 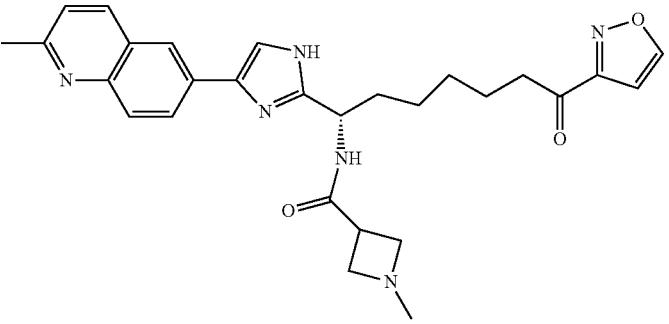<br>Exact Mass: 500.25 | Calc'd 501.3 | 501.1 |

-continued
| Example # | Structure | Exact Mass [M + H]⁺ | Observed [M + H]⁺ |
|---|---|---|---|
| 44 | 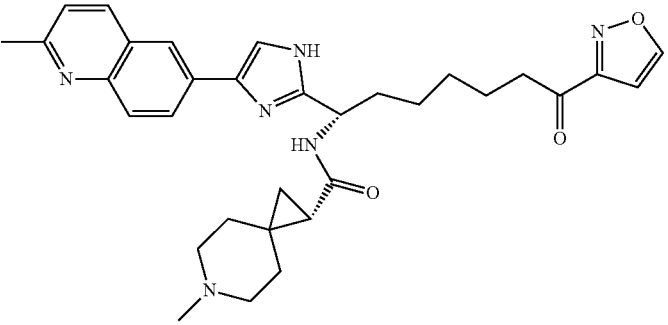<br>Exact Mass: 554.30 | Calc'd 555.3 | 555.2 |
| 45 | 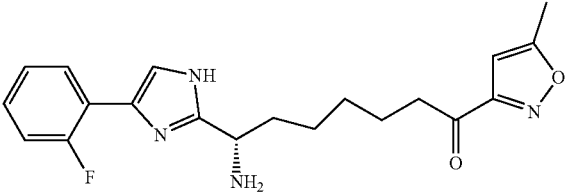<br>Exact Mass: 370.18 | Calc'd 371.3 | 371.1 |
| 46 | 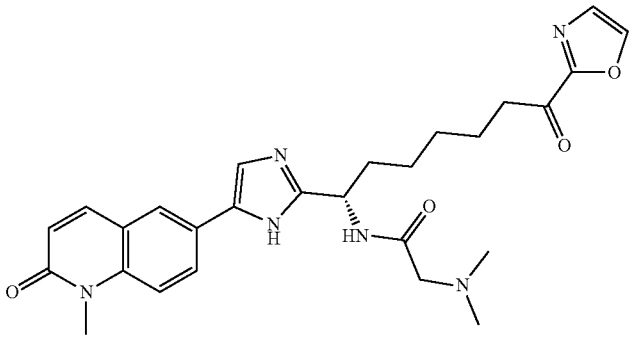 [SMILES: CN(C)CC(=O)N[C@@H](CCCCCC(=O)c1ncco1)c1ncc(-c2ccc3c(ccc(=O)n3C)c2)[nH]1] | Calc'd 505.3 | 505.3 |
| 47 | 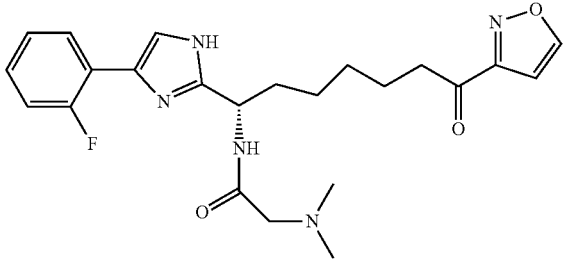 [SMILES: CN(C)CC(=O)N[C@@H](CCCCCC(=O)c1ccon1)c1nc(-c2ccccc2F)c[nH]1] | Calc'd 442.3 | 442.1 |
| 48 | 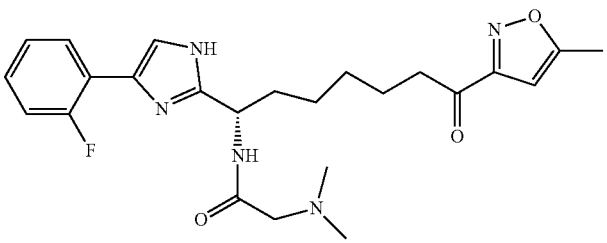 [SMILES: Cc1cc(C(=O)CCCCC[C@H](NC(=O)CN(C)C)c2nc(-c3ccccc3F)c[nH]2)no1] | Calc'd 456.3 | 456.0 |

-continued
| Example # | Structure | Exact Mass [M + H]+ | Observed [M + H]+ |
|---|---|---|---|
| 49 | 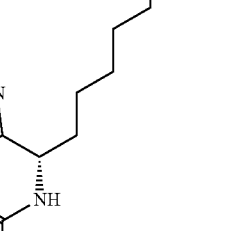 | Calc'd 454.3 | 454.2 |
| 50 | 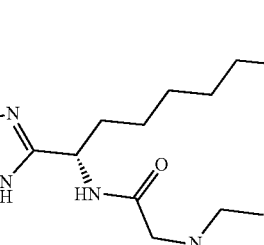 | Calc'd 533.3 | 533.4 |
| 51 | 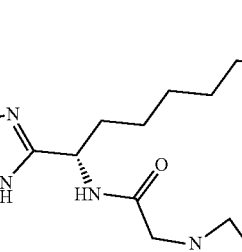 | Calc'd 517.3 | 517.4 |
| 52 | 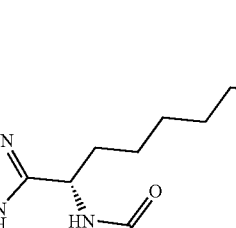 | Calc'd 531.3 | 531.4 |

-continued

| Example # | Structure | Exact Mass [M + H]+ | Observed [M + H]+ |
|---|---|---|---|
| 53 | 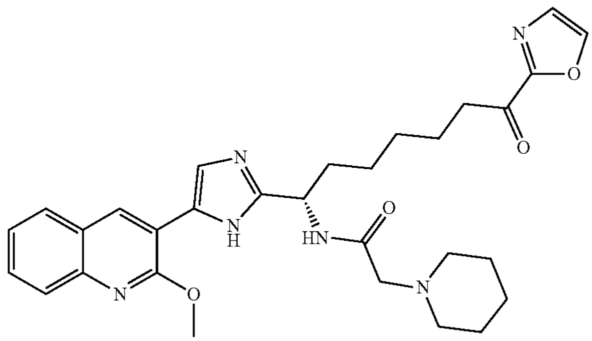 [SMILES: COc1nc2ccccc2cc1-c1cnc([C@H](CCCCCC(=O)c2ncco2)NC(=O)CN2CCCCC2)[nH]1] | Calc'd 545.3 | 545.4 |
| 54 | 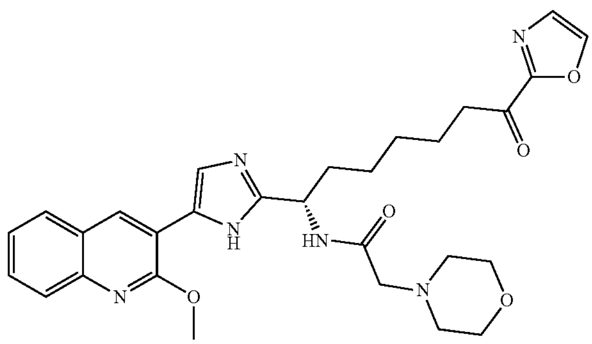 [SMILES: COc1nc2ccccc2cc1-c1cnc([C@H](CCCCCC(=O)c2ncco2)NC(=O)CN2CCOCC2)[nH]1] | Calc'd 547.3 | 547.4 |
| 55 | 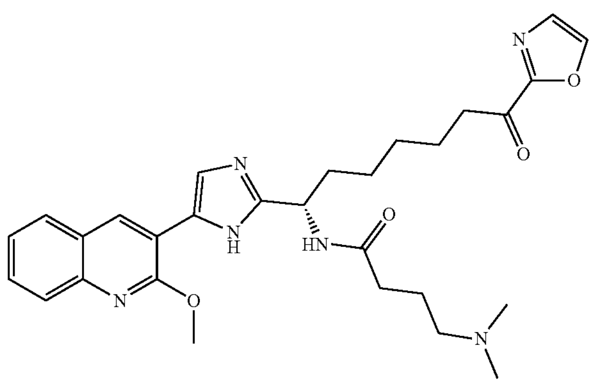 [SMILES: COc1nc2ccccc2cc1-c1cnc([C@H](CCCCCC(=O)c2ncco2)NC(=O)CCCN(C)C)[nH]1] | Calc'd 533.3 | 533.5 |
| 56 | 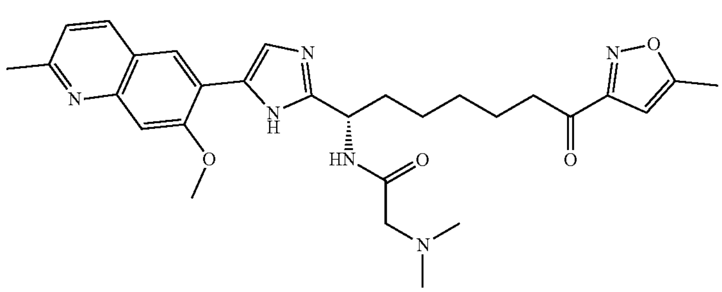 | Calc'd 533.3 | 533.4 |

-continued

| Example # | Structure | Exact Mass [M + H]+ | Observed [M + H]+ |
|---|---|---|---|
| 57 | 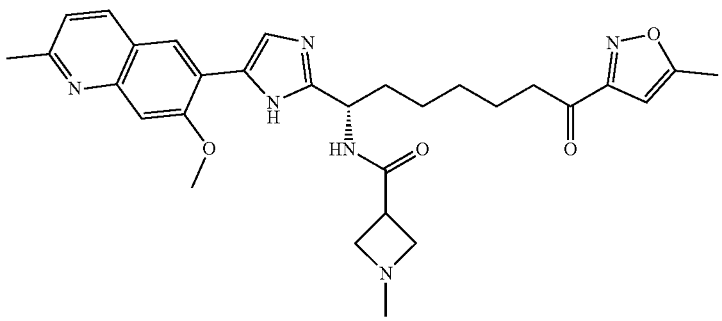 | Calc'd 545.3 | 545.4 |
| 58 | 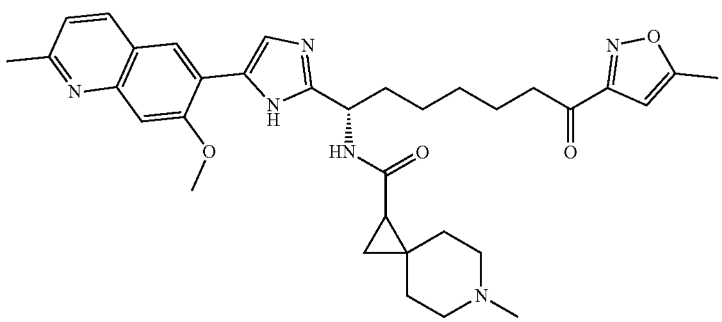 | Calc'd 599.3 | 599.5 |
| 59 | 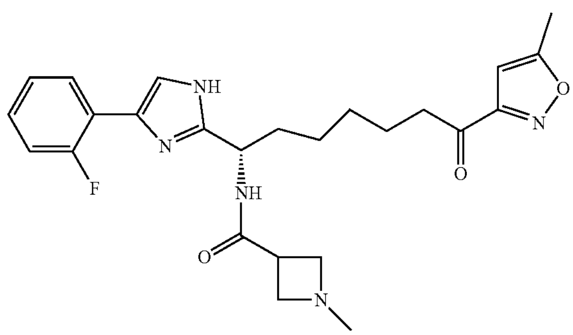 [SMILES: Cc1cc(C(=O)CCCCC[C@H](NC(=O)C2CN(C)C2)c2nc(-c3ccccc3F)c[nH]2)no1] | Calc'd 468.3 | 468.1 |
| 60 | 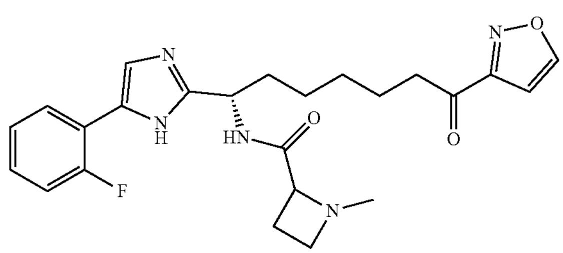 [SMILES: CN1CCC1C(=O)N[C@@H](CCCCCC(=O)c1ccon1)c1ncc(-c2ccccc2F)[nH]1] | Calc'd 454.3 | 454.4 |
| 61 | 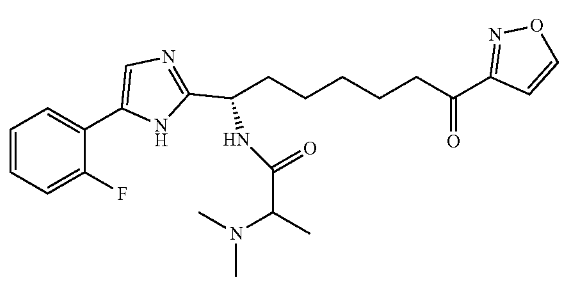 [SMILES: CC(C(=O)N[C@@H](CCCCCC(=O)c1ccon1)c1ncc(-c2ccccc2F)[nH]1)N(C)C] | Calc'd 456.3 | 456.5 |

| Example # | Structure | Exact Mass [M + H]+ | Observed [M + H]+ |
|---|---|---|---|
| 62 | 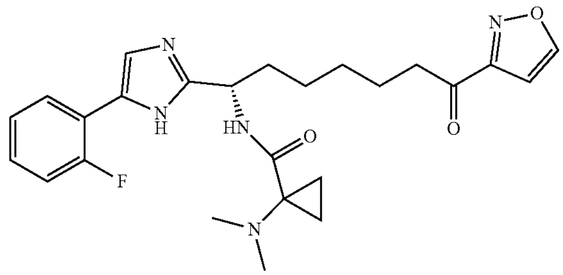 [SMILES: CN(C)C1(C(=O)N[C@@H](CCCCCC(=O)c2ccon2)c2ncc(-c3ccccc3F)[nH]2)CC1] | Calc'd 468.3 | 468.4 |
| 63 | 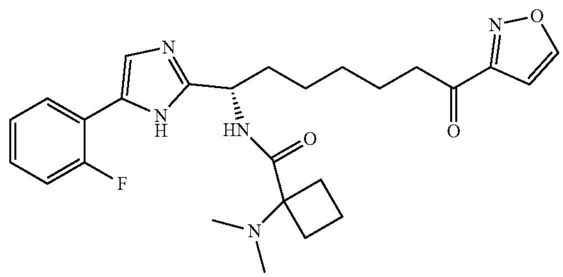 [SMILES: CN(C)C1(C(=O)N[C@@H](CCCCCC(=O)c2ccon2)c2ncc(-c3ccccc3F)[nH]2)CCC1] | Calc'd 482.3 | 482.5 |
| 64 | 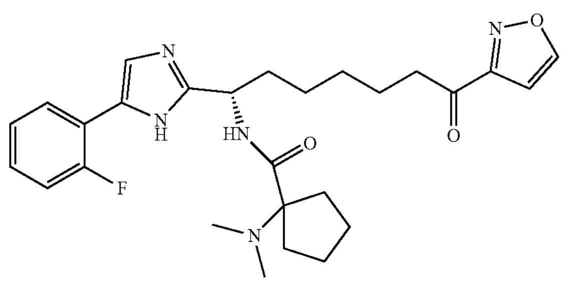 [SMILES: CN(C)C1(C(=O)N[C@@H](CCCCCC(=O)c2ccon2)c2ncc(-c3ccccc3F)[nH]2)CCCC1] | Calc'd 496.3 | 496.5 |
Example 65
(R)-5-(5-(4-fluorophenyl)-1H-imidazol-2-yl)-5-(6-(oxazol-2-yl)-6-oxohexyl)pyrrolidin-2-one
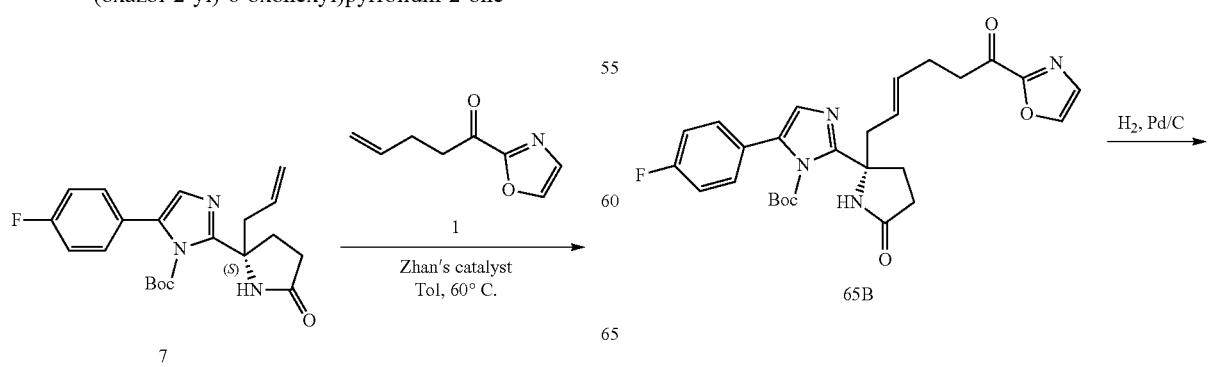

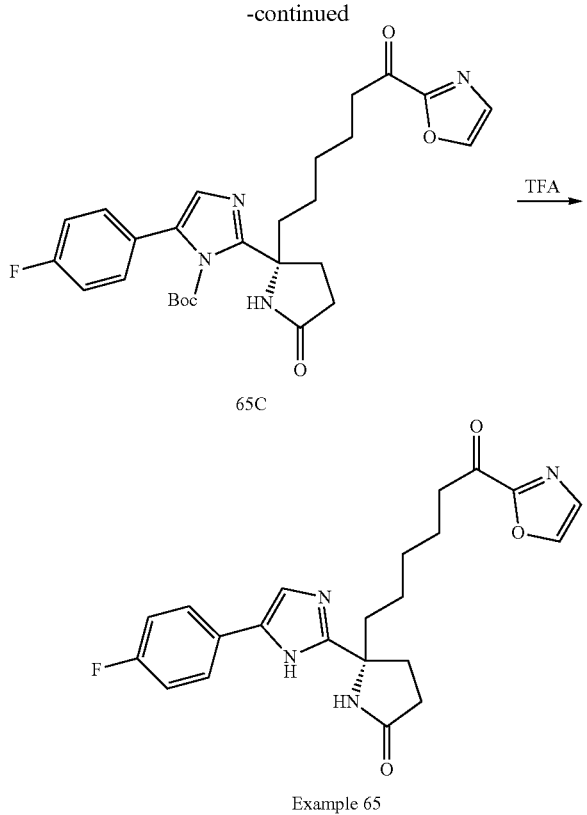

Example 65

Step 1: Preparation of (S,E)-tert-butyl 5-(4-fluorophenyl)-2-(2-(6-(oxazol-2-yl)-6-oxohex-2-en-1-yl)-5-oxopyrrolidin-2-yl)-1H-imidazole-1-carboxylate (65B)

Toluene (1 ml) was added to (S)-tert-butyl 2-(2-allyl-5-oxopyrrolidin-2-yl)-5-(4-fluorophenyl)-1H-imidazole-1-carboxylate (7, 105 mg, 0.272 mmol) and 1-(oxazol-2-yl)pent-4-en-1-one (165 mg, 1.090 mmol) and Zhan catalyst-1B (10 mg, 0.014 mmol), the solvent was degassed, then it was stirred at 60° C. for 20 h. The reaction mixture was concentrated in vacuo and the residue was purified by silica gel flash chromatography (ISCORF75; Sepa flash column), eluting with petroleum ether/EtOAc=10:1-1:1 to give (S,E)-tert-butyl 5-(4-fluorophenyl)-2-(2-(6-(oxazol-2-yl)-6-oxohex-2-en-1-yl)-5-oxopyrrolidin-2-yl)-1H-imidazole-1-carboxylate (65B). LCMS (ESI) calc'd for $C_{27}H_{29}FN_4O_5$ [M+H]$^+$: 509.2, found: 509.3.

Step 2: Preparation of (R)-tert-butyl 5-(4-fluorophenyl)-2-(2-(6-(oxazol-2-yl)-6-oxohexyl)-5-oxopyrrolidin-2-yl)-1H-imidazole-1-carboxylate (65C)

A solution of (S,E)-tert-butyl 5-(4-fluorophenyl)-2-(2-(6-(oxazol-2-yl)-6-oxohex-2-en-1-yl)-5-oxopyrrolidin-2-yl)-1H-imidazole-1-carboxylate (65B, 37 mg, 0.073 mmol) in ethanol (5 ml) was added to a 100 mL three-necked bottle and then Pd—C (20 mg, 0.019 mmol) (10%, dry) was added under Ar. The suspension was degassed under vacuum and purged with H$_2$ several times. The mixture was then stirred under H$_2$ (15 psi) at 25° C. for 1 h. The mixture was filtered and the filter cake was washed with ethanol (5 mL), concentrated to give (R)-tert-butyl 5-(4-fluorophenyl)-2-(2-(6-(oxazol-2-yl)-6-oxohexyl)-5-oxopyrrolidin-2-yl)-1H-imidazole-1-carboxylate (65C) which was used in the next step without purification. LCMS (ESI) calc'd for $C_{17}H_{31}FN_4O_5$ [M+H]$^+$: 511.2, found: 511.3.

Step 5: Preparation of (R)-5-(5-(4-fluorophenyl)-1H-imidazol-2-yl)-5-(6-(oxazol-2-yl)hept-6-en-1-yl)pyrrolidin-2-one (Example 65)

TFA (200 µl, 2.60 mmol) was added to the solution of (R)-tert-butyl 5-(4-fluorophenyl)-2-(2-(6-(oxazol-2-yl)-6-oxohexyl)-5-oxopyrrolidin-2-yl)-1H-imidazole-1-carboxylate (65C, 150 mg, 0.294 mmol) in DCM (1 ml) at rt and stirred at rt for 2 h. The mixture was concentrated in vacuo and the residue was purified by preparative HPLC (reverse phase C-18 column), eluting with acetonitrile/water+0.1% TFA, to give (R)-5-(5-(4-fluorophenyl)-1H-imidazol-2-yl)-5-(6-(oxazol-2-yl)-6-oxohexyl)pyrrolidin-2-one (Example 65). LCMS (ESI) calc'd for $C_{12}H_{23}FN_4O_3$[M+H]$^+$: 411.2, found: 411.1. $^1$H NMR (400 MHz, MeOD) δ 8.09 (s, 1H), 7.73-7.83 (m, 3H), 7.38 (s, 1H), 7.27 (t, J=8.80 Hz, 2H), 3.06 (t, J=7.24 Hz, 2H), 2.44-2.54 (m, 5H), 2.06-2.24 (m, 2H), 1.75 (quin, J=7.24 Hz, 2H), 1.38-1.58 (m, 4H).

Example 66

4-(4-(4-fluorophenyl)-1H-imidazol-2-yl)-4-(6-(oxazol-2-yl)-6-oxohexyl)oxazolidin-2-one

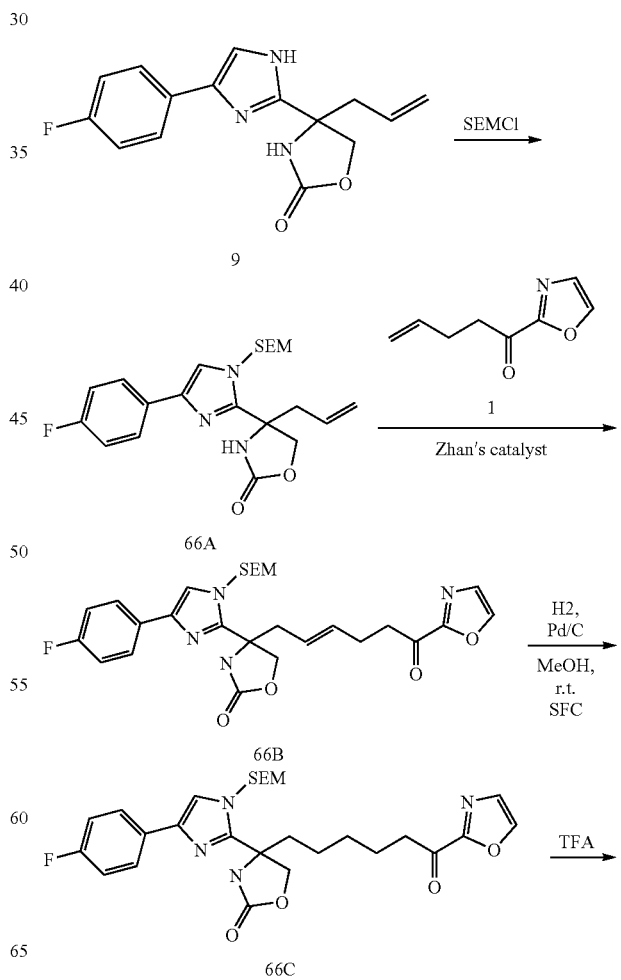

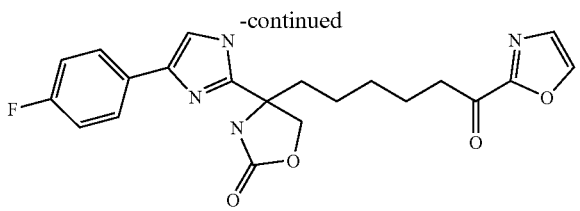

Example 66E1 and Example 66E2

Step 1: Preparation of 4-allyl-4-(4-(4-fluorophenyl)-1-((2-(trimethylsilyl)ethoxy)methyl)-1H-imidazol-2-yl)oxazolidin-2-one (66A)

SEMCl (2.223 ml, 12.53 mmol) was added to the solution of 4-allyl-4-(4-(4-fluorophenyl)-1H-imidazol-2-yl)oxazolidin-2-one (9, 900 mg, 3.13 mmol), DMAP (10 mg, 0.082 mmol) and DIPEA (2.74 ml, 15.66 mmol) in DMF (15 ml), the resultant mixture was stirred at rt for 16 h. The mixture was quenched with brine (saturated, 10 mL), and the mixture was extracted with ethyl acetate (2×15 mL). The combined organic fractions were washed with brine (saturated, 20 mL), dried ($Na_2SO_4$), filtered and the solvent was evaporated under reduced pressure. The residue was purified by silica gel flash chromatography (ISCORF75; Sepa flash column), eluting with petroleum ether/EtOAc=10:1-2:1 to give 4-allyl-4-(4-(4-fluorophenyl)-1-((2-(trimethylsilyl)ethoxy)methyl)-1H-imidazol-2-yl)oxazolidin-2-one (66A). LCMS (ESI) calc'd for $C_{21}H_{28}FN_3O_3Si$ [M+H]$^+$: 418.2, found: 418.2

Step 2: Preparation of (E)-4-(4-(4-fluorophenyl)-1-((2-(trimethylsilyl)ethoxy)methyl)-1H-imidazol-2-yl)-4-(6-(oxazol-2-yl)-6-oxohex-2-en-1-yl)oxazolidin-2-one (66B)

Zhan's catalyst (88 mg, 0.120 mmol) (in three potions by a interval of 3 h) was added to the solution of 1-(oxazol-2-yl)pent-4-en-1-one (1, 1086 mg, 7.18 mmol) in 4 potions with catalyst) and 4-allyl-4-(4-(4-fluorophenyl)-1-((2-(trimethylsilyl)ethoxy)methyl)-1H-imidazol-2-yl)oxazolidin-2-one (66A, 500 mg, 1.197 mmol) in degassed toluene (10 ml), the resultant mixture was stirred at 105° C. for 16 h under $N_2$ atmosphere. The mixture was concentrated in vacuo. The residue was purified by silica gel flash chromatography (ISCORF75; Sepa flash column), eluting with petroleum ether/EtOAc=10:1-1:1 to give (E)-4-(4-(4-fluorophenyl)-1-((2-(trimethylsilyl)ethoxy)methyl)-1H-imidazol-2-yl)-4-(6-(oxazol-2-yl)-6-oxohex-2-en-1-yl)oxazolidin-2-one (66B). LCMS (ESI) calc'd for $C_{27}H_{33}FN_4O_5Si$ [M+H]$^+$: 541.2, found: 541.3

Step 3: Preparation of 4-(4-(4-fluorophenyl)-1-((2-(trimethylsilyl)ethoxy)methyl)-1H-imidazol-2-yl)-4-(6-(oxazol-2-yl)-6-oxohexyl)oxazolidin-2-one (66C)

A solution of (E)-4-(4-(4-fluorophenyl)-1-((2-(trimethylsilyl)ethoxy)methyl)-1H-imidazol-2-yl)-4-(6-(oxazol-2-yl)-6-oxohex-2-en-1-yl)oxazolidin-2-one (66A, 150 mg, 0.277 mmol) in MeOH (10 ml) was added to a 100 mL bottle and then Pd/C (30 mg, 0.028 mmol) (10%, wet) was added under $N_2$. The suspension was degassed under vacuum and purged with $H_2$ several times. The mixture was then stirred under $H_2$ (Pressure: 15 psi) at room temperature for 4 h. The mixture was filtered through Celite and the filter cake was washed with MeOH (2*20 mL). The filtrate was concentrated to dryness and the residue was purified by preparative HPLC (reverse phase C-18 column), eluting with acetonitrile/water+0.1% TFA, to give 4-(4-(4-fluorophenyl)-1-((2-(trimethylsilyl)ethoxy)methyl)-1H-imidazol-2-yl)-4-(6-(oxazol-2-yl)-6-oxohexyl)oxazolidin-2-one (66C). LCMS (ESI) calc'd for $C_{27}H_{35}FN_4O_5Si$ [M+H]$^+$: 543.2, found: 543.3

The racemate was further separated by chiral SFC using a ChiralPak AD column, to afford two singer isomers.

Step 4: Preparation of 4-(4-(4-fluorophenyl)-1H-imidazol-2-yl)-4-(6-(oxazol-2-yl)-6-oxohexyl)oxazolidin-2-one (Example 66E1 and Example 66E2)

TFA (5 ml, 64.9 mmol) was added to the solution of 4-(4-(4-fluorophenyl)-1-((2-(trimethylsilyl)ethoxy)methyl)-1H-imidazol-2-yl)-4-(6-(oxazol-2-yl)-6-oxohexyl)oxazolidin-2-one (66CE1, peak 1, 40 mg, 0.074 mmol) in DCM (1 ml), and the resultant mixture was stirred at rt for 16 h. The reaction mixture was concentrated in vacuo and the residue was purified by preparative HPLC (reverse phase C-18 column), eluting with acetonitrile/water+0.1% TFA, to give 4-(4-(4-fluorophenyl)-1H-imidazol-2-yl)-4-(6-(oxazol-2-yl)-6-oxohexyl)oxazolidin-2-one (Example 66E1). LCMS (ESI) calc'd for $C_{21}H_{21}FN_4O_4$[M+H]$^+$: 413.2, found: 413.2. $^1$H NMR (400 MHz, MeOD) δ 8.08 (s, 1H), 7.78 (brs, 3H), 7.38 (s, 1H), 7.23 (t, J=8.41 Hz, 2H), 4.58 (q, J=9.13 Hz, 2H), 3.06 (t, J=7.04 Hz, 2H), 2.20 (t, J=7.73 Hz, 2H), 1.68-1.83 (m, 2H), 1.23-1.63 (m, 4H).

Compound Example 66E2 was prepared using similar methodology from peak 2, yield 94%, white solid. LCMS (ESI) calc'd for $C_{21}H_{21}FN_4O_4$[M+H]$^+$: 413.2, found: 413.2. $^1$H NMR (400 MHz, MeOD) δ 8.09 (s, 1H), 7.67-7.82 (m, 3H), 7.38 (s, 1H), 7.23 (t, J=8.71 Hz, 2H), 4.46-4.65 (m, 2H), 3.07 (t, J=7.24 Hz, 2H), 2.18 (t, J=7.92 Hz, 2H), 1.76 (quin, J=7.19 Hz, 2H), 1.24-1.62 (m, 4H).

Example 67

(S)-5-(4-(2-fluoro-4-(oxazol-2-yl)phenyl)-1H-imidazol-2-yl)-5-(6-(isoxazol-3-yl)-6-oxohexyl)pyrrolidin-2-one

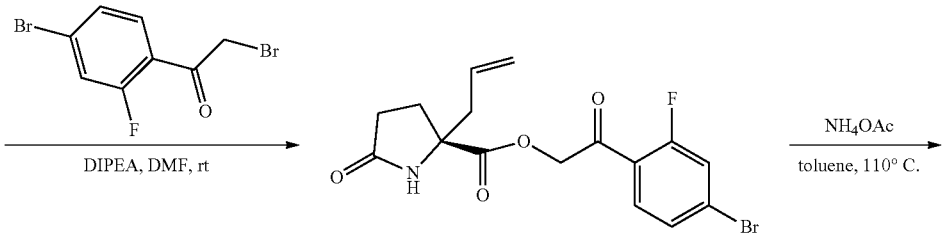

67A

-continued
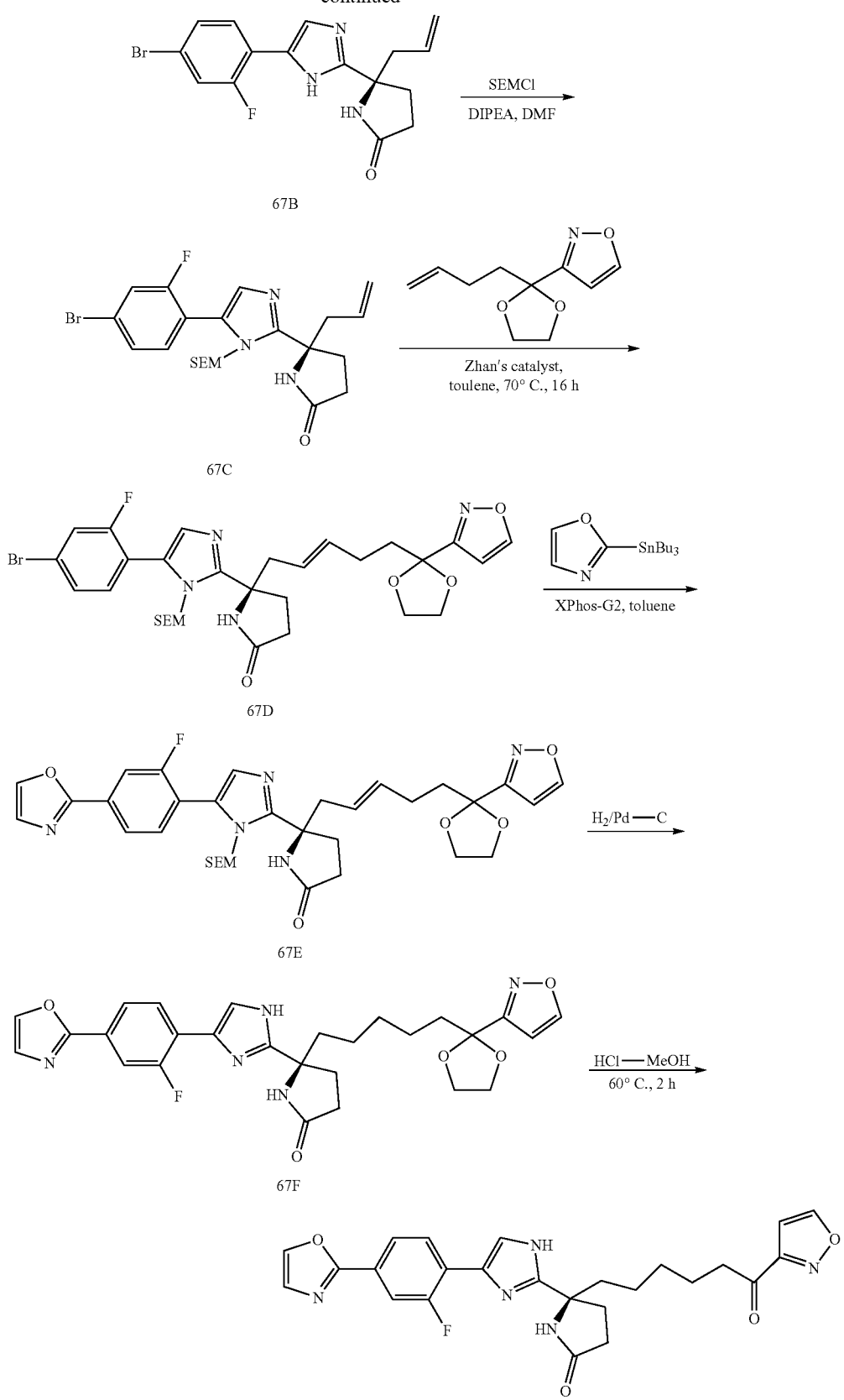
Example 67

Step 1: Preparation of (R)-2-(4-bromo-2-fluorophenyl)-2-oxoethyl 2-allyl-5-oxopyrrolidine-2-carboxylate (67A)

DIPEA (0.883 ml, 5.05 mmol) was added to the solution of (R)-2-allyl-5-oxopyrrolidine-2-carboxylic acid (7-3, 570 mg, 3.37 mmol) and 2-bromo-1-(4-bromo-2-fluorophenyl) ethanone (1007 mg, 3.40 mmol) in DMF (20 ml), and the resultant mixture was stirred at rt for 1.5 h. The mixture was quenched with aqueous NH$_4$Cl (saturated, 10 mL), and the mixture was extracted with ethyl acetate (3×30 mL). The combined organic fractions were washed with brine (saturated, 15 mL), dried (Na$_2$SO$_4$), filtered and the solvent was evaporated under reduced pressure to give (R)-2-(4-bromo-2-fluorophenyl)-2-oxoethyl 2-allyl-5-oxopyrrolidine-2-carboxylate (67A) which was used to the next step without further purification. LCMS (ESI) calc'd for C$_{16}$H$_{15}$BrFNO$_4$ [M+H]$^+$: 384.0, found: 386.1

Step 2: Preparation of (R)-5-allyl-5-(5-(4-bromo-2-fluorophenyl)-1H-imidazol-2-yl)pyrrolidin-2-one (67B)

NH$_4$OAc (1023 mg, 13.27 mmol) was added to the solution of (R)-2-(4-bromo-2-fluorophenyl)-2-oxoethyl 2-allyl-5-oxopyrrolidine-2-carboxylate (67A, 5100 mg, 13.27 mmol) in toluene (10 ml), the resultant mixture was stirred at 110° C. for 2 h. The mixture was concentrated in vacuo. The residue was purified by silica gel flash chromatography (ISCORF75; Sepa flash column), eluting with petroleum ether/EtOAc=10:1-1:2 to give (R)-5-allyl-5-(5-(4-bromo-2-fluorophenyl)-1H-imidazol-2-yl)pyrrolidin-2-one (67B). LCMS (ESI) calc'd for C$_{16}$H$_{15}$BrFN$_3$O [M+H]$^+$: 364, found: 363.9

Step 3: Preparation of (R)-5-allyl-5-(4-(4-bromo-2-fluorophenyl)-1-((2-(trimethylsilyl)ethoxy)methyl)-1H-imidazol-2-yl)pyrrolidin-2-one (67C)

DIPEA (1.3 ml, 7.14 mmol) was added to the solution of (R)-5-allyl-5-(5-(4-bromo-2-fluorophenyl)-1H-imidazol-2-yl)pyrrolidin-2-one (67B, 1300 mg, 3.57 mmol) in DMF (25 ml) at 0° C., the resultant mixture was stirred at rt for 0.5 h. (2-(chloromethoxy)ethyl)trimethylsilane (1.9 ml, 10.71 mmol) was added to the mixture, and the resultant mixture was stirred at rt for 16 h. The mixture was quenched with aqueous NH$_4$Cl (saturated, 25 mL) and the mixture was extracted with ethyl acetate (2×10 mL). The combined organic fractions were washed with brine (saturated, 20 mL), dried (Na$_2$SO$_4$), filtered and the solvent was evaporated under reduced pressure. The residue was purified by silica gel flash chromatography (ISCORF75; Sepa flash column), eluting with petroleum ether/EtOAc=10:1-2:1 to give (R)-5-allyl-5-(4-(4-bromo-2-fluorophenyl)-1-((2-(trimethylsilyl)ethoxy)methyl)-1H-imidazol-2-yl)pyrrolidin-2-one (67C). LCMS (ESI) calc'd for C$_{22}$H$_{29}$BrFN$_3$O$_2$Si [M+H]$^+$: 494.1, found: 496.1

Step 4: Preparation of (R,E)-5-(5-(4-bromo-2-fluorophenyl)-1-((2-(trimethylsilyl)ethoxy)methyl)-1H-imidazol-2-yl)-5-(5-(2-(isoxazol-3-yl)-1,3-dioxolan-2-yl)pent-2-en-1-yl)pyrrolidin-2-one (67D)

Zhan's catalyst (54 mg, 0.074 mmol) was added to a mixture of (R)-5-allyl-5-(5-(4-bromo-2-fluorophenyl)-1-((2-(trimethylsilyl)ethoxy)methyl)-1H-imidazol-2-yl)pyrrolidin-2-one (67C, 600 mg, 1.213 mmol) and 3-(2-(but-3-en-1-yl)-1,3-dioxolan-2-yl)isoxazole (Prepared from 2, 474 mg, 2.427 mmol) in toluene (5 ml) which was bubbled with N$_2$ for 20 mins at rt. The mixture was degassed and backfilled with N$_2$ three times and stirred at 70° C. for 16 h. The reaction mixture was concentrated to dryness, and purified by silica gel chromatography eluted with Petro.Ether:EtOAc=1:1 to give (R,E)-5-(5-(4-bromo-2-fluorophenyl)-1-((2-(trimethylsilyl)ethoxy)methyl)-1H-imidazol-2-yl)-5-(5-(2-(isoxazol-3-yl)-1,3-dioxolan-2-yl)pent-2-en-1-yl)pyrrolidin-2-one (67D). LCMS (ESI) calc'd for C$_{30}$H$_{38}$BrFN$_4$O$_5$Si [M+H]$^+$: 661.2, found: 663.2

Step 5: Preparation of (R,E)-5-(5-(2-fluoro-4-(oxazol-2-yl)phenyl)-1-((2-(trimethylsilyl)ethoxy)methyl)-1H-imidazol-2-yl)-5-(5-(2-(isoxazol-3-yl)-1,3-dioxolan-2-yl)pent-2-en-1-yl)pyrrolidin-2-one (67E)

A mixture of (R,E)-5-(5-(4-bromo-2-fluorophenyl)-1-((2-(trimethylsilyl)ethoxy)methyl)-1H-imidazol-2-yl)-5-(5-(2-(isoxazol-3-yl)-1,3-dioxolan-2-yl)pent-2-en-1-yl)pyrrolidin-2-one (67D, 45 mg, 0.068 mmol), 2-(tributylstannyl)oxazole (50 mg, 0.140 mmol) XPhos Pd-G2 (10.70 mg, 0.014 mmol) in toluene (4 ml) was degassed and backfilled with N$_2$ three times. The mixture was heated to 85° C. for 18 h, the mixture was filtered and the filter cake was washed with ethyl acetate (20 mL). The filtrate was concentrated to dryness. The residue was purified by silica gel flash chromatography (ISCORF75; Sepa flash column), eluting with Petro.Ether/EtOAc=1:2 to give (R,E)-5-(5-(2-fluoro-4-(oxazol-2-yl)phenyl)-1-((2-(trimethylsilyl)ethoxy)methyl)-1H-imidazol-2-yl)-5-(5-(2-(isoxazol-3-yl)-1,3-dioxolan-2-yl)pent-2-en-1-yl)pyrrolidin-2-one (67E). LCMS (ESI) calc'd for C$_{33}$H$_{40}$FN$_5$O$_6$Si [M+H]$^+$: 650.3, found: 650.3.

Step 6: Preparation of (S)-5-(5-(2-fluoro-4-(oxazol-2-yl)phenyl)-1-((2-(trimethylsilyl)ethoxy)methyl)-1H-imidazol-2-yl)-5-(5-(2-(isoxazol-3-yl)-1,3-dioxolan-2-yl)pentyl)pyrrolidin-2-one (67F)

A solution of (R,E)-5-(5-(2-fluoro-4-(oxazol-2-yl)phenyl)-1-((2-(trimethylsilyl)ethoxy)methyl)-1H-imidazol-2-yl)-5-(5-(2-(isoxazol-3-yl)-1,3-dioxolan-2-yl)pent-2-en-1-yl)pyrrolidin-2-one (67E, 36 mg, 0.055 mmol) in MeOH (5 ml) was added Pd/C (6 mg, 5.64 µmol) (10%, wet) under Ar. The suspension was degassed under vacuum and purged with N$_2$ several times. The mixture was then stirred under H$_2$ (Pressure: 15 psi) at 25° C. for 2 h. It was filtered on Celite, and the filter cake was washed with methanol (3×5 mL). The filtrate was concentrated under reduced pressure to give (S)-5-(5-(2-fluoro-4-(oxazol-2-yl)phenyl)-1-((2-(trimethylsilyl)ethoxy)methyl)-1H-imidazol-2-yl)-5-(5-(2-(isoxazol-3-yl)-1,3-dioxolan-2-yl)pentyl)pyrrolidin-2-one (67F) which was used directly for next step without purification. LCMS (ESI) calc'd for C$_{33}$H$_{42}$FN$_5$O$_6$Si [M+H]$^+$: 652.3, found: 652.3

Step 7: Preparation of (S)-5-(5-(2-fluoro-4-(oxazol-2-yl)phenyl)-1H-imidazol-2-yl)-5-(6-(isoxazol-3-yl)-6-oxohexyl)pyrrolidin-2-one (Example 67)

HCl (1 ml, 4.00 mmol) was added to the solution of (S)-5-(5-(2-fluoro-4-(oxazol-2-yl)phenyl)-1-((2-(trimethylsilyl)ethoxy)methyl)-1H-imidazol-2-yl)-5-(5-(2-(isoxazol-3-yl)-1,3-dioxolan-2-yl)pentyl)pyrrolidin-2-one (67F, 30 mg, 0.046 mmol) in MeOH (1.0 ml) and Water (1 ml), and the resultant mixture was stirred at 65° C. for 12 h. The mixture was quenched with aqueous NaHCO₃ (saturated) to pH=7-8 and the mixture was extracted with DCM (3×3 mL). The combined organic fractions were washed with brine (saturated, 20 mL), dried (Na₂SO₄), filtered and the solvent was evaporated under reduced pressure to afford (S)-5-(5-(2-fluoro-4-(oxazol-2-yl)phenyl)-1H-imidazol-2-yl)-5-(6-(isoxazol-3-yl)-6-oxohexyl)pyrrolidin-2-one (Example 67). LCMS (ESI) calc'd for C₂₅H₂₄FN₅O₄[M+H]⁺: 478.2, found: 478.1.

(S)-5-(5-(2-fluoro-4-(oxazol-2-yl)phenyl)-1H-imidazol-2-yl)-5-(6-(isoxazol-3-yl)-6-oxohexyl)pyrrolidin-2-one (Example 67, 15 mg, 0.029 mmol) was added to L-(+)-tartaric acid (5 mg, 0.033 mmol) in water (2 ml) at rt and the mixture was stirred at the same temperature for 15 min. The mixture was lyophilized to give (S)-5-(5-(2-fluoro-4-(oxazol-2-yl)phenyl)-1H-imidazol-2-yl)-5-(6-(isoxazol-3-yl)-6-oxohexyl)pyrrolidin-2-one 2,3-dihydroxysuccinate (67). ¹H NMR (400 MHz, MeOD) δ 8.76 (d, J=1.76 Hz, 1H), 8.14 (t, J=8.12 Hz, 1H), 8.02 (d, J=0.78 Hz, 1H), 7.86-7.92 (m, 1H), 7.76-7.82 (m, 1H), 7.53 (d, J=3.91 Hz, 1H), 7.34 (d, J=0.78 Hz, 1H), 6.77 (d, J=1.76 Hz, 1H), 4.54 (s, 5H), 3.32 (td, J=1.59, 3.28 Hz, 1H), 3.01-3.08 (m, 2H), 2.47 (d, J=7.04 Hz, 3H), 2.33-2.40 (m, 1H), 2.02-2.20 (m, 2H), 1.70-1.80 (m, 2H), 1.25-1.49 (m, 6H).

Example 68

(S)-5-(4-(4-cyclopropyl-2-fluorophenyl)-1H-imidazol-2-yl)-5-(6-(isoxazol-3-yl)-6-oxohexyl)pyrrolidin-2-one

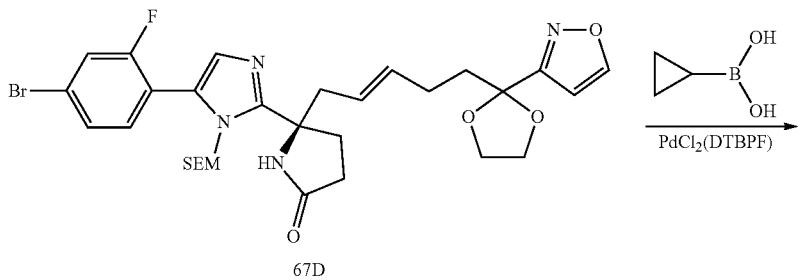
67D

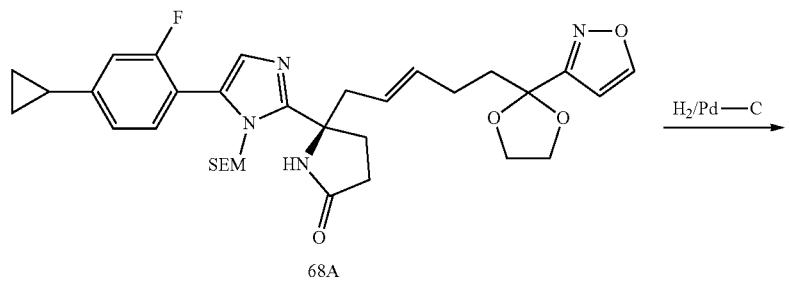
68A

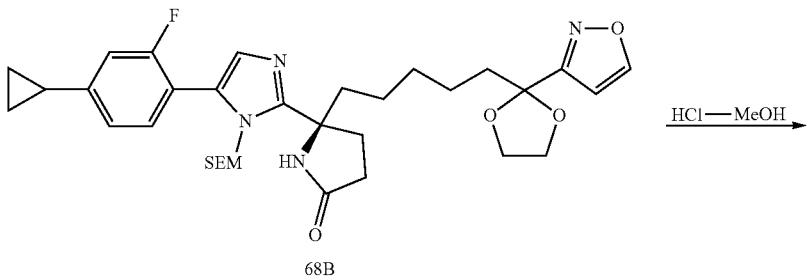
68B

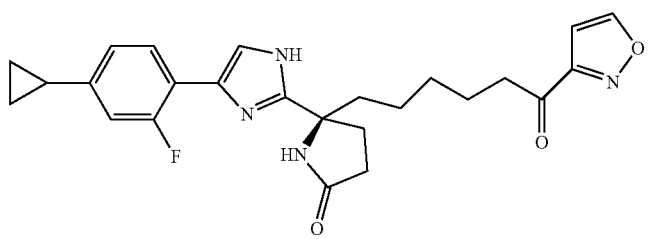
Example 68

Step 1: Preparation of (R,E)-5-(5-(4-cyclopropyl-2-fluorophenyl)-1-((2-(trimethylsilyl)ethoxy)methyl)-1H-imidazol-2-yl)-5-(5-(2-(isoxazol-3-yl)-1,3-dioxolan-2-yl)pent-2-en-1-yl)pyrrolidin-2-one (68A)

PdCl$_2$(DTBPF) (6 mg, 9.21 μmol) was added to a stirred mixture of cyclopropylboronic acid (13 mg, 0.151 mmol), (R,E)-5-(5-(4-bromo-2-fluorophenyl)-1-((2-(trimethylsilyl)ethoxy)methyl)-1H-imidazol-2-yl)-5-(5-(2-(isoxazol-3-yl)-1,3-dioxolan-2-yl)pent-2-en-1-yl)pyrrolidin-2-one (67D, 50 mg, 0.076 mmol) and Cs$_2$CO$_3$ (74 mg, 0.227 mmol) in co-solvents of toluene (2 ml) and water (0.05 ml) at rt and the mixture was stirred at 100° C. for 18 h. The mixture was concentrated in vacuo and the residue was purified by silica gel flash chromatography (ISCORF75; Sepa flash column), eluting with petroleum ether/EtOAc=10:1-1:2 to give (R,E)-5-(5-(4-cyclopropyl-2-fluorophenyl)-1-((2-(trimethylsilyl)ethoxy)methyl)-1H-imidazol-2-yl)-5-(5-(2-(isoxazol-3-yl)-1,3-dioxolan-2-yl)pent-2-en-1-yl)pyrrolidin-2-one (68A). LCMS (ESI) calc'd for C$_{33}$H$_{43}$FN$_4$O$_5$Si [M+H]$^+$: 623.3, found: 623.3

Step 2: Preparation of (S)-5-(5-(4-cyclopropyl-2-fluorophenyl)-1-((2-(trimethylsilyl)ethoxy)methyl)-1H-imidazol-2-yl)-5-(5-(2-(isoxazol-3-yl)-1,3-dioxolan-2-yl)pentyl)pyrrolidin-2-one (68B)

A solution of (R,E)-5-(5-(4-cyclopropyl-2-fluorophenyl)-1-((2-(trimethylsilyl)ethoxy)methyl)-1H-imidazol-2-yl)-5-(5-(2-(isoxazol-3-yl)-1,3-dioxolan-2-yl)pent-2-en-1-yl)pyrrolidin-2-one (68A, 21 mg, 0.034 mmol)) in MeOH (3 ml) was added Pd/C (35.9 mg, 0.034 mmol) (10%, wet) was added under Ar. The suspension was degassed under vacuum and purged with N$_2$ several times. The mixture was then stirred under H$_2$ (Pressure: 15 psi) at rt for 2 h. The mixture was filtered and concentrated to afford the title compound (68B) which was used directly for next step without purification. LCMS (ESI) calc'd for C$_{33}$H$_{45}$FN$_4$O$_5$Si [M+H]$^+$: 625.3, found: 625.4.

Step 3: Preparation of (S)-5-(5-(4-cyclopropyl-2-fluorophenyl)-1H-imidazol-2-yl)-5-(6-(isoxazol-3-yl)-6-oxohexyl)pyrrolidin-2-one (Example 68)

HCl (2 μl, 8.00 μmol) was added to the solution of (S)-5-(5-(4-cyclopropyl-2-fluorophenyl)-1-((2-(trimethylsilyl)ethoxy)methyl)-1H-imidazol-2-yl)-5-(5-(2-(isoxazol-3-yl)-1,3-dioxolan-2-yl)pentyl)pyrrolidin-2-one (68B, 20 mg, 0.032 mmol) in MeOH (2 ml) and water (2 ml) the resultant mixture was stirred at 65° C. for 12 h. The mixture was purified by preparative HPLC (reverse phase C-18 column), eluting with acetonitrile/water, to give (S)-5-(5-(4-cyclopropyl-2-fluorophenyl)-1H-imidazol-2-yl)-5-(6-(isoxazol-3-yl)-6-oxohexyl)pyrrolidin-2-one (Example 68). LCMS (ESI) calc'd for C$_{25}$H$_{27}$FN$_4$O$_3$[M+H]$^+$: 451.2, found: 451.0. $^1$H NMR (400 MHz, MeOD) δ 8.77 (d, J=1.6 Hz, 1H), 7.61-7.68 (m, 2H), 7.04-7.09 (m, 1H), 6.96-7.03 (m, 1H), 6.75-6.78 (m, 1H), 3.06 (s, 2H), 2.49 (s, 4H), 2.09-2.20 (m, 2H), 1.95-2.04 (m, 1H), 1.71-1.81 (m, 2H), 1.40-1.53 (m, 3H), 1.20-1.31 (m, 1H), 1.08 (dd, J=2.0, 8.31 Hz, 2H), 0.77 (dd, J=2.0, 4.70 Hz, 2H).

Example 69

(S)-5-(4-(2-fluorophenyl)-1H-imidazol-2-yl)-5-(6-(isoxazol-3-yl)-6-oxohexyl)pyrrolidin-2-one

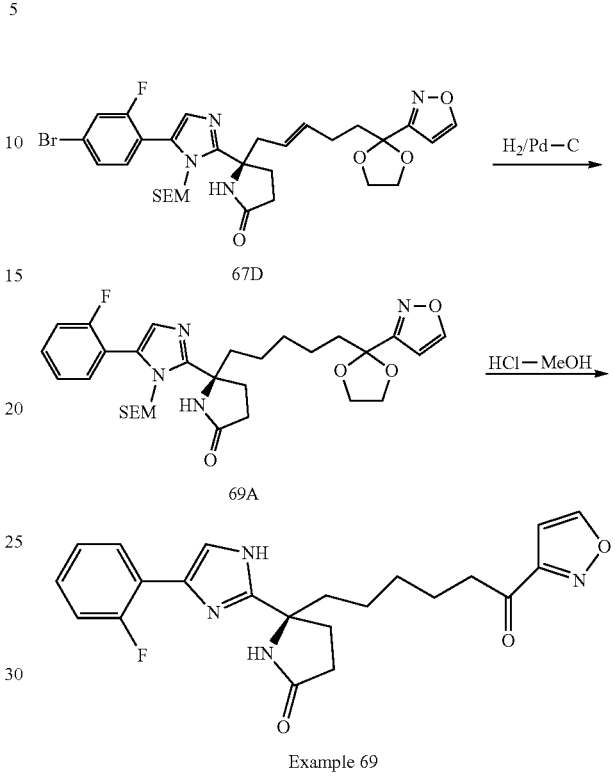

Example 69

Step 1: Preparation of (S)-5-(4-(2-fluorophenyl)-1-((2-(trimethylsilyl)ethoxy)methyl)-1H-imidazol-2-yl)-5-(6-(isoxazol-3-yl)-6-oxohexyl)pyrrolidin-2-one (69A)

A solution of (R,E)-5-(5-(4-bromo-2-fluorophenyl)-1-((2-(trimethylsilyl)ethoxy)methyl)-1H-imidazol-2-yl)-5-(5-(2-(isoxazol-3-yl)-1,3-dioxolan-2-yl)pent-2-en-1-yl)pyrrolidin-2-one (67D, 14 mg, 0.021 mmol) in MeOH (1.5 ml) was added Pd/C (4 mg, 3.76 μmol) (10%, wet) was added under Ar. The suspension was degassed under vacuum and purged with N$_2$ several times. The mixture was then stirred under H$_2$ (Pressure: 15 psi) at 25° C. for 2 h. The mixture was filtered and concentrated to afford (S)-5-(4-(2-fluorophenyl)-1-((2-(trimethylsilyl)ethoxy)methyl)-1H-imidazol-2-yl)-5-(6-(isoxazol-3-yl)-6-oxohexyl)pyrrolidin-2-one (69A) which was used directly for next step without purification. LCMS (ESI) calc'd for C$_{30}$H$_{41}$FN$_4$O$_5$Si [M+H]$^+$: 585.3, found: 585.4

Step 3: Preparation of (S)-5-(5-(2-fluorophenyl)-1H-imidazol-2-yl)-5-(6-(isoxazol-3-yl)-6-oxohexyl)pyrrolidin-2-one (Example 69)

HCl (1 mL, 4.00 mmol) was added to the solution of (S)-5-(5-(2-fluorophenyl)-1-((2-(trimethylsilyl)ethoxy)methyl)-1H-imidazol-2-yl)-5-(5-(2-(isoxazol-3-yl)-1,3-dioxolan-2-yl)pentyl)pyrrolidin-2-one (69A, 18 mg, 0.031 mmol) in MeOH (1 ml) and water (1 mL), and the resultant mixture was stirred at 65° C. for 12 h. The residue was purified by preparative HPLC (reverse phase C-18 column), eluting with acetonitrile/water, to give (S)-5-(5-(2-fluorophenyl)-1H-imidazol-2-yl)-5-(6-(isoxazol-3-yl)-6-oxohexyl)pyrrolidin-2-one (Example 69). LCMS (ESI) calc'd for $C_{22}H_{23}FN_4O_3[M+H]^+$: 411.2, found: 411.2. $^1$H NMR (400 MHz, MeOD) δ 8.78 (d, J=1.8 Hz, 1H), 7.78-7.84 (m, 1H), 7.75 (d, J=2.2 Hz, 1H), 7.48-7.55 (m, 1H), 7.28-7.39 (m, 2H), 6.77 (d, J=1.6 Hz, 1H), 3.07 (t, J=7.2 Hz, 2H), 2.50 (s, 4H), 2.11-2.21 (m, 2H), 1.72-1.82 (m, 2H), 1.41-1.58 (m, 3H), 1.21-1.32 (m, 1H).

Example 70

(R)-5-(6-(isoxazol-3-yl)-6-oxohexyl)-5-(5-(7-methoxy-2-methylquinolin-6-yl)-1H-imidazol-2-yl)pyrrolidin-2-one

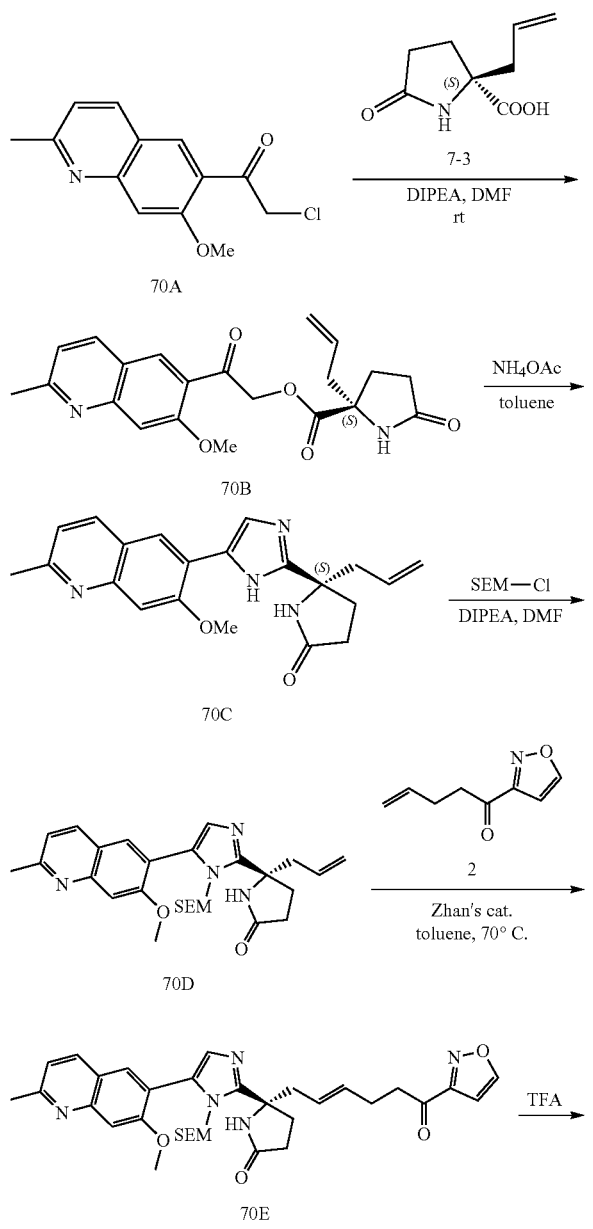

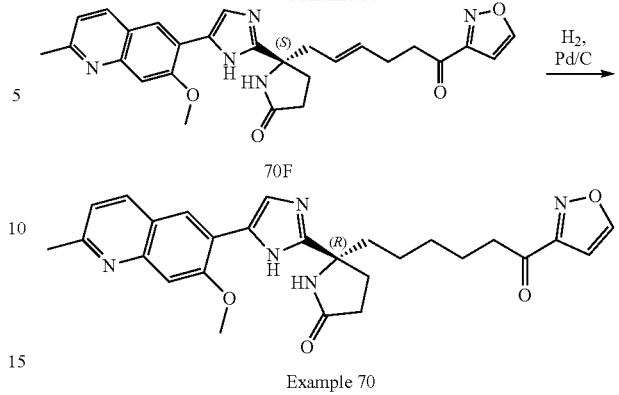

Example 70

Step 1: Preparation of (S)-2-(7-methoxy-2-methylquinolin-6-yl)-2-oxoethyl 2-allyl-5-oxopyrrolidine-2-carboxylate (70BA)

DIPEA (1.38 ml, 7.90 mmol) was added to a stirred mixture of 2-chloro-1-(7-methoxy-2-methylquinolin-6-yl)ethanone (70A, 850 mg, 3.40 mmol) and (S)-2-allyl-5-oxopyrrolidine-2-carboxylic acid (7-3, 634 mg, 3.74 mmol) in DMF (10 ml) at room temperature and the mixture was stirred at room temperature for 24 h. Another acid (100 mg) and DIPEA (0.2 mL) were added then it was continued to be stirred at rt for 20 h. Water (10 mL) was added and the mixture was extracted with ethyl acetate (3×10 mL). The combined organic fractions were washed with aqueous NaHCO₃ (saturated, 1×10 mL), dried (Na₂SO₄), filtered and the solvent was evaporated under reduced pressure. The residue was purified by silica gel flash chromatography (ISCORF75; Sepa flash column), eluting with petroleum ether/EtOAc=50%~100% to give (S)-2-(7-methoxy-2-methylquinolin-6-yl)-2-oxoethyl-2-allyl-5-oxopyrrolidine-2-carboxylate (70B). LCMS (ESI) calc'd for $C_{21}H_{22}N_2O_5$ [M+H]⁺: 383.2, found: 383.1

Step 2: Preparation of (S)-5-allyl-5-(5-(7-methoxy-2-methylquinolin-6-yl)-1H-imidazol-2-yl)pyrrolidin-2-one (70C)

Ammonium acetate (1.8 g, 23.35 mmol) was added to a stirred mixture of (S)-2-(7-methoxy-2-methylquinolin-6-yl)-2-oxoethyl-2-allyl-5-oxopyrrolidine-2-carboxylate (70B, 900 mg, 2.353 mmol) in toluene (30 ml) at room temperature and the mixture was heated with stirring at 110° C. for 18 h. All the volatiles were removed by evaporator. Water (30 mL) was added and the mixture was extracted with DCM (5×30 mL). The combined organic fractions were washed with aqueous NaHCO₃ (saturated, 2×30 mL), then washed with brine (1×30 mL), dried (Na₂SO₄), filtered and the solvent was evaporated under reduced pressure to give (S)-5-allyl-5-(5-(7-methoxy-2-methylquinolin-6-yl)-1H-imidazol-2-yl)pyrrolidin-2-one (70C) which was used directly for next step.

Step 3: Preparation of (S)-5-allyl-5-(5-(7-methoxy-2-methylquinolin-6-yl)-1-((2-(trimethylsilyl)ethoxy)methyl)-1H-imidazol-2-yl)pyrrolidin-2-one (70D)

DIPEA (1.2 ml, 6.87 mmol) was added to a stirred mixture of (S)-5-allyl-5-(5-(7-methoxy-2-methylquinolin-6- yl)-1H-imidazol-2-yl)pyrrolidin-2-one (70C, 750 mg, 2.069 mmol) and (2-(chloromethoxy)ethyl)trimethylsilane (0.5 ml, 2.83 mmol) in DMF (10 ml) at room temperature and the mixture was stirred at room temperature for 3 h. Water (20 mL) was added and the mixture was extracted with ethyl acetate (3×20 mL). The combined organic fractions were washed with brine (saturated, 1×20 mL), dried ($Na_2SO_4$), filtered and the solvent was evaporated under reduced pressure. The residue was purified by silica gel flash chromatography (ISCORF75; Sepa flash column), eluting with petroleum ether/EtOAc=0~50% to give (S)-5-allyl-5-(5-(7-methoxy-2-methylquinolin-6-yl)-1-((2-(trimethylsilyl) ethoxy)methyl)-1H-imidazol-2-yl)pyrrolidin-2-one (70D). LCMS (ESI) calc'd for $C_{27}H_{36}N_4O_3Si$ [M+H]$^+$: 493.3, found: 493.3.

Step 4: Preparation of (S, E)-5-(6-(isoxazol-3-yl)-6-oxohex-2-en-1-yl)-5-(5-(7-methoxy-2-methylquinolin-6-yl)-1-((2-(trimethylsilyl)ethoxy)methyl)-1H-imidazol-2-yl)pyrrolidin-2-one (70E)

UMICORE M71 SIPR (50 mg, 0.061 mmol) was added to a stirred mixture of (S)-5-allyl-5-(5-(7-methoxy-2-methylquinolin-6-yl)-1-((2-(trimethylsilyl)ethoxy)methyl)-1H-imidazol-2-yl)pyrrolidin-2-one (70D, 300 mg, 0.609 mmol) and 1-(isoxazol-3-yl)pent-4-en-1-one (2, 92 mg, 0.609 mmol) in degassed toluene (5 mL) at room temperature and the mixture was heated with stirring at 100° C. for 18 h. Then UMICORE M71 SIPR (50 mg, 0.061 mmol) and 1-(isoxazol-3-yl)pent-4-en-1-one (2, 92 mg, 0.609 mmol) were added again twice every 2 hours. Excess toluene was removed by evaporator. The residue was purified by silica gel flash chromatography (ISCORF75; Sepa flash column), eluting with petroleum ether/EtOAc=50%~100% to give (S, E)-5-(6-(isoxazol-3-yl)-6-oxohex-2-en-1-yl)-5-(5-(7-methoxy-2-methylquinolin-6-yl)-1-((2-(trimethylsilyl) ethoxy)methyl)-1H-imidazol-2-yl)pyrrolidin-2-one (70E). LCMS (ESI) calc'd for $C_{33}H_{41}N_5O_5Si$ [M+H]$^+$: 616.3, found: 616.4.

Step 5: Preparation of (S, E)-5-(6-(isoxazol-3-yl)-6-oxohex-2-en-1-yl)-5-(5-(7-methoxy-2-methylquinolin-6-yl)-1H-imidazol-2-yl)pyrrolidin-2-one 2,2,2-trifluoroacetate (70F)

TFA (1.0 mL, 12.98 mmol) was added to (S, E)-5-(6-(isoxazol-3-yl)-6-oxohex-2-en-1-yl)-5-(5-(7-methoxy-2-methylquinolin-6-yl)-1-((2-(trimethylsilyl)ethoxy)methyl)-1H-imidazol-2-yl)pyrrolidin-2-one (70E, 90 mg, 0.146 mmol) at room temperature and the mixture was stirred at room temperature for 4 h. All the volatiles were removed by evaporator to give (S, E)-5-(6-(isoxazol-3-yl)-6-oxohex-2-en-1-yl)-5-(5-(7-methoxy-2-methylquinolin-6-yl)-1H-imidazol-2-yl)pyrrolidin-2-one 2,2,2-trifluoroacetate (70F) which was used directly for the next step. LCMS (ESI) calc'd for $C_{27}H_{27}N_5O_4$ [M+H]$^+$: 486.2, found: 486.3.

Step 6: Preparation of (R)-5-(6-(isoxazol-3-yl)-6-oxohexyl)-5-(5-(7-methoxy-2-methylquinolin-6-yl)-1H-imidazol-2-yl)pyrrolidin-2-one (Example 70)

A solution of (S, E)-5-(6-(isoxazol-3-yl)-6-oxohex-2-en-1-yl)-5-(5-(7-methoxy-2-methylquinolin-6-yl)-1H-imidazol-2-yl)pyrrolidin-2-one 2,2,2-trifluoroacetate (70F, 88 mg, 0.147 mmol) in MeOH (2 ml) was added to a 100 mL three-necked bottle and then Pd/C (10 mg, 9.40 µmol) (10%, wet) was added under Ar. The suspension was degassed under vacuum and purged with $N_2$ several times. The mixture was then stirred under $H_2$ (Pressure: 15 psi) at 25° C. for 10 h. The mixture was filtered and the filter cake was washed with MeOH (3×5 mL). The filtrate was concentrated to dryness. The residue was purified by preparative HPLC (reverse phase C-18 column), eluting with acetonitrile/water+0.1% TFA, to give the TFA salt of the target compound. Then it was made dry by lyophilization and neutralized with Sat. $NaHCO_3$ (1 mL), extracted with ethyl acetate (3×5 mL), dried with anhydrous $Na_2SO_4$, filtered and concentrated to give (R)-5-(6-(isoxazol-3-yl)-6-oxohexyl)-5-(5-(7-methoxy-2-methylquinolin-6-yl)-1H-imidazol-2-yl)pyrrolidin-2-one (Example 70). LCMS (ESI) calc'd for $C_{17}H_{29}N_5O_4$ [M+H]$^+$: 488.2, found: 488.3

L-(+)-tartaric acid (6 mg, 0.040 mmol) was added to a stirred mixture of (R)-5-(6-(isoxazol-3-yl)-6-oxohexyl)-5-(5-(7-methoxy-2-methylquinolin-6-yl)-1H-imidazol-2-yl) pyrrolidin-2-one (18 mg, 0.037 mmol) in acetonitrile (2 ml) and water (2 mL) at room temperature. Then it was made dry by lyophilization to give (R)-5-(6-(isoxazol-3-yl)-6-oxohexyl)-5-(5-(7-methoxy-2-methylquinolin-6-yl)-1H-imidazol-2-yl)pyrrolidin-2-one (2R,3R)-2,3-dihydroxysuccinate (Example 70). $^1$H NMR (400 MHz, MeOD) δ 8.74 (d, J=1.6 Hz, 1H), 8.48 (s, 1H), 8.41 (d, J=8.6 Hz, 1H), 7.67 (s, 1H), 7.48 (s, 1H), 7.42 (d, J=8.6 Hz, 1H), 6.73 (d, J=1.6 Hz, 1H), 4.50 (s, 2H), 4.13 (s, 3H), 3.02 (t, J=7.2 Hz, 2H), 2.78 (s, 3H), 2.51-2.61 (m, 1H), 2.43-2.50 (m, 2H), 2.32-2.42 (m, 1H), 1.99-2.23 (m, 2H), 1.72-1.76 (m, 2H), 1.38-1.45 (m, 2H), 1.25-1.34 (m, 2H).

Example 71

(S)-6-(6-(isoxazol-3-yl)-6-oxohexyl)-6-(4-(2-methoxypyridin-3-yl)-1H-imidazol-2-yl)piperidin-2-one

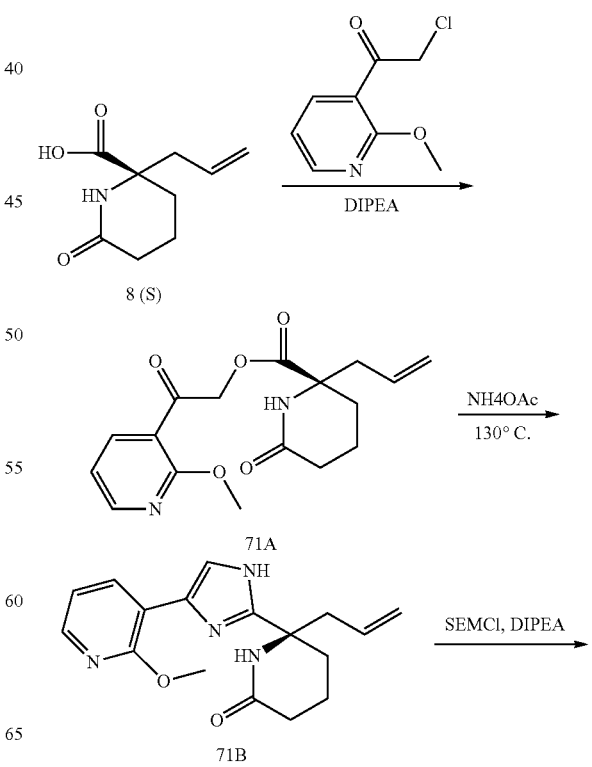

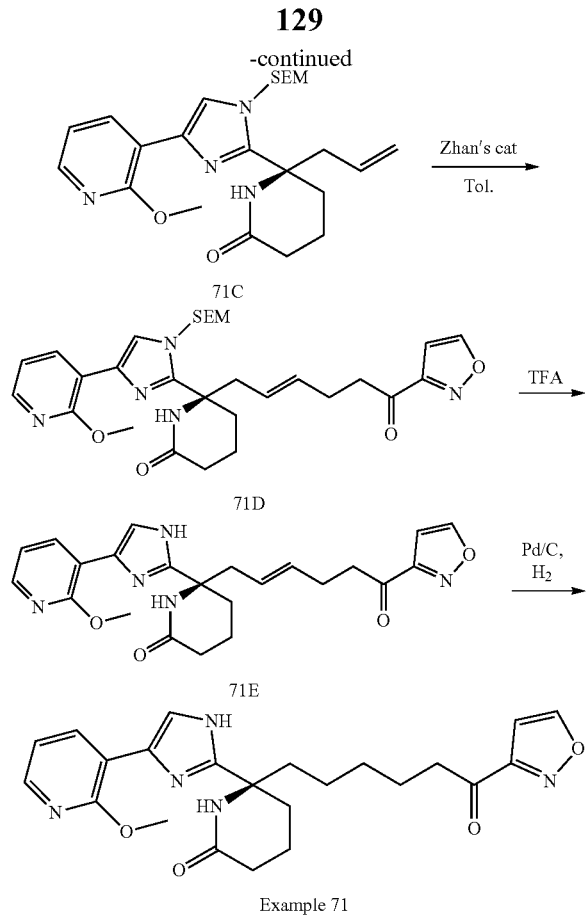

Example 71

Step 1: Preparation of (S)-2-(2-methoxypyridin-3-yl)-2-oxoethyl 2-allyl-6-oxopiperidine-2-carboxylate (71A)

2-chloro-1-(2-methoxypyridin-3-yl)ethanone (760 mg, 3.28 mmol) was added to a stirred mixture of DIPEA (1 ml, 5.73 mmol), and (S)-2-allyl-6-oxopiperidine-2-carboxylic acid (8-S, 600 mg, 3.28 mmol) in DMF (20 ml) at room temperature and the mixture was stirred at room temperature for 30 h. The mixture was diluted with ethyl acetate (15 mL), washed with brine (saturated, 3×15 mL), dried ($Na_2SO_4$), filtered and the solvent was evaporated under reduced pressure. The residue was purified by silica gel column flash chromatography, eluting with EtOAc/petroleum ether=0-30% to give (S)-2-(2-methoxypyridin-3-yl)-2-oxoethyl 2-allyl-6-oxopiperidine-2-carboxylate (71A). LCMS (ESI) calc'd for $C_{17}H_{20}N_2O_5$ [M+H]$^+$: 333.1, found: 333.1

Step 2: Preparation of (S)-6-allyl-6-(4-(2-methoxypyridin-3-yl)-1H-imidazol-2-yl)piperidin-2-one (71B)

NH$_4$OAc (2.0 g, 25.9 mmol) was added to a stirred mixture of (S)-2-(2-methoxypyridin-3-yl)-2-oxoethyl 2-allyl-6-oxopiperidine-2-carboxylate (71A, 0.8 g, 2.407 mmol) in toluene (8 ml) at room temperature and the mixture was stirred at 130° C. for 5 h. The mixture was cooled, diluted with ethyl acetate (20 mL), washed with brine (saturated, 3×20 mL), dried ($Na_2SO_4$), filtered and the solvent was evaporated under reduced pressure. The residue was purified by silica gel column flash chromatography, eluting with MeOH/DCM=0-20% to give (S)-6-allyl-6-(4-(2-methoxypyridin-3-yl)-1H-imidazol-2-yl)piperidin-2-one (71B). LCMS (ESI) calc'd for $C_{17}H_{20}N_4O_2$ [M+H]$^+$: 313.2, found: 313.1

Step 3: Preparation of (S)-6-allyl-6-(4-(2-methoxypyridin-3-yl)-1-((2-(trimethylsilyl)ethoxy)methyl)-1H-imidazol-2-yl)piperidin-2-one (71C)

SEMCl (0.5 ml, 2.82 mmol) was added to a stirred mixture of DIEA (1.2 ml, 6.87 mmol) and (S)-6-allyl-6-(4-(2-methoxypyridin-3-yl)-1H-imidazol-2-yl)piperidin-2-one (71B, 600 mg, 1.921 mmol) in DMF (3 ml) at 0° C. and the mixture was stirred at room temperature for 12 h. The mixture was cooled to 0° C., water (15 mL) was added and the mixture was extracted with DCM (3×10 mL). The combined organic fractions were washed with brine (saturated, 2×15 mL), dried ($Na_2SO_4$), filtered and the solvent was evaporated under reduced pressure. The residue was purified by silica gel column flash chromatography, eluting with EtOAc/petroleum ether=0-20% to give (S)-6-allyl-6-(4-(2-methoxypyridin-3-yl)-1-((2-(trimethylsilyl)ethoxy)methyl)-1H-imidazol-2-yl)piperidin-2-one (71C). LCMS (ESI) calc'd for $C_{23}H_{34}N_4O_3Si$ [M+H]$^+$: 443.2, found: 443.2

Step 4: Preparation of (S,E)-6-(6-(isoxazol-3-yl)-6-oxohex-2-en-1-yl)-6-(4-(2-methoxypyridin-3-yl)-1-((2-(trimethylsilyl)ethoxy)methyl)-1H-imidazol-2-yl)piperidin-2-one (71D)

Zhan's catalyst (30 mg, 0.041 mmol) was added to a stirred mixture of 1-(isoxazol-3-yl)pent-4-en-1-one (2, 205 mg, 1.356 mmol), and (S)-6-allyl-6-(4-(2-methoxypyridin-3-yl)-1-((2-(trimethylsilyl)ethoxy)methyl)-1H-imidazol-2-yl)piperidin-2-one (71C, 300 mg, 0.678 mmol) in toluene (3 ml) at room temperature under $N_2$ atmosphere and the mixture was stirred at 65° C. for 12 h under $N_2$. The mixture was cooled, diluted with ethyl acetate (10 mL), washed with brine (saturated, 3×10 mL), dried ($Na_2SO_4$), filtered and the solvent was evaporated under reduced pressure. The residue was purified by silica gel column flash chromatography, eluting with EtOAc/petroleum ether=0-50% to give (S,E)-6-(6-(isoxazol-3-yl)-6-oxohex-2-en-1-yl)-6-(4-(2-methoxypyridin-3-yl)-1-((2-(trimethylsilyl)ethoxy)methyl)-1H-imidazol-2-yl)piperidin-2-one (71D). LCMS (ESI) calc'd for $C_{29}H_{39}N_5O_5Si$ [M+H]$^+$: 566.3, found: 566.4

Step 5: Preparation of (S,E)-6-(6-(isoxazol-3-yl)-6-oxohex-2-en-1-yl)-6-(4-(2-methoxypyridin-3-yl)-1H-imidazol-2-yl)piperidin-2-one (71E)

(S,E)-6-(6-(isoxazol-3-yl)-6-oxohex-2-en-1-yl)-6-(4-(2-methoxypyridin-3-yl)-1-((2-(trimethylsilyl)ethoxy)methyl)-1H-imidazol-2-yl)piperidin-2-one (71D, 54 mg, 0.095 mmol) was added in TFA (1 ml, 12.98 mmol) at room temperature, the mixture was stirred at room temperature for 2 h and concentrated to afford (S,E)-6-(6-(isoxazol-3-yl)-6-oxohex-2-en-1-yl)-6-(4-(2-methoxypyridin-3-yl)-1H-imidazol-2-yl)piperidin-2-one (71E). LCMS (ESI) calc'd for $C_{23}H_{25}N_5O_4$ [M+H]$^+$: 436.2, found: 436.2, tR=0.924 min.

Step 6: Preparation of (R)-6-(6-(isoxazol-3-yl)-6-oxohexyl)-6-(4-(2-methoxypyridin-3-yl)-1H-imidazol-2-yl)piperidin-2-one (Example 71)

10% Pd—C (10 mg, 9.40 μmol) was added to a stirred mixture of (S,E)-6-(6-(isoxazol-3-yl)-6-oxohex-2-en-1-yl)-

6-(4-(2-methoxypyridin-3-yl)-1H-imidazol-2-yl)piperidin-2-one (71E, 40 mg, 0.092 mmol) in MeOH (1 ml) at room temperature and the mixture was stirred at room temperature for 0.5 h under H$_2$. The mixture was filtered and concentrated, the residue was purified by preparative HPLC, eluting with acetonitrile/water+0.05% NH$_3$, to give (R)-6-(6-(isoxazol-3-yl)-6-oxohexyl)-6-(4-(2-methoxypyridin-3-yl)-1H-imidazol-2-yl)piperidin-2-one (77). LCMS (ESI) calc'd for C$_{23}$H$_{27}$N$_5$O$_4$ [M+H]$^+$: 438.2, found: 438.2

L-(+)-tartaric acid (8 mg, 0.053 mmol) in water (1 ml) was added to a stirred mixture of (R)-6-(6-(isoxazol-3-yl)-6-oxohexyl)-6-(4-(2-methoxypyridin-3-yl)-1H-imidazol-2-yl)piperidin-2-one (Example 71, 25 mg free, 0.057 mmol) in MeCN (1 ml) at room temperature and the mixture was concentrated to give (R)-6-(6-(isoxazol-3-yl)-6-oxohexyl)-6-(4-(2-methoxypyridin-3-yl)-1H-imidazol-2-yl)piperidin-2-one (2R,3R)-2,3-dihydroxysuccinate (Example 71). $^1$H NMR (400 MHz, MeOD) δ 8.76 (d, J=1.5 Hz, 1H), 8.22 (dd, J=1.8, 7.5 Hz, 1H), 8.05 (dd, J=1.9, 5.0 Hz, 1H), 7.57 (s, 1H), 7.04 (dd, J=5.0, 7.6 Hz, 1H), 6.75 (d, J=1.8 Hz, 1H), 4.53 (s, 3H), 4.05 (s, 3H), 3.03 (t, J=7.3 Hz, 2H), 2.38 (d, J=5.1 Hz, 3H), 1.98-2.03 (m, 3H), 1.81-1.87 (m, 1H), 1.69-1.75 (m, 2H), 1.54 (br s, 1H), 1.36-1.43 (m, 2H), 1.22-1.33 (m, 2H), 1.17-1.19 (m, 1H).

Example 72

(S)-7-(4-(2-fluorophenyl)-1H-imidazol-2-yl)-7-(6-(isoxazol-3-yl)-6-oxohexyl)azepan-2-one

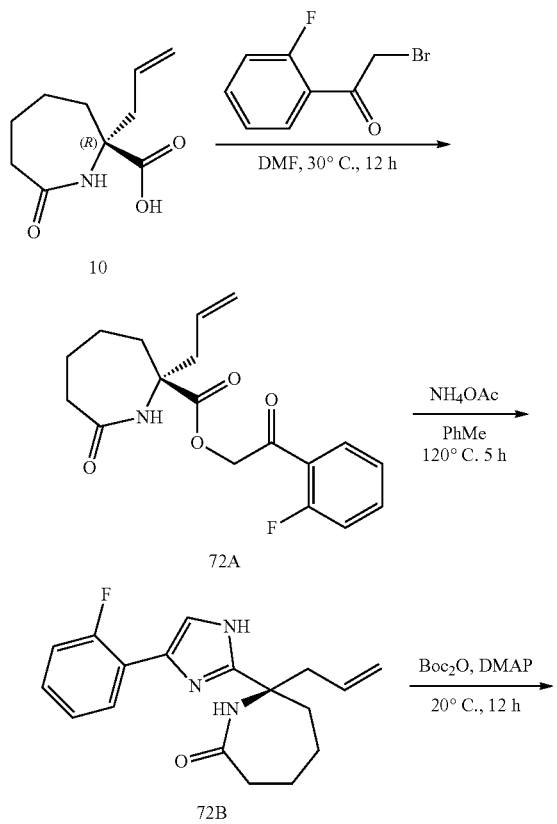

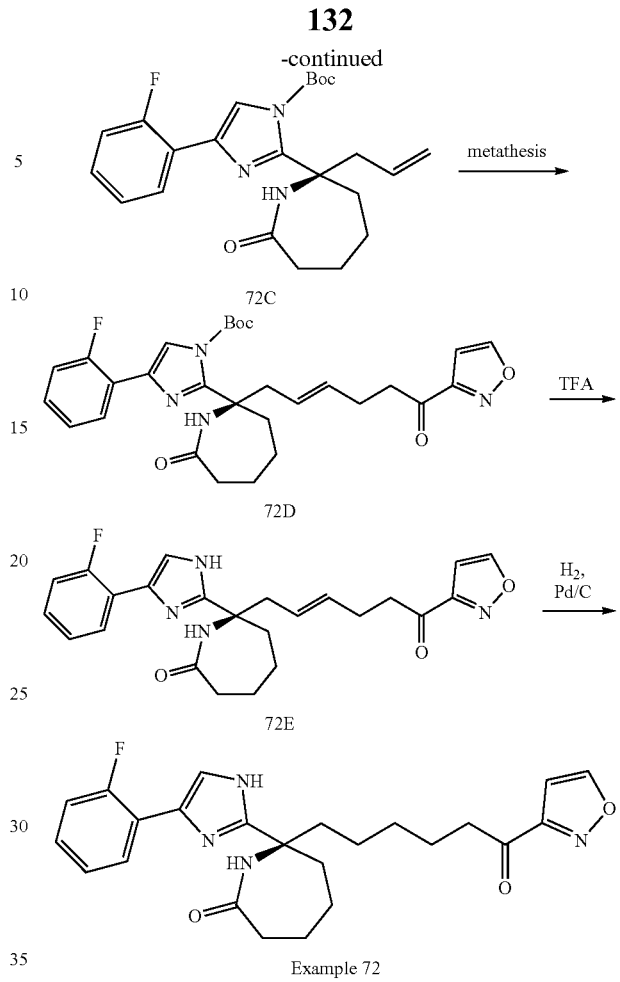

Example 72

Step 1: Preparation of (S)-2-(2-fluorophenyl)-2-oxoethyl 2-allyl-7-oxoazepane-2-carboxylate (72A)

In a 50 mL round bottomed flask was added (S)-2-allyl-7-oxoazepane-2-carboxylic acid (10, 1 g, 5.07 mmol) in THF (10 ml). 2-bromo-1-(2-fluorophenyl)ethanone (1.100 g, 5.07 mmol) and DIEA (1.328 ml, 7.61 mmol) were added. The mixture was stirred at room temperature for 16 h. The mixture was diluted with ethyl acetate (10 mL), washed with brine (saturated, 2*10 ml), dried (Na$_2$SO$_4$), filtered and the solvent was evaporated under reduced pressure. The residue was purified by silica gel column flash chromatography, eluting with petroleum ether/EtOAc=10:1-1:1 to give (S)-2-(2-fluorophenyl)-2-oxoethyl 2-allyl-7-oxoazepane-2-carboxylate (72A). LCMS (ESI) calc'd for C$_{18}$H$_{20}$FNO$_4$ [M+H]$^+$: 334.1. found: 334.5

Step 2: Preparation of (R)-7-allyl-7-(4-(2-fluorophenyl)-1H-imidazol-2-yl)azepan-2-one (72B)

NH$_4$OAc (1041 mg, 13.50 mmol) was added to a stirred mixture of (S)-2-(2-fluorophenyl)-2-oxoethyl 2-allyl-7-oxoazepane-2-carboxylate (72A, 900 mg, 2.70 mmol) in toluene at room temperature and the mixture was heated to 120° C. and stirred for 18 h. The mixture was diluted with ethyl acetate, washed with water (saturated, 2×20 mL), dried (Na$_2$SO$_4$), filtered and the solvent was evaporated under reduced pressure. The residue was purified by silica gel column flash chromatography, eluting with petroleum ether/

EtOAc=5:1-1:5 to give (R)-7-allyl-7-(4-(2-fluorophenyl)-1H-imidazol-2-yl)azepan-2-one (72B). LCMS (ESI) calc'd for $C_{18}H_{20}FN_3O$ [M+H]$^+$: 314.2, found: 314.1

Step 3: Preparation of (R)-tert-butyl 2-(2-allyl-7-oxoazepan-2-yl)-4-(2-fluorophenyl)-1H-imidazole-1-carboxylate (72C)

Bo15O (0.372 ml, 1.604 mmol) was added to the solution of DMAP (10 mg, 0.082 mmol) and (R)-7-allyl-7-(4-(2-fluorophenyl)-1H-imidazol-2-yl)azepan-2-one (72B, 304 mg, 0.970 mmol) in DCM (10 ml), the resultant mixture was stirred at rt for 16 h. The mixture was quenched with water (10 mL), and the mixture was extracted with DCM (20 mL). The combined organic fractions were washed with water (10 mL) and brine (10 ml), dried (Na$_2$SO$_4$), filtered and the solvent was evaporated under reduced pressure. The residue was purified by silica gel column flash chromatography, eluting with petroleum ether/EtOAc=5:1 to give (R)-tert-butyl 2-(2-allyl-7-oxoazepan-2-yl)-4-(2-fluorophenyl)-1H-imidazole-1-carboxylate (72C, 220 mg, 55% yield) as a colorless gum. LCMS (ESI) calc'd for $C_{23}H_{28}FN_3O_3$[M+H]$^+$: 414.2, found: 414.2

Step 4: Preparation of (R,E)-tert-butyl 4-(2-fluorophenyl)-2-(2-(6-(isoxazol-3-yl)-6-oxohex-2-en-1-yl)-7-oxoazepan-2-yl)-1H-imidazole-1-carboxylate (72D)

UMICORE M71 SIPR (80 mg, 0.097 mmol) (in 4 batches with an interval of 4 h) was added to the mixture of 1-(isoxazol-3-yl)pent-4-en-1-one (2, 439 mg, 2.90 mmol) and (R)-tert-butyl 2-(2-allyl-7-oxoazepan-2-yl)-4-(2-fluorophenyl)-1H-imidazole-1-carboxylate (72C, 200 mg, 0.484 mmol) (in 4 batches with catalyst) in degassed toluene (5 ml), the resultant mixture was stirred at 75° C. for 20 h. The reaction mixture was concentrated in vacuo. The residue was purified by silica gel flash chromatography (ISCORF75; Sepa flash column), eluting with petroleum ether/EtOAc=10:1-2:1 to give (R,E)-tert-butyl 4-(2-fluorophenyl)-2-(2-(6-(isoxazol-3-yl)-6-oxohex-2-en-1-yl)-7-oxoazepan-2-yl)-1H-imidazole-1-carboxylate (72D). LCMS (ESI) calc'd for $C_{29}H_{33}FN_4O_5$[M+H]$^+$: 537.2, found: 537.3

Step 5: Preparation of (R,E)-7-(4-(2-fluorophenyl)-1H-imidazol-2-yl)-7-(6-(isoxazol-3-yl)-6-oxohex-2-en-1-yl)azepan-2-one (72E)

TFA (50 µl, 0.037 mmol) was added to the solution of (R,E)-tert-butyl 4-(2-fluorophenyl)-2-(2-(6-(isoxazol-3-yl)-6-oxohex-2-en-1-yl)-7-oxoazepan-2-yl)-1H-imidazole-1-carboxylate (72D, 20 mg, 0.037 mmol) in DCM (1 ml), and the resultant mixture was stirred at rt for 2 h. The mixture was concentrated in vacuo to give (R,E)-7-(4-(2-fluorophenyl)-1H-imidazol-2-yl)-7-(6-(isoxazol-3-yl)-6-oxohex-2-en-1-yl)azepan-2-one (72E) which was used in next step without further purification. LCMS (ESI) calc'd for $C_{24}H_{25}FN_4O_3$[M+H]$^+$: 437.2, found: 437.2

Step 6: Preparation of (S)-7-(4-(2-fluorophenyl)-1H-imidazol-2-yl)-7-(6-(isoxazol-3-yl)-6-oxohexyl)azepan-2-one (Example 72)

A solution of (R,E)-7-(4-(2-fluorophenyl)-1H-imidazol-2-yl)-7-(6-(isoxazol-3-yl)-6-oxohex-2-en-1-yl)azepan-2-one (72E, 56 mg, 0.128 mmol) in MeOH (5 ml) was added to a 100 mL bottle and then Pd/C (30 mg, 0.014 mmol) (10%, wet) was added under N$_2$. The suspension was degassed under vacuum and purged with H$_2$ several times. The mixture was then stirred under H$_2$ (15 psi) at rt for 4 h. The reaction mixture was filtered and concentrated in vacuo. The residue was purified by preparative HPLC (reverse phase C-18 column), eluting with acetonitrile/water+0.1% TFA and lyophilized to give the TFA salt of product. The solid was dissolved in MeOH (1 mL) and aq.NaHCO$_3$ (3 mL) was added, the aqueous layer was extracted with EtOAc (3*5 mL). The combined organic layer was concentrated in vacuo to give (S)-7-(4-(2-fluorophenyl)-1H-imidazol-2-yl)-7-(6-(isoxazol-3-yl)-6-oxohexyl)azepan-2-one (Example 72). LCMS (ESI) calc'd for $C_{24}H_{27}FN_4O_3$[M+H]$^+$: 439.2, found: 439.3

A solution of L-(+)-tartaric acid (6 mg, 0.040 mmol) in water (5.0 ml) was added to the solution of (S)-7-(4-(2-fluorophenyl)-1H-imidazol-2-yl)-7-(6-(isoxazol-3-yl)-6-oxohexyl)azepan-2-one (Example 72, 15 mg, 0.034 mmol) in MeOH (2 ml), MeOH was removed in vacuo, the aqueous residue was lyophilized to give (S)-7-(4-(2-fluorophenyl)-1H-imidazol-2-yl)-7-(6-(isoxazol-3-yl)-6-oxohexyl)azepan-2-one (2R,3R)-2,3-dihydroxysuccinate (92). $^1$H NMR (400 MHz, MeOD) δ 8.72 (d, J=0.78 Hz, 1H), 7.91 (t, J=7.73 Hz, 1H), 7.41 (d, J=3.13 Hz, 1H), 7.08-7.30 (m, 3H), 6.71 (d, J=0.98 Hz, 1H), 4.51 (s, 2H), 2.96 (t, J=7.14 Hz, 2H), 2.58 (d, J=10.76 Hz, 1H), 2.36 (dd, J=7.73, 13.99 Hz, 1H), 2.05-2.17 (m, 1H), 1.78-1.94 (m, 4H), 1.57-1.72 (m, 3H), 1.21-1.29 (m, 6H).

Example 73

7-(5-(2-methoxyquinolin-3-yl)-1H-imidazol-2-yl)-1-(oxazol-2-yl)heptan-1-one

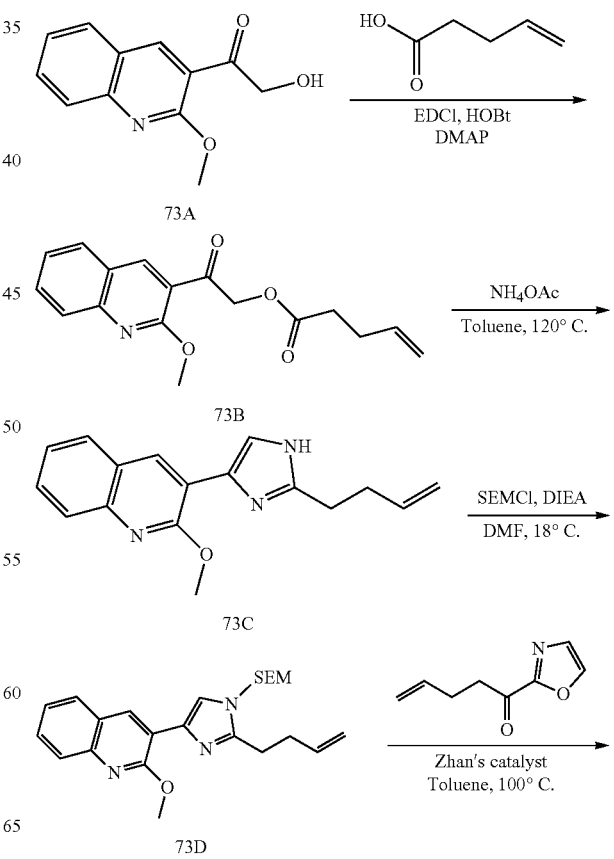

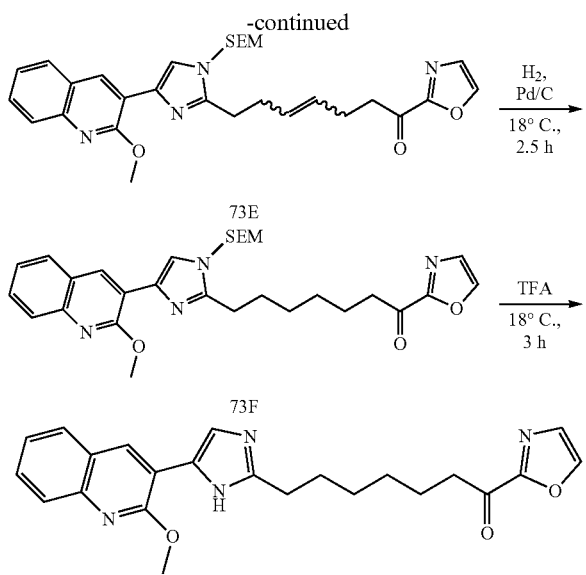

Example 73

Step 1: Preparation of 2-(2-methoxyquinolin-3-yl)-2-oxoethyl pent-4-enoate (73B)

2-hydroxy-1-(2-methoxyquinolin-3-yl)ethanone (73A, 1 g, 4.60 mmol) and DMAP (0.169 g, 1.381 mmol) were added to a stirred mixture of pent-4-enoic acid (0.922 g, 9.21 mmol), HOBT (0.775 g, 5.06 mmol), EDCI (1.139 g, 6.45 mmol) in DMF (5 ml) at room temperature and the mixture was stirred at rt for 18 h. The mixture was diluted with ethyl acetate (50 mL*2), washed with water (30 mL) and brine (30 mL), dried ($Na_2SO_4$), filtered and the solvent was evaporated under reduced pressure. The residue was purified by silica gel column flash chromatography, eluting with Petro.Ether/EtOAc=0-40% to give 2-(2-methoxyquinolin-3-yl)-2-oxoethyl pent-4-enoate (73B). LCMS (ESI) calc'd for $C_{17}H_{17}NO_4$ [M+H]$^+$: 300.1, found: 300.0

Step 2: 3-(2-(but-3-en-1-yl)-1H-imidazol-4-yl)-2-methoxyquinoline (73C)

$NH_4OAc$ (3.208 g, 41.6 mmol) was added to a stirred mixture of 2-(2-methoxyquinolin-3-yl)-2-oxoethyl pent-4-enoate (73B, 820 mg, 2.74 mmol) in toluene (40 ml) at rt and the mixture was stirred at 120° C. for 2.5 h. The mixture was evaporated under reduced pressure. The residue was purified by silica gel column flash chromatography, eluting with DCM/MeOH=0~7% to give 3-(2-(but-3-en-1-yl)-1H-imidazol-5-yl)-2-methoxyquinoline (73C). LCMS (ESI) calc'd for $C_{17}H_{17}N_3O$ [M+H]$^+$: 280.3, found: 280.4

Step 3: 3-(2-(but-3-en-1-yl)-1-((2-(trimethylsilyl)ethoxy)methyl)-1H-imidazol-4-yl)-2-methoxyquinoline (73D)

SEM-Cl (0.6 ml, 3.38 mmol) was added to a stirred mixture of 3-(2-(but-3-en-1-yl)-1H-imidazol-5-yl)-2-methoxyquinoline (73C, 440 mg, 1.575 mmol) and DIEA (1.1 ml, 6.30 mmol) in DMF (6 ml) at rt and the mixture was stirred at rt for 2 h. The mixture was diluted with water (30 mL) and extracted with ethyl acetate (3×15 mL). The combined organic fractions were washed with water (3×10 mL), dried ($Na_2SO_4$), filtered and the solvent was evaporated under reduced pressure. The residue was purified by silica gel column flash chromatography, eluting with petroleum ether/EtOAc=0-5% to give 3-(2-(but-3-en-1-yl)-1-((2-(trimethylsilyl)ethoxy)methyl)-1H-imidazol-5-yl)-2-methoxyquinoline (73D). LCMS (ESI) calc'd for $C_{23}H_{31}N_3O_2Si$ [M+H]$^+$: 410.5, found: 411.0. $^1$H NMR (400 MHz, $CDCl_3$) δ 8.81 (brs, 1H), 7.81 (brs, 2H), 7.50-7.64 (m, 3H), 7.36 (brs, 1H), 7.26 (d, J=3.33 Hz, 1H), 5.28 (d, J=3.33 Hz, 2H), 5.15 (brs, 1H), 5.11 (brs, 1H), 5.04 (d, J=10.76 Hz, 1H), 4.21 (d, J=3.13 Hz, 4H), 3.57 (brs, 2H), 2.91 (brs, 2H), 2.62 (brs, 2H), 0.93 (d, J=7.43 Hz, 3H), 0.07-0.05 (m, 11H).

Step 4: 7-(4-(2-methoxyquinolin-3-yl)-1-((2-(trimethylsilyl)ethoxy)methyl)-1H-imidazol-2-yl)-1-(oxazol-2-yl)hept-4-en-1-one (73E)

Zhan's catalyst (22 mg, 0.030 mmol) was added to a mixture of 3-(2-(but-3-en-1-yl)-1-((2-(trimethylsilyl)ethoxy)methyl)-1H-imidazol-4-yl)-2-methoxyquinoline (73D, 130 mg, 0.317 mmol) and 1-(oxazol-2-yl)pent-4-en-1-one (1, 110 mg, 0.728 mmol) in toluene (1.5 ml) which was bubbled with $N_2$ for 10 mins at rt. The mixture was degassed and backfilled with $N_2$ three times and stirred at 100° C. for 16 h. The mixture was combined with two parallel reactions, concentrated in vacuo. The residue was purified by silica gel column flash chromatography, eluting with DCM/MeOH=0~3% to give 7-(4-(2-methoxyquinolin-3-yl)-1-((2-(trimethylsilyl)ethoxy)methyl)-1H-imidazol-2-yl)-1-(oxazol-2-yl)hept-4-en-1-one (73E). LCMS (ESI) calc'd for $C_{29}H_{36}N_4O_4Si$ [M+H]$^+$: 533.7, found: 533.2

Step 5: 7-(4-(2-methoxyquinolin-3-yl)-1-((2-(trimethylsilyl)ethoxy)methyl)-1H-imidazol-2-yl)-1-(oxazol-2-yl)heptan-1-one (73F)

10% Pd—C (28 mg, 0.263 mmol) was added to a stirred mixture of (E)-7-(4-(2-methoxyquinolin-3-yl)-1-((2-(trimethylsilyl)ethoxy)methyl)-1H-imidazol-2-yl)-1-(oxazol-2-yl)hept-4-en-1-one (33E, 40 mg, 0.075 mmol) in MeOH (10 ml). The mixture was degassed and backfilled with $H_2$ (three times), then stirred at 18° C. for 2.5 h under $H_2$ atmosphere (15 psi). The mixture was filtered and the filter cake was washed with MeOH (30 mL). The filtrate was concentrated to give 7-(4-(2-methoxyquinolin-3-yl)-1-((2-(trimethylsilyl)ethoxy)methyl)-1H-imidazol-2-yl)-1-(oxazol-2-yl)heptan-1-one (73F), which was used to the next step without purification. LCMS (ESI) calc'd for $C_{29}H_{38}N_4O_4Si$ [M+H]$^+$: 535.7, found: 535.3

Step 6: 7-(5-(2-methoxyquinolin-3-yl)-1H-imidazol-2-yl)-1-(oxazol-2-yl)heptan-1-one (Example 73)

TFA (3 mL, 38.9 mmol) was added to 7-(4-(2-methoxyquinolin-3-yl)-1-((2-(trimethylsilyl)ethoxy)methyl)-1H-imidazol-2-yl)-1-(oxazol-2-yl)heptan-1-one (73F, 38 mg, 0.071 mmol) and the mixture was stirred at rt for 3 h. The solvent was evaporated under reduced pressure. The residue was purified by preparative HPLC (reverse phase C-18 column), eluting with acetonitrile/water+0.1% TFA, to give 7-(4-(2-methoxyquinolin-3-yl)-1H-imidazol-2-yl)-1-(oxazol-2-yl)heptan-1-one (Example 73). LCMS (ESI) calc'd for $C_{23}H_{24}N_4O_3$ [M+Na]$^+$: 427.4, found: 427.2, tR=1.038 min. $^1$H NMR (400 MHz, MeOD) δ 8.50-8.52 (m, 1H), 8.51 (s, 1H), 8.09 (s, 1H), 7.83-7.92 (m, 3H), 7.71 (t, J=7.24 Hz, 1H), 7.48 (t, J=7.19 Hz, 1H), 7.39 (s, 1H), 4.20 (s, 3H), 3.30 (td, J=1.57, 3.25 Hz, 4H), 3.07 (dt, J=2.87, 7.50 Hz, 4H), 1.83-1.95 (m, 2H), 1.75 (t, J=7.17 Hz, 2H), 1.41-1.54 (m, 4H).

Example 74

(S)-7-(ethylamino)-7-(5-(2-methylquinolin-6-yl)-1H-imidazol-2-yl)-1-(oxazol-2-yl)heptan-1-one

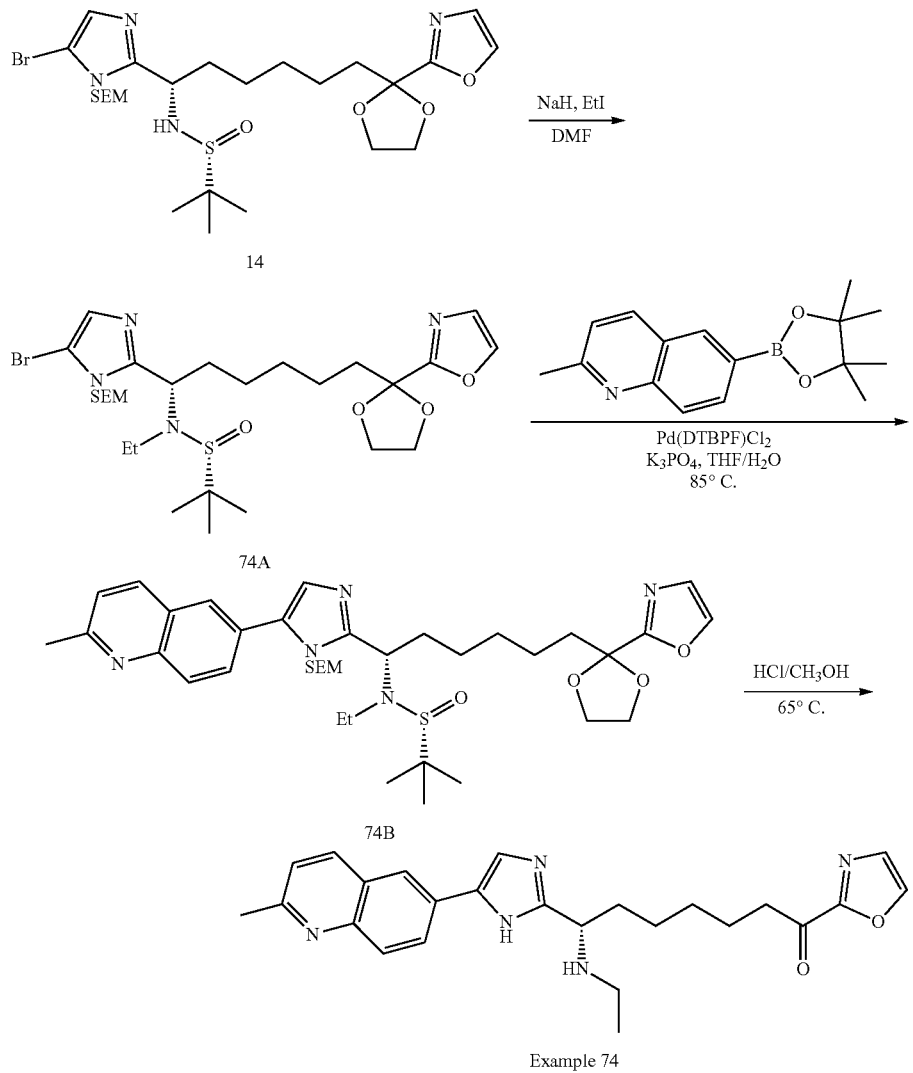

Step 1: Preparation of (R)-N-(1-(5-bromo-1-((2-(trimethylsilyl)ethoxy)methyl)-1H-imidazol-2-yl)-6-(2-(oxazol-2-yl)-1,3-dioxolan-2-yl)hexyl)-N-ethyl-2-methylpropane-2-sulfinamide (74A)

To a solution of (R)-N-(1-(5-bromo-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (14, 100 mg, 0.161 mmol) in DMF (1 mL) was added NaH (60%, 8 mg, 0.2 mmol) at 0° C. The mixture was stirred at 0° C. for 30 min. Then iodoethane (25 mg, 0.161 mmol) was added. The mixture was stirred at rt for 2 h. Aqueous NH$_4$Cl (saturated, 10 mL) was added and the mixture was extracted with ethyl acetate (5×2 mL). The combined organic fractions were washed with brine (saturated, 10 mL), dried (Na$_2$SO$_4$), filtered and the solvent was evaporated under reduced pressure. The crude product was purified by preparative TLC on silica gel, eluting with petroleum ether/EtOAc=1:1 to give (R)-N-(1-(5-bromo-1-((2-(trimethylsilyl)ethoxy)methyl)-1H-imidazol-2-yl)-6-(2-(oxazol-2-yl)-1,3-dioxolan-2-yl)hexyl)-N-ethyl-2-methylpropane-2-sulfinamide (74A). LCMS (ESI) calc'd for C$_{27}$H$_{47}$BrN$_4$O$_5$SSi [M+H]$^+$: 647.2, 649.2, found: 647.3, 649.3. $^1$H NMR (400 MHz, MeOD) δ 7.96-8.04 (m, 1H), 7.87-7.94 (m, 1H), 7.22-7.31 (m, 1H), 7.09-7.20 (m, 1H), 5.84-6.05 (m, 1H), 5.13-5.23 (m, 1H), 4.60-4.71 (m, 1H), 4.04-4.07 (m, 2H), 4.01-4.04 (m, 2H), 3.38-3.62 (m, 4H), 2.95-3.10 (m, 5H), 2.81-2.93 (m, 4H), 2.00-2.11 (m, 3H), 1.77-1.92 (m, 1H), 1.14-1.42 (m, 16H), 0.91-0.98 (m, 4H), −0.02-0.03 (m, 9H).

Step 2: Preparation of (R)-N-ethyl-2-methyl-N-((S)-1-(5-(2-methylquinolin-6-yl)-1-((2-(trimethylsilyl)ethoxy)methyl)-1H-imidazol-2-yl)-6-(2-(oxazol-2-yl)-1,3-dioxolan-2-yl)hexyl)propane-2-sulfinamide (74B)

A mixture of Pd(DTBPF)Cl$_2$ (6 mg, 9.21 μmol), 2-methyl-6-(4,4,5,5-tetramethyl-1,3,2-dioxaborolan-2-yl)quinoline (25 mg, 0.093 mmol), (R)-N-((S)-1-(5-bromo-1-((2-(trimethylsilyl)ethoxy)methyl)-1H-imidazol-2-yl)-6-(2-(oxazol-2-yl)-1,3-dioxolan-2-yl)hexyl)-N-ethyl-2- methylpropane-2-sulfinamide (74A, 60 mg, 0.093 mmol) and K$_3$PO$_4$ (50 mg, 0.236 mmol) in THF (2 mL) and water (0.4 mL) was degassed and backfilled with N$_2$ three times. The mixture was heated at 85° C. for 3 h. The mixture was filtered and the filter cake was washed with ethyl acetate (20 mL). The filtrate was concentrated to dryness. The residue was purified by silica gel flash chromatography (ISCORF75; Sepa flash column), eluting with DCM/MeOH=100:1-9:1 to give (R)-N-ethyl-2-methyl-N-((S)-1-(5-(2-methylquinolin-6-yl)-1-((2-(trimethylsilyl)ethoxy)methyl)-1H-imidazol-2-yl)-6-(2-(oxazol-2-yl)-1,3-dioxolan-2-yl)hexyl)propane-2-sulfinamide (74B). LCMS (ESI) calc'd for C$_{27}$H$_{55}$N$_5$O$_5$SSi [M+H]$^+$: 710.4, found: 710.4

Step 3: Preparation of (S)-7-(ethylamino)-7-(5-(2-methylquinolin-6-yl)-1H-imidazol-2-yl)-1-(oxazol-2-yl)heptan-1-one (Example 74)

HCl (0.5 mL, 6.09 mmol) was added to a stirred mixture of (R)-N-ethyl-2-methyl-N-((S)-1-(5-(2-methylquinolin-6-yl)-1-((2-(trimethylsilyl)ethoxy)methyl)-1H-imidazol-2-yl)-6-(2-(oxazol-2-yl)-1,3-dioxolan-2-yl)hexyl)propane-2-sulfinamide (74B, 40 mg, 0.056 mmol) in co-solvents of MeOH (2 mL) and water (0.2 mL) at rt and the mixture was stirred at 65° C. for 10 h. The solvent was evaporated under reduced pressure. The residue was purified by preparative HPLC (reverse phase C-18 column), eluting with acetonitrile/water+0.1% TFA, to give (S)-7-(ethylamino)-7-(5-(2-methylquinolin-6-yl)-1H-imidazol-2-yl)-1-(oxazol-2-yl)heptan-1-one (Example 74). LCMS (ESI) calc'd for C$_{25}$H$_{29}$N$_5$O$_2$ [M+H]$^+$: 432.2, found: 432.3

Hydrogen chloride (0.1 M, 1 mL, 0.1 mmol) was added to a stirred mixture of (S)-7-(ethylamino)-7-(5-(2-methylquinolin-6-yl)-1H-imidazol-2-yl)-1-(oxazol-2-yl)heptan-1-one (Example 74, 20 mg, 0.046 mmol) in acetonitrile (2 mL) at room temperature, then it was lyophilized to give (S)-7-(ethylamino)-7-(5-(2-methylquinolin-6-yl)-1H-imidazol-2-yl)-1-(oxazol-2-yl)heptan-1-one hydrochloride (41). LCMS (ESI) calc'd for C$_{25}$H$_{30}$ClN$_5$O$_2$[M+H]$^+$: 432.2, found: 432.1. $^1$H NMR (400 MHz, MeOD) δ 8.95-9.05 (m, 1H), 8.63-8.74 (m, 1H), 8.55-8.62 (m, 1H), 8.15-8.23 (m, 1H), 8.02-8.08 (m, 1H), 7.95-8.01 (m, 1H), 7.89-7.96 (m, 1H), 7.31-7.39 (m, 1H), 4.47-4.58 (m, 1H), 3.06-3.19 (m, 1H), 3.00 (s, 5H), 2.93-3.06 (m, 1H), 2.10-2.35 (m, 2H), 2.10-2.35 (m, 2H), 1.60-1.78 (m, 2H), 1.22-1.46 (m, 7H).

Example 75

(S)-7-(methylamino)-7-(5-(2-methylquinolin-6-yl)-1H-imidazol-2-yl)-1-(oxazol-2-yl)heptan-1-one

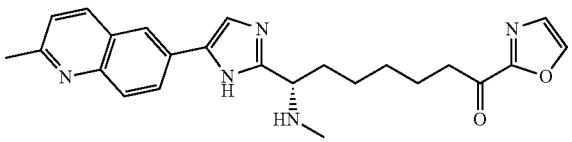 [SMILES: CN[C@@H](CCCCCC(=O)c1ncco1)c1ncc(-c2ccc3nc(C)ccc3c2)[nH]1]

Example 75 was obtained from 14 using a similar method starting with MeI. LCMS (ESI) calc'd for C$_{24}$H$_{27}$N$_5$O$_2$ [M+H]$^+$: 418.2, found: 418.1. $^1$H NMR (400 MHz, MeOD) δ 8.73-8.86 (m, 1H), 8.44-8.60 (m, 2H), 8.00-8.13 (m, 2H), 7.75-7.91 (m, 2H), 7.28-7.38 (m, 1H), 4.32-4.45 (m, 1H), 2.98-3.05 (m, 2H), 2.90-2.95 (m, 3H), 2.90-2.95 (m, 1H), 2.63-2.73 (m, 3H), 2.05-2.31 (m, 2H), 1.63-1.76 (m, 2H), 1.36-1.45 (m, 2H), 1.22-1.33 (m, 3H).

Example 76

(S)-7-methoxy-1-methyl-6-(2-(1-(methylamino)-7-(oxazol-2-yl)-7-oxoheptyl)-1H-imidazol-5-yl)quinolin-2(1H)-one

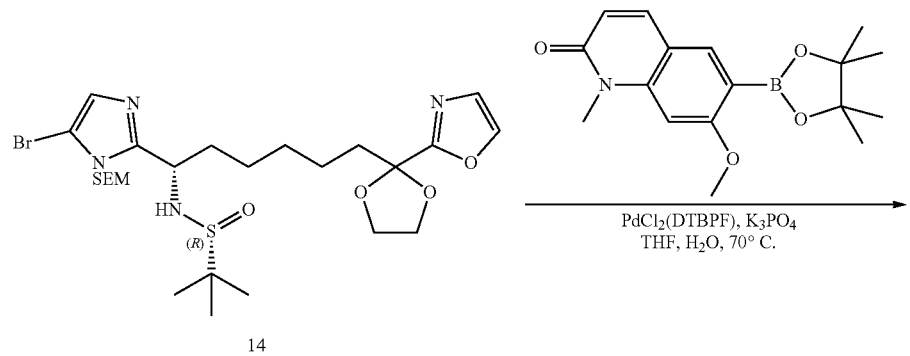

14

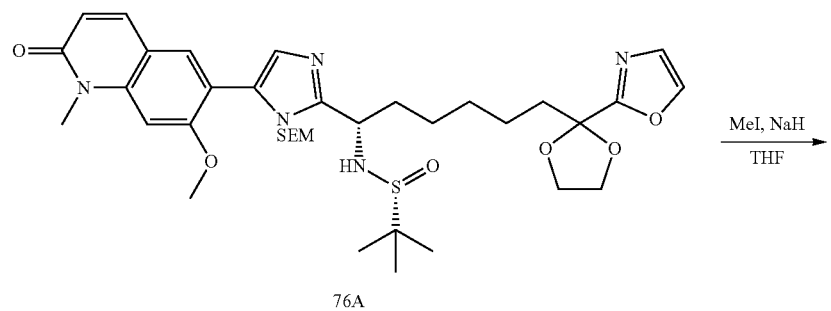

76A

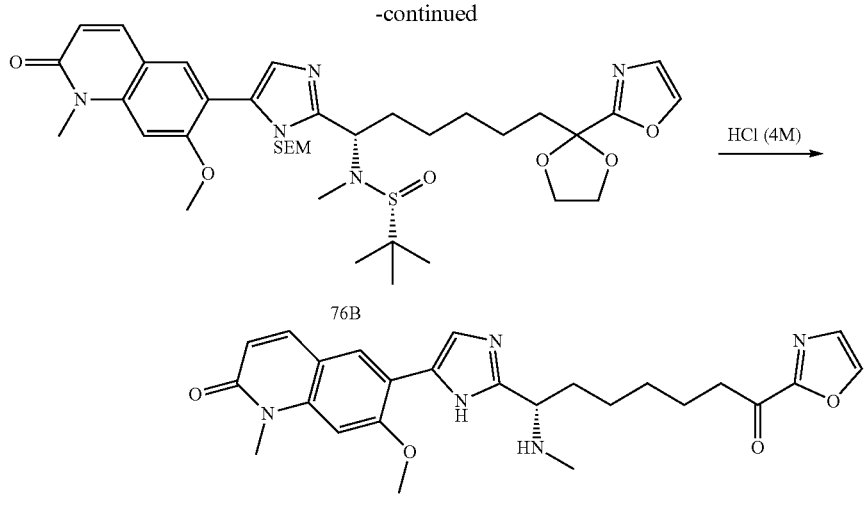

Example 76

Step 1: Preparation of (S)-N-((S)-1-(5-(7-methoxy-1-methyl-2-oxo-1,2-dihydroquinolin-6-yl)-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (76A)

PdCl$_2$(DTBPF) (45 mg, 0.069 mmol) was added to a mixture of (S)-N-((S)-1-(5-bromo-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (14, 400 mg, 0.645 mmol), 7-methoxy-1-methyl-6-(4,4,5,5-tetramethyl-1,3,2-dioxaborolan-2-yl)quinolin-2(1H)-one (415 mg, 0.658 mmol) and K$_3$PO$_4$ (411 mg, 1.936 mmol) in co-solvents of THF (4 ml) and water (0.4 ml) at room temperature and the mixture was stirred at 70° C. for 2.5 h. Water (5 mL) was added, and the mixture was extracted with ethyl acetate (3×10 mL). The combined organic fractions were washed with brine (saturated, 10 mL), dried (Na$_2$SO$_4$), filtered and the solvent was evaporated under reduced pressure. The residue was purified by silica gel column flash chromatography, eluting with DCM/MeOH=0~10% to give (S)-N-((S)-1-(5-(7-methoxy-1-methyl-2-oxo-1,2-dihydroquinolin-6-yl)-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (76A). LCMS (ESI) calc'd for C$_{36}$H$_{53}$N$_5$O$_7$SSi [M+H]$^+$: 728.3, found: 728.4

Step 2: Preparation of (S)-N-((S)-1-(5-(7-methoxy-1-methyl-2-oxo-1,2-dihydroquinolin-6-yl)-1-((2-(trimethylsilyl)ethoxy)methyl)-1H-imidazol-2-yl)-6-(2-(oxazol-2-yl)-1,3-dioxolan-2-yl)hexyl)-N,2-dimethylpropane-2-sulfinamide (76B)

NaH (60%, 7 mg, 0.175 mmol) was added to a stirred mixture of (S)-N-((S)-1-(5-(7-methoxy-1-methyl-2-oxo-1,2-dihydroquinolin-6-yl)-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (76A, 100 mg, 0.137 mmol) in THF (1 ml) at room temperature then MeI (0.02 ml, 0.320 mmol) was added and the mixture was stirred at room temperature for 2 h. It was done twice in the same way then they were combined together for further operation. Water (5 mL) was added and the mixture was extracted with ethyl acetate (3×5 mL). The combined organic fractions were washed with brine (saturated, 1×5 mL), dried (Na$_2$SO$_4$), filtered and the solvent was evaporated under reduced pressure. The residue was purified by silica gel flash chromatography (ISCORF75; Sepa flash column), eluting with petroleum ether/EtOAc=0~100% to give (S)-N-((S)-1-(5-(7-methoxy-1-methyl-2-oxo-1,2-dihydroquinolin-6-yl)-1-((2-(trimethylsilyl)ethoxy)methyl)-1H-imidazol-2-yl)-6-(2-(oxazol-2-yl)-1,3-dioxolan-2-yl)hexyl)-N,2-dimethylpropane-2-sulfinamide (76B). LCMS (ESI) calc'd for C$_{37}$H$_{55}$N$_5$O$_7$SSi [M+H]$^+$: 742.4, found: 742.4

Step 3: Preparation of (S)-7-methoxy-1-methyl-6-(2-(1-(methylamino)-7-(oxazol-2-yl)-7-oxoheptyl)-1H-imidazol-5-yl)quinolin-2(1H)-one (Example 76)

HCl (0.2 mL, 0.800 mmol) was added to a stirred mixture of (S)-N-((S)-1-(5-(7-methoxy-1-methyl-2-oxo-1,2-dihydroquinolin-6-yl)-1-((2-(trimethylsilyl)ethoxy)methyl)-1H-imidazol-2-yl)-6-(2-(oxazol-2-yl)-1,3-dioxolan-2-yl)hexyl)-N,2-dimethylpropane-2-sulfinamide (76B, 90 mg, 0.121 mmol) in MeOH (1.0 mL) and water (0.2 ml) at room temperature and the mixture was stirred at 50° C. for 28 h. It was done twice in the same way and they were combined together for purification. The residue was purified by preparative HPLC (reverse phase C-18 column), eluting with acetonitrile/water+0.1% TFA, to give its TFA salt of the target compound. It was then dissolved in the mixture of 3 mL water and 1 mL CH$_3$CN, neutralized with NaHCO$_3$ (sat.), extracted with ethyl acetate (3×5 mL), dried with anhydrous Na$_2$SO$_4$, and concentrated under reduced pressure to give (S)-7-methoxy-1-methyl-6-(2-(1-(methylamino)-7-(oxazol-2-yl)-7-oxoheptyl)-1H-imidazol-5-yl)quinolin-2(1H)-one (Example 76). LCMS (ESI) calc'd for C$_{25}$H$_{29}$N$_5$O$_4$[M+H]$^+$: 464.2, found: 464.3

L-(+)-tartaric acid (26 mg, 0.173 mmol) was added to a stirred mixture of (S)-7-methoxy-1-methyl-6-(2-(1-(methylamino)-7-(oxazol-2-yl)-7-oxoheptyl)-1H-imidazol-5-yl)quinolin-2(1H)-one (Example 76, 80 mg, 0.173 mmol) in acetonitrile (2 ml) and water (2 mL) at room temperature. Then, it was lyophilized to give (S)-7-methoxy-1-methyl-6-(2-(1-(methylamino)-7-(oxazol-2-yl)-7-oxoheptyl)-1H-imidazol-5-yl)quinolin-2(1H)-one (2R,3R)-2,3-dihydroxysuccinate (Example 76). $^1$H NMR (400 MHz, MeOD) δ 8.23 (s, 1H), 8.05 (s, 1H), 7.86 (d, J=9.3 Hz, 1H), 7.65 (s, 1H), 7.34

(s, 1H), 7.03 (brs, 1H), 6.54 (d, J=9.3 Hz, 1H), 4.49 (s, 2H), 4.40 (d, J=5.95 Hz, 1H), 4.10 (s, 3H), 3.75 (s, 3H), 2.99 (t, J=7.1 Hz, 2H), 2.63 (s, 3H), 2.06-2.37 (m, 2H), 1.61-1.77 (m, 2H), 1.20-1.50 (m, 4H).

Example 77

(S)-6-(2-(1-(ethylamino)-7-(oxazol-2-yl)-7-oxoheptyl)-1H-imidazol-5-yl)-7-methoxy-1-methylquinolin-2(1H)-one

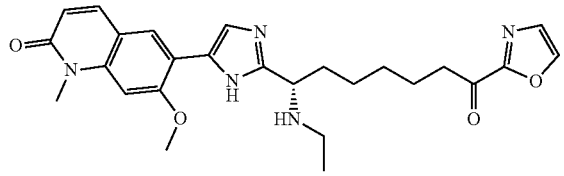 [SMILES: CCN[C@@H](CCCCCC(=O)c1ncco1)c1ncc(-c2cc3ccc(=O)n(C)c3cc2OC)[nH]1]

Example 77 was obtained from 76B using a similar method starting with EtI. LCMS (ESI) calc'd for $C_{26}H_{31}N_5O_4 \cdot 17H_6O_6[M+H]^+$: 478.2, found: 478.3. $^1$H NMR (400 MHz, MeOD) δ 8.21 (s, 1H), 8.03 (s, 1H), 7.86 (d, J=9.00 Hz, 1H), 7.64 (s, 1H), 7.33 (s, 1H), 7.01 (s, 1H), 6.52 (d, J=9.39 Hz, 1H), 4.45 (s, 2H), 4.39 (brs, 1H), 4.09 (s, 3H), 3.74 (s, 3H), 2.98 (t, J=7.04 Hz, 1H), 2.82-3.05 (m, 1H), 2.89 (brs, 1H), 2.80-2.93 (m, 1H), 2.28 (brs, 1H), 2.10 (brs, 1H), 1.66 (d, J=6.65 Hz, 2H), 1.38 (brs, 4H), 1.24-1.32 (m, 3H).

Example 78

(S)-7-((1-methylpiperidin-4-yl)amino)-7-(5-(2-methylquinolin-6-yl)-1H-imidazol-2-yl)-1-(oxazol-2-yl)heptan-1-one

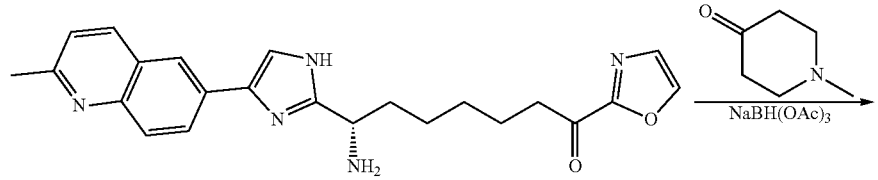

Example 9

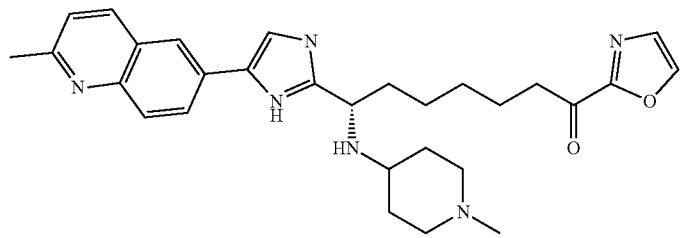

Example 78 aBH(OAc)₃ (193 mg, 0.909 mmol) was added to a stirred mixture of (S)-7-amino-7-(4-(2-methylquinolin-6-yl)-1H-imidazol-2-yl)-1-(oxazol-2-yl)heptan-1-one hydrochloride (Example 9, 40 mg, 0.091 mmol) and 1-methylpiperidin-4-one (103 mg, 0.909 mmol) in MeOH (2.0 ml) at room temperature. The mixture was stirred at 40° C. for 12 h. The residue was purified by preparative HPLC (reverse phase C-18 column), eluting with acetonitrile/water+0.1% TFA, to give (S)-7-((1-methylpiperidin-4-yl) amino)-7-(5-(2-methylquinolin-6-yl)-1H-imidazol-2-yl)-1-(oxazol-2-yl)heptan-1-one (Example 78). LCMS (ESI) calc'd for $C_{29}H_{36}N_6O_2$ $[M+H]^+$: 501.3, found: 501.3. $^1$H NMR (400 MHz, MeOD) δ 8.94 (d, J=8.60 Hz, 1H), 8.63 (s, 1H), 8.56 (d, J=8.82 Hz, 1H), 8.16 (d, J=8.82 Hz, 1H), 8.07 (s, 1H), 7.86-7.99 (m, 2H), 7.36 (s, 1H), 4.63 (brs, 1H), 3.54-3.69 (m, 2H), 2.94-3.20 (m, 7H), 2.84 (brs, 3H), 2.53 (d, J=13.45 Hz, 1H), 1.92-2.33 (m, 6H), 1.62-1.77 (m, 2H), 1.42 (d, J=6.17 Hz, 3H), 1.28 (d, J=16.76 Hz, 1H).

Example 79

(S)-7-(5-(2-methylquinolin-6-yl)-1H-imidazol-2-yl)-1-(oxazol-2-yl)-7-((tetrahydro-2H-pyran-4-yl)amino)heptan-1-one

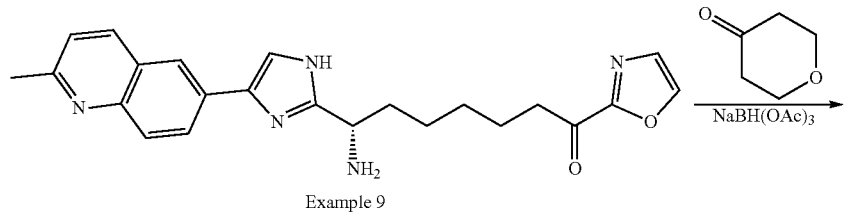

Example 9

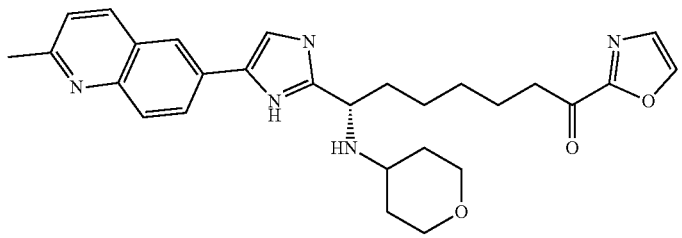

Example 79

NaBH(OAc)$_3$ (193 mg, 0.909 mmol) was added to a stirred mixture of (S)-7-amino-7-(4-(2-methylquinolin-6-yl)-1H-imidazol-2-yl)-1-(oxazol-2-yl)heptan-1-one hydrochloride (Example 9, 40 mg, 0.091 mmol) and dihydro-2H-pyran-4(3H)-one (91 mg, 0.909 mmol) in MeOH (2.0 ml) at room temperature and the mixture was stirred at 40° C. for 12 h. The residue was purified by preparative HPLC (reverse phase C-18 column), eluting with acetonitrile/water+0.1% TFA, to give (S)-7-(5-(2-methylquinolin-6-yl)-1H-imidazol-2-yl)-1-(oxazol-2-yl)-7-((tetrahydro-2H-pyran-4-yl)amino)heptan-1-one (Example 79). LCMS (ESI) calc'd for C$_{28}$H$_{33}$N$_5$O$_3$ [M+H]$^+$: 488.3, found: 488.1. $^1$H NMR (400 MHz, MeOD) δ 8.95 (d, J=8.60 Hz, 1H), 8.50-8.67 (m, 2H), 8.15 (d, J=8.82 Hz, 1H), 8.07 (s, 1H), 7.85-7.95 (m, 2H), 7.36 (s, 1H), 4.56-4.63 (m, 1H), 4.00 (dd, J=12.24, 18.63 Hz, 2H), 3.34-3.41 (m, 2H), 3.26 (brs, 1H), 2.95-3.06 (m, 4H), 2.25 (brs, 1H), 2.15 (d, J=12.35 Hz, 2H), 1.92 (d, J=13.01 Hz, 1H), 1.63-1.79 (m, 4H), 1.14-1.51 (m, 5H).

Example 80

(S)-7-(5-(7-methoxy-2-methylquinolin-6-yl)-1H-imidazol-2-yl)-1-(oxazol-2-yl)-7-((tetrahydro-2H-pyran-4-yl)amino)heptan-1-one

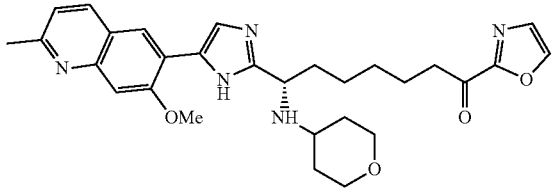 [SMILES: COc1cc2nc(C)ccc2cc1-c1cnc([C@H](CCCCCC(=O)c2ncco2)NC2CCOCC2)[nH]1]

Example 80 was obtained from compound Example 12 using a similar method. LCMS (ESI) calc'd for C$_{29}$H$_{35}$N$_5$O$_4$ [M+H]$^+$: 518.3, found: 518.1, tR=1.908 min. $^1$H NMR (400 MHz, MeOD) δ 8.84-8.90 (m, 2H), 8.06 (s, 1H), 7.91 (s, 1H), 7.73 (d, J=8.38 Hz, 1H), 7.56 (s, 1H), 7.35 (s, 1H), 4.61 (dd, J=4.08, 10.47 Hz, 1H), 4.24 (s, 3H), 3.91-4.07 (m, 3H), 3.33-3.40 (m, 2H), 3.19-3.26 (m, 1H), 3.00 (t, J=7.39 Hz, 2H), 2.96 (s, 3H), 2.25 (brs, 1H), 2.15 (d, J=9.70 Hz, 1H), 1.91 (d, J=11.03 Hz, 1H), 1.64-1.79 (m, 4H), 1.40 (brs, 3H), 1.22 (brs, 1H).

Example 81

(S)-7-(benzylamino)-7-(5-(2-methylquinolin-6-yl)-1H-imidazol-2-yl)-1-(oxazol-2-yl)heptan-1-one

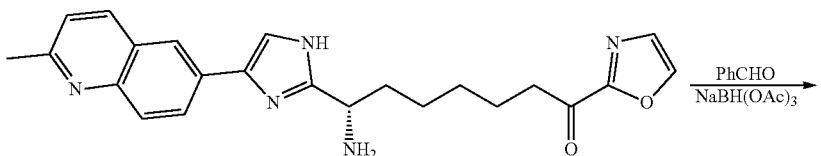

Example 9

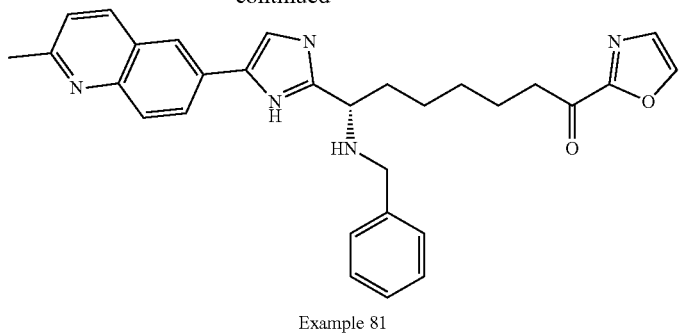

Example 81

Benzaldehyde (50 mg, 0.471 mmol) was added to a stirred mixture of (S)-7-amino-7-(4-(2-methylquinolin-6-yl)-1H-imidazol-2-yl)-1-(oxazol-2-yl)heptan-1-one hydrochloride (Example 9, 30 mg, 0.068 mmol) in MeOH (1.0 ml) at room temperature and the mixture was stirred at room temperature for 2 h. NaBH(OAc)$_3$ (145 mg, 0.682 mmol) was added. The mixture was stirred at room temperature for 12 h. The residue was purified by preparative HPLC (reverse phase C-18 column), eluting with acetonitrile/water+0.1% TFA, to give (S)-7-(benzylamino)-7-(5-(2-methylquinolin-6-yl)-1H-imidazol-2-yl)-1-(oxazol-2-yl)heptan-1-one (Example 81). LCMS (ESI) calc'd for $C_{20}H_{31}N_5O_2$ [M+H]$^+$: 494.3, found: 494.1. $^1$H NMR (400 MHz, MeOD) δ 8.96 (d, J=8.38 Hz, 1H), 8.66 (d, J=1.54 Hz, 1H), 8.58-8.64 (m, 1H), 8.17 (d, J=8.82 Hz, 1H), 8.08 (d, J=0.66 Hz, 1H), 7.89-7.94 (m, 2H), 7.45 (s, 5H), 7.37 (s, 1H), 4.47 (dd, J=4.19, 10.36 Hz, 1H), 4.28 (d, J=13.01 Hz, 1H), 4.14 (d, J=13.01 Hz, 1H), 2.97-3.06 (m, 5H), 2.16-2.27 (m, 2H), 1.64-1.73 (m, 2H), 1.41 (brs, 3H), 1.28 (d, J=11.91 Hz, 1H).

Example 82

(S)-7-(benzylamino)-7-(5-(7-methoxy-2-methylquinolin-6-yl)-1H-imidazol-2-yl)-1-(oxazol-2-yl)heptan-1-one

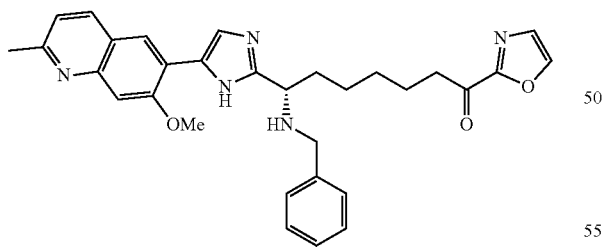

Example 82 was obtained from compound Example 12 using a similar method. LCMS (ESI) calc'd for $C_{21}H_{33}N_5O_3$ [M+H]$^+$: 524.3, found: 524.1. $^1$H NMR (400 MHz, MeOD) δ 8.85-8.93 (m, 2H), 8.06 (s, 1H), 7.92 (s, 1H), 7.74 (d, J=8.60 Hz, 1H), 7.57 (s, 1H), 7.44 (s, 5H), 7.36 (s, 1H), 4.48 (d, J=5.51 Hz, 1H), 4.20-4.31 (m, 4H), 4.13 (d, J=13.23 Hz, 1H), 2.91-3.04 (m, 5H), 2.25 (d, J=9.92 Hz, 1H), 2.20 (dd, J=5.18, 10.47 Hz, 1H), 1.65-1.76 (m, 2H), 1.36-1.47 (m, 3H), 1.25 (brs, 1H).

Example 83

(S)-7-(5-(2-methylquinolin-6-yl)-1H-imidazol-2-yl)-7-morpholino-1-(oxazol-2-yl)heptan-1-one

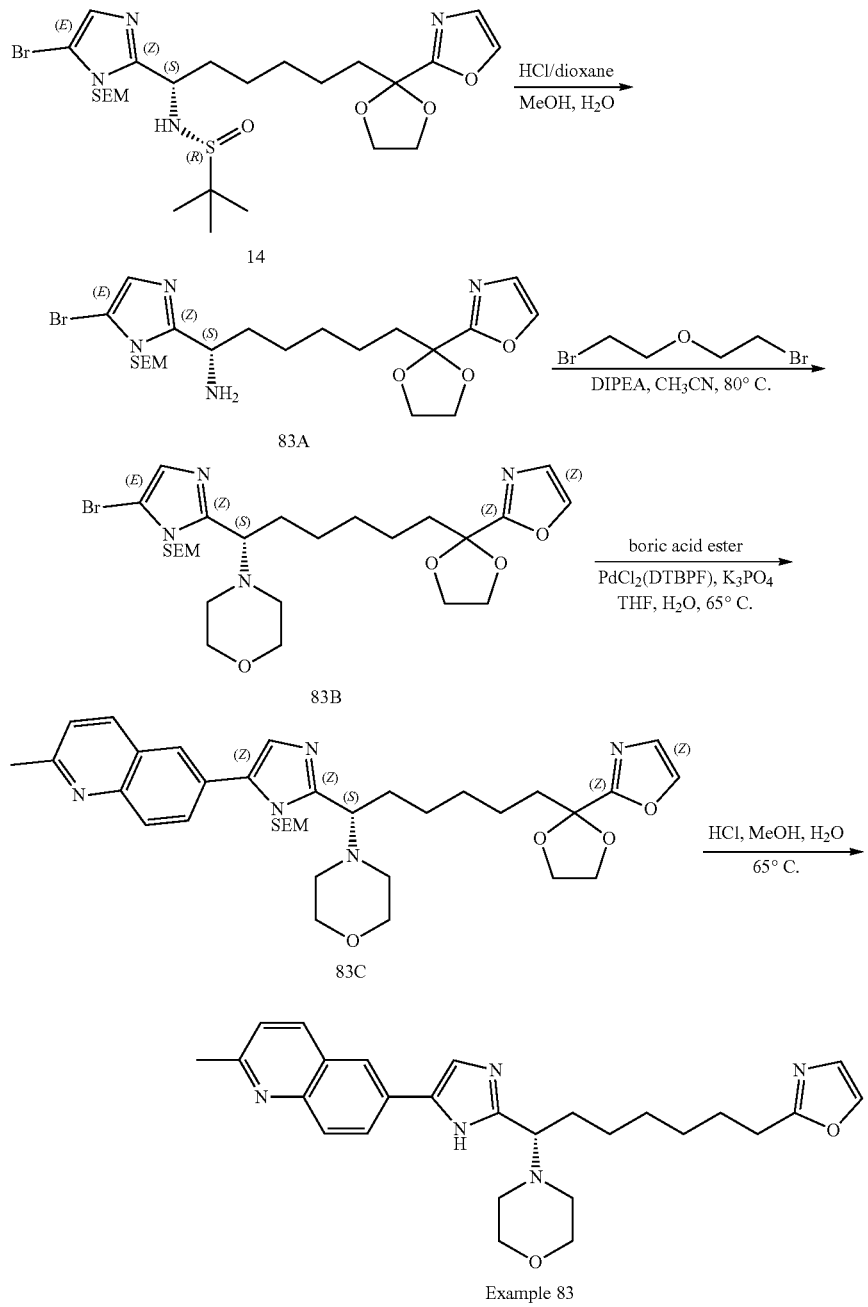

Example 83

Step 1: Preparation of (S)-1-(5-bromo-1-((2-(trimethylsilyl)ethoxy)methyl)-1H-imidazol-2-yl)-6-(2-(oxazol-2-yl)-1,3-dioxolan-2-yl)hexan-1-amine (83A)

HCl/dioxane (3.75 mL, 15.00 mmol) was added to a stirred mixture of (R)-N-((S)-1-(5-bromo-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (14, 1.5 g, 2.421 mmol) in MeOH (15 ml) and water (7.5 mL) at room temperature and the mixture was stirred at room temperature for 2 h. 2 mL HCl/dioxane was added and the mixture continued to be stirred at room temperature for 2 h. Aqueous NaHCO$_3$ (saturated, 15 mL) was added to adjust the pH to around 7 and the mixture was extracted with DCM (3×15 mL). The combined organic fractions were washed with brine (saturated, 1×15 mL), dried (Na$_2$SO$_4$), filtered and the solvent was evaporated under reduced pressure to give (S)-1-(5-bromo-1-((2-(trimethylsilyl)ethoxy)methyl)-1H-imidazol-2-yl)-6-(2-(oxazol-2-yl)-1,3-dioxolan-2-yl)hexan-1-amine (49A). LCMS (ESI) calc'd for C$_{21}$H$_{35}$BrN$_4$O$_4$Si [M+H]$^+$: 515.2, 517.2, found: 515.1, 517.1

Step 2: Preparation of (S)-4-(1-(5-bromo-1-((2-(trimethylsilyl)ethoxy)methyl)-1H-imidazol-2-yl)-6-(2-(oxazol-2-yl)-1,3-dioxolan-2-yl)hexyl)morpholine (83B)

DIPEA (0.08 ml, 0.458 mmol) was added to a stirred mixture of (S)-1-(5-bromo-1-((2-(trimethylsilyl)ethoxy)methyl)-1H-imidazol-2-yl)-6-(2-(oxazol-2-yl)-1,3-dioxolan-2-yl)hexan-1-amine (83A, 130 mg, 0.252 mmol) and 1-bromo-2-(2-bromoethoxy)ethane (60 mg, 0.259 mmol) in acetonitrile (7 ml) at room temperature and the mixture was heated with stirring at 80° C. for 42 h. Then NaI (40 mg, 0.267 mmol) and 1-bromo-2-(2-bromoethoxy)ethane (60 mg, 0.259 mmol) was added and it continued to be stirred at 80° C. for 24 h. The mixture was cooled to room temperature, the solvent was removed by evaporator, then water (5 mL) was added and the mixture was extracted with DCM (3×10 mL). The combined organic fractions were washed with brine (saturated, 1×10 mL), dried (Na$_2$SO$_4$), filtered and the solvent was evaporated under reduced pressure. The residue was purified by silica gel flash chromatography (ISCORF75; Sepa flash column), eluting with petroleum ether/EtOAc=0~60% to give (S)-4-(1-(5-bromo-1-((2-(trimethylsilyl)ethoxy)methyl)-1H-imidazol-2-yl)-6-(2-(oxazol-2-yl)-1,3-dioxolan-2-yl)hexyl)morpholine (83B). LCMS (ESI) calc'd for C$_{25}$H$_{41}$BrN$_4$O$_5$Si [M+H]$^+$: 585.2, 587.2, found: 585.3, 587.3

Step 3: Preparation of (S)-4-(1-(5-(2-methylquinolin-6-yl)-1-((2-(trimethylsilyl)ethoxy)methyl)-1H-imidazol-2-yl)-6-(2-(oxazol-2-yl)-1,3-dioxolan-2-yl)hexyl)morpholine (83C)

Pd(DTBPF)Cl$_2$ (11 mg, 0.017 mmol) was added to a stirred mixture of 2-methyl-6-(4,4,5,5-tetramethyl-1,3,2-dioxaborolan-2-yl)quinoline (46 mg, 0.171 mmol), (S)-4-(1-(5-bromo-1-((2-(trimethylsilyl)ethoxy)methyl)-1H-imidazol-2-yl)-6-(2-(oxazol-2-yl)-1,3-dioxolan-2-yl)hexyl)morpholine (83B, 100 mg, 0.171 mmol), K$_3$PO$_4$ (109 mg, 0.512 mmol) in THF (1 ml)/water (0.25 ml) at room temperature and the mixture was stirred at 65° C. for 18 h. The mixture was concentrated and the residue was purified by silica gel flash chromatography (ISCORF75; Sepa flash column), eluting with petroleum ether/EtOAc=0~100% to give (S)-4-(1-(5-(2-methylquinolin-6-yl)-1-((2-(trimethylsilyl)ethoxy)methyl)-1H-imidazol-2-yl)-6-(2-(oxazol-2-yl)-1,3-dioxolan-2-yl)hexyl)morpholine (83C). LCMS (ESI) calc'd for C$_{25}$H$_{49}$N$_5$O$_5$Si [M+H]$^+$: 648.4, found: 648.4

Step 4: Preparation of (S)-7-(5-(2-methylquinolin-6-yl)-1H-imidazol-2-yl)-7-morpholino-1-(oxazol-2-yl)heptan-1-one (Example 83)

HCl (0.7 mL, 2.80 mmol) was added to a stirred mixture of (S)-4-(1-(5-(2-methylquinolin-6-yl)-1-((2-(trimethylsilyl)ethoxy)methyl)-1H-imidazol-2-yl)-6-(2-(oxazol-2-yl)-1,3-dioxolan-2-yl)hexyl)morpholine (83C, 65 mg, 0.100 mmol) in MeOH (2.8 ml) and water (0.28 mL) at room temperature and the mixture was stirred at 65° C. for 16 h. The mixture was cooled to room temperature, and aqueous NaHCO$_3$ (saturated, 3 mL) was added to adjust the pH to 7. Most of the solvent was removed by evaporator. The residue was purified by preparative HPLC (reverse phase C-18 column), eluting with acetonitrile/water+0.05% NH$_3$·H$_2$O, to give (S)-7-(5-(2-methylquinolin-6-yl)-1H-imidazol-2-yl)-7-morpholino-1-(oxazol-2-yl)heptan-1-one (Example 83). LCMS (ESI) calc'd for C$_{27}$H$_{31}$N$_5$O$_3$ [M+H]$^+$: 474.2, found: 474.2.

L-(+)-Tartaric acid (12 mg, 0.080 mmol) was added to a stirred mixture of (S)-7-(5-(2-methylquinolin-6-yl)-1H-imidazol-2-yl)-7-morpholino-1-(oxazol-2-yl)heptan-1-one (Example 83, 35 mg, 0.074 mmol) in acetonitrile (2 ml) and water (2 ml) at room temperature and the mixture was made dry by lyophilization to give (S)-7-(5-(2-methylquinolin-6-yl)-1H-imidazol-2-yl)-7-morpholino-1-(oxazol-2-yl)heptan-1-one (2R,3R)-2,3-dihydroxysuccinate (Example 83). LCMS (ESI) calc'd for C$_{27}$H$_{31}$N$_5$O$_3$ [M+H]$^+$: 474.2, found: 474.1. $^1$H NMR (400 MHz, MeOD) δ 8.29 (d, J=8.6 Hz, 1H), 8.25 (d, J=1.5 Hz, 1H), 8.12 (dd, J=2.0, 8.8 Hz, 1H), 8.05 (s, 1H), 7.97 (d, J=8.8 Hz, 1H), 7.68 (s, 1H), 7.47 (d, J=8.6 Hz, 1H), 7.35 (s, 1H), 4.50 (s, 2H), 3.84-3.91 (m, 1H), 3.68-3.78 (m, 4H), 2.99-3.06 (m, 2H), 2.74 (s, 5H), 2.56-2.67 (m, 2H), 2.07 (d, J=7.7 Hz, 2H), 1.65-1.75 (m, 2H), 1.15-1.50 (m, 4H).

Example 84

(S)-7-(5-(7-methoxy-2-methylquinolin-6-yl)-1H-imidazol-2-yl)-7-((3-methoxycyclobutyl)amino)-1-(oxazol-2-yl)heptan-1-one

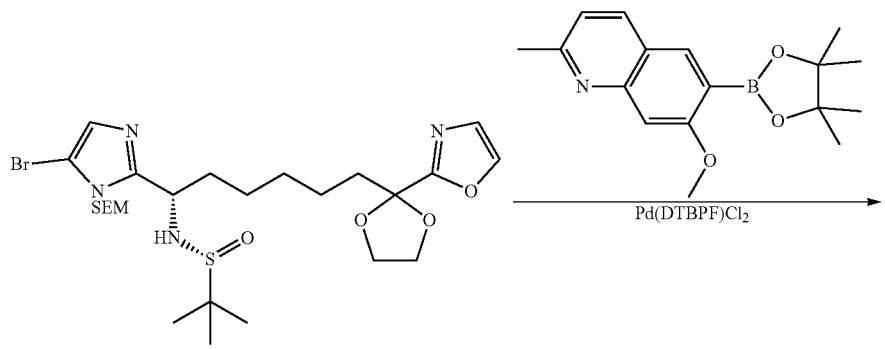

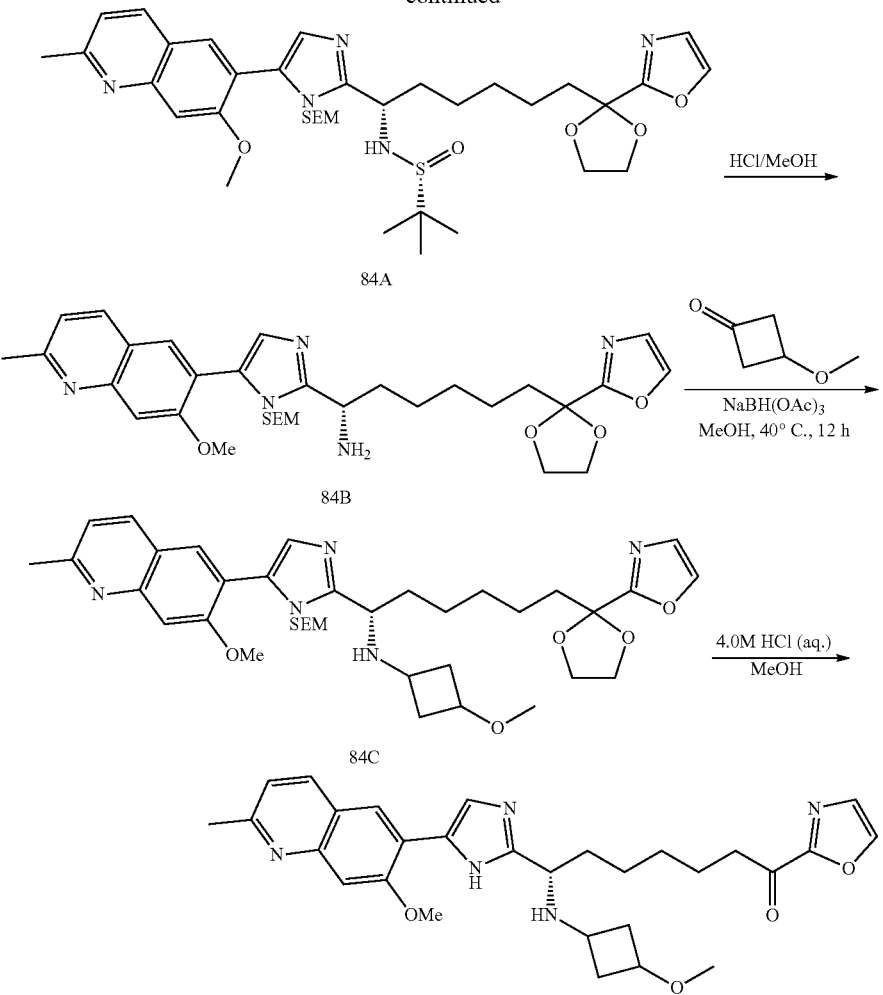

Example 84

Step 1: Preparation of (R)-N-((S)-1-(5-(7-methoxy-2-methylquinolin-6-yl)-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (84A)

Pd(DTBPF)Cl$_2$ (0.13 g, 0.199 mmol) was added to a stirred mixture of 7-methoxy-2-methyl-6-(4,4,5,5-tetramethyl-1,3,2-dioxaborolan-2-yl)quinoline (1.01 g, 3.38 mmol), (R)-N-((S)-1-(5-bromo-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (14, 2.0 g, 3.23 mmol) and K$_3$PO$_4$ (2.056 g, 9.69 mmol) in THF (20 ml) and water (1.0 ml) at room temperature and the mixture was stirred at 80° C. for 4 h under N$_2$. The mixture was concentrated. The residue was purified by silica gel column flash chromatography, eluting with petroleum ether/EtOAc=1:1-0:1 to give (R)-N-((S)-1-(5-(7-methoxy-2-methylquinolin-6-yl)-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (84A). LCMS (ESI) calc'd for C$_{26}$H$_{53}$N$_5$O$_6$SSi [M+H]$^+$: 712.4, found: 712.4

Step 2: Preparation of (S)-1-(5-(7-methoxy-2-methylquinolin-6-yl)-1-((2-(trimethylsilyl)ethoxy)methyl)-1H-imidazol-2-yl)-6-(2-(oxazol-2-yl)-1,3-dioxolan-2-yl)hexan-1-amine (84B)

Hydrogen chloride (3.0 ml, 12.00 mmol) was added to a stirred mixture of (R)-N-((S)-1-(5-(7-methoxy-2-methylquinolin-6-yl)-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (84A, 800 mg, 1.124 mmol) in MeOH (3.0 ml) at room temperature and the mixture was stirred at room temperature for 12 h. The mixture was quenched with aqueous NaHCO$_3$ (saturated) to pH=7-9 and the mixture was extracted with DCM (3×30 mL). The combined organic fractions were washed with brine (saturated, 30 mL), dried (Na$_2$SO$_4$), filtered and the solvent was evaporated under reduced pressure. The residue was purified by silica gel column flash chromatography, eluting with DCM/MeOH=10:1 to give (S)-1-(5-(7-methoxy-2-methylquinolin-6-yl)-1-((2-(trimethylsilyl)ethoxy)methyl)-1H-imidazol-2-yl)-6-(2-(oxazol-2-yl)-1,3-dioxolan-2-yl)hexan-1-amine (84B). LCMS (ESI) calc'd for C$_{22}$H$_{45}$N$_5$O$_5$Si [M+H]$^+$: 608.3, found: 608.4

Step 3: Preparation of (S)-3-methoxy-N-(1-(5-(7-methoxy-2-methylquinolin-6-yl)-1-((2-(trimethylsilyl)ethoxy)methyl)-1H-imidazol-2-yl)-6-(2-(oxazol-2-yl)-1,3-dioxolan-2-yl)hexyl)cyclobutanamine (84C)

3-methoxycyclobutanone (40 mg, 0.400 mmol) was added to a stirred mixture of (S)-1-(5-(7-methoxy-2-methylquinolin-6-yl)-1-((2-(trimethylsilyl)ethoxy)methyl)-1H-imidazol-2-yl)-6-(2-(oxazol-2-yl)-1,3-dioxolan-2-yl)hexan-1-amine (84B, 60 mg, 0.099 mmol) in MeOH (1.0 ml) at room temperature and the mixture was stirred at 40° C. for 12 h. The residue was purified by silica gel column flash chromatography, eluting with petroleum ether/EtOAc=1:1-0:1 to give (S)-3-methoxy-N-(1-(5-(7-methoxy-2-methylquinolin-6-yl)-1-((2-(trimethylsilyl)ethoxy)methyl)-1H-imidazol-2-yl)-6-(2-(oxazol-2-yl)-1,3-dioxolan-2-yl)hexyl) cyclobutanamine (84C). LCMS (ESI) calc'd for $C_{27}H_{53}N_5O_6Si$ [M+H]$^+$: 692.4, found: 692.4 preparative HPLC (reverse phase C-18 column), eluting with acetonitrile/water+0.1% TFA, to give (S)-7-(5-(7-methoxy-2-methylquinolin-6-yl)-1H-imidazol-2-yl)-7-((3-methoxycyclobutyl)amino)-1-(oxazol-2-yl)heptan-1-one (Example 84). LCMS (ESI) calc'd for $C_{29}H_{35}N_5O_4$ [M+H]$^+$: 518.3, found: 518.0. $^1$H NMR (400 MHz, MeOD) δ 8.83-8.92 (m, 2H), 8.06 (s, 1H), 7.90 (s, 1H), 7.73 (d, J=8.60 Hz, 1H), 7.57 (brs, 1H), 7.35 (s, 1H), 4.38 (d, J=10.80 Hz, 1H), 4.24 (s, 3H), 3.78-4.02 (m, 1H), 3.67 (td, J=7.06, 13.67 Hz, 1H), 3.33-3.39 (m, 1H), 3.19 (s, 3H), 3.00 (t, J=7.39 Hz, 2H), 2.96 (s, 3H), 2.74 (dt, J=6.39, 11.91 Hz, 1H), 2.35-2.51 (m, 1H), 2.22-2.33 (m, 1H), 2.05-2.17 (m, 2H), 1.92 (td, J=8.30, 11.41 Hz, 1H), 1.64-1.75 (m, 2H), 1.40 (brs, 3H), 1.22 (brs, 1H).

Example 85

(S)-7-(5-(7-methoxy-2-methylquinolin-6-yl)-1H-imidazol-2-yl)-1-(oxazol-2-yl)-7-(pyrimidin-2-ylamino)heptan-1-one

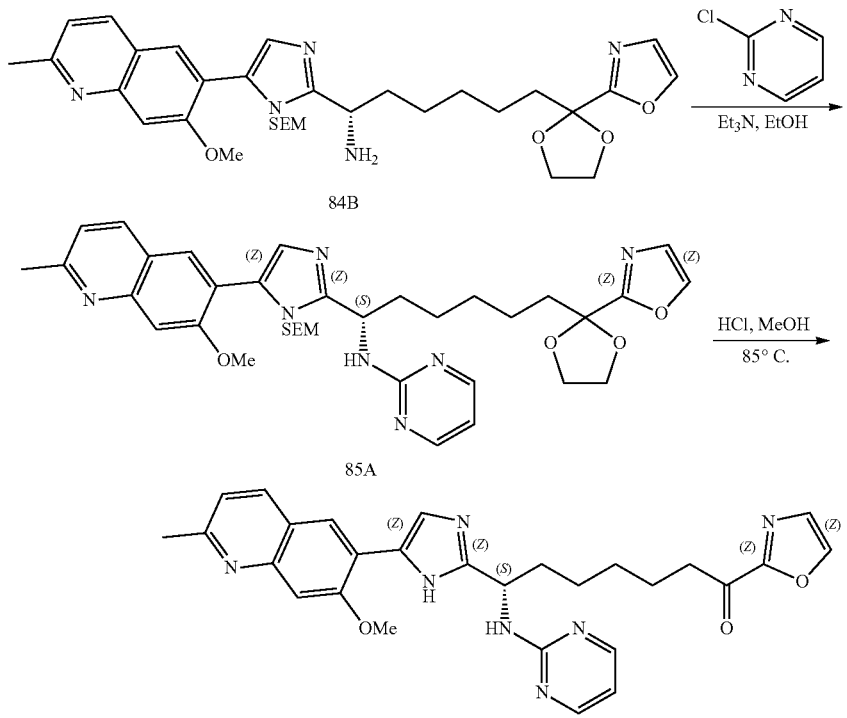

Step 4: Preparation of (S)-7-(5-(7-methoxy-2-methylquinolin-6-yl)-1H-imidazol-2-yl)-7-((3-methoxycyclobutyl)amino)-1-(oxazol-2-yl)heptan-1-one (Example 84)

Hydrogen chloride (1.5 ml, 6.00 mmol) was added to a stirred mixture of (S)-3-methoxy-N-(1-(5-(7-methoxy-2-methylquinolin-6-yl)-1-((2-(trimethylsilyl)ethoxy)methyl)-1H-imidazol-2-yl)-6-(2-(oxazol-2-yl)-1,3-dioxolan-2-yl) hexyl)cyclobutanamine (84C, 40 mg, 0.058 mmol) in MeOH (2.0 ml) at room temperature and the mixture was stirred at 50° C. for 6 h. The residue was purified by

Step 1: Preparation of (S)-N-(1-(5-(7-methoxy-2-methylquinolin-6-yl)-1-((2-(trimethylsilyl)ethoxy)methyl)-1H-imidazol-2-yl)-6-(2-(oxazol-2-yl)-1,3-dioxolan-2-yl)hexyl)pyrimidin-2-amine (85A)

To a solution of (S)-1-(5-(7-methoxy-2-methylquinolin-6-yl)-1-((2-(trimethylsilyl)ethoxy)methyl)-1H-imidazol-2-yl)-6-(2-(oxazol-2-yl)-1,3-dioxolan-2-yl)hexan-1-amine (84B, 100 mg, 0.165 mmol) and TEA (0.1 mL, 0.717 mmol) in ethanol (1 mL) was added 2-chloropyrimidine (19 mg, 0.166 mmol) at rt. The mixture was stirred at 90° C. for 48 h. The mixture was concentrated to dryness and the residue was purified by silica gel flash chromatography (ISCORF75; Sepa flash column), eluting with DCM/MeOH=100:1-9:1 to give (S)-N-(1-(5-(7-methoxy-2-methylquinolin-6-yl)-1-((2-(trimethylsilyl)ethoxy)methyl)-1H-imidazol-2-yl)-6-(2-(oxazol-2-yl)-1,3-dioxolan-2-yl)hexyl)pyrimidin-2-amine (85A). LCMS (ESI) calc'd for $C_{36}H_{47}N_7O_5Si$ [M+H]$^+$: 686.3, found: 686.3

Step 2: Preparation of (S)-7-(5-(7-methoxy-2-methylquinolin-6-yl)-1H-imidazol-2-yl)-1-(oxazol-2-yl)-7-(pyrimidin-2-ylamino)heptan-1-one (Example 85)

HCl (0.5 mL, 6.09 mmol) was added to a stirred mixture of (S)-N-(1-(5-(7-methoxy-2-methylquinolin-6-yl)-1-((2-(trimethylsilyl)ethoxy)methyl)-1H-imidazol-2-yl)-6-(2-(oxazol-2-yl)-1,3-dioxolan-2-yl)hexyl)pyrimidin-2-amine (85A, 40 mg, 0.058 mmol) in co-solvents of MeOH (2 mL) and water (0.2 mL) at rt and the mixture was stirred at 65° C. for 10 h. The residue was purified by preparative HPLC (reverse phase C-18 column), eluting with Acetonitrile/Water+0.1% TFA, and HCl (0.1 M, 0.6 mL, 0.060 mmol) was added before lyophilization to give (S)-7-(5-(7-methoxy-2-methylquinolin-6-yl)-1H-imidazol-2-yl)-1-(oxazol-2-yl)-7-(pyrimidin-2-ylamino)heptan-1-one hydrochloride (Example 85). LCMS (ESI) calc'd for ClH $C_{28}H_{29}N_7O_3$ [M+H]$^+$: 512.2, found: 512.1. $^1$H NMR (400 MHz, MeOD) δ 8.81-8.96 (m, 1H), 8.50-8.62 (m, 1H), 8.27-8.39 (m, 2H), 8.04-8.13 (m, 1H), 7.95-8.00 (m, 1H), 7.74-7.83 (m, 1H), 7.59-7.70 (m, 1H), 7.33-7.44 (m, 1H), 6.67-6.78 (m, 1H), 5.25-5.35 (m, 1H), 5.25-5.35 (m, 1H), 4.15-4.25 (m, 3H), 3.01-3.10 (m, 2H), 2.91-3.00 (m, 3H), 2.06-2.23 (m, 2H), 1.68-1.82 (m, 2H), 1.42-1.64 (m, 4H).

Example 86

(S)-methyl (1-(5-(7-methoxy-2-methylquinolin-6-yl)-1H-imidazol-2-yl)-7-(oxazol-2-yl)-7-oxoheptyl)carbamate Step 1: Preparation of (S)-methyl (1-(5-(7-methoxy-2-methylquinolin-6-yl)-1-((2-(trimethylsilyl)ethoxy)methyl)-1H-imidazol-2-yl)-6-(2-(oxazol-2-yl)-1,3-dioxolan-2-yl)hexyl)carbamate (86A)

To a solution of (S)-1-(5-(7-methoxy-2-methylquinolin-6-yl)-1-((2-(trimethylsilyl)ethoxy)methyl)-1H-imidazol-2-yl)-6-(2-(oxazol-2-yl)-1,3-dioxolan-2-yl)hexan-1-amine (84B, 100 mg, 0.165 mmol) and triethylamine (2 mL, 14.35 mmol) in DCM (2 mL) was added methyl carbonochloridate (600 mg, 6.35 mmol) at 0° C. The mixture was stirred at 0° C. for 1 h. The mixture was washed with water (10 mL) and extracted with ethyl acetate (10×3 mL), dried (Na$_2$SO$_4$), filtered and the solvent was evaporated under reduced pressure to give (S)-methyl (1-(5-(7-methoxy-2-methylquinolin-6-yl)-1-((2-(trimethylsilyl)ethoxy)methyl)-1H-imidazol-2-yl)-6-(2-(oxazol-2-yl)-1,3-dioxolan-2-yl)hexyl)carbamate (84A) which was used directly in next step. LCMS (ESI) calc'd for $C_{34}H_{47}N_5O_7Si$ [M+H]$^+$: 666.3, found: 666.4

Step 2: Preparation of (S)-methyl (1-(5-(7-methoxy-2-methylquinolin-6-yl)-1H-imidazol-2-yl)-7-(oxazol-2-yl)-7-oxoheptyl)carbamate hydrochloride (Example 86)

HCl (0.5 ml, 6.09 mmol) was added to a stirred mixture of (S)-methyl (1-(5-(7-methoxy-2-methylquinolin-6-yl)-1-((2-(trimethylsilyl)ethoxy)methyl)-1H-imidazol-2-yl)-6-(2-(oxazol-2-yl)-1,3-dioxolan-2-yl)hexyl)carbamate (86A, 100 mg, 0.15 mmol) in co-solvents of MeOH (2 ml) and water (0.2 ml) at rt and the mixture was stirred at 65° C. for 10 h. The residue was purified by preparative HPLC (reverse phase C-18 column), eluting with acetonitrile/water+0.1% TFA, to give (S)-methyl (1-(5-(7-methoxy-2-methylquinolin-6-yl)-1H-imidazol-2-yl)-7-(oxazol-2-yl)-7-oxoheptyl) carbamate (Example 86). HCl (0.1 M, 1.7 mL, 0.170 mmol)

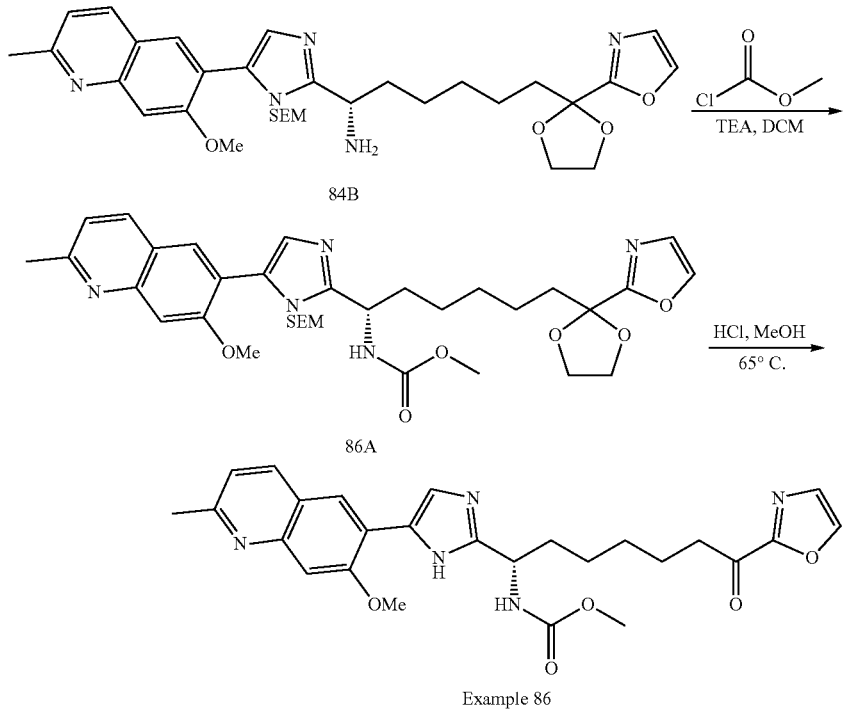

Example 86 was added to a stirred mixture of (S)-methyl (1-(5-(7-methoxy-2-methylquinolin-6-yl)-1H-imidazol-2-yl)-7-(oxazol-2-yl)-7-oxoheptyl)carbamate (Example 86, 40 mg, 0.081 mmol) in acetonitrile (2 ml) at room temperature, then it was lyophilized to give (S)-methyl (1-(5-(7-methoxy-2-methylquinolin-6-yl)-1H-imidazol-2-yl)-7-(oxazol-2-yl)-7-oxoheptyl)carbamate hydrochloride (43). LCMS (ESI) calc'd for $C_{26}H_{29}N_5O_5 \cdot ClH$ [M+H]$^+$: 492.2, found: 492.1. $^1$H NMR (400 MHz, MeOD) δ 8.89-8.98 (m, 1H), 8.53-8.64 (m, 1H), 8.05-8.11 (m, 1H), 7.96-8.04 (m, 1H), 7.76-7.84 (m, 1H), 7.62-7.68 (m, 1H), 7.32-7.41 (m, 1H), 4.93-5.03 (m, 1H), 4.22 (s, 3H), 3.61-3.71 (m, 3H), 3.03-3.10 (m, 2H), 2.93-3.01 (m, 3H), 1.98-2.09 (m, 2H), 1.68-1.80 (m, 2H), 1.36-1.55 (m, 4H).

Example 87

(S)-N-(1-(5-(2-methylquinolin-6-yl)-1H-imidazol-2-yl)-7-(oxazol-2-yl)-7-oxoheptyl)acetamide

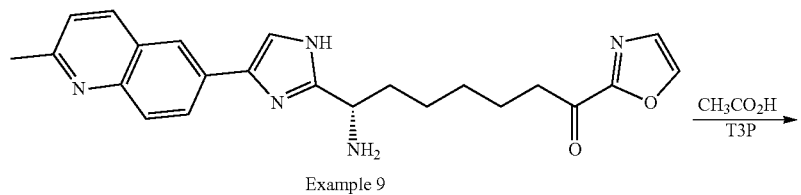

Example 9

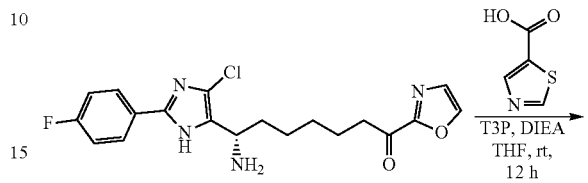

Example 87

T3H (116 mg, 0.182 mmol) was added to a stirred mixture of (S)-7-amino-7-(4-(2-methylquinolin-6-yl)-1H-imidazol-2-yl)-1-(oxazol-2-yl)heptan-1-one hydrochloride (Example 9, 40 mg, 0.091 mmol), acetic acid (11 mg, 0.183 mmol) and DIPEA (60 mg, 0.46 mmol) in DMF (2.0 ml) at room temperature and the mixture was stirred at room temperature for 12 h. The residue was purified by preparative HPLC (reverse phase C-18 column), eluting with acetonitrile/water+0.1% TFA, to give (S)-N-(1-(5-(2-methylquinolin-6-yl)-1H-imidazol-2-yl)-7-(oxazol-2-yl)-7-oxoheptyl) acetamide (Example 87). LCMS (ESI) calc'd for $C_{25}H_{27}N_5O_3$ [M+H]$^+$: 446.2, found: 446.1. $^1$H NMR (400 MHz, MeOD) δ 8.85 (d, J=7.28 Hz, 1H), 8.56 (brs, 1H), 8.37 (brs, 1H), 8.23 (brs, 1H), 8.00-8.12 (m, 2H), 7.89 (d, J=7.72 Hz, 1H), 7.40 (s, 1H), 5.11 (t, J=6.95 Hz, 1H), 3.08 (t, J=7.17 Hz, 2H), 2.97 (s, 3H), 2.06 (s, 4H), 1.74-1.79 (m, 1H), 1.63-1.71 (m, 1H), 1.43-1.58 (m, 3H), 1.37 (dd, J=3.53, 6.39 Hz, 1H), 0.98-1.06 (m, 1H).

Example 88

(S)-N-(1-(4-chloro-2-(4-fluorophenyl)-1H-imidazol-5-yl)-7-(oxazol-2-yl)-7-oxoheptyl)thiazole-5-carboxamide

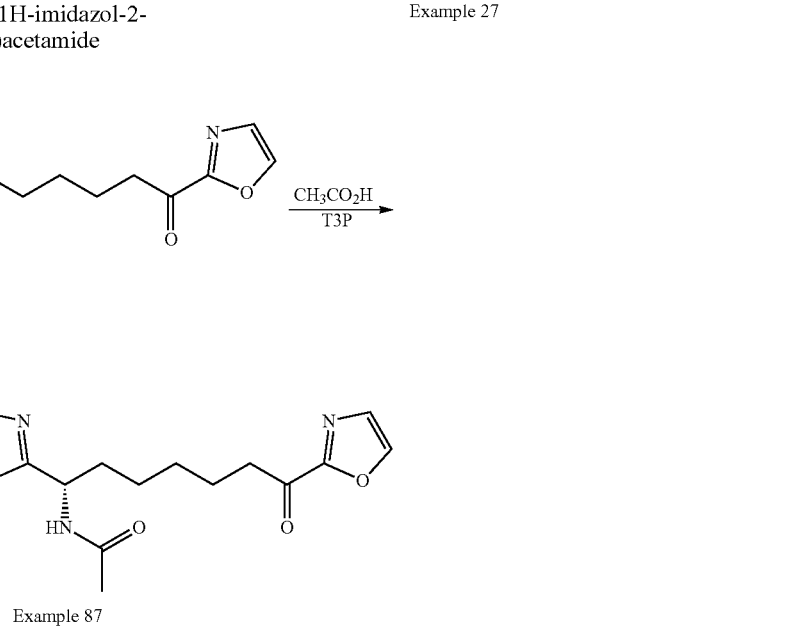

-continued

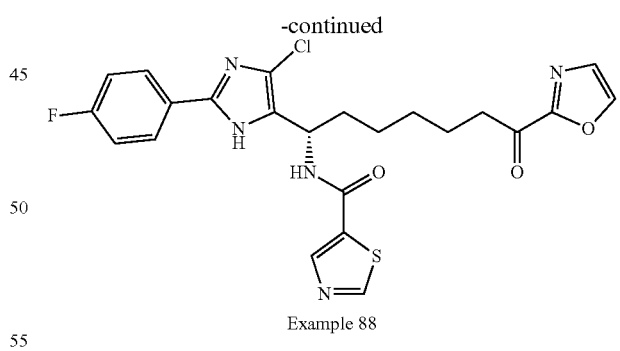

Example 88

T3P (244 mg, 0.384 mmol) was added to a stirred mixture of thiazole-5-carboxylic acid (34 mg, 0.263 mmol), (S)-7-amino-7-(4-chloro-2-(4-fluorophenyl)-1H-imidazol-5-yl)-1-(oxazol-2-yl)heptan-1-one (88D, 100 mg, 0.256 mmol) and DIEA (0.089 ml, 0.511 mmol) in THF (2.0 ml) at room temperature and the mixture was stirred at room temperature for 12 h. The mixture was concentrated and the residue was purified by preparative HPLC (reverse phase C-18 column), eluting with acetonitrile/water+0.1% TFA, to give (S)-N-(1-(4-chloro-2-(4-fluorophenyl)-1H-imidazol-5-yl)-7-(oxazol-2-yl)-7-oxoheptyl)thiazole-5-carboxamide (Example 88).

LCMS (ESI) calc'd for $C_{23}H_{21}ClFN_5O_3S$ [M+H]$^+$: 502.1, found: 501.9. $^1$H NMR (400 MHz, MeOD) δ 9.06-9.32 (m, 1H), 8.49 (s, 1H), 8.09 (s, 1H), 7.82-7.96 (m, 2H), 7.39 (s, 1H), 7.26 (t, J=8.66 Hz, 2H), 5.15 (t, J=7.78 Hz, 1H), 3.07 (t, J=7.15 Hz, 2H), 1.99-2.19 (m, 2H), 1.68-1.83 (m, 2H), 1.40-1.56 (m, 3H), 1.40-1.55 (m, 1H).

Example 89

(S)-2-(dimethylamino)-N-(1-(5-(7-methoxy-2-methylquinolin-6-yl)-1H-imidazol-2-yl)-7-(oxazol-2-yl)-7-oxoheptyl)acetamide

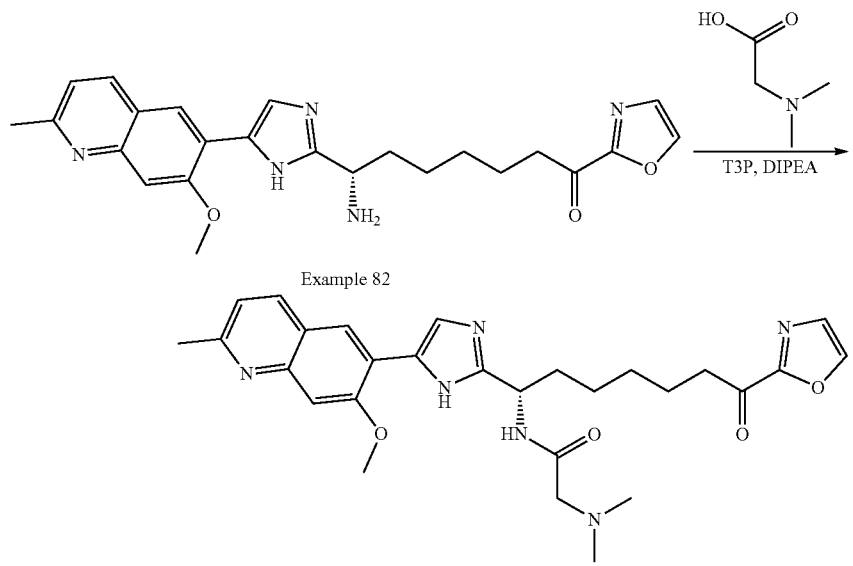

T₃P (348 mg, 0.547 mmol) was added to a stirred mixture of 2-(dimethylamino)acetic acid (38 mg, 0.369 mmol), (S)-7-amino-7-(5-(7-methoxy-2-methylquinolin-6-yl)-1H-imidazol-2-yl)-1-(oxazol-2-yl)heptan-1-one (Example 82, 158 mg, 0.364 mmol) and DIEA (0.2 mL, 1.145 mmol) in THF (2.0 mL) at room temperature and the mixture was stirred at room temperature for 12 h. The mixture was concentrated and the residue was purified by preparative HPLC (reverse phase C-18 column), eluting with acetonitrile/water+0.05% NH₃·H₂O, to give (S)-2-(dimethylamino)-N-(1-(5-(7-methoxy-2-methylquinolin-6-yl)-1H-imidazol-2-yl)-7-(oxazol-2-yl)-7-oxoheptyl)acetamide (Example 89). LCMS (ESI) calc'd for $C_{28}H_{34}N_6O_4$ [M+H]$^+$: 519.2, found: 519.4. $^1$H NMR (400 MHz, MeOD) δ 8.73-8.84 (m, 1H), 8.54-8.66 (m, 1H), 8.02-8.12 (m, 1H), 7.84-7.93 (m, 1H), 7.66-7.75 (m, 1H), 7.51-7.61 (m, 1H), 7.31-7.42 (m, 1H), 5.13-5.28 (m, 1H), 4.14-4.26 (m, 3H), 3.96-4.13 (m, 2H), 3.01-3.10 (m, 2H), 2.93 (d, J=4.89 Hz, 9H), 1.96-2.18 (m, 2H), 1.69-1.81 (m, 2H), 1.59-1.65 (m, 1H), 1.59-1.65 (m, 1H), 1.37-1.52 (m, 4H), 0.97-1.05 (m, 1H).

The following compounds were prepared using similar procedures to those described above using T3P as coupling reagent:

| Example # | Structure | Exact Mass [M + H]$^+$ | Observed [M + H]$^+$ |
|---|---|---|---|
| 90 | 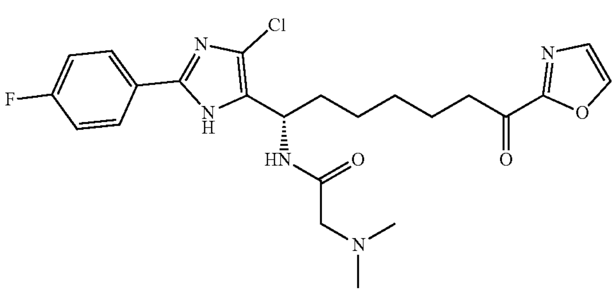 [SMILES: CN(C)CC(=O)N[C@@H](CCCCCC(=O)c1ncco1)c1[nH]c(-c2ccc(F)cc2)nc1Cl] | Calc'd 476.2, found | 476.0 |

-continued
| Example # | Structure | Exact Mass [M + H]+ | Observed [M + H]+ |
|---|---|---|---|
| 91 | 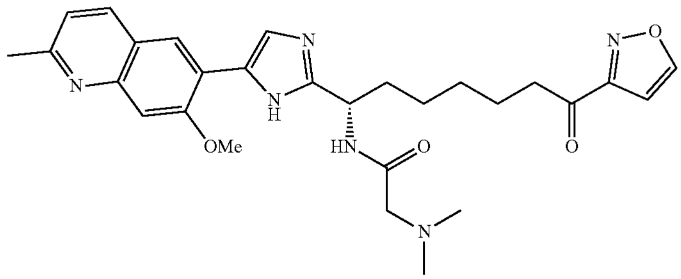 [SMILES: COc1cc2nc(C)ccc2cc1-c1cnc([C@H](CCCCCC(=O)c2ccon2)NC(=O)CN(C)C)[nH]1] | Calc'd 519.3, found | 519.3 |
| 92 | 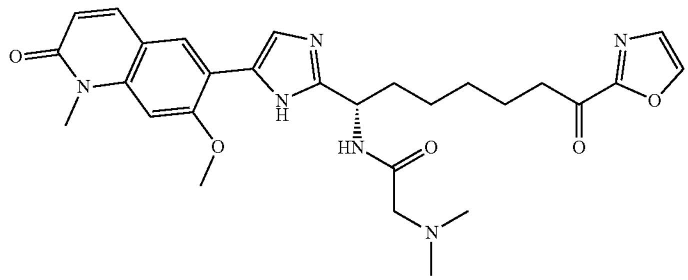 [SMILES: COc1cc2c(ccc(=O)n2C)cc1-c1cnc([C@H](CCCCCC(=O)c2ncco2)NC(=O)CN(C)C)[nH]1] | Calc'd 535.3, found | 535.3 |
| 93 | 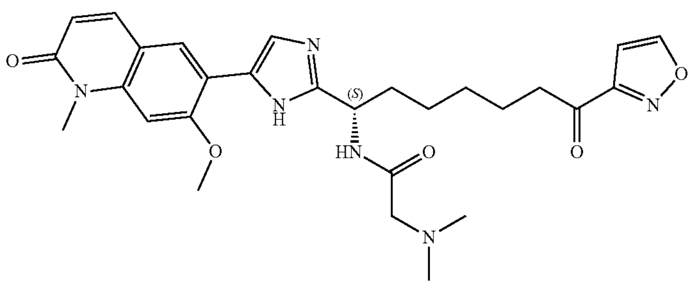 | Calc'd 535.2, found | 535.3 |
Example 94
(S)-2-(dimethylamino)-N-(1-(5-(2-ethyl-7-methoxy-1-oxo-1,2-dihydroisoquinolin-6-yl)-1H-imidazol-2-yl)-7-(isoxazol-3-yl)-7-oxoheptyl)acetamide
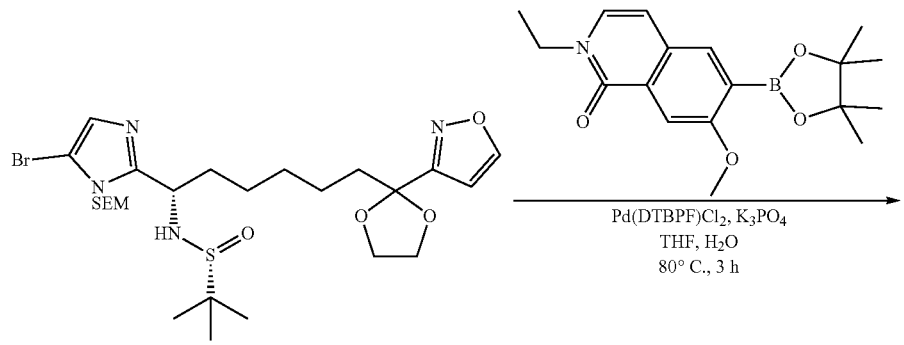

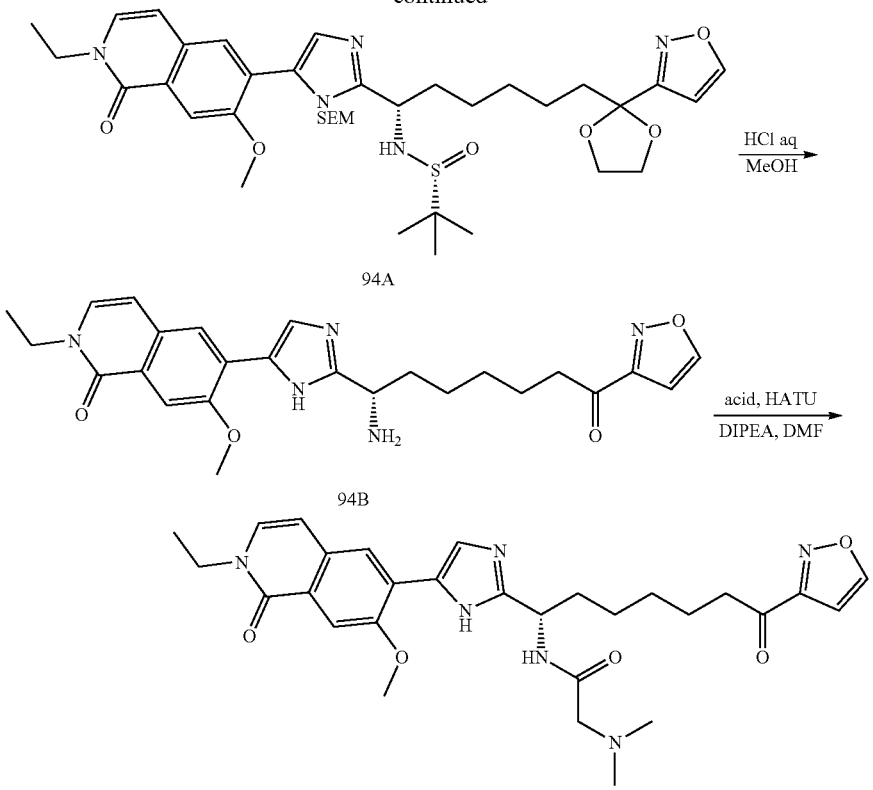

Example 94

Step 1. Preparation of (R)-N-((S)-1-N₅-(2-ethyl-7-methoxy-1-oxo-1,2-dihydroisoquinolin-6-yl)-1-(2-(trimethylsilyl)ethoxy)methyl)-1H-imidazol-2-yl)-6-(2-(isoxazol-3-yl)-1,3-dioxolan-2-yl)hexyl)-2-methylpropane-2-sulfinamide (94A)

Pd(DTBPF)Cl₂ (11 mg, 0.017 mmol) was added to a stirred mixture of 2-ethyl-7-methoxy-6-(4,4,5,5-tetramethyl-1,3,2-dioxaborolan-2-yl)isoquinolin-1(2H)-one (53 mg, 0.161 mmol), (R)-N-((S)-1-(5-bromo-1-((2-(trimethylsilyl)ethoxy)methyl)-1H-imidazol-2-yl)-6-(2-(isoxazol-3-yl)-1,3-dioxolan-2-yl)hexyl)-2-methylpropane-2-sulfinamide (15, 100 mg, 0.161 mmol), K₃PO₄ (103 mg, 0.484 mmol) in THF (1 ml)/water (0.25 ml) at room temperature and the mixture was stirred at 80° C. for 2 h. The mixture was cooled to room temperature then evaporated under reduced pressure. The residue was purified by silica gel column flash chromatography, eluting with petroleum ether/EtOAc=0-100% to give (R)-N-((S)-1-(5-(2-ethyl-7-methoxy-1-oxo-1,2-dihydroisoquinolin-6-yl)-1-((2-(trimethylsilyl)ethoxy)methyl)-1H-imidazol-2-yl)-6-(2-(isoxazol-3-yl)-1,3-dioxolan-2-yl)hexyl)-2-methylpropane-2-sulfinamide (94A). LCMS (ESI) calc'd for C₃₇H₅₅N₅O₇SSi [M+H]⁺: 742.4, found: 742.4

Step 2: Preparation of (S)-6-(2-(1-amino-7-(isoxazol-3-yl)-7-oxoheptyl)-1H-imidazol-5-yl)-2-ethyl-7-methoxyisoquinolin-1(2H)-one dihydrochloride (94B)

Hydrogen chloride (4 M) (0.6 ml, 2.400 mmol) was added to a stirred mixture of (R)-N-((S)-1-(5-(2-ethyl-7-methoxy-1-oxo-1,2-dihydroisoquinolin-6-yl)-1-((2-(trimethylsilyl)ethoxy)methyl)-1H-imidazol-2-yl)-6-(2-(isoxazol-3-yl)-1,3-dioxolan-2-yl)hexyl)-2-methylpropane-2-sulfinamide (94A, 60 mg, 0.081 mmol) in co-solvents of MeOH (2.4 ml) and water (0.24 ml) at room temperature and the mixture was stirred at 65° C. for 20 h. All the volatiles were removed by evaporator to give (S)-6-(2-(1-amino-7-(isoxazol-3-yl)-7-oxoheptyl)-1H-imidazol-5-yl)-2-ethyl-7-methoxyisoquinolin-1(2H)-one dihydrochloride (94B) which was used to the next step without further purification. LCMS (ESI) calc'd for C₂₅H₂₉N₅O₄[M+H]⁺: 464.2, found: 464.3

Step 3: Preparation of (S)-2-(dimethylamino)-N-(1-(5-(2-ethyl-7-methoxy-1-oxo-1,2-dihydroisoquinolin-6-yl)-1H-imidazol-2-yl)-7-(isoxazol-3-yl)-7-oxoheptyl)acetamide (Example 94)

DIPEA (0.08 mL, 0.458 mmol) was added to a stirred mixture of 2-(dimethylamino)acetic acid (10 mg, 0.097 mmol) and HATU (37 mg, 0.097 mmol) in DMF (0.5 mL) at room temperature and the mixture was stirred at room temperature for 15 min. Then (S)-6-(2-(1-amino-7-(isoxazol-3-yl)-7-oxoheptyl)-1H-imidazol-5-yl)-2-ethyl-7-methoxyisoquinolin-1(2H)-one dihydrochloride (94B, 50 mg, 0.093 mmol) in DMF (0.5 mL) was added. The mixture was stirred at rt for 1 h. The mixture was purified by preparative HPLC (reverse phase C-18 column), eluting with acetonitrile/water+0.05% NH₃·H₂O, to give (S)-2-(dimethylamino)-N-(1-(5-(2-ethyl-7-methoxy-1-oxo-1,2-dihydroisoquinolin-6-yl)-1H-imidazol-2-yl)-7-(isoxazol-3-yl)-7-oxoheptyl)acetamide (Example 94).

L-(+)-tartaric acid (13 mg, 0.087 mmol) was added to a stirred mixture of (S)-2-(dimethylamino)-N-(1-(5-(2-ethyl- 7-methoxy-1-oxo-1,2-dihydroisoquinolin-6-yl)-1H-imidazol-2-yl)-7-(isoxazol-3-yl)-7-oxoheptyl)acetamide (Example 94, 45 mg, 0.082 mmol) in acetonitrile (2 ml) and water (2 ml) at room temperature. Then the mixture was made dry by lyophilization to give (S)-2-(dimethylamino)-N-(1-(5-(2-ethyl-7-methoxy-1-oxo-1,2-dihydroisoquinolin-6-yl)-1H-imidazol-2-yl)-7-(isoxazol-3-yl)-7-oxoheptyl)acetamide (2R,3R)-2,3-dihydroxysuccinate (Example 94). LCMS (ESI) calc'd for $C_{29}H_{36}N_6O_5$ [M+H]$^+$: 549.3, found: 549.1. $^1$H NMR (400 MHz, MeOD) δ 8.75 (d, J=1.8 Hz, 1H), 8.14 (s, 1H), 7.79 (s, 1H), 7.72 (s, 1H), 7.25 (d, J=7.3 Hz, 1H), 6.75 (d, J=1.8 Hz, 1H), 6.70 (d, J=7.3 Hz, 1H), 5.13-5.23 (m, 1H), 4.49 (s, 2H), 4.04 (s, 7H), 3.03 (t, J=7.2 Hz, 2H), 2.91 (s, 6H), 2.02 (brs, 2H), 1.72 (t, J=6.8 Hz, 2H), 1.32-1.52 (m, 7H).

Example 95

(S)-2-(dimethylamino)-N-(7-(oxazol-2-yl)-7-oxo-1-(5-(quinoxalin-6-yl)-1H-imidazol-2-yl)heptyl)acetamide Step 1: Preparation of (S)-7-amino-7-(5-bromo-1H-imidazol-2-yl)-1-(oxazol-2-yl)heptan-1-one (95A)

HCl (0.242 mL, 0.968 mmol) was added to a stirred mixture of (R)-N-((S)-1-(4-bromo-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (14, 100 mg, 0.161 mmol) in MeOH (0.2 mL) and water (0.04 ml) at room temperature and the mixture was stirred at 40° C. for 16 h and then at 60° C. for 5 h. It was then concentrated to afford (S)-7-amino-7-(4-bromo-1H-imidazol-2-yl)-1-(oxazol-2-yl)heptan-1-one dihydrochloride (95A) which was used to the next step without further purification. LCMS (ESI) calc'd for $C_{13}H_{17}BrN_4O_2 \cdot 2HCl$ [M+H]$^+$: 341.1, found: 343.0

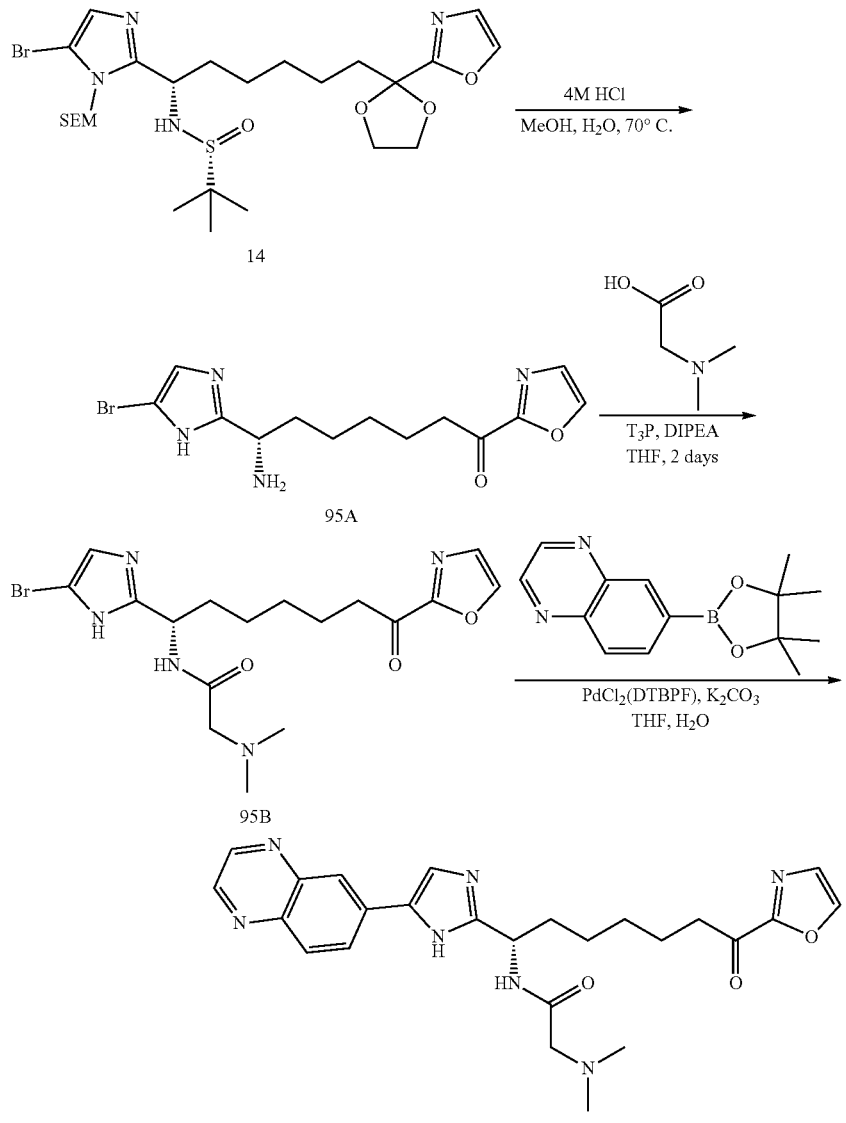

Example 95

Step 2: Preparation of (S)-N-(1-(5-bromo-1H-imidazol-2-yl)-7-(oxazol-2-yl)-7-oxoheptyl)-2-(dimethylamino)acetamide (95B)

T₃P (154 mg, 0.242 mmol) was added to a stirred mixture of (S)-7-amino-7-(4-bromo-1H-imidazol-2-yl)-1-(oxazol-2-yl)heptan-1-one (95A, 55 mg, 0.161 mmol), 2-(dimethylamino)acetic acid (35 mg, 0.339 mmol) and DIEA (0.084 ml, 0.484 mmol) in THF (3.0 mL) at room temperature and the mixture was stirred at rt for 2 h. Another batch of 2-(dimethylamino)acetic acid (35 mg, 0.339 mmol), DIEA (0.084 ml, 0.484 mmol) and T₃P (154 mg, 0.242 mmol) were added to the mixture and it was stirred at rt for 24 h. The mixture was washed with water (2.0 ml), and extracted with ethyl acetate (10 mL). The combined organic fractions were washed with brine (saturated, 5 mL), dried (Na₂SO₄), filtered and the solvent was evaporated under reduced pressure. The product was purified by preparative HPLC (reverse phase C-18 column), eluting with acetonitrile/water+ 0.1% TFA, to give (S)-N-(1-(4-bromo-1H-imidazol-2-yl)-7-(oxazol-2-yl)-7-oxoheptyl)-2-(dimethylamino)acetamide (95B). LCMS (ESI) calc'd for $C_{17}H_{24}BrN_5O_3[M+H]^+$: 426.1, found: 426.0.

Step 3: Preparation of (S)-2-(dimethylamino)-N-(7-(oxazol-2-yl)-7-oxo-1-(5-(quinoxalin-6-yl)-1H-imidazol-2-yl)heptyl)acetamide (Example 95)

Pd(DTBPF)Cl₂ (10 mg, 0.015 mmol) was added to a stirred mixture of 6-(4,4,5,5-tetramethyl-1,3,2-dioxaborolan-2-yl)quinoxaline (36 mg, 0.141 mmol), (S)-N-(1-(4-bromo-1H-imidazol-2-yl)-7-(oxazol-2-yl)-7-oxoheptyl)-2-(dimethylamino)acetamide (95B, 40 mg, 0.094 mmol) and K₃PO₄ (60 mg, 0.283 mmol) in THF (2.0 mL) and water (0.5 mL) at room temperature and the mixture was stirred at 70° C. for 2 h. It was then heated to 90° C. for 4 h, filtered and the residue was purified by preparative HPLC (reverse phase C-18 column), eluting with acetonitrile/water+0.1% TFA, to give (S)-2-(dimethylamino)-N-(7-(oxazol-2-yl)-7-oxo-1-(4-(quinoxalin-6-yl)-1H-imidazol-2-yl)heptyl)acetamide (95). LCMS (ESI) calc'd for $C_{25}H_{29}N_7O_3$ [M+H]⁺: 476.2, found: 476.3.

HCl (0.1 M, 0.213 ml, 0.021 mmol) was added to a stirred mixture of (S)-2-(dimethylamino)-N-(7-(oxazol-2-yl)-7-oxo-1-(4-(quinoxalin-6-yl)-1H-imidazol-2-yl)heptyl)acetamide bis(2,2,2-trifluoroacetate) (95, 5 mg, 7.11 µmol) in water (1.0 ml) at room temperature and the mixture was lyophilized to give (S)-2-(dimethylamino)-N-(7-(oxazol-2-yl)-7-oxo-1-(4-(quinoxalin-6-yl)-1H-imidazol-2-yl)heptyl)acetamide dihydrochloride (95). ¹H NMR (400 MHz, MeOD) δ 8.88-9.01 (m, 2H), 8.51 (s, 1H), 8.22 (d, J=0.98 Hz, 2H), 8.01-8.20 (m, 2H), 7.38 (s, 1H), 5.24 (t, J=7.24 Hz, 1H), 4.16 (s, 2H), 3.07 (t, J=7.24 Hz, 2H), 2.95 (d, J=9.00 Hz, 7H), 2.06-2.24 (m, 2H), 1.67-1.83 (m, 2H), 1.39-1.63 (m, 5H).

Example 96

(S)-2-(dimethylamino)-N-(1-(5-(2-ethyl-7-methoxy-1-oxo-1,2-dihydroisoquinolin-6-yl)-1H-imidazol-2-yl)-7-(oxazol-2-yl)-7-oxoheptyl)acetamide

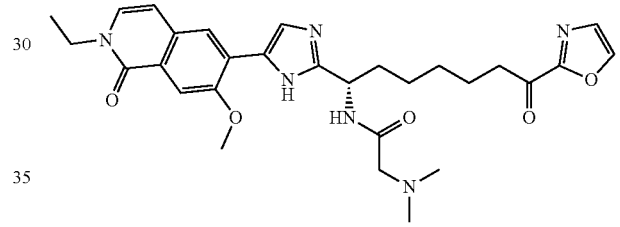

Compound 96 was obtained from compound 95B utilizing a similar method. LCMS (ESI) calc'd for $C_{29}H_{36}N_6O_5 \cdot 2ClH$ [M+H]⁺: 549.3, found: 549.1. ¹H NMR (400 MHz, MeOD) δ 8.10 (s, 2H), 7.89-8.02 (m, 2H), 7.33-7.43 (m, 2H), 6.75 (s, 1H), 5.22-5.31 (m, 1H), 4.88-4.90 (m, 2H), 4.19 (d, J=3.97 Hz, 2H), 4.07-4.14 (m, 5H), 3.08 (t, J=7.17 Hz, 2H), 2.97 (d, J=9.26 Hz, 6H), 2.13 (d, J=7.50 Hz, 2H), 1.71-1.82 (m, 2H), 1.44-1.58 (m, 4H), 1.37 (t, J=7.17 Hz, 3H).

Example 97

(S)-N-((S)-1-(4-chloro-2-(4-fluorophenyl)-1H-imidazol-5-yl)-7-(oxazol-2-yl)-7-oxoheptyl)-6-ethyl-6-azaspiro[2.5]octane-1-carboxamide

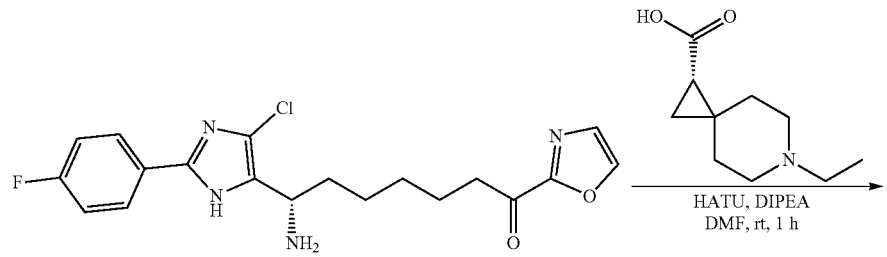

Example 27

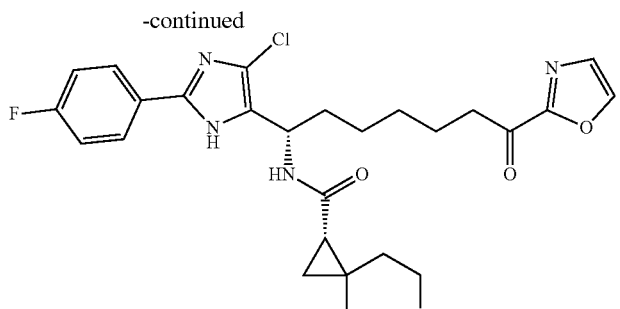

Example 97

(S)-7-amino-7-(4-chloro-2-(4-fluorophenyl)-1H-imidazol-5-yl)-1-(oxazol-2-yl)heptan-1-one (27D, 100 mg, 0.256 mmol) was added to a stirred mixture of (S)-6-ethyl-6-azaspiro[2.5]octane-1-carboxylic acid (70 mg, 0.382 mmol), HATU (145 mg, 0.381 mmol) and DIPEA (0.18 ml, 1.031 mmol) in DMF (1 ml) at room temperature and the mixture was stirred at room temperature for 1 h. Another batch of (S)-6-ethyl-6-azaspiro[2.5]octane-1-carboxylic acid (35 mg, 0.191 mmol), HATU (72 mg, 0.191 mmol) and DIPEA (0.09 mL, 0.515 mmol) were added and it was stirred at rt for 1 h. Water (2 mL) was added and the mixture was extracted with DCM (3×5 mL). The combined organic fractions were washed with brine (saturated, 1×5 mL), dried (Na$_2$SO$_4$), filtered and the solvent was evaporated under reduced pressure. The residue was purified by preparative HPLC (reverse phase C-18 column), eluting with acetonitrile/water+0.1% TFA, to give (S)-N-((S)-1-(4-chlorophenyl-2-(4-fluorophenyl)-1H-imidazol-5-yl)-7-(oxazol-2-yl)-7-oxoheptyl)-6-ethyl-6-azaspiro[2.5]octane-1-carboxamide (Example 97). LCMS (ESI) calc'd for C$_{29}$H$_{35}$ClFN$_5$O$_3$[M+H]$^+$: 556.2, found: 556.2

HCl (2.5 mL, 0.250 mmol) was added to a stirred mixture of (S)-N-((S)-1-(4-chloro-2-(4-fluorophenyl)-1H-imidazol-5-yl)-7-(oxazol-2-yl)-7-oxoheptyl)-6-ethyl-6-azaspiro[2.5]octane-1-carboxamide bis(2,2,2-trifluoroacetate) (97, 60 mg, 0.077 mmol) in acetonitrile (1 ml) at rt and the mixture was made dry by lyophilization to give (S)-N-((S)-1-(4-chloro-2-(4-fluorophenyl)-1H-imidazol-5-yl)-7-(oxazol-2-yl)-7-oxoheptyl)-6-ethyl-6-azaspiro[2.5]octane-1-carboxamide dihydrochloride (97). $^1$H NMR (400 MHz, MeOD) δ 8.14-8.21 (m, 1H), 7.99-8.13 (m, 2H), 7.33-7.46 (m, 3H), 4.78-4.93 (m, 1H), 3.43-3.65 (m, 2H), 2.99-3.27 (m, 4H), 2.22-2.52 (m, 1H), 1.70-2.10 (m, 7H), 1.27-1.56 (m, 7H), 1.19-1.24 (m, 1H), 1.06-1.18 (m, 3H), 0.98-1.06 (m, 1H).

Example 98

(S)-N-(1-(5-(7-methoxy-2-methylquinolin-6-yl)-1H-imidazol-2-yl)-7-(oxazol-2-yl)-7-oxoheptyl)-1-methylpiperidine-4-carboxamide

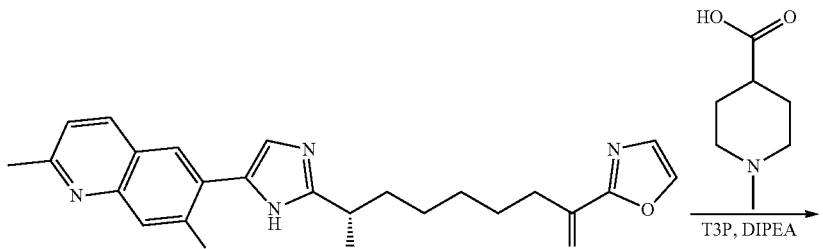

Example 12

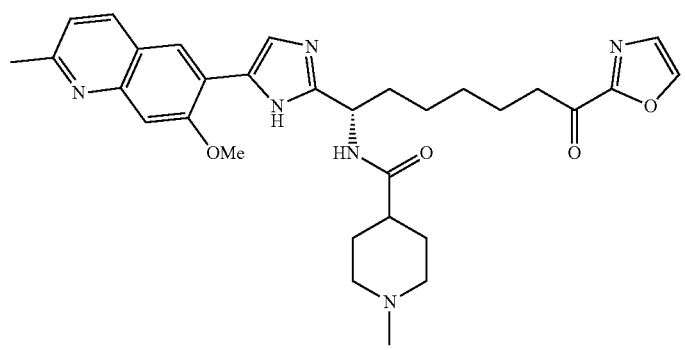

Example 98

(S)-7-amino-7-(5-(7-methoxy-2-methylquinolin-6-yl)-1H-imidazol-2-yl)-1-(oxazol-2-yl)heptan-1-one hydrochloride (Example 12, 40 mg, 0.085 mmol) was added to a stirred mixture of 1-methylpiperidine-4-carboxylic acid (37 mg, 0.258 mmol), DIPEA (110 mg, 0.851 mmol) and T3P (162 mg, 0.255 mmol) in DMF (2.0 ml) at room temperature and the mixture was stirred at room temperature and for 2 h. The residue was purified by preparative HPLC (reverse phase C-18 column), eluting with acetonitrile/water+0.1% TFA, to give (S)-N-(1-(5-(7-methoxy-2-methylquinolin-6-yl)-1H-imidazol-2-yl)-7-(oxazol-2-yl)-7-oxoheptyl)-1-methylpiperidine-4-carboxamide (Example 98). LCMS (ESI) calc'd for $C_{31}H_{38}N_6O_4$ [M+H]$^+$: 559.3, found: 559.1. $^1$H NMR (400 MHz, MeOD) δ 8.89 (brs, 1H), 8.57-8.70 (m, 1H), 8.11 (s, 1H), 8.00 (brs, 1H), 7.72-7.82 (m, 1H), 7.67 (brs, 1H), 7.40 (s, 1H), 5.19 (brs, 1H), 4.22 (brs, 3H), 3.63-3.75 (m, 1H), 3.57 (brs, 1H), 3.08 (t, J=7.28 Hz, 2H), 2.93-3.01 (m, 3H), 2.87 (brs, 2H), 2.81-2.90 (m, 1H), 2.69 (brs, 1H), 2.11 (brs, 2H), 1.94 (brs, 1H), 1.73-1.81 (m, 2H), 1.61-1.69 (m, 2H), 1.46 (d, J=6.84 Hz, 3H), 1.37 (dd, J=3.53, 6.62 Hz, 1H), 1.02 (q, J=7.50 Hz, 3H), 0.01-0.01 (m, 1H).

Example 99

(S)-N-(1-(5-(7-methoxy-2-methylquinolin-6-yl)-1H-imidazol-2-yl)-7-(oxazol-2-yl)-7-oxoheptyl)-1-methylazetidine-3-carboxamide T3P (162 mg, 0.255 mmol) was added to a stirred mixture of 1-methylazetidine-3-carboxylic acid (30 mg, 0.261 mmol), N-ethyl-N-isopropylpropan-2-amine (55 mg, 0.426 mmol), (S)-7-amino-7-(5-(7-methoxy-2-methylquinolin-6-yl)-1H-imidazol-2-yl)-1-(oxazol-2-yl)heptan-1-one hydrochloride (Example 12, 40 mg, 0.085 mmol) in DMF (2.0 ml) at room temperature and the mixture was stirred at room temperature for 2 h. The residue was purified by preparative HPLC (reverse phase C-18 column), eluting with acetonitrile/water+0.1% TFA, to give (S)-N-(1-(5-(7-methoxy-2-methylquinolin-6-yl)-1H-imidazol-2-yl)-7-(oxazol-2-yl)-7-oxoheptyl)-1-methylazetidine-3-carboxamide (Example 99). LCMS (ESI) calc'd for $C_{29}H_{34}N_6O_4$ [M+H]$^+$: 531.3, found: 531.1. $^1$H NMR (400 MHz, MeOD) δ 8.86 (d, J=8.16 Hz, 1H), 8.64 (s, 1H), 8.10 (s, 1H), 7.99 (brs, 1H), 7.77 (d, J=8.16 Hz, 1H), 7.60-7.70 (m, 1H), 7.39 (s, 1H), 5.22 (brs, 1H), 4.39-4.57 (m, 2H), 4.05-4.24 (m, 4H), 3.73 (brs, 1H), 3.07 (t, J=7.17 Hz, 2H), 2.97 (s, 2H), 2.92 (brs, 3H), 2.08 (d, J=5.51 Hz, 1H), 1.71-1.84 (m, 2H), 1.58-1.70 (m, 2H), 1.45 (dd, J=6.39, 12.35 Hz, 2H), 1.02 (q, J=7.28 Hz, 2H).

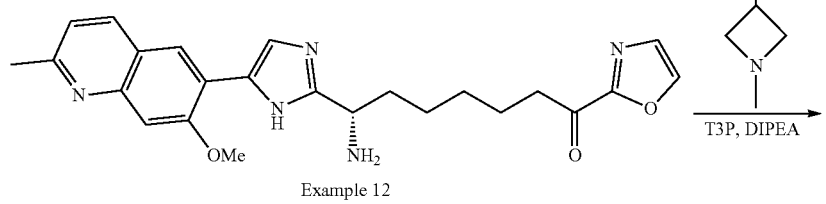

Example 12

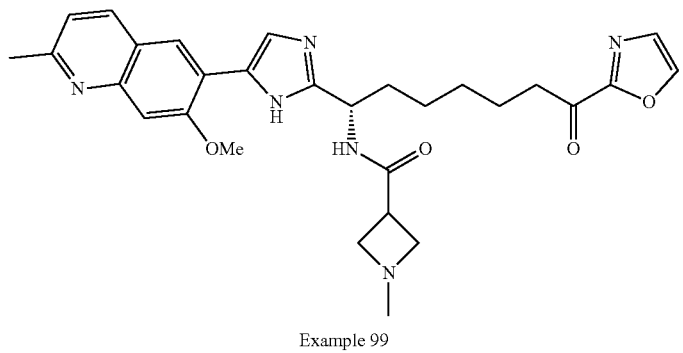

Example 99

Example 100

(S)-N-(1-(5-(7-methoxy-2-methylquinolin-6-yl)oxazol-2-yl)-7-(oxazol-2-yl)-7-oxoheptyl)-1-methylazetidine-3-carboxamide

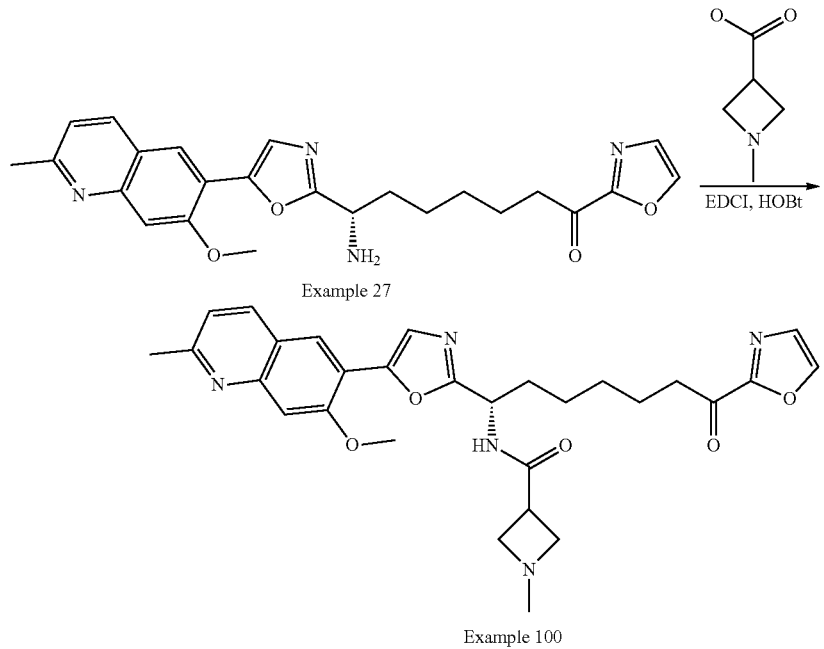

EDCI (222 mg, 1.160 mmol) and HOBT (159 mg, 1.036 mmol) was added to the solution of DIPEA (0.724 ml, 4.14 mmol) and 1-methylazetidine-3-carboxylic acid (143 mg, 1.243 mmol) in DMF (20 ml), the resultant mixture was stirred at 27° C. for 0.5 h. (S)-7-amino-7-(5-(7-methoxy-2-methylquinolin-6-yl)oxazol-2-yl)-1-(oxazol-2-yl)heptan-1-one (Example 27, 180 mg, 0.414 mmol) in DMF (3 ml) was added, and the resultant mixture was stirred for another 5 h. The excess DMF was removed by vacuum. The residue was purified by preparative HPLC (reverse phase C-18 column), eluting with acetonitrile/water+0.1% TFA, to give (S)-N-(1-(5-(7-methoxy-2-methylquinolin-6-yl)oxazol-2-yl)-7-(oxazol-2-yl)-7-oxoheptyl)-1-methylazetidine-3-carboxamide (Example 100). LCMS (ESI) calc'd for $C_{29}H_{33}N_5O_5$ [M+H]$^+$: 532.2 found: 532.3.

(S)-N-(1-(5-(7-methoxy-2-methylquinolin-6-yl)oxazol-2-yl)-7-(oxazol-2-yl)-7-oxoheptyl)-1-methylazetidine-3-carboxamide 2,2,2-trifluoroacetate (100, 75 mg, 0.116 mmol) was dissolved in EtOAc (20 mL), the resultant mixture was washed with aq.NaHCO$_3$ (sat., 5 mL), and the aqueous layer was back extracted with EtOAc (5*5 ml). The combined organic layer was dried over Na$_2$SO$_4$, concentrated in vacuo to give free base. L-(+)-tartaric acid (18 mg, 0.120 mmol) in water (3 ml) was added to the above residue, the resultant solution was lyophilized to give (S)-N-(1-(5-(7-methoxy-2-methylquinolin-6-yl)oxazol-2-yl)-7-(oxazol-2-yl)-7-oxoheptyl)-1-methylazetidine-3-carboxamide (2R,3R)-2,3-dihydroxysuccinate (100). $^1$H NMR (400 MHz, MeOD) δ 8.18-8.27 (m, 2H), 8.06 (s, 1H), 7.57 (s, 1H), 7.41 (s, 1H), 7.29-7.37 (m, 2H), 5.20 (dd, J=6.36, 8.31 Hz, 1H), 4.46 (s, 4H), 4.38 (brs, 2H), 4.21 (brs, 2H), 4.10 (s, 3H), 3.70 (t, J=7.53 Hz, 1H), 3.04 (t, J=7.24 Hz, 2H), 2.91 (s, 3H), 2.69 (s, 3H), 1.90-2.16 (m, 2H), 1.66-1.80 (m, 2H), 1.45 (brs, 4H).

Example 101

(S)-N-(1-(4-chloro-2-(4-fluorophenyl)-1H-imidazol-5-yl)-7-(oxazol-2-yl)-7-oxoheptyl)-1-methylazetidine-3-carboxamide

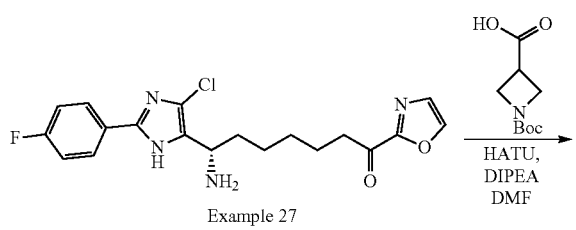

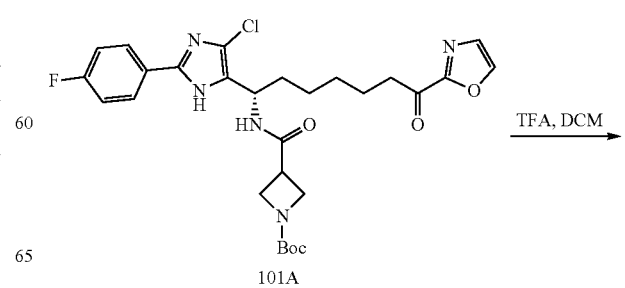

101A

177

-continued

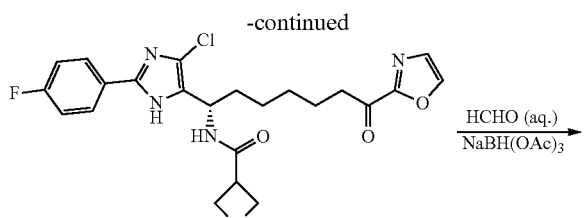

101B

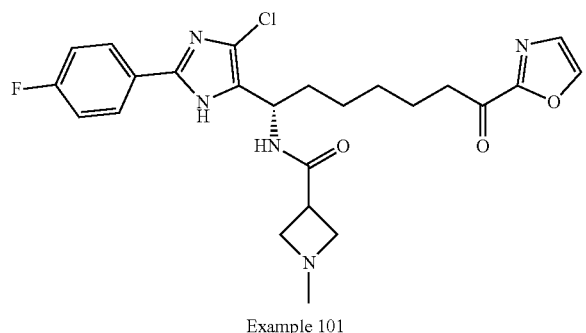

Example 101

Step 1: Preparation of (S)-tert-butyl-3-((1-(4-chloro-2-(4-fluorophenyl)-1H-imidazol-5-yl)-7-(oxazol-2-yl)-7-oxoheptyl)carbamoyl)azetidine-1-carboxylate (101A)

(S)-7-amino-7-(4-chloro-2-(4-fluorophenyl)-1H-imidazol-5-yl)-1-(oxazol-2-yl)heptan-1-one (Example 27, 180 mg, 0.461 mmol) was added to a stirred mixture of 1-(tert-butoxycarbonyl)azetidine-3-carboxylic acid (463 mg, 2.303 mmol), HATU (876 mg, 2.303 mmol) and DIPEA (0.8 ml, 4.58 mmol) in DMF (2 ml) at room temperature and the mixture was stirred at room temperature for 1 h. Then 1-(tert-butoxycarbonyl)azetidine-3-carboxylic acid (230 mg, 1.151 mmol) and HATU (438 mg, 1.151 mmol) were added. It was stirred at rt for 16 h. Another acid (115 mg, 0.576 mmol) and HATU (219 mg, 0.576 mmol) were added again. It continued to be stirred at rt for 16 h. Water (5 mL) was added and the mixture was extracted with DCM (3×10 mL). The combined organic fractions were washed with brine (saturated, 1×10 mL), dried (Na$_2$SO$_4$), filtered and the solvent was evaporated under reduced pressure. The residue was purified by silica gel flash chromatography (ISCORF75; Sepa flash column), eluting with petroleum ether/EtOAc=20%~100% to give (S)-tert-butyl-3-((1-(4-chloro-2-(4-fluorophenyl)-1H-imidazol-5-yl)-7-(oxazol-2-yl)-7-oxoheptyl)carbamoyl)azetidine-1-carboxylate (101A). LCMS (ESI) calc'd for C$_{28}$H$_{33}$ClFN$_5$O$_5$[M+H]$^+$: 574.2, found: 574.2

Step 2: Preparation of (S)-N-(1-(4-chloro-2-(4-fluorophenyl)-1H-imidazol-5-yl)-7-(oxazol-2-yl)-7-oxoheptyl)azetidine-3-carboxamide 2,2,2-trifluoroacetate (101B)

TFA (0.2 mL, 2.60 mmol) was added to a stirred mixture of (S)-tert-butyl 3-((1-(4-chloro-2-(4-fluorophenyl)-1H-imidazol-5-yl)-7-(oxazol-2-yl)-7-oxoheptyl)carbamoyl)azetidine-1-carboxylate (101A, 100 mg, 0.174 mmol) in DCM (2 ml) at room temperature and the mixture was stirred at room temperature for 2 h. All the volatiles were removed by evaporator to give (S)-N-(1-(4-chloro-2-(4-fluorophenyl)-

178

1H-imidazol-5-yl)-7-(oxazol-2-yl)-7-oxoheptyl)azetidine-3-carboxamide 2,2,2-trifluoroacetate (101B) which was used directly for next step. LCMS (ESI) calc'd for C$_{23}$H$_{25}$ClFN$_5$O$_3$[M+H]$^+$: 474.2, found: 474.2

Step 3: Preparation of (S)-N-(1-(4-chloro-2-(4-fluorophenyl)-1H-imidazol-5-yl)-7-(oxazol-2-yl)-7-oxoheptyl)-1-methylazetidine-3-carboxamide (Example 101)

Formaldehyde (0.2 mL, 2.69 mmol) was added to a stirred mixture of (S)-N-(1-(4-chloro-2-(4-fluorophenyl)-1H-imidazol-5-yl)-7-(oxazol-2-yl)-7-oxoheptyl)azetidine-3-carboxamide (101B, 100 mg, 0.211 mmol) in MeOH (2 ml) at room temperature and the mixture was stirred at room temperature for 1 h. Sodium triacetoxyborohydride (134 mg, 0.633 mmol) was added and the mixture was stirred at rt for 1 h. The residue was purified by preparative HPLC (reverse phase C-18 column), eluting with acetonitrile/water+0.1% TFA, to give 30 mg TFA salt of the target compound. Then, it was neutralized with NaHCO$_3$ (sat.). The residue was purified by preparative HPLC (reverse phase C-18 column), eluting with acetonitrile/water, to give (S)-N-(1-(4-chloro-2-(4-fluorophenyl)-1H-imidazol-5-yl)-7-(oxazol-2-yl)-7-oxoheptyl)-1-methylazetidine-3-carboxamide (Example 101). LCMS (ESI) calc'd for C$_{24}$H$_{27}$ClFN$_5$O$_3$ [M+H]$^+$: 488.2, found: 488.2

L-(+)-tartaric acid (5 mg, 0.033 mmol) was added to the solution of (S)-N-(1-(4-chloro-2-(4-fluorophenyl)-1H-imidazol-5-yl)-7-(oxazol-2-yl)-7-oxoheptyl)-1-methylazetidine-3-carboxamide (101, 15 mg, 0.031 mmol) in acetonitrile (4 ml) and water (3 ml), and the mixture was made dry by lyophilization to give (S)-N-(1-(4-chloro-2-(4-fluorophenyl)-1H-imidazol-5-yl)-7-(oxazol-2-yl)-7-oxoheptyl)-1-methylazetidine-3-carboxamide (2R,3R)-2,3-dihydroxysuccinate (101). $^1$H NMR (400 MHz, MeOD) δ 8.09 (s, 1H), 7.88 (brs, 2H), 7.39 (s, 1H), 7.19 (brs, 2H), 5.04 (brs, 1H), 4.53 (brs, 2H), 3.31-3.33 (m, 3H), 3.05 (t, J=7.1 Hz, 2H), 2.92 (brs, 3H), 1.94 (brs, 2H), 1.72 (brs, 2H), 1.26-1.49 (m, 6H).

Example 102

(S)-N-(7-(isoxazol-3-yl)-1-(5-(7-methoxy-1-methyl-2-oxo-1,2-dihydroquinolin-6-yl)-1H-imidazol-2-yl)-7-oxoheptyl)-1-methylazetidine-3-carboxamide

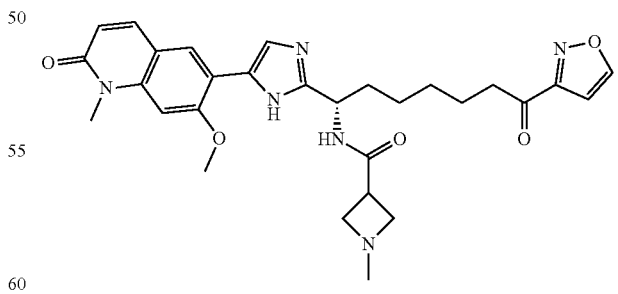

Example 102 was obtained from compound Example 21 using a similar method as described above. LCMS (ESI) calc'd for C$_{29}$H$_{34}$N$_6$O$_5$ [M+H]$^+$: 547.2, found: 547.1. $^1$H NMR (400 MHz, MeOD) δ 8.76 (s, 1H), 8.03 (s, 1H), 7.86 (d, J=9.6 Hz, 1H), 7.77 (s, 1H), 7.14 (s, 1H), 6.76 (d, J=2.0 Hz, 1H), 6.58 (d, J=9.2 Hz, 1H), 5.13-5.25 (m, 1H), 4.20-

4.27 (m, 1H), 4.13 (s, 3H), 3.78 (s, 3H), 3.28-3.33 (m, 5H), 3.06 (t, J=8.8 Hz, 2H), 2.92 (s, 2H), 2.00-2.13 (m, 2H), 1.69-1.81 (m, 2H), 1.37-1.55 (m, 4H).

Example 103

(S)-N-(7-(isoxazol-3-yl)-1-(5-(7-methoxy-2-methylquinolin-6-yl)-1H-imidazol-2-yl)-7-oxoheptyl)-1-methylazetidine-3-carboxamide

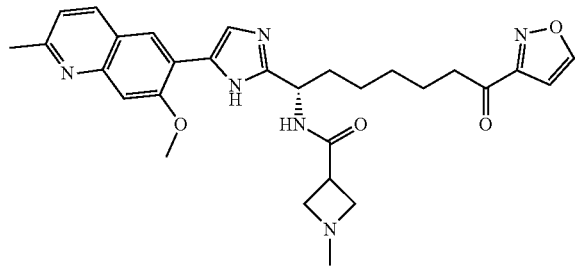 [SMILES: COc1cc2nc(C)ccc2cc1-c1cnc([C@H](CCCCCC(=O)c2ccon2)NC(=O)C2CN(C)C2)[nH]1]

Example 103 was obtained from compound Example 31 using a similar method as described above. LCMS (ESI) calc'd for $C_{29}H_{34}N_6O_4 \cdot 17H_6O_6[M+H]^+$: 531.3, found: 531.3. $^1$H NMR (400 MHz, D$_2$O) δ 8.50 (s, 1H), 8.39 (s, 1H), 8.11 (s, 1H), 7.57 (s, 1H), 7.41 (d, J=8.41 Hz, 1H), 7.17 (s, 1H), 6.46 (s, 1H), 4.88-4.96 (m, 1H), 4.38 (s, 3H), 4.28 (m, 2H), 4.22 (m, 3H), 4.02 (m, 2H), 3.92 (s, 3H), 3.85-3.97 (m, 1H), 3.62 (m, 1H), 2.77 (s, 4H), 2.72-2.83 (m, 1H), 2.68 (brs, 3H), 1.83 (brs, 2H), 1.49 (brs, 2H), 1.06-1.31 (m, 4H).

Example 104

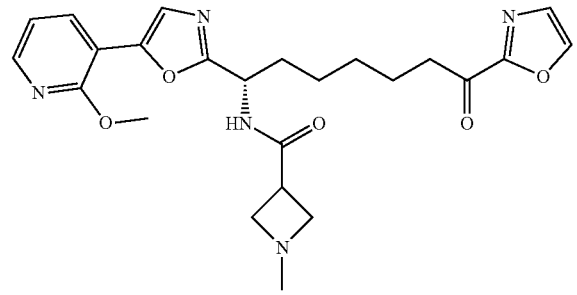 [SMILES: COc1ncccc1-c1cnc([C@H](CCCCCC(=O)c2ncco2)NC(=O)C2CN(C)C2)o1]

N-(1-(5-(2-methoxypyridin-3-yl)oxazol-2-yl)-7-(oxazol-2-yl)-7-oxoheptyl)-1-methylazetidine-3-carboxamide Example 104 was obtained from compound Example 28 using a similar method as described above. LCMS (ESI) calc'd for $C_{24}H_{29}N_5O_5[M+H]^+$: 468.2, found: 468.3. $^1$H NMR (400 MHz, MeOD) δ 8.09 (d, J=12.32 Hz, 2H), 8.00-8.21 (m, 1H), 8.00-8.21 (m, 1H), 7.47 (brs, 1H), 7.37 (brs, 1H), 7.06 (brs, 1H), 5.14 (brs, 1H), 4.35-4.44 (m, 2H), 4.17-4.28 (m, 2H), 4.16-4.25 (m, 1H), 4.14-4.25 (m, 2H), 4.06 (brs, 3H), 3.65 (brs, 1H), 3.01-3.01 (m, 1H), 2.97-2.98 (m, 1H), 2.90 (brs, 1H), 2.86-2.96 (m, 1H), 2.85-2.98 (m, 1H), 2.84-3.08 (m, 1H), 1.85-2.10 (m, 2H), 1.71 (brs, 3H), 1.43 (brs, 5H).

Example 105

(S)-N-(1-(4-chloro-2-(2-fluorophenyl)-1H-imidazol-5-yl)-7-(isoxazol-3-yl)-7-oxoheptyl)-1-methylazetidine-3-carboxamide

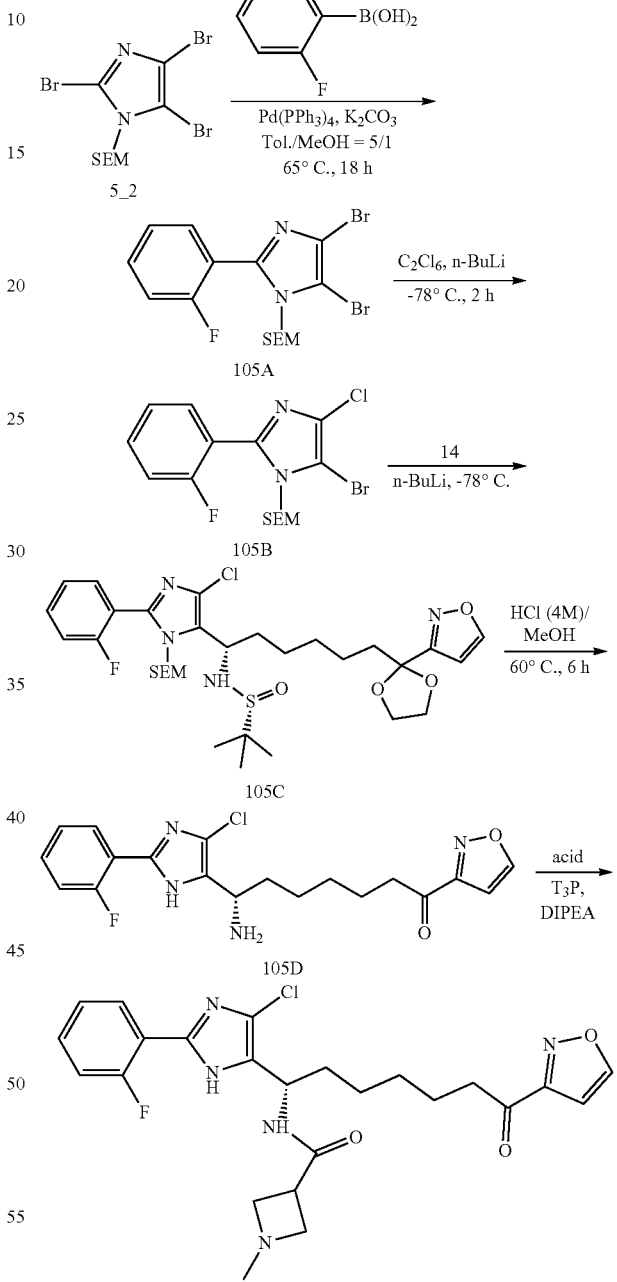

Example 105

Step 1: Preparation of 4,5-dibromo-2-(2-fluorophenyl)-1-((2-(trimethylsilyl)ethoxy)methyl)-1H-imidazole (105A)

Pd(PPh$_3$)$_4$ (1.594 g, 1.379 mmol) was added to a stirred mixture of potassium carbonate (3.81 g, 27.6 mmol), 2,4,5- tribromo-1-((2-(trimethylsilyl)ethoxy)methyl)-1H-imidazole (5_2, 6.0 g, 13.79 mmol), and (2-fluorophenyl)boronic acid (2.1 g, 15.01 mmol) in toluene (15 ml)/MeOH (3 ml) at room temperature and the mixture was stirred at 65° C. for 12 h. The mixture was cooled, diluted with ethyl acetate (10 mL), washed with brine (saturated, 2×10 mL), dried (Na$_2$SO$_4$), filtered and the solvent was evaporated under reduced pressure. The residue was purified by silica gel column flash chromatography, eluting with EtOAc/petroleum ether=0-15% to give 4,5-dibromo-2-(2-fluorophenyl)-1-((2-(trimethylsilyl)ethoxy)methyl)-1H-imidazole (105A). LCMS (ESI) calc'd for C$_{15}$H$_{19}$Br$_2$FN$_2$OSi [M+H]$^+$: 449.0, found: 451.0. $^1$H NMR (400 MHz, CDCl$_3$) δ 7.46-7.60 (m, 2H), 7.27 (s, 1H), 7.20 (t, J=9.1 Hz, 1H), 5.29 (s, 2H), 3.30 (t, J=8.8 Hz, 2H), 1.59 (s, 1H), 0.76 (t, J=8.8 Hz, 2H), −0.079 (s, 9H).

Step 2: Preparation of 5-bromo-4-chloro-2-(2-fluorophenyl)-1-((2-(trimethylsilyl)ethoxy)methyl)-1H-imidazole (105B)

n-BuLi (1.8 ml, 4.50 mmol) was added to a stirred mixture of 4,5-dibromo-2-(2-fluorophenyl)-1-((2-(trimethylsilyl)ethoxy)methyl)-1H-imidazole (105A, 2.0 g, 4.44 mmol) in THF (2 ml) at −78° C. and the mixture was stirred at −78° C. for 30 min. Then perchloroethane (1.6 g, 6.76 mmol) was added slowly at −78° C., and the mixture was stirred at −78° C. for 2 h. Aqueous ammonium chloride (saturated, 10 mL) was added and the mixture was extracted with ethyl acetate (3×15 mL). The combined organic fractions were washed with brine (saturated, 2×15 mL), dried (Na$_2$SO$_4$), filtered and the solvent was evaporated under reduced pressure. The residue was purified by silica gel column flash chromatography, eluting with EtOAc/petroleum ether=0-15% to give 5-bromo-4-chloro-2-(2-fluorophenyl)-1-((2-(trimethylsilyl)ethoxy)methyl)-1H-imidazole (105B). LCMS (ESI) calc'd for C$_{15}$H$_{19}$BrClFN$_2$OSi [M+H]$^+$: 405.0, found: 407.0

Step 3: Preparation of (R)-N-((S)-1-(4-chloro-2-(2-fluorophenyl)-1-((2-(trimethylsilyl)ethoxy)methyl)-1H-imidazol-5-yl)-6-(2-(isoxazol-3-yl)-1,3-dioxolan-2-yl)hexyl)-2-methylpropane-2-sulfinamide (105C)

n-BuLi (1.1 ml, 2.75 mmol) was added to a stirred mixture of 5-bromo-4-chloro-2-(2-fluorophenyl)-1-((2-(trimethylsilyl)ethoxy)methyl)-1H-imidazole (105B, 1.15 g, 2.83 mmol) in THF (2 ml) at −78° C. and the mixture was stirred at −78° C. for 30 min. Then (R,E)-N-(6-(2-(isoxazol-3-yl)-1,3-dioxolan-2-yl)hexylidene)-2-methylpropane-2-sulfinamide (13, 900 mg, 2.63 mmol) in THF (1 ml) was added drop-wise. The mixture was warmed to 20° C. and stirred for 2 h. Aqueous ammonium chloride (saturated, 20 mL) was added and the mixture was extracted with ethyl acetate (3×15 mL). The combined organic fractions were washed with brine (saturated, 2×30 mL), dried (Na$_2$SO$_4$), filtered and the solvent was evaporated under reduced pressure. The residue was purified by silica gel column flash chromatography, eluting with MeOH/DCM=0-15% to give (R)-N-((S)-1-(4-chloro-2-(2-fluorophenyl)-1-((2-(trimethylsilyl)ethoxy)methyl)-1H-imidazol-5-yl)-6-(2-(isoxazol-3-yl)-1,3-dioxolan-2-yl)hexyl)-2-methylpropane-2-sulfinamide (105C). LCMS (ESI) calc'd for C$_{31}$H$_{46}$ClFN$_4$O$_5$SSi [M+H]$^+$: 669.3, found: 669.3

Step 4: Preparation of (S)-7-amino-7-(4-chloro-2-(2-fluorophenyl)-1H-imidazol-5-yl)-1-(isoxazol-3-yl)heptan-1-one (105D)

HCl (1.5 ml, 6.00 mmol) was added to a stirred mixture of (R)-N-((S)-1-(4-chloro-2-(2-fluorophenyl)-1-((2-(trimethylsilyl)ethoxy)methyl)-1H-imidazol-5-yl)-6-(2-(isoxazol-3-yl)-1,3-dioxolan-2-yl)hexyl)-2-methylpropane-2-sulfinamide (105C, 300 mg, 0.448 mmol) in MeOH (1.5 ml) at room temperature and the mixture was stirred at 50° C. for 1.5 h. Most of the MeOH and water was removed, and it was concentrated to give (S)-7-amino-7-(4-chloro-2-(2-fluorophenyl)-1H-imidazol-5-yl)-1-(isoxazol-3-yl)heptan-1-one (105D) which was used to the next without further purification. LCMS (ESI) calc'd for C$_{19}$H$_{20}$ClFN$_4$O$_2$[M+H]$^+$: 391.1, found: 374.1 (M−17).

Step 5: Preparation of (S)-N-(1-(4-chloro-2-(2-fluorophenyl)-1-((2-(trimethylsilyl)ethoxy)methyl)-1H-imidazol-5-yl)-7-(isoxazol-3-yl)-7-oxoheptyl)-1-methylazetidine-3-carboxamide (Example 105)

HOBT (51 mg, 0.333 mmol), EDCI (98 mg, 0.512 mmol) was added to a stirred mixture of DIPEA (0.5 ml, 2.86 mmol), and 1-methylazetidine-3-carboxylic acid (40 mg, 0.347 mmol) in DMF (1 ml) at room temperature and the mixture was stirred at room temperature for 15 min. Then (S)-7-amino-7-(4-chloro-2-(2-fluorophenyl)-1H-imidazol-5-yl)-1-(isoxazol-3-yl)heptan-1-one (105D, 100 mg, 0.256 mmol) in DMF (1 ml) was added. The mixture was stirred at rt for 12 h. The residue was purified by preparative HPLC, eluting with acetonitrile/water, to give (S)-N-(1-(4-chloro-2-(2-fluorophenyl)-1-((2-(trimethylsilyl)ethoxy)methyl)-1H-imidazol-5-yl)-7-(isoxazol-3-yl)-7-oxoheptyl)-1-methylazetidine-3-carboxamide (Example 105). LCMS (ESI) calc'd for C$_{20}$H$_{41}$ClFN$_5$O$_4$Si [M+H]$^+$: 488.2, found: 488.2

L-tartaric acid (10 mg, 0.067 mmol) in MeCN (2 ml) was added to a stirred mixture of (S)-N-(1-(4-chloro-2-(2-fluorophenyl)-1H-imidazol-5-yl)-7-(isoxazol-3-yl)-7-oxoheptyl)-1-methylazetidine-3-carboxamide (105, 40 mg, 0.082 mmol) in water (2 ml) at room temperature and the mixture was lyophilized to give (S)-N-(1-(4-chloro-2-(2-fluorophenyl)-1H-imidazol-5-yl)-7-(isoxazol-3-yl)-7-oxoheptyl)-1-methylazetidine-3-carboxamide (2R,3R)-2,3-dihydroxysuccinate (105). $^1$H NMR (400 MHz, MeOD) δ 8.77 (d, J=1.8 Hz, 1H), 7.83-7.90 (m, 1H), 7.41-7.49 (m, 1H), 7.21-7.32 (m, 2H), 6.77 (d, J=1.5 Hz, 1H), 5.06 (t, J=7.9 Hz, 1H), 4.46 (m, 2H), 4.34 (m, 2H), 4.02-4.24 (m, 2H), 3.65 (m, 1H), 3.05 (t, J=7.3 Hz, 2H), 2.90 (s, 3H), 1.96 (q, J=7.0 Hz, 2H), 1.74 (quin, J=7.2 Hz, 2H), 1.34-1.48 (m, 4H).

Example 106

(S)-N-(1-(5-(2-fluorophenyl)-1,3,4-oxadiazol-2-yl)-7-(isoxazol-3-yl)-7-oxoheptyl)-1-methylazetidine-3-carboxamide

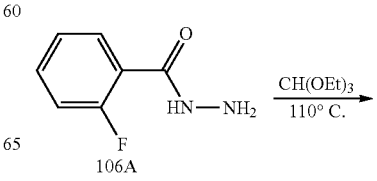

106A

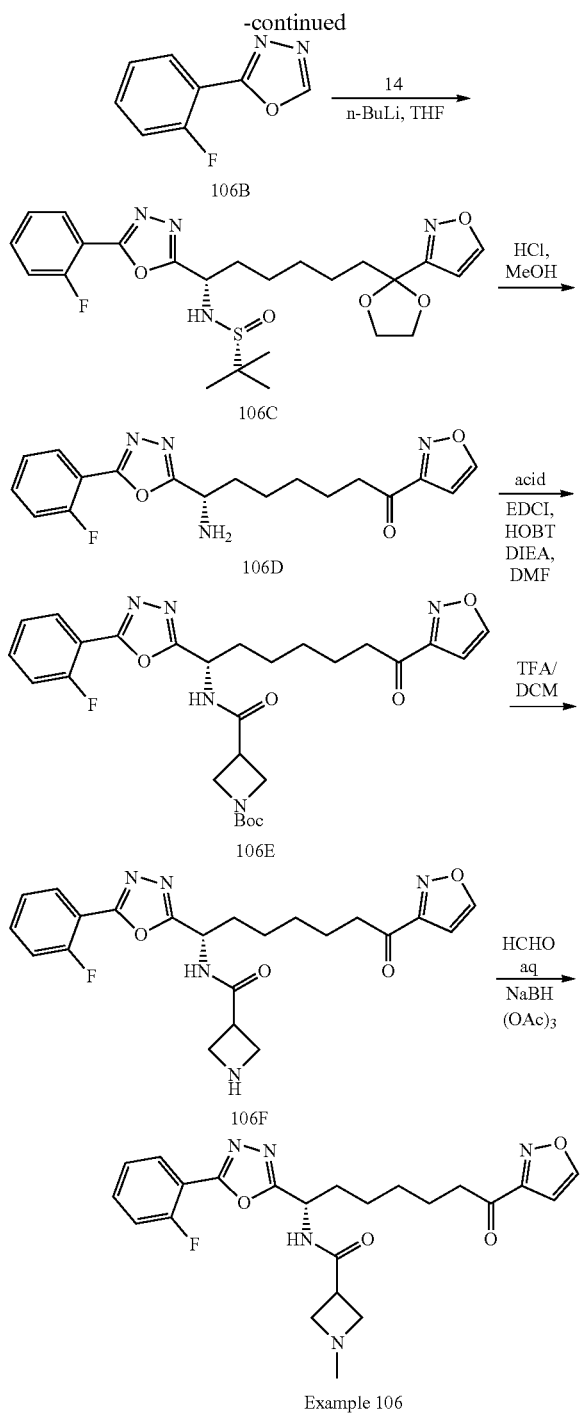

Step 1: Preparation of 2-(2-fluorophenyl)-1,3,4-oxadiazole (106B)

A mixture of 2-fluorobenzohydrazide (106A, 2 g, 12.98 mmol) and triethoxymethane (3 g, 20.24 mmol) was stirred at 110° C. for 10 h. The reaction mixture was cooled to room temperature and concentrated. The residue was purified by column chromatography on silica gel using eluent 0-5% ethyl acetate in petroleum ether to give 2-(2-fluorophenyl)-1,3,4-oxadiazole (106B). LCMS (ESI) calc'd for $C_8H_5FN_2O$ [M+H]$^+$: 165.0, found: 165.2.

Step 2: Preparation of 2-(2-fluorophenyl)-1,3,4-oxadiazole (106C)

nBuLi (2.92 mL, 7.31 mmol) was added dropwise into a stirring solution of 2-(2-fluorophenyl)-1,3,4-oxadiazole (106B, 1 g, 6.09 mmol) in THF (30 mL) at −78° C. under $N_2$ atmosphere. The mixture was stirred at −78° C. for 1 h. (R,E)-N-(6-(2-(isoxazol-3-yl)-1,3-dioxolan-2-yl)hexylidene)-2-methylpropane-2-sulfinamide (14, 2.086 g, 6.09 mmol) in THF (20 mL) was added into the mixture slowly at −78° C. After stirring at −78° C. for 2 h, the mixture was then stirred at rt for 1 h. Aqueous NH$_4$Cl (saturated, 30 mL) was added and the mixture was extracted with ethyl acetate (3×30 mL). The combined organic fractions were washed with brine (saturated, 20 mL), dried (Na$_2$SO$_4$), filtered and the solvent was evaporated under reduced pressure. The residue was purified by silica gel column flash chromatography, eluting with petroleum ether/EtOAc=1:1-1:100 to give (R)-N-((S)-1-(5-(2-fluorophenyl)-1,3,4-oxadiazol-2-yl)-6-(2-(isoxazol-3-yl)-1,3-dioxolan-2-yl)hexyl)-2-methylpropane-2-sulfinamide (82C). LCMS (ESI) calc'd for $C_{24}H_{31}FN_4O_5S$ [M+H]$^+$: 507.2, found: 507.1

Step 3: (S)-7-amino-7-(5-(2-fluorophenyl)-1,3,4-oxadiazol-2-yl)-1-(isoxazol-3-yl)heptan-1-one (106D)

HCl (0.5 mL, 6.09 mmol) was added to a stirred mixture of (R)-N-((S)-1-(5-(2-fluorophenyl)-1,3,4-oxadiazol-2-yl)-6-(2-(isoxazol-3-yl)-1,3-dioxolan-2-yl)hexyl)-2-methylpropane-2-sulfinamide (106C, 400 mg, 0.790 mmol) in MeOH (2 mL) and water (0.2 mL) at rt and the mixture was stirred at 50° C. for 2 h. The mixture was basified by NaHCO$_3$ aq and purified by Pre-HPLC (reverse phase C-18 column), eluting with acetonitrile/water+0.1% TFA, to give (S)-7-amino-7-(5-(2-fluorophenyl)-1,3,4-oxadiazol-2-yl)-1-(isoxazol-3-yl)heptan-1-one (106D). LCMS (ESI) calc'd for $C_{18}H_{19}FN_4O_3$[M+H]$^+$: 359.2, found: 359.2.

Step 4: (S)-tert-butyl 3-((1-(5-(2-fluorophenyl)-1,3,4-oxadiazol-2-yl)-7-(isoxazol-3-yl)-7-oxoheptyl)carbamoyl)azetidine-1-carboxylate (106E)

1-(tert-butoxycarbonyl)azetidine-3-carboxylic acid (54 mg, 0.268 mmol) was added to a solution of HOBT (45 mg, 0.294 mmol), EDCI (86 mg, 0.446 mmol) and DIPEA (0.390 mL, 2.232 mmol) in DMF (1 mL) at room temperature and the mixture was stirred at room temperature for 15 min. (S)-7-amino-7-(5-(2-fluorophenyl)-1,3,4-oxadiazol-2-yl)-1-(isoxazol-3-yl)heptan-1-one (106D, 80 mg, 0.223 mmol) in DMF (1 mL) was then added. The mixture was stirred at rt for 1 h. The mixture was cooled, diluted with ethyl acetate (10 mL), washed with water (20 mL), dried (Na$_2$SO$_4$), filtered and the solvent was evaporated under reduced pressure to give (S)-tert-butyl 3-((1-(5-(2-fluorophenyl)-1,3,4-oxadiazol-2-yl)-7-(isoxazol-3-yl)-7-oxoheptyl)carbamoyl)azetidine-1-carboxylate (106E). LCMS (ESI) calc'd for $C_{27}H_{32}FN_5O_6$ [M+H]$^+$: 542.2, found: 486.3 (M−55).

Step 5: (S)-N-(1-(5-(2-fluorophenyl)-1,3,4-oxadiazol-2-yl)-7-(isoxazol-3-yl)-7-oxoheptyl)azetidine-3-carboxamide (106F)

TFA (0.5 mL) was added to a stirred mixture of (S)-tert-butyl 3-((1-(5-(2-fluorophenyl)-1,3,4-oxadiazol-2-yl)-7-(isoxazol-3-yl)-7-oxoheptyl)carbamoyl)azetidine-1-carboxylate (106E, 90 mg, 0.166 mmol) in DCM (1 mL) at room temperature and the mixture was stirred at room temperature for 1 h. The solvent was evaporated under reduced pressure to give (S)-N-(1-(5-(2-fluorophenyl)-1,3,4-oxadiazol-2-yl)-7-(isoxazol-3-yl)-7-oxoheptyl)azetidine-3-carboxamide (106F). LCMS (ESI) calc'd for $C_{22}H_{24}FN_5O_4[M+H]^+$: 442.2, found: 442.2

Step 6: (S)-N-(1-(5-(2-fluorophenyl)-1,3,4-oxadiazol-2-yl)-7-(isoxazol-3-yl)-7-oxoheptyl)-1-methyl-azetidine-3-carboxamide (Example 106)

Sodium triacetoxyhydroborate (117 mg, 0.554 mmol) was added to a stirred mixture of (S)-tert-butyl 3-((1-(5-(2-fluorophenyl)-1,3,4-oxadiazol-2-yl)-7-(isoxazol-3-yl)-7-oxoheptyl)carbamoyl)azetidine-1-carboxylate (106F, 100 mg, 0.185 mmol) and formaldehyde (37 mg, 0.370 mmol) in MeOH (2 mL) at room temperature and the mixture was stirred at room temperature for 10 h. The mixture was purified twice by preparative HPLC (reverse phase C-18 column), eluting with acetonitrile/water+0.1% TFA, to give (S)-N-(1-(5-(2-fluorophenyl)-1,3,4-oxadiazol-2-yl)-7-(isoxazol-3-yl)-7-oxoheptyl)-1-methylazetidine-3-carboxamide (Example 106). LCMS (ESI) calc'd for $C_{17}H_{29}N_5O_4$ $[M+H]^+$: 456.2, found: 456.0. ¹HNMR (400 MHz, MeOD) δ 8.76 (d, J=1.6 Hz, 1H), 7.97-8.08 (m, 1H), 7.57-7.71 (m, 1H), 7.29-7.42 (m, 2H), 6.76 (d, J=1.6 Hz, 1H), 5.22-5.35 (m, 1H), 4.40-4.53 (m, 1H), 4.13-4.26 (m, 2H), 3.55-3.81 (m, 1H), 3.28-3.30 (m, 3H), 3.05 (d, J=7.2 Hz, 1H), 2.89-2.95 (m, 2H), 1.92-2.13 (m, 2H), 1.66-1.80 (m, 2H), 1.42-1.53 (m, 4H).

Example 107

N-(1-(5-(2-fluorophenyl)oxazol-2-yl)-7-(isoxazol-3-yl)-7-oxoheptyl)-1-methylazetidine-3-carboxamide

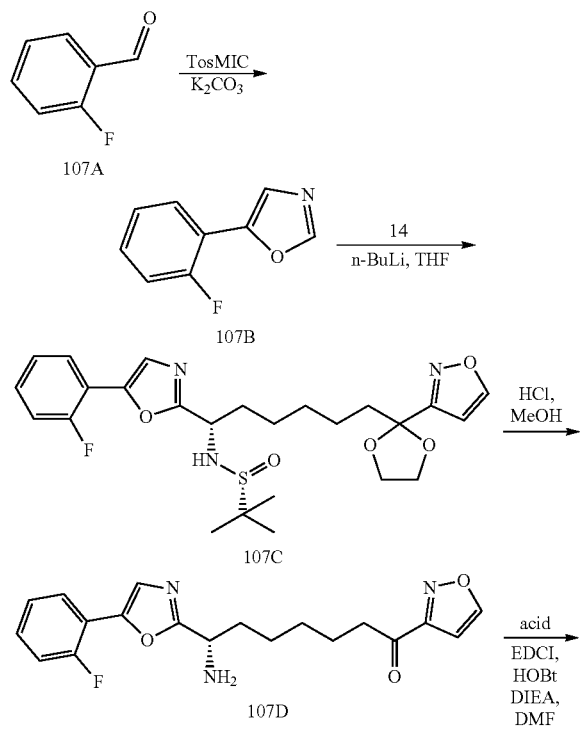

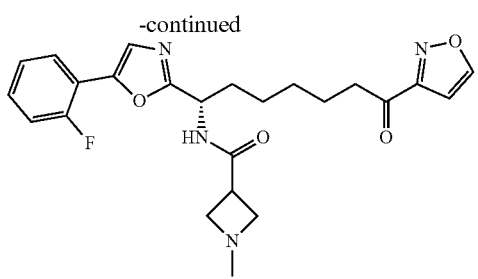

Example 107

Step 1: Preparation of 5-(2-fluorophenyl)oxazole (107B)

$K_2CO_3$ (5.88 g, 42.5 mmol), TosMIC (8.31 g, 42.5 mmol) was added to a stirred mixture of 2-fluorobenzaldehyde (107A, 4.8 g, 38.7 mmol) in MeOH (150 ml) at room temperature and the mixture was heated with stirring at 50° C. for 18 h. The mixture was extracted with ethyl acetate (3×30 mL). The combined organic fractions were washed with brine (saturated, 3×20 mL), dried ($Na_2SO_4$), filtered and the solvent was evaporated under reduced pressure. The residue was purified by silica gel column flash chromatography, eluting with petroleum ether/EtOAc=5:1 to give 5-(2-fluorophenyl)oxazole (107B). LCMS (ESI) calc'd for $C_9H_6FNO$ $[M+H]^+$: 164.0, found: 164.0.

Step 2: (R)-N-((S)-1-(5-(2-fluorophenyl)oxazol-2-yl)-6-(2-(isoxazol-3-yl)-1,3-dioxolan-2-yl)hexyl)-2-methylpropane-2-sulfinamide (109C)

(R,E)-N-(6-(2-(isoxazol-3-yl)-1,3-dioxolan-2-yl)hexylidene)-2-methylpropane-2-sulfinamide (13, 2204 mg, 6.44 mmol) was added to a stirred mixture of n-BuLi (2.70 ml, 6.76 mmol), 5-(2-fluorophenyl)oxazole (109B, 1050 mg, 6.44 mmol) in THF (30 ml) at −78° C. and the mixture was stirred at −78° C. for 2 h. The mixture was added aqueous $NH_4Cl$ (20%, 20 mL) and the mixture was extracted with ethyl acetate (3×30 mL). The combined organic fractions were washed with brine (saturated, 3×20 mL), dried ($Na_2SO_4$), filtered and the solvent was evaporated under reduced pressure. The residue was purified by silica gel column flash chromatography, eluting with petroleum ether/EtOAc=1:1 to give (R)-N-((S)-1-(5-(2-fluorophenyl)oxazol-2-yl)-6-(2-(isoxazol-3-yl)-1,3-dioxolan-2-yl)hexyl)-2-methylpropane-2-sulfinamide (107C). LCMS (ESI) calc'd for $C_{25}H_{32}FN_3O_5S$ $[M+H]^+$: 506.2, found: 506.2. The compound was further purified by silica gel column flash chromatography, eluting with petroleum ether/EtOAc=1:2 to give two isomers, isomer1, which is less polar and isomer2, which is more polar.

Step 3: (S)-7-amino-7-(5-(2-fluorophenyl)oxazol-2-yl)-1-(isoxazol-3-yl)heptan-1-one hydrochloride (107D)

HCl (0.2 ml, 2.435 mmol) was added to a stirred mixture of (R)-N-((S)-1-(5-(2-fluorophenyl)oxazol-2-yl)-6-(2-(isoxazol-3-yl)-1,3-dioxolan-2-yl)hexyl)-2-methylpropane-2-sulfinamide (107C, isomer 2, 150 mg, 0.297 mmol) in MeOH (1.5 ml) and water (0.5 ml) at room temperature and the mixture was heated with stirring at 60° C. for 8 h. The mixture was filtered and the filter cake was washed with MeOH (2×10 ml). The filtrate was concentrated to dryness to give (S)-7-amino-7-(5-(2-fluorophenyl)oxazol-2-yl)-1-(isoxazol-3-yl)heptan-1-one hydrochloride (107D). LCMS (ESI) calc'd for $C_{19}H_{21}ClFN_3O_3[M+H]^+$: 358.1, found: 358.1

Step 4: (S)-N-(1-(5-(2-fluorophenyl)oxazol-2-yl)-7-(isoxazol-3-yl)-7-oxoheptyl)-1-methylazetidine-3-carboxamide (107)

HOBT (31 mg, 0.202 mmol) and EDCI (60 mg, 0.313 mmol) was added to a stirred mixture of DIPEA (0.266 ml, 1.523 mmol) and 1-methylazetidine-3-carboxylic acid (22 mg, 0.191 mmol) in DMF (1 ml) at room temperature and the mixture was stirred at room temperature for 15 min. Then, (S)-7-amino-7-(5-(2-fluorophenyl)oxazol-2-yl)-1-(isoxazol-3-yl)heptan-1-one hydrochloride (107D, 60 mg, 0.152 mmol) in DMF (1 ml) was added. The mixture was stirred at rt for 12 h. The mixture was quenched with water (20 mL), and extracted with EtOAc (30 mL*3). The combined organic fractions were washed with brine (30 mL), dried ($Na_2SO_4$), filtered and the solvent was evaporated under reduced pressure. The residue was purified by preparative HPLC (reverse phase C-18 column), eluting with acetonitrile/water+0.1% TFA, to give (S)-N-(1-(5-(2-fluorophenyl)oxazol-2-yl)-7-(isoxazol-3-yl)-7-oxoheptyl)-1-methylazetidine-3-carboxamide (Example 107). LCMS (ESI) calc'd for $C_{24}H_{27}FN_4O_4[M+H]^+$: 455.2, found: 455.2. $^1$H NMR (400 MHz, MeOD) δ 8.76 (d, J=1.76 Hz, 1H), 7.77 (dd, J=5.97, 7.53 Hz, 1H), 7.34-7.44 (m, 2H), 7.19-7.32 (m, 2H), 6.76 (d, J=1.76 Hz, 1H), 5.17 (m, 1H), 4.35-4.52 (m, 2H), 4.04-4.21 (m, 2H), 3.62 (m, 1H), 3.04 (t, J=7.24 Hz, 2H), 2.92 (brs, 3H), 1.92-2.06 (m, 2H), 1.72 (m, 2H), 1.44 (m, 2H), 1.17-1.32 (m, 1H), 0.82-0.90 (m, 1H).

Example 108

(S)-N-(7-(isoxazol-3-yl)-1-(5-(7-methoxy-2-methylquinolin-6-yl)oxazol-2-yl)-7-oxoheptyl)-1-methylazetidine-3-carboxamide

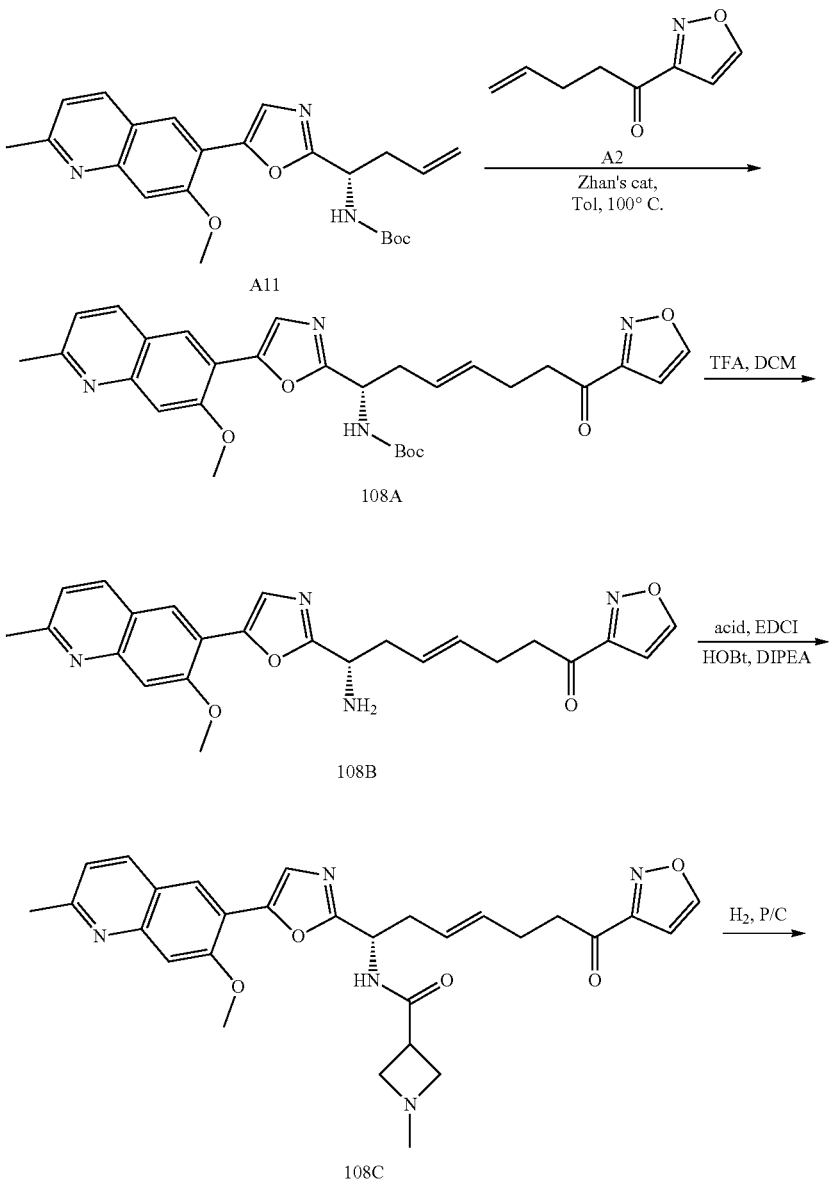

-continued

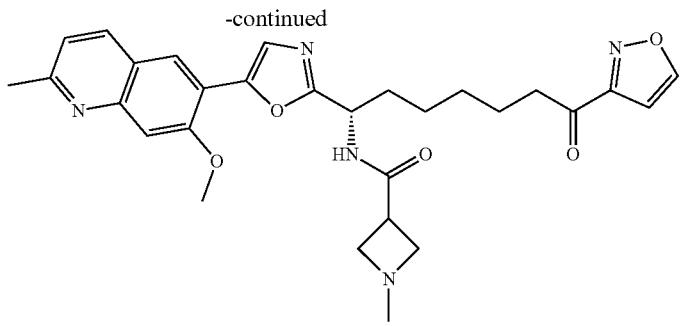

Example 108

Step 1: Preparation of (S,E)-tert-butyl (7-(isoxazol-3-yl)-1-(5-(7-methoxy-2-methylquinolin-6-yl)oxazol-2-yl)-7-oxohept-3-en-1-yl)carbamate (108A)

Zhan's catalyst (48 mg, 0.065 mmol) was added to a stirring mixture of 1-(isoxazol-3-yl)pent-4-en-1-one (A2, 491 mg, 3.25 mmol) and (S)-tert-butyl (1-(5-(7-methoxy-2-methylquinolin-6-yl)oxazol-2-yl)but-3-en-1-yl)carbamate (A11, 266 mg, 0.650 mmol) in toluene (8.0 mL) at rt under $N_2$ atmosphere and the mixture was stirred at 80° C. for 18 h under $N_2$ atmosphere. The reaction mixture was cooled to rt and filtered through Celite and the resulting filtrate was concentrated under reduced pressure. The residue was purified by preparative TLC on silica gel, eluting with petroleum ether/EtOAc=2:1 to give (S,E)-tert-butyl (7-(isoxazol-3-yl)-1-(5-(7-methoxy-2-methylquinolin-6-yl)oxazol-2-yl)-7-oxohept-3-en-1-yl)carbamate (108A). LCMS (ESI) calc'd for $C_{29}H_{32}N_4O_6$ [M+H]$^+$: 533.2, found: 533.3

Step 2: Preparation of (S,E)-7-amino-1-(isoxazol-3-yl)-7-(5-(7-methoxy-2-methylquinolin-6-yl)oxazol-2-yl)hept-4-en-1-one (108B)

TFA (0.4 mL, 5.19 mmol) was added to a stirring mixture of (S,E)-tert-butyl (7-(isoxazol-3-yl)-1-(5-(7-methoxy-2-methylquinolin-6-yl)oxazol-2-yl)-7-oxohept-3-en-1-yl)carbamate (108A, 53 mg, 0.100 mmol) in DCM (1.6 mL) at rt and the mixture was stirred at rt for 1 h. The mixture was concentrated under reduced pressure to give (S,E)-7-amino-1-(isoxazol-3-yl)-7-(5-(7-methoxy-2-methylquinolin-6-yl)oxazol-2-yl)hept-4-en-1-one 2,2,2-trifluoroacetate (108B) which was used to the next step without further purification. LCMS (ESI) calc'd for $_4H_{24}N_4O_4$ [M+H]$^+$: 433.2, found: 433.2

Step 3: Preparation of (S,E)-N-(7-(isoxazol-3-yl)-1-(5-(7-methoxy-2-methylquinolin-6-yl)oxazol-2-yl)-7-oxohept-3-en-1-yl)-1-methylazetidine-3-carboxamide (108C)

EDCI (36 mg, 0.188 mmol), HOBT (30 mg, 0.196 mmol) were added to a stirred mixture of (S,E)-7-amino-1-(isoxazol-3-yl)-7-(5-(7-methoxy-2-methylquinolin-6-yl)oxazol-2-yl)hept-4-en-1-one (108B, 80 mg, 0.185 mmol), 1-methylazetidine-3-carboxylic acid (22 mg, 0.191 mmol) and DIPEA (0.18 mL, 1.031 mmol) in DMF (1 ml) at room temperature and the mixture was stirred at room temperature for 2 h. Water (2 mL) was added and the mixture was extracted with ethyl acetate (3×4 mL). The combined organic fractions were washed with brine (saturated, 1×4 mL), dried ($Na_2SO_4$), filtered and the solvent was evaporated under reduced pressure to give (S,E)-N-(7-(isoxazol-3-yl)-1-(5-(7-methoxy-2-methylquinolin-6-yl)oxazol-2-yl)-7-oxohept-3-en-1-yl)-1-methylazetidine-3-carboxamide (108C) which was used directly for hydrogenation. LCMS (ESI) calc'd for $C_{29}H_{31}N_5O_5$[M+H]$^+$: 530.3, found: 530.3

Step 4: Preparation of (S)-N-(7-(isoxazol-3-yl)-1-(5-(7-methoxy-2-methylquinolin-6-yl)oxazol-2-yl)-7-oxoheptyl)-1-methylazetidine-3-carboxamide (108)

A solution of (S,E)-N-(7-(isoxazol-3-yl)-1-(5-(7-methoxy-2-methylquinolin-6-yl)oxazol-2-yl)-7-oxohept-3-en-1-yl)-1-methylazetidine-3-carboxamide (108C, 98 mg, 0.185 mmol) was added to a 100 mL three-necked bottle and then Pd/C (10 mg, 0.094 mmol) (10%, wet) was added under Ar. The suspension was degassed under vacuum and purged with $N_2$ several times. The mixture was then stirred under $H_2$ (Pressure: 15 psi) at rt for 2 h. The mixture was filtered and the filter cake was washed with MeOH (3×5 mL). The filtrate was concentrated to dryness. The residue was purified by preparative HPLC (reverse phase C-18 column), eluting with acetonitrile/water+0.1% TFA, to give (S)-N-(7-(isoxazol-3-yl)-1-(5-(7-methoxy-2-methylquinolin-6-yl)oxazol-2-yl)-7-oxoheptyl)-1-methylazetidine-3-carboxamide (108). LCMS (ESI) calc'd for $C_{29}H_{33}N_5O_5$ [M+H]$^+$: 532.3, found: 532.1. $^1$H NMR (400 MHz, MeOD) δ 8.84 (d, J=8.3 Hz, 1H), 8.77 (d, J=1.8 Hz, 1H), 8.54 (s, 1H), 7.73 (s, 1H), 7.71 (d, J=8.5 Hz, 1H), 7.59 (s, 1H), 6.76 (d, J=1.8 Hz, 1H), 5.24 (brs, 1H), 4.93-4.97 (m, 1H), 4.59-4.64 (m, 1H), 4.40-4.63 (m, 1H), 4.24 (s, 3H), 4.07-4.16 (m, 1H), 3.72 (brs, 1H), 3.06 (s, 2H), 2.93 (s, 6H), 2.06-2.18 (m, 1H), 1.93-2.01 (m, 1H), 1.70-1.83 (m, 2H), 1.49 (brs, 4H).

Example 109

(S)-6-methyl-N-((S)-1-(5-(2-methylquinolin-6-yl)oxazol-2-yl)-7-(oxazol-2-yl)-7-oxoheptyl)-6-azaspiro[2.5]octane-1-carboxamide

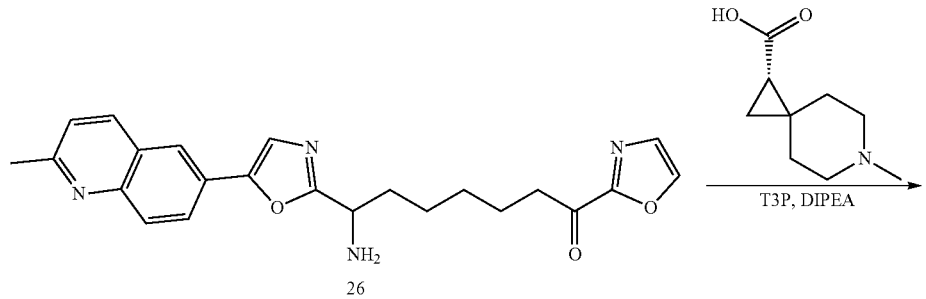

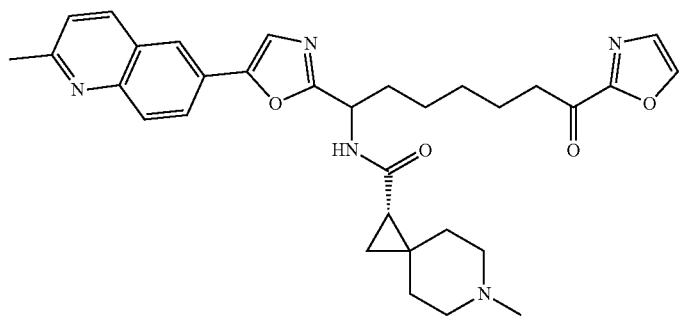 [SMILES: Cc1ccc2cc(-c3cnc(C(CCCCCC(=O)c4ncco4)NC(=O)[C@H]4CC45CCN(C)CC5)o3)ccc2n1]

Example 109

T3P (472 mg, 0.742 mmol) was added to the solution of (S)-7-amino-7-(5-(2-methylquinolin-6-yl)oxazol-2-yl)-1-(oxazol-2-yl)heptan-1-one (26, 60 mg, 0.148 mmol), (S)-6-methyl-6-azaspiro[2.5]octane-1-carboxylic acid (50 mg, 0.295 mmol) and DIPEA (0.259 ml, 1.483 mmol) in DMF (3 ml), and the resultant mixture was stirred at rt for 16 h. The mixture was quenched with brine (10 mL), and the mixture was extracted with ethyl acetate (3×20 mL). The combined organic fractions were washed with brine (saturated, 20 mL), dried (Na$_2$SO$_4$), filtered and the solvent was evaporated under reduced pressure. The residue was purified by preparative HPLC (reverse phase C-18 column), eluting with acetonitrile/water+0.1% TFA, to give (S)-6-methyl-N-((S)-1-(5-(2-methylquinolin-6-yl)oxazol-2-yl)-7-(oxazol-2-yl)-7-oxoheptyl)-6-azaspiro[2.5]octane-1-carboxamide (109). LCMS (ESI) calc'd for C$_{32}$H$_{37}$N$_5$O$_4$ [M+H]$^+$: 556.3, found: 556.1. $^1$H NMR (400 MHz, MeOD) δ 8.86 (d, J=8.60 Hz, 1H), 8.47 (s, 1H), 8.34 (d, J=8.60 Hz, 1H), 8.16 (d, J=9.04 Hz, 1H), 8.09 (s, 1H), 7.84 (d, J=8.60 Hz, 1H), 7.74 (d, J=2.43 Hz, 1H), 7.39 (s, 1H), 5.13-5.25 (m, 1H), 3.48-3.63 (m, 2H), 3.00-3.21 (m, 4H), 2.87-2.98 (m, 6H), 2.72-2.84 (m, 1H), 1.67-2.37 (m, 9H), 1.16-1.60 (m, 7H), 1.02-1.20 (m, 1H).

Example 110

(S)-N-((S)-7-(isoxazol-3-yl)-1-(5-(7-methoxy-2-methylquinolin-6-yl)-1H-imidazol-2-yl)-7-oxoheptyl)-6-methyl-6-azaspiro[2.5]octane-1-carboxamide

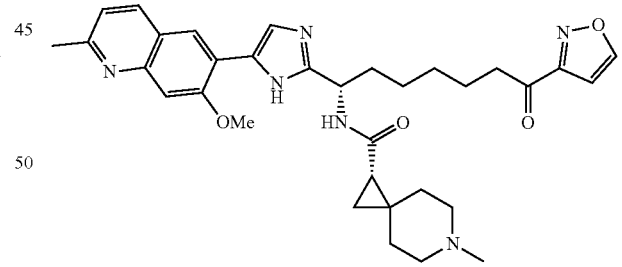

Compound 110 was obtained from compound 31 using a similar method as described above. LCMS (ESI) calc'd for C$_{33}$H$_{40}$N$_6$O$_4$ [M+H]$^+$: 585.3, found: 585.1. $^1$H NMR (400 MHz, MeOD) δ 8.74 (d, J=1.8 Hz, 1H), 8.31-8.36 (m, 1H), 8.19-8.25 (m, 1H), 7.62-7.67 (m, 1H), 7.41 (s, 1H), 7.32 (d, J=8.2 Hz, 1H), 6.74 (d, J=1.8 Hz, 1H), 5.02-5.09 (m, 1H), 4.45 (s, 5H), 4.09 (s, 4H), 3.00-3.08 (m, 4H), 2.70 (s, 6H), 1.95-2.07 (m, 3H), 1.74 (brs, 6H), 1.35-1.54 (m, 6H), 1.28 (t, J=7.14 Hz, 1H), 1.15-1.22 (m, 1H), 0.92-1.00 (m, 1H).

Example 111

(1S)-6-methyl-N-(1-(5-(2-methylquinolin-6-yl)oxazol-2-yl)-7-(oxazol-2-yl)-7-oxoheptyl)-6-azaspiro[2.5]octane-1-carboxamide

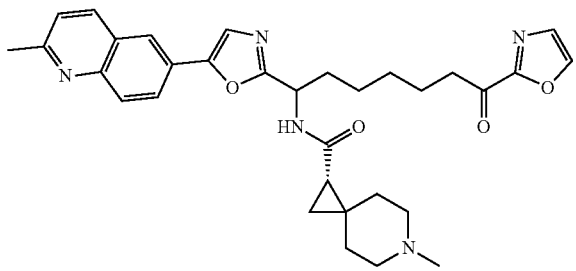

Compound 111 was obtained from compound 26 using a similar method as described above. LCMS (ESI) calc'd for $C_{32}H_{37}N_5O_4$ [M+H]$^+$: 556.3, found: 556.1. $^1$H NMR (400 MHz, METHANOL-d$_4$) δ 8.81 (d, J=8.38 Hz, 1H), 8.45 (d, J=5.95 Hz, 1H), 8.31 (d, J=9.26 Hz, 1H), 8.05-8.18 (m, 3H), 7.81 (d, J=8.60 Hz, 1H), 7.68-7.74 (m, 1H), 7.38 (s, 1H), 5.16 (brs, 1H), 3.06-3.12 (m, 3H), 2.85-2.93 (m, 8H), 2.13-2.32 (m, 2H), 1.97 (brs, 3H), 1.78 (dd, J=6.28, 13.56 Hz, 3H), 1.49 (brs, 4H), 1.23-1.29 (m, 2H), 0.97-1.11 (m, 1H).

Example 112

(S)-N-((S)-1-(4-chloro-2-(2-fluorophenyl)-1H-imidazol-5-yl)-7-(isoxazol-3-yl)-7-oxoheptyl)-6-methyl-6-azaspiro[2.5]octane-1-carboxamide

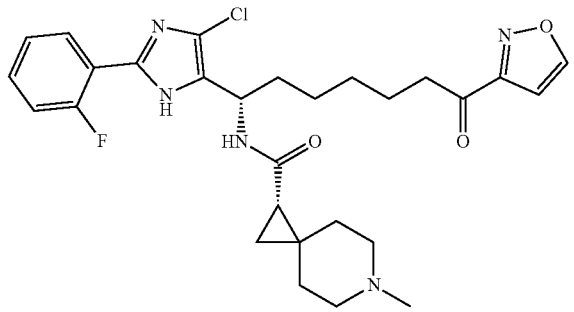 [SMILES: CN1CCC2(CC1)C[C@@H]2C(=O)N[C@@H](CCCCCC(=O)c1ccon1)c1[nH]c(-c2ccccc2F)nc1Cl]

Compound 112 was obtained from compound 105D using a similar method as described above. LCMS (ESI) calc'd for $C_{28}H_{33}ClFN_5O_3 \cdot 17H_6O_6$[M+H]$^+$: 542.2, found: 542.0. $^1$H NMR (400 MHz, MeOD) δ 8.78 (d, J=1.8 Hz, 1H), 7.88 (t, J=7.7 Hz, 1H), 7.42-7.49 (m, 1H), 7.23-7.33 (m, 2H), 6.78 (d, J=1.8 Hz, 1H), 5.01-5.07 (m, 1H), 4.42 (s, 2H), 3.04-3.20 (m, 4H), 2.76-2.83 (m, 3H), 2.76-2.83 (m, 3H), 2.76-2.83 (m, 3H), 1.83-2.04 (m, 5H), 1.72-1.79 (m, 3H), 1.35-1.51 (m, 5H), 1.20 (d, J=4.3 Hz, 1H), 0.99 (dd, J=4.5, 8.3 Hz, 1H).

Example 113

(S)-N-((S)-1-(5-(7-methoxy-2-methylquinolin-6-yl)oxazol-2-yl)-7-(oxazol-2-yl)-7-oxoheptyl)-6-methyl-6-azaspiro[2.5]octane-1-carboxamide

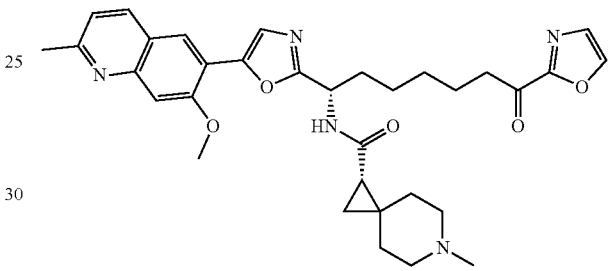

Compound 113 was obtained from compound 27 using a similar method as described above. LCMS (ESI) calc'd for $C_{33}H_{39}N_5O_5$ [M+H]$^+$: 586.3, found: 586.3. $^1$H NMR (400 MHz, MeOD) δ 8.24-8.30 (m, 2H), 8.10 (s, 1H), 7.61 (s, 1H), 7.46 (s, 1H), 7.34-7.40 (m, 2H), 5.20 (dd, J=6.15, 8.41 Hz, 1H), 4.46 (s, 3H), 4.14 (s, 3H), 3.09 (t, J=7.15 Hz, 2H), 2.85 (s, 3H), 2.73 (s, 3H), 1.91-2.18 (m, 5H), 1.71-1.88 (m, 4H), 1.52 (d, J=6.27 Hz, 5H), 1.25 (t, J=4.77 Hz, 1H), 1.04 (dd, J=4.77, 8.03 Hz, 1H).

Example 114

(1S)-N-(1-(5-(2-methoxypyridin-3-yl)oxazol-2-yl)-7-(oxazol-2-yl)-7-oxoheptyl)-6-methyl-6-azaspiro[2.5]octane-1-carboxamide

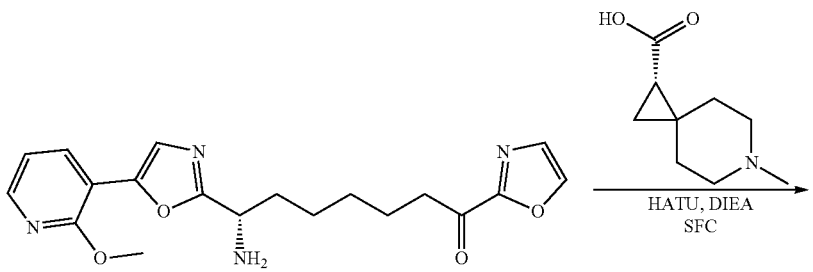

-continued

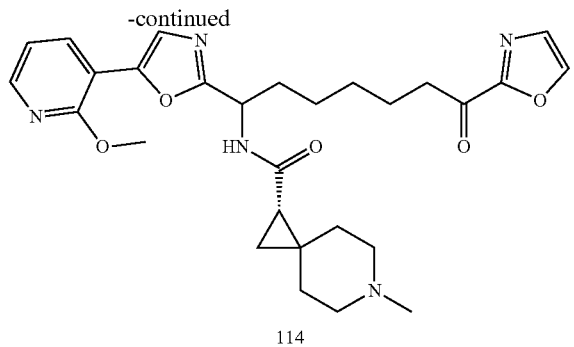

114

A mixture of HATU (166 mg, 0.437 mmol), (S)-6-methyl-6-azaspiro[2.5]octane-1-carboxylic acid (90 mg, 0.532 mmol) and DIPEA (0.3 ml, 1.718 mmol) in DMF (0.5 ml) was stirred at rt for 30 mins, then (S)-7-amino-7-(5-(2-methoxypyridin-3-yl)oxazol-2-yl)-1-(oxazol-2-yl)heptan-1-one (28, 80 mg, 0.216 mmol) dissolved in DMF (0.5 mL) was added and the mixture was stirred at rt for 2 h. The mixture was filtered and the residue was purified by preparative HPLC (reverse phase C-18 column), eluting with acetonitrile/water (10 mM NH$_4$HCO$_3$), to give (1S)-N-(1-(5-(2-methoxypyridin-3-yl)oxazol-2-yl)-7-(oxazol-2-yl)-7-oxoheptyl)-6-methyl-6-azaspiro[2.5]octane-1-carboxamide (114). LCMS (ESI) calc'd for $15_8H_{35}N_5O_5$ [M+H]$^+$: 522.3, found: 522.3. (1S)-N-(1-(5-(2-methoxypyridin-3-yl)oxazol-2-yl)-7-(oxazol-2-yl)-7-oxoheptyl)-6-methyl-6-azaspiro [2.5]octane-1-carboxamide (114, 10 mg, 0.019 mmol) was further purified by preparative HPLC (reverse phase C-18 column), eluting with acetonitrile/water+0.1% TFA. LCMS (ESI) calc'd for C$_{28}$H$_{35}$N$_5$O$_5$ [M+H]$^+$: 522.3, found: 522.3. $^1$H NMR (400 MHz, MeOD) δ 8.10 (d, J=12.13 Hz, 2H), 8.05 (brs, 1H), 7.48 (brs, 1H), 7.38 (brs, 1H), 7.06 (brs, 1H), 5.14 (brs, 1H), 4.06 (brs, 3H), 3.53 (d, J=9.00 Hz, 2H), 2.99-3.16 (m, 1H), 2.99-3.19 (m, 3H), 2.85-2.94 (m, 1H), 2.90 (d, J=11.15 Hz, 2H), 2.09-2.11 (m, 1H), 2.07-2.11 (m, 1H), 1.68-2.11 (m, 1H), 1.65-2.15 (m, 7H), 1.16-1.50 (m, 7H).

Example 115

(S)-N-((S)-1-(4-(6-cyclopropyl-2-methoxypyridin-3-yl)-1H-imidazol-2-yl)-7-(oxazol-2-yl)-7-oxoheptyl)-6-methyl-6-azaspiro[2.5]octane-1-carboxamide

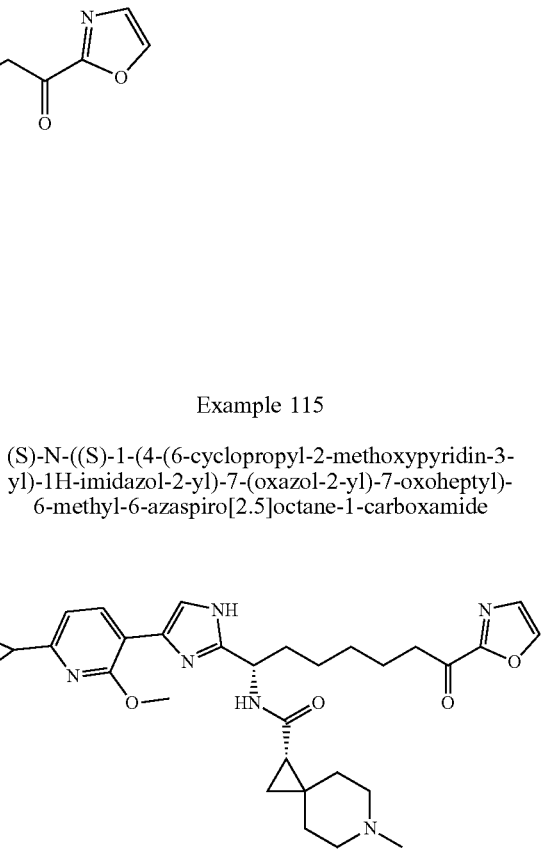

Compound 115 was obtained from compound 24 using a similar method as described above. LCMS (ESI) calc'd for C$_{31}$H$_{40}$N$_6$O$_4$·17H$_6$O$_6$[M+H]$^+$: 561.3, found: 561.3. $^1$H NMR (400 MHz, MeOD) δ 8.08 (s, 1H), 8.02 (brs, 1H), 7.61 (brs, 1H), 7.38 (s, 1H), 6.95 (d, J=7.50 Hz, 1H), 5.00-5.14 (m, 1H), 4.49 (s, 7H), 3.98 (s, 4H), 3.32-3.56 (m, 4H), 3.04-3.07 (m, 1H), 3.05 (t, J=7.17 Hz, 1H), 2.68-2.90 (m, 3H), 1.93-2.12 (m, 1H), 1.93-2.10 (m, 1H), 1.92-2.12 (m, 1H), 1.80-1.89 (m, 1H), 1.67-1.78 (m, 1H), 1.66-1.78 (m, 1H), 1.64-1.91 (m, 3H), 1.31-1.58 (m, 1H), 1.29-1.59 (m, 1H), 1.12-1.58 (m, 4H), 0.91-1.00 (m, 1H), 0.88-1.09 (m, 4H), 0.87-0.92 (m, 1H).

Example 116

(S)-8-methyl-N-(1-(5-(2-methylquinolin-6-yl)oxazol-2-yl)-7-(oxazol-2-yl)-7-oxoheptyl)-1-oxa-2,8-diazaspiro[4.5]dec-2-ene-3-carboxamide

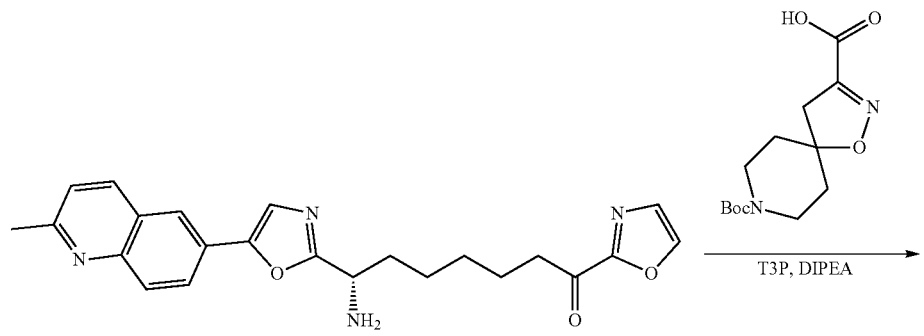

26

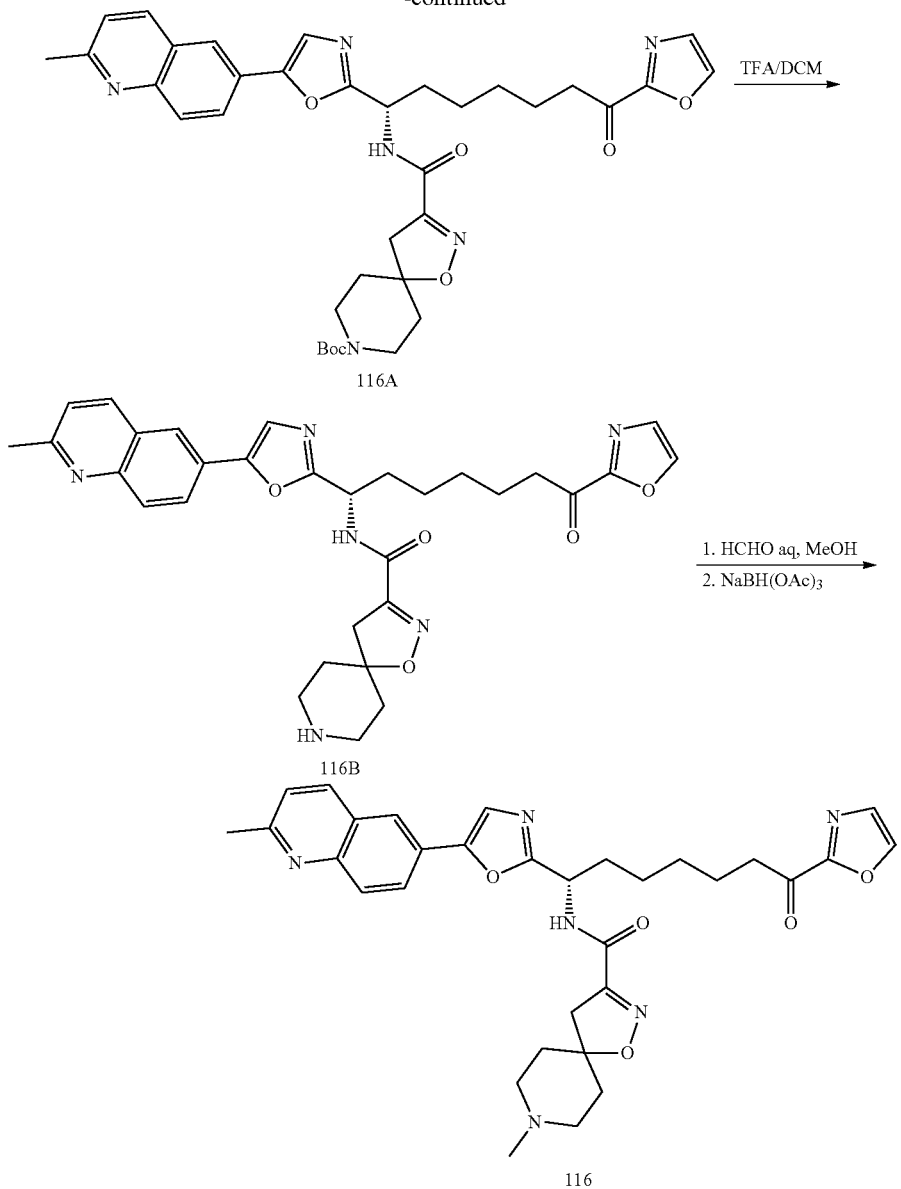

Step 1: Preparation of (S)-tert-butyl 3-((1-(5-(2-methylquinolin-6-yl)oxazol-2-yl)-7-(oxazol-2-yl)-7-oxoheptyl)carbamoyl)-1-oxa-2,8-diazaspiro[4.5]dec-2-ene-8-carboxylate (116A)

T3P (0.6 ml, 0.185 mmol) was added to a stirred mixture of DIEA (0.5 ml, 2.86 mmol), 8-(tert-butoxycarbonyl)-1-oxa-2,8-diazaspiro[4.5]dec-2-ene-3-carboxylic acid (63 mg, 0.222 mmol), (S)-7-amino-7-(5-(2-methylquinolin-6-yl)oxazol-2-yl)-1-(oxazol-2-yl)heptan-1-one (26, 150 mg, 0.185 mmol) in DMF (2 ml) at room temperature and the mixture was stirred at rt for 15 h. The residue was purified by preparative HPLC (reverse phase C-18 column), eluting with acetonitrile/water+0.1% TFA, to give (S)-tert-butyl 3-((1-(5-(2-methylquinolin-6-yl)oxazol-2-yl)-7-(oxazol-2-yl)-7-oxoheptyl)carbamoyl)-1-oxa-2,8-diazaspiro[4.5]dec-2-ene-8-carboxylate (116A). LCMS (ESI) calc'd for $C_{36}H_{42}N_6O_7$ [M+H]$^+$: 671.3, found: 671.4

Step 2: Preparation of (S)-N-(1-(5-(2-methylquinolin-6-yl)oxazol-2-yl)-7-(oxazol-2-yl)-7-oxoheptyl)-1-oxa-2,8-diazaspiro[4.5]dec-2-ene-3-carboxamide (116B)

TFA (0.5 ml, 6.49 mmol) was added to a stirred mixture of (S)-tert-butyl 3-((1-(5-(2-methylquinolin-6-yl)oxazol-2-yl)-7-(oxazol-2-yl)-7-oxoheptyl)carbamoyl)-1-oxa-2,8-diazaspiro[4.5]dec-2-ene-8-carboxylate (116A, 40 mg, 0.054 mmol) in DCM (2 ml) at room temperature and the mixture was stirred at room temperature for 3 h. The mixture was concentrated to afford (S)-N-(1-(5-(2-methylquinolin-6-yl)oxazol-2-yl)-7-(oxazol-2-yl)-7-oxoheptyl)-1-oxa-2,8-diazaspiro[4.5]dec-2-ene-3-carboxamide (116B) which was used directly to next step without further purification. LCMS (ESI) calc'd for $C_{31}H_{34}N_6O_5$ [M+H]$^+$: 571.2, found: 571.4

Step 3: Preparation of (S)-8-methyl-N-(1-(5-(2-methylquinolin-6-yl)oxazol-2-yl)-7-(oxazol-2-yl)-7-oxoheptyl)-1-oxa-2,8-diazaspiro[4.5]dec-2-ene-3-carboxamide (116)

Formaldehyde (0.5 ml, 0.053 mmol) was added to a stirred mixture of ((S)-N-(1-(5-(2-methylquinolin-6-yl)oxazol-2-yl)-7-(oxazol-2-yl)-7-oxoheptyl)-1-oxa-2,8-diazaspiro[4.5]dec-2-ene-3-carboxamide (116B, 30 mg, 0.053 mmol) in MeOH (0.5 ml) at room temperature and the mixture was stirred at room temperature for 1 h. Then triacetoxyhydroborate (10 mg, 0.053 mmol) was added into the mixture and the mixture was stirred at room temperature for 2 h. The residue was purified by preparative HPLC (reverse phase C-18 column), eluting with acetonitrile/water+0.1% TFA, then transferred to HCl salt to give (S)-8-methyl-N-(1-(5-(2-methylquinolin-6-yl)oxazol-2-yl)-7-(oxazol-2-yl)-7-oxoheptyl)-1-oxa-2,8-diazaspiro[4.5]dec-2-ene-3-carboxamide hydrochloride (116). LCMS (ESI) calc'd for $C_{32}H_{36}N_6O_5 \cdot ClH$ [M+H]$^+$: 585.3, found: 585.1.
$^1$H NMR (400 MHz, MeOD) δ 7.41-7.50 (m, 2H), 7.01 (s, 1H), 6.89 (d, J=9.04 Hz, 1H), 6.66 (d, J=9.04 Hz, 1H), 6.54 (s, 1H), 6.40 (d, J=8.60 Hz, 1H), 6.24 (s, 1H), 5.83 (s, 1H), 3.71-3.79 (m, 1H), 1.95 (d, J=12.79 Hz, 1H), 1.78 (s, 3H), 1.73-1.74 (m, 7H), 1.61-1.73 (m, 1H), 1.58-1.61 (m, 1H), 1.60 (d, J=5.73 Hz, 1H), 1.51 (t, J=7.17 Hz, 2H), 1.45 (s, 3H), 1.36 (s, 3H), 0.43-0.71 (m, 6H), 0.14-0.24 (m, 1H), −0.07 (d, J=5.51 Hz, 2H), −0.27 (brs, 2H).

Example 117

(S)-N-(1-(5-(7-methoxy-2-methylquinolin-6-yl)-1H-imidazol-2-yl)-7-(oxazol-2-yl)-7-oxoheptyl)-2-methyl-2-azaspiro[3.5]nonane-7-carboxamide

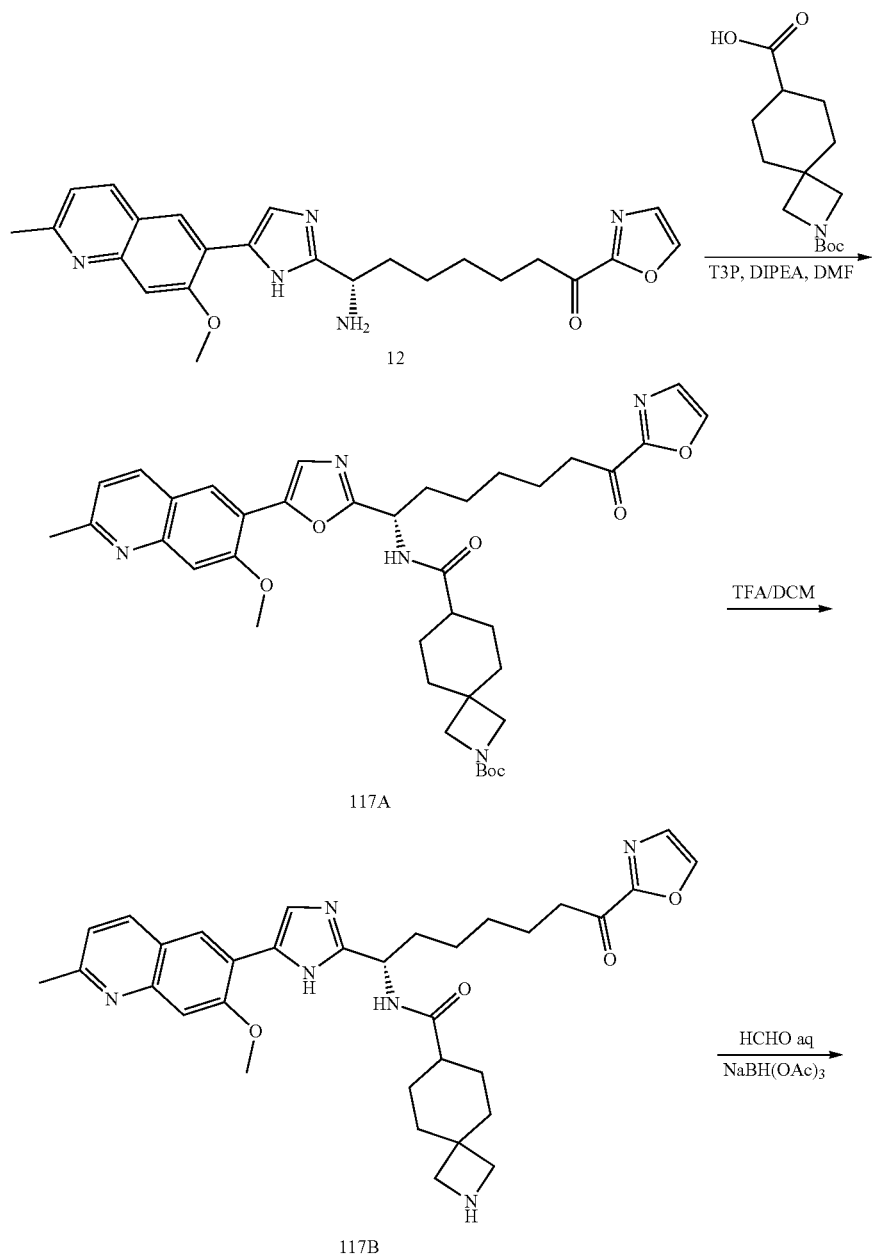

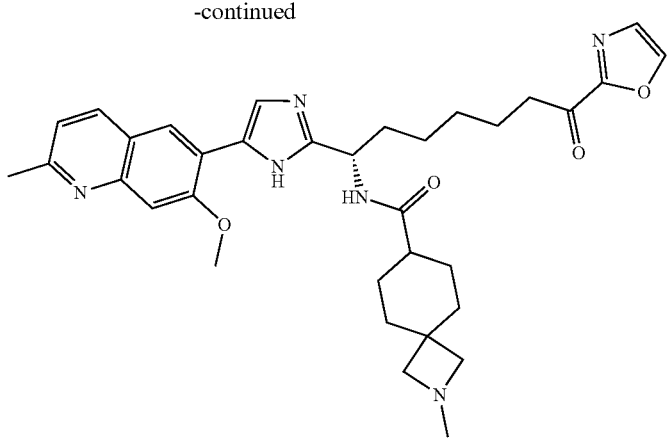

117

Step 1: Preparation of (S)-tert-butyl 7-((1-(5-(7-methoxy-2-methylquinolin-6-yl)-1H-imidazol-2-yl)-7-(oxazol-2-yl)-7-oxoheptyl)carbamoyl)-2-azaspiro[3.5]nonane-2-carboxylate (117A)

T3P (220 mg, 0.346 mmol) was added to a stirred mixture of DIEA (1 ml, 5.73 mmol), (S)-7-amino-7-(5-(7-methoxy-2-methylquinolin-6-yl)-1H-imidazol-2-yl)-1-(oxazol-2-yl)heptan-1-one (12, 100 mg, 0.231 mmol), and 2-(tert-butoxycarbonyl)-2-azaspiro[3.5]nonane-7-carboxylic acid (75 mg, 0.278 mmol) in DMF (2 ml) at room temperature and the mixture was stirred at rt for 2 h. The residue was purified by silica gel column flash chromatography, eluting with DCM/MeOH=0-20% to give (S)-tert-butyl 7-((1-(5-(7-methoxy-2-methylquinolin-6-yl)-1H-imidazol-2-yl)-7-(oxazol-2-yl)-7-oxoheptyl)carbamoyl)-2-azaspiro[3.5]nonane-2-carboxylate (117A). LCMS (ESI) calc'd for $C_{38}H_{48}N_6O_6$ $[M+H]^+$: 685.4, found: 685.4

Step 2: Preparation of (S)-N-(1-(5-(7-methoxy-2-methylquinolin-6-yl)-1H-imidazol-2-yl)-7-(oxazol-2-yl)-7-oxoheptyl)-2-azaspiro[3.5]nonane-7-carboxamide (117B)

TFA (0.1 ml, 1.298 mmol) was added to a stirred mixture of (S)-tert-butyl 7-((1-(5-(7-methoxy-2-methylquinolin-6-yl)-1H-imidazol-2-yl)-7-(oxazol-2-yl)-7-oxoheptyl)carbamoyl)-2-azaspiro[3.5]nonane-2-carboxylate (117A, 80 mg, 0.082 mmol) in DCM (1 ml) at rt and the mixture was stirred at rt for 1 h. The mixture was concentrated to afford (S)-N-(1-(5-(7-methoxy-2-methylquinolin-6-yl)-1H-imidazol-2-yl)-7-(oxazol-2-yl)-7-oxoheptyl)-2-azaspiro[3.5]nonane-7-carboxamide (117B) which was used directly to next step without further purification. LCMS (ESI) calc'd for $C_{33}H_{40}N_6O_4$ $[M+H]^+$: 585.3, found: 585.3

Step 3: Preparation of (S)-N-(1-(5-(7-methoxy-2-methylquinolin-6-yl)-1H-imidazol-2-yl)-7-(oxazol-2-yl)-7-oxoheptyl)-2-methyl-2-azaspiro[3.5]nonane-7-carboxamide (117)

Formaldehyde (1 ml, 0.096 mmol) was added to a stirred mixture of (S)-N-(1-(5-(7-methoxy-2-methylquinolin-6-yl)-1H-imidazol-2-yl)-7-(oxazol-2-yl)-7-oxoheptyl)-2-azaspiro[3.5]nonane-7-carboxamide (117B, 80 mg, 0.096 mmol) in MeOH (1 ml) at room temperature and the mixture was stirred at room temperature for 2 h. Then, sodium triacetoxyhydroborate (362 mg, 1.7 mmol) was added and the mixture was stirred at room temperature for 2 h. The residue was purified by preparative HPLC (reverse phase C-18 column), eluting with MeCN/Water+0.1% TFA, to give (S)-N-(1-(5-(7-methoxy-2-methylquinolin-6-yl)-1H-imidazol-2-yl)-7-(oxazol-2-yl)-7-oxoheptyl)-2-methyl-2-azaspiro[3.5]nonane-7-carboxamide (117). LCMS (ESI) calc'd for $C_{34}H_{42}N_6O_4$ $[M+H]^+$: 599.3, found: 599.1. $^1H$ NMR (400 MHz, MeOD) δ 8.31 (brs, 2H), 7.99 (s, 1H), 7.60 (s, 1H), 7.33-7.40 (m, 2H), 7.29 (s, 1H), 4.97 (t, J=7.43 Hz, 1H), 4.04 (s, 3H), 2.90-3.00 (m, 4H), 2.82 (s, 3H), 2.69 (s, 3H), 2.60 (s, 2H), 2.05-2.12 (m, 2H), 1.89-1.97 (m, 3H), 1.59-1.68 (m, 2H), 1.50 (brs, 4H), 1.30-1.39 (m, 4H), 1.27 (dd, J=3.33, 6.65 Hz, 4H), 0.80 (t, J=6.75 Hz, 3H).

Example 118

(S)-7-amino-7-(5-(4-fluorophenyl)isoxazol-3-yl)-1-(isoxazol-3-yl)heptan-1-one

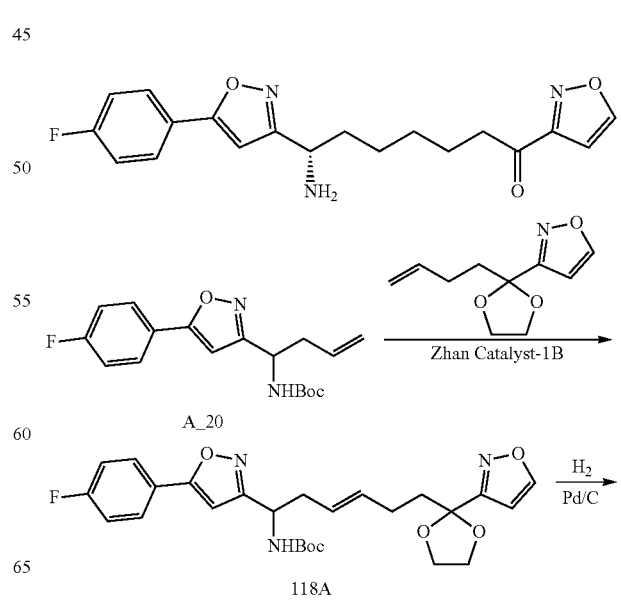

118A

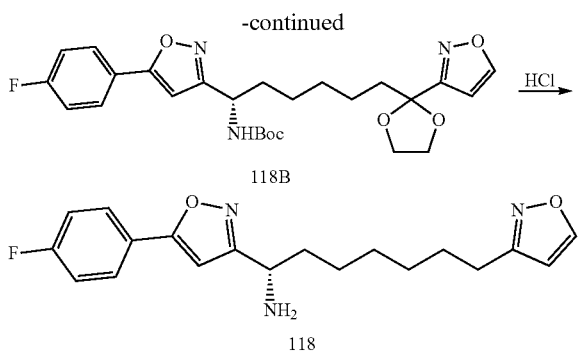

Step A: tert-butyl (E)-(1-(5-(4-fluorophenyl)isoxazol-3-yl)-6-(2-(isoxazol-3-yl)-1,3-dioxolan-2-yl)hex-3-en-1-yl)carbamate (118A)

To a solution of tert-butyl (1-(5-(4-fluorophenyl)isoxazol-3-yl)but-3-en-1-yl)carbamate (A_20, 434 mg, 1.306 mmol) and 3-(2-(but-3-en-1-yl)-1,3-dioxolan-2-yl)isoxazole (Prepared from 2, 0.549 ml, 3.26 mmol) in CH₂Cl₂ (10 ml) was added 1,3-bis(2,4,6-trimethylphenyl)-4,5-dihydroimidazol-2-ylidene[2-(i-propoxy)-5-(N,N-dimethylaminosulfonyl)phenyl]methyleneruthenium(II) dichloride (96 mg, 0.131 mmol). The reaction mixture was heated at reflux under N₂ overnight. The reaction mixture was cooled to RT and concentrated by rotorvap. The crude product was purified by normal phase silica gel column chromatography using EtOAc/Hexanes to yield tert-butyl (E)-(1-(5-(4-fluorophenyl)isoxazol-3-yl)-6-(2-(isoxazol-3-yl)-1,3-dioxolan-2-yl)hex-3-en-1-yl)carbamate (118A).

Step B: tert-butyl (S)-(1-(5-(4-fluorophenyl)isoxazol-3-yl)-6-(2-(isoxazol-3-yl)-1,3-dioxolan-2-yl)hexyl)carbamate (118B)

To a solution of (E)-tert-butyl (1-(5-(4-fluorophenyl)isoxazol-3-yl)-6-(2-(isoxazol-3-yl)-1,3-dioxolan-2-yl)hex-3-en-1-yl)carbamate (118A, 250 mg, 0.500 mmol) in ethanol (10 ml) was added Pd/C (53.3 mg, 0.050 mmol) (10 wt %). The reaction mixture was stirred at RT under 1 atm of H₂. After 4 h, the reaction mixture was filtered through a pad of Celite and the filtrate was concentrated. The crude product was separated using SFC chiral separation to yield tert-butyl (S)-(1-(5-(4-fluorophenyl)isoxazol-3-yl)-6-(2-(isoxazol-3-yl)-1,3-dioxolan-2-yl)hexyl)carbamate (118B) (SFC purification first peak) and tert-butyl (R)-(1-(5-(4-fluorophenyl)isoxazol-3-yl)-6-(2-(isoxazol-3-yl)-1,3-dioxolan-2-yl)hexyl)carbamate (118R) (SFC purification second peak).

Step C: (S)-7-amino-7-(5-(4-fluorophenyl)isoxazol-3-yl)-1-(isoxazol-3-yl)heptan-1-one (118)

To a solution of tert-butyl (S)-(1-(5-(4-fluorophenyl)isoxazol-3-yl)-6-(2-(isoxazol-3-yl)-1,3-dioxolan-2-yl)hexyl)carbamate (118B, 46.7 mg, 0.093 mmol) in MeOH (2 ml) and H₂O (1 ml) was added HCl (300 µL, 1.200 mmol) (4.0M in dioxane). The reaction mixture was heated at 50° C. under N₂ overnight. The reaction mixture was cooled to RT and concentrated by rotorvap. The crude product was purified by reverse phase prep HPLC to yield the title compound. LC-MS (ES, m/z): 358 [M+H]⁺

Example 119

(R)-7-amino-7-(5-(4-fluorophenyl)isoxazol-3-yl)-1-(isoxazol-3-yl)heptan-1-one

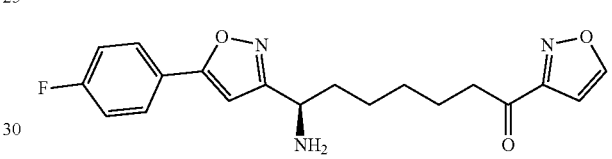

To a solution of tert-butyl (R)-(1-(5-(4-fluorophenyl)isoxazol-3-yl)-6-(2-(isoxazol-3-yl)-1,3-dioxolan-2-yl)hexyl)carbamate (118R, 54.1 mg, 0.108 mmol) in MeOH (2 ml) and H₂O (1 ml) was added HCl (300 µL, 1.200 mmol) (4.0M in dioxane). The reaction mixture was heated at 50° C. under N₂ overnight. The reaction mixture was cooled to RT and concentrated by rotorvap. The crude product purified by reverse phase prep HPLC to yield the title compound as white solid. LC-MS (ES, m/z): 358 [M+H]⁺

The Examples in the following table were prepared from the appropriate intermediates as the starting materials described previously or commercially available starting materials using procedures similar to those described in Examples 118 and 119.

| Example # | Structure | IUPAC Name | Exact Mass [M + H]⁺ |
|---|---|---|---|
| 120 | 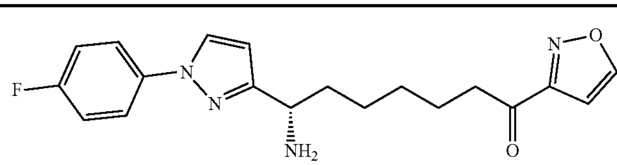 | (7S)-7-amino-7-[1-(4-fluorophenyl)-1H-pyrazol-3-yl]-1-isoxazol-3-ylheptan-1-one | 357 |
| 121 | 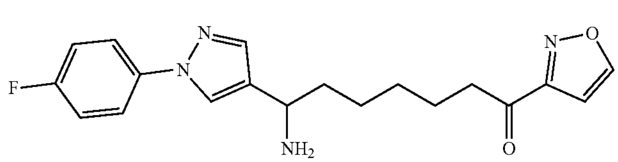 [SMILES: NC(CCCCCC(=O)c1ccon1)c1cnn(-c2ccc(F)cc2)c1] | 7-amino-7-[1-(4-fluorophenyl)-1H-pyrazol-4-yl]-1-isoxazol-3-ylheptan-1-one | 357 |

| Example # | Structure | IUPAC Name | Exact Mass [M + H]+ |
|---|---|---|---|
| 122 | 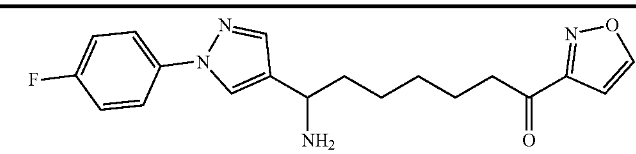 | 7-amino-7-[1-(4-fluorophenyl)-1H-pyrazol-4-yl]-1-isoxazol-3-ylheptan-1-one | 357 |
| 123 | 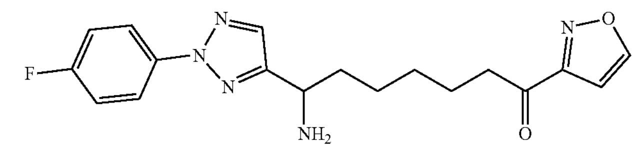 [SMILES: NC(CCCCCC(=O)c1ccon1)c1cnn(-c2ccc(F)cc2)c1] | 7-amino-7-[2-(4-fluorophenyl)-2H-1,2,3-triazol-4-yl]-1-isoxazol-3-ylheptan-1-one | 358 |
| 124 | 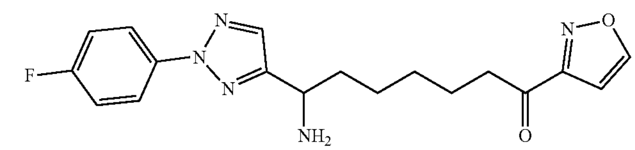 | 7-amino-7-[2-(4-fluorophenyl)-2H-1,2,3-triazol-4-yl]-1-isoxazol-3-ylheptan-1-one | 358 |
| 125 | 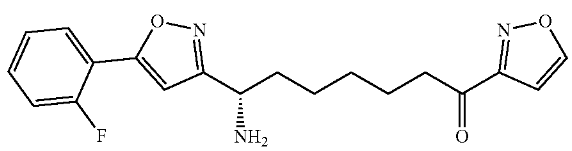 [SMILES: N[C@@H](CCCCCC(=O)c1ccon1)c1cc(-c2ccccc2F)on1] | (7S)-7-amino-7-[5-(2-fluorophenyl)isoxazol-3-yl]-1-isoxazol-3-ylheptan-1-one | 358 |
| 126 | 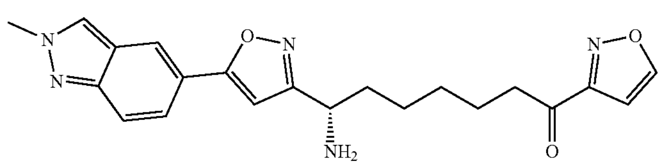 [SMILES: Cn1cc2cc(-c3cc([C@@H](N)CCCCCC(=O)c4ccon4)no3)ccc2n1] | (7S)-7-amino-1-isoxazol-3-yl-7-[5-(2-methyl-2H-indazol-5-yl)isoxazol-3-yl]heptan-1-one | 394 |
| 127 | 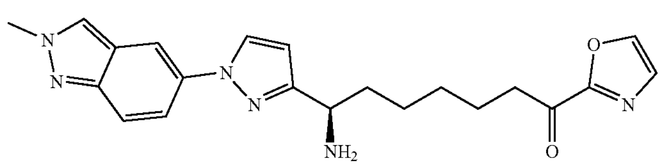 [SMILES: Cn1cc2cc(-n3ccc([C@H](N)CCCCCC(=O)c4ncco4)n3)ccc2n1] | (7R)-7-amino-7-[1-(2-methyl-2H-indazol-5-yl)-1H-pyrazol-3-yl]-1-(1,3-oxazol-2-yl)heptan-1-one | 393 |
| 128 | 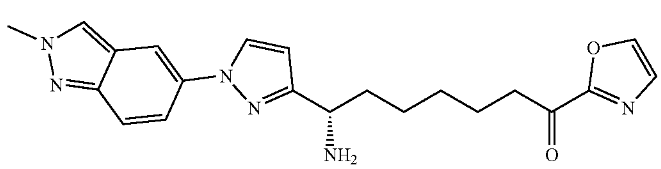 [SMILES: Cn1cc2cc(-n3ccc([C@@H](N)CCCCCC(=O)c4ncco4)n3)ccc2n1] | (7S)-7-amino-7-[1-(2-methyl-2H-indazol-5-yl)-1H-pyrazol-3-yl]-1-(1,3-oxazol-2-yl)heptan-1-one | 393 |

Example 129

(S)-7-amino-7-(5-(5-fluoro-2-methoxypyridin-4-yl)-1H-imidazol-2-yl)-1-(oxazol-2-yl)heptan-1-one

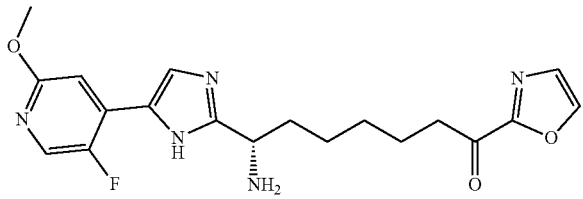

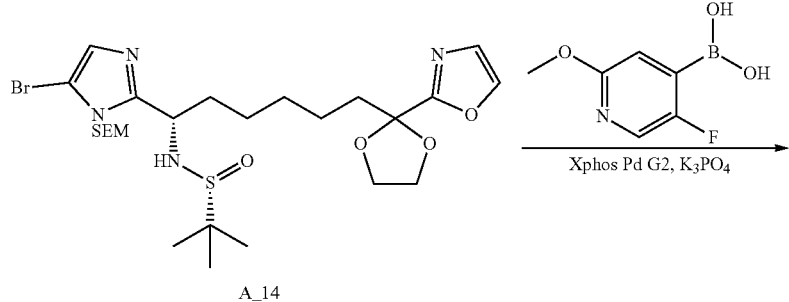

A_14

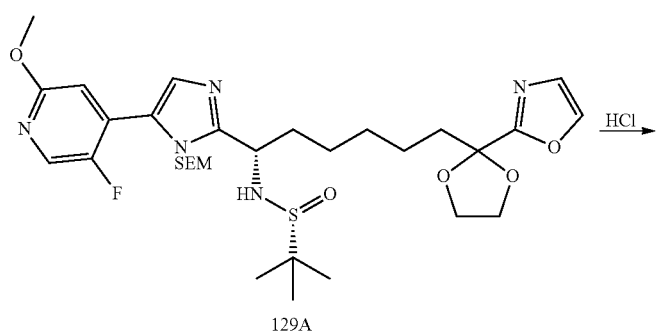

129A

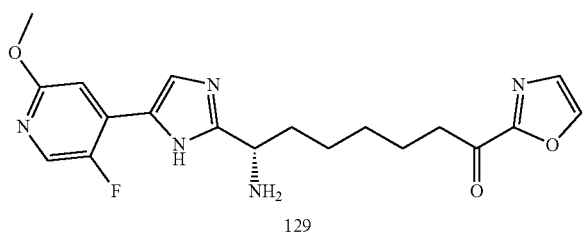

129

Step A: (R)-N-((S)-1-(5-(5-fluoro-2-methoxypyridin-4-yl)-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (129A)

To a suspension of (R)-N-((S)-1-(5-bromo-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (A_14, 320.1 mg, 0.517 mmol) and (5-fluoro-2-methoxypyridin-4-yl)boronic acid (115 mg, 0.672 mmol) in 1,4-dioxane (3 ml) and water (0.600 ml) were added 2nd generation xphos precatalyst (40.6 mg, 0.052 mmol) and potassium phosphate tribasic (329 mg, 1.550 mmol). The reaction mixture was degassed by $N_2$ stream for 10 min. Then the reaction mixture was stirred at 90° C. under $N_2$ overnight. The reaction mixture was cooled to RT. The reaction mixture was concentrated by rotorvap. The crude reaction mixture was purified by normal phase silica gel column chromatography using EtOAc/$CH_2Cl_2$ as eluents to yield (R)-N-((S)-1-(5-(5-fluoro-2-methoxypyridin-4-yl)-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (129A).

Step B: (S)-7-amino-7-(5-(5-fluoro-2-methoxypyridin-4-yl)-1H-imidazol-2-yl)-1-(oxazol-2-yl)heptan-1-one (129)

To a solution of (R)-N-((S)-1-(5-(5-fluoro-2-methoxypyridin-4-yl)-1-((2-(trimethylsilyl)ethoxy)methyl)-1H-imidazol-2-yl)-6-(2-(oxazol-2-yl)-1,3-dioxolan-2-yl)hexyl)-2-methylpropane-2-sulfinamide (129B, 265.1 mg, 0.398 mmol) in MeOH (5 ml) and water (0.5 ml) was added HCl (2 ml, 8.00 mmol) (4.0 M in dioxane). The reaction mixture was heated at 50° C. under $N_2$ overnight. The crude product was purified by reverse phase prep HPLC to yield (S)-7-amino-7-(5-(5-fluoro-2-methoxypyridin-4-yl)-1H-imidazol-2-yl)-1-(oxazol-2-yl)heptan-1-one (129). LC-MS (ES, m/z): 388 [M+H]$^+$ The Examples in the following table were prepared from appropriate intermediates as the starting materials described previously or commercially available starting materials using procedures similar to those in Example 129.

| Example # | Structure | IUPAC Name | Exact Mass [M + H]+ |
|---|---|---|---|
| 130 | 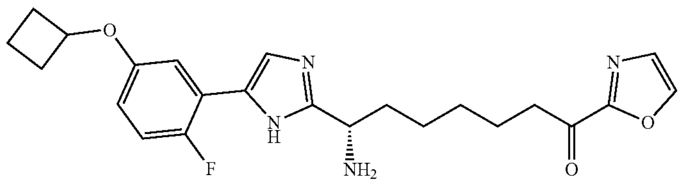 [SMILES: N[C@@H](CCCCCC(=O)c1ncco1)c1ncc(-c2cc(OC3CCC3)ccc2F)[nH]1] | (7S)-7-amino-7-{5-[5-(cyclobutyloxy)-2-fluorophenyl]-1H-imidazol-2-yl}-1-(1,3-oxazol-2-yl)heptan-1-one | 427 |
| 131 | 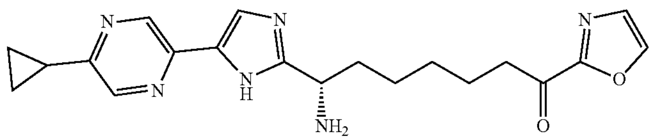 [SMILES: N[C@@H](CCCCCC(=O)c1ncco1)c1ncc(-c2cnc(C3CC3)cn2)[nH]1] | (7S)-7-amino-7-[5-(5-cyclopropylpyrazin-2-yl)-1H-imidazol-2-yl]-1-(1,3-oxazol-2-yl)heptan-1-one | 381 |
| 132 | 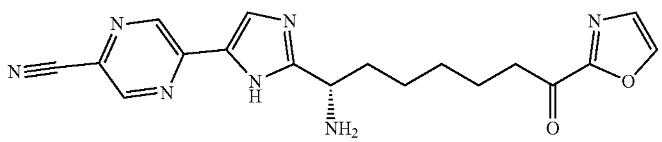 [SMILES: N#Cc1cnc(-c2cnc([C@@H](N)CCCCCC(=O)c3ncco3)[nH]2)cn1] | 5-{2-[(1S)-1-amino-7-(1,3-oxazol-2-yl)-7-oxoheptyl]-1H-imidazol-5-yl}pyrazine-2-carbonitrile | 365 |
| 133 | 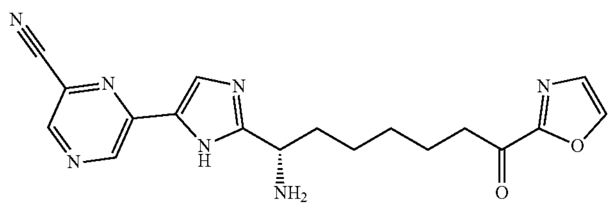 [SMILES: N#Cc1cncc(-c2cnc([C@@H](N)CCCCCC(=O)c3ncco3)[nH]2)n1] | 6-{2-[(1S)-1-amino-7-(1,3-oxazol-2-yl)-7-oxoheptyl]-1H-imidazol-5-yl}pyrazine-2-carbonitrile | 365 |
| 134 | 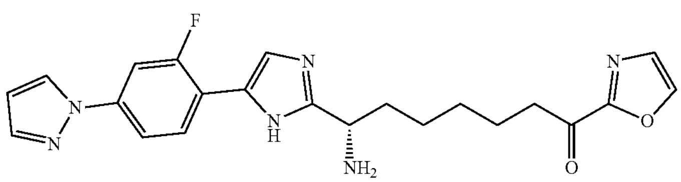 [SMILES: N[C@@H](CCCCCC(=O)c1ncco1)c1ncc(-c2ccc(-n3cccn3)cc2F)[nH]1] | (7S)-7-amino-7-{5-[2-fluoro-4-(1H-pyrazol-1-yl)phenyl]-1H-imidazol-2-yl}-1-(1,3-oxazol-2-yl)heptan-1-one | 423 |
| 135 | 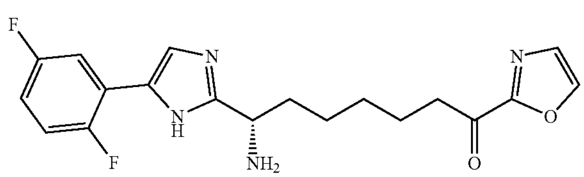 [SMILES: N[C@@H](CCCCCC(=O)c1ncco1)c1ncc(-c2cc(F)ccc2F)[nH]1] | (7S)-7-amino-7-[5-(2,5-difluorophenyl)-1H-imidazol-2-yl]-1-(1,3-oxazol-2-yl)heptan-1-one | 375 |
| 136 | 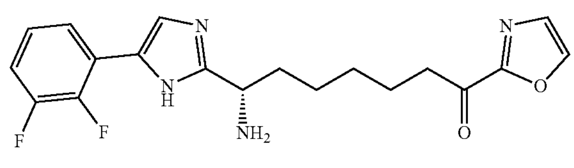 [SMILES: N[C@@H](CCCCCC(=O)c1ncco1)c1ncc(-c2cccc(F)c2F)[nH]1] | (7S)-7-amino-7-[5-(2,3-difluorophenyl)-1H-imidazol-2-yl]-1-(1,3-oxazol-2-yl)heptan-1-one | 375 |
| 137 | 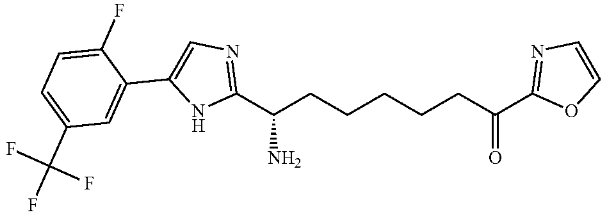 [SMILES: N[C@@H](CCCCCC(=O)c1ncco1)c1ncc(-c2cc(C(F)(F)F)ccc2F)[nH]1] | (7S)-7-amino-7-{5-[2-fluoro-5-(trifluoromethyl)phenyl]-1H-imidazol-2-yl}-1-(1,3-oxazol-2-yl)heptan-1-one | 425 |

-continued

| Example # | Structure | IUPAC Name | Exact Mass [M + H]+ |
|---|---|---|---|
| 138 | 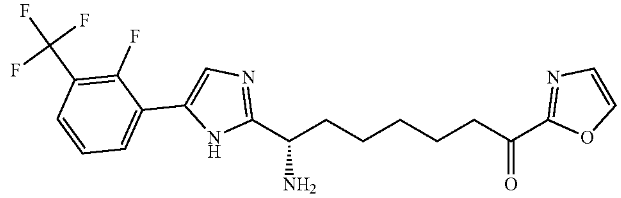 [SMILES: N[C@@H](CCCCCC(=O)c1ncco1)c1ncc(-c2cccc(C(F)(F)F)c2F)[nH]1] | (7S)-7-amino-7-{5-[2-fluoro-3-(trifluoromethyl)phenyl]-1H-imidazol-2-yl}-1-(1,3-oxazol-2-yl)heptan-1-one | 425 |
| 139 | 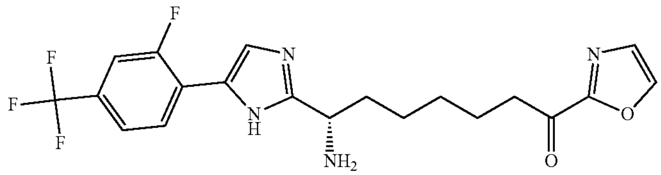 [SMILES: N[C@@H](CCCCCC(=O)c1ncco1)c1ncc(-c2ccc(C(F)(F)F)cc2F)[nH]1] | (7S)-7-amino-7-{5-[2-fluoro-4-(trifluoromethyl)phenyl]-1H-imidazol-2-yl}-1-(1,3-oxazol-2-yl)heptan-1-one | 425 |
| 140 | 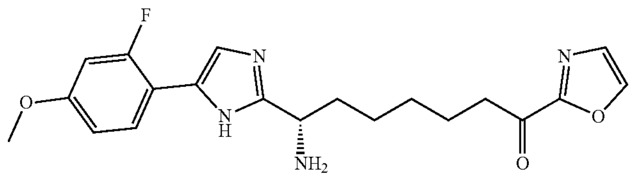 [SMILES: COc1ccc(-c2cnc([C@@H](N)CCCCCC(=O)c3ncco3)[nH]2)c(F)c1] | (7S)-7-amino-7-[5-(2-fluoro-4-methoxyphenyl)-1H-imidazol-2-yl]-1-(1,3-oxazol-2-yl)heptan-1-one | 387 |
| 141 | 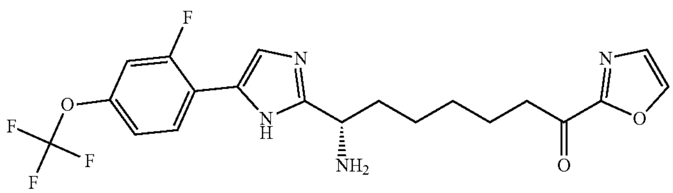 [SMILES: N[C@@H](CCCCCC(=O)c1ncco1)c1ncc(-c2ccc(OC(F)(F)F)cc2F)[nH]1] | (7S)-7-amino-7-{5-[2-fluoro-4-(trifluoromethoxy)phenyl]-1H-imidazol-2-yl}-1-(1,3-oxazol-2-yl)heptan-1-one | 441 |
| 142 | 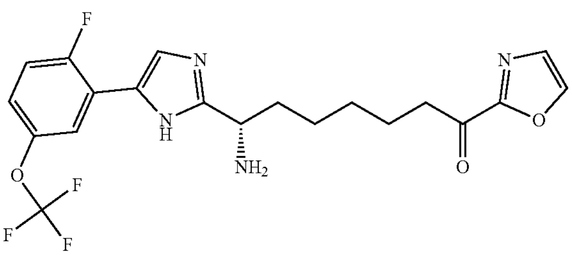 [SMILES: N[C@@H](CCCCCC(=O)c1ncco1)c1ncc(-c2cc(OC(F)(F)F)ccc2F)[nH]1] | (7S)-7-amino-7-{5-[2-fluoro-5-(trifluoromethoxy)phenyl]-1H-imidazol-2-yl}-1-(1,3-oxazol-2-yl)heptan-1-one | 441 |
| 143 | 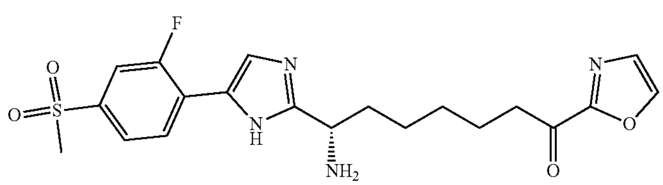 [SMILES: CS(=O)(=O)c1ccc(-c2cnc([C@@H](N)CCCCCC(=O)c3ncco3)[nH]2)c(F)c1] | (7S)-7-amino-7-{5-[2-fluoro-4-(methylsulfonyl)phenyl]-1H-imidazol-2-yl}-1-(1,3-oxazol-2-yl)heptan-1-one | 435 |
| 144 | 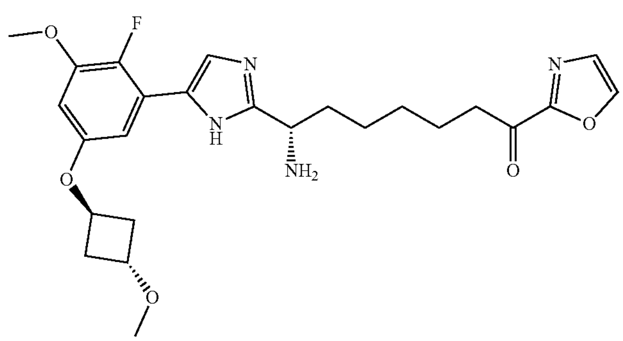 [SMILES: COc1cc(O[C@H]2C[C@H](OC)C2)cc(-c2cnc([C@@H](N)CCCCCC(=O)c3ncco3)[nH]2)c1F] | (7S)-7-amino-7-(5-{2-fluoro-3-methoxy-5-[(trans-3-methoxycyclobutyl)oxy]phenyl}-1H-imidazol-2-yl)-1-(1,3-oxazol-2-yl)heptan-1-one | 487 |

Example 145
(S)-6-ethyl-N-((S)-7-(isoxazol-3-yl)-1-(5-(7-methoxy-2-methylquinolin-6-yl)isoxazol-3-yl)-7-oxoheptyl)-6-azaspiro[2.5]octane-1-carboxamide
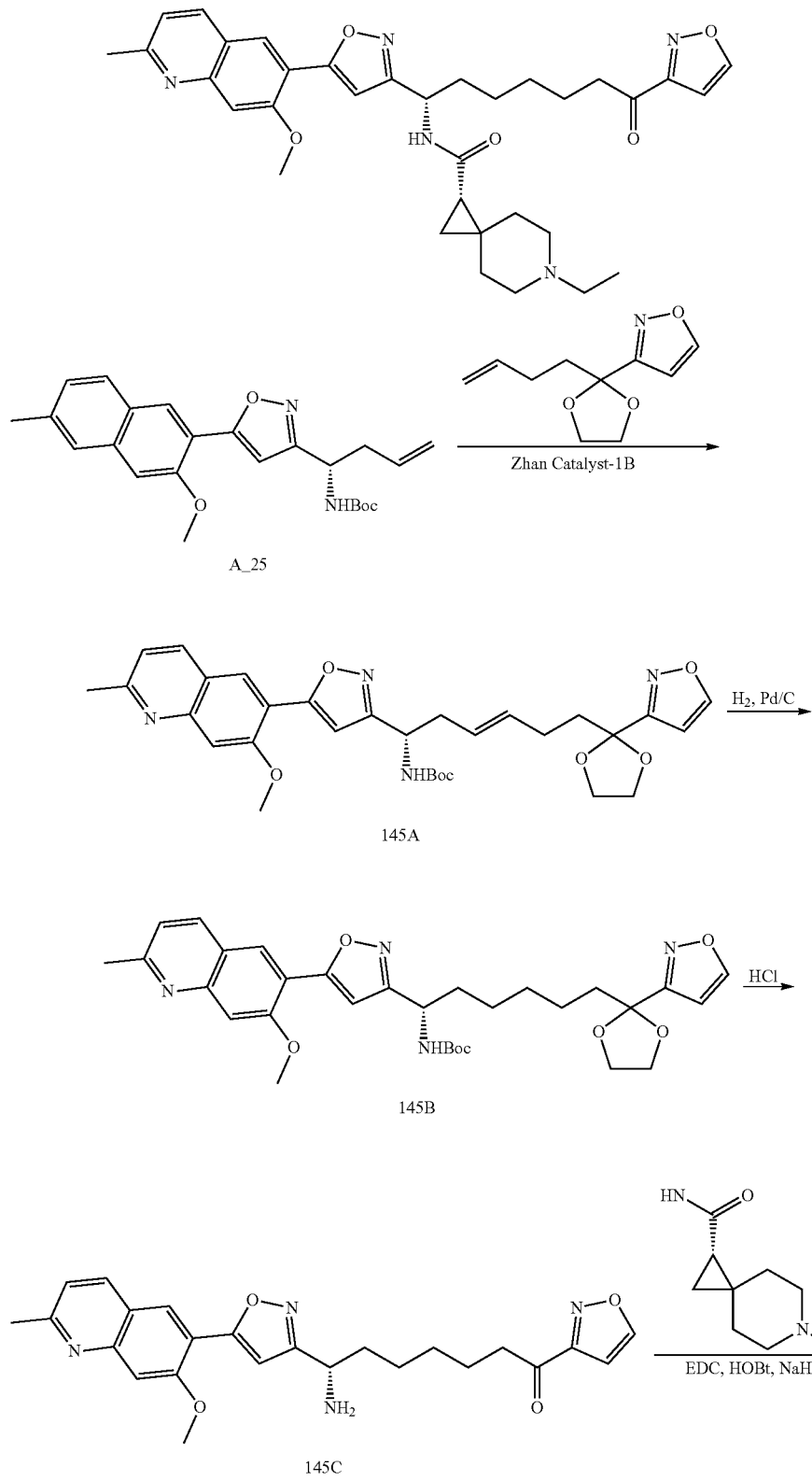

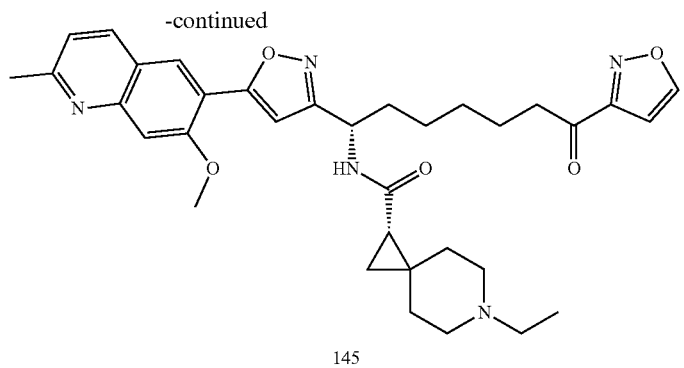

145

Step 1: tert-butyl (S,E)-(6-(2-(isoxazol-3-yl)-1,3-dioxolan-2-yl)-1-(5-(7-methoxy-2-methylquinolin-6-yl)isoxazol-3-yl)hex-3-en-1-yl)carbamate (145A)

To a solution of (S)-tert-butyl (1-(5-(7-methoxy-2-methylquinolin-6-yl)isoxazol-3-yl)but-3-en-1-yl)carbamate (A_25, 132.1 mg, 0.323 mmol) and 3-(2-(but-3-en-1-yl)-1,3-dioxolan-2-yl)isoxazole (0.217 ml, 1.290 mmol) in CH$_2$Cl$_2$ (5 ml) was added 1,3-bis(2,4,6-trimethylphenyl)-4,5-dihydroimidazol-2-ylidene[2-(i-propoxy)-5-(N,N-dimethylaminosulfonyl)phenyl]methyleneruthenium(II) dichloride (23.67 mg, 0.032 mmol). The reaction mixture was heated at reflux under N$_2$. After 18 hr of stirring, the reaction mixture was treated with additional 1,3-bis(2,4,6-trimethylphenyl)-4,5-dihydroimidazol-2-ylidene[2-(i-propoxy)-5-(N,N-dimethylaminosulfonyl)phenyl]methyleneruthenium(II) dichloride (23.67 mg, 0.032 mmol). The reaction mixture was heated at reflux under N$_2$. After another 18 hr of stirring, the reaction mixture was cooled to RT and concentrated by rotorvap. The crude product was purified by normal phase silica gel column chromatography using CH$_3$CN/CH$_2$Cl$_2$ as eluents to yield tert-butyl (S,E)-(6-(2-(isoxazol-3-yl)-1,3-dioxolan-2-yl)-1-(5-(7-methoxy-2-methylquinolin-6-yl)isoxazol-3-yl)hex-3-en-1-yl)carbamate (145A).

Step 2: tert-butyl (S)-(6-(2-(isoxazol-3-yl)-1,3-dioxolan-2-yl)-1-(5-(7-methoxy-2-methylquinolin-6-yl)isoxazol-3-yl)hexyl)carbamate (145B)

To a solution of (S,E)-tert-butyl (6-(2-(isoxazol-3-yl)-1,3-dioxolan-2-yl)-1-(5-(7-methoxy-2-methylquinolin-6-yl)isoxazol-3-yl)hex-3-en-1-yl)carbamate (145A, 70.9 mg, 0.123 mmol) in ethanol (5 ml) was added Pd/C (13.08 mg, 0.012 mmol). The reaction mixture was stirred at RT under 1 atm of H$_2$. After 3 h, the reaction mixture was filtered through a pad of Celite and the filtrate was concentrated. The crude product was purified by normal phase silica gel column chromatography using MeOH/CH$_2$Cl$_2$ as eluents to yield tert-butyl (S)-(6-(2-(isoxazol-3-yl)-1,3-dioxolan-2-yl)-1-(5-(7-methoxy-2-methylquinolin-6-yl)isoxazol-3-yl)hexyl)carbamate (145B).

Step 3: (S)-7-amino-1-(isoxazol-3-yl)-7-(5-(7-methoxy-2-methylquinolin-6-yl)isoxazol-3-yl)heptan-1-one (145C)

To a solution of (S)-tert-butyl (6-(2-(isoxazol-3-yl)-1,3-dioxolan-2-yl)-1-(5-(7-methoxy-2-methylquinolin-6-yl)isoxazol-3-yl)hexyl)carbamate (145B, 58.1 mg, 0.100 mmol) in MeOH (1 ml) and water (0.2 ml) was added HCl (0.5 ml, 2.000 mmol) (4.0M in dioxane). The reaction mixture was heated at 50° C. under N$_2$ overnight. The reaction mixture was cooled to RT and concentrated by rotorvap. The crude product purified by reverse phase prep HPLC to (S)-7-amino-1-(isoxazol-3-yl)-7-(5-(7-methoxy-2-methylquinolin-6-yl)isoxazol-3-yl)heptan-1-one (145C). LC-MS (ES, m/z): 435 [M+H]$^+$

Step 4: (S)-6-ethyl-N-((S)-7-(isoxazol-3-yl)-1-(5-(7-methoxy-2-methylquinolin-6-yl)isoxazol-3-yl)-7-oxoheptyl)-6-azaspiro[2.5]octane-1-carboxamide (145)

To a solution of (S)-7-amino-1-(isoxazol-3-yl)-7-(5-(7-methoxy-2-methylquinolin-6-yl)isoxazol-3-yl)heptan-1-one hydrochloride (145C, 37 mg, 0.079 mmol) in DMF (1 ml) at RT was added (S)-6-ethyl-6-azaspiro[2.5]octane-1-carboxylic acid (28.8 mg, 0.157 mmol), EDC (33.1 mg, 0.173 mmol), HOBt (2.406 mg, 0.016 mmol), and NaHCO$_3$ (200 mg, 2.381 mmol). The reaction mixture was stirred at RT under N$_2$ overnight. The reaction mixture was filtered with 0.5 mL DMF and the filtrate was purified by reverse phase prep HPLC to yield (S)-6-ethyl-N-((S)-7-(isoxazol-3-yl)-1-(5-(7-methoxy-2-methylquinolin-6-yl)isoxazol-3-yl)-7-oxoheptyl)-6-azaspiro[2.5]octane-1-carboxamide (145). LC-MS (ES, m/z): 600 [M+H]$^+$ The Examples in the following table were prepared from the appropriate starting materials described previously or commercially available starting materials using procedures similar to those in the Example 145.

| Example # | Structure | IUPAC Name | Exact Mass [M + H]+ |
|---|---|---|---|
| 146 | 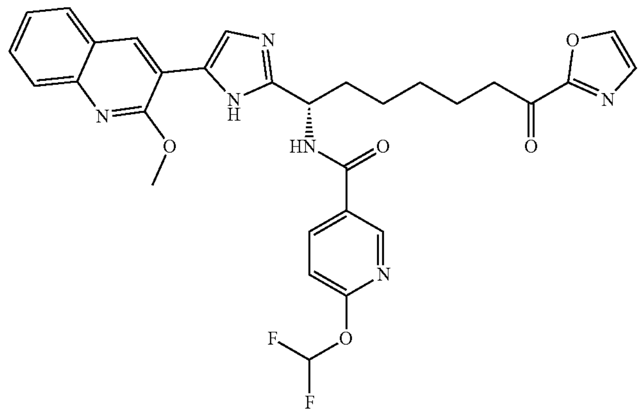 [SMILES: COc1nc2ccccc2cc1-c1cnc([C@H](CCCCCC(=O)c2ncco2)NC(=O)c2ccc(OC(F)F)nc2)[nH]1] | 6-(difluoromethoxy)-N-[(1S)-1-[5-(2-methoxyquinolin-3-yl)-1H-imidazol-2-yl]-7-(1,3-oxazol-2-yl)-7-oxoheptyl]pyridine-3-carboxamide | 591 |
| 147 | 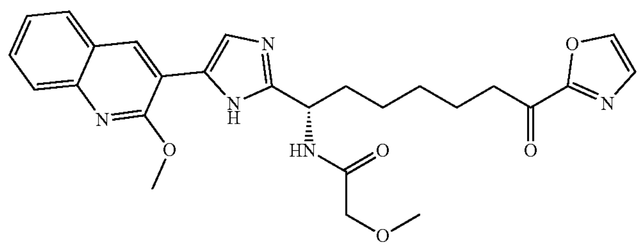 [SMILES: COCC(=O)N[C@@H](CCCCCC(=O)c1ncco1)c1ncc(-c2cc3ccccc3nc2OC)[nH]1] | 2-methoxy-N-[(1S)-1-[5-(2-methoxyquinolin-3-yl)-1H-imidazol-2-yl]-7-(1,3-oxazol-2-yl)-7-oxoheptyl]acetamide | 492 |
| 148 | 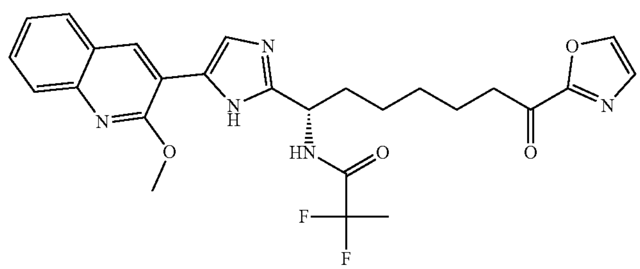 [SMILES: COc1nc2ccccc2cc1-c1cnc([C@H](CCCCCC(=O)c2ncco2)NC(=O)C(C)(F)F)[nH]1] | 2,2-difluoro-N-[(1S)-1-[5-(2-methoxyquinolin-3-yl)-1H-imidazol-2-yl]-7-(1,3-oxazol-2-yl)-7-oxoheptyl]propanamide | 512 |
| 149 | 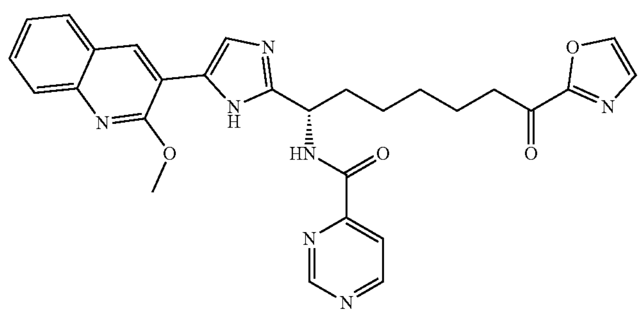 [SMILES: COc1nc2ccccc2cc1-c1cnc([C@H](CCCCCC(=O)c2ncco2)NC(=O)c2ccncn2)[nH]1] | N-[(1S)-1-[5-(2-methoxyquinolin-3-yl)-1H-imidazol-2-yl]-7-(1,3-oxazol-2-yl)-7-oxoheptyl]pyrimidine-4-carboxamide | 526 |
| 150 | 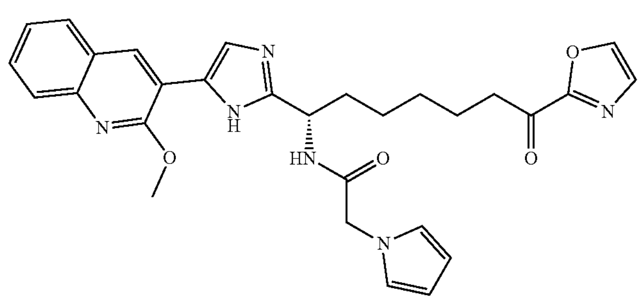 [SMILES: COc1nc2ccccc2cc1-c1cnc([C@H](CCCCCC(=O)c2ncco2)NC(=O)Cn2cccc2)[nH]1] | N-[(1S)-1-[5-(2-methoxyquinolin-3-yl)-1H-imidazol-2-yl]-7-(1,3-oxazol-2-yl)-7-oxoheptyl]-2-(1H-pyrrol-1-yl)acetamide | 527 |

| Example # | Structure | IUPAC Name | Exact Mass [M + H]+ |
|---|---|---|---|
| 151 | 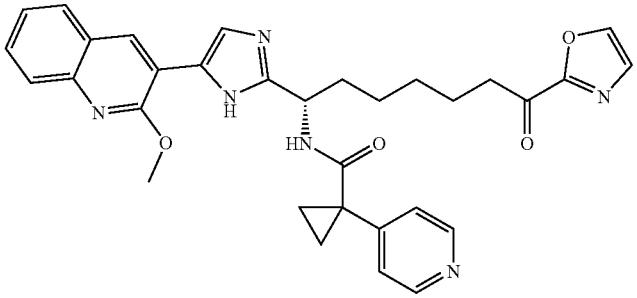 [SMILES: COc1nc2ccccc2cc1-c1cnc([C@H](CCCCCC(=O)c2ncco2)NC(=O)C2(c3ccncc3)CC2)[nH]1] | N-[(1S)-1-[5-(2-methoxyquinolin-3-yl)-1H-imidazol-2-yl]-7-(1,3-oxazol-2-yl)-7-oxoheptyl]-1-pyridin-4-ylcyclopropanecarboxamide | 565 |
| 152 | 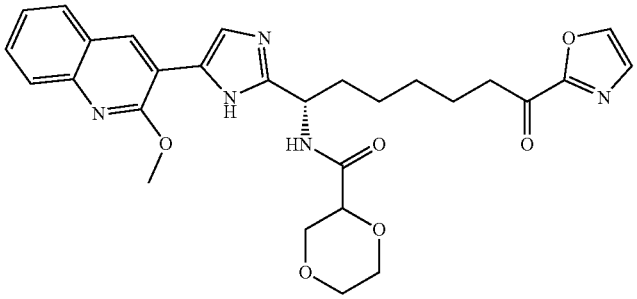 [SMILES: COc1nc2ccccc2cc1-c1cnc([C@H](CCCCCC(=O)c2ncco2)NC(=O)C2COCCO2)[nH]1] | N-[(1S)-1-[5-(2-methoxyquinolin-3-yl)-1H-imidazol-2-yl]-7-(1,3-oxazol-2-yl)-7-oxoheptyl]-1,4-dioxane-2-carboxamide | 534 |
| 153 | 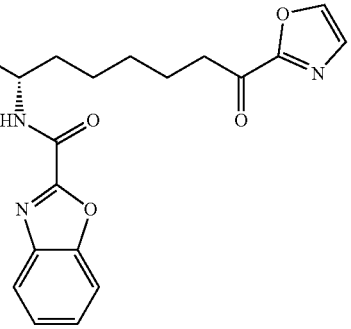 | N-[(1S)-1-[5-(2-methoxyquinolin-3-yl)-1H-imidazol-2-yl]-7-(1,3-oxazol-2-yl)-7-oxoheptyl]-1,3-benzoxazole-2-carboxamide | 565 |
| 154 | 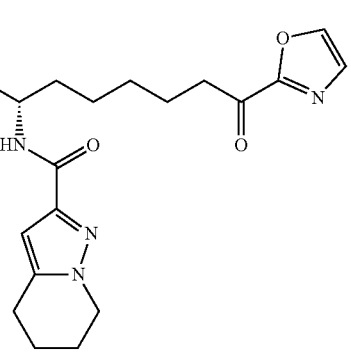 | N-[(1S)-1-[5-(2-methoxyquinolin-3-yl)-1H-imidazol-2-yl]-7-(1,3-oxazol-2-yl)-7-oxoheptyl]-4,5,6,7-tetrahydropyrazolo[1,5-a]pyridine-2-carboxamide | 568 |

| Example # | Structure | IUPAC Name | Exact Mass [M + H]+ |
|---|---|---|---|
| 155 | 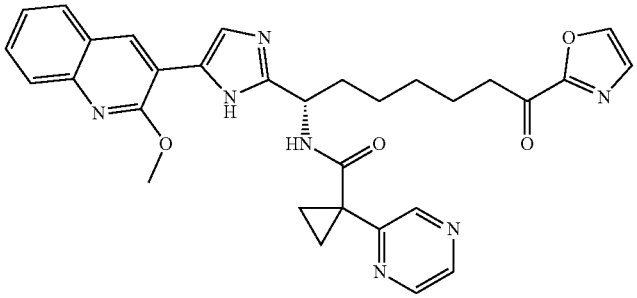 [SMILES: COc1nc2ccccc2cc1-c1cnc([C@H](CCCCCC(=O)c2ncco2)NC(=O)C2(c3cnccn3)CC2)[nH]1] | N-[(1S)-1-[5-(2-methoxyquinolin-3-yl)-1H-imidazol-2-yl]-7-(1,3-oxazol-2-yl)-7-oxoheptyl]-1-pyrazin-2-ylcyclopropanecarboxamide | 566 |
| 156 | 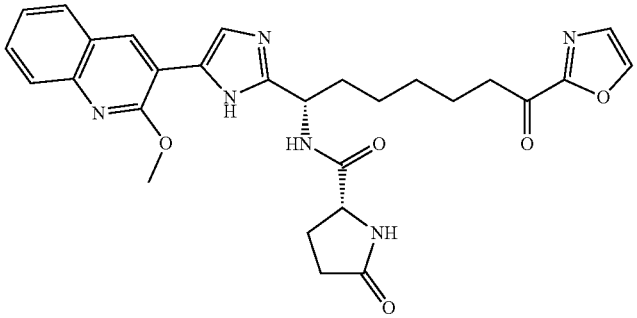 [SMILES: COc1nc2ccccc2cc1-c1cnc([C@H](CCCCCC(=O)c2ncco2)NC(=O)[C@H]2CCC(=O)N2)[nH]1] | N-[(1S)-1-[5-(2-methoxyquinolin-3-yl)-1H-imidazol-2-yl]-7-(1,3-oxazol-2-yl)-7-oxoheptyl]-5-oxo-D-prolinamide | 531 |
| 157 | 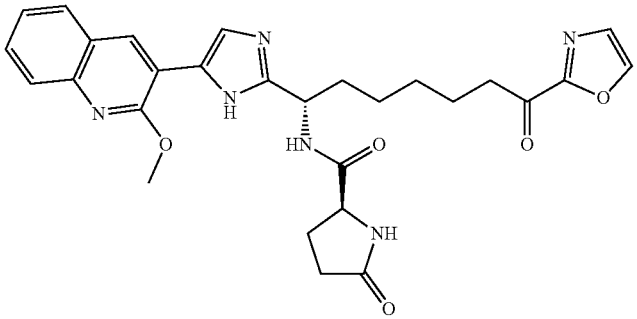 [SMILES: COc1nc2ccccc2cc1-c1cnc([C@H](CCCCCC(=O)c2ncco2)NC(=O)[C@@H]2CCC(=O)N2)[nH]1] | N-[(1S)-1-[5-(2-methoxyquinolin-3-yl)-1H-imidazol-2-yl]-7-(1,3-oxazol-2-yl)-7-oxoheptyl]-5-oxo-L-prolinamide | 531 |
| 158 | 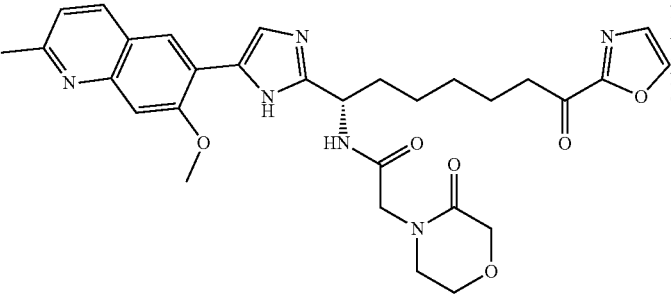 [SMILES: COc1cc2nc(C)ccc2cc1-c1cnc([C@H](CCCCCC(=O)c2ncco2)NC(=O)CN2CCOCC2=O)[nH]1] | N-[(1S)-1-[5-(7-methoxy-2-methylquinolin-6-yl)-1H-imidazol-2-yl]-7-(1,3-oxazol-2-yl)-7-oxoheptyl]-2-(3-oxomorpholin-4-yl)acetamide | 575 |
| 159 | 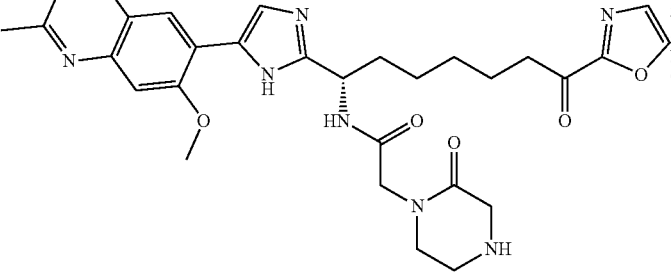 | N-[(1S)-1-[5-(7-methoxy-2-methylquinolin-6-yl)-1H-imidazol-2-yl]-7-(1,3-oxazol-2-yl)-7-oxoheptyl]-2-(2-oxopiperazin-1-yl)acetamide | 574 |

| Example # | Structure | IUPAC Name | Exact Mass [M + H]+ |
|---|---|---|---|
| 160 | 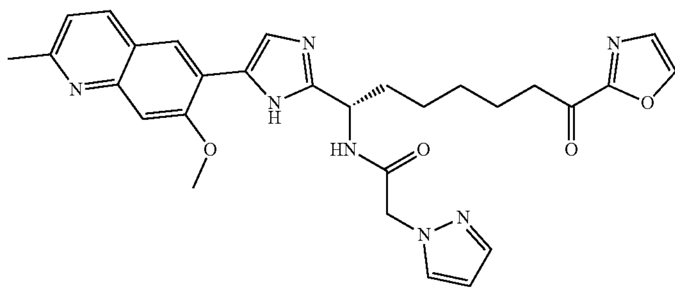 [SMILES: COc1cc2nc(C)ccc2cc1-c1cnc([C@H](CCCCCC(=O)c2ncco2)NC(=O)Cn2cccn2)[nH]1] | N-[(1S)-1-[5-(7-methoxy-2-methylquinolin-6-yl)-1H-imidazol-2-yl]-7-(1,3-oxazol-2-yl)-7-oxoheptyl]-2-(1H-pyrazol-1-yl)acetamide | 542 |
| 161 | 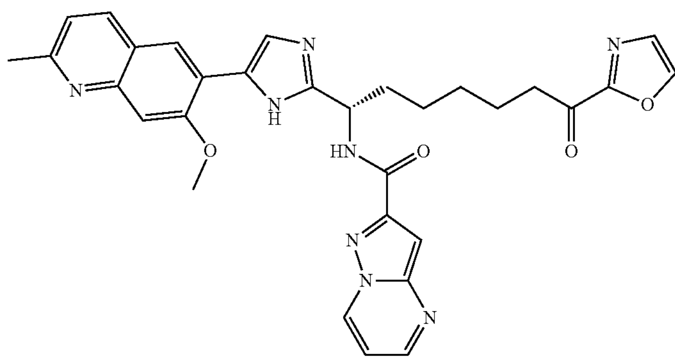 [SMILES: COc1cc2nc(C)ccc2cc1-c1cnc([C@H](CCCCCC(=O)c2ncco2)NC(=O)c2cc3ncccn3n2)[nH]1] | N-[(1S)-1-[5-(7-methoxy-2-methylquinolin-6-yl)-1H-imidazol-2-yl]-7-(1,3-oxazol-2-yl)-7-oxoheptyl]pyrazolo[1,5-a]pyrimidine-2-carboxamide | 579 |
| 162 | 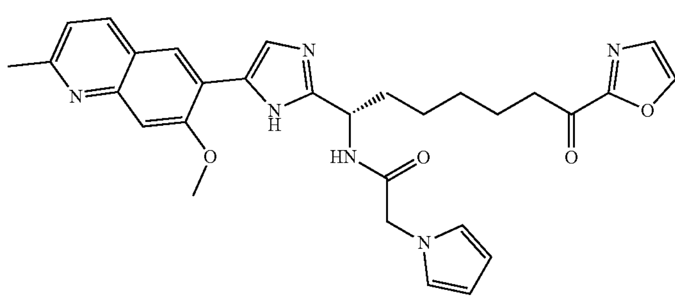 [SMILES: COc1cc2nc(C)ccc2cc1-c1cnc([C@H](CCCCCC(=O)c2ncco2)NC(=O)Cn2cccc2)[nH]1] | N-[(1S)-1-[5-(7-methoxy-2-methylquinolin-6-yl)-1H-imidazol-2-yl]-7-(1,3-oxazol-2-yl)-7-oxoheptyl]-2-(1H-pyrrol-1-yl)acetamide | 541 |
| 163 | 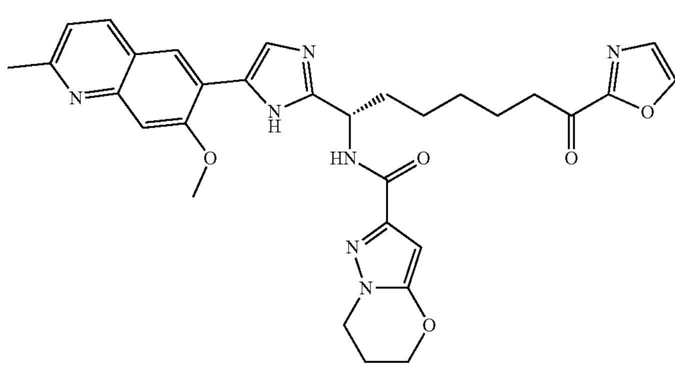 [SMILES: COc1cc2nc(C)ccc2cc1-c1cnc([C@H](CCCCCC(=O)c2ncco2)NC(=O)c2cc3n(n2)CCCO3)[nH]1] | N-[(1S)-1-[5-(7-methoxy-2-methylquinolin-6-yl)-1H-imidazol-2-yl]-7-(1,3-oxazol-2-yl)-7-oxoheptyl]-6,7-dihydro-5H-pyrazolo[5,1-b][1,3]oxazine-2-carboxamide | 584 |

| Example # | Structure | IUPAC Name | Exact Mass [M + H]+ |
|---|---|---|---|
| 164 | 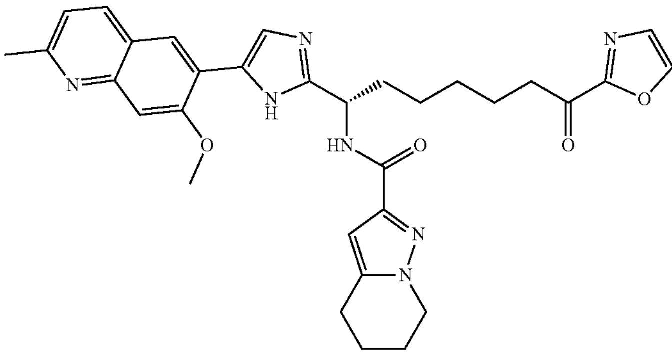 [SMILES: COc1cc2nc(C)ccc2cc1-c1cnc([C@H](CCCCCC(=O)c2ncco2)NC(=O)c2cc3n(n2)CCCC3)[nH]1] | N-[(1S)-1-[5-(7-methoxy-2-methylquinolin-6-yl)-1H-imidazol-2-yl]-7-(1,3-oxazol-2-yl)-7-oxoheptyl]-4,5,6,7-tetrahydropyrazolo[1,5-a]pyridine-2-carboxamide | 582 |
| 165 | 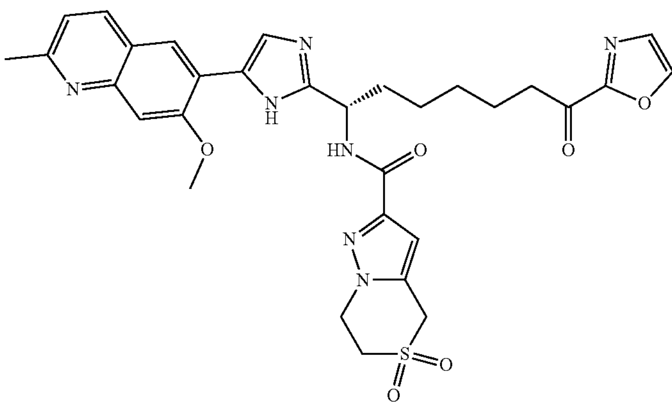 [SMILES: COc1cc2nc(C)ccc2cc1-c1cnc([C@H](CCCCCC(=O)c2ncco2)NC(=O)c2cc3n(n2)CCS(=O)(=O)C3)[nH]1] | N-[(1S)-1-[5-(7-methoxy-2-methylquinolin-6-yl)-1H-imidazol-2-yl]-7-(1,3-oxazol-2-yl)-7-oxoheptyl]-6,7-dihydro-4H-pyrazolo[5,1-c][1,4]thiazine-2-carboxamide 5,5-dioxide | 632 |
| 166 | 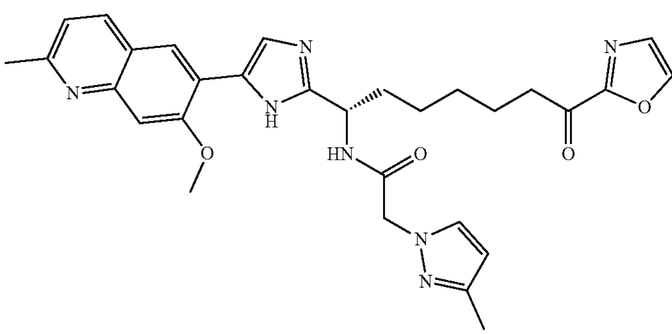 [SMILES: COc1cc2nc(C)ccc2cc1-c1cnc([C@H](CCCCCC(=O)c2ncco2)NC(=O)Cn2ccc(C)n2)[nH]1] | N-[(1S)-1-[5-(7-methoxy-2-methylquinolin-6-yl)-1H-imidazol-2-yl]-7-(1,3-oxazol-2-yl)-7-oxoheptyl]-2-(3-methyl-1H-pyrazol-1-yl)acetamide | 556 |
| 167 | 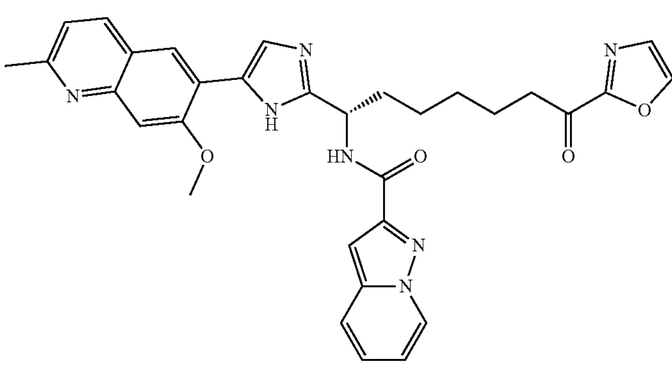 [SMILES: COc1cc2nc(C)ccc2cc1-c1cnc([C@H](CCCCCC(=O)c2ncco2)NC(=O)c2cc3ccccn3n2)[nH]1] | N-[(1S)-1-[5-(7-methoxy-2-methylquinolin-6-yl)-1H-imidazol-2-yl]-7-(1,3-oxazol-2-yl)-7-oxoheptyl]pyrazolo[1,5-a]pyridine-2-carboxamide | 578 |

-continued

| Example # | Structure | IUPAC Name | Exact Mass [M + H]+ |
|---|---|---|---|
| 168 | 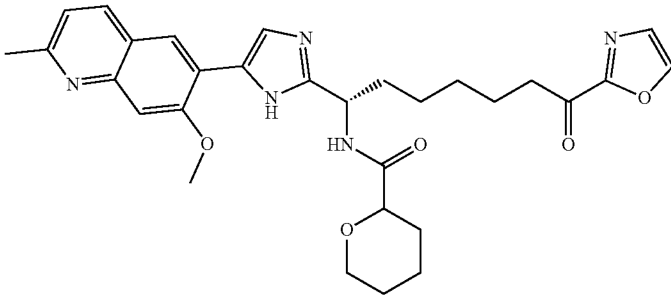 [SMILES: COc1cc2nc(C)ccc2cc1-c1cnc([C@H](CCCCCC(=O)c2ncco2)NC(=O)C2CCCCO2)[nH]1] | N-[(1S)-1-[5-(7-methoxy-2-methylquinolin-6-yl)-1H-imidazol-2-yl]-7-(1,3-oxazol-2-yl)-7-oxoheptyl]tetrahydro-2H-pyran-2-carboxamide | 546 |
| 169 | 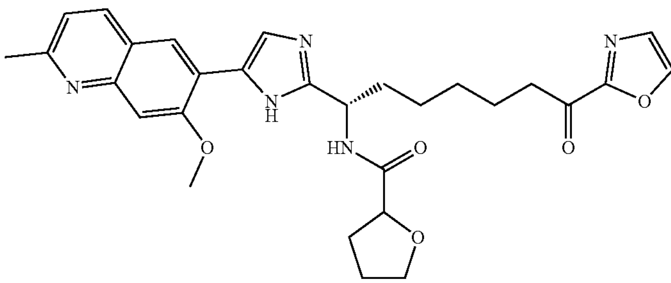 [SMILES: COc1cc2nc(C)ccc2cc1-c1cnc([C@H](CCCCCC(=O)c2ncco2)NC(=O)C2CCCO2)[nH]1] | N-[(1S)-1-[5-(7-methoxy-2-methylquinolin-6-yl)-1H-imidazol-2-yl]-7-(1,3-oxazol-2-yl)-7-oxoheptyl]tetrahydrofuran-2-carboxamide | 532 |
| 170 | 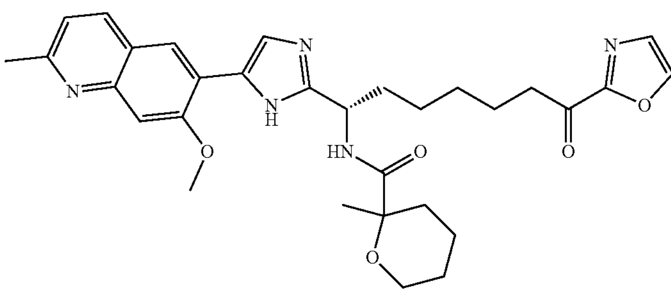 [SMILES: COc1cc2nc(C)ccc2cc1-c1cnc([C@H](CCCCCC(=O)c2ncco2)NC(=O)C2(C)CCCCO2)[nH]1] | N-[(1S)-1-[5-(7-methoxy-2-methylquinolin-6-yl)-1H-imidazol-2-yl]-7-(1,3-oxazol-2-yl)-7-oxoheptyl]-2-methyltetrahydro-2H-pyran-2-carboxamide | 560 |
| 171 | 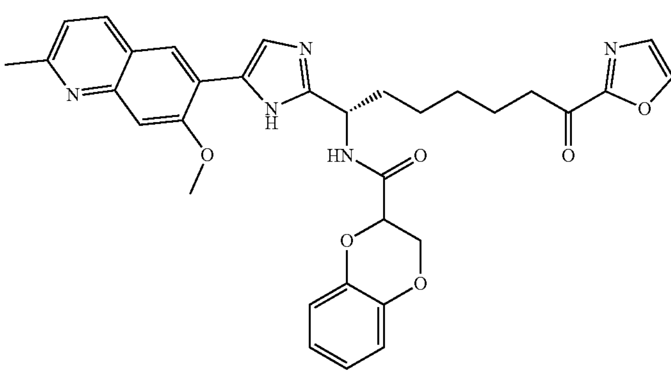 [SMILES: COc1cc2nc(C)ccc2cc1-c1cnc([C@H](CCCCCC(=O)c2ncco2)NC(=O)C2COc3ccccc3O2)[nH]1] | N-[(1S)-1-[5-(7-methoxy-2-methylquinolin-6-yl)-1H-imidazol-2-yl]-7-(1,3-oxazol-2-yl)-7-oxoheptyl]-2,3-dihydro-1,4-benzodioxine-2-carboxamide | 596 |

| Example # | Structure | IUPAC Name | Exact Mass [M + H]+ |
|---|---|---|---|
| 172 | 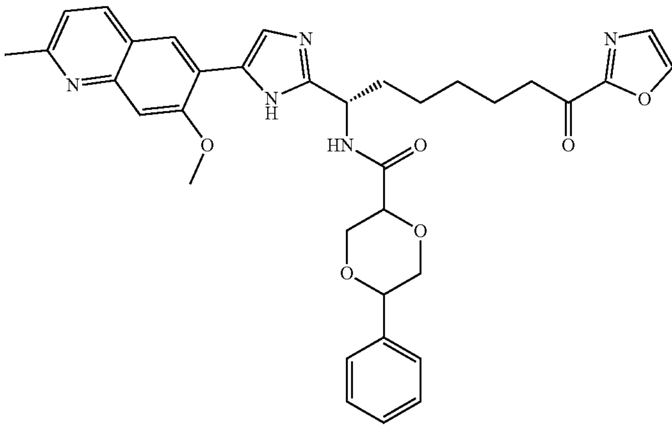 [SMILES: COc1cc2nc(C)ccc2cc1-c1cnc([C@H](CCCCCC(=O)c2ncco2)NC(=O)C2COC(c3ccccc3)CO2)[nH]1] | N-[(1S)-1-[5-(7-methoxy-2-methylquinolin-6-yl)-1H-imidazol-2-yl]-7-(1,3-oxazol-2-yl)-7-oxoheptyl]-5-phenyl-1,4-dioxane-2-carboxamide | 624 |
| 173 | 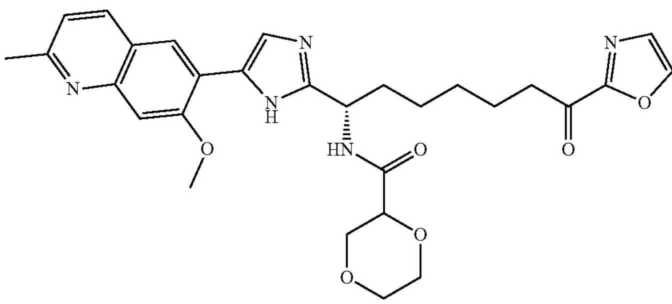 [SMILES: COc1cc2nc(C)ccc2cc1-c1cnc([C@H](CCCCCC(=O)c2ncco2)NC(=O)C2COCCO2)[nH]1] | N-[(1S)-1-[5-(7-methoxy-2-methylquinolin-6-yl)-1H-imidazol-2-yl]-7-(1,3-oxazol-2-yl)-7-oxoheptyl]-1,4-dioxane-2-carboxamide | 548 |
| 174 | 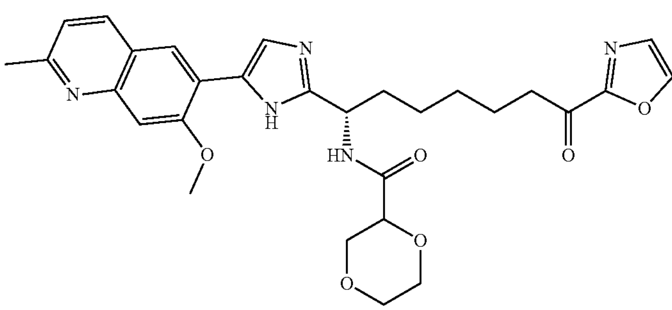 [SMILES: COc1cc2nc(C)ccc2cc1-c1cnc([C@H](CCCCCC(=O)c2ncco2)NC(=O)C2COCCO2)[nH]1] | N-[(1S)-1-[5-(7-methoxy-2-methylquinolin-6-yl)-1H-imidazol-2-yl]-7-(1,3-oxazol-2-yl)-7-oxoheptyl]-1,4-dioxane-2-carboxamide | 548 |
| 175 | 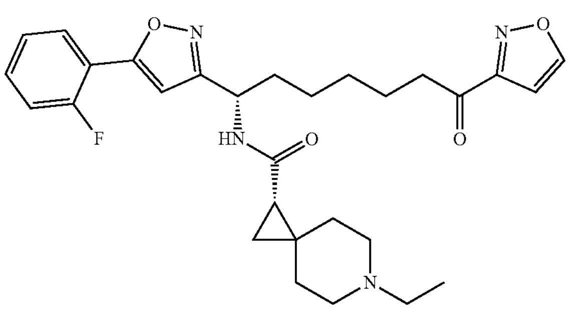 [SMILES: CCN1CCC2(CC1)C[C@@H]2C(=O)N[C@@H](CCCCCC(=O)c1ccon1)c1cc(-c2ccccc2F)on1] | (1S)-6-ethyl-N-{(1S)-1-[5-(2-fluorophenyl)isoxazol-3-yl]-7-isoxazol-3-yl-7-oxoheptyl}-6-azaspiro[2.5]octane-1-carboxamide | 524 |

-continued

| Example # | Structure | IUPAC Name | Exact Mass [M + H]+ |
|---|---|---|---|
| 176 | 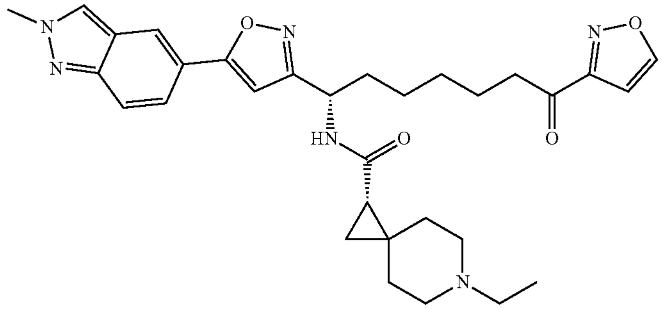 [SMILES: CCN1CCC2(CC1)C[C@@H]2C(=O)N[C@@H](CCCCCC(=O)c1ccon1)c1cc(-c2ccc3nn(C)cc3c2)on1] | (1S)-6-ethyl-N-{(1S)-7-isoxazol-3-yl-1-[5-(2-methyl-2H-indazol-5-yl)isoxazol-3-yl]-7-oxoheptyl}-6-azaspiro[2.5]octane-1-carboxamide | 560 |
| 177 | 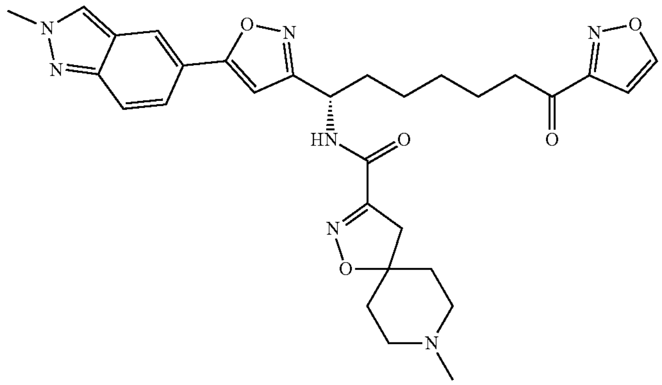 [SMILES: CN1CCC2(CC1)CC(C(=O)N[C@@H](CCCCCC(=O)c1ccon1)c1cc(-c3ccc4nn(C)cc4c3)on1)=NO2] | N-{(1S)-7-isoxazol-3-yl-1-[5-(2-methyl-2H-indazol-5-yl)isoxazol-3-yl]-7-oxoheptyl}-8-methyl-1-oxa-2,8-diazaspiro[4.5]dec-2-ene-3-carboxamide | 575 |
| 178 | 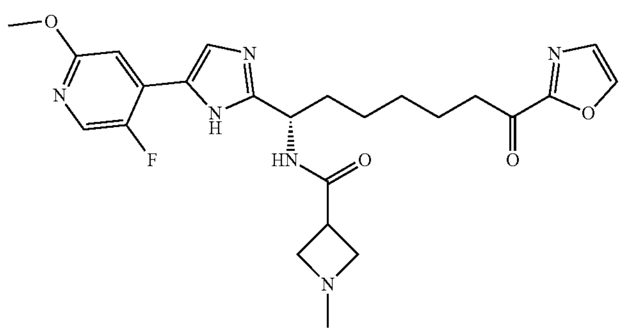 [SMILES: COc1cc(-c2cnc([C@H](CCCCCC(=O)c3ncco3)NC(=O)C3CN(C)C3)[nH]2)c(F)cn1] | N-[(1S)-1-[5-(5-fluoro-2-methoxypyridin-4-yl)-1H-imidazol-2-yl]-7-(1,3-oxazol-2-yl)-7-oxoheptyl]-1-methylazetidine-3-carboxamide | 485 |
| 179 | 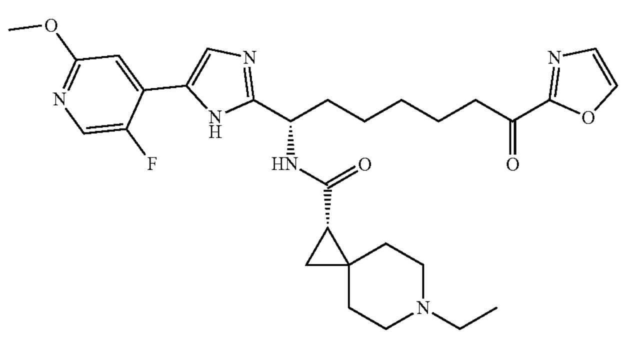 [SMILES: CCN1CCC2(CC1)C[C@@H]2C(=O)N[C@@H](CCCCCC(=O)c1ncco1)c1ncc(-c2cc(OC)ncc2F)[nH]1] | (1S)-6-ethyl-N-[(1S)-1-[5-(5-fluoro-2-methoxypyridin-4-yl)-1H-imidazol-2-yl]-7-(1,3-oxazol-2-yl)-7-oxoheptyl]-6-azaspiro[2.5]octane-1-carboxamide | 553 |

-continued

| Example # | Structure | IUPAC Name | Exact Mass [M + H]+ |
|---|---|---|---|
| 180 | 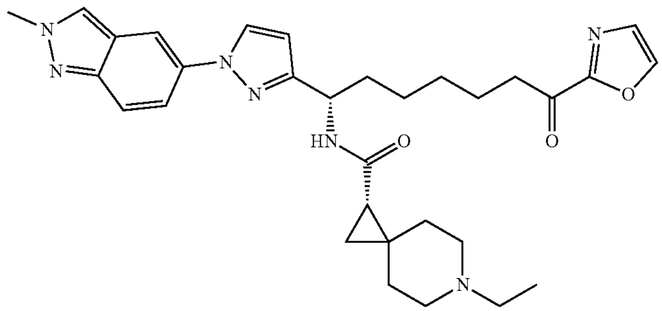 [SMILES: CCN1CCC2(CC1)C[C@@H]2C(=O)N[C@@H](CCCCCC(=O)c1ncco1)c1ccn(-c2ccc3nn(C)cc3c2)n1] | (1S)-6-ethyl-N-[(1S)-1-[1-(2-methyl-2H-indazol-5-yl)-1H-pyrazol-3-yl]-7-(1,3-oxazol-2-yl)-7-oxoheptyl]-6-azaspiro[2.5]octane-1-carboxamide | 559 |
| 181 | 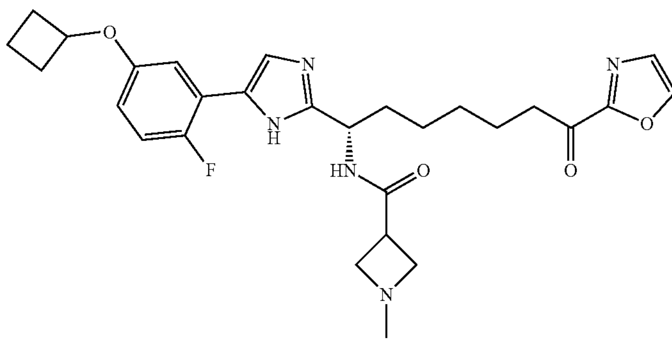 [SMILES: CN1CC(C(=O)N[C@@H](CCCCCC(=O)c2ncco2)c2ncc(-c3cc(OC4CCC4)ccc3F)[nH]2)C1] | N-[(1S)-1-{5-[5-(cyclobutyloxy)-2-fluorophenyl]-1H-imidazol-2-yl}-7-(1,3-oxazol-2-yl)-7-oxoheptyl]-1-methylazetidine-3-carboxamide | 524 |
| 182 | 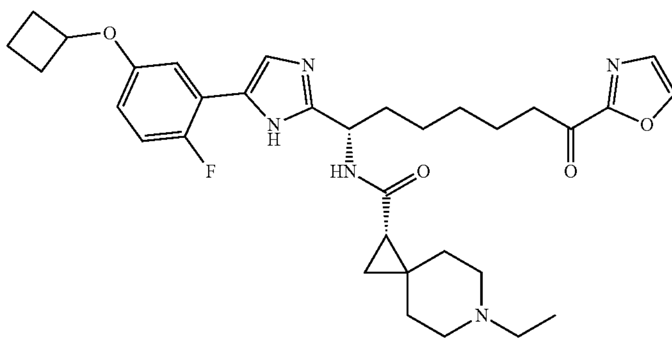 [SMILES: CCN1CCC2(CC1)C[C@@H]2C(=O)N[C@@H](CCCCCC(=O)c1ncco1)c1ncc(-c2cc(OC3CCC3)ccc2F)[nH]1] | (1S)-N-[(1S)-1-{5-[5-(cyclobutyloxy)-2-fluorophenyl]-1H-imidazol-2-yl}-7-(1,3-oxazol-2-yl)-7-oxoheptyl]-6-ethyl-6-azaspiro[2.5]octane-1-carboxamide | 593 |

Example 183

(S)-6-ethyl-N-((S)-2-(5-(2-fluorophenyl)-1H-imidazol-2-yl)-8-(isoxazol-3-yl)-8-oxooctan-2-yl)-6-azaspiro[2.5]octane-1-carboxamide

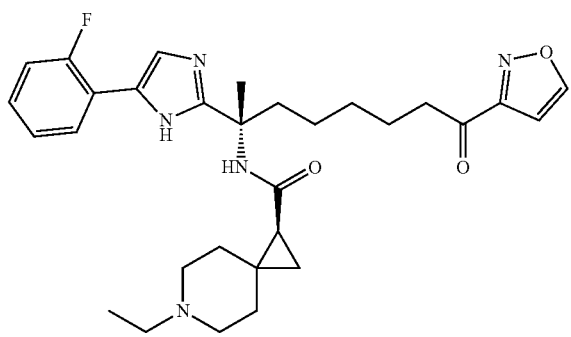

Step 1: (S)-2-((tert-butoxycarbonyl)amino)-2-methylpent-4-enoic acid

A 50 ml one neck round bottom flask was charged with (S)-2-amino-2-methylpent-4-enoic acid (500 mg, 3.87 mmol) along with triethylamine (1 ml, 7.33 mmol) and sodium hydroxide (1 ml, 1.000 mmol). The mixture was stirred and di-tert-butyl dicarbonate (887 mg, 4.06 mmol) was added in one portion. The resulting reaction mixture was stirred at room temperature for 18 hrs overnight. The mixture was then concentrated, the residue was acidified to pH ~2 by 5 N HCl and extracted with ethyl acetate (3×20 ml). The combined organic phases were washed with brine, dried over MgSO$_4$, filtered and concentrated. The crude was used directly to next step without further purification. LCMS (ESI) calc'd for C$_{11}$H$_{19}$NO$_4$ [M+H]+: 230.3, found: 229.9.

Step 2: (S)-2-(2-fluorophenyl)-2-oxoethyl 2-((tert-butoxycarbonyl)amino)-2-methylpent-4-enoate A 100 ml one neck round bottom flask was charged with (S)-2-((tert-butoxycarbonyl)amino)-2-methylpent-4-enoic acid, 376469-113 (888 mg, 3.87 mmol) along with DMF (10 ml), 2-bromo-1-(2-fluorophenyl)ethanone (925 mg, 4.26 mmol) and cesium carbonate (1262 mg, 3.87 mmol). The reaction mixture was then stirred at room temperature for 18 hrs overnight. The reaction mixture was diluted with ethyl acetate (30 mL), filtered and washed with ethyl acetate (3×). The filtrate was concentrated and the crude was purified by MPLC (40 g silica gel, 5 to 40% ethyl acetate in hexanes, 18 CV) to afford the product (S)-2-(2-fluorophenyl)-2-oxoethyl 2-((tert-butoxycarbonyl)amino)-2-methylpent-4-enoate. LCMS (ESI) calc'd for $C_{19}H_{24}FNO_5$ [M+H]$^+$: 366.2, found: 366.0.

Step 3: (S)-tert-butyl (2-(5-(2-fluorophenyl)-1H-imidazol-2-yl)pent-4-en-2-yl)carbamate A 100 mL one neck round bottom flask was charged with (S)-2-(2-fluorophenyl)-2-oxoethyl 2-((tert-butoxycarbonyl)amino)-2-methylpent-4-enoate, 376469-114 (1360 mg, 3.72 mmol) along with ammonium acetate (2869 mg, 37.2 mmol) in toluene (10 ml). The mixture was then stirred and heated in an oil bath at 110° C. for 18 hrs over night. After it cooled to room temperature, the mixture was diluted with ethyl acetate (50 mL), washed with NaHCO$_3$ (sat, 50 mL), brine, dried over MgSO$_4$, filtered and concentrated to afford the product, which is carried on to next step without further purification. LCMS (ESI) calc'd for $C_{19}H_{24}FN_3O_2$[M+H]$^+$: 346.3, found: 346.1.

Step 4: (S)-tert-butyl 2-(2-((tert-butoxycarbonyl)amino)pent-4-en-2-yl)-4-(2-fluorophenyl)-1H-imidazole-1-carboxylate A 100 mL one neck round bottom flask was charged with (S)-tert-butyl (2-(5-(2-fluorophenyl)-1H-imidazol-2-yl)pent-4-en-2-yl)carbamate (directly from step 3) along with di-tert-butyl dicarbonate (840 mg, 3.85 mmol) in CH$_2$Cl$_2$ (10 ml). The mixture was then stirred and N,N-dimethylpyridin-4-amine (22.39 mg, 0.183 mmol) was added. The mixture was then stirred at room temperature for 1 hr. The mixture was then loaded to MPLC directly for purification (40 g silica gel, 0 to 40% ethyl acetate in hexanes, 18 CV) to the product (S)-tert-butyl 2-(2-((tert-butoxycarbonyl)amino)pent-4-en-2-yl)-4-(2-fluorophenyl)-1H-imidazole-1-carboxylate. LCMS (ESI) calc'd for $C_{24}H_{32}FN_3O_4$[M+H]$^+$: 446.3, found: 446.1.

Step 5: (S,E)-tert-butyl 2-(2-((tert-butoxycarbonyl)amino)-8-(isoxazol-3-yl)-8-oxoocta-4-en-2-yl)-4-(2-fluorophenyl)-1H-imidazole-1-carboxylate A 50 ml one neck round bottom flask was charged with (S)-tert-butyl 2-(2-((tert-butoxycarbonyl)amino)pent-4-en-2-yl)-4-(2-fluorophenyl)-1H-imidazole-1-carboxylate (439 mg, 0.985 mmol) along with 1-(isoxazol-3-yl)pent-4-en-1-one (447 mg, 2.96 mmol) and 1-(isoxazol-3-yl)pent-4-en-1-one (447 mg, 2.96 mmol), followed by metathesis catalyst M71-S1PR (40.5 mg, 0.049 mmol). The flask was capped with septum and connected to manifold through syringe, and was vacuumed and refilled with nitrogen three times. The mixture was then stirred and heated in an oil bath at 60° C. for 15 hrs. The mixture was loaded to MPLC (12 g silica gel, 0 to 30% ethyl acetate in hexanes, 48 CV) to afford product (S,E)-tert-butyl 2-(2-((tert-butoxycarbonyl)amino)-8-(isoxazol-3-yl)-8-oxoocta-4-en-2-yl)-4-(2-fluorophenyl)-1H-imidazole-1-carboxylate. LCMS (ESI) calc'd for $C_{30}H_{37}FN_4O_6$[M+H]$^+$: 569.4, found: 569.2.

Step 6: (S,E)-7-amino-7-(4-(2-fluorophenyl)-1H-imidazol-2-yl)-1-(isoxazol-3-yl)oct-4-en-1-one 2,2,2-trifluoroacetate A 50 ml sample vial was charged with (S,E)-tert-butyl 2-(2-((tert-butoxycarbonyl)amino)-8-(isoxazol-3-yl)-8-oxooct-4-en-2-yl)-4-(2-fluorophenyl)-1H-imidazole-1-carboxylate (367 mg, 0.645 mmol) along with CH$_2$Cl$_2$ (2 ml) and then 2,2,2-trifluoroacetic acid (2 ml, 25.4 mmol). The mixture was then stirred at room temperature for 2 hrs. The mixture was then concentrated by rotary evaporation to provide the crude product which is used directly to next step without further purification. LCMS (ESI) calc'd for $C_{20}H_{21}FN_4O_2$[M+H]$^+$: 369.3, found: 369.0.

Step 7: (S)-7-amino-7-(4-(2-fluorophenyl)-1H-imidazol-2-yl)-1-(isoxazol-3-yl)octan-1-one A 50 ml round bottom flask was charged with (S,E)-7-amino-7-(4-(2-fluorophenyl)-1H-imidazol-2-yl)-1-(isoxazol-3-yl)oct-4-en-1-one 2,2,2-trifluoroacetate (311 mg, 0.645 mmol) along with palladium on carbon (34.3 mg, 0.032 mmol) in MeOH (3 ml) with a few drops of water. The flask was connected to a hydrogen balloon through a three way joint. The system was vacuumed and refilled with hydrogen three times. The mixture was then stirred under a hydrogen atmosphere for 2 hrs. The catalyst was filtered and washed with methanol (3×). The filtrate was concentrated, the residue was dissolved in ethyl acetate and washed with NaHCO$_3$(sat) dried over MgSO$_4$, filtered and concentrated to afford product (S)-7-amino-7-(4-(2-fluorophenyl)-1H-imidazol-2-yl)-1-(isoxazol-3-yl)octan-1-one. LCMS (ESI) calc'd for $C_{20}H_{23}FN_4O_2$[M+H]$^+$: 371.3, found: 371.1.

Step 8: (S)-6-ethyl-N-((S)-2-(5-(2-fluorophenyl)-1H-imidazol-2-yl)-8-(isoxazol-3-yl)-8-oxooctan-2-yl)-6-azaspiro[2.5]octane-1-carboxamide 2,2,2-trifluoroacetate A 20 ml sample vial was charged with (S)-7-amino-7-(5-(2-fluorophenyl)-1H-imidazol-2-yl)-1-(isoxazol-3-yl)octan-1-one (62 mg, 0.167 mmol) along with (S)-6-ethyl-6-azaspiro[2.5]octane-1-carboxylic acid compound with 2,2,2-trifluoroacetic acid (1:1) (54.7 mg, 0.184 mmol), N-ethyl-N-isopropylpropan-2-amine (64.9 mg, 0.502 mmol) in CH$_2$Cl$_2$ (15 ml). The mixture was stirred and HATU (70.0 mg, 0.184 mmol) was added in one portion and the resulting reaction mixture was then stirred at room temperature for 2 hrs. The mixture was diluted with methylenechloride (20 mL), washed with NaHCO$_3$ (sat, 5 mL), water, dried over MgSO$_4$, filtered and concentrated. The crude was purified by Mass-Link HPLC to afford product (S)-6-ethyl-N-((S)-2-(5-(2-fluorophenyl)-1H-imidazol-2-yl)-8-(isoxazol-3-yl)-8-oxooctan-2-yl)-6-azaspiro[2.5]octane-1-carboxamide 2,2,2-trifluoroacetate. LCMS (ESI) calc'd for $C_{30}H_{38}FN_5O_3$[M+H]$^+$: 536.3, found: 536.3.

Example 184

(S)-N-(2-(5-(2-fluorophenyl)-1H-imidazol-2-yl)-8-(isoxazol-3-yl)-8-oxooctan-2-yl)-1-methylazetidine-3-carboxamide

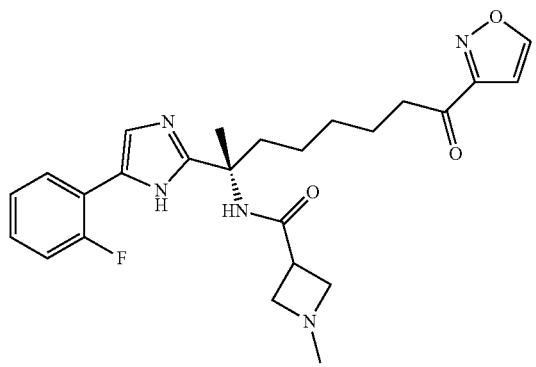

Using similar procedures as described in Example 183, (S)-N-(2-(5-(2-fluorophenyl)-1H-imidazol-2-yl)-8-(isoxazol-3-yl)-8-oxooctan-2-yl)-1-methylazetidine-3-carboxamide was prepared. LCMS (ESI) calc'd for $C_{25}H_{30}FN_5O_3$ [M+H]$^+$: 468.3, found: 468.4.

Example 185

(S)-5-(1-amino-7-(oxazol-2-yl)-7-oxoheptyl)-2-(4-fluorophenyl)-1H-imidazole-4-carbonitrile

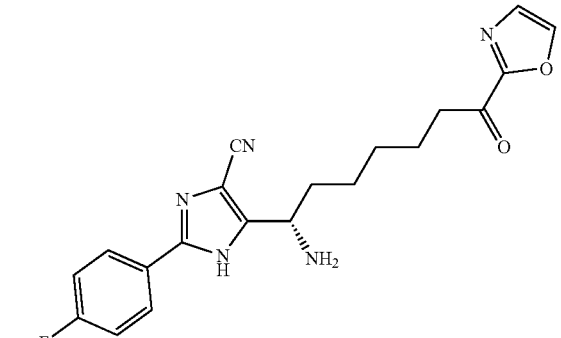

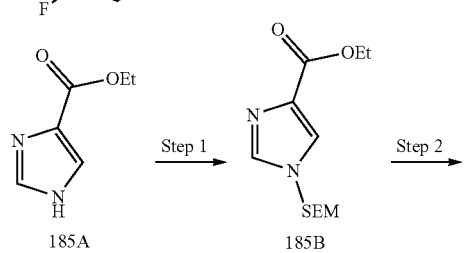

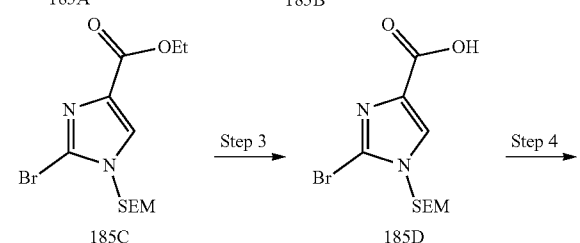

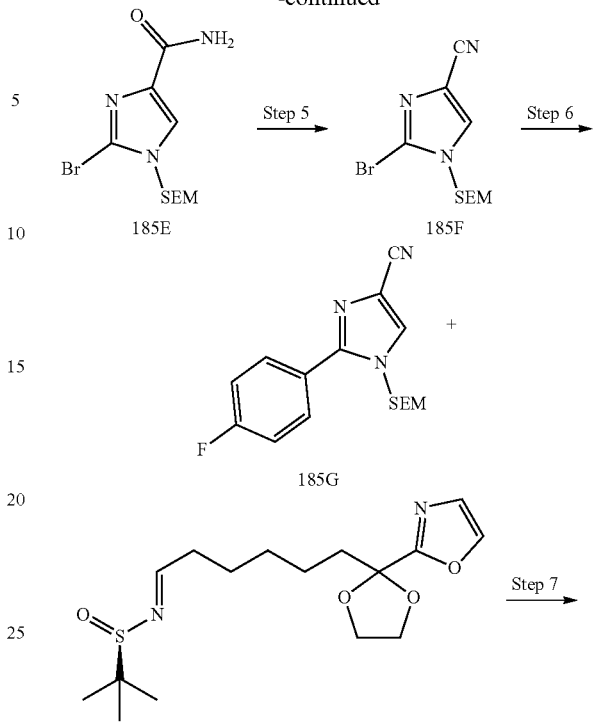

Intermediate 12

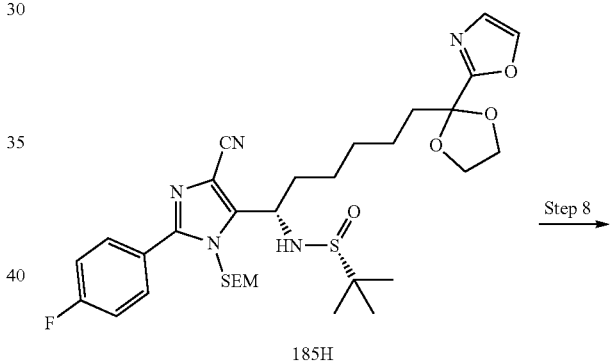

185H

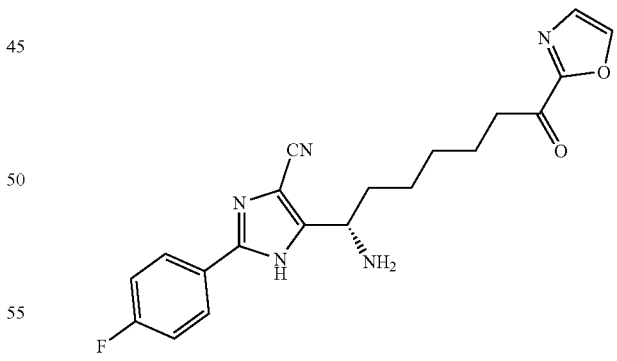

185

Step 1: Ethyl 1-((2-(trimethylsilyl)ethoxy)methyl)-1H-imidazole-4-carboxylate (185B)

To a solution of ethyl 1H-imidazole-4-carboxylate (185A) (560 mg, 4.00 mmol) in DMF (3996 μl) at ambient temperature was added NaH (160 mg, 4.00 mmol) and the reaction mixture was stirred for 15 minutes. The mixture was cooled to 0° C. and SEM-Cl (780 µl, 4.40 mmol) was added dropwise. The reaction continued to stir for 1 hour before quenching with H₂O (5 mL), taking up in EtOAc (20 mL), washing with H₂O (15 mL×3), drying over Na₂SO₄, and concentrating. The residue was purified by column chromatography on silica (2-50% 1:3 EtOH:EtOAc/hexanes) to afford the title compound. MS: 271.1 (M+1).

Step 2: Ethyl 2-bromo-1-((2-(trimethylsilyl)ethoxy) methyl)-1H-imidazole-4-carboxylate (185C)

To a solution of ethyl 1-((2-(trimethylsilyl)methoxy)methyl)-1H-imidazole-4-carboxylate (185B) (682 mg, 2.52 mmol) in chloroform (8407 µl) at ambient temperature was added NBS (494 mg, 2.77 mmol) and AIBN (41.4 mg, 0.252 mmol). The reaction mixture was heated to 60° C. for 2 hours before cooling and concentrating. The residue was purified by column chromatography on silica (2-40% 1:3 EtOH:EtOAc/hexanes) to afford the title compound. MS: 349.1, 351.1 (M+1).

Step 3: 2-bromo-1-((2-(trimethylsilyl)ethoxy) methyl)-1H-imidazole-4-carboxylic acid (185D)

To a solution of ethyl 2-bromo-1-((2-(trimethylsilyl)ethoxy)methyl)-1H-imidazole-4-carboxylate (185C) (5.00 g, 14.31 mmol) in EtOH (28.6 ml) at ambient temperature was added aqueous LiOH (9.54 ml, 28.6 mmol). The mixture was stirred for 3 hours before concentrating. The mixture was taken up in minimal DMSO and acidified with AcOH. The resulting solution was purified by column chromatography on C18 (5-95% MeCN/water with 0.1% TFA modifier) to afford the title compound. MS: 321.1, 323.1 (M+1).

Step 4: 2-bromo-1-((2-(trimethylsilyl)ethoxy) methyl)-1H-imidazole-4-carboxamide (185E)

To a solution of 2-bromo-1-((2-(trimethylsilyl)ethoxy)methyl)-1H-imidazole-4-carboxylic acid (185D) (4.00 g, 12.45 mmol) in DMF (12.45 ml) at ambient temperature was added HATU (5.68 g, 14.94 mmol) and DIPEA (3.26 ml, 18.68 mmol). After stirring for 5 minutes, 7.0 M ammonia (3.56 ml, 24.90 mmol) in methanol was added. The mixture was stirred for 30 minutes before acidifying with AcOH (5 mL) and concentrating. The resulting residue was purified by column chromatography on C18 (5-95% MeCN/water with 0.1% TFA modifier) to afford the title compound. MS: 320.1, 322.1 (M+1).

Step 5: 2-bromo-1-((2-(trimethylsilyl)ethoxy) methyl)-1H-imidazole-4-carbonitrile (185F)

To a solution of 2-bromo-1-((2-(trimethylsilyl)ethoxy)methyl)-1H-imidazole-4-carboxamide (185E) (3.30 g, 10.30 mmol) in DCM (51.5 ml) at 0° C. was added pyridine (2.083 ml, 25.8 mmol) and trifluoromethanesulfonic anhydride (11.33 ml, 11.33 mmol). The reaction was stirred for 1 hour before quenching with a sat'd solution of NaHCO₃ (50 mL), extracting with DCM (50 mL×3), dried over Na₂SO₄, and concentrated. The resulting residue was purified by column chromatography on silica (2-80% 1:3 EtOH:EtOAc/hexanes) to afford the title compound. MS: 302.1, 304.1 (M+1).

Step 6: 2-(4-fluorophenyl)-1-((2-(trimethylsilyl) ethoxy)methyl)-1H-imidazole-4-carbonitrile (185G)

To a solution of 2-bromo-1-((2-(trimethylsilyl)ethoxy)methyl)-1H-imidazole-4-carbonitrile (185F) (5.50 g, 18.20 mmol) in dioxane (48.5 ml) at ambient temperature was added (4-fluorophenyl)boronic acid (3.06 g, 21.84 mmol) and K₃PO₄ (9.66 g, 45.5 mmol) dissolved in water (12.13 ml). The mixture then had XPhos Pd G3 (0.462 g, 0.546 mmol) added and was heated to 110° C. for 2 hours. The mixture was cooled and extracted with EtOAc (30 mL×3), dried over Na₂SO₄, and concentrated. The resulting residue was purified by column chromatography on silica (2-60% 1:3 EtOH:EtOAc/hexanes) to afford the title compound. MS: 318.0 (M+1).

Step 7: (R)-N-((S)-1-(4-cyano-2-(4-fluorophenyl)-1-((2-(trimethylsilyl)ethoxy)methyl)-1H-imidazol-5-yl)-6-(2-(oxazol-2-yl)-1,3-dioxolan-2-yl)hexyl)-2-methylpropane-2-sulfinamide (185H To a solution of 2-(4-fluorophenyl)-1-((2-(trimethylsilyl)ethoxy)methyl)-1H-imidazole-4-carbonitrile (185G) (1.808 g, 5.69 mmol) in THF (13.27 ml) at −78° C. was added LDA (2.74 ml, 5.48 mmol) in THF dropwise. The reaction mixture was stirred for 20 min before adding (R,E)-2-methyl-N-(6-(2-(oxazol-2-yl)-1,3-dioxolan-2-yl)hexylidene)propane-2-sulfinamide (Intermediate A_12) (1.50 g, 4.38 mmol) in THF (3.0 mL) dropwise. The mixture was stirred for 1 hour before quenching with a sat'd solution of NH₄Cl (30 mL), extracted with EtOAc (30 mL×3), dried over Na₂SO₄, and concentrated. The resulting residue was purified by column chromatography on silica (10-100% 1:3 EtOH:EtOAc/hexanes) to afford the title compound. MS: 660.4 (M+1).

Step 8: (S)-5-(1-amino-7-(oxazol-2-yl)-7-oxoheptyl)-2-(4-fluorophenyl)-1H-imidazole-4-carbonitrile (185)

To a mixture of (R)-N-((S)-1-(4-cyano-2-(4-fluorophenyl)-1-((2-(trimethylsilyl)ethoxy)methyl)-1H-imidazol-5-yl)-6-(2-(oxazol-2-yl)-1,3-dioxolan-2-yl)hexyl)-2-methylpropane-2-sulfinamide (185H) (2.30 g, 3.49 mmol) in methanol (10.56 ml) at ambient temperature was added 4.0 M HCl (2.61 ml, 10.46 mmol) in dioxanes. The mixture was stirred for 8 hours. The mixture was concentrated and the resulting residue was purified using column chromatography on C18 (5-95% MeCN/water with 0.1% TFA modifier) to afford a complex mixture of products. The resulting mixture was taken up in MeOH (11.60 ml) at ambient temperature and TFA (2.68 ml, 34.8 mmol) was added. After 2 hours, the mixture was heated to 50° C. After an additional 2 hours, 4.0 M HCl (5.22 ml, 20.87 mmol) via dioxanes was added and it continued to stir overnight. The mixture was concentrated and the resulting residue was purified using column chromatography on C18 (5-95% MeCN/water with 0.1% TFA modifier) to afford the desired product. The product was submitted to chiral SFC separation to afford the title compound. MS: 382.2 (M+1). NMR: 1H NMR (500 MHz, DMSO-d6) δ 8.43 (s, 3H), 8.35 (s, 1H), 7.99 (dd, J=8.4, 5.5 Hz, 2H), 7.48 (s, 1H), 7.38 (t, J=8.8 Hz, 2H), 4.40 (s, 1H), 2.98 (t, J=7.3 Hz, 2H), 1.96 (m, 2H), 1.57 (m, 2H), 1.38-1.13 (m, 4H).

Example 186

(S)-N-(1-(4-cyano-2-(4-fluorophenyl)-1H-imidazol-5-yl)-7-(oxazol-2-yl)-7-oxoheptyl)-2-(dimethyl-amino)acetamide

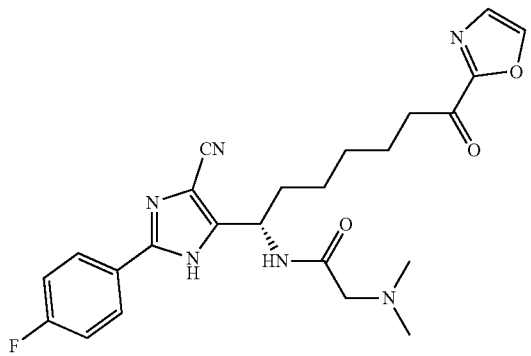

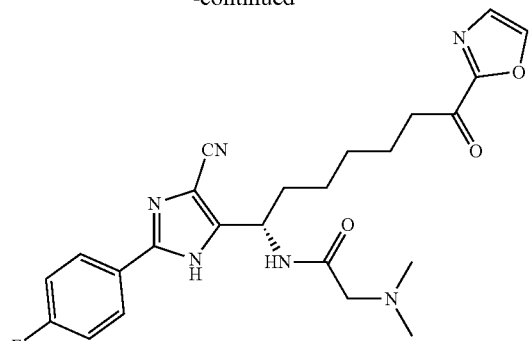

186

Step 1: (S)-N-(1-(4-cyano-2-(4-fluorophenyl)-1H-imidazol-5-yl)-7-(oxazol-2-yl)-7-oxoheptyl)-2-(dimethylamino)acetamide (186)

To a mixture of (S)-5-(1-amino-7-(oxazol-2-yl)-7-oxoheptyl)-2-(4-fluorophenyl)-1H-imidazole-4-carbonitrile (185) (40 mg, 0.105 mmol) in DMF (1049 µl) at ambient temperature was added 2-(dimethylamino)acetic acid (16.22 mg, 0.157 mmol), HATU (59.8 mg, 0.157 mmol), and DIPEA (55.0 µl, 0.315 mmol). After two hours the resulting mixture was quenched with a few drops of AcOH. The resulting solution was purified by mass triggered reverse phase HPLC (MeCN/water with 0.1% TFA modifier) to afford the title compound. MS: 467.2 (M+1). NMR: 1H NMR (500 MHz, DMSO-d6) δ 9.70 (s, 1H), 9.16 (d, J=7.1 Hz, 1H), 8.36 (s, 1H), 7.96 (dd, J=8.3, 5.6 Hz, 2H), 7.49 (s, 1H), 7.33 (t, J=8.8 Hz, 2H), 4.97 (q, J=7.3 Hz, 1H), 4.02 (d, J=16.2 Hz, 1H), 3.86 (d, J=15.9 Hz, 1H), 3.00 (t, J=7.2 Hz, 2H), 2.80 (s, 3H), 2.78 (s, 3H), 2.00-1.88 (m, 1H), 1.83 (m, 1H), 1.65-1.56 (m, 2H), 1.31 (m, 4H).

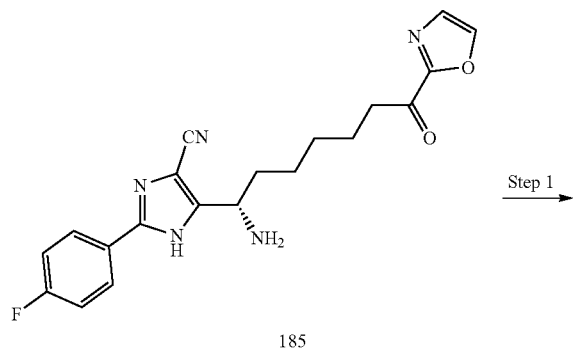

185

Step 1 →

Using similar methodology as described above, the following examples were prepared by using different acid in Step 1 to provide the final amide coupling products:

| Example # | Structure | IUPAC Name | Exact Mass [M + H]+ |
|---|---|---|---|
| 187 | 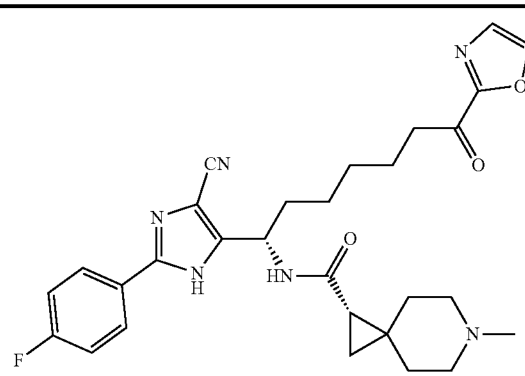 | (S)-N-((S)-1-(4-cyano-2-(4-fluorophenyl)-1H-imidazol-5-yl)-7-(oxazol-2-yl)-7-oxoheptyl)-6-methyl-6-azaspiro[2.5]octane-1-carboxamide | 533.3 |

US 12,331,044 B2
243                                                                                                 244
-continued
| Example # | Structure | IUPAC Name | Exact Mass [M + H]⁺ |
|---|---|---|---|
| 188 | 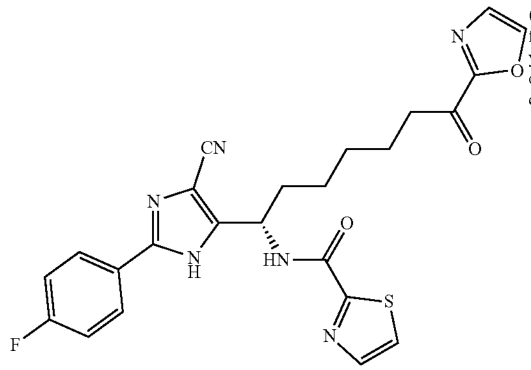 [SMILES: N#Cc1nc(-c2ccc(F)cc2)[nH]c1[C@H](CCCCCC(=O)c1ncco1)NC(=O)c1nccs1] | (S)-N-(1-(4-cyano-2-(4-fluorophenyl)-1H-imidazol-5-yl)-7-(oxazol-2-yl)-7-oxoheptyl)thiazole-5-carboxamide | 493.2 |
Example 189
(S)-5-(1-amino-7-(oxazol-2-yl)-7-oxoheptyl)-2-(4-fluorophenyl)oxazole-4-carbonitrile
-continued
189C
Step 3 →
189D
Step 4 →
189A
Step 1 →
189E
189B
Step 2 →
Intermediate 12
Step 5 →

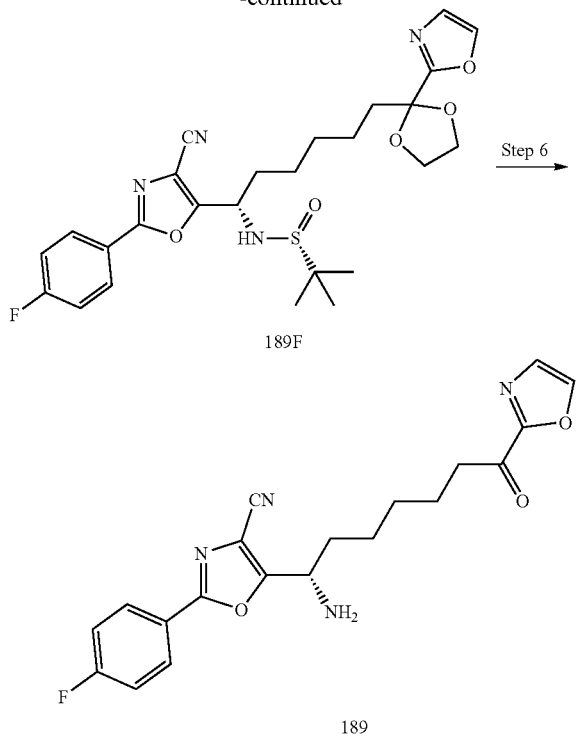

Step 1: ethyl 2-(4-fluorophenyl)oxazole-4-carboxylate (189B)

To a solution of ethyl 2-bromooxazole-4-carboxylate (5.00 g, 22.73 mmol) in dioxane (36.4 ml) at ambient temperature was added (4-fluorophenyl)boronic acid (6.36 g, 45.5 mmol) and $K_3PO_4$ (12.06 g, 56.8 mmol) dissolved in water (9.09 ml). XPhos Pd G3 (0.962 g, 1.136 mmol) was added to the mixture and the solution was heated to 100° C. for 2 hours. The mixture was cooled and quenched with $H_2O$ (100 mL), extracted with EtOAc (100 mL×3), dried over $Na_2SO_4$, and concentrated to afford the crude title compound. MS: 236.1 (M+1).

Step 2: 2-(4-fluorophenyl)oxazole-4-carboxylic acid (189C)

To a solution of ethyl 2-(4-fluorophenyl)oxazole-4-carboxylate (189B) (5.35 g, 22.75 mmol) in ethanol (114 ml) at ambient temperature was added aq. LiOH (18.95 ml, 56.9 mmol). The mixture stirred for 2 hours before concentrating. The mixture was taken up in 10 mL DMSO, add AcOH (10 mL), and $H_2O$ (400 mL). The solid was collected by filtration, washed with $H_2O$, and placed under vacuum to obtain the title compound. MS: 208.1 (M+1).

Step 3: 2-(4-fluorophenyl)oxazole-4-carboxamide (189D)

To a solution of 2-(4-fluorophenyl)oxazole-4-carboxylic acid (189C) (4.00 g, 19.31 mmol) in DMF (38.6 ml) at ambient temperature was added HATU (8.08 g, 21.24 mmol) and DIPEA (3.71 ml, 21.24 mmol). The mixture was stirred for 10 minutes before adding 7.0 M ammonia (4.14 ml, 29.0 mmol) in MeOH. The mixture was stirred for 1 hour before adding 400 mL of $H_2O$ to the mixture. A solid precipitated and was collected using filtration. The solid was washed with $H_2O$ and placed under vacuum to afford the title compound. MS: 207.1 (M+1).

Step 4: 2-(4-fluorophenyl)oxazole-4-carbonitrile (189E)

To a solution of 2-(4-fluorophenyl)oxazole-4-carboxamide (189D) (3.30 g, 16.01 mmol) in DCM (16.01 ml)/dioxane (16.01 ml) at 0° C. was added pyridine (2.85 ml, 35.2 mmol) followed by 1.0 M triflic anhydride (17.61 ml, 17.61 mmol) in DCM dropwise. The mixture was stirred for 1 hour before quenching with a sat'd solution of $NaHCO_3$ (50 mL), extracted with DCM (50 mL×3), dried over $Na_2SO_4$, and concentrated. The resulting residue was purified by column chromatography on silica (2% to 70% EtOAc/Hexanes) to afford the title compound. MS: 189.2 (M+1).

Step 5: (R)-N-((S)-1-(4-cyano-2-(4-fluorophenyl)oxazol-5-yl)-6-(2-(oxazol-2-yl)-1,3-dioxolan-2-yl)hexyl)-2-methylpropane-2-sulfinamide (189F)

To a solution of 2-(4-fluorophenyl)oxazole-4-carbonitrile (189E) (0.714 g, 3.80 mmol) in THF (8.85 ml) at −78° C. was added 2.0 M LDA (1.825 ml, 3.65 mmol) in THF dropwise. The reaction mixture stirred for 20 min before adding (R,E)-2-methyl-N-(6-(2-(oxazol-2-yl)-1,3-dioxolan-2-yl)hexylidene)propane-2-sulfinamide (Intermediate A_12) (1.00 g, 2.92 mmol) in THF (3.0 mL) dropwise. The mixture was stirred for 1 hour before quenching with a sat'd solution of $NH_4Cl$ (30 mL), extracted with EtOAc (30 mL×3), dried over $Na_2SO_4$, and concentrated. The resulting residue was purified by column chromatography on silica (10-100% 1:3 EtOH:EtOAc/hexanes) to afford the title compound. MS: 531.2 (M+1).

Step 6: (S)-5-(1-amino-7-(oxazol-2-yl)-7-oxoheptyl)-2-(4-fluorophenyl)oxazole-4-carbonitrile (189)

To a mixture of (R)-N-((S)-1-(4-cyano-2-(4-fluorophenyl)oxazol-5-yl)-6-(2-(oxazol-2-yl)-1,3-dioxolan-2-yl)hexyl)-2-methylpropane-2-sulfinamide (189F) (1.40 g, 2.64 mmol) in MeOH (8.00 ml) at ambient temperature was added 4.0 M HCl (1.979 ml, 7.92 mmol) in dioxanes. The mixture was stirred for 8 hours. The mixture was concentrated and the resulting residue was purified using column chromatography on C18 (5-95% MeCN/water with 0.1% TFA modifier) to afford a complex mixture of products. The resulting mixture was taken up in MeOH (7.82 ml) at ambient temperature and TFA (1.987 ml, 25.8 mmol) was added. After 2 hours, it was heated to 50° C. After an additional 2 hours, 4.0 M HCl HCl (3.87 ml, 15.48 mmol) was added via dioxanes and it continued to stir overnight. The mixture was concentrated and the resulting residue was purified using column chromatography on C18 (5-95% MeCN/water with 0.1% TFA modifier) to afford the desired product. The product was submitted to chiral SFC separation to afford the title compound. MS: 383.2 (M+1). NMR: 1H NMR (500 MHz, DMSO-d6) δ 8.75 (s, 2H), 8.35 (s, 1H), 8.08 (dd, J=8.6, 5.4 Hz, 2H), 7.46 (dd, J=15.1, 6.4 Hz, 3H), 4.78 (s, 1H), 2.99 (t, J=7.3 Hz, 2H), 2.02 (m, 2H), 1.59 (m, 2H), 1.39-1.20 (m, 4H).

Example 190

(S)-N-(1-(4-cyano-2-(4-fluorophenyl)-1H-imidazol-5-yl)-7-(oxazol-2-yl)-7-oxoheptyl)-2-(dimethylamino)acetamide

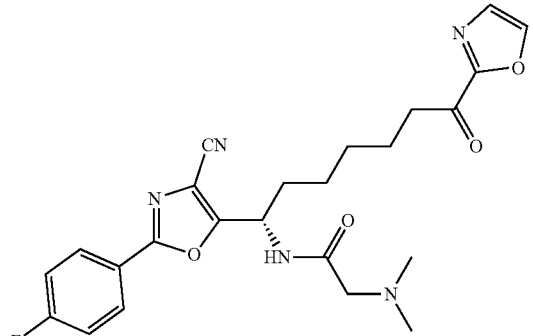

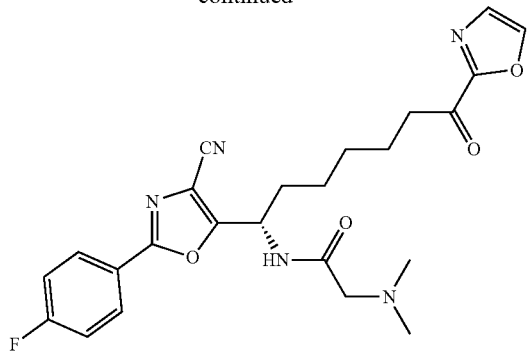

190

Step 1: (S)-N-(1-(4-cyano-2-(4-fluorophenyl)-1H-imidazol-5-yl)-7-(oxazol-2-yl)-7-oxoheptyl)-2-(dimethylamino)acetamide (190)

To a mixture of (S)-5-(1-amino-7-(oxazol-2-yl)-7-oxoheptyl)-2-(4-fluorophenyl)oxazole-4-carbonitrile (189) (40 mg, 0.105 mmol) in DMF (1046 µl) at ambient temperature was added 2-(dimethylamino)acetic acid (16.18 mg, 0.157 mmol), HATU (59.7 mg, 0.157 mmol), and DIPEA (54.8 µl, 0.314 mmol). After two hours the resulting mixture was quenched with a few drops of AcOH. The resulting solution was purified by mass triggered reverse phase HPLC (MeCN/water with 0.1% TFA modifier) to afford the title compound. MS: 468.2 (M+1). NMR: 1H NMR (500 MHz, DMSO-d6) δ 9.71 (s, 1H), 9.31 (d, J=7.1 Hz, 1H), 8.36 (s, 1H), 8.02 (dd, J=7.7, 5.5 Hz, 2H), 7.50 (s, 1H), 7.42 (t, J=8.5 Hz, 2H), 5.14 (q, J=7.2 Hz, 1H), 4.15-3.98 (m, 1H), 3.98-3.85 (m, 1H), 3.01 (t, J=7.2 Hz, 2H), 2.80 (s, 3H), 2.78 (s, 3H), 1.98 (m, 1H), 1.87 (m, 1H), 1.66-1.58 (m, 2H), 1.37 (m, 4H).

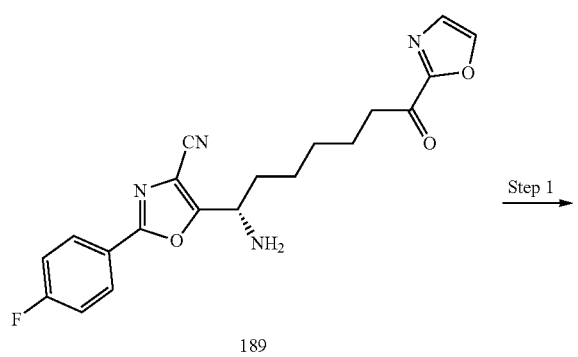

189

Step 1 →

Using similar methodology as described above, the following examples were prepared by using different acid in Step 1 to provide the final amide coupling products:

| Example # | Structure | IUPAC Name | Exact Mass [M + H]+ |
|---|---|---|---|
| 191 | 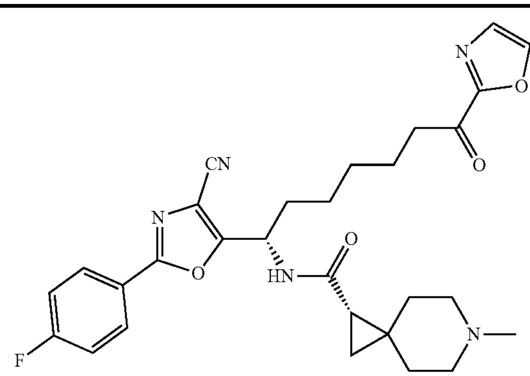 | (S)-N-((S)-1-(4-cyano-2-(4-fluorophenyl)oxazol-5-yl)-7-(oxazol-2-yl)-7-oxoheptyl)-6-methyl-6-azaspiro[2.5]octane-1-carboxamide | 534.2 |

| Example # | Structure | IUPAC Name | Exact Mass [M + H]+ |
|---|---|---|---|
| 192 | 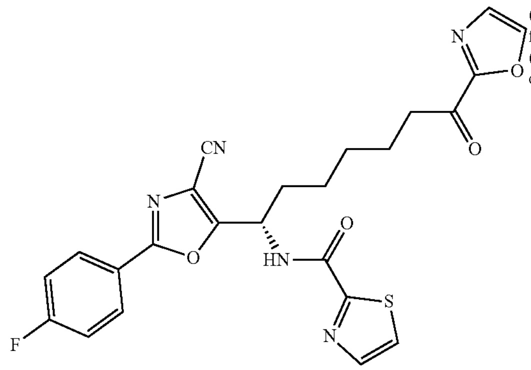 [SMILES: N#Cc1nc(-c2ccc(F)cc2)oc1[C@H](CCCCCC(=O)c1ncco1)NC(=O)c1nccs1] | (S)-N-(1-(4-cyano-2-(4-fluorophenyl)oxazol-5-yl)-7-(oxazol-2-yl)-7-oxoheptyl)thiazole-5-carboxamide | 494.2 |
Example 193
(S)-7-amino-7-(4-chloro-5-(4-fluorophenyl)-1H-imidazol-2-yl)-1-(isoxazol-3-yl)heptan-1-one
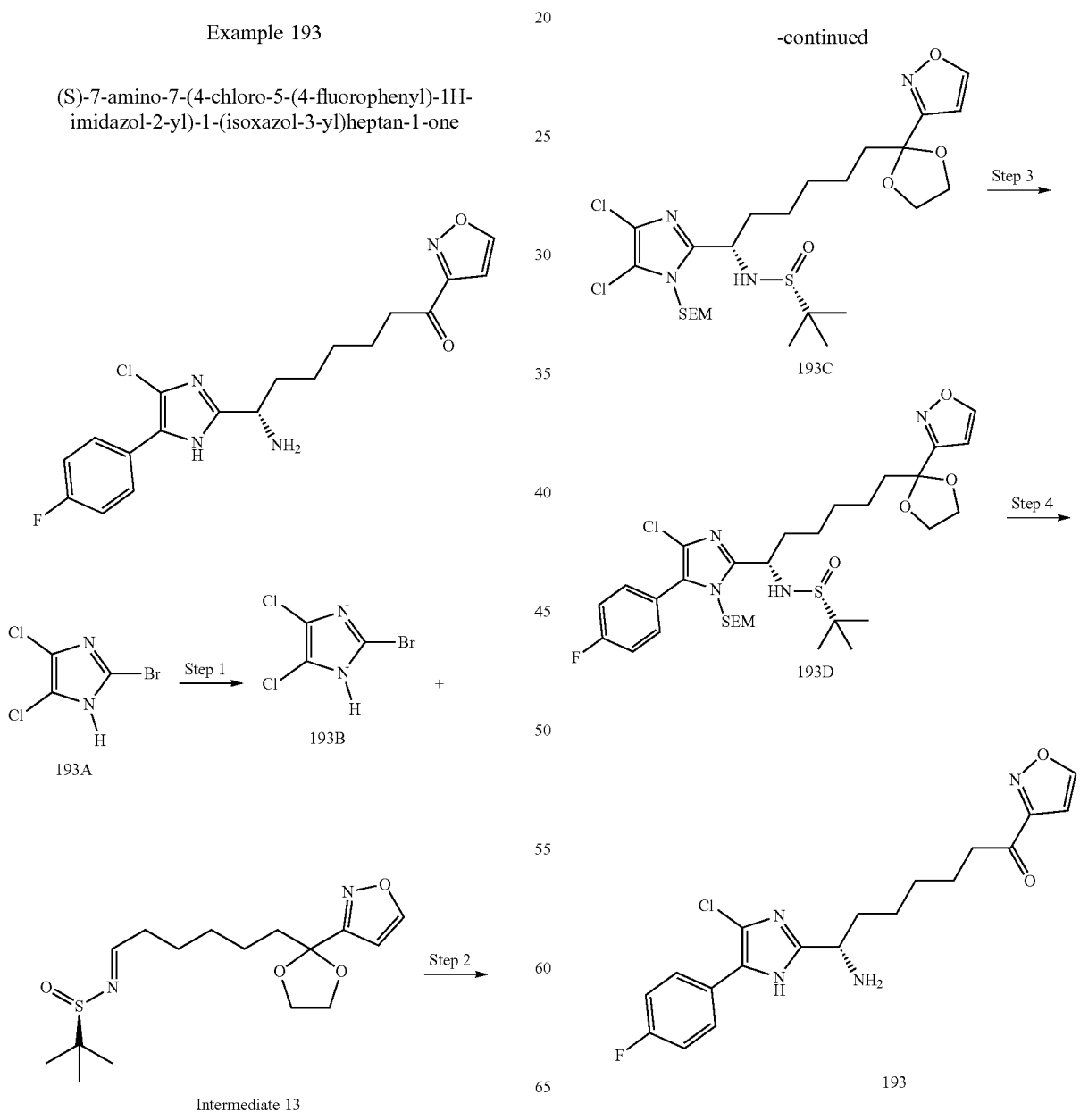

Step 1: 2-bromo-4,5-dichloro-1-((2-(trimethylsilyl)ethoxy)methyl)-1H-imidazole (193B)

To a mixture of 2-bromo-4,5-dichloro-1H-imidazole (193A) (25.0 g, 116 mmol) in THF (351 ml) at 0° C. was added NaH (5.10 g, 127 mmol). The mixture was stirred for 30 min before adding SEM-Cl (22.60 ml, 127 mmol). The mixture was allowed to warm to ambient temperature. After 2 hours the mixture was quenched with $H_2O$ (250 mL). The mixture was extracted with EtOAc (200 mL×3), dried over $Na_2SO_4$, and concentrated to afford the title compound. MS: 347.1, 349.1 (M+1).

Step 2: (R)-N-((S)-1-(4,5-dichloro-1-((2-(trimethylsilyl)ethoxy)methyl)-1H-imidazol-2-yl)-6-(2-(isoxazol-3-yl)-1,3-dioxolan-2-yl)hexyl)-2-methylpropane-2-sulfinamide (193C)

To a mixture of 2-bromo-4,5-dichloro-1-((2-(trimethylsilyl)ethoxy)methyl)-1H-imidazole (195B) (1.516 g, 4.38 mmol) in THF (9.73 ml) at −78° C. was added 2.5 M nBuLi (1.752 ml, 4.38 mmol) in hexanes. The mixture was stirred for 20 minutes before adding (R,E)-N-(6-(2-(isoxazol-3-yl)-1,3-dioxolan-2-yl)hexylidene)-2-methylpropane-2-sulfinamide (Intermediate 13) (1.00 g, 2.92 mmol) in THF (2 mL) dropwise. The mixture was stirred for 30 minutes before being quenching with a sat'd solution of $NH_4Cl$ (25 mL). The mixture was warmed to room temp, extracted with EtOAc (25 mL×3), dried over $Na_2SO_4$, and concentrated. The resulting residue was purified by column chromatography on silica (2-85% 1:3 EtOH:EtOAc/hexanes) to afford the title compound. MS: 609.4, 611.4 (M+1).

Step 3: (R)-N-((S)-1-(4-chloro-5-(4-fluorophenyl)-1-((2-(trimethylsilyl)ethoxy)methyl)-1H-imidazol-2-yl)-6-(2-(isoxazol-3-yl)-1,3-dioxolan-2-yl)hexyl)-2-methylpropane-2-sulfinamide (193D)

To a mixture of (R)-N-((S)-1-(4,5-dichloro-1-((2-(trimethylsilyl)ethoxy)methyl)-1H-imidazol-2-yl)-6-(2-(isoxazol-3-yl)-1,3-dioxolan-2-yl)hexyl)-2-methylpropane-2-sulfinamide (195C) (1.10 g, 1.804 mmol) in dioxane (7.22 ml) at ambient temperature was added (4-fluorophenyl)boronic acid (0.278 g, 1.985 mmol) and $K_3PO_4$ (0.957 g, 4.51 mmol) dissolved in water (1.804 ml). XPhos Pd G3 (0.076 g, 0.090 mmol) was added and the mixture was heated to 80° C. and stirred for 2 hours. The mixture was cooled and taken up in EtOAc (20 mL) and water (20 mL). It was extracted with EtOAc (20 mL×3), dried over $Na_2SO_4$, and concentrated. The resulting residue was purified by column chromatography on silica (2-80% 1:3 EtOH:EtOAc/hexanes) to afford the title compound. MS: 669.5, 671.4 (M+1).

Step 4: (S)-7-amino-7-(4-chloro-5-(4-fluorophenyl)-1H-imidazol-2-yl)-1-(isoxazol-3-yl)heptan-1-one (193)

To a mixture of (R)-N-((S)-1-(4-chloro-5-(4-fluorophenyl)-1-((2-(trimethylsilyl)ethoxy)methyl)-1H-imidazol-2-yl)-6-(2-(isoxazol-3-yl)-1,3-dioxolan-2-yl)hexyl)-2-methylpropane-2-sulfinamide (193D) (999 mg, 1.493 mmol) in MeOH (7463 µl) at ambient temperature was added 6.0 M HCl (1493 µl, 8.96 mmol). The mixture was heated to 50° C. and stirred overnight. The mixture was cooled and concentrated. The resulting residue was purified using column chromatography on C18 (5-95% MeCN/water with 0.1% TFA modifier) to afford the title compound. MS: 391.3, 393.3 (M+1). NMR: 1H NMR (500 MHz, DMSO-d6) δ 9.17-9.07 (m, 1H), 8.50 (d, J=17.2 Hz, 3H), 7.79-7.65 (m, 2H), 7.43-7.25 (m, 2H), 6.89 (s, 1H), 4.32 (s, 1H), 3.01 (t, J=7.1 Hz, 2H), 1.91 (m, 2H), 1.59 (m, 2H), 1.39-1.18 (m, 4H).

Example 194

(S)-N-(1-(4-chloro-5-(4-fluorophenyl)-1H-imidazol-2-yl)-7-(isoxazol-3-yl)-7-oxoheptyl)-2-(dimethylamino)acetamide

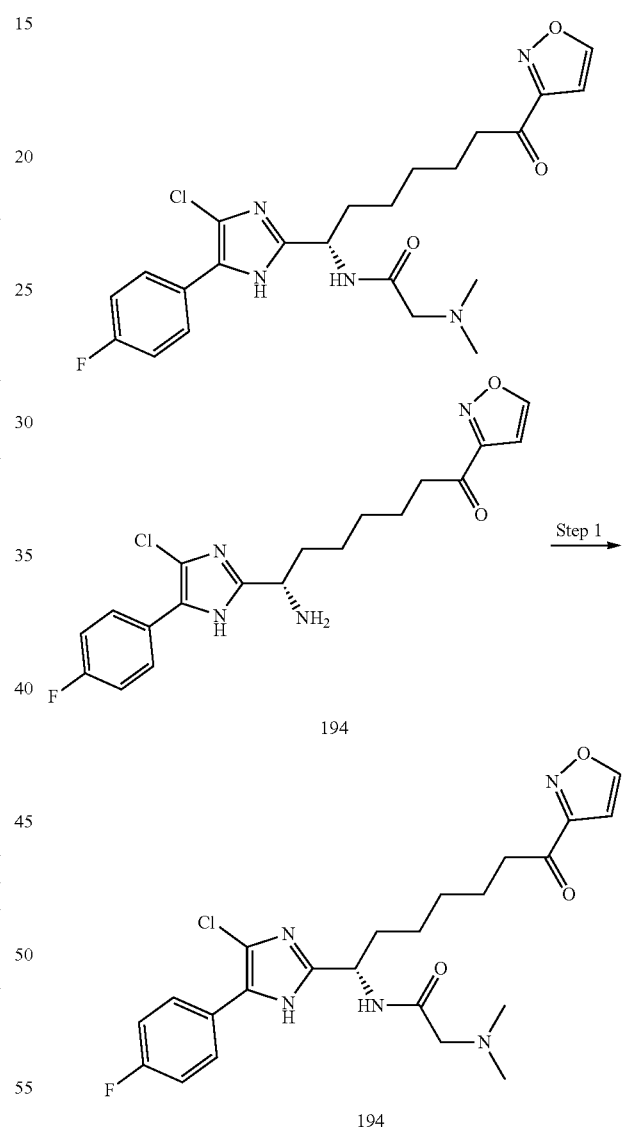

Step 1: (S)-N-(1-(4-chloro-5-(4-fluorophenyl)-1H-imidazol-2-yl)-7-(isoxazol-3-yl)-7-oxoheptyl)-2-(dimethylamino)acetamide (194)

To a mixture of 2-(dimethylamino)acetic acid (59.4 mg, 0.576 mmol) in DMF (959 µl) at ambient temperature was added HATU (146 mg, 0.384 mmol) and DIPEA (84 µl, 0.480 mmol). The mixture was stirred for 15 min before adding (S)-7-amino-7-(4-chloro-5-(4-fluorophenyl)-1H-imidazol-2-yl)-1-(isoxazol-3-yl)heptan-1-one (193) (75 mg, 0.192 mmol) in DMF (0.2 mL) to the solution. The mixture was stirred for two hours before quenching with a few drops of TFA. The resulting solution was purified by mass triggered reverse phase HPLC (MeCN/water with 0.1% TFA modifier) to afford the title compound. MS: 476.4, 476.3 (M+1). NMR: 1H NMR (500 MHz, DMSO-d6) δ 12.70 (s, 1H), 9.24-9.03 (m, 1H), 8.67 (s, 1H), 7.81-7.59 (m, 2H), 7.32 (t, J=8.7 Hz, 2H), 6.98-6.77 (m, 1H), 4.94 (q, J=8.0 Hz, 1H), 4.26 (s, 2H), 3.54 (s, 2H), 3.01 (t, J=7.2 Hz, 2H), 2.57 (s, 3H), 2.49 (s, 3H), 1.84 (m, 1H), 1.80-1.64 (m, 1H), 1.44-1.09 (m, 4H).

Using similar methodology as described above, the following examples were prepared by using different acid in Step 1 to provide the final amide coupling products:

Boston BioProducts, Tween-20 from Fisher Scientific (BP337), TCEP from Calbiochem and 7.5% bovine serum albumin (BSA) from Life Technologies (15260037). 384-well, black assay plates were obtained from Corning (3575).

Recombinant human HDAC1, HDAC2, and HDAC3/SMRT heterodimer were prepared by Merck Research Laboratories. Full length human HDAC1-FLAG was stably expressed in HEK-293F cells and purified using an anti-FLAG affinity chromatography with FLAG peptide (100 μg/ml) elution. The final concentration of HDAC1 was 1.98 uM by Western Blot analysis and 1.39 uM by active site titration. Full length human HDAC2-FLAG was expressed in baculovirus infected Sf9 cells and purified using an anti-FLAG affinity chromatography with FLAG peptide (100 g/ml) elution. The eluted protein was then passed over an anti-HDAC1 immunoaffinity column to remove any

| Example # | Structure | IUPAC Name | Exact Mass [M + H]$^+$ |
|---|---|---|---|
| 195 | 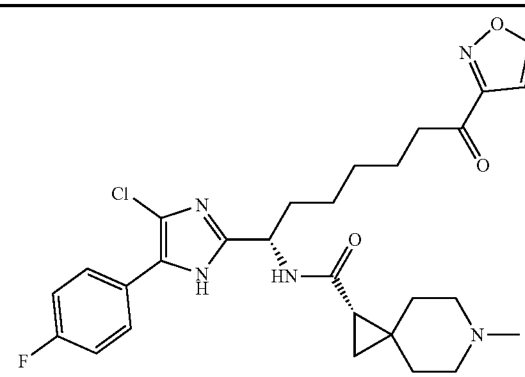 | (S)-N-((S)-1-(4-chloro-5-(4-fluorophenyl)-1H-imidazol-2-yl)-7-(isoxazol-3-yl)-7-oxoheptyl)-6-methyl-6-azaspiro[2.5]octane-1-carboxamide 2,3-dihydroxysuccinate | 542.4 |
| 196 | 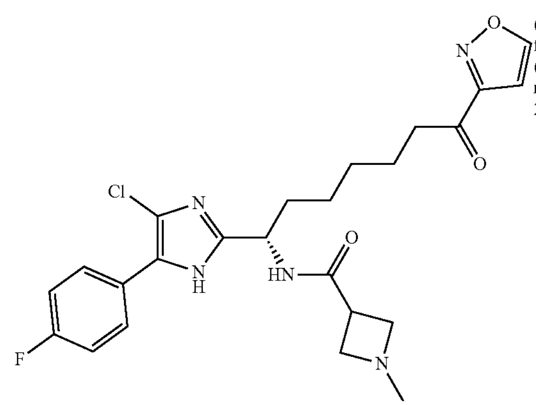 [SMILES: CN1CC(C(=O)N[C@@H](CCCCCC(=O)c2ccon2)c2nc(Cl)c(-c3ccc(F)cc3)[nH]2)C1] | (S)-N-(1-(4-chloro-5-(4-fluorophenyl)-1H-imidazol-2-yl)-7-(isoxazol-3-yl)-7-oxoheptyl)-1-methylazetidine-3-carboxamide 2,3-dihydroxysuccinate | 488.3 |

Human HDAC Enzyme Inhibitor Fluor-De-Lys Assay
Materials

Recombinant human HDAC8 (BML-SE145-0100) and HDAC10 (BML-SE559-0050) enzymes, HDAC substrates BML-KI104 and BML-KI178, and HDAC developer solutions BML-KI105 and BML-K1176 were purchased from Enzo Life Sciences. Recombinant human HDAC5 and HDAC11 were purchased from BPS Bioscience (catalog numbers 50045 and 50021). Substrate Boc-Lys(TFA)-AMC was obtained from Bachem (catalog number I-1985). HDAC inhibitor suberoylanilide hydroxamic acid (SAHA) was obtained from Indofine and trichostatin A (TSA) was obtained from Sigma-Aldrich. D-myo inositol-1,4,5,6-tetraphosphate potassium salt (IP$_4$) was obtained from Carbosynth (catalog MI 16761). HEPES pH 8.0 was obtained from complexes containing HDAC1. The final concentration of HDAC2 was 16.8 uM by Western Blot analysis and 7.6 uM by active site titration. Full length human HDAC3-FLAG was expressed in HEK-293F cells along with SMRT (amino acids 1-899)-6×His; plasmid APP-0024) and purified using an anti-FLAG affinity chromatography with FLAG peptide (100 g/ml) elution. The eluted protein was then passed over an anti-HDAC1 immunoaffinity column to remove any complexes containing HDAC1. The final concentration of the HDAC3/SMRT complex was 2.03 uM by Western Blot analysis and 1.37 uM by active site titration.

HDAC Inhibition Assays

The histone deacetylase activities of HDAC1, HDAC2, HDAC3, HDAC6, and HDAC8 were measured in modified FLUOR DE LYS assays in 384-well format. In this assay, HDAC enzymes are initially incubated with an F-acetyl (or -trifluoroacetyl)-L-lysine-containing substrate with a C-terminal amide having aminomethylcoumarin as the amine component. HDACs cleave the F-acetyl group, rendering the resulting product susceptible to AMC cleavage by trypsin. The released AMC is then detected by its fluorescence.

The HDAC 1, 2 assays employed buffer A, which contained 20 mM HEPES, pH 8.0, 1 mM $MgCl_2$, 137 mM NaCl, 2.7 mM KCl, 0.05% BSA. The HDAC3/SMRT assay employed buffer B, consisting of 20 mM HEPES, pH 8.0, 1 mM $MgCl_2$, 50 mM NaCl, 2.7 mM KCl, 0.05% BSA, 0.005% Tween 20, and 10 µM $IP_4$. The HDAC6 assay employed buffer C, consisting of 20 mM HEPES, pH 8.0, 1 mM $MgCl_2$, 137 mM NaCl, 2.7 mM KCl, 0.5 mM TCEP (Calbiochem) and 0.05% BSA. The HDAC8 assay employed buffer D, consisting of 20 mM HEPES, pH 8.0, 1 mM $MgCl_2$, 100 mM NaCl, 20 mM KCl, 0.1% n-octyl-β-D-glucoside (Anatrace) and 0.05% BSA. All steps were performed at room temperature (23° C.). The assay was performed by pre-incubating serial dilutions of test compounds with the target HDAC prior to initiation with substrate. Each compound was titrated in a 10-point dose response, using a 1:3 fold dilution scheme, with 0.15 ul of solution added by ECH0555 to the plate, followed by the addition of 20 µl of the appropriate HDAC isoform diluted in appropriate assay buffer. The incubation was allowed to proceed for 3 hours, then the appropriate substrate diluted in assay buffer (final substrate concentration ~$K_m$) was added and the reaction allowed to proceed for 60 min. Final conditions used for each assay were: 1. HDAC 1, 0.3 nM total enzyme, 20 µM substrate BML-KI104; 2. HDAC 2, 1.5 nM total enzyme, 40 µM substrate BML-KI104; 3. HDAC 3/SMRT, 0.3 nM total enzyme, 20 µM substrate BML-KI104; 4. HDAC 6, 1.3 nM total enzyme, 2.5 µM substrate BML-KI104; 5. HDAC 8, 1.3 nM total enzyme, 200 µM substrate BML-KI178; the final high dose of test compound was 30 µM. For potent compounds, 900 nM was used as the final high dose. The reactions were stopped and developed by addition of 30 ul of HDAC developer solution containing a saturating level of HDAC inhibitor as follows: 1. HDACs 1, 2, 3 and 6, developer BML-KI105 (stock diluted 1:125, containing 20 uM SAHA, 2. HDAC 8, developer BML-K1176 (1:100 plus 40 uM SAHA, and the plates were shaken to assure good mixing, briefly centrifuged, incubated for 30 minutes at room temperature and then the fluorescence intensity (excitation 380 nm, emission 460 nm) measured using a PHERAstar plate reader. For each assay plate, both minimal inhibition (100% DMSO; 0% inhibition) and maximal inhibition (either 10 uM SAHA or 100 uM TSA; 100% inhibition) controls were added. For data analysis, background subtracted product (fluorescence) vs. time data for each inhibitor concentration was fitted using a 4-parameter fit.

All compounds prepared were tested in the binding assays with HDAC1, 2, 3, 6 and 8.

| Ex. # | HDAC1 $IC_{50}$ (nM) | HDAC2 $IC_{50}$ (nM) | HDAC3 $IC_{50}$ (nM) | HDAC6 $IC_{50}$ (nM) | HDAC8 $IC_{50}$ (nM) |
|---|---|---|---|---|---|
| 1 | 1.1 | 7.1 | 3.1 | 45000 | 100 |
| 2 | 0.37 | 6.3 | 1.6 | 45000 | 30 |
| 3 | 0.26 | 4.0 | 0.84 | 45000 | 31 |
| 4 | 2205 | 67 | 310 | | |
| 5 | 0.62 | 7.2 | 2.6 | 45000 | 47 |
| 6 | 2.9 | 14 | 1.5 | 45000 | 55 |
| 7 | 19 | 57 | 3.1 | 45000 | 600 |
| 8 | 8.3 | 50 | 50 | 15000 | 8000 |
| 9 | 2.4 | 12 | 1.5 | 2300 | 2000 |
| 10 | 2.6 | 9.9 | 2.8 | 45000 | 2345 |
| 11 | 5.6 | 26 | 5.1 | 45000 | 2800 |
| 12 | 1.8 | 5.6 | 1.6 | 8300 | 710 |
| 13 | 1.8 | 5.5 | 1.7 | 45000 | 650 |
| 14 | 0.90 | 4.5 | 1.1 | 45000 | 3100 |
| 15 | 5.2 | 18 | 7.3 | 40000 | 720 |
| 16 | 2.7 | 8.8 | 2.6 | 33000 | 1400 |
| 17 | 2.1 | 17 | 4.1 | 45000 | 2900 |
| 18 | 1.1 | 6.2 | 1.5 | >1500 | 4500 |
| 19 | 2.0 | 9.4 | 1.5 | >1500 | 3600 |
| 20 | 1.5 | 4.5 | 1.5 | 45000 | 4300 |
| 21 | 1.9 | 8.4 | 1.5 | >4500 | 490 |
| 22 | 10 | 38 | 6.7 | 45000 | 1500 |
| 23 | 1.9 | 9.5 | 1.8 | 31000 | 660 |
| 24 | 7.1 | 39 | 3.5 | 45000 | 3200 |
| 25 | 0.66 | 5.0 | 0.38 | 45000 | 6300 |
| 26 | 11 | 35 | 13 | 45000 | 8000 |
| 27 | 1.9 | 9.5 | 1.5 | 1111 | 1200 |
| 28 | 9.0 | 32 | 9.4 | 655.4 | >900 |
| 29 | 15 | 63 | 18 | 5156 | 20000 |
| 30 | 49 | 230 | 48 | 38800 | 21000 |
| 31 | 1.4 | 4.3 | 1.8 | 22000 | 100 |
| 32 | 0.51 | 2.5 | 0.60 | 15000 | 150 |
| 33 | 0.73 | 4.3 | 0.84 | 45000 | 110 |
| 34 | 1.4 | 5.1 | 1.5 | 5600 | 120 |
| 35 | 1.2 | 4.7 | 1.3 | 15000 | 150 |
| 36 | 170 | 740 | 150 | >900 | >900 |
| 37 | 1.4 | 8.5 | 1.18 | 45000 | 280 |
| 38 | 0.14 | 0.91 | 0.19 | 45000 | 2.9 |
| 39 | 0.10 | 0.57 | 0.13 | 45000 | 2.0 |
| 40 | 1.5 | 1.8 | 1.5 | 2000 | 3.3 |
| 41 | 0.39 | 2.6 | 0.71 | 3300 | 65 |
| 42 | 1.7 | 5.4 | 1.5 | 13000 | 27 |
| 43 | 0.20 | 1.0 | 0.25 | 1800 | 3.6 |
| 44 | 0.24 | 0.97 | 0.26 | 45000 | 5.7 |
| 45 | 8.9 | 76 | 19 | 45000 | 1200 |
| 46 | 1.7 | 9.6 | 1.5 | 45000 | 91 |
| 47 | 0.11 | 0.92 | 0.20 | 9100 | 5.0 |
| 48 | 0.18 | 1.0 | 0.15 | 45000 | 220 |
| 49 | 0.55 | 3.0 | 0.96 | 9100 | 6.8 |
| 50 | 0.99 | 3.2 | 1.3 | 1700 | 47 |
| 51 | 0.38 | 2.3 | 0.66 | 690 | 31 |
| 52 | 0.56 | 2.5 | 1.1 | 210 | 44 |
| 53 | 2.4 | 4.9 | 1.6 | 1100 | 92 |
| 54 | 2.0 | 6.3 | 1.5 | 960 | 88 |
| 55 | 0.30 | 2.1 | 0.48 | 140 | 41 |
| 56 | 0.40 | 1.8 | 0.37 | 45000 | 310 |
| 57 | 0.23 | 1.0 | 0.24 | 45000 | 150 |
| 58 | 0.18 | 0.90 | 0.18 | 45000 | 120 |
| 59 | 0.16 | 0.76 | 0.068 | 45000 | 16 |
| 60 | 0.13 | 0.41 | 0.093 | >900 | 1.7 |
| 61 | 0.25 | 0.88 | 0.23 | >900 | 3.1 |
| 62 | 1.2 | 4.9 | 0.77 | >900 | 7.0 |
| 63 | 0.54 | 2.1 | 0.46 | >900 | 3.8 |
| 64 | 0.58 | 2.1 | 0.64 | >900 | 3.5 |
| 65 | 2.2 | 11 | 2.2 | 45000 | 3100 |
| 66 | 4.4 | 15 | 3.1 | 45000 | 4400 |
| 67 | 1.8 | 4.3 | 1.5 | 45000 | 400 |
| 68 | 1.0 | 5.0 | 0.55 | >900 | 230 |
| 69 | 0.92 | 4.2 | 0.79 | >900 | 210 |
| 70 | 0.78 | 3.5 | 1.1 | >900 | 260 |
| 71 | 1.19 | 6.1 | 1.8 | >900 | 690 |
| 72 | 17 | 89 | 17 | >900 | >900 |
| 73 | 3.3 | 16 | 4.2 | 2500 | 3900 |
| 74 | 1.6 | 5.0 | 1.8 | 45000 | 4500 |
| 75 | 2.4 | 7.0 | 3.9 | 26000 | 3400 |
| 76 | 2.2 | 6.7 | 2.7 | >900 | >900 |
| 77 | 1.3 | 3.7 | 1.7 | >900 | >900 |
| 78 | 2.8 | 8.3 | 2.5 | 45000 | 6900 |
| 79 | 6.6 | 35 | 12 | 45000 | 17000 |
| 80 | 2.7 | 10 | 5.7 | 15000 | 3500 |
| 81 | 3.4 | 16 | 3.7 | 21000 | 4900 |
| 82 | 3.1 | 7.8 | 2.7 | 1500 | 1800 |
| 83 | 14 | 62 | 31 | 45000 | 12000 |
| 84 | 4.0 | 22 | 7.9 | 13000 | 3100 |

| Ex. # | HDAC1 IC$_{50}$ (nM) | HDAC2 IC$_{50}$ (nM) | HDAC3 IC$_{50}$ (nM) | HDAC6 IC$_{50}$ (nM) | HDAC8 IC$_{50}$ (nM) |
|---|---|---|---|---|---|
| 85 | 2.3 | 11 | 1.5 | 250 | 210 |
| 86 | 2.0 | 9.9 | 1.5 | 40 | 160 |
| 87 | 0.69 | 5.7 | 1.8 | 8600 | 130 |
| 88 | 0.22 | 1.4 | 0.37 | 45000 | 61 |
| 89 | 0.80 | 3.4 | 1.5 | 1700 | 69 |
| 90 | 0.14 | 0.82 | 0.14 | 26000 | 280 |
| 91 | 1.5 | 1.9 | 1.5 | 11000 | 14 |
| 92 | 0.92 | 6.2 | 1.1 | 4500 | 57 |
| 93 | 0.37 | 2.2 | 0.46 | 4500 | 3.5 |
| 94 | 0.26 | 1.0 | 0.24 | 20000 | 5.2 |
| 95 | 1.3 | 8.6 | 2.2 | 700 | 68 |
| 96 | 0.51 | 3.8 | 0.94 | 920 | 57 |
| 97 | 0.049 | 0.38 | 0.066 | 19000 | 210 |
| 98 | 0.34 | 3.6 | 0.64 | 1000 | 25 |
| 99 | 0.30 | 2.6 | 0.47 | 1300 | 56 |
| 100 | 0.45 | 1.3 | 0.28 | 620 | 130 |
| 101 | 1.5 | 1.5 | 1.5 | 45000 | 340 |
| 102 | 0.24 | 0.78 | 0.25 | >900 | 3.1 |
| 103 | 0.13 | 0.44 | 0.18 | >900 | 3.0 |
| 104 | 1.3 | 6.7 | 0.63 | >900 | 260 |
| 105 | 0.12 | 0.37 | 0.046 | 8500 | 29 |
| 106 | 51 | 101 | 23 | >900 | >900 |
| 107 | 0.20 | 0.82 | 0.17 | >900 | 32 |
| 108 | 0.18 | 0.35 | 0.19 | >900 | 5.8 |
| 109 | 7.5 | 39 | 7.5 | 23000 | 5000 |
| 110 | 0.18 | 0.87 | 0.18 | 2500 | 2.7 |
| 111 | 0.76 | 5.2 | 1.4 | 430 | 520 |
| 112 | 0.083 | 0.25 | 0.035 | 4600 | 23 |
| 113 | 0.41 | 2.5 | 0.58 | 200 | 180 |
| 114 | 26 | 120 | 13 | >900 | >900 |
| 115 | 0.66 | 3.9 | 0.84 | 300 | 51 |
| 116 | 4.8 | 9.7 | 1.5 | 4100 | 250 |
| 117 | 0.82 | 5.8 | 1.4 | 680 | 21 |
| 118 | 2.4 | 8.0 | 1.6 | 45000 | 300 |
| 119 | 96 | 420 | 100 | 45000 | 260 |
| 120 | 21 | 86 | 15 | 45000 | 210 |
| 121 | 15 | 61 | 14 | 45000 | 470 |
| 122 | 500 | 1600 | 570 | | |
| 123 | 25 | 81 | 20 | 45000 | 440 |
| 124 | 450 | 1200 | 480 | | |
| 125 | 3.1 | 21 | 3.1 | >900 | 600 |
| 126 | 5.5 | 14 | 5.5 | >900 | 100 |
| 127 | 480 | 2600 | 770 | | |
| 128 | 8.0 | 55 | 10 | 45000 | 4300 |
| 129 | 16 | 100 | 16 | 45000 | 2300 |
| 130 | 62 | 150 | 43 | >900 | 310 |
| 131 | 3.3 | 23 | 9.0 | >900 | >900 |
| 132 | 380 | 900 | 500 | >900 | >900 |
| 133 | 260 | 900 | 27 | >900 | >900 |
| 134 | | | | | |
| 135 | 91 | 450 | 85 | >900 | >900 |
| 136 | 110 | 380 | 100 | >900 | >900 |
| 137 | 61 | 240 | 45 | >900 | >900 |
| 138 | 4.3 | 37 | 3.9 | >900 | 250 |
| 139 | 5.6 | 28 | 5.9 | >900 | >900 |
| 140 | 1.0 | 6.0 | 1.3 | >900 | >900 |
| 141 | 4.0 | 28 | 4.3 | >900 | >900 |
| 142 | 10 | 61 | 7.5 | >900 | 560 |
| 143 | 7.2 | 35 | 7.9 | >900 | >900 |
| 144 | 7.0 | 39 | 6.4 | >900 | 210 |
| 145 | 3.4 | 14 | 4.2 | >900 | 5.1 |
| 146 | 5.3 | 16 | 2.3 | 45000 | 96 |
| 147 | 0.70 | 3.8 | 1.4 | 15000 | 120 |
| 148 | 0.75 | 6.5 | 1.7 | 3400 | 63 |
| 149 | 1.7 | 6.6 | 1.5 | 21000 | 140 |
| 150 | 2.1 | 8.8 | 1.5 | 2700 | 120 |
| 151 | 2.0 | 7.8 | 1.5 | 41000 | 57 |
| 152 | 0.68 | 5.8 | 1.6 | 12000 | 78 |
| 153 | 8.5 | 15 | 4.2 | 45000 | 167 |
| 154 | 5.1 | 20 | 2.0 | 45000 | 110 |
| 155 | 0.81 | 5.3 | 1.3 | 35000 | 53 |
| 156 | 1.1 | 5.4 | 1.1 | 1400 | 55 |
| 157 | 0.64 | 4.1 | 1.0 | 380 | 28 |
| 158 | 1.1 | 5.6 | 1.5 | 590 | 48 |
| 159 | 0.82 | 5.8 | 1.7 | 2900 | 58 |
| 160 | 1.2 | 5.5 | 0.54 | >900 | 71 |
| 161 | 1.7 | 11 | 0.57 | >900 | 44 |
| 162 | 4.2 | 24 | 1.5 | >900 | 300 |
| 163 | 1.6 | 8.4 | 0.53 | >900 | 38 |
| 164 | 3.3 | 18 | 0.87 | >900 | 74 |
| 165 | 2.3 | 7.2 | 0.46 | >900 | 41 |
| 166 | 1.7 | 6.2 | 0.56 | 660 | 75 |
| 167 | 2.2 | 13 | 0.59 | >900 | 63 |
| 168 | 3.0 | 12 | 1.2 | >900 | 120 |
| 169 | 3.4 | 15 | 1.2 | >900 | 180 |
| 170 | 4.1 | 17 | 1.6 | >900 | 220 |
| 171 | 11 | 56 | 4.0 | >900 | 340 |
| 172 | 20 | 100 | 6.4 | >900 | 490 |
| 173 | 1.1 | 3.2 | 0.43 | >900 | 83 |
| 174 | 1.4 | 3.7 | 0.54 | >900 | 110 |
| 175 | 0.14 | 0.68 | 0.11 | >900 | 17 |
| 176 | 2.1 | 9.7 | 3.1 | >900 | 2.0 |
| 177 | 0.61 | 4.6 | 1.2 | >900 | 6 |
| 178 | 2.0 | 7.8 | 1.5 | 5300 | 83 |
| 179 | 2.3 | 7.1 | 1.5 | 4300 | 65 |
| 180 | 0.90 | 5.2 | 1.5 | >900 | 170 |
| 181 | 2.6 | 13 | 1.0 | >900 | 12 |
| 182 | 2.0 | 9.1 | 0.79 | >900 | 5.6 |
| 183 | 0.56 | 2.3 | 0.48 | 43000 | 550 |
| 184 | 0.41 | 1.4 | 0.48 | >900 | 210 |
| 185 | 2.9 | 15 | 3.9 | 45000 | 6700 |
| 186 | 0.28 | 1.7 | 0.39 | 45000 | 220 |
| 187 | 0.16 | 0.83 | 0.16 | 45000 | 170 |
| 188 | 0.19 | 2.6 | 0.44 | 45000 | 37 |
| 189 | 26 | 250 | 45 | 45000 | 25000 |
| 190 | 4.6 | 21 | 3.2 | 45000 | 3200 |
| 191 | 2.5 | 12 | 1.9 | 45000 | 2300 |
| 192 | 9.1 | 45 | 5.5 | 45000 | 1700 |
| 193 | 1.8 | 7.4 | 1.8 | 45000 | 1600 |
| 194 | 0.20 | 0.69 | 0.10 | 9500 | 19 |
| 195 | 0.14 | 0.32 | 0.046 | 3100 | 9.6 |
| 196 | 0.18 | 0.58 | 0.087 | 4600 | 8.7 |

KARN Assay

Cell Maintenance

KARN cells (Jurkat 2C4) were licensed from the laboratory of Dr. John Karn, Case Western Reserve University, School of Medicine. The details regarding this cell line are published (Pearson, R., Kin, Y. K., Hokello, J., Lassen, K., Friedman, J., Tyagi, M., Karn, J., 2008, *J. Virol.* 82:12291-12303). The cells were grown in a T175 flask (Thermo Fisher, catalog number 159910) in RPMI 1640 containing L-glutamine and phenol red (Life Technologies, catalog number 11875-085), 5% heat inactivated fetal bovine serum (FBS; Life Technologies, catalog number 10100-147) and 100 μg/ml Penicillin-Streptomycin (Life Technologies, catalog number 15140-122) at 37° C. An atmosphere of 5% $CO_2$ and 90% humidity was used for all culture work. Cells were split and reseeded into T175 flasks at a density of $0.2 \times 10^6$ cells/ml, in 40 ml of media, every 3-4 days.

KARN Assay

Day 1: After the 3-4 day growth period, the cells were transferred from the T175 flask to a 50 ml conical tube and gently pelleted at 1000 rpm for 5 minutes. The supernatant was removed and the cells gently resuspended in assay media RPMI 1640 medium containing L-glutamine but without Phenol Red (Life Technologies, catalog number 11835-030), 5% FBS and 100 μg/ml Penicillin-Streptomycin, and then reseeded such that the original flask is now divided into two T175 flasks. These flasks were returned to the incubator.

Day 2: Cell Preparation: The next day, the cells were transferred from each T175 flask to an individual 50 ml conical tube and gently pelleted at 1000 rpm for 5 minutes. The cells were gently resuspended in assay media (30 ml)

and pelleted again. The cell pellets were each resuspended in 30 ml of RPMI 1640 medium containing L-glutamine but without Phenol Red, 100 µg/ml Penicillin-Streptomycin and containing either 0.1% or 5% normal human serum (NHS; Biospecialty, catalog number 115-00 Anticoagulant free). The cells were counted using the ViCell (Beckman Coulter) and diluted as necessary. A Multidrop (Combi, Thermo Scientific) with a sterile head was used to seed the cells into the wells of a 384-well solid black plate with lid (Perkin Elmer, catalog number 6007660) at 4000 cells/30 µl/well for the 5% NHS assay media and 6000 cells/30 µl/well for 0.1% NHS assay. The plates were covered and returned to the incubator prior to compound addition.

Compound Preparation: Solutions of control inhibitor suberoylanilide hydroxamic acid (SAHA; Sigma, catalog number SML0061) and test compounds in 100% DMSO were titrated into 384-well polypropylene plates (Labcyte, catalog number P-05525) using a 20-point dose response and 2-fold dilutions. The reference compounds, DMSO and SAHA were then added to the compound plate. Using the Access system (Labcyte), 120 nl of these inhibitor and control solutions were added to the individual wells of the plates containing the cells, and the plates were then returned to the incubator for ~20 hr (range from 18-24 hr). The final high concentration for SAHA and the test compounds in the assays was 40 µM. The final DMSO concentration in all wells was 0.4%. The minimal induction reference compound used was DMSO and the maximal induction reference compound used was SAHA (2 µM final concentration in the assay).

Day 3: The luciferase detection reagent was prepared by transferring the contents of one bottle of Steady-Glo buffer to one bottle of Steady-Glo aubstrate (Steady-Glo Luciferase Assay System, Promega, catalog number E2520), followed by gently mixing until the substrate was thoroughly dissolved and the solution was equilibrated to room temperature. The cell culture assay plates were removed from the incubator and brought to room temperature (15 min). The Steady-Glo Reagent was added to the plates (30 µl/well), which were then covered with a black lid and incubated for 10 minutes at room temperature. The plates were then read for luminescence on an Envision (Perkin Elmer) using the ultrasensitive mode (US LUM), 0.1 counts per second and 384-well aperture. Luminescence counts in the DMSO reference wells were considered as 0% induction, while those in the 2 µM SAHA reference wells were considered as 100% induction. Dose response curves were plotted as test compound concentration (X-axis) vs. percent activation (Y-axis) using a 4-parameter fit based on the Levenberg-Marquardt algorithm.

All HIDAC inhibitors were tested in the KARN assays for their cell functional activity:

| Ex. # | Karn $EC_{50}$ nM 0.1% NHS | Karn $EC_{50}$ nM 5% NHS |
| --- | --- | --- |
| 1 | 37 | 39 |
| 2 | 44 | 97 |
| 3 | 18 | 26 |
| 4 | | |
| 5 | 63 | 130 |
| 6 | 87 | 160 |
| 7 | 23 | 8400 |
| 8 | 2000 | 2300 |
| 9 | 160 | 160 |
| 10 | 300 | 450 |
| 11 | 620 | 670 |
| 12 | 66 | 80 |
| 13 | 94 | 140 |
| 14 | 390 | 270 |
| 15 | 180 | 670 |
| 16 | 120 | 170 |
| 17 | 650 | 590 |
| 18 | 93 | 130 |
| 19 | 210 | 420 |
| 20 | 450 | 340 |
| 21 | 110 | 110 |
| 22 | 130 | 290 |
| 23 | 100 | 210 |
| 24 | 1400 | 2000 |
| 25 | 340 | 650 |
| 26 | 6200 | 6900 |
| 27 | 120 | 140 |
| 28 | 1900 | 2000 |
| 29 | 1800 | 1800 |
| 30 | 2500 | 4000 |
| 31 | 18 | 26 |
| 32 | 26 | 35 |
| 33 | 61 | 84 |
| 34 | 23 | 44 |
| 35 | 72 | 50 |
| 36 | 24000 | 40000 |
| 37 | 74 | 180 |
| 38 | 5.7 | 3.5 |
| 39 | 3.0 | 4.0 |
| 40 | 15 | 58 |
| 41 | 16 | 140 |
| 42 | 52 | 340 |
| 43 | 8.5 | 14 |
| 44 | 9.5 | 9.1 |
| 45 | 460 | 1900 |
| 46 | 31 | 44 |
| 47 | 3.7 | 10 |
| 48 | 28 | 69 |
| 49 | 29 | 81 |
| 50 | 21 | 140 |
| 51 | 11 | 56 |
| 52 | 23 | 81 |
| 53 | 26 | 220 |
| 54 | 76 | 680 |
| 55 | 12 | 32 |
| 56 | 6.4 | 11 |
| 57 | 5.5 | 13 |
| 58 | 6.8 | 11 |
| 59 | 18 | 20 |
| 60 | 4.2 | 9.0 |
| 61 | 3.6 | 5.8 |
| 62 | 50 | 100 |
| 63 | 11 | 32 |
| 64 | 16 | 28 |
| 65 | 470 | 630 |
| 66 | 380 | 530 |
| 67 | 51 | 95 |
| 68 | 34 | 110 |
| 69 | 96 | 260 |
| 70 | 31 | 110 |
| 71 | 330 | 490 |
| 72 | 650 | 1900 |
| 73 | 840 | 15 |
| 74 | 140 | 200 |
| 75 | 300 | 220 |
| 76 | 200 | 220 |
| 77 | 120 | 120 |
| 78 | 660 | 620 |
| 79 | 1000 | 1300 |
| 80 | 550 | 680 |
| 81 | 430 | 690 |
| 82 | 180 | 320 |
| 83 | 3400 | 4200 |
| 84 | 490 | 540 |
| 85 | 67 | 210 |
| 86 | 80 | 160 |

| Ex. # | Karn EC$_{50}$ nM 0.1% NHS | Karn EC$_{50}$ nM 5% NHS |
|---|---|---|
| 87 | 43 | 60 |
| 88 | 25 | 380 |
| 89 | 13 | 32 |
| 90 | 14 | 34 |
| 91 | 17 | 22 |
| 92 | 32 | 64 |
| 93 | 6.6 | 14 |
| 94 | 3.8 | 8.8 |
| 95 | 63 | 84 |
| 96 | 14 | 24 |
| 97 | 4.1 | 11 |
| 98 | 58 | 170 |
| 99 | 77 | 73 |
| 100 | 19 | 21 |
| 101 | 27 | 22 |
| 102 | 170 | 270 |
| 103 | 6.0 | 8.3 |
| 104 | 40 | 44 |
| 105 | 2.8 | 3.5 |
| 106 | 3300 | 2100 |
| 107 | 14 | 14 |
| 108 | 6.4 | 6.1 |
| 109 | 1700 | 2500 |
| 110 | 11 | 11 |
| 111 | 70 | 48 |
| 112 | 1.4 | 1.4 |
| 113 | 18 | 12 |
| 114 | 3400 | 4200 |
| 115 | 37 | 58 |
| 116 | 95 | 120 |
| 117 | 320 | 320 |
| 118 | 780 | 1600 |
| 119 | 10000 | |
| 120 | 1300 | 1400 |
| 121 | 3500 | 4300 |
| 122 | | |
| 123 | 1500 | 3600 |
| 124 | | |
| 125 | 1200 | 1700 |
| 126 | 170 | 250 |
| 127 | | |
| 128 | 1200 | 1500 |
| 129 | 1600 | 2900 |
| 130 | 1600 | 4600 |
| 131 | 1300 | 1500 |
| 132 | 25000 | 30000 |
| 133 | 23000 | 25000 |
| 134 | | |
| 135 | 5600 | 13000 |
| 138 | 2200 | 3400 |
| 139 | 1700 | 2700 |
| 140 | 390 | 860 |
| 141 | 2400 | 3500 |
| 142 | 1200 | 270 |
| 143 | 1200 | 1600 |
| 144 | 650 | 870 |
| 145 | 49 | 66 |
| 146 | 130 | 440 |
| 147 | 50 | 490 |
| 148 | 54 | 450 |
| 149 | 69 | 360 |
| 150 | 94 | 500 |
| 151 | 68 | 790 |
| 152 | 49 | 350 |
| 153 | 100 | 560 |
| 154 | 120 | 570 |
| 155 | 50 | 600 |
| 156 | 88 | 420 |
| 157 | 77 | 380 |
| 158 | 210 | 210 |
| 159 | 1500 | 2900 |
| 160 | 48 | 120 |
| 161 | 75 | 210 |
| 162 | 650 | 1200 |
| 163 | 84 | 210 |
| 164 | 85 | 290 |
| 165 | 370 | 760 |
| 166 | 77 | 200 |
| 167 | 83 | 400 |
| 168 | 100 | 200 |
| 169 | 99 | 270 |
| 170 | 160 | 260 |
| 171 | 180 | 470 |
| 172 | 340 | 990 |
| 173 | 42 | 74 |
| 174 | 37 | 80 |
| 175 | 13 | 19 |
| 176 | 14 | 13 |
| 177 | 33 | 55 |
| 178 | 80 | 1000 |
| 179 | 36 | 48 |
| 180 | 200 | 190 |
| 181 | 84 | 630 |
| 182 | 41 | 190 |
| 183 | 37 | 37 |
| 184 | 56 | 57 |
| 185 | 250 | 690 |
| 186 | 12 | 21 |
| 187 | 20 | 25 |
| 188 | 22 | 120 |
| 189 | 3000 | 7400 |
| 190 | 240 | 260 |
| 191 | 110 | 100 |
| 192 | 750 | 930 |
| 193 | 130 | 1800 |
| 194 | 3.2 | 15 |
| 195 | 1.4 | 1.9 |
| 196 | 3.8 | 7.5 |

Treatment or Prevention of HIV Infection

The Compounds of Formula I may be useful in the activation of HIV latency, the the treatment of HIV infection and/or reduction of the likelihood or severity of symptoms of HIV infection and the inhibition of HIV viral replication and/or HIV viral production in a cell-based system. For example, the Compounds of Formula I may be useful in treating infection by HIV after suspected past exposure to HIV by such means as blood transfusion, exchange of body fluids, bites, accidental needle stick, or exposure to subject blood during surgery or other medical procedures.

Accordingly, in one embodiment, the invention provides methods for treating HIV infection in a subject, the methods comprising administering to the subject an effective amount of at least one Compound of Formula I or a pharmaceutically acceptable salt or prodrug thereof. In a specific embodiment, the amount administered is effective to treat or prevent infection by HIV in the subject. In another specific embodiment, the amount administered is effective to inhibit HIV viral replication and/or viral production in the subject. In one embodiment, the HIV infection has progressed to AIDS.

The Compounds of Formula I are also useful in the preparation and execution of screening assays for antiviral compounds. For example the Compounds of Formula I may be useful for identifying resistant HIV cell lines harboring mutations, which are excellent screening tools for more powerful antiviral compounds. Furthermore, the Compounds of Formula I may be useful in establishing or determining the binding site of other antivirals to the HIV Integrase.

The compositions and combinations of the present invention may be useful for treating a subject suffering from infection related to any HIV genotype.

Combination Therapy

In another embodiment, the present methods for treating or preventing HIV infection can further comprise the administration of one or more additional therapeutic agents which are not Compounds of Formula I.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: I at least one Compound of Formula I (which may include two or more different Compounds of Formula I), or a pharmaceutically acceptable salt or prodrug thereof, and (ii) at least one additional therapeutic agent that is other than a Compound of Formula I, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Tricyclic Heterocycle Compound and an additional therapeutic agent may be present in fixed amounts (dosage amounts) in a single dosage unit (e.g., a capsule, a tablet and the like).

In one embodiment, at least one Compound of Formula I is administered during a time when the additional therapeutic agent(s) exert their prophylactic or therapeutic effect, or vice versa.

In another embodiment, at least one Compound of Formula I and the additional therapeutic agent(s) are administered in doses commonly employed when such agents are used as monotherapy for treating a viral infection.

In another embodiment, at least one Compound of Formula I and the additional therapeutic agent(s) are administered in doses lower than the doses commonly employed when such agents are used as monotherapy for treating a viral infection.

In still another embodiment, at least one Compound of Formula I and the additional therapeutic agent(s) act synergistically and are administered in doses lower than the doses commonly employed when such agents are used as monotherapy for treating a viral infection.

In one embodiment, at least one Compound of Formula I and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that may be treated or prevented using the combination therapy methods of the present invention include, but are not limited to, those listed above.

In one embodiment, the viral infection is HIV infection.

In another embodiment, the viral infection is AIDS.

The at least one Compound of Formula I and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Compound of Formula I and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS. Suitable HIV antivirals for use in combination with the compounds of the present invention include, for example, those listed in Table A as follows:

TABLE A

| Name | Trade Name |
|---|---|
| abacavir, ABC | Ziagen ® |
| abacavir + lamivudine | Epzicom ® |
| abacavir + lamivudine + zidovudine | Trizivir ® |
| amprenavir | Agenerase ® |
| atazanavir | Reyataz ® |
| AZT, zidovudine, azidothymidine | Retrovir ® |
| darunavir | Prezista ® |
| ddC, zalcitabine, dideoxycytidine | Hivid ® |
| ddI, didanosine, dideoxyinosine | Videx® |
| ddI (enteric coated) | Videx EC ® |
| delavirdine, DLV | Rescriptor ® |
| dolutegravir | Tivicay ® |
| doravirine | |
| efavirenz, EFV | Sustiva ®, Stocrin ® |
| efavirenz + emtricitabine + tenofovir DF | Atripla ® |
| EFdA (4'-ethynyl-2-fluoro-2'-deoxyadenosine) | |
| emtricitabine, FTC | Emtriva ® |
| emtricitabine + tenofovir DF | Truvada ® |
| emvirine | Coactinon ® |
| enfuvirtide | Fuzeon ® |
| enteric coated didanosine | Videx EC ® |
| etravirine, TMC-125 | Intelence ® |
| fosamprenavir calcium | Lexiva ® |
| indinavir | Crixivan ® |
| lamivudine, 3TC | Epivir ® |
| lamivudine + zidovudine | Combivir ® |
| lopinavir | |
| lopinavir + ritonavir | Kaletra ® |
| maraviroc | Selzentry ® |
| nelfinavir | Viracept ® |
| nevirapine, NVP | Viramune ® |

TABLE A-continued

| Name | Trade Name |
| --- | --- |
| raltegravir | Isentress ® |
| rilpivirine, TMC-278 | Edurant ® |
| ritonavir | Norvir ® |
| saquinavir | Invirase ®, Fortovase ® |
| stavudine, d4T, didehydrodeoxythymidine | Zerit ® |
| tenofovir DF (DF = disoproxil fumarate), TDF | Viread ® |
| tipranavir | Aptivus ® |

Some of the drugs listed in the table are used in a salt form; e.g., abacavir sulfate, indinavir sulfate, atazanavir sulfate, nelfinavir mesylate.

In one embodiment, one or more anti-HIV drugs are selected from, raltegravir, lamivudine, abacavir, ritonavir, darunavir, atazanavir, emtricitabine, tenofovir, rilpivirine, doravirine, EFdA and lopinavir.

In another embodiment, the compound of formula I is used in combination with raltegravir.

In another embodiment, the compound of formula I is used in combination with lamivudine.

In still another embodiment, the compound of formula I is used in combination atazanavir.

In another embodiment, the compound of formula I is used in combination with darunavir.

In another embodiment, the compound of formula I is used in combination with rilpivirine.

In one embodiment, the compound of formula I is used in combination with lamivudine and abacavir.

In another embodiment, the compound of formula I is used in combination with EFdA.

In another embodiment, the compound of formula I is used in combination with emtricitabine and tenofovir.

In still another embodiment, the compound of formula I is used in combination doravirine.

In another embodiment, the compound of formula I is used in combination with ritonavir and lopinavir.

In one embodiment, the compound of formula I is used in combination with abacavir and lamivudine.

In another embodiment, the compound of formula I is used in combination with lopinavir and ritonavir.

In one embodiment, the present invention provides pharmaceutical compositions comprising (i) a compound of formula I or a pharmaceutically acceptable salt or prodrug thereof, (ii) a pharmaceutically acceptable carrier; and (iii) one or more additional anti-HIV agents selected from lamivudine, abacavir, ritonavir and lopinavir, or a pharmaceutically acceptable salt or prodrug thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula I or a pharmaceutically acceptable salt or prodrug thereof and (ii) one or more additional anti-HIV agents selected from lamivudine, abacavir, ritonavir and lopinavir, or a pharmaceutically acceptable salt or prodrug thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, $57^{th}$ edition (2003), the $58^{th}$ edition (2004), the $59^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection may be determined by the attending clinician, taking into consideration the approved doses and dosage regimen in the package insert; the age, sex and general health of the subject; and the type and severity of the viral infection or related disease or disorder. When administered in combination, the Tricyclic Heterocycle Compound(s) and the other agent(s) may be administered simultaneously (i.e., in the same composition or in separate compositions one right after the other) or sequentially. This is particularly useful when the components of the combination are given on different dosing schedules, e.g., one component is administered once daily and another component is administered every six hours, or when the pharmaceutical compositions are different, e.g., one is a tablet and one is a capsule. A kit comprising the separate dosage forms is therefore advantageous.

Compositions and Administration

When administered to a subject, the Compounds of Formula I may be administered as a component of a composition that comprises a pharmaceutically acceptable carrier or vehicle. The present invention provides pharmaceutical compositions comprising an effective amount of at least one Compound of Formula I and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules may be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methyl-cellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Compounds of Formula I are administered orally.

In another embodiment, the one or more Compounds of Formula I are administered intravenously.

In one embodiment, a pharmaceutical preparation comprising at least one Compound of Formula I is in unit dosage form. In such form, the preparation is subdivided into unit doses containing effective amounts of the active components.

Compositions may be prepared according to conventional mixing, granulating or coating methods, respectively, and the present compositions can contain, in one embodiment, from about 0.1% to about 99% of the Compound(s) of Formula I by weight or volume. In various embodiments, the present compositions can contain, in one embodiment, from about 1% to about 70% or from about 5% to about 60% of the Compound(s) of Formula I by weight or volume.

The compounds of Formula I may be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions may be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The unit dosages of the Compounds of Formula I may be administered at varying frequencies. In one embodiment, a unit dosage of a Compound of Formula I may be administered once daily. In another embodiment, a unit dosage of a Compound of Formula I may be administered twice weekly. In another embodiment, a unit dosage of a Compound of Formula I may be administered once weekly. In still another embodiment, a unit dosage of a Compound of Formula I may be administered once biweekly. In another embodiment, a unit dosage of a Compound of Formula I may be administered once monthly. In yet another embodiment, a unit dosage of a Compound of Formula I may be administered once bimonthly. In another embodiment, a unit dosage of a Compound of Formula I may be administered once every 3 months. In a further embodiment, a unit dosage of a Compound of Formula I may be administered once every 6 months. In another embodiment, a unit dosage of a Compound of Formula I may be administered once yearly.

The amount and frequency of administration of the Compounds of Formula I will be regulated according to the judgment of the attending clinician considering such factors as age, condition and size of the subject as well as severity of the symptoms being treated. The compositions of the invention can further comprise one or more additional therapeutic agents, selected from those listed above herein.

Kits

In one aspect, the present invention provides a kit comprising a therapeutically effective amount of at least one Compound of Formula I, or a pharmaceutically acceptable salt or prodrug of said compound and a pharmaceutically acceptable carrier, vehicle or diluent.

In another aspect the present invention provides a kit comprising an amount of at least one Compound of Formula I, or a pharmaceutically acceptable salt or prodrug of said compound and an amount of at least one additional therapeutic agent listed above, wherein the amounts of the two or more active ingredients result in a desired therapeutic effect. In one embodiment, the one or more Compounds of Formula I and the one or more additional therapeutic agents are provided in the same container. In one embodiment, the one or more Compounds of Formula I and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound of the formula:

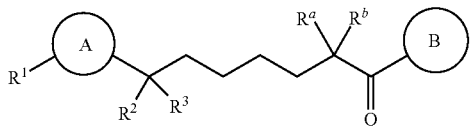

wherein

is a five-membered heteroaryl ring which is optionally substituted with halo, cyano or $C_{1-3}$ alkyl;

is a-five-membered heteroaryl ring selected from the group consisting of isoxazolyl, oxazolyl, or thiazolyl, which is optionally substituted with $C_{1-3}$ alkyl;
$R^1$ is phenyl or heteroaryl, which may be monocyclic or bicyclic, wherein said phenyl and heteroaryl groups are optionally substituted with one to three groups independently selected from the group consisting of halo, oxo, cyano, $R^4$, $R^6$, $OR^4$, $OR^6$ and $SO_2R^4$;
$R^2$ is selected from the group consisting of hydrogen, $NH(C=O)R^6$, $NH(C=O)CH_2R^6$, $NH(C=O)R^4$, $NH(C=O)R^5$, $NH(C=O)OR^5$, $NH_2$, $NHR^4$, $NHR^6$, $NHCH_2R^6$ and $R^6$;
$R^3$ is selected from hydrogen or $C_{1-6}$ alkyl;
or $R^2$ and $R^3$ can be taken together with the atoms to which they are attached to form a 5, 6 or 7 membered heterocyclyl group which is optionally substituted with oxo;
each $R^4$ is independently hydrogen or $C_{1-6}$ alkyl, which is optionally substituted with one to three halo;
each $R^5$ is independently hydrogen or $C_{1-6}$ alkyl, which is optionally substituted with $N(R^4)_2$ or $OR^4$;
$R^6$ is
(a) heterocyclyl, which may be monocyclic or bicyclic,
(b) $C_{3-6}$ cycloalkyl, or
(c) heteroaryl, which may be monocyclic or bicyclic,
wherein said $R^6$ heterocyclyl, cycloalkyl, and heteroaryl groups are optionally substituted with one to two groups independently selected from the group of oxo, $R^5$, $OR^4$ and heteroaryl;
$R^a$ is hydrogen or halo;
$R^b$ is hydrogen or halo;
or a pharmaceutically acceptable salt thereof.

2. The compound of claim 1 wherein

is selected from imidazolyl, isoxazolyl, oxadiazolyl, oxazolyl, pyrazolyl or triazolyl, wherein said groups are optionally substituted with halo, cyano or $C_{1-3}$ alkyl; or a pharmaceutically acceptable salt thereof.

3. The compound of claim 1 wherein $R^1$ is imidazolyl, isoquinolinyl, napthyridinyl, phenyl, pyrazinyl, pyridinyl, quinolinyl or quinoxalinyl, wherein said groups are optionally substituted with one to three groups optionally selected from the group consisting of halo, oxo, cyano, $R^4$, $R^6$, $OR^4$, $OR^6$ and $SO_2R^4$; or a pharmaceutically acceptable salt thereof.

4. The compound of claim 1 wherein $R^2$ is $NH(C=O)R^6$ or $NH(C=O)CH_2R^6$, and $R^6$ is selected from the group consisting of azaindolyl, azaspirononanyl, azaspirooctanyl, azetidinyl, benzisoxazolyl, cyclobutyl, cyclopentyl, cyclopropyl, dihydrobenzodioxinyl, dihydropyrazoloxazinyl, dihydropyrazolyothiazinedioxidyl, dioxanyl, morpholinyl, oxadiazaspirodecenyl, oxaspirooctanyl, oxazolidinonyl, oxazolyl, piperazinyl, piperidinyl, pyrazolopyrimidinyl, pyrazolyl, pyrimidinyl, pyrrolidinyl, pyrrolyl, tetrahydrofuranyl, tetrahydropyranyl and thiazolyl; or a pharmaceutically acceptable salt thereof.

5. The compound of claim 1 wherein $R^2$ is $NH_2$, or a pharmaceutically acceptable salt thereof.

6. A compound selected from the group consisting of
(S)-N-(1-(4-(4-fluorophenyl)-1H-imidazol-2-yl)-7-(oxazol-2-yl)-7-oxoheptyl)-1-methylazetidine-3-carboxamide,
(S)-N-(1-(4-(4-fluorophenyl)-1H-imidazol-2-yl)-7-(oxazol-2-yl)-7-oxoheptyl)thiazole-5-carboxamide,
(S)-N-(1-(4-(4-fluorophenyl)-1H-imidazol-2-yl)-7-(oxazol-2-yl)-7-oxoheptyl)methylpiperidine-4-carboxamide,
(S)-N-((S)-(1-(4-(4-fluorophenyl)-1H-imidazol-2-yl)-7-(oxazol-2-yl)-7-oxoheptyl)-6-methyl-6-azaspirol[2.5]octane-1-carboxamide,
N-((S)-(1-(4-(4-fluorophenyl)-1H-imidazol-2-yl)-7-(oxazol-2-yl)-7-oxoheptyl)-6-oxaspiro[2.5]octane-1-carboxamide,
(S)-N-(1-(4-(4-fluorophenyl)-1H-imidazol-2-yl)-7-oxo-7-(thiazol-2-yl)heptyl)-1-methylpiperidine-4-carboxamide,
(S)-N-(1-(4-(4-fluorophenyl)-1H-imidazol-2-yl)-7-oxo-7-(thiazol-2-yl)heptyl)thiazole-5-carboximide,
(S)-N-(1-(4-(4-fluorophenyl)-1H-imidazol-2-yl)-7-(4-methyloxazol-2-yl)-7-oxoheptyl)-1-methylpiperdine-4-carboxamide,
(S)-7-amino-7-(4-(2-methylquinolin-6-yl)-1H-imidazol-2-yl)-1-(oxazol-2-yl)heptan-1-one,
(S)-6-(2-(1-amino-7-(oxazol-2-yl)-7-oxoheptyl)-1H-imidazol-4-yl)-2-ethylisoquinolin-1(2H)-one,
(S)-7-amino-1-(oxazol-2-yl)-7-(5-(quinoline-6-yl)-1H-imidazol-2-yl)heptan-1-one, 16
(S)-7-amino-7-(4-(7-methoxyquinolin-6-yl)-1H-imidazol-2-yl)-1-(oxazol-2-yl)heptan-1-one,
(S)-7-amino-7-(4-(6-cyclopropyl-2-methoxypyridin-3-yl)-1H-imidazol-2-yl)-1-(oxazol-2-yl)heptan-1-one,
(S)-7-amino-7-(4-chloro-2-(4_fluorophenyl)-1H-imidazol-5-yl)-1-(oxazol-2-yl)heptan-1-one,
7-amino-7-(5-(2-methylquinonlin-6-yl)oxazol-2-yl)-1-(oxazol-2-yl)heptan-1-one,
(S)-7-amino-7-(5-(7-methoxy-2-methylquinolin-6-yl_oxazol-2-yl)-1-(oxazol-2-yl)heptan-1-one,
(S)-7-amino-7-(5-(2-methoxypiperdin-3-yl)oxazol-2-yl)-1-(oxazol-2-yl)heptan-1-one,
(S)-7-amino-7-(-methyl-4-(2-methylquinolin-6-yl)-1H-imidazol-2-yl)-1-(oxazol-2-yl)heptan-1-one,
(S)-7-amino-(1-ethyl-4-(2-methylquinolin-6-yl)-1H-imidazol-2-yl)-1-(oxazol-2-yl)heptan-1-one, (S)-7-amino-1-(isoxazole-3-yl)-7-(4-(7-methoxy-2-methylquinolin-6-yl)-1H-imidazol-2-yl)heptan-1-one,
(S)-6-(2-(I-amino-7-(isoxazol-3-yl)-7-oxoheptyl)-1H-imidazol-4-yl)-1-methylquinolin-2(1H)-one,
(S)-7-amino-1-(isoxazol-3-yl)-7-(4-(2-methoxypyridin-3-yl)-1H-imidazol-2-yl)heptan-1-one,
(S)-7-amino-1-(isoxazol-3-yl)-7-(4-(7-methoxyquinolin-6-yl)-1H-imidazol-2-yl)heptan-1-one,
(S)-6-(2-(1-amino-7-(isoxazol-3-yl)-7-oxoheptyl)-1H-imidazol-5-yl)-7-methoxy-1-methylquinolin-2(1H)-one,
(S)-7-amino-7-(5-(2-fluorophenyl)-1H-imidazol-2-yl)-1-(oxazol-4-yl)heptan-1-one,
(S)-7-amino-7-(5-(2-fluorophenyl)-1H-imidazol-2-yl)-1-(isoxazol-3-yl)heptan-1-one,
(S)-N-(1-(5-(2-fluorophenyl)-1H-imidazol-2-yl)-7-(isoxazol-3-yl)-7-oxoheptyl)-1-methylazetidine-3-carboxamide,
(R)-5-(5-(4-fluorophenyl)-1H-imidazol-2-yl)-5-(6-(oxazol-2-yl)-6-oxohexyl)pyrrolidin-2-one,
4-(4-(4-fluorophenyl)-1H-imidazol-2-yl)-4-(6-(oxazol-2-yl)-6-oxohexyl)oxazolidin-2-one,
(S)-5-(4-(2-fluoro-4-(oxazol-2-yl)phenyl)-1H-imidazol-2-yl)-5-(6-(isoxazol-3-yl)-6-oxohexyl)pyrrolidin-2-one,
(S)-5-(4-(4-cyclopropyl-2-fluorophenyl)-1H-imidazol-2-yl)-5-(6-(isoxazol-3-yl)-6-oxohexyl)pyrrolidin-2-one,
(S)-5-(4-(2-fluorophenyl)-1H-imidazol-2-yl)-5-(6-(isoxazol-3-yl)-6-oxohexyl)pyrrolidin-2-one,
(R)-5-(6-(isoxazol-3-yl)-6-oxohexyl)-5-(5-(7-methoxy-2-methylquinolin-6-yl)-1H-imidazol-2-yl)pyrrolidin-2-one,
(S)-6-(6-(isoxazol-3-yl)-6-oxohexyl)-6-(4-(2-methoxypyridin-3-yl)-1H-imidazol-2-yl)piperidin-2-one,
(S)-7-(4-(2-fluorophenyl)-1H-imidazol-2-yl)-7-(6-(isoxazol-3-yl)-6-oxohexyl)azepan-2-one,
7-(5-(2-methoxyquinolin-3-yl)-1H-imidazol-2-yl)-1-(oxazol-2-yl)heptan-1-one,
(S)-7-(ethyl amino)-7-(5-(2-methylquinolin-6-yl)-1H-imidazol-2-yl)-1-(oxazol-2-yl)heptan-1-one,
(S)-7-(methylamino)-7-(5-(2-methylquinolin-6-yl)-1H-imidazol-2-yl)-1-(oxazol-2-yl)heptan-1-one,
(S)-7-methoxy-1-methyl-6-(2-(1-(methylamino)-7-(oxazol-2-yl)-7-oxoheptyl)-1H-imidazol-5-yl)quinolin-2(1H)-one,
(S)-6-(2-(1-(ethyl amino)-7-(oxazol-2-yl)-7-oxoheptyl)-1H-imidazol-5-yl)-7-methoxy-1-methylquinolin-2(1H)-one,
(S)-7-((1-methylpiperidin-4-yl)amino)-7-(5-(2-methylquinolin-6-yl)-1H-imidazol-2-yl)-1-(oxazol-2-yl)heptan-1-one,
(S)-7-(5-(2-methylquinolin-6-yl)-1H-imidazol-2-yl)-1-(oxazol-2-yl)-7-((tetrahydro-2H-pyran-4-yl)amino)heptan-1-one,
(S)-7-(5-(7-methoxy-2-methylquinolin-6-yl)-1H-imidazol-2-yl)-1-(oxazol-2-yl)-7-((tetrahydro-2H-pyran-4-yl)amino)heptan-1-one,
(S)-7-(benzylamino)-7-(5-(2-methylquinolin-6-yl)-1H-imidazol-2-yl)-1-(oxazol-2-yl)heptan-1-one,
(S)-7-(benzylamino)-7-(5-(7-methoxy-2-methylquinolin-6-yl)-1H-imidazol-2-yl)-1-(oxazol-2-yl)heptan-1-one,
(S)-7-(5-(2-methylquinolin-6-yl)-1H-imidazol-2-yl)-7-morpholino-1-(oxazol-2-yl)heptan-1-one,
(S)-7-(5-(7-methoxy-2-methylquinolin-6-yl)-1H-imidazol-2-yl)-1-(oxazol-2-yl)-7-(pyrimidin-2-ylamino)heptan-1-one,
(S)-N-(1-(5-(2-methylquinolin-6-yl)-1H-imidazol-2-yl)-7-(oxazol-2-yl)-7-oxoheptyl)acetamide,
(S)-N-(1-(4-chloro-2-(4-fluorophenyl)-1H-imidazol-5-yl)-7-(oxazol-2-yl)-7-oxoheptyl)thiazole-5-carboxamide,
(S)-N-(1-(4-chloro-2-(4-fluorophenyl)-1H-imidazol-5-yl)-7-(oxazol-2-yl)-7-oxoheptyl)-2-(dimethylamino)acetamide,
(S)-2-(dimethylamino)-N-(1-(5-(2-ethyl-7-methoxy-1-oxo-1,2-dihydroisoquinolin-6-yl)-1H-imidazol-2-yl)-7-(isoxazol-3-yl)-7-oxoheptyl)acetamide,
(S)-2-(dimethylamino)-N-(7-(oxazol-2-yl)-7-oxo-1-(5-(quinoxalin-6-yl)-1H-imidazol-2-yl)heptyl)acetamide,
(S)-2-(dimethylamino)-N-(1-(5-(2-ethyl-7-methoxy-1-oxo-1,2-dihydroisoquinolin-6-yl)-1H-imidazol-2-yl)-7-(oxazol-2-yl)-7-oxoheptyl)acetamide,
(S)-N-((S)-1-(4-chloro-2-(4-fluorophenyl)-1H-imidazol-5-yl)-7-(oxazol-2-yl)-7-oxoheptyl)-6-ethyl-6-azaspiro[2.5]octane-1-carboxamide,
(S)-N-(1-(5-(7-methoxy-2-methylquinolin-6-yl)-1H-imidazol-2-yl)-7-(oxazol-2-yl)-7-oxoheptyl)-1-methyl piperidine-4-carboxamide,
(S)-N-(1-(5-(7-methoxy-2-methylquinolin-6-yl)-1H-imidazol-2-yl)-7-(oxazol-2-yl)-7-oxoheptyl)-1-methylazetidine-3-carboxamide,
(S)-N-(1-(5-(7-methoxy-2-methylquinolin-6-yl)oxazol-2-yl)-7-(oxazol-2-yl)-7-oxoheptyl)-1-methylazetidine-3-carboxamide,
(S)-N-(1-(4-chloro-2-(4-fluorophenyl)-1H-imidazol-5-yl)-7-(oxazol-2-yl)-7-oxoheptyl)-1-methylazetidine-3-carboxamide,
(S)-N-(7-(isoxazol-3-yl)-1-(5-(7-methoxy-1-methyl-2-oxo-1,2-dihydroquinolin-6-yl)-1H-imidazol-2-yl)-7-oxoheptyl)-1-methylazetidine-3-carboxamide,
(S)-N-(7-(isoxazol-3-yl)-1-(5-(7-methoxy-2-methylquinolin-6-yl)-1H-imidazol-2-yl)-7-oxoheptyl)-1-methylazetidine-3-carboxamide,
N-(1-(5-(2-methoxypyridin-3-yl)oxazol-2-yl)-7-(oxazol-2-yl)-7-oxoheptyl)-1-methylazetidine-3-carboxamide,
(S)-N-(1-(4-chloro-2-(2-fluorophenyl)-1H-imidazol-5-yl)-7-(isoxazol-3-yl)-7-oxoheptyl)-1-methylazetidine-3-carboxamide,
(S)-N-(1-(5-(2-fluorophenyl)-1,3,4-oxadiazol-2-yl)-7-(isoxazol-3-yl)-7-oxoheptyl)-1-methylazetidine-3-carboxamide,
N-(1-(5-(2-fluorophenyl)oxazol-2-yl)-7-(isoxazol-3-yl)-7-oxoheptyl)-1-methylazetidine-3-carboxamide,
(S)-N-(7-(isoxazol-3-yl)-1-(5-(7-methoxy-2-methylquinolin-6-yl)oxazol-2-yl)-7-oxoheptyl)-1-methylazetidine-3-carboxamide,
(S)-6-methyl-N-((S)-1-(5-(2-methylquinolin-6-yl)oxazol-2-yl)-7-(oxazol-2-yl)-7-oxoheptyl)-6-azaspiro[2.5]octane-1-carboxamide,
(S)-N-((S)-7-(isoxazol-3-yl)-1-(5-(7-methoxy-2-methylquinolin-6-yl)-1H-imidazol-2-yl)-7-oxoheptyl)-6-methyl-6-azaspiro[2.5]octane-1-carboxamide,
(1S)-6-methyl-N-(1-(5-(2-methylquinolin-6-yl)oxazol-2-yl)-7-(oxazol-2-yl)-7-oxoheptyl)-6-azaspiro[2.5]octane-1-carboxamide,
(S)-N-((S)-1-(4-chloro-2-(2-fluorophenyl)-1H-imidazol-5-yl)-7-(isoxazol-3-yl)-7-oxoheptyl)-6-methyl-6-azaspiro[2.5]octane-1-carboxamide,
(S)-N-((S)-1-(5-(7-methoxy-2-methylquinolin-6-yl)oxazol-2-yl)-7-(oxazol-2-yl)-7-oxoheptyl)-6-methyl-6-azaspiro[2.S]octane-1-carboxamide, (1S)-N-(1-(5-(2-methoxypyridin-3-yl)oxazol-2-yl)-7-(oxazol-2-yl)-7-oxoheptyl)-6-methyl-6-azaspiro[2.5]octane-1-carboxamide, (S)-N-((S)-1-(4-(6-cyclopropyl-2-methoxypyridin-3-yl)-1H-imidazol-2-yl)-7-(oxazol-2-yl)-7-oxoheptyl)-6-methyl-6-azaspiro[2.5]octane-1-carboxamide, (S)-8-methyl-N-(1-(5-(2-methylquinolin-6-yl)oxazol-2-yl)-7-(oxazol-2-yl)-7-oxoheptyl)-1-oxa-2,8-diazaspiro[4.5]dec-2-ene-3-carboxamide, (S)-N-(1-(5-(7-methoxy-2-methylquinolin-6-yl)-1H-imidazol-2-yl)-7-(oxazol-2-yl)-7-oxoheptyl)-2-methyl-2-azaspiro[3.5]nonane-7-carboxamide, (S)-7-amino-7-(5-(4-fluorophenyl)isoxazol-3-yl)-1-(isoxazol-3-yl)heptan-1-one, (R)-7-amino-7-(5-(4-fluorophenyl)isoxazol-3-yl)-1-(isoxazol-3-yl)heptan-1-one, (7S)-7-amino-7-[1-(4-fluorophenyl)-1H-pyrazol-3-yl]-1-isoxazol-3-ylheptan-1-one, 7-amino-7-[1-(4-fluorophenyl)-1H-pyrazol-4-yl]-1-isoxazol-3-vlheptan-1-one, 7-amino-7-[2-(4-fluorophenyl)-2H-1,2,3-triazol-4-yl]-1-isoxazol-3-vlheptan-1-one, (7S)-7-amino-7-(5-(2-fluorophenyl)isoxazol-3-yl]-1-isoxazol-3-ylheptan-1-one, (7S)-7-amino-1-isoxazol-3-yl-7-[5-(2-methyl-2H-indazol-5-yl)isoxazol-3-yl]heptan-1-one, (7R)-7-amino-7-[1-(2-methyl-2H-indazol-5-yl)-1H-pyrazol-3-yl]-1-(1,3-oxazol-2-yl)heptan-1-one, (7S)-7-amino-7-[1-(2-methyl-2H-indazol-5-yl)-1H-pyrazol-3-yl]-1-(1,3-oxazol-2-yl)heptan-1-one, (S)-7-amino-7-(5-(5-fluoro-2-methoxypyridin-4-yl)-1H-imidazol-2-yl)-1-(oxazol-2-yl)heptan-1-one, (7S)-7-amino-7-{5-[5-(cyclobutyloxy)-2-fluorophenyl]-1H-imidazol-2-yl}-1-(1,3-oxazol-2-yl)heptan-1-one, (7S)-7-amino-7-[5-(5-cyclopropyl pyrazin-2-yl)-1H-imidazol-2-yl]-1-(1,3-oxazol-2-yl)heptan-1-one, 5-{2-[(1S)-1-amino-7-(1,3-oxazol-2-yl)-7-oxoheptyl]-1H-imidazol-5-yl}pvrazine-2-carbonitrile, 6-{2-[(1S)-1-amino-7-(1,3-oxazol-2-yl)-7-oxoheptyl]-1H-imidazol-5-yl}pyrazine-2-carbonitrile, (7S)-7-amino-7-{5-[2-fluoro-4-(1H-pyrazol-1-yl)phenyl]-1H-imidazol-2-yl}-1-(1,3-oxazol-2-yl)heptan-1-one, (7S)-7-amino-7-[5-(2,5-difluorophenyl)-1H-imidazol-2-yl]-1-(1,3-oxazol-2-yl)heptan-1-one, (7S)-7-amino-7-{5-[2-fluoro-5-(trifluoromethyl)phenyl]-1H-imidazol-2-yl}-1-(1,3-oxazol-2-yl)heptan-1-one, (7S)-7-amino-7-{5-[2-fluoro-3-(trifluoromethyl)phenyl]-1H-imidazol-2-yl}-1-(1,3-oxazol-2-yl)heptan-1-one, (7S)-7-amino-7-{5-[2-fluoro-4-(trifluoromethyl)phenyl]-1H-imidazol-2-yl}-1-(1,3-oxazol-2-yl)heptan-1-one, (7S)-7-amino-7-[5-(2-fluoro-4-methoxyphenyl)-1H-imidazol-2-yl]-1-(1,3-oxazol-2-yl)heptan-1-one, (7S)-7-amino-7-{5-[2-fluoro-4-(trifluoromethoxy)phenyl]-1H-imidazol-2-yl}-1-(1,3-oxazol-2-yl)heptan-1-one, (7S)-7-amino-7-{5-[2-fluoro-5-(trifluoromethoxy)phenyl]-1H-imidazol-2-yl}-1-(1,3-oxazol-2-yl)heptan-1-one, (7S)-7-amino-7-{5-[2-fluoro-4-(methylsulfonyl)phenyl]-1H-imidazol-2-yl}-1-(1,3-oxazol-2-yl)heptan-1-one, (7S)-7-amino-7-(5-{2-fluoro-3-methoxy-5-[(trans-3-methoxycyclobutyl)oxy]phenyl}-1H-imidazol-2-yl)-1-(1,3-oxazol-2-yl)heptan-1-one, (S)-6-ethyl-N-((S)-7-(isoxazol-3-yl)-1-(5-(7-methoxy-2-methylquinolin-6-yl)isoxazol-3-yl)-7-oxoheptyl)-6-azaspiro[2.5]octane-1-carboxamide, 6-(difluoromethoxy)-N-[(1S)-1-[5-(2-methoxyquinolin-3-yl)-1H-imidazol-2-yl]-7-(1,3-oxazol-2-yl)-7-oxoheptyl]pyridine-3-carboxamide, 2-methoxy-N-[(1S)-1-[5-(2-methoxyquinolin-3-yl)-1H-imidazol-2-yl]-7-(1,3-oxazol-2-vi)-7-oxoheptyl lacetamide, 2,2-difluoro-N-[(1S)-1-[5-(2-methoxyquinolin-3-yl)-1H-imidazol-2-yl]-7-(1,3-oxazol-2-yl)-7-oxoheptyl]propenamide, N-[(1S)-1-[5-(2-methoxyquinolin-3-yl)-1H-imidazol-2-yl]-7-(1,3-oxazol-2-yl)-7-oxoheptyl]pyrimidine-4-carboxamide, N-[(1S)-1-[5-(2-methoxyquinolin-3-yl)-1H-imidazol-2-yl]-7-(1,3-oxazol-2-yl)-7-oxoheptyl]-2-(1H-pyrrol-1-yl)acetamide, N-[(1S)-1-[5-(2-methoxyquinolin-3-yl)-1H-imidazol-2-yl]-7-(1,3-oxazol-2-yl)-7-oxoheptyl]-1-pyridin-4-ylcyclopropanecarboxamide, N-[(1S)-1-[5-(2-methoxyquinolin-3-yl)-1H-imidazol-2-yl]-7-(1,3-oxazol-2-yl)-7-oxoheptyl]-1,4-dioxane-2-carboxamide, N-[(1S)-1-[5-(2-methoxyquinolin-3-yl)-1H-imidazol-2-yl]-7-(1,3-oxazol-2-yl)-7-oxoheptyl]-1,3-benzoxazole-2-carboxamide, N-[(1S)-1-[5-(2-methoxyquinolin-3-yl)-1H-imidazol-2-yl]-7-(1,3-oxazol-2-yl)-7-oxoheptyl]-4,5,6,7-tetrahydropyrazolo[1,5-a]pyridine-2-carboxamide, N-[(1S)-1-[5-(2-methoxyquinolin-3-yl)-1H-imidazol-2-yl]-7-(1,3-oxazol-2-yl)-7-oxoheptyl]-1-pyrazin-2-ylcyclopropanecarboxamide, N-[(1S)-1-[5-(2-methoxyquinolin-3-yl)-1H-imidazol-2-yl]-7-(1,3-oxazol-2-yl)-7-oxoheptyl]-5-oxo-D-prolinamide, N-[(1S)-1-[5-(2-methoxyquinolin-3-yl)-1H-imidazol-2-yl]-7-(1,3-oxazol-2-yl)-7-oxoheptyl]-5-oxo-L-prolinamide, N-[(1S)-1-[5-(7-methoxy-2-methylquinolin-6-yl)-1H-imidazol-2-yl]-7-(1,3-oxazol-2-yl)-7-oxoheptyl]-2-(3-oxomorpholin-4-yl)acetamide, N-[(1S)-1-[5-(7-methoxy-2-methylquinolin-6-yl)-1H-imidazol-2-yl]-7-(1,3-oxazol-2-yl)-7-oxoheptyl]-2-(2-oxopiperazin-1-yl)acetamide, N-[(1S)-1-[5-(7-methoxy-2-methylquinolin-6-yl)-1H-imidazol-2-yl]-7-(1,3-oxazol-2-yl)-7-oxoheptyl]-2-(1H-pyrazol-1-yl)acetamide, N-[(1S)-1-[5-(7-methoxy-2-methylquinolin-6-yl)-1H-imidazol-2-yl]-7-(1,3-oxazol-2-yl)-7-oxoheptyl]pyrazolo[1,5-a]pyrimidine-2-carboxamide, N-[(1S)-1-[5-(7-methoxy-2-methylquinolin-6-yl)-1H-imidazol-2-yl]-7-(1,3-oxazol-2-yl)-7-oxoheptyl]-2-(1H-pyrrol-1-yl)acetamide, N-[(1S)-1-[5-(7-methoxy-2-methylquinolin-6-yl)-1H-imidazol-2-yl]-7-(1,3-oxazol-2-yl)-7-oxoheptyl]-6,7-dihydro-5H-pyrazolo[5,1-b][1,3]oxazine-2-carboxamide, N-[(1S)-1-[5-(7-methoxy-2-methylquinolin-6-yl)-1H-imidazol-2-yl]-7-(1,3-oxazol-2-yl)-7-oxoheptyl]-4,5,6,7-tetrahydropyrazolo[1,5-a]pyridine-2-carboxamide, N-[(1S)-1-[5-(7-methoxy-2-methylquinolin-6-yl)-1H-imidazol-2-yl]-7-(1,3-oxazol-2-yl)-7-oxoheptyl]-6,7-dihydro-4H-pyrazolo[5,1-c][1,4]thiazine-2-carboxamide 5,5-dioxide, N-[(1S)-1-[5-(7-methoxy-2-methylquinolin-6-yl)-1H-imidazol-2-yl]-7-(1,3-oxazol-2-yl)-7-oxoheptyl]-2-(3-methyl-1H-pyrazol-1-yl)acetamide, N-[(1S)-1-[5-(7-methoxy-2-methylquinolin-6-yl)-1H-imidazol-2-yl]-7-(1,3-oxazol-2-yl)-7-oxoheptyl]pyrazolo[1,5-a]pyridine-2-carboxamide,
N-[(1S)-1-[5-(7-methoxy-2-methylquinolin-6-yl)-1H-imidazol-2-yl]-7-(1,3-oxazol-2-yl)-7-oxoheptyl]tetrahydro-2H-pyran-2-carboxamide,
N N-[(1S)-1-[5-(7-methoxy-2-methylquinolin-6-yl)-1H-imidazol-2-yl]-7-(1,3-oxazol-2-yl)-7-oxoheptyl]-2-methyltetrahydro-2H-pyran-2-carboxamide,
N-[(1S)-1-[5-(7-methoxy-2-methylquinolin-6-yl)-1H-imidazol-2-yl]-7-(1,3-oxazol-2-yl)-7-oxoheptyl]tetrahydrofuran-2-carboxamide,
N-[(1S)-1-[5-(7-methoxy-2-methylquinolin-6-yl)-1H-imidazol-2-yl]-7-(1,3-oxazol-2-yl)-7-oxoheptyl]-2,3-dihydro-1,4-benzodioxine-2-carboxamide,
N-[(1S)-1-[5-(7-methoxy-2-methylquinolin-6-yl)-1H-imidazol-2-yl]-7-(1,3-oxazol-2-yl)-7-oxoheptyl]-5-phenyl-1,4-dioxane-2-carboxamide,
N-[(1S)-1-[5-(7-methoxy-2-methylquinolin-6-yl)-1H-imidazol-2-yl]-7-(1,3-oxazol-2-yl)-7-oxoheptyl]-1,4-dioxane-2-carboxamide,
N-[(1S)-1-[5-(7-methoxy-2-methylquinolin-6-yl)-1H-imidazol-2-yl]-7-(1,3-oxazol-2-yl)-7-oxoheptyl]-1,4-dioxane-2-carboxamide,
(1S)-6-ethyl-N-{(1S)-1-[5-(2-fluorophenyl)isoxazol-3-yl]-7-isoxazol-3-yl-7-oxoheptyl}-6-azaspiro[2.5]octane-1-carboxamide,
(1S)-6-ethyl-N-{(1S)-7-isoxazol-3-yl-1-[5-(2-methyl-2H-indazol-5-yl)isoxazol-3-yl]-7-oxoheptyl}-6-azaspiro[2.5]octane-1-carboxamide,
N-{(1S)-7-isoxazol-3-yl-1-[5-(2-methyl-2H-indazol-5-yl)isoxazol-3-yl]-7-oxoheptyl}-8-methyl-1-oxa-2,8-diazaspiro[4.5]dec-2-ene-3-carboxamide,
N-[(1S)-1-[5-(5-fluoro-2-methoxypyridin-4-yl)-1H-imidazol-2-yl]-7-(1,3-oxazol-2-yl)-7-oxoheptyl]-1-methylazetidine-3-carboxamide,
(1S)-6-ethyl-N-[(1S)-1-[5-(5-fluoro-2-methoxypyridin-4-yl)-1H-imidazol-2-yl]-7-(1,3-oxazol-2-yl)-7-oxoheptyl]-6-azaspiro[2.5]octane-1-carboxamide,
(1S)-6-ethyl-N-[(1S)-1-[1-(2-methyl-2H-indazol-5-yl)-1H-pyrazol-3-yl]-7-(1,3-oxazol-2-yl)-7-oxoheptyl]-6-azaspiro[2.5]octane-1-carboxamide,
N-[(1S)-1-{5-[5-(cyclobutyloxy)-2-fluorophenyl]-1H-imidazol-2-yl}-7-(1,3-oxazol-2-yl)-7-oxoheptyl]-1-methylazetidine-3-carboxamide,
(1S)-N-[(1S)-1-{5-[5-(cyclobutyloxy)-2-fluorophenyl]-1H-imidazol-2-yl}-7-(1,3-oxazol-2-yl)-7-oxoheptyl]-6-ethyl-6-azaspiro[2.5]octane-1-carboxamide,
(S)-6-ethyl-N-((S)-2-(5-(2-fluorophenyl)-1H-imidazol-2-yl)-8-(isoxazol-3-yl)-8-oxooctan-2-yl)-6-azaspiro[2.5]octane-1-carboxamide,
(S)-N-(2-(5-(2-fluorophenyl)-1H-imidazol-2-yl)-8-(isoxazol-3-yl)-8-oxooctan-2-yl)-1-10 methylazetidine-3-carboxamide,
(S)-5-(1-amino-7-(oxazol-2-yl)-7-oxoheptyl)-2-(4-fluorophenyl)-1H-imidazole-4-carbonitrile,
(S)-N-(1-(4-cyano-2-(4-fluorophenyl)-1H-imidazol-5-yl)-7-(oxazol-2-yl)-7-oxoheptyl)-2-(dimethylamino)acetamide,
(S)-N-((S)-1-(4-cyano-2-(4-fluorophenyl)-1H-imidazol-5-yl)-7-(oxazol-2-yl)-7-oxoheptyl)-6-methyl-6-azaspiro[2.5]octane-1-carboxamide,
(S)-N-(1-(4-cyano-2-(4-fluorophenyl)-1H-imidazol-5-yl)-7-(oxazol-2-yl)-7-oxoheptyl)thiazole-5-carboxamide,
(S)-5-(1-amino-7-(oxazol-2-yl)-7-oxoheptyl)-2-(4-fluorophenyl)oxazole-4-carbonitrile,
(S)-N-(1-(4-cyano-2-(4-fluorophenyl)-1H-imidazol-5-yl)-7-(oxazol-2-yl)-7-oxoheptyl)-2-(dimethylamino)acetamide,
(S)-N-((S)-1-(4-cyano-2-(4-fluorophenyl)oxazol-5-yl)-7-(oxazol-2-yl)-7-oxoheptyl)-6-methyl-6-azaspiro[2.5]octane-1-carboxamide,
(S)-N-(1-(4-cyano-2-(4-fluorophenyl)oxazol-5-yl)-7-(oxazol-2-yl)-7-oxoheptyl)thiazole-5-carboxamide,
(S)-7-amino-7-(4-chloro-5-(4-fluorophenyl)-1H-imidazol-2-yl)-1-(isoxazol-3-yl)heptan-1-one,
(S)-N-(1-(4-chloro-5-(4-fluorophenyl)-1H-imidazol-2-yl)-7-(isoxazol-3-yl)-7-oxoheptyl)-2-25 (dimethylamino)acetamide,
(S)-N-((S)-1-(4-chloro-5-(4-fluorophenyl)-1H-imidazol-2-yl)-7-(isoxazol-3-yl)-7-oxoheptyl)-6-methyl-6-azaspiro[2.5]octane-1-carboxamide 2,3-dihydroxysuccinate,
(S)-N-(1-(4-chloro-5-(4-fluorophenyl)-1H-imidazol-2-yl)-7-(isoxazol-3-yl)-7-oxoheptyl)-1-methylazetidine-3-carboxamide 2,3-dihydroxysuccinate,
or a pharmaceutically acceptable salt thereof.

7. A pharmaceutical composition comprising an effective amount of a compound of claim 1, or a pharmaceutically acceptable salt thereof, and a pharmaceutically acceptable carrier.

8. A method for the inhibition of HDAC in a subject in need thereof which comprises administering to the subject an effective amount of a compound of claim 1, or a pharmaceutically acceptable salt thereof.

9. A method for the treatment of infection by HIV or for the treatment of AIDS in a subject in need thereof, which comprises administering to the subject an effective amount of a compound of claim 1, or a pharmaceutically acceptable salt thereof.

10. The pharmaceutical composition of claim 7, further comprising one or more additional therapeutic agents selected from raltegravir, lamivudine, abacavir, ritonavir, darunavir, atazanavir, emtricitabine, tenofovir, rilpivirine, doravirine, EFdA and lopinavir.

11. The method of claim 9, further comprising administering to the subject one or more additional therapeutic agents selected from raltegravir, lamivudine, abacavir, ritonavir, darunavir, atazanavir, emtricitabine, tenofovir, rilpivirine, doravirine, EFdA and lopinavir, wherein the amounts administered of the compounds are B together effective to treat infection by HIV or to treat AIDS.

12. A compound of claim 1, selected from the group consisting of

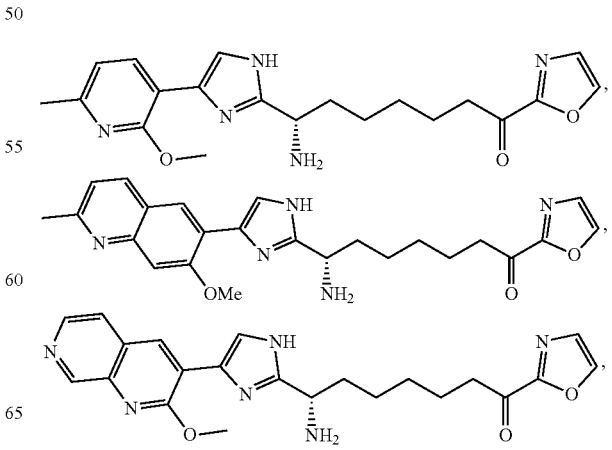

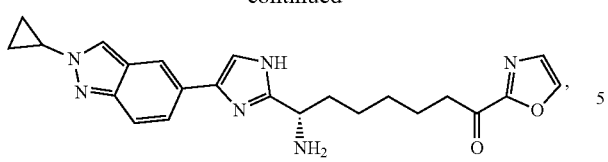
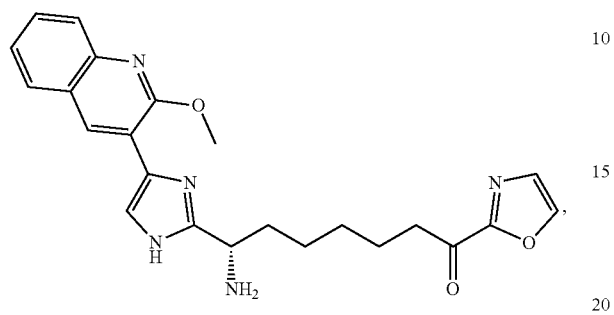
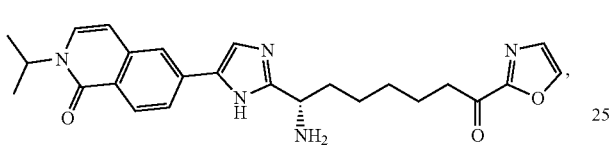
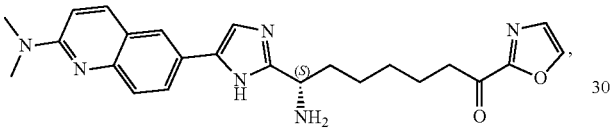
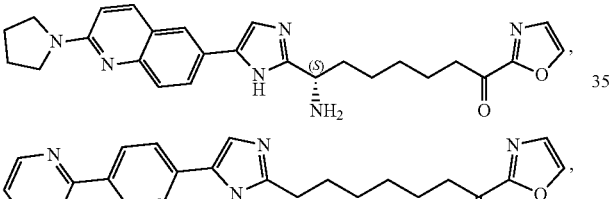
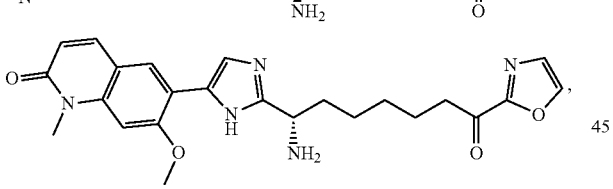
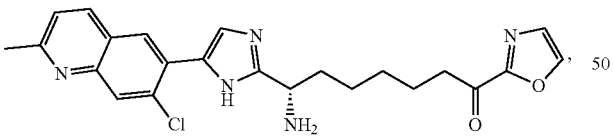
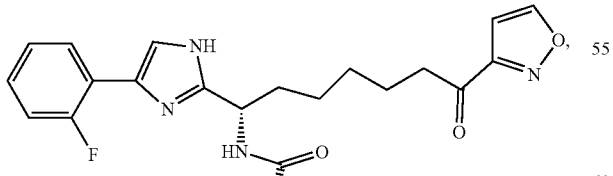
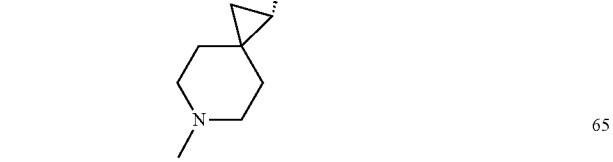
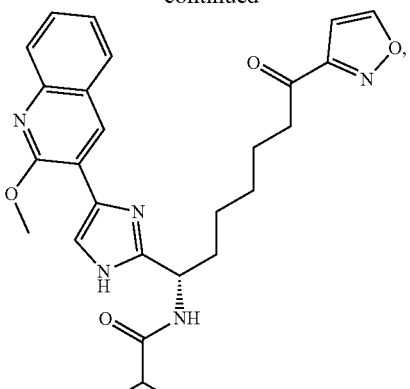
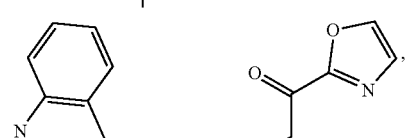
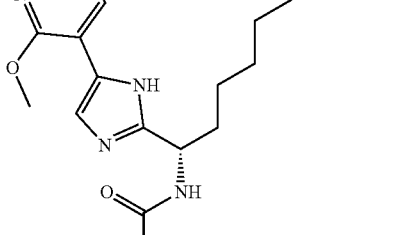
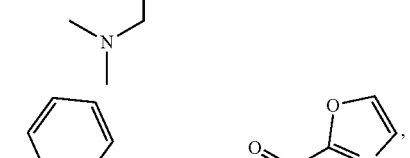
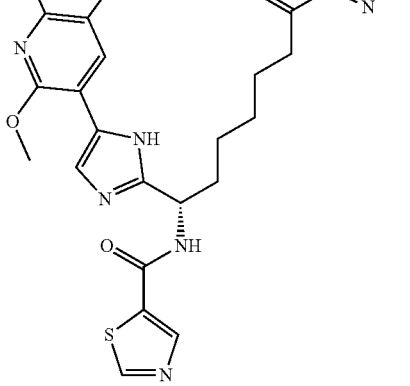
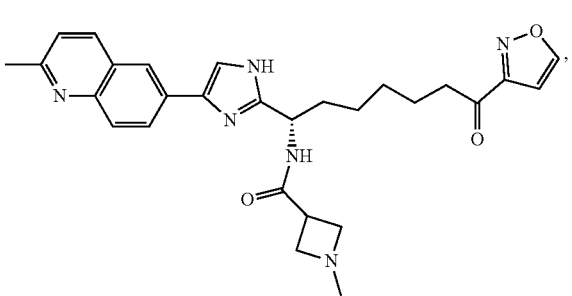

279
-continued
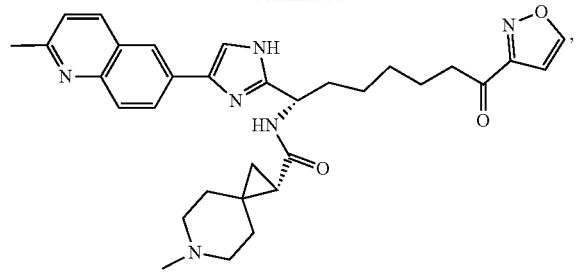
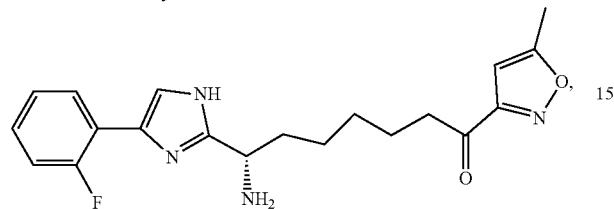
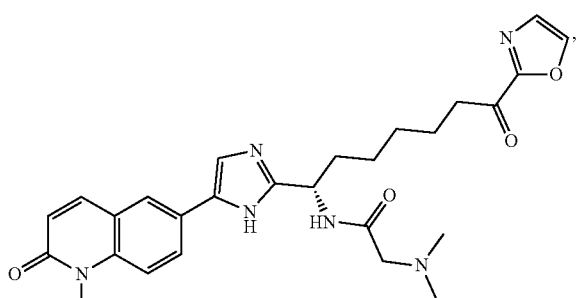
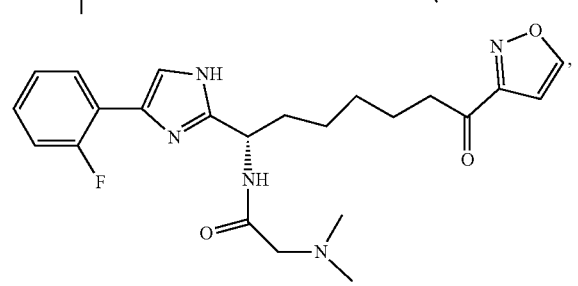
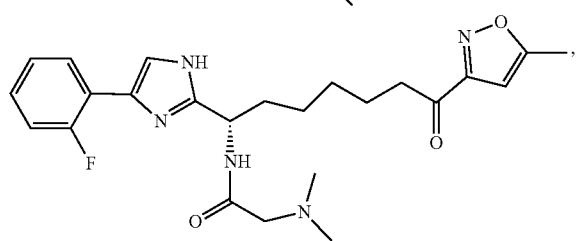
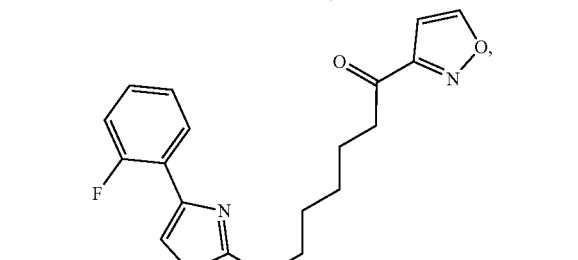
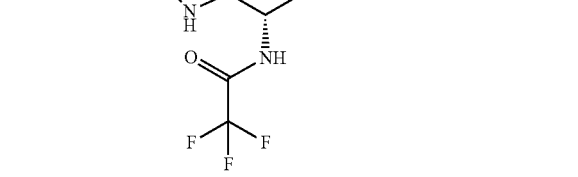
280
-continued
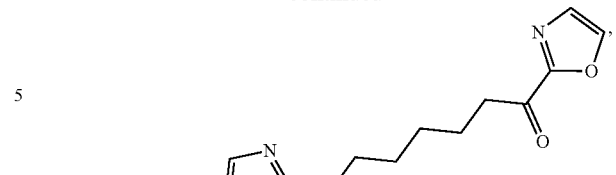
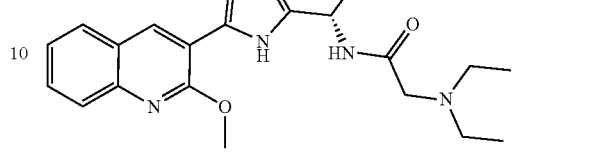
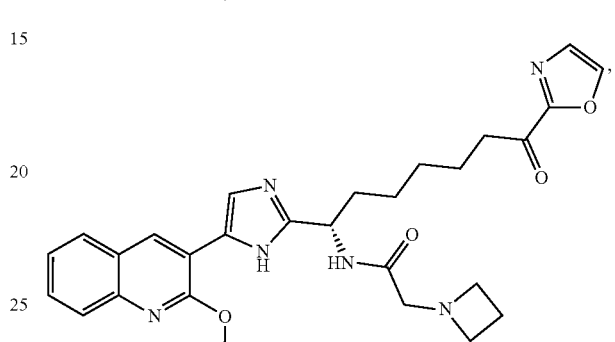
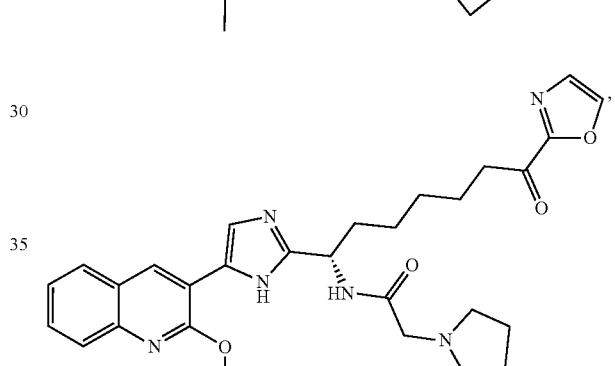
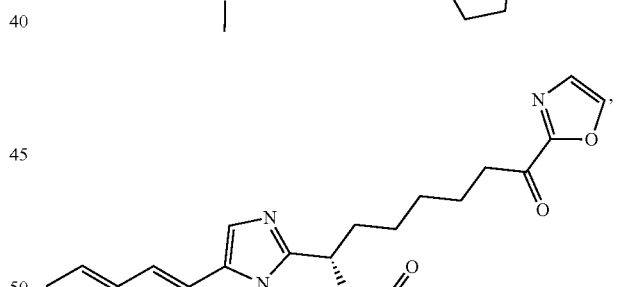
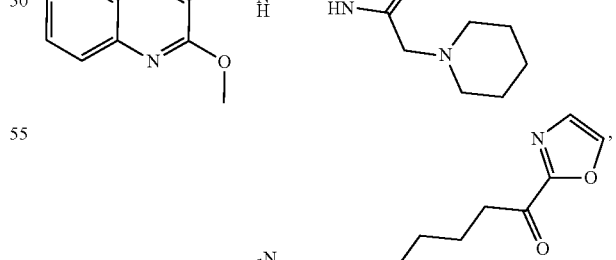
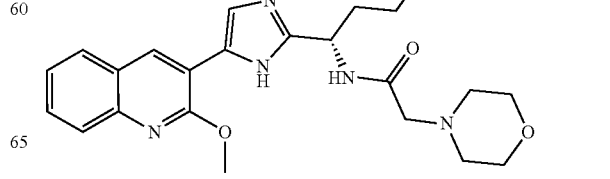

281
-continued
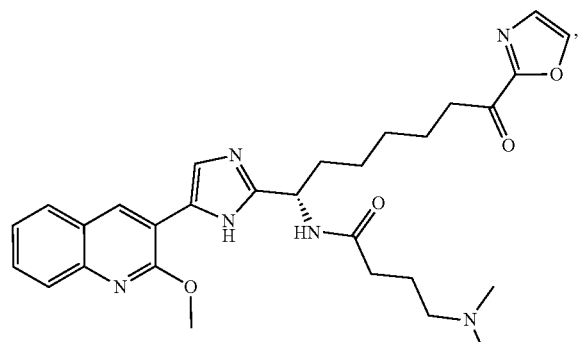
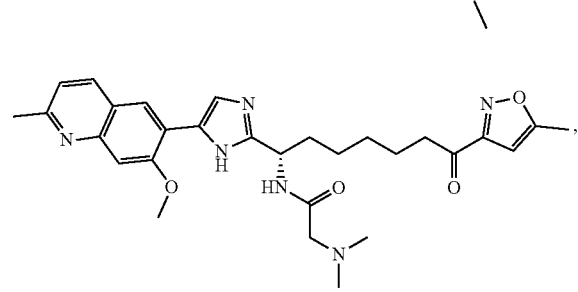
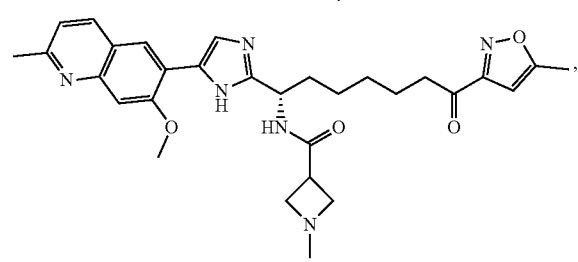
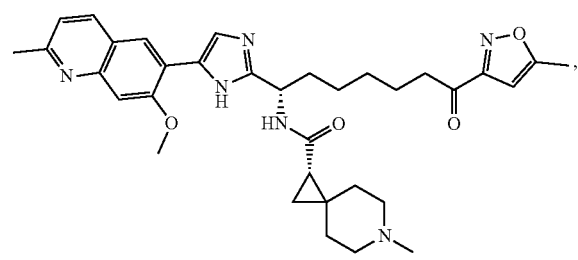
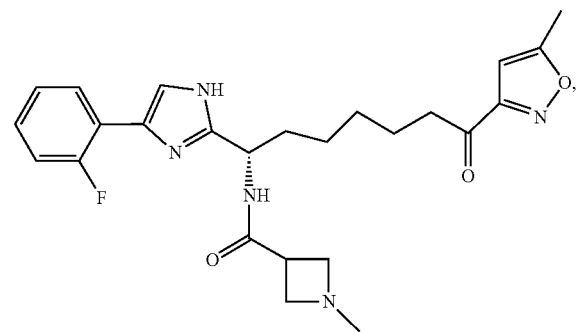
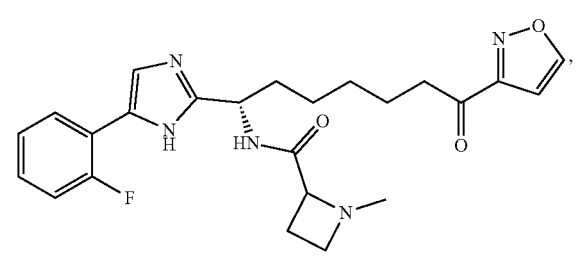
282
-continued
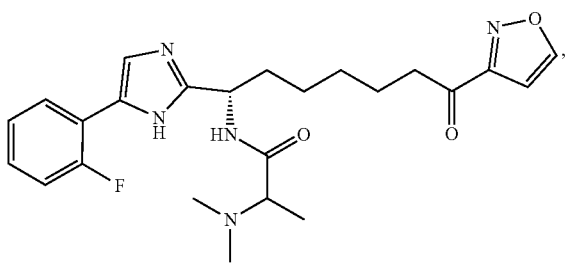
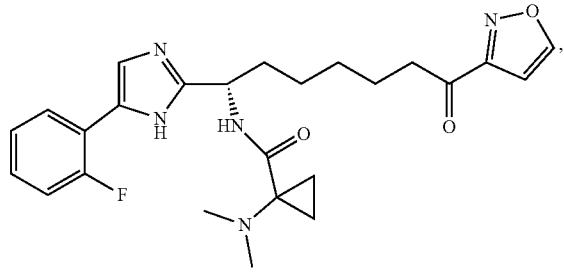
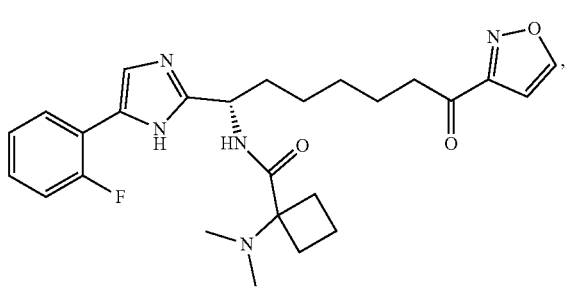
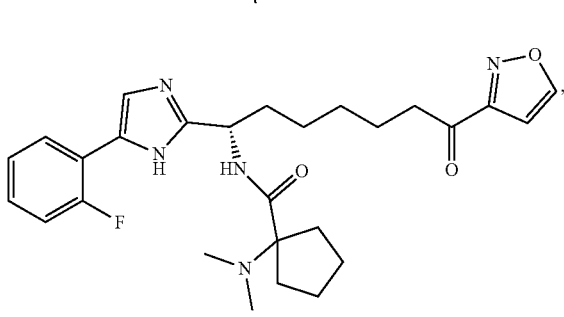
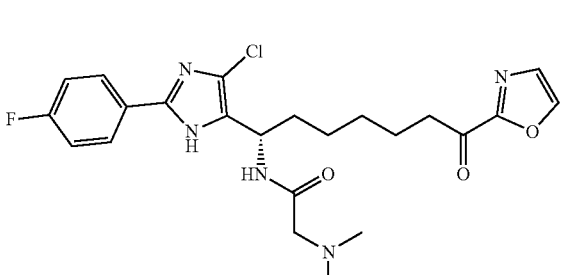
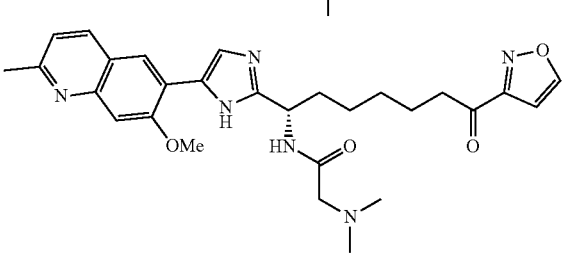

-continued
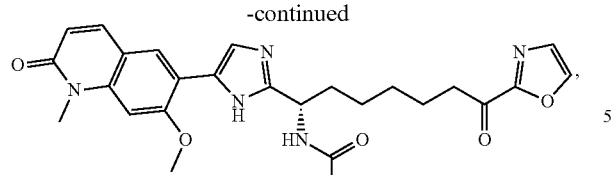
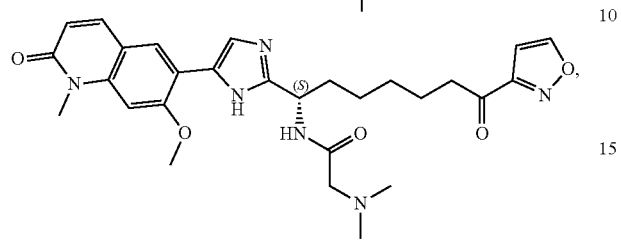
or a pharmaceutically acceptable salt thereof.
* * * * *